United States Patent
Schwink et al.

(10) Patent No.: US 7,223,788 B2
(45) Date of Patent: May 29, 2007

(54) SUBSTITUTED N-ARYL HETEROCYCLES, PROCESS FOR THEIR PREPARATION AND THEIR USE AS MEDICAMENTS

(75) Inventors: Lothar Schwink, Stadtallendorf (DE); Siegfried Stengelin, Eppstein (DE); Matthias Gossel, Hofheim (DE); Thomas Boehme, Ruesselsheim (DE); Gerhard Hessler, Hofheim (DE); Petra Stahl, Frankfurt (DE); Dirk Gretzke, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 217 days.

(21) Appl. No.: 10/779,853

(22) Filed: Feb. 17, 2004

(65) Prior Publication Data

US 2004/0220191 A1 Nov. 4, 2004

Related U.S. Application Data

(60) Provisional application No. 60/488,545, filed on Jul. 18, 2003.

(30) Foreign Application Priority Data

Feb. 14, 2003 (DE) ................ 103 06 250

(51) Int. Cl.
  *A61K 31/40* (2006.01)
  *A61K 31/4025* (2006.01)
  *C07D 207/14* (2006.01)
  *C07D 211/56* (2006.01)

(52) U.S. Cl. ............ 514/426; 514/218; 514/318; 514/326; 514/329; 546/279.1; 546/304; 548/557

(58) Field of Classification Search ........ 548/557; 546/306, 279.1, 304; 514/326, 329, 429, 514/218, 318, 426
See application file for complete search history.

(56) References Cited

FOREIGN PATENT DOCUMENTS

| | | |
|---|---|---|
| EP | 1176140 | 1/2002 |
| WO | WO 96/13502 | 5/1996 |
| WO | WO 99/24406 | 5/1999 |
| WO | WO 00/35454 | 6/2000 |
| WO | WO 00/61569 | 10/2000 |
| WO | WO 00/71529 | 11/2000 |
| WO | WO 02/06232 | 1/2002 |
| WO | WO 02/06278 | 1/2002 |
| WO | WO 02/10146 | 2/2002 |
| WO | WO 02/20501 | 3/2002 |
| WO | WO 02/42271 | 5/2002 |
| WO | WO 02/098839 | 12/2002 |
| WO | WO 02/098871 | 12/2002 |
| WO | WO 02/099388 | 12/2002 |
| WO | WO 03/091256 | 11/2003 |
| WO | WO 2004/002948 | 1/2004 |

OTHER PUBLICATIONS

Wood, M., et. al., Benzodiazepines as Potent and Selective Bradkinin B1 Antagonists, J. Med. Chem. vol. 46, No. 10 pp. 1803-1806 (2003).

*Primary Examiner*—Bernard Dentz
(74) *Attorney, Agent, or Firm*—Barbara E. Kurys

(57) ABSTRACT

The invention relates to substituted N-aryl heterocycles and to the physiologically tolerated salts and physiologically functional derivatives thereof.

Compounds of the formula I

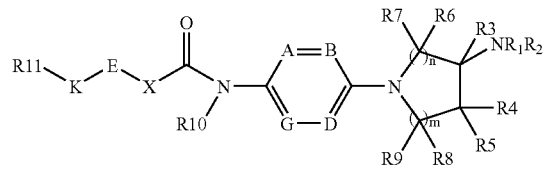

in which the radicals have the stated meanings, the N-oxides and the physiologically tolerated salts thereof and process for the preparation thereof are described. The compounds are suitable for example as anorectic agents.

14 Claims, No Drawings

SUBSTITUTED N-ARYL HETEROCYCLES, PROCESS FOR THEIR PREPARATION AND THEIR USE AS MEDICAMENTS

This application claims priority from Provisional Application 60/488,545 filed Jul. 18, 2003.

The invention relates to substituted N-aryl heterocycles and to the physiologically tolerated salts and physiologically functional derivatives thereof.

Compounds having a pharmacological effect and similar in their overall structure to the N-aryl heterocycles described herein have already been described in the prior art. Thus, for example, WO 00/35454 describes ureido-substituted phenylpiperidines and -pyrrolidines as agents for the treatment of inflammatory and autoimmune diseases. Acylamido-substituted phenylpyrrolidines are proposed in WO 02/042271 for the treatment of diabetes, obesity and disorders of lipid metabolism.

The invention was based on the object of providing compounds which bring about a weight reduction in mammals and are suitable for preventing and treating obesity and diabetes.

The invention therefore relates to compounds of the formula I

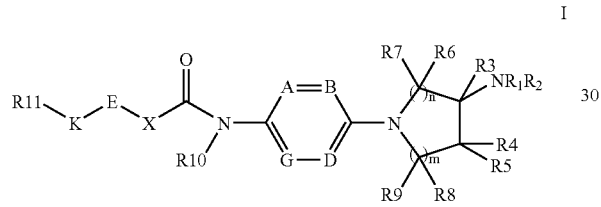

I wherein

R1, R2 are each independently H, $(C_1-C_8)$-alkyl, —$(CR78R79)_o$-R12, $(C_1-C_4)$-alkoxy-$(C_1-C_4)$-alkyl, aryloxy-$(C_1-C_4)$-alkyl, $(C_3-C_8)$-alkenyl, $(C_3-C_8)$-alkynyl, CO—$(C_1-C_8)$-alkyl, —CO—$(CH_2)_o$-R12, CO-aryloxy-$(C_1-C_4)$-alkyl, CO—$(C_2-C_8)$-alkenyl, CO—$(C_2-C_8)$-alkynyl, COCH=CH(R13), COCC(R14), CO—$(C_1-C_4)$-alkyl-S(O)$_p$-$(C_1-C_4)$-alkyl, CO(C(R15)(R16))$_q$N(R17)(R18), CO(C(R19)(R20))$_r$CON(R21)(R22) or CO(C(R23)(R24))$_s$O(R25); or R1 and R2, together with the nitrogen atom to which they are attached, form a 4-, 5-, 6-, 7-, 8-, 9- or 10-membered mono-, bi- or spirocyclic ring which, apart from said nitrogen atom of attachment, optionally contains 1, 2, 3 or 4 additional heteroatoms selected from the group of oxygen, nitrogen and sulfur, and is optionally substituted by F, Cl, Br, CF$_3$, NO$_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R26), CON(R27)(R28), hydroxy, COO(R29), N(R30)CO$(C_1-C_6)$-alkyl, N(R31)(R32) or SO$_2$CH$_3$;
wherein
o is 0, 1, 2, 3, 4, 5 or 6;
p is 0, 1 or 2
q, r, s are each independently 0, 1, 2, 3 or 4;
R13, R14 are each independently a 5-, 6-, 7-, 8-, 9- or 10-membered aromatic ring system optionally containing 1 or 2 heteroatoms selected from the group of nitrogen, oxygen and sulfur, and is optionally substituted by F, Cl, Br, CF$_3$, NO$_2$, CN, $(C_1-C_6)$-alkyl or O—$(C_1-C_8)$-alkyl;

R15, R16, R17, R19, R20, R21, R22, R23, R24, R25, R26, R27, R28, R29, R30, R31, R32 are each independently H or $(C_1-C_6)$-alkyl;
R18 is H, $(C_1-C_6)$-alkyl, CO($C_1-C_6$)-alkyl or CO(R33);
or
substituent pairs R17 and R18, R21 and R22, R27 and R28, and R31 and R32, independently of one another and taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur;
R33 is a 5-, 6-, 7-, 8-, 9- or 10-membered aromatic ring system which optionally contains 1 or 2 heteroatoms selected from the group of nitrogen, oxygen and sulfur, and is optionally substituted by F, Cl, Br, CF$_3$, NO$_2$, CN, $(C_1-C_6)$-alkyl or O—$(C_1-C_8)$-alkyl;
R12 is OH, O—$(C_1-C_6)$-alkyl, O$(C_0-C_8)$-alkylene-aryl, CN, S—$(C_1-C_6)$-alkyl, COO(R80), CON(R81)(R93), N(R82)(R83) or a 3-, 4-, 5-, 6-, 7-, 8-, 9-, 10-, 11-, or 12-membered mono-, bi- or spirocyclic ring which optionally contains one or more heteroatoms selected from the group of N, O and S, and is optionally substituted with F, Cl, Br, I, OH, CF$_3$, NO$_2$, CN, OCF$_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, O—$(C_0-C_8)$-alkylene-aryl, N(R34)(R35), COCH=CH(R36), (C(R37)(R38))$_t$(R39), CO(C(R37)(R38))$_t$(R39), CO$(C_1-C_6)$-alkyl, COCOO$(C_1-C_6)$-alkyl, COO(R40), S(O)$_u$(R41) or COOH;
t is 0, 1, 2, 3, 4, 5 or 6;
u is 0, 1 or 2;
R34, R35, R37, R38 are each independently H or $(C_1-C_8)$-alkyl; or
R34 and R35, taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur, and is optionally substituted by 1 or 2 oxo groups;
R36, R39 are each independently $(C_3-C_8)$-cycloalkyl or a 5-, 6-, 7-, 8-, 9- or 10-membered aromatic ring system wherein said aromatic ring system optionally contains one or two additional heteroatoms selected from the group of nitrogen, oxygen and sulfur, and is optionally substituted by F, Cl, Br, CF$_3$, NO$_2$, CN, $(C_1-C_6)$-alkyl or O—$(C_1-C_8)$-alkyl;
R40 is H, $(C_1-C_8)$-alkyl, $(C_2-C_6)$-alkenyl or $(C_0-C_8)$-alkylene-aryl;
R41 is $(C_1-C_6)$-alkyl or a 5-, 6-, 7-, 8-, 9-, or 10-membered aromatic ring system optionally containing one or two heteroatoms from the group of nitrogen, oxygen and sulfur, and optionally substituted by F, Cl, Br, CF$_3$, NO$_2$, CN, $(C_1-C_6)$-alkyl or O—$(C_1-C_8)$-alkyl;
R78, R79 are each independently H, $(C_1-C_8)$-alkyl, hydroxy-$(C_1-C_4)$-alkyl, OH or $(C_1-C_4)$-alkoxy-$(C_1-C_4)$-alkyl;
R80, R81, R93 are each independently $(C_1-C_8)$-alkyl, $(C_2-C_6)$-alkenyl or $(C_0-C_8)$-alkylene-aryl;
R82, R83 are each independently H or $(C_1-C_6)$-alkyl; or
R82 and R83, taken together with the nitrogen atom to which they are attached, optionally form a 5- or 6-membered ring which, apart from said nitrogen atom of attachment, optionally contains one additional heteroatom component selected from the group of N—$(C_1$-$C_6)$-alkyl, oxygen and sulfur, and is optionally substituted by 1 or 2 oxo groups;

R3 is H or $(C_1$-$C_6)$-alkyl;

R4, R5 are each independently H, $(C_1$-$C_6)$-alkyl, OH, O—$(C_1$-$C_6)$-alkyl, O—$CO(C_1$-$C_6)$-alkyl or S—$(C_1$-$C_6)$-alkyl;

R6, R7, R8, R9 are each independently H or $(C_1$-$C_8)$-alkyl; or substituent pairs R6 and R7, and R8 and R9, optionally form, independently of one another, an oxo group;

n, m are each independently 0, 1 or 2;

A, B, D, G are each independently N or C(R42); or said radicals A and B, or said radicals D and G are each C(R42) and, taken together, optionally form a 5- or 6 membered carbocyclic or heterocyclic radical resulting in an overall bicyclic ring system;

wherein

R42 is H, F, Cl, Br, I, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, $(C_0$-$C_8)$-alkylene-aryl, O—$(C_0$-$C_8)$-alkylene-aryl, S-aryl, N(R43)(R44), $SO_2$—$CH_3$, COOH, COO—$(C_1$-$C_6)$-alkyl, CON(R45)(R46), N(R47)CO(R48), N(R49)$SO_2$(R50), CO(R51) or —$(CR84R85)_x$—O(R86);

wherein

R43, R44, R45, R46, R47, R49 are each independently H or $(C_1$-$C_8)$-alkyl; or substituent pairs R43 and R44, and R45 and R46, independently of one another and taken together with the nitrogen atom to which they are attached, optionally form a 5- or 6-membered ring which, apart from said nitrogen atom of attachment, optionally contains an additional heteroatom component selected from the group of N—$(C_1$-$C_6)$-alkyl, oxygen and sulfur;

R48, R50, R51 are each independently H, $(C_1$-$C_8)$-alkyl or aryl;

R84, R85 are each independently H or $(C_1$-$C_8)$-alkyl;

R86 is H, $(C_1$-$C_6)$-alkyl or aryl;

x is 1, 2, 3, 4, 5 or 6;

R10 is H, $(C_1$-$C_8)$-alkyl, $(C_3$-$C_6)$-alkenyl or $(C_3$-$C_6)$-alkynyl;

X is N(R52), O, a bond, C=C, C(R53)(R54), C(R55)(R56) O, CO, C≡C, or a group of the formula —$(CR87R88)_y$- wherein one or more —(CR87R88)-units contained in said group of formula —$(CR87R88)_y$— is optionally replaced by Y;

wherein

Y is O, S or N(R89) wherein R89 is H or $(C_1$-$C_8)$-alkyl;

R52, R53, R54, R55, R56 are each independently H or $(C_1$-$C_8)$-alkyl;

R87, R88 are each independently H or $(C_1$-$C_4)$-alkyl, and may be defined the same or differently in each of said —(CR87R88)-units contained in said group of formula —$(CR87R88)_y$-;

y is 2, 3, 4, 5 or 6;

E is a 3, 4, 5, 6, 7, 8, 9, 10, 11, 12, 13- or 14-membered bivalent carbo- or heterocyclic ring structure with 0, 1, 2, 3 or 4 heteroatoms selected from the group of N, O and S, and optionally substituted with H, F, Cl, Br, I, OH, $CF_3$, $NO_2$, CN, $OCF_3$, oxo, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, $(C_0$-$C_8)$-alkylene-aryl, O—$(C_0$-$C_8)$-alkylene-aryl, S-aryl, N(R57)(R58), $SO_2$—$CH_3$, COOH, COO—$(C_1$-$C_6)$-alkyl, CON(R59)(R60), N(R61)CO(R62), N(R63)$SO_2$(R64) or CO(R65), and wherein said bivalent carbo- or heterocyclic ring structure is mono- or bicyclic;

wherein

R57, R58, R59, R60, R61, R63 are each independently H or $(C_1$-$C_8)$-alkyl; or substituent pairs R57 and R58, and R59 and R60, independently of one another and taken together with the nitrogen atom to which they are attached, optionally form a 5- or 6-membered ring which, apart from said nitrogen atom of attachment, optionally contains one further heteroatom component selected from the group of N—$(C_1$-$C_6)$-alkyl, oxygen and sulfur;

R62, R64, R65 are each independently H, $(C_1$-$C_8)$-alkyl or aryl;

K is a bond, O, $OCH_2$, $CH_2O$, S, SO, $SO_2$, N(R66), N(R67)CO, CON(R68), $(C(R69)(R70))_v$, CO, C≡C, C=C or a group of the formula —$(CR90R91)_Z$-in which one or more of the —(CR90R91)-units contained in said group of the formula —$(CR90R91)_Z$-is optionally replaced by Z;

wherein v is 1, 2, 3 or 4

R66, R67, R68, R69, R70 are each independently H or $(C_1$-$C_8)$-alkyl;

Z is O, S, N(R92), CO, SO or $SO_2$;

R90, R91 are each independently H, $(C_1$-$C_8)$-alkyl, hydroxy-$(C_1$-$C_4)$-alkyl, hydroxy or $(C_1$-$C_4)$-alkoxy-$(C_1$-$C_4)$-alkyl, and wherein R90 and R91 may be defined the same or differently in each of said —(CR90R91)-units contained in said group of formula —$(CR90R91)_Z$-;

z is 2, 3, 4, 5 or 6;

R92 is H or $(C_1$-$C_8)$-alkyl;

R11 is H, $(C_1$-$C_8)$-alkyl, $(C_1$-$C_4)$-alkoxy-$(C_1$-$C_4)$-alkyl, $(C_3$-$C_8)$-alkenyl, $(C_3$-$C_8)$-alkynyl or a 3-, 4-, 5-, 6-, 7-, 8-, 9- or 10-membered mono-, bi- or spirocyclic ring, optionally containing 1, 2, 3 or 4 heteroatoms selected from the group of oxygen, nitrogen and sulfur, and optionally substituted by F, Cl, Br, $CF_3$, $NO_2$, CN, $(C_1$-$C_6)$-alkyl, O—$(C_1$-$C_8)$-alkyl, $(C_1$-$C_4)$-alkoxy-$(C_1$-$C_4)$-alkyl, $(C_0$-$C_8)$-alkylene-aryl, oxo, CO(R71), CON(R72)(R73), hydroxy, hydroxy-$(C_1$-$C_4)$-alkyl, COO(R74), N(R75)CO $(C_1$-$C_6)$-alkyl, N(R76)(R77), $SO_2CH_3$ or $SCF_3$;

wherein

R71, R72, R73, R74, R75, R76, R77 are each independently H or $(C_1$-$C_8)$-alkyl; or substituent pairs R72 and R73, and R76 and R77, independently of one another and taken together with the nitrogen atom to which they are attached, optionally form a 5- or 6-membered ring which, apart from the nitrogen atom, optionally contain one additional heteroatom component selected from the group of N—$(C_1$-$C_6)$-alkyl, oxygen and sulfur; or E, K and R11 taken together form a tricyclic system where each of the rings in said tricyclic system are, independently of one another, saturated, partially saturated or unsaturated, and wherein each ring is comprised of 3-8 ring atoms;

and the N-oxides and pharmaceutically acceptable salts thereof.

In a further embodiment, the invention therefore relates to compounds of the formula I in which the meanings are:

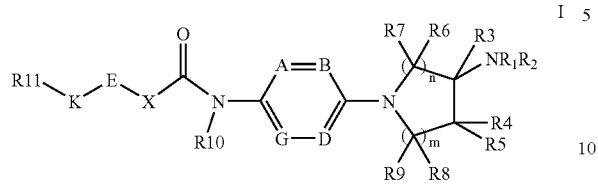

wherein

R1, R2 are each independently H, $(C_1-C_8)$-alkyl, $-(CR78R79)_o$-R12, $(C_1-C_4)$-alkoxy-$(C_1-C_4)$-alkyl, aryloxy-$(C_1-C_4)$-alkyl, $(C_3-C_8)$-alkenyl, $(C_3-C_8)$-alkynyl, CO—$(C_1-C_8)$-alkyl, —CO—$(CH_2)_o$—R12, CO-aryloxy-$(C_1-C_4)$-alkyl, CO—$(C_2-C_8)$-alkenyl, CO—$(C_2-C_8)$-alkynyl, COCH=CH(R13), COCC(R14), CO—$(C_1-C_4)$-alkyl-$S(O)_p$—$(C_1$-$C_{CO(C(R}15)(R16))_q$N(R17)(R18), CO(C(R19)(R20))$_r$CON(R21)(R22) or CO(C(R23)(R24))$_s$O(R25); or R1 and R2, together with the nitrogen atom to which they are attached, form a 4-, 5-, 6-, 7-, 8-, 9- or 10-membered mono-, bi- or spirocyclic ring which, apart from said nitrogen atom of attachment, optionally contains 1, 2, 3 or 4 additional heteroatoms selected from the group of oxygen, nitrogen and sulfur, and is optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R26), CON(R27)(R28), hydroxy, COO(R29), N(R30)CO($C_1$-$C_6$)-alkyl, N(R31)(R32) or $SO_2CH_3$;

wherein o is, 0, 1, 2, 3, 4, 5 or 6;

p is 0, 1 or 2 q, r, s are each independently 0, 1, 2, 3 or 4;

R13, R14 are each independently a 5-, 6-, 7-, 8-, 9- or 10-membered aromatic ring system optionally containing 1 or 2 heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R15, R16, R17, R19, R20, R21, R22, R23, R24, R25, R26, R27, R28, R29, R30, R31, R32 are each independently H or $(C_1-C_6)$-alkyl;

R18 is H, $(C_1-C_6)$-alkyl, CO($C_1-C_6$)-alkyl or CO(R33); or substituent pairs R17 and R18, R21 and R22, R27 and R28, and R31 and R32, independently of one another and taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur;

R33 is a 5-, 6-, 7-, 8-, 9- or 10-membered aromatic ring system which optionally contains 1 or 2 heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R12 is OH or a 3-, 4-, 5-, 6-, 7-, 8-, 9-, 10-, 11-, or 12-membered mono-, bi- or spirocyclic ring which optionally contains one or more heteroatoms selected from the group of N, O and S, and is optionally substituted with F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, O—$(C_0-C_8)$-alkylene-aryl, N(R34)(R35), COCH=CH(R36), $(C(R37)(R38))_t$(R39), CO(C(R37)(R38))$_t$(R39), CO($C_1-C_6$)-alkyl, COCOO($C_1-C_6$)-alkyl, COO(R40), $S(O)_u$(R41) or COOH;

t is 0, 1, 2, 3, 4, 5 or 6;

u is 0, 1 or 2;

R34, R35, R37, R38 are each independently H or $(C_1-C_8)$-alkyl; or

R34 and R35, taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur, and is optionally substituted by 1 or 2 oxo groups;

R36, R39 are each independently $(C_3-C_8)$-cycloalkyl or a 5-, 6-, 7-, 8-, 9- or 10-membered aromatic ring system wherein said aromatic ring system optionally contains one or two additional heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R40 is H, $(C_1-C_8)$-alkyl, $(C_2-C_6)$-alkenyl or $(C_0-C_8)$-alkylene-aryl;

R41 is $(C_1-C_6)$-alkyl or a 5-, 6-, 7-, 8-, 9-, or 10-membered aromatic ring system optionally containing one or two heteroatoms from the group of nitrogen, oxygen and sulfur, and optionally substituted by F, Cl, Br, $CF_3$, $NO_2$, CN, $(C_1-C_6)$-alkyl or O—$(C_1-C_8)$-alkyl;

R3 is H or $(C_1-C_6)$-alkyl;

R4, R5 are each independently H, $(C_1-C_6)$-alkyl, OH, O—$(C_1-C_6)$-alkyl, O—CO($C_1-C_6$)-alkyl or S—$(C_1-C_6)$-alkyl;

R6, R7, R8, R9 are each independently H or $(C_1-C_8)$-alkyl; or substituent pairs R6 and R7, and R8 and R9, optionally form, independently of one another, an oxo group;

n, m are each independently 0, 1 or 2;

A, B, D, G are each independently N or C(R42);

wherein

R42 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R43)(R44), $SO_2$—$CH_3$, COOH, COO—$(C_1-C_6)$-alkyl, CON(R45)(R46), N(R47)CO(R48), N(R49)$SO_2$(R50) or CO(R51);

wherein

R43, R44, R45, R46, R47, R49 are each independently H or $(C_1-C_8)$-alkyl; or substituent pairs R43 and R44, and R45 and R46, independently of one another and taken together with the nitrogen atom to which they are attached, optionally form a 5- or 6-membered ring which, apart from said nitrogen atom of attachment, optionally contains an additional heteroatom component selected from the group of N—$(C_1-C_6)$-alkyl, oxygen and sulfur;

R48, R50, R51 are each independently H, $(C_1-C_8)$-alkyl or aryl;

R10 is H, $(C_1-C_8)$-alkyl, $(C_3-C_6)$-alkenyl or $(C_3-C_6)$-alkynyl;

X is N(R52), O, a bond, C=C, C(R53)(R54) or C(R55)(R56)O;
  wherein
    R52, R53, R54, R55, R56 are each independently H or $(C_1-C_8)$-alkyl;

E is a 3, 4, 5, 6, 7 or 8-membered bivalent carbo- or heterocyclic ring structure with 0, 1, 2, 3 or 4 heteroatoms selected from the group of N, O and S, and optionally substituted with H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R57)(R58), $SO_2$—$CH_3$, COOH, COO—$(C_1-C_6)$-alkyl, CON(R59)(R60), N(R61)CO(R62), N(R63)$SO_2$(R64) or CO(R65), and wherein said bivalent carbo- or heterocyclic ring structure is mono- or bicyclic;
  wherein
    R57, R58, R59, R60, R61, R63 are each independently H or $(C_1-C_8)$-alkyl; or
    substituent pairs R57 and R58, and R59 and R60, independently of one another and taken together with the nitrogen atom to which they are attached, optionally form a 5- or 6-membered ring which, apart from said nitrogen atom of attachment, optionally contains one further heteroatom component selected from the group of N—$(C_1-C_6)$-alkyl, oxygen and sulfur;
    R62, R64, R65 are each independently H, $(C_1-C_8)$-alkyl or aryl;

K is a bond, O, $OCH_2$, $CH_2O$, S, SO, SO2, N(R66), N(R67)CO, CON(R68), (C(R69)(R70))v, CO or C≡C;
  wherein
    v is 1, 2, 3 or 4
    R66, R67, R68, R69, R70 are each independently H or $(C_1-C_8)$-alkyl;

R11 is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl or a 3-, 4-, 5-, 6-, 7-, 8-, 9- or 10-membered mono-, bi- or spirocyclic ring, optionally containing 1, 2, 3 or 4 heteroatoms selected from the group of oxygen, nitrogen and sulfur, and optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R71), CON(R72)(R73), hydroxy, COO(R74), N(R75)CO($C_1-C_6$)-alkyl, N(R76)(R77) or $SO_2CH_3$;
  wherein
    R71, R72, R73, R74, R75, R76, R77 are each independently H or $(C_1-C_8)$-alkyl; or
    substituent pairs R72 and R73, and R76 and R77, independently of one another and taken together with the nitrogen atom to which they are attached, optionally form a 5- or 6-membered ring which, apart from the nitrogen atom, optionally contain one additional heteroatom component selected from the group of N—$(C_1-C_6)$-alkyl, oxygen and sulfur; or E, K and R11 taken together form a tricyclic system where each of the rings in said tricyclic system are, independently of one another, saturated, partially saturated or unsaturated, and wherein each ring is comprised of 3-8 ring atoms;

and the N-oxides and pharmaceutically acceptable salts thereof.

The invention relates to compounds of the formula I in the form of their racemates, enantiomer-enriched mixtures and pure enantiomers, and to their diastereomers and mixtures thereof.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92 and R93 may be either straight-chain, branched or optionally halogenated.

The term "aryl" means in particular a phenyl or naphthyl group.

A "tricyclic system" means structures having 3 rings which are connected together by more than one bond. Examples of such systems are fused systems with 3 rings and spirocycles with a ring system fused on.

In the case where R1 and R2 form together with the nitrogen atom to which they are bonded a ring, this ring may be substituted by one or more of the substituents mentioned.

The bivalent carbo- or heterocyclic ring structure E includes structures which are linked by one and the same atom to the two adjacent groups K and X.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric, sulfonic and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. For medical purposes the chlorine salt is particularly preferably used. Suitable pharmaceutically acceptable basic salts are ammonium salts, alkali metal salts (such as sodium and potassium salts), alkaline earth metal salts (such as magnesium and calcium salts).

Salts with a pharmaceutically unacceptable anion likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula (I)" hereinafter refer to compound(s) of the formula (I) as described above, and their salts, solvates and physiologically functional derivatives as described herein.

If radicals or substituents can occur more than once in the compounds of the formula I, they may all have independently of one another the stated meanings and be identical or different.

In a particularly preferred embodiment, the present invention relates to compounds of the formula I in which the meanings are:

R1, R2 are each independently H, $(C_1-C_8)$-alkyl, —$(CH_2)_o$—R12, $(C_1-C_4)$-alkoxy-$(C_1-C_4)$-alkyl, CO—$(C_1-C_8)$-alkyl, —CO—$(CH_2)_o$—R12, COCH═CH(R13), COCC(R14), CO—$(C_1-C_4)$-alkyl-S(O)$_p$—$(C_1-C_4)$-alkyl, CO(C(R15)(R16))$_q$N(R17)(R18), CO(C(R19)(R20))$_r$, CON(R21)(R22) or CO(C(R23)(R24))$_s$O(R25); or R1 and R2 together with the nitrogen atom to which they are attached, optionally form a 4-, 5-, 6-, 7, 8-, 9- or 10-membered mono-, bi- or spirocyclic ring which, apart from he nitrogen atom, may comprise 0 to 2 additional heteroatoms selected from the group of oxygen, nitrogen and sulfur, where the heterocyclic ring system may additionally be substituted by F, $(C_1-C_6)$-alkyl, O—$(C_1-C_8)$-alkyl, $(C_0-C_8)$-alkylene-aryl, oxo, CO(R26), CON(R27)(R28), hydroxy, COO(R29), N(R30)CO($C_1-C_6$)-alkyl, N(R31)(R32) or SO$_2$CH$_3$, where R1 and R2 are preferably not both H, and R1 and R2 together with the nitrogen atom are preferably not a morpholino radical;

o 0, 1, 2, 3, 4;

p 0, 1, 2;

q, r, s independently of one another 0, 1, 2, 3, preferably q, s are independently of one another 1, 2, 3 and r is 0, 1, 2, 3;

R13, R14 independently of one another a 5-10 membered aromatic ring system which may comprise a further heteroatom from the group of nitrogen, oxygen and sulfur and may be substituted by F, Cl, $(C_1-C_6)$-alkyl, O—$(C_1-C_8)$-alkyl;

R15, R16, R17, R19, R20, R21, R22, R23, R24, R25, R26, R27, R28, R29, R30, R31, R32
independently of one another H, $(C_1-C_6)$-alkyl;

R18 H, $(C_1-C_6)$-alkyl, CO($C_1-C_6$)-alkyl, CO(R33);

R17 and R18, R21 and R22, R27 and R28, R31 and R32 independently of one another optionally together with the nitrogen atom to which they are bonded a 5-6 membered ring which, apart from the nitrogen atom, may also comprise 0-1 further heteroatoms from the group of N—$(C_1-C_6)$-alkyl, oxygen and sulfur;

R33 a 5-10 membered aromatic ring system which may comprise a further heteroatom from the group of nitrogen, oxygen and sulfur and may be substituted by F, Cl, $(C_1-C_6)$-alkyl, O—$(C_1-C_8)$-alkyl;

R12 OH, 3-12 membered mono-, bi- or spirocyclic ring which may comprise one or more heteroatoms from the group of N, O and S, and the 3-12 membered ring may comprise further substituents such as F, Cl, CF$_3$, CN, oxo, O—$(C_1-C_6)$-alkyl, $(C_1-C_6)$-alkyl, O—$(C_0-C_8)$-alkylene-aryl, N(R34)(R35), COCH═CH(R36), (C(R37)(R38))$_t$ (R39), CO(C(R37)(R38))$_t$ (R39), CO($C_1-C_6$)-alkyl, COCOO($C_1-C_6$)-alkyl, COO(R40) and S(O)$_u$ (R41), where in a preferred embodiment the substituent O—$(C_1-C_6)$-alkyl is excluded when the 3-12 membered ring is phenyl;

t 0, 1, 2, 3, 4;

u 0, 1, 2;

R34, R35, R37, R38
independently of one another H, $(C_1-C_8)$-alkyl;

R34 and R35
optionally together with the nitrogen atom to which they are bonded a 5-6 membered ring which, apart from the nitrogen atom, may also comprise 0-1 further heteroatoms from the group of N—$(C_1-C_6)$-alkyl, oxygen and sulfur and may optionally be substituted by 1-2 oxo groups;

R36, R39 independently of one another $(C_3-C_8)$-cycloalkyl, 5-10 membered aromatic ring system which may comprise a further heteroatom from the group of nitrogen, oxygen and sulfur and may be substituted by F, Cl, $(C_1-C_6)$-alkyl, O—$(C_1-C_8)$-alkyl;

R40 H, $(C_1-C_8)$-alkyl, $(C_2-C_6)$-alkenyl, $(C_0-C_8)$-alkylene-aryl;

R41 $(C_1-C_6)$-alkyl, 5-10 membered aromatic ring system which may comprise 0-2 further heteroatoms from the group of nitrogen, oxygen and sulfur and may be substituted by F, Cl, $(C_1-C_6)$-alkyl, O—$(C_1-C_8)$-alkyl;

R3 H, $(C_1-C_6)$-alkyl;

R4, R5 independently of one another H, $(C_1-C_6)$-alkyl, OH, O—$(C_1-C_6)$-alkyl, O—CO($C_1-C_6$)-alkyl;

R6, R7, R8, R9
independently of one another H, $(C_1-C_8)$-Alkyl;

R6 and R7, R8 and R9
independently of one another optionally oxo;

n, m independently of one another 0, 1, 2, preferably m is 0, 1, 2 and n is 1;

A, B, D, G independently of one another N, C(R42);

R42 is H, F, Cl, Br, CF$_3$, CN, O—$(C_1-C_6)$-alkyl, $(C_1-C_6)$-alkyl, $(C_3-C_8)$-cycloalkyl, $(C_0-C_2)$-alkylene-aryl, O—$(C_0-C_2)$-alkylene-aryl, N(R43)(R44), SO$_2$—CH$_3$, COO—$(C_1-C_6)$-alkyl, CON(R45)(R46), N(R47)CO(R48), N(R49)SO$_2$(R50), CO(R51)

R43, R44, R45, R46, R47, R49
independently of one another H, $(C_1-C_8)$-alkyl;

R43 and R44, R45 and R46
independently of one another optionally together with the nitrogen atom to which they are bonded a 5-6 membered ring which, apart from the nitrogen atom, may also comprise 0-1 further heteroatoms from the group of N—$(C_1-C_6)$-alkyl, oxygen and sulfur;

R48, R50, R51
independently of one another H, $(C_1-C_8)$-alkyl, aryl;

R10 H, $(C_1-C_8)$-alkyl;

X N(R52), O, a bond, C═C, C(R53)(R54), C(R55)(R56)O;

R52, R53, R54, R55, R56
independently of one another H, $(C_1-C_8)$-alkyl

E 3-8 membered bivalent carbo- or heterocyclic ring structure with 0-4 heteroatoms from the group of N, O and S, which may optionally have substituents from the group of H, F, Cl, CF$_3$, NO$_2$, OH, CN, O—$(C_1-C_6)$-alkyl, $(C_1-C_6)$-alkyl, $(C_0-C_8)$-alkylene-aryl, O—$(C_0-C_8)$-alkylene-aryl, N(R57)(R58), SO$_2$—CH$_3$, COO—$(C_1-C_6)$-alkyl, CON(R59)(R60), N(R61)CO(R62), N(R63)SO$_2$(R64), CO(R65) and may be mono- or bicyclic, preferably the group E has no substituents from the group of $(C_0-C_8)$-alkylene-aryl, O—$(C_0-C_8)$-alkylene-aryl and N(R57)(R58), in which R57 and R58 form together with the nitrogen atom a 5-6 membered ring, in the position ortho to the point of attachment of X; particularly preferably E is monocyclic;

R57, R58, R59, R60, R61, R63
independently of one another H, $(C_1-C_8)$-alkyl;

R57 and R58, R59 and R60
independently of one another optionally together with the nitrogen atom to which they are bonded a 5-6 membered ring which, apart from the nitrogen atom, may also comprise 0-1 further heteroatoms from the group of N—($C_1$-$C_6$)-alkyl, oxygen and sulfur, where R59 and R60 are preferably not both H;

R62, R64, R65
independently of one another H, ($C_1$-$C_8$)-alkyl, aryl;

K a bond, O, $CH_2O$, N(R66), $(C(R69)(R70))_v$, C≡C, $OCH_2$, CON(R68), preferably a bond, O, $CH_2O$, $((CR69)(R70))_v$, C≡C, N(R66);

v 1, 2;

R66, R68, R69, R70
independently of one another H, ($C_1$-$C_8$)-alkyl;

R11 H, ($C_1$-$C_8$)-alkyl, ($C_1$-$C_4$)-alkoxy-($C_1$-$C_4$)-alkyl, ($C_3$-$C_8$)-alkenyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, ($C_0$-$C_8$)-alkylene-aryl, oxo, CO(R71), CON(R72)(R73), hydroxy, COO(R74), N(R75)CO($C_1$-$C_6$)-alkyl, N(R76)(R77) or $SO_2CH_3$, preferably R11 is not COO(R74);

R71, R72, R73, R74, R75, R76, R77
independently of one another H, ($C_1$-$C_8$)-alkyl;

R72 and R73, R76 and R77
independently of one another optionally together with the nitrogen atom to which they are bonded a 5-6 membered ring which, apart from the nitrogen atom, may also comprise 0-1 further heteroatoms from the group of N—($C_1$-$C_6$)-alkyl, oxygen and sulfur.

Particularly preferred compounds of the formula I are those in which

A, B, D, G are independently of one another N or C(R42), and the total number of nitrogen atoms in this ring is 0-2, preferably 0 or 1.

Very particularly preferred compounds of the formula I are those in which n is 1 and m is 1 or 2.

Especially preferred compounds of the formula I are those in which

A, B, D, G are independently of one another N or C(R42) and the total number of nitrogen atoms in this ring is 0-2, preferably 0 or 1;

n is 1 and m is 1 or 2.

In a further preferred embodiment, the present invention relates to compounds of the formula I in which the meanings are:

R1, R2 independently of one another are H, ($C_1$-$C_8$)-alkyl, —$(CR78R79)_o$—R12, ($C_1$-$C_4$)-alkoxy-($C_1$-$C_4$)-alkyl, ($C_3$-$C_8$)-alkenyl, CO—($C_1$-$C_8$)-alkyl, —CO—$(CH_2)_o$—R12, CO-aryloxy-($C_1$-$C_4$)-alkyl, COCH═CH(R13), COCC(R14), $CO(C(R15)(R16))_q$N(R17)(R18), $CO(C(R19)(R20))_r$CON(R21)(R22), $CO(C(R23)(R24))_s$O(R25); or $R_1$ and R2 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, $CF_3$, ($C_1$-$C_6$)-alkyl, O—($C_1$-$C_4$)-alkyl, ($C_1$-$C_4$)-alkoxy-($C_1$-$C_4$)-alkyl, hydroxy-($C_1$-$C_4$)-alkyl, ($C_0$-$C_2$)-alkylene-aryl, oxo, CO(R26), CON(R27)(R28), hydroxy, COO(R29), N(R30)CO($C_1$-$C_6$)-alkyl, N(R31)(R32) or $SO_2CH_3$;

preferably independently of one another H, ($C_1$-$C_8$)-alkyl, —$(CR78R79)_o$—R12, ($C_1$-$C_4$)-alkoxy-($C_1$-$C_4$)-alkyl, CO—($C_1$-$C_8$)-alkyl, —CO—$(CH_2)_o$—R12, COCH═CH(R13), COCC(R14), $CO(C(R15)(R16))_q$N(R17)(R18), $CO(C(R23)(R24))_s$O(R25);

or $R_1$ and R2 form together with the nitrogen atom to which they are bonded a 4 to 10-membered mono- or bicyclic ring which, apart from the nitrogen atom, may comprise 0 to 2 additional heteroatoms selected from the group of oxygen, nitrogen and sulfur, where the heterocyclic ring system may additionally be substituted by F, Cl, $CF_3$, ($C_1$-$C_6$)-alkyl, O—($C_1$-$C_4$)-alkyl, ($C_1$-$C_4$)-alkoxy-($C_1$-$C_4$)-alkyl, ($C_0$-$C_2$)-alkylene-aryl, oxo, CO(R26), hydroxy, N(R31)(R32) or $SO_2CH_3$;

particularly preferably independently of one another H, ($C_1$-$C_8$)-alkyl, —$(CR78R79)_o$—R12, ($C_1$-$C_4$)-alkoxy-($C_1$-$C_4$)-alkyl, CO—($C_1$-$C_8$)-alkyl, —CO—$(CH_2)_o$—R12, $CO(C(R15)(R16))_q$N(R17)(R18), or R1 and R2 form together with the nitrogen atom to which they are bonded a 4 to 10-membered mono- or bicyclic ring which, apart from the nitrogen atom, may comprise 0 to 2 additional heteroatoms selected from the group of oxygen and nitrogen, where the heterocyclic ring system may be additionally substituted by F, ($C_1$-$C_6$)-alkyl, ($C_1$-$C_4$)-alkoxy-($C_1$-$C_4$)-alkyl, oxo, CO(R26), hydroxy, N(R31)(R32);

o 0, 1, 2, 3, 4, 5, 6; preferably 0, 1, 2, 3, 4; particularly preferably 0, 1, 2, 3;

q, r independently of one another 1, 2, 3; preferably q is 1 or 2;

s 0, 1, 2, 3, 4; preferably 0, 1, 2, 3; particularly preferably 0, 1, 2;

R13, R14 independently of one another are a phenyl ring which may comprise 0-1 nitrogen atoms;

R15, R16, R17, R19, R20, R21, R22, R23, R24, R25, R26, R27, R28, R29, R30, R31, R32
independently of one another H, ($C_1$-$C_6$)-alkyl;

R18 H, ($C_1$-$C_6$)-alkyl, CO($C_1$-$C_6$)-alkyl, CO(R33); preferably H, ($C_1$-$C_6$)-alkyl, CO($C_1$-$C_6$)-alkyl; particularly preferably H, ($C_1$-$C_6$)-alkyl;

or

R17 and R18, R21 and R22, R27 and R28, R31 and R32 independently of one another optionally form together with the nitrogen atom to which they are bonded a 5-6 membered ring which, apart from the nitrogen atom, may also comprise 0-1 further heteroatoms from the group of N—($C_1$-$C_6$)-alkyl, oxygen and sulfur; preferably the ring is pyrrolidine, piperidine, N-methylpiperazine, morpholine;

R33 a 5-10 membered aromatic ring system which may comprise a further heteroatom from the group of nitrogen, oxygen and sulfur and may be substituted by F, Cl, ($C_1$-$C_6$)-alkyl, O—($C_1$-$C_8$)-alkyl;

R12 OH, O—($C_1$-$C_6$)-alkyl, O—($C_0$-$C_8$)-alkylene-aryl, CN, S—($C_1$-$C_6$)-alkyl, COO(R80), CON(R81)(R82), 3-12 membered mono-, bi- or spirocyclic ring which may comprise one or more heteroatoms from the group of N, O and S, and the 3-12 membered ring may comprise further substituents such as F, Cl, Br, OH, $CF_3$, CN, oxo, O—($C_1$-$C_6$)-alkyl, ($C_1$-$C_4$)-alkoxy-($C_1$-$C_4$)-alkyl, ($C_1$-$C_6$)-alkyl, O—($C_0$-$C_8$)-alkylene-aryl, ($C_0$-$C_8$)-alkylene-aryl, N(R34)(R35), COCH═CH(R36), $(C(R37)(R38))_t$(R39), $CO(C(R37)(R38))_t$(R39), CO($C_1$-$C_6$)-alkyl, $COCOO(C_1$-$C_6$)-alkyl, COO(R40), $S(O)_u$(R41);

preferably OH, O—($C_1$-$C_6$)-alkyl, O—($C_0$-$C_8$)-alkylene-aryl, CN, 3-10 membered mono- or bicyclic ring which may comprise 1-3 heteroatoms from the group of N, O and S, and the 3-10 membered ring may comprise further substituents such as F, Cl, Br, OH, $CF_3$, CN, oxo, O—(C$_1$-C$_6$)-alkyl, (C$_1$-C$_4$)-alkoxy-(C$_1$-C$_4$)-alkyl, (C$_1$-C$_6$)-alkyl, (C$_0$-C$_2$)-alkylene-aryl, N(R34)(R35), CO(C$_1$-C$_6$)-alkyl;
particularly preferably OH, O—(C$_1$-C$_6$)-alkyl, 3-10 membered mono- or bicyclic ring which may comprise 1-2 heteroatoms from the group of N, O and S, and the 3-10 membered ring may comprise further substituents such as F, OH, oxo, (C$_1$-C$_6$)-alkyl, CO(C$_1$-C$_6$)-alkyl;

t 0, 1, 2, 3, 4, 5, 6;
u 0, 1, 2; preferably 0 or 2; particularly preferably 2;
R34, R35, R37, R38
independently of one another H, (C$_1$-C$_8$)-alkyl;

or

R34 and R35
optionally together with the nitrogen atom to which they are bonded a 5-6 membered ring which, apart from the nitrogen atom, may also comprise 0-1 further heteroatoms from the group of N—(C$_1$-C$_6$)-alkyl, oxygen and sulfur and may optionally be substituted by 1-2 oxo groups;

R36, R39 independently of one another (C$_3$-C$_8$)-cycloalkyl, 5-10 membered aromatic ring system which may comprise 0-2 further heteroatoms from the group of nitrogen, oxygen and sulfur and may be substituted by F, Cl, (C$_1$-C$_6$)-alkyl, O—(C$_1$-C$_8$)-alkyl;

R40 H, (C$_1$-C$_8$)-alkyl, (C$_2$-C$_6$)-alkenyl, (C$_0$-C$_8$)-alkylene-aryl;

R41 (C$_1$-C$_6$)-alkyl, 5-10 membered aromatic ring system which may comprise 0-2 further heteroatoms from the group of nitrogen, oxygen and sulfur and may be substituted by F, Cl, (C$_1$-C$_6$)-alkyl, O—(C$_1$-C$_8$)-alkyl;

R78, R79 independently of one another H, (C$_1$-C$_8$)-alkyl, hydroxy-(C$_1$-C$_4$)-alkyl, OH, (C$_1$-C$_4$)-alkoxy-(C$_1$-C$_4$)-alkyl;

R80, R81 independently of one another H, (C$_1$-C$_8$)-alkyl;
R3 H, (C$_1$-C$_6$)-alkyl; preferably H;
R4, R5 independently of one another H, (C$_1$-C$_6$)-alkyl, OH, O—(C$_1$-C$_6$)-alkyl, O—CO—(C$_1$-C$_6$)-alkyl, S—(C$_1$-C$_6$)-alkyl;
preferably independently of one another H, (C$_1$-C$_6$)-alkyl, OH, O—(C$_1$-C$_6$)-alkyl, O—CO—(C$_1$-C$_6$)-alkyl; particularly preferably independently of one another H, OH, O—(C$_1$-C$_6$)-alkyl;

R6, R7, R8, R9
H;

or

R6 and R7, R8 and R9
independently of one another optionally oxo;
preferably R6, R7, R8, R9 are H;
n 1
m 1 or 2; preferably 1;
A, B, D, G independently of one another N, C(R42);

or the groups A and B or D and G are each C(R42) and together form an ortho-phenylene unit to result overall in a 1,4-bisubstituted naphthalene system;
preferably
B is N, C(R42); and A, D, G C(R42);
particularly preferably
A, B, D, G are C(R42);

R42 H, F, Cl, Br, CF$_3$, CN, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_0$-C$_8$)-alkylene-aryl, O—(C$_0$-C$_8$)-alkylene-aryl, N(R43)(R44), SO$_2$—CH$_3$, CON(R45)(R46), N(R47)CO(R48), CO(R51), —(CR84R85)$_x$—O(R86);

preferably H, F, Cl, Br, CF$_3$, CN, O—(C$_1$-C$_6$)-alkyl, (C$_1$-C$_6$)-alkyl, SO$_2$—CH$_3$, CON(R45)(R46), N(R47)CO(R48), CO(R51), —(CR84R85)$_x$—O(R86);
particularly preferably H, F, Cl, CF$_3$, CN, (C$_1$-C$_6$)-alkyl, —(CR84R85)$_x$—O(R86);

R43, R44, R45, R46, R47
independently of one another H, (C$_1$-C$_8$)-alkyl;

or

R43 and R44, R45 and R46
independently of one another optionally together with the nitrogen atom to which they are bonded a 5-6 membered ring which, apart from the nitrogen atom, may also comprise 0-1 further heteroatoms from the group of N—(C$_1$-C$_6$)-alkyl, oxygen and sulfur;

R48, R50, R51
independently of one another H, (C$_1$-C$_8$)-alkyl, aryl; preferably independently of one another H, (C$_1$-C$_8$)-alkyl;

R84, R85 H;
R86 H, (C$_1$-C$_6$)-alkyl;
x 0, 1, 2; preferably 0, 1; particularly preferably 1;
R10 H, (C$_1$-C$_8$)-alkyl;
x N(R52), a bond, C═C, C(R53)(R54), C(R55)(R56)O, C≡C, CH$_2$—CH$_2$, YCH$_2$; preferably N(R52), a bond, C═C, C(R53)(R54), CH$_2$—CH$_2$; particularly preferably a bond, C═C, C(R53)(R54), CH$_2$—CH$_2$;
y O, S, N(R89);
R89 H, (C$_1$-C$_8$)-alkyl;
R52, R53, R54, R55, R56
independently of one another H, (C$_1$-C$_8$)-alkyl;

E 3-8 membered bivalent carbo- or heterocyclic ring structure with 0-4 heteroatoms from the group of N, O and S, which may optionally have substituents from the group of H, F, Cl, Br, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R57)(R58), SO$_2$—CH$_3$, N(R61)CO(R62), N(R63)SO$_2$(R64), CO(R65) and may be mono- or bicyclic;

preferably 5-7 membered bivalent carbo- or heterocyclic ring structure with 0-3 heteroatoms from the group of N, O and S, which may optionally have substituents from the group of H, F, Cl, Br, OH, CF$_3$, NO$_2$, CN, OCF$_3$, O—(C$_1$-C$_6$)-alkyl, S—(C$_1$-C$_6$)-alkyl, (C$_1$-C$_6$)-alkyl, (C$_2$-C$_6$)-alkenyl, O—(C$_0$-C$_8$)-alkylene-aryl, S-aryl, N(R57)(R58), SO$_2$—CH$_3$,
N(R61)CO(R62), CO(R65) and may be mono- or bicyclic; particularly preferably 5-7 membered bivalent carbo- or heterocyclic ring structure with 0-2 heteroatoms from the group of N, O and S, which may optionally have substituents from the group of H, F, Cl, Br, OH, CF$_3$, NO$_2$, OCF$_3$, O—(C$_1$-C$_6$)-alkyl, (C$_1$-C$_6$)-alkyl, (C$_2$-C$_6$)-alkenyl, N(R57)(R58), SO$_2$—CH$_3$, CO(R65)

e.g. E is selected from the group consisting of

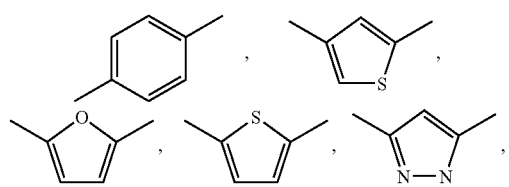

-continued

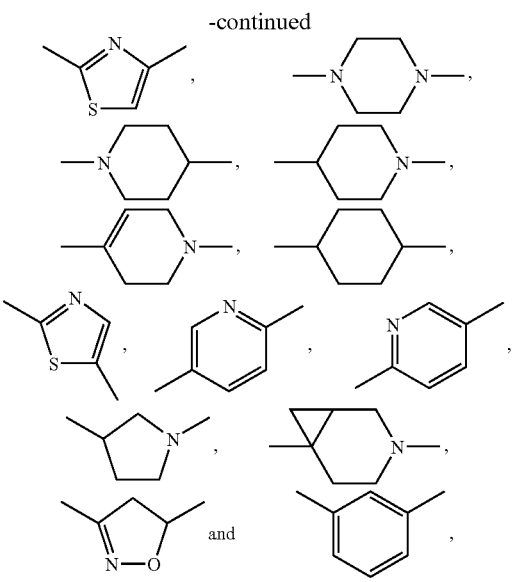

which may optionally have substituents from the group of H, F, Cl, Br, OH, CF$_3$, NO$_2$, OCF$_3$, O—(C$_1$-C$_6$)-alkyl, (C$_1$-C$_6$)-alkyl, (C$_2$-C$_6$)-alkenyl, N(R57)(R58), SO$_2$—CH$_3$, CO(R65);

preferably

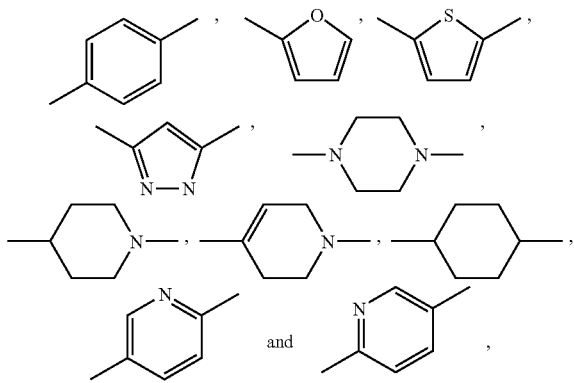

which may optionally have the aforementioned substituents;
R57, R58, R61, R63
  independently of one another H, (C$_1$-C$_8$)-alkyl;
R62, R64, R65
  independently of one another H, (C$_1$-C$_8$)-alkyl, aryl; preferably independently of one another H, (C$_1$-C$_8$)-alkyl;
K a bond, O, OCH$_2$, CH$_2$O, S, SO, SO$_2$, N(R66), N(R67)CO, CON(R68), (C(R69)(R70))$_v$, CO, C=C, C≡C, SCH$_2$, SO$_2$CH$_2$; preferably a bond, O, OCH$_2$, CH$_2$O, N(R66), CON(R68), (C(R69)(R70))$_v$, CO, C≡C, SCH$_2$; particularly preferably a bond, O, OCH$_2$, CH$_2$O, CON(R68), (C(R69)(R70))$_v$, CO, C≡C;
v 1, 2, 3, 4; preferably 1, 2, 3; particularly preferably 1, 2;
R66, R67, R68, R69, R70
  independently of one another H, (C$_1$-C$_8$)-alkyl;
R11 H, (C$_1$-C$_8$)-alkyl, (C$_1$-C$_4$)-alkoxy-(C$_1$-C$_4$)-alkyl, (C$_3$-C$_8$)-alkenyl, (C$_3$-C$_8$)-alkynyl, a 3 to 10-membered mono-, bi-, tri- or spirocyclic ring, which may comprise 0 to 4 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, (C$_1$-C$_4$)-alkoxy-(C$_1$-C$_4$)-alkyl hydroxy-(C$_1$-C$_4$)-alkyl, (C$_0$-C$_8$)-alkylene-aryl, oxo, CO(R71), CON(R72)(R73), hydroxy, COO(R74), N(R75)CO(C$_1$-C$_6$)-alkyl, N(R76)(R77) or SO$_2$CH$_3$;
preferably (C$_1$-C$_8$)-alkyl, (C$_1$-C$_4$)-alkoxy-(C$_1$-C$_4$)-alkyl, a 3 to 10-membered mono-, bi-, tri- or spirocyclic ring which may comprise 0 to 3 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, (C$_0$-C$_2$)-alkylene-aryl, oxo, CO(R71), CON(R72)(R73), hydroxy, N(R75)CO(C$_1$-C$_6$)-alkyl, N(R76)(R77) or SO$_2$CH$_3$;
particularly preferably (C$_1$-C$_8$)-alkyl, (C$_1$-C$_4$)-alkoxy-(C$_1$-C$_4$)-alkyl, a 3 to 10-membered mono- or bicyclic ring which may comprise 0 to 2 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, oxo, CO(R71), CON(R72)(R73), N(R75)CO(C$_1$-C$_6$)-alkyl, or SO$_2$CH$_3$;
R71, R72, R73, R74, R75, R76, R77
  independently of one another H, (C$_1$-C$_8$)-alkyl;
or
R72 and R73, R76 and R77
  independently of one another optionally together with the nitrogen atom to which they are bonded a 5-6 membered ring which, apart from the nitrogen atom, may also comprise 0-1 further heteroatoms from the group of N—(C$_1$-C$_6$)-alkyl, oxygen and sulfur; or the N-oxides and the physiologically tolerated salts thereof.
In a further preferred embodiment, A, B, G and D in formula I are CH or:
If E is 1,4-phenylene, the preferred meanings for A, B, G and D are furthermore those listed in table I below:

TABLE I

| A | B | G | D |
|---|---|---|---|
| N | CH | CH | CH |
| CH | N | CH | CH |
| C—Cl | N | CH | CH |
| C—F | CH | C—F | CH |
| CH | CH | C—F | CH |
| CH | C—F | CH | CH |
| CH | CH | CH | CF |
| CH | C—Br | CH | CH |
| CH | CH | C—Br | CH |
| CH | C—Cl | CH | CH |
| CH | CH | C—Cl | CH |
| CH | CH | C—CN | CH |
| CH | CH | CH | C—CN |
| CH | CH | C—CH$_3$ | CH |
| CH | CH | CH | C—CH$_3$ |
| CH | CH | C—CF$_3$ | CH |
| CH | CH | CH | C—CF$_3$ |
| CH | CH | CH | CH$_2$OH |
| CH | C—F | CH | C—F |
| CH | C—F | C—F | CH |
| CH | CH | C—F | C—F |
| CH | CH | C—F | C—Cl |
| CH | CH | C—Cl | C—CN |
| CH | C—CH$_3$ | C—Cl | CH |
| CH | N | CH | C—CH$_3$ |
| CH | C—CH$_3$ | CH | N |

TABLE I-continued

| A | B | G | D |
|---|---|---|---|
| CH | N | C—CH₃ | CH |
| CH | CH | | |

If E is

the preferred meanings for A, B, G and D are furthermore those listed in table 11 below:

TABLE II

| A | B | G | D |
|---|---|---|---|
| CH | C—CH₃ | CH | CH |
| CH | C—F | CH | CH |
| CH | CH | C—CH₃ | CH |
| CH | CH | C—F | CH |
| CH | N | CH | CH |
| CH | CH | CH | N |
| C—F | CH | C—F | CH |

If E is

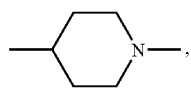

the preferred meanings for A, B, G and D are furthermore those listed in table III below:

TABLE III

| A | B | G | D |
|---|---|---|---|
| CH | CH | C—F | CH |
| CH | N | CH | CH |
| CH | CH | CH | N |

Further preferred combinations for E and A, B, G and D are listed in table IV.

TABLE IV

| E | A | B | G | D |
|---|---|---|---|---|
| cyclohexyl | CH | C—F | CH | CH |
| cyclohexyl | CH | CH | C—F | CH |
| 2,5-dimethylfuran | CH | C—F | CH | CH |
| 2,5-dimethylthiophene | CH | C—F | CH | CH |
| 2,5-dimethylindole | CH | CF | CH | CH |
| 2-methyl-5-amino-phenyl | CH | CF | CH | CH |
| 2-methyl-5-nitro-phenyl | CH | C—F | CH | CH |
| 3-chloro-2,5-dimethyl-phenyl | CH | C—F | CH | CH |
| 3,4-dichloro-2,5-dimethyl-6-methoxy-phenyl | CH | C—F | CH | CH |
| tetrafluoro-phenyl | CH | C—F | CH | CH |
| 3-fluoro-2,5-dimethyl-phenyl | CH | C—F | CH | CH |
| 3-chloro-2,5-dimethyl-phenyl | CH | C—F | CH | CH |
| 2,5-dimethyl-acetyl-phenyl | CH | C—F | CH | CH |

TABLE IV-continued

| E | A | B | G | D |
|---|---|---|---|---|
| (4-methyl-phenoxy) | CH | C—F | CH | CH |
| (5-methylpyridin-2-yl) | CH | C—F | CH | CH |
| (5-methylthiophen-2-yl) | CH | C—F | CH | CH |

The radicals R11, K, X and E in formula I have in a particularly preferred embodiment one of the following meanings:

R11 is preferably selected from the group consisting of: n-propyl, n-butyl, iso-butyl, iso-pentyl, cyclopropyl, cyclobutyl, cyclopentyl, cyclohexyl, cyclohex-(1)-enyl, phenyl, p-fluorophenyl, p-chlorophenyl, p-bromophenyl, p-tolyl, p-methoxyphenyl, p-trifluoromethylphenyl, p-methylthiophenyl, o-fluorophenyl, o-chlorophenyl, o-cyanophenyl, m-fluorophenyl, 2,4-difluorophenyl, 3-fluoro-4-methylphenyl, 2-nitro-4-methylphenyl, 2-amino-4-methylphenyl,

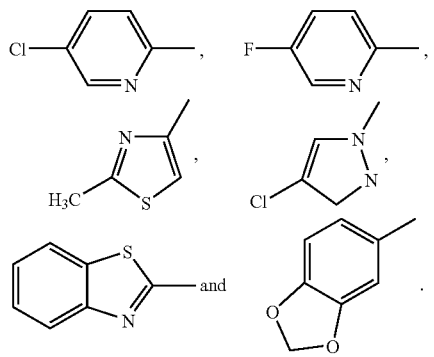

K is preferably selected from the group consisting of: —O—, bond, C≡C, CH$_2$, CH$_2$O, CONH, OCH$_2$, CO, SCH$_2$ and (CH$_2$)$_2$O.

X is preferably selected from the group consisting of bond, NH and CH$_2$.

E is preferably selected from the group consisting of:

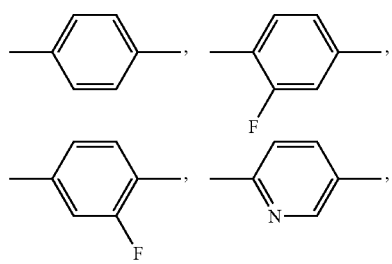

Preferred combinations of R11, K, X and E are listed below:

If K and X are each a bond, the particularly preferred meanings for E and R11 areas follows:

If E is 1,4-phenylene, R11 is selected from the group consisting of:
cyclohexyl, p-tolyl, p-fluorophenyl, o-fluorophenyl, p-methoxyphenyl, p-chlorophenyl, o-chlorophenyl, 2,4-difluorophenyl, 3-fluoro-4-methylphenyl, o-cyanophenyl,

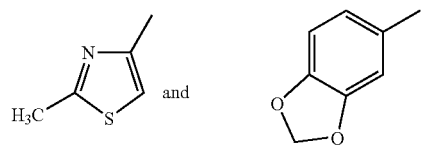

If E is

R 11 selected from the group consisting of: p-chlorophenyl, p-tolyl, p-fluorophenyl, p-methoxyphenyl, p-trifluoromethylphenyl, o-fluorophenyl, phenyl and

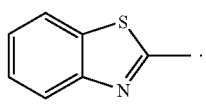

Further combinations of E and R11 or the case where K and X are each a bond are listed in table V:

TABLE V

| R11 | E |
|---|---|
| p-Chlorophenyl | 1,4-Cyclohexylene |
| 2-Nitro-4-methylphenyl | (2,5-furylene) |

TABLE V-continued

| R11 | E |
|---|---|
| p-Chlorophenyl | 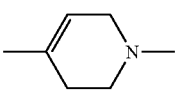 |
| p-Bromophenyl | 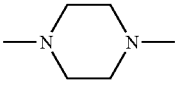 |
| p-Fluorophenyl | 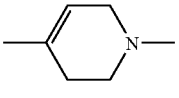 |
| p-Chlorophenyl | 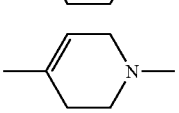 |
| 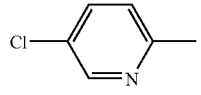 | 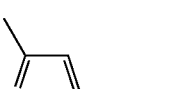 |
| p-Tolyl | 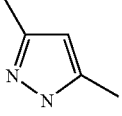 |
| n-Butyl | 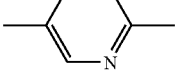 |
| p-Chlorophenyl | 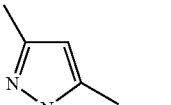 |
| 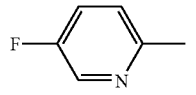 | 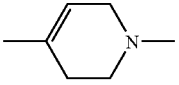 |
| 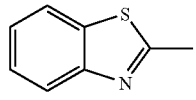 | 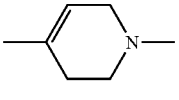 |
| p-Methylthiophenyl | 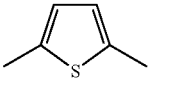 |
| 2-Amino-4-methylphenyl | 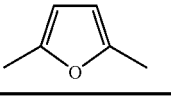 |

If K is —O— and X is a bond, NH or CH$_2$, the particularly preferred meanings for E and R11 are as follows:

If E is 1,4-phenylene, R11 is selected from the group consisting of:
phenyl, cyclopentyl, n-butyl, iso-butyl, iso-pentyl, 2,4-difluorophenyl and p-fluorophenyl.

Further combinations of E and R11 for the case where K is —O— and X is a bond, NH or CH$_2$ are listed in table VI:

TABLE VI

| R11 | E |
|---|---|
| Phenyl | 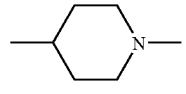 |
| Cyclopentyl | 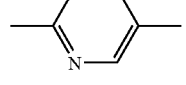 |
| Phenyl | 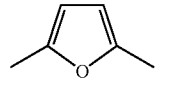 |
| n-Butyl | 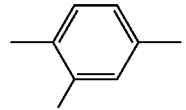 |
| n-Butyl | 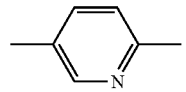 |

If K is C≡C and X is a bond, the particularly preferred meanings of E and R11 are as follows:
If E is

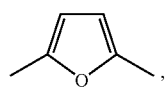

R11 is selected from the group consisting of:
phenyl, p-fluorophenyl and p-chlorophenyl.

If K is CH$_2$ and X is a bond, the particularly preferred meanings of E and R11 are indicated in table VII below:

TABLE VII

| R11 | E |
|---|---|
| Phenyl | 1,4-Phenylene |
| 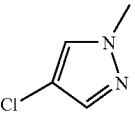 | 1,4-Phenylene |
| p-Chlorophenyl | 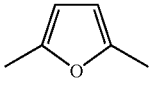 |

If K is CH$_2$O and X is a bond, the particularly preferred meanings of E and R11 areas follows:
If E is 1,4-phenylene, R11 is selected from the group consisting of:
phenyl, cyclopropyl and cyclohexyl.

If K is CONH and X is a bond, the particularly preferred meanings of E and R11 are indicated in table VIII below:

TABLE VIII

| R11 | E |
|---|---|
| Cyclopentyl | 1,4-Phenylene |
| Cyclohex-(1)-enyl | 1,4-Phenylene |
| Cyclopentyl | (3-fluoro-1,4-phenylene) |

If K is $OCH_2$ and X is a bond, the particularly preferred meanings of E and R11 are indicated in table IX below:

TABLE IX

| R11 | E |
|---|---|
| o-Chlorophenyl | (2,5-furandiyl) |
| p-Tolyl | 1,4-Phenylene |
| n-Propyl | 1,4-Phenylene |
| Cyclobutyl | 1,4-Phenylene |

The combinations of R11, K and E listed in table X below are furthermore particularly preferred in addition to the aforementioned combinations, with X very particularly preferably being a bond:

TABLE X

| R11 | K | E |
|---|---|---|
| o-Fluorophenyl | CO | (2,5-furandiyl) |
| Phenyl | $SCH_2$ | 1,4-Phenylene |
| Cyclopropyl | $(CH_2)_2O$ | (3-fluoro-1,4-phenylene) |

The compounds of the formula I are in a very particularly preferred embodiment compounds of the formula Ia

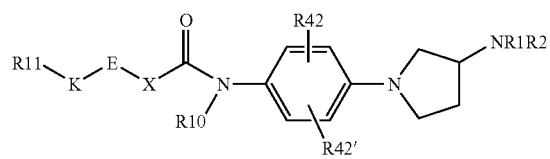

Ia in which the radicals R1, R2, R10, R11, R42, and groups X, E, K have the aforementioned meanings, and R42' is defined as R42, where R42 and R42' in the compounds of the formula Ia may be identical or different, or the N-oxides and the physiologically tolerated salts thereof.

In a preferred embodiment of the invention, the radicals R1, R2, R10, R11, R42, R42' and groups X, E, K have the following meanings:

R1, R2 independently of one another H, $(C_1-C_8)$-alkyl, —$(CR78R79)_o$—R12, $(C_1-C_4)$-alkoxy-$(C_1-C_4)$-alkyl, or R1 and R2 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, $(C_1-C_6)$-alkyl, O—$(C_1-C_4)$-alkyl, $(C_1-C_4)$-alkoxy-$(C_1-C_4)$-alkyl, hydroxy-$(C_1-C_4)$-alkyl, $(C_0-C_2)$-alkylene-aryl, oxo, CO(R26), CON(R27)(R28), hydroxy, N(R31)(R32) or $SO_2CH_3$; where $R^1$ and $R^2$ are not both CO(R26),
preferably H, $(C_1-C_8)$-alkyl, —$(CR78R79)_o$—R12, $(C_1-C_4)$-alkoxy-$(C_1-C_4)$-alkyl, or R1 and R2 form together with the nitrogen atom to which they are bonded a 4 to 10-membered mono- or bicyclic ring which, apart from the nitrogen atom, may comprise 0 to 2 additional heteroatoms selected from the group of oxygen and nitrogen, where the heterocyclic ring system may additionally be substituted by F, $(C_1-C_6)$-alkyl, $(C_1-C_4)$-alkoxy-$(C_1-C_4)$-alkyl, oxo, CO(R26), hydroxy, N(R31)(R32);

o 0, 1, 2, 3, 4, preferably
0, 1, 2, 3;
q 1, 2, 3, preferably
1 or 2;
s 0, 1, 2;
R15, R16, R17, R18, R23, R24, R25, R26, R27, R28, R31, R32
independently of one another H, $(C_1-C_6)$-alkyl;
or
R17 and R18, R27 and R28, R31 and R32
independently of one another optionally together with the nitrogen atom to which they are bonded a 5-6 membered ring which, apart from the nitrogen atom, may also comprise 0-1 further heteroatoms from the group of N—$(C_1-C_6)$-alkyl, oxygen and sulfur, preferably the ring is a pyrrolidine, piperidine, N-methylpiperazine, morpholine ring;
R12 OH, O—$(C_1-C_6)$-alkyl, O—$(C_0-C_2)$-alkylene-aryl, CN, S—$(C_1-C_6)$-alkyl, 3-12 membered mono-, bi- or spirocyclic ring which may comprise 1 to 3 heteroatoms from the group of N, O and S, and the 3-12 membered ring may comprise further substituents such as F, OH, $CF_3$, CN, oxo, $(C_1-C_6)$-alkyl, $(C_0-C_2)$-alkylene-aryl, N(R34)(R35), COO(R40), CO$(C_1-C_6)$-alkyl, preferably OH, O—$(C_1-C_6)$-alkyl, 3-10 membered mono- or bicyclic ring which may comprise 1-2 heteroatoms from the group of N, O and S, and the 3-10 membered ring may comprise further substituents such as F, OH, oxo, $(C_1-C_6)$-alkyl, CO$(C_1-C_6)$-alkyl;
R34, R35
independently of one another H, $(C_1-C_4)$-alkyl;
R40 H, $(C_1-C_6)$-alkyl, $(C_0-C_2)$-alkylene-aryl;
R78, R79 independently of one another H, $(C_1-C_8)$-alkyl, hydroxy-$(C_1-C_4)$-alkyl, OH, $(C_1-C_4)$-alkoxy-$(C_1-C_4)$-alkyl;
R42, R42' independently of one another H, F, Cl, Br, $CF_3$, CN, $(C_1-C_6)$-alkyl;
R10 H, $(C_1-C_8)$-alkyl;
X N(R52), a bond, C=C, C(R53)(R54), $CH_2CH_2$;
R52, R53, R54
independently of one another H, $(C_1-C_8)$-alkyl;

E 5-7 membered bivalent carbo- or heterocyclic ring structure with 0-3 heteroatoms from the group of N, O and S, which may optionally have substituents from the group of H, F, Cl, Br, $CF_3$, OH, CN, $OCF_3$, $NO_2$, O—($C_1$-$C_6$)-alkyl, ($C_1$-$C_6$)-alkyl, $SO_2$—$CH_3$, CO(R65);

preferably 5-7 membered bivalent carbo- or heterocyclic ring structure with 0-2 heteroatoms from the group of N, O and S, which may optionally have substituents from the group of H, F, Cl, Br, OH, $CF_3$, $NO_2$, $OCF_3$, O—($C_1$-$C_6$)-alkyl, ($C_1$-$C_6$)-alkyl, ($C_2$-$C_6$)-alkenyl, N(R57)(R58), $SO_2$—$CH_3$, CO(R65) e.g. E is selected from the group consisting of

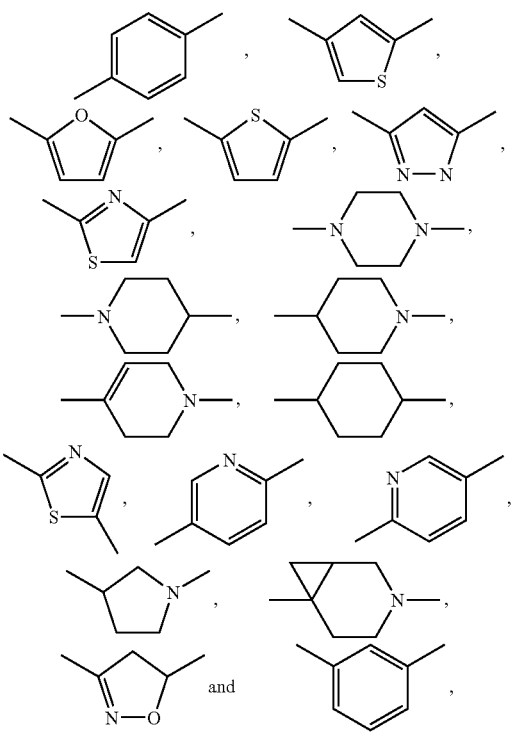

which may optionally have substituents from the group of H, F, Cl, Br, OH, $CF_3$, $NO_2$, $OCF_3$, O—($C_1$-$C_6$)-alkyl, ($C_1$-$C_6$)-alkyl, ($C_2$-$C_6$)-alkenyl, N(R57)(R58), $SO_2$—$CH_3$, CO(R65);

preferably

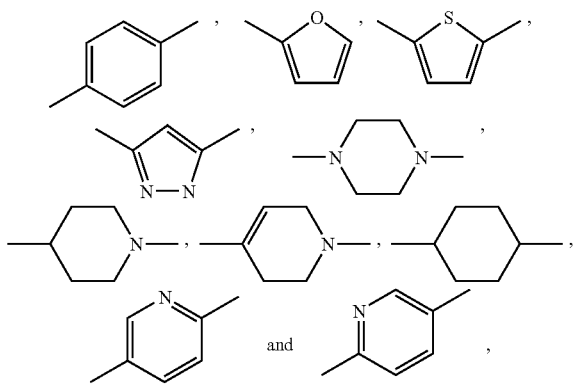

which may optionally have the aforementioned substituents;

R65 H, ($C_1$-$C_8$)-alkyl;

K a bond, O, $OCH_2$, $CH_2O$, S, $SO_2$, N(R66), N(R67)CO, CON(R68), (C(R69)(R70))$_v$, CO, C≡C, $SCH_2$, $SO_2CH_2$;

preferably a bond, O, $OCH_2$, $CH_2O$, CON(R68), (C(R69)(R70))$_v$, particularly preferably $CH_2$, CO, C≡C;

v 1, 2, 3, preferably
1, 2;

R66, R67, R68, R69, R70
independently of one another H, ($C_1$-$C_8$)-alkyl;

R11 ($C_1$-$C_8$)-alkyl, ($C_1$-$C_4$)-alkoxy-($C_1$-$C_4$)-alkyl, a 3 to 10-membered mono-, bi-, tri- or spirocyclic ring which may comprise 0 to 4 heteroatoms selected from the group of oxygen, nitrogen and sulfur, where the ring system may additionally be substituted by F, Cl, Br, $CF_3$, CN, ($C_1$-$C_6$)-alkyl, O—($C_1$-$C_8$)-alkyl, oxo, CO(R71), hydroxy, N(R75)CO($C_1$-$C_6$)-alkyl, or $SO_2CH_3$;

preferably ($C_1$-$C_8$)-alkyl, ($C_1$-$C_4$)-alkoxy-($C_1$-$C_4$)-alkyl, a 3 to 10-membered mono- or bicyclic ring which may comprise 0 to 2 heteroatoms selected from the group of oxygen, nitrogen and sulfur, where the ring system may additionally be substituted by F, Cl, Br, $CF_3$, CN, ($C_1$-$C_6$)-alkyl, O—($C_1$-$C_8$)-alkyl, oxo, CO(R71), CON(R72)(R73), N(R75)CO($C_1$-$C_6$)-alkyl, or $SO_2CH_3$;

R71, R72, R73, R74, R75, R76, R77
independently of one another H, ($C_1$-$C_8$)-alkyl;

or

R72 and R73, R76 and R77
independently of one another optionally together with the nitrogen atom to which they are bonded a 5-6 membered ring which, apart from the nitrogen atom, may also comprise 0-1 further heteroatoms from the group of N—($C_1$-$C_6$)-alkyl, oxygen and sulfur.

In a preferred embodiment, the present invention relates to compounds of the formula Ia, in which X is $CH_2CH_2$, N(R52), $CH_2$, $OCH_2$, $SCH_2$, CH═CH, preferably $CH_2CH_2$, CH═CH;

E is

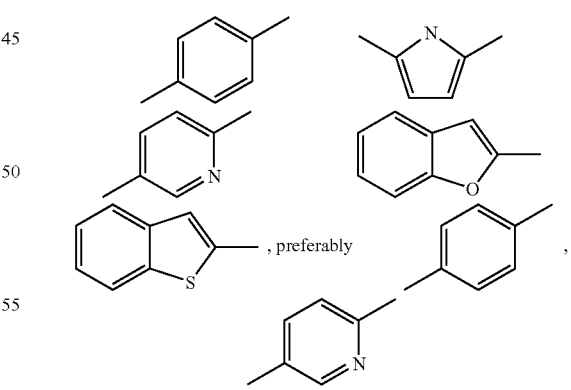

K is a bond, O or C(R69)(R70);

and the other symbols R1, R2, R10, R11, R42, R42', R52, R69 and R70 have the meanings indicated above in relation to a definition of the radicals of the compound of the formula Ia.

In a further preferred embodiment, the present invention relates to compounds of the formula Ia, in which
X is N(R52), preferably NH, or C(R53)(R54);
E is , preferably , or ;

K is a bond, O or C(R69)(R70), preferably O;
preferably O and the other symbols R1, R2, R10, R11, R42, R42', R52, R53, R54, R69 and R70 have the meanings indicated above in relation to a definition of the radicals of the compound of the formula Ia.

In a further particularly preferred embodiment, the compounds of the formula I are compounds of the formula Ib (Ib)

in which the radicals R1, R2, R10 and R11 and the groups E and D have the aforementioned meanings, or the N-oxides and the physiologically tolerated salts thereof.

In a preferred embodiment, the radicals R1, R2, R10 and R11 the groups E and D have the following meanings:

R1, R2 independently of one another H, $(C_1-C_8)$-alkyl, —$(CR78R79)_o$—R12, $(C_1-C_4)$-alkoxy-$(C_1-C_4)$-alkyl, $(C_3-C_8)$-alkenyl, CO—$(C_1-C_8)$-alkyl, —CO—$(CH_2)_o$—R12, CO-aryloxy-$(C_1-C_4)$-alkyl, COCH=CH(R13), COCC(R14), CO(C(R15)(R16))$_q$N(R17)(R18), CO(C(R19)(R20))$_r$CON(R21)(R22), CO(C(R23)(R24))$_s$O(R25); or R1 and R2 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, $CF_3$, $(C_1-C_6)$-alkyl, O—$(C_1-C_4)$-alkyl, $(C_1-C_4)$-alkoxy-$(C_1-C_4)$-alkyl, hydroxy-$(C_1-C_4)$-alkyl, $(C_0-C_2)$-alkylene-aryl, oxo, CO(R26), CON(R27)(R28), hydroxy, COO(R29), N(R30)CO($C_1-C_6$)-alkyl, N(R31)(R32) or $SO_2CH_3$, where R1 and R2 are not both CO(R26);
preferably independently of one another H, $(C_1-C_8)$-alkyl, —$(CR78R79)_o$—R12, $(C_1-C_4)$-alkoxy-$(C_1-C_4)$-alkyl, CO—$(C_1-C_8)$-alkyl, —CO—$(CH_2)_o$—R12, COCH=CH(R13), COCC(R14), CO(C(R15)(R16))$_q$N(R17)(R18), CO(C(R23)(R24))$_s$O(R25);

or R1 and R2 form together with the nitrogen atom to which they are bonded a 4 to 10-membered mono- or bicyclic ring which, apart from the nitrogen atom, may comprise 0 to 2 additional heteroatoms selected from the group of oxygen, nitrogen and sulfur, where the heterocyclic ring system may additionally be substituted by F, Cl, $CF_3$, $(C_1-C_6)$-alkyl, O—$(C_1-C_4)$-alkyl, $(C_1-C_4)$-alkoxy-$(C_1-C_4)$-alkyl, $(C_0-C_2)$-alkylene-aryl, oxo, hydroxy, N(R31)(R32) or $SO_2CH_3$, where R1 and R2 are not both CO—$(C_1-C_8)$-alkyl;
particularly preferably independently of one another H, $(C_1-C_8)$-alkyl, —$(CR78R79)_o$—R12, $(C_1-C_4)$-alkoxy-$(C_1-C_4)$-alkyl, CO—$(C_1-C_8)$-alkyl, —CO—$(CH_2)_o$—R12, CO(C(R15)(R16))$_q$N(R17)(R18), or R1 and R2 form together with the nitrogen atom to which they are bonded a 4 to 10-membered mono- or bicyclic ring which, apart from the nitrogen atom, may comprise 0 to 2 additional heteroatoms selected from the group of oxygen and nitrogen, where the heterocyclic ring system may additionally be substituted by F, $(C_1-C_6)$-alkyl, $(C_1-C_4)$-alkoxy-$(C_1-C_4)$-alkyl, oxo, CO($C_1-C_8$)-alkyl, hydroxy, N(R31)(R32), where R1 and R2 are not both CO($C_1-C_8$)-alkyl;

o 0, 1, 2, 3, 4, 5, 6; preferably 0, 1, 2, 3, 4; particularly preferably 0, 1, 2, 3;
q, r independently of one another 1, 2, 3; preferably q is 1 or 2;
s 0, 1, 2, 3, 4; preferably 0, 1, 2, 3; particularly preferably 0, 1, 2;
R13, R14 independently of one another a phenyl ring which may comprise 0-1 nitrogen atoms;
R15, R16, R17, R19, R20, R21, R22, R23, R24, R25, R26, R27, R28, R29, R30, R31, R32
independently of one another H, $(C_1-C_6)$-alkyl;
R18 H, $(C_1-C_6)$-alkyl, CO($C_1-C_6$)-alkyl, CO(R33); preferably H, $(C_1-C_6)$-alkyl, CO($C_1-C_6$)-alkyl; particularly preferably H, $(C_1-C_6)$-alkyl;

or

R17 and R18, R21 and R22, R27 and R28, R31 and R32 independently of one another optionally together with the nitrogen atom to which they are bonded a 5-6 membered ring which, apart from the nitrogen atom, may also comprise 0-1 further heteroatoms from the group of N—$(C_1-C_6)$-alkyl, oxygen and sulfur; preferably the ring is pyrrolidine, piperidine, N-methylpiperazine, morpholine;

R33 a 5-10 membered aromatic ring system which may comprise a further heteroatom from the group of nitrogen, oxygen and sulfur and may be substituted by F, Cl, $(C_1-C_6)$-alkyl, O—$(C_1-C_8)$-alkyl;

R12 is OH, O—$(C_1-C_6)$-alkyl, O—$(C_0-C_8)$-alkylene-aryl, CN, S—$(C_1-C_6)$-alkyl, COO(R80), CON(R81)(R82), 3-12 membered mono-, bi- or spirocyclic ring which may comprise one or more heteroatoms from the group of N, O and S and the 3-12 membered ring may comprise further substituents such as F, Cl, Br, OH, $CF_3$, CN, oxo, O—$(C_1-C_6)$-alkyl, $(C_1-C_4)$-alkoxy-$(C_1-C_4)$-alkyl, $(C_1-C_6)$-alkyl, O—$(C_0-C_8)$-alkylene-aryl, $(C_0-C_8)$-alkylene-aryl, N(R34)(R35), COCH=CH(R36), (C(R37)(R38))$_t$(R39), CO(C(R37)(R38)) (R39), CO($C_1-C_6$)-alkyl, COCOO($C_1-C_6$)-alkyl, COO(R40), S(O)$_u$ (R41);
preferably OH, O—$(C_1-C_6)$-alkyl, O—$(C_0-C_8)$-alkylene-aryl, CN, 3-10 membered mono- or bicyclic ring which may comprise 1-3 heteroatoms from the group of N, O and S, and the 3-10 membered ring may comprise further substituents such as F, Cl, Br, OH, $CF_3$, CN, oxo, O—($C_1$-$C_6$)-alkyl, ($C_1$-$C_4$)-alkoxy-($C_1$-$C_4$)-alkyl, ($C_1$-$C_6$)-alkyl, ($C_0$-$C_2$)-alkylene-aryl, N(R34)(R35), CO($C_1$-$C_6$)-alkyl;
  particularly preferably OH, O—($C_1$-$C_6$)-alkyl, 3-10 membered mono- or bicyclic ring which may comprise 1-2 heteroatoms from the group of N, O and S and the 3-10 membered ring may comprise further substituents such as F, OH, oxo, ($C_1$-$C_6$)-alkyl, CO($C_1$-$C_6$)-alkyl;
t 0, 1, 2, 3, 4, 5, 6;
u 0, 1, 2; preferably 0 or 2; particularly preferably 2;
R34, R35, R37, R38
  independently of one another H, ($C_1$-$C_8$)-alkyl;

or

R34 and R35
  optionally together with the nitrogen atom to which they are bonded a 5-6 membered ring which, apart from the nitrogen atom, may also comprise 0-1 further heteroatoms from the group of N—($C_1$-$C_6$)-alkyl, oxygen and sulfur and may optionally be substituted by 1-2 oxo groups;
R36, R39 independently of one another ($C_3$-$C_8$)-cycloalkyl, 5-10 membered aromatic ring system which may comprise 0-2 further heteroatoms from the group of nitrogen, oxygen and sulfur and may be substituted by F, Cl, ($C_1$-$C_6$)-alkyl, O—($C_1$-$C_8$)-alkyl;
R40 H, ($C_1$-$C_8$)-alkyl, ($C_2$-$C_6$)-alkenyl, ($C_0$-$C_8$)-alkylene-aryl;
R41 ($C_1$-$C_6$)-alkyl, 5-10 membered aromatic ring system which may comprise 0-2 further heteroatoms from the group of nitrogen, oxygen and sulfur and may be substituted by F, Cl, ($C_1$-$C_6$)-alkyl, O—($C_1$-$C_8$)-alkyl;
R78, R79 independently of one another H, ($C_1$-$C_8$)-alkyl, hydroxy-($C_1$-$C_4$)-alkyl, OH, ($C_1$-$C_4$)-alkoxy-($C_1$-$C_4$)-alkyl;
R80, R81 independently of one another H, ($C_1$-$C_8$)-alkyl;
R10 H, ($C_1$-$C_8$)-alkyl;
E 3-8 membered bivalent carbo- or heterocyclic ring structure with 0-4 heteroatoms from the group of N, O and S, which may optionally have substituents from the group of H, F, Cl, Br, OH, $CF_3$, $NO_2$, CN, $OCF_3$, O—($C_1$-$C_6$)-alkyl, O—($C_1$-$C_4$)-alkoxy-($C_1$-$C_4$)-alky S—($C_1$-$C_6$)-alkyl, ($C_1$-$C_6$)-alkyl, ($C_2$-$C_6$)-alkenyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R57)(R58), $SO_2$—$CH_3$, N(R61)CO(R62), N(R63)$SO_2$(R64), CO(R65) and may be mono- or bicyclic;
  preferably 5-7 membered bivalent carbo- or heterocyclic ring structure with 0-3 heteroatoms from the group of N, O and S, which may optionally have substituents from the group of H, F, Cl, Br, OH, $CF_3$, $NO_2$, CN, $OCF_3$, O—($C_1$-$C_6$)-alkyl, S—($C_1$-$C_6$)-alkyl, ($C_1$-$C_6$)-alkyl, ($C_2$-$C_6$)-alkenyl, O—($C_0$-$C_8$)-alkylene-aryl, S-aryl, N(R57)(R58), $SO_2$—$CH_3$, N(R61)CO(R62), CO(R65) and may be mono- or bicyclic;
  particularly preferably 5-7 membered bivalent carbo- or heterocyclic ring structure with 0-2 heteroatoms from the group of N, O and S, which may optionally have substituents from the group of H, F, Cl, Br, OH, $CF_3$, $NO_2$, $OCF_3$, O—($C_1$-$C_6$)-alkyl, ($C_1$-$C_6$)-alkyl, ($C_2$-$C_6$)-alkenyl, N(R57)(R58), $SO_2$—$CH_3$, CO(R65)
  e.g. E is selected from the group consisting of

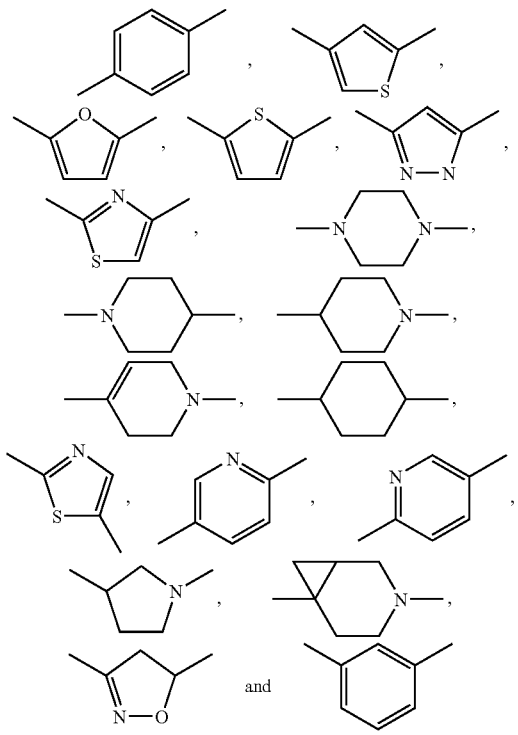

which may optionally have substituents from the group of H, F, Cl, Br, OH, $CF_3$, $NO_2$, $OCF_3$, O—($C_1$-$C_6$)-alkyl, ($C_1$-$C_6$)-alkyl, ($C_2$-$C_6$)-alkenyl, N(R57)(R58), $SO_2$—$CH_3$, CO(R65);

preferably

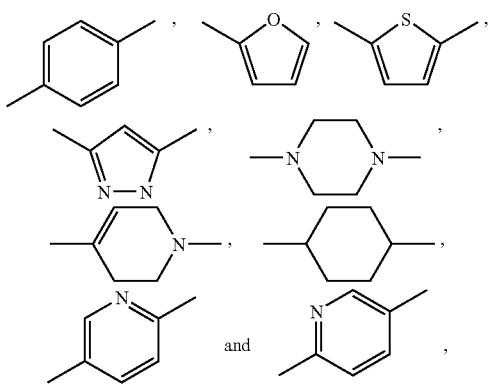

which may optionally have the aforementioned substituents;
R57, R58, R61, R63
  independently of one another H, ($C_1$-$C_8$)-alkyl;
R62, R64, R65
  independently of one another H, ($C_1$-$C_8$)-alkyl, aryl;
  preferably independently of one another H, ($C_1$-$C_8$)-alkyl;
K a bond, O, $OCH_2$, $CH_2O$, S, SO, $SO_2$, N(R66), N(R67)CO, CON(R68), (C(R69)(R70))$_v$, CO, C=C, C≡C, $SCH_2$, $SO_2CH_2$;

preferably a bond, O, OCH$_2$, CH$_2$O, N(R66), CON(R68), (C(R69)(R70))$_v$, CO, C≡C, SCH$_2$; particularly preferably a bond, O, OCH$_2$, CH$_2$O, CON(R68), (C(R69)(R70))$_v$, CO, C≡C;

v 1, 2, 3, 4; preferably 1, 2, 3; particularly preferably 1, 2;

R66, R67, R68, R69, R70
   independently of one another H, (C$_1$-C$_8$)-alkyl;

R11 H, (C$_1$-C$_8$)-alkyl, (C$_1$-C$_4$)-alkoxy-(C$_1$-C$_4$)-alkyl, (C$_3$-C$_8$)-alkenyl, (C$_3$-C$_8$)-alkynyl, a 3 to 10-membered mono-, bi-, tri- or spirocyclic ring which may comprise 0 to 4 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, (C$_0$-C$_8$)-alkylene-aryl, oxo, CO(R71), CON(R72)(R73), hydroxy, COO(R74), N(R75)CO(C$_1$-C$_6$)-alkyl, N(R76)(R77) or SO$_2$CH$_3$SCF$_3$;
   preferably (C$_1$-C$_8$)-alkyl, (C$_1$-C$_4$)-alkoxy-(C$_1$-C$_4$)-alkyl, a 3 to 10-membered mono-, bi-, tri- or spirocyclic ring which may comprise 0 to 3 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, (C$_0$-C$_2$)-alkylene-aryl, oxo, CO(R71), CON(R72)(R73), hydroxy, N(R75)CO(C$_1$-C$_6$)-alkyl, N(R76)(R77) or SO$_2$CH$_3$;
   particularly preferably (C$_1$-C$_8$)-alkyl, (C$_1$-C$_4$)-alkoxy-(C$_1$-C$_4$)-alkyl, a 3 to 10-membered mono- or bicyclic ring which may comprise 0 to 2 heteroatoms selected from the group of oxygen, nitrogen and sulfur, where the ring system may additionally be substituted by F, Cl, Br, CF$_3$, CN, (C$_1$-C$_6$)-alkyl, O—(C$_1$-C$_8$)-alkyl, oxo, CO(R71), CON(R72)(R73), N(R75)CO(C$_1$-C$_6$)-alkyl, or SO$_2$CH$_3$;

R71, R72, R73, R74, R75, R76, R77
   independently of one another H, (C$_1$-C$_8$)-alkyl;

or

R72 and R73, R76 and R77
   independently of one another optionally together with the nitrogen atom to which they are bonded a 5-6 membered ring which, apart from the nitrogen atom, may also comprise 0-1 further heteroatoms from the group of N—(C$_1$-C$_6$)-alkyl, oxygen and sulfur.

In a preferred embodiment, the present invention relates to compounds of the formula Ib in which X is a bond, E is where the aforementioned groups may optionally have substituents from the group of H, F, Cl, Br, OH, CF$_3$, NO$_2$, OCF$_3$, O—(C$_1$-C$_6$)-alkyl, (C$_1$-C$_6$)-alkyl, (C$_2$-C$_6$)-alkenyl, N(R57)(R58), SO$_2$—CH$_3$, CO(R65);

preferably E is in which the groups may have the aforementioned substituents;

K is a bond; and the other radicals R1, R2, R10 and R11 and the group D have the meanings indicated above in relation to the definition of the radicals of the compound of the formula Ib.

R11 in the aforementioned compounds of the formula Ib is particularly preferably a substituted mono- or bicyclic ring system with 5-10 members, which may have 0-3 heteroatoms, in particular N, O and/or S, particularly preferably phenyl with 0-1 N atom, cyclohexyl or a bicyclic system with 8-10 members and 1-2 heteroatoms, in particular N, O and/or S.

In a further preferred embodiment, the present invention relates to compounds of the formula Ib in which X is a bond;

E is

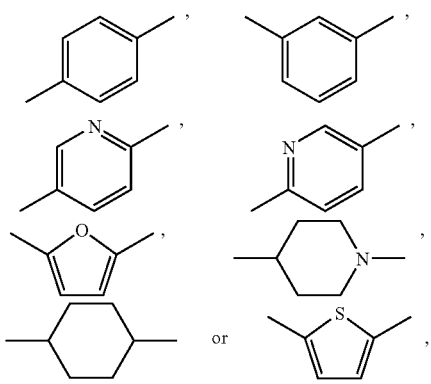

where the aforementioned groups may optionally have substituents from the group of H, F, Cl, Br, OH, $CF_3$, $NO_2$, $OCF_3$, O—$(C_1$-$C_6)$-alkyl, $(C_1$-$C_6)$-alkyl, $(C_2$-$C_6)$-alkenyl, N(R57)(R58), $SO_2CH_3$ and CO(R65);

preferably

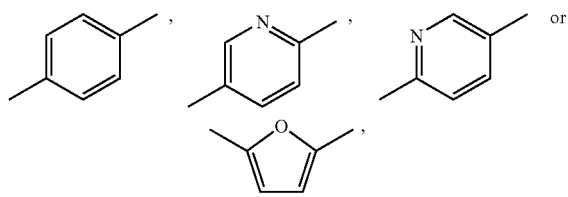

in which the groups may have the aforementioned substituents;

K is $CH_2$, $CH_2CH_2$, O, $CH_2O$, $OCH_2$, CON(R68), N(R67)CO, S, $SO_2$, $SCH_2$, $SO_2$, $SO_2CH_2$, CO or a triple bond; preferably $CH_2$, O, $CH_2O$, $OCH_2$, CON(R68), $SCH_2$, CO or a triple bond; and the other radicals R1, R2, R3, R4, R5, R6, R7, R8, R9, R10, R11, R67 and R68 and the group D have the meanings indicated above in relation to the definition of the radicals of the compound of the formula Ib.

The amount of a compound of formula (I) necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 1.0 to 1000 mg, typically from 10 to 600 mg. In the case of pharmaceutically acceptable salts, the aforementioned weight data are based on the weight of the free compound from which the salt is derived. For the prophylaxis and therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula (I) with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and they also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure. The compounds act as MCH antagonists and are also suitable for the treatment of disturbances of wellbeing and of psychiatric indications such as, for example, depressions, anxiety states, anxiety neuroses, schizophrenia and for the treatment of disorders associated with the circadian rhythm and for the treatment of drug abuse.

In a further aspect of the invention, the compounds of the formula I can be administered in combination with one or more other pharmacologically active substances which are selected, for example, from antidiabetics, antiobesity agents, active ingredients which lower blood pressure, lipid-lowering agents and active ingredients for the treatment and/or prevention of complications caused by diabetes or associated with diabetes.

Further pharmacologically active substances suitable in particular are:

all antidiabetics mentioned in the Rote Liste 2001, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Suitable antidiabetics include insulin and insulin derivatives such as, for example, Lantus® or HMR 1964, fast-acting insulins (see U.S. Pat. No. 6,221,633), amylin, GLP-1 and GLP-2 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon receptor antagonists, GLP-1 agonists, potassium channel openers such as, for example, those disclosed in WO 97/26265 and WO 99/03861 of Novo Nordisk A/S, insulin sensitizers, activators of insulin receptor kinase, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism, such as antihyperlipidemic active ingredients and antilipidemic active ingredients, e.g. HMG-CoA reductase inhibitors, inhibitors of cholesterol transport/ of cholesterol uptake, inhibitors of bile acid reabsorption or inhibitors of microsomal triglyceride transfer protein (MTP), compounds which reduce food intake, PPAR and RXR agonists and active ingredients which act on the ATP-dependent potassium channel of the beta cells.

In one embodiment of the invention, the present compounds are administered in combination with insulin.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyse inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidined In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc. The compounds of the invention may moreover be administered in combination with one or more antiobesity agents or appetite-controlling active ingredients.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexyl-methyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g.1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In one embodiment, the other active ingredient is fenfluramine or dexfenfluramine.

In another embodiment, the other active ingredient is sibutramine or the mono- and bisdemethylated active metabolites of sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

-continued

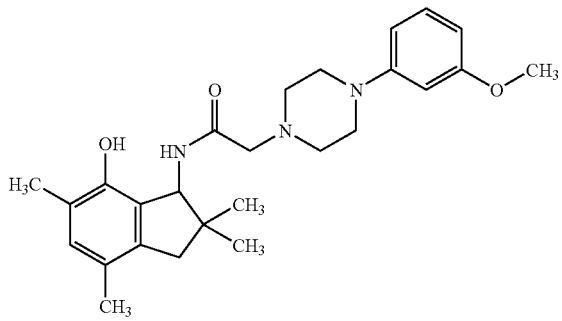
OPC-14117

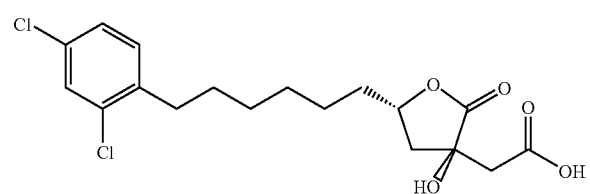
SB-204990

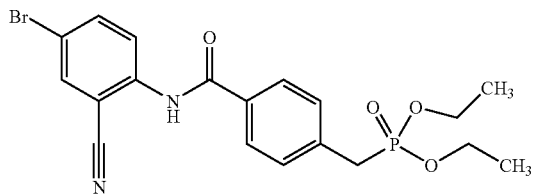
NO-1886

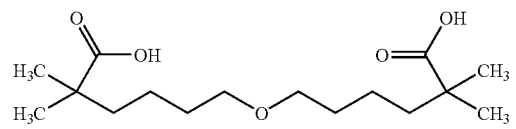
CI-1027

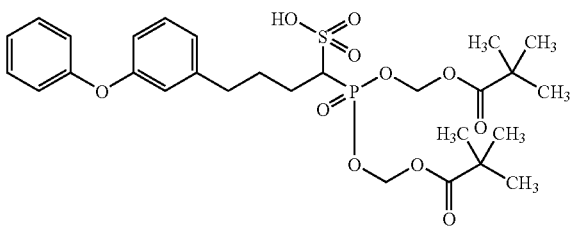
BMS-188494

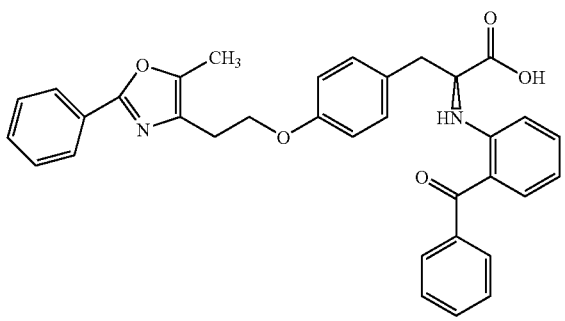
GI 262570

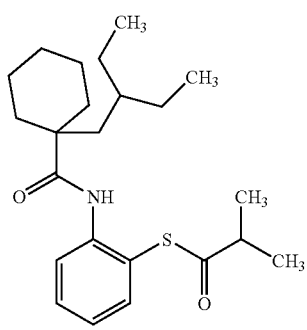
JTT-705

-continued

JTT-501

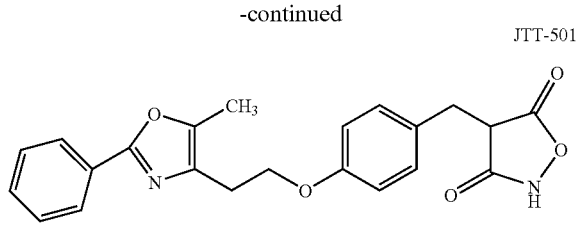

The present compounds may additionally be administered in combination with one or more antihypertensive active ingredients. Examples of antihypertensive active ingredients are beta blockers such as alprenolol,atenol, timolol, pindolol, propanolol and metoprolol, ACE (angiotensin converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and alpha blockers such as doxazosin, urapidil, prazosin and terazosin. Reference may furthermore be made to Remington: The Science and Practice of Pharmacy, 19th edition, Gennaro, editor, Mack Publishing Co., Easton, Pa., 1995.

It will be appreciated that every suitable combination of the compounds of the invention with one or more of the aforementioned compounds and optionally one or more other pharmacologically active substances is to be regarded as covered by the scope of protection of the present invention.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

EXAMPLES

The efficacy of the compounds was tested as follows:

Biological Test Model:

The anorectic effect was tested on female NMRI mice. After withdrawal of food for 17 hours, the test product was administered by gavage. The animals were housed singly with free access to drinking water and were offered condensed milk 30 minutes after administration of the product. The condensed milk consumption was determined every half hour for 7 hours, and the general wellbeing of the animals was observed. The measured milk consumption was compared with the vehicle-treated control animals.

TABLE 1

Anorectic effect measured as the reduction in the cumulative milk consumption of treated compared with control animals

| Example | Oral dose [mg/kg] | Number of animals/-cumulative milk consumption of the treated animals N/[ml] | Number of animals/-cumulative milk consumption of the control animals N/[ml] | Reduction in the cumulative milk consumption as % of the control |
|---|---|---|---|---|
| Example 4 | 30 | 5/3.55 | 5/1.76 | 50 |
| Example 13 | 30 | 5/3.70 | 5/1.34 | 64 |

DESCRIPTION OF EXPERIMENTS

Functional Measurements to Find IC50 Values

The cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554-13562, 2001). A difference from the reference was, however, the use of the plasmid pEAK8 from EDGE Biosystems (USA) to construct the expression vector. The host used for the transfection was a transformed HEK cell line named "PEAK Stable Cells" (likewise from EDGE Biosystems). The functional measurements of the cellular calcium flux after addition of agonist (MCH) in the presence of ligand of the invention took place with the aid of the FLIPR apparatus from Molecular Devices (USA) using the protocols of the apparatus manufacturer.

The examples and preparation methods detailed below serve to illustrate the invention without, however, restricting it.

The compounds of the formula I of the invention can be prepared with the aid of reactions which are known in principle. For example, the compounds were obtained in accordance with the following general reaction schemes.

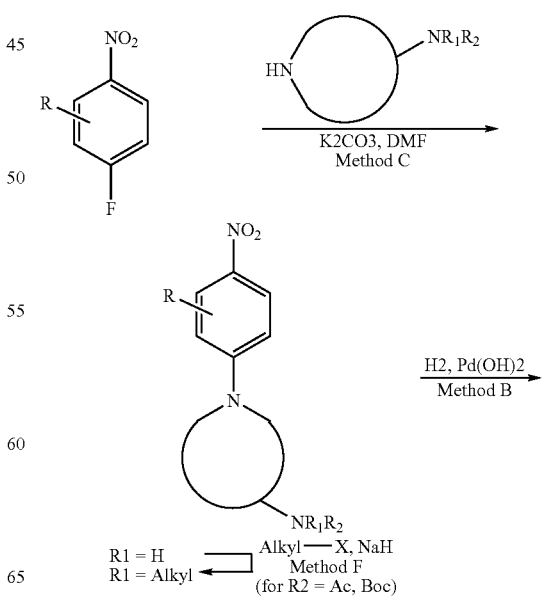

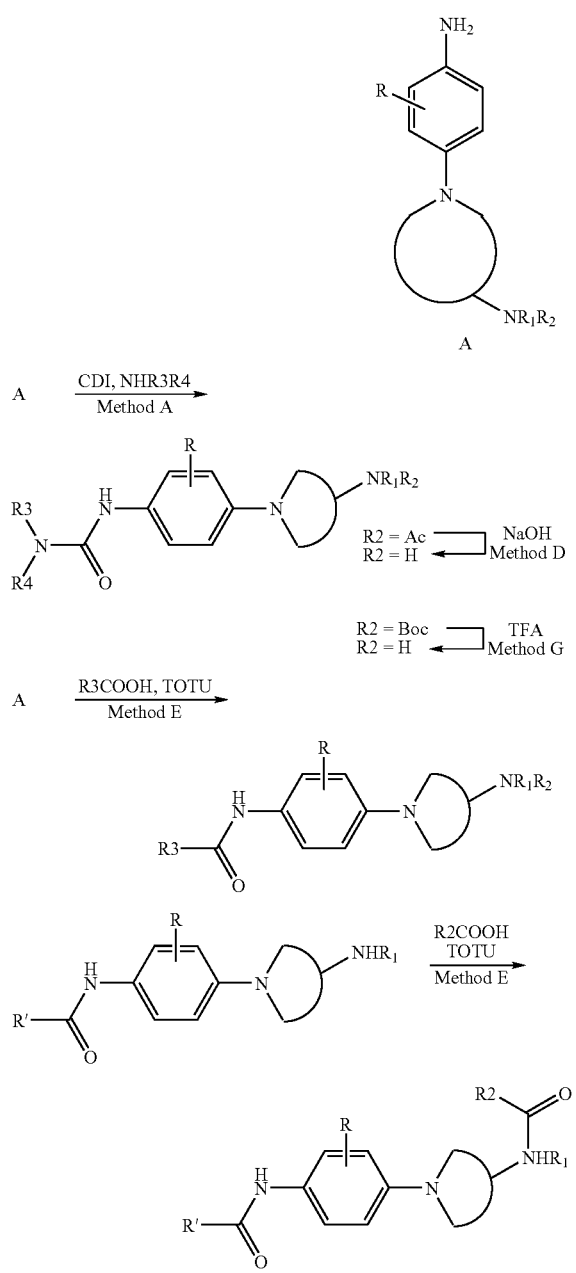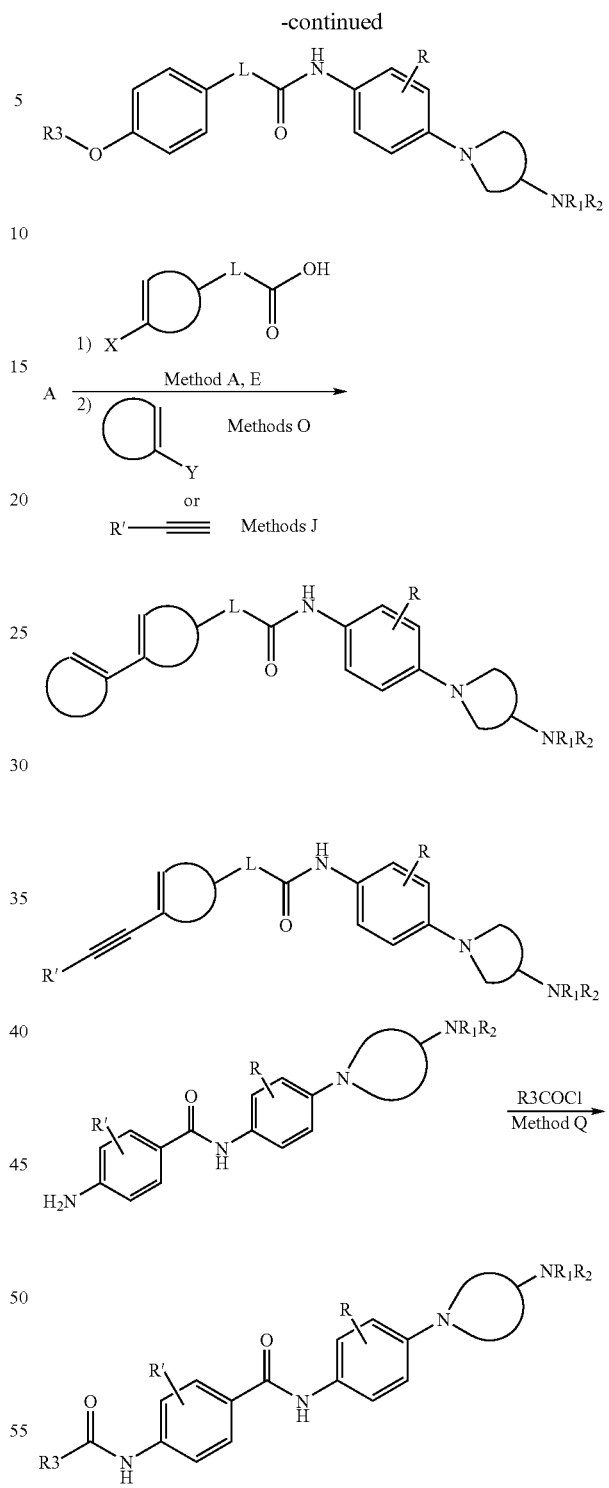
Other compounds of the invention can be obtained by further routes which are outlined by way of example in the following scheme.
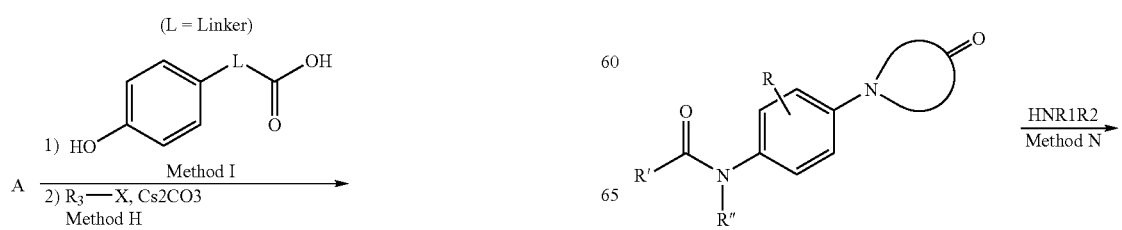

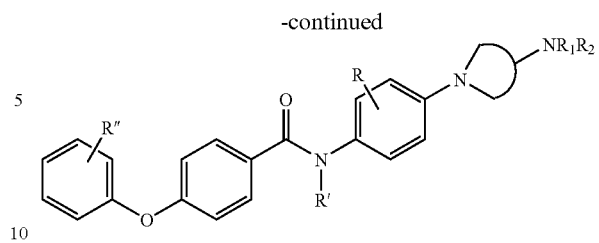

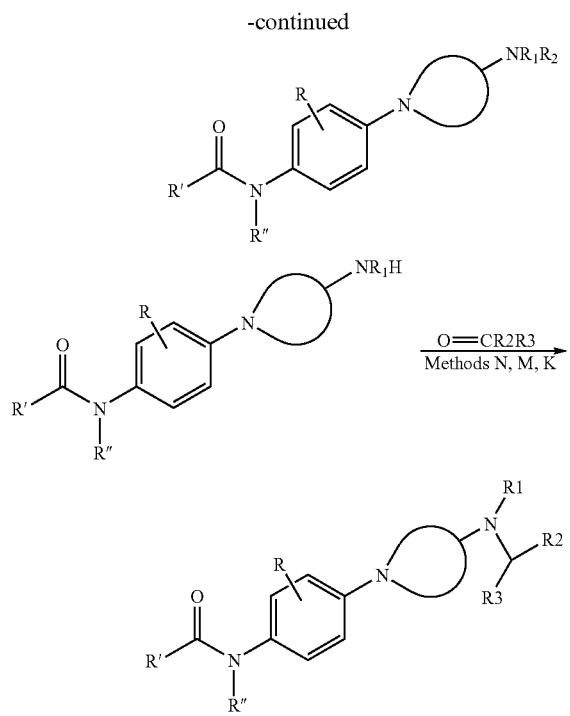

Yet other examples were obtained as indicated in the following scheme.

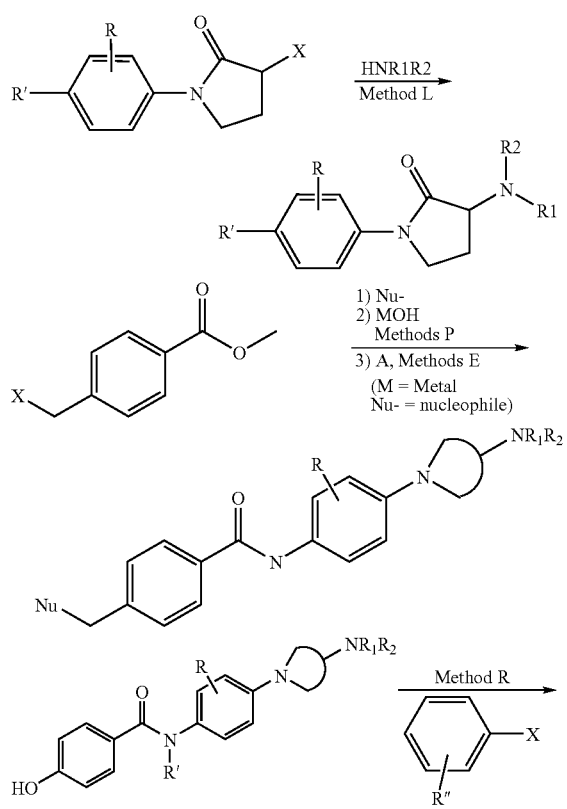

Descriptions of the general methods used are to be found by way of example described at the following places:

Methods A, B and C in example 1;
Method D in example 2;
Method E in example 3;
Method E-a in example 275;
Method E-b in example 286;
Method F in example 4;
Method F-a in example 264;
Method G in example 15;
Method H in example 237;
Method H-a in example 298;
Method I in example 238;
Method J in example 245;
Method J-a in example 297;
Method K in example 250;
Method L in example 254;
Method M in example 274;
Method N in example 277;
Method O in example 279;
Method O-a in example 292;
Method O-b in example 280;
Method P in example 285;
Method Q in example 290;
Method R in example 309.

General Explanations a) Mode of Drawing the Structural Formulae

Only non-hydrogen atoms are depicted for clarity in the structural formulae of the given examples.

In tables 6-13, enantiomer-enriched compounds are identified by a marked hydrogen atom on the stereogenic center. Unless expressly noted otherwise, the enantiomer-enriched examples shown have the (R) configuration on the 3-aminopyrrolidine stereocenter.

b) Salt Forms

Many of the compounds of the invention are bases and can form salts with appropriately strong acids. In particular, after purification of the compounds by HPLC chromatography using a trifluoroacetic acid-containing mobile phase they may be in the form of hydrotrifluoroacetates. These can be converted into the free bases shown by simple treatment of a solution of the salts for example with sodium carbonate solution.

c) Units of the Characterizing Data

The unit of the stated molecular weight is "g/mol". Peaks observed in the mass spectrum are indicated as the integral quotient of the molar molecular ion mass and the charge of the molecular ion (m/z).

Example 1

N-Methyl-N-(1-{4-[3-(4-phenoxyphenyl)ureido]phenyl}pyrrolidin-3-yl)acetamide

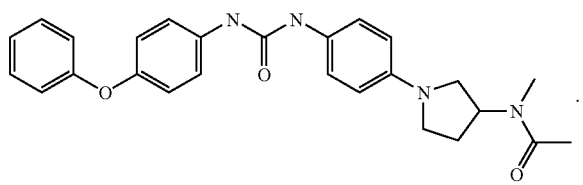

Method A

A solution of 4-phenoxyaniline (3.33 g) in DMF (10 ml) was added dropwise to a solution of carbonyldiimidazole (2.92 g) in DMF (12 ml) cooled to 0° C. After 30 minutes, N-[1-(4-aminophenyl)pyrrolidin-3-yl]-N-methylacetamide (3.80 g) in DMF (10 ml) was added dropwise. The reaction solution was kept initially at room temperature for 2 hours and then at 80° C. for 30 minutes. The mixture was added dropwise to water (600 ml) and the resulting precipitate was filtered off with suction and washed with water. Alternatively, the product can also be extracted with ethyl acetate and purified by chromatography after concentration. This resulted in the product with the molecular weight of 444.54 (C26H28N4O3); MS (ESI): 445 (M+H+).

N-[1-(4-Aminophenyl)pyrrolidin-3-yl]-N-methylacetamide

Method B

A suspension of N-methyl-N-[1-(4-nitrophenyl)pyrrolidin-3-yl]acetamide (3.5 g) and palladium(II) hydroxide (20% on carbon; 0.9 g) in ethanol (150 ml) and ethyl acetate (300 ml) was vigorously stirred under a hydrogen atmosphere (atmospheric pressure) for 3 hours. The catalyst was then removed by filtration, and the filtrate was concentrated. This resulted in the product with the molecular weight of 233.32 (C13H19N3O); MS (ESI): 234 (M+H+).

N-Methyl-N-[1-(4-nitrophenyl)pyrrolidin-3-yl]acetamide

Method C

4-Fluoronitrobenzene (25.0 g) was slowly added to a suspension of N-methyl-N-pyrrolidin-3-ylacetamide (25.2 g) and cesium carbonate (57.6 g) in DMF (300 ml). After 2 hours, the reaction mixture was poured into water, and the resultant precipitate was filtered off with suction. Alternatively, the product can also be extracted with ethyl acetate and purified by chromatography after concentration. This results in the product with the molecular weight of 263.30 (C13H17N3O3): MS (ESI): 264 (M+H+).

Example 2

1-[4-(3-Methylaminopyrrolidin-1-yl)phenyl]-3-(4-phenoxyphenyl)urea

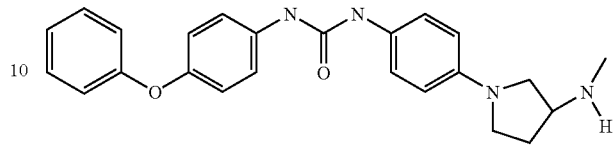

Method D

A mixture of N-methyl-N-(1-{4-[3-(4-phenoxyphenyl)ureido]phenyl}pyrroldin-3-yl)acetamide (6.0 g), ethanol (250 ml), water (60 ml) and sodium hydroxide solution (10 M; 80 ml) was heated under reflux for 12 hours. The alcohol was distilled out and the resulting precipitate was filtered off with suction and washed with dichloromethane. Additional product was obtained by concentration of the organic phase and chromatography (silica gel, dichloromethane/methanol 9:1 with 1% triethylamine). This resulted in the product with the molecular weight of 402.50 (C24H26N4O2); MS (ESI): 403 (M+H+).

Example 3

N-Methyl-N-(1-{4-[3-(4-phenoxyphenyl)ureido]phenyl}pyrrolidin-3-yl)-2-phenylacetamide

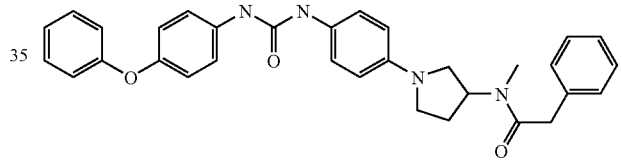

Method E

TOTU (327 mg) was added to a solution of 1-[4-(3-methylaminopyrrolidin-1-yl)phenyl]-3-(4-phenoxyphenyl)urea (402 mg) in DMF (3 ml) at 0° C. After 10 minutes, Hünig's base (130 mg) and then a solution of phenylacetic acid (136 mg) in DMF (1 ml) was added. After a reaction time of 12 hours at room temperature, water was added to the mixture, and it was extracted with ethyl acetate. The organic phase was dried over magnesium sulfate and concentrated. The residue was purified by preparative HPLC. This resulted in the product with the molecular weight of 520.64 (C32H32N4O3); MS (ESI): 521 (M+H+) as hydrotrifluoroacetate.

Example 4

(R)-N-Methyl-N-(1-{4-[3-(4-phenoxyphenyl)ureido]phenyl}pyrrolidin-3-yl)acetamide

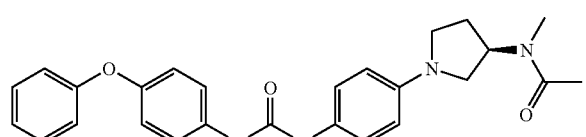

(R)-N-[1-(4-Aminophenyl)pyrrolidin-3-yl]-N-methylacetamide was reacted with 4-phenoxyaniline by method A.

This resulted in the product with the molecular weight of 444.54 (C26H28N4O3); MS (ESI): 445 (M+H+).

(R)-N-[1-(4-Aminophenyl)pyrrolidin-3-yl]-N-methylacetamide (R)-N-Methyl-N-[1-(4-nitrophenyl)pyrrolidin-3-yl]acetamide was hydrogenated by method B. This resulted in the product with the molecular weight of 233.32 (C13H19N3O); MS (ESI): 234 (M+H+).

(R)-N-Methyl-N-[1-(4-nitrophenyl)pyrrolidin-3-yl]acetamide

Method F (R)-N-[1-(4-Nitrophenyl)pyrrolidin-3-yl]acetamide (1.3 g) was added in portions to a suspension of sodium hydride (50% in oil; 0.25 g) in DMF (50 ml). After gas evolution had ceased, iodomethane (0.82 g) was added. After one hour, the reaction mixture was cautiously hydrolyzed with water and extracted with ethyl acetate. The organic phase was dried over magnesium sulfate and concentrated. This resulted in the product with the molecular weight of 263.30 (C13H17N3O3); MS (ESI): 264 (M+H+).

(R)-N-[1-(4-Nitrophenyl)pyrrolidin-3-yl]acetamide (R)-N-pyrrolidin-3-ylacetamide was reacted with 4-fluoronitrobenzene by method C. This resulted in the product with the molecular weight of 249.27 (C12H15N3O3); MS (ESI): 250 (M+H+).

Example 5

(S)-N-Methyl-N-(1-{4-[3-(4-phenoxyphenyl)ureido]phenyl}pyrrolidin-3-yl)acetamide

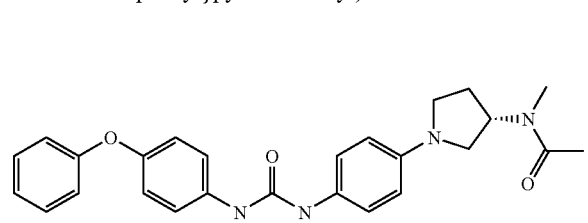

The sequence described in example 4 was applied to (S)-N-pyrrolidin-3-ylacetamide. This resulted in the product with the molecular weight of 444.54 (C26H28N4O3); MS (ESI): 445 (M+H+).

Example 6

(R)-1-[4-(3-Methylaminopyrrolidin-1-yl)phenyl]-3-(4-phenoxyphenyl)urea

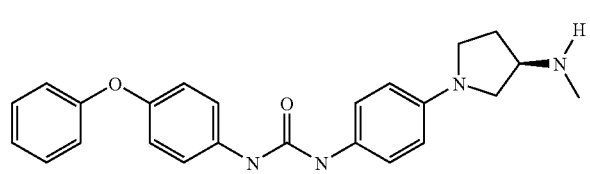

(R)-N-Methyl-N-(1-{4-[3-(4-phenoxyphenyl)ureido]phenyl}pyrrolidin-3-yl)acetamide was reacted by method D.

This resulted in the product with the molecular weight of 402.50 (C24H26N4O2); MS (ESI): 403 (M+H+).

Example 7

(S)-1-[4-(3-Methylaminopyrrolidin-1-yl)phenyl]-3-(4-phenoxyphenyl)urea

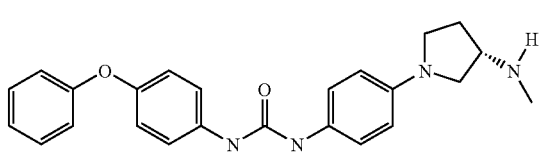

(S)-N-Methyl-N-(1-{4-[3-(4-phenoxyphenyl)ureido]phenyl}pyrrolidin-3-yl)acetamide was reacted by method D. This resulted in the product with the molecular weight of 402.50 (C24H26N4O2); MS (ESI): 403 (M+H+).

Example 8

(R)-N-(1-{4-[3-(4-Cyclopentyloxyphenyl)ureido]phenyl}pyrrolidin-3-yl)-N-methylacetamide

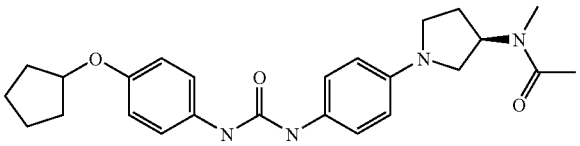

(R)-N-[1-(4-Aminophenyl)pyrrolidin-3-yl)-N-methylacetamide was reacted with 4-cyclopentyloxyaniline by method A. This resulted in the product with the molecular weight of 436.56 (C25H32N4O3); MS (ESI): 437 (M+H+).

(S)-N-(1-{4-[3-(4-cyclopentyloxy-phenyl)-ureido]-phenyl}-pyrrolidin-3-yl)-N-methyl-acetamide was obtained analogously from (S)-N-[1-(4-amino-phenyl)-pyrrolidin-3-yl]-N-methyl-acetamide.

4-Cyclopentyloxyaniline

A mixture of 4-nitrophenol (63.7 g), bromocyclopentane (68.2 g), potassium carbonate (63.3 g) and DMF (300 ml) was heated at 80° C. for 24 hours. After cooling, it was diluted with water and extracted with ethyl acetate. The organic phase was washed with water, dried over magnesium sulfate and concentrated. The residue was hydrogenated by method B. This resulted in the product with the molecular weight of 177.25 (C11H15NO); MS (ESI): 178 (M+H+).

Example 9

1-(4-Cyclopentyloxyphenyl)-3-[4-(3-methylaminopyrrolidin-1-yl)phenyl]urea

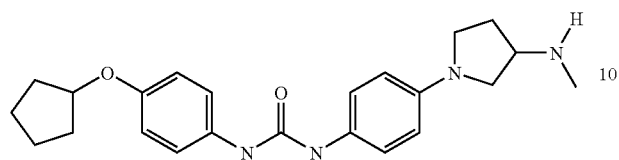

N-(1-{4-[3-(4-Cyclopentyloxyphenyl)ureido]phenyl}pyrrolidin-3-yl)-N-methylacetamide was reacted by method D. This resulted in the product with the molecular weight of 394.52 (C23H30N4O2); MS (ESI): 395 (M+H+).

(R)- and (S)-1-(4-cyclopentyloxy-phenyl)-3-[4-(3-methylamino-pyrrolidin-1-yl)-phenyl]-urea was obtained analogously from (R)- and (S)-N-(1-{4-[3-(4-cyclopentyloxyphenyl)-ureido]-phenyl}-pyrrolidin-3-yl)-N-methyl-acetamide.

Example 10

Ethyl (1-{4-[3-(4-Cyclopentyloxyphenyl)ureido]phenyl}pyrrolidin-3-yl)methyl-carbamate

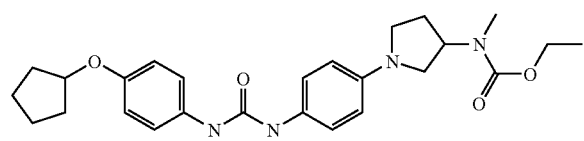

Ethyl chloroformate (8 µl) was added dropwise to a solution of 1-(4-cyclopentyloxyphenyl)-3-[4-(3-methylaminopyrrolidin-1-yl)phenyl]urea (20 mg) and Hünig's base (10 mg) in dichloromethane (3 ml). After 12 hours, the reaction mixture was concentrated and the residue was purified by preparative HPLC. This resulted in the product with the molecular weight of 466.59 (C26H34N4O4); MS (ESI): 467 (M+H+) as hydrotrifluoroacetate.

Example 11

1-(1-{4-[3-(4-Cyclopentyloxyphenyl)ureido]phenyl}pyrrolidin-3-yl)-3-ethyl-1-methylurea

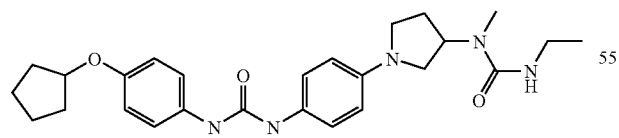

Ethyl isocyanate (7 µl) was added dropwise to a solution of 1-(4-cyclopentyloxyphenyl)-3-[4-(3-methylaminopyrrolidin-1-yl)phenyl]urea (20 mg) and Hünig's base (10 mg) in dichloromethane (3 ml). After 12 hours, the reaction mixture was concentrated and the residue was purified by preparative HPLC. This resulted in the product with the molecular weight of 465.60 (C26H35N5O3); MS (ESI): 466 (M+H+) as hydrotrifluoroacetate.

Example 12

1-(4-Cyclopentyloxyphenyl)-3-(4-{3-[methyl-((R)-5-oxo-pyrrolidin-2-ylmethyl)amino]pyrrolidin-1-yl}phenyl)urea

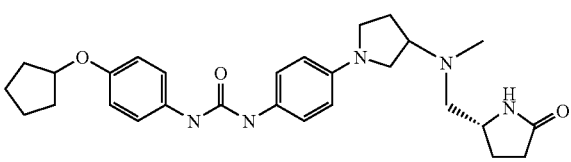

(R)-5-Bromomethylpyrrolidin-2-one (15 mg) was added to a suspension of 1-(4-cyclopentyloxyphenyl)-3-[4-(3-methyaminopyrrolidin-1-yl)phenyl]urea (30 mg) and potassium carbonate (20 mg) in DMF (3 ml). After 2 hours, the reaction mixture was filtered and concentrated, and the residue was purified by preparative HPLC. This resulted in the product with the molecular weight of 491.64 (C28H37N5O3); MS (ESI): 492 (M+H+) as hydrotrifluoroacetate.

Example 13

4-(4-Chlorophenyl)piperidine-1-carboxylic acid {4-[3-(acetylmethylamino)-pyrrolidin-1-yl]phenyl}amide

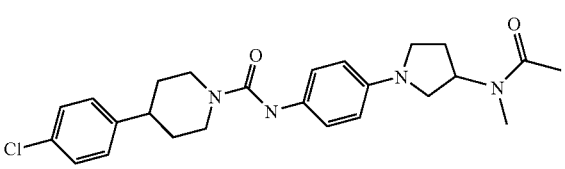

N-[1-(4-Aminophenyl)pyrrolidin-3-yl]-N-methylacetamide was reacted with carbonyldiimidazole and then with 4-(4-chlorophenyl)piperidine by method A. This resulted in the product with the molecular weight of 455.00 (C25H31ClN4O2); MS (ESI): 455 (M+H+).

(R)- and (S)-4-(4-chlorophenyl)piperidine-1-carboxylic acid {4-[3-(acetyl-methylamino)pyrrolidin-1-yl]phenyl}amide were obtained analogously from (R)- and (S)-N-[1-(4-aminophenyl)pyrrolidin-3-yl]-N-methylacetamide.

Example 14 tert-Butyl (R)-[1-(4-{[4-(4-chlorophenyl)piperidine-1-carbonyl]amino}-phenyl)pyrrolidin-3-yl]methyl-carbamate

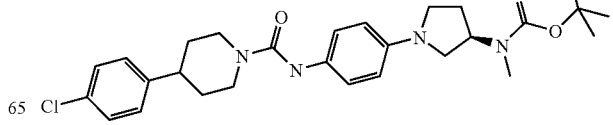

tert-Butyl (R)-[1-(4-aminophenyl)pyrrolidin-3-yl]methylcarbamate was reacted with carbonyldiimidazole and then with 4-(4-chlorophenyl)piperidine by method A. This resulted in the product with the molecular weight of 513.09 (C28H37ClN4O3); MS (ESI): 513 (M+H+).

tert-Butyl (R)-[1-(4-aminophenyl)pyrrolidin-3-yl]methylcarbamate tert-Butyl (R)-methyl-[1-(4-nitrophenyl)pyrrolidin-3-yl]carbamate was hydrogenated by method B. This resulted in the product with the molecular weight of 291.40 (C16H25N3O2); MS (ESI): 292 (M+H+).

tert-Butyl (R)-methyl-[1-(4-nitrophenyl)pyrrolidin-3-yl]carbamate tert-Butyl (R)-[1-(4-nitrophenyl)pyrrolidin-3-yl]carbamate was alkylated with iodomethane by method F. This resulted in the product with the molecular weight of 321.38 (C16H23N3O4); MS (ESI): 322 (M+H+).

tert-Butyl (R)-[1-(4-nitrophenyl)pyrrolidin-3-yl]carbamate tert-Butyl (R)-pyrrolidin-3-ylcarbamate was reacted with 4-fluoronitro-benzene by method C. This resulted in the product with the molecular weight of 307.35 (C15H21N3O4); MS (ESI): 308 (M+H+).

Example 15

(R)-4-(4-Chlorophenyl)piperidine-1-carboxylic acid [4-(3-methylamino-pyrrolidin-1-yl)phenyl]amide

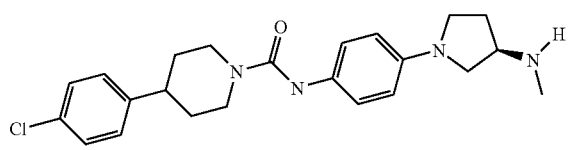

Method G

Trifluoroacetic acid (6.67 g) was added to a solution of tert-butyl (R)-[1-(4-{[4-(4-chlorophenyl)piperidin-1-carbonyl]amino}phenyl)pyrrolidin-3-yl]methylcarbamate (1.5 g) in dichloromethane (50 ml). After 3 hours, volatile fractions were removed and the residue was taken up in dichloromethane. After washing with sodium carbonate solution, the organic phase was dried over magnesium sulfate and concentrated. This resulted in the product with the molecular weight of 412.97 (C23H29ClN4O); MS (ESI): 413 (M+H+).

Example 16

4-(4-Chlorophenyl)piperidine-1-carboxylic acid (4-{(R)-3-[methyl-(1-methyl-piperidin-3-ylcarbonyl)amino]pyrrolidin-1-yl}phenyl)amide

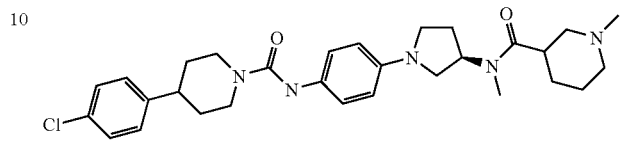

(R)-4-(4-Chlorophenyl)piperidine-1-carboxylic acid [4-(3-methylamino-pyrrolidin-1-yl)phenyl]amide was reacted with 1-methylpiperidine-3-carboxylic acid by method E. This resulted in the product with the molecular weight of 538.14 (C30H40ClN5O2); MS (ESI): 538 (M+H+).

Example 17

4-(4-Chlorophenyl)piperidine-1-carboxylic acid (4-(R)-{3-[methyl-(2-piperidin-1-ylacetyl)amino]pyrrolidin-1-yl}phenyl)amide (R)-4-(4-Chlorophenyl)piperidine-1-carboxylic acid [4-(3-methylamino-pyrrolidin-1-yl)phenyl]amide was reacted with piperidin-1-ylacetic acid by method E. This resulted in the product with the molecular weight of 538.14 (C30H40ClN5O2); MS (ESI): 538 (M+H+).

Example 18

4-(4-Chlorophenyl)piperidine-1-carboxylic acid (4-(R)-{3-[methyl-(2-oxo-thiazolidine-4-carbonyl)amino]pyrrolidin-1-yl}phenyl)amide (R)-4-(4-Chlorophenyl)piperidin-1-carboxylic acid [4-(3-methylamino-pyrrolidin-1-yl)phenyl]amide was reacted with 2-oxothiazolidine-4-carboxylic acid by method E. This resulted in the product with the molecular weight of 542.10 (C27H32ClN5O3S); MS (ESI): 542 (M+H+).

Example 19

(R)-4-(4-Chlorophenyl)piperidine-1-carboxylic acid (4-{3-[methyl-(2,2,2-trifluoroacetyl)amino]pyrrolidin-1-yl}phenyl)amide

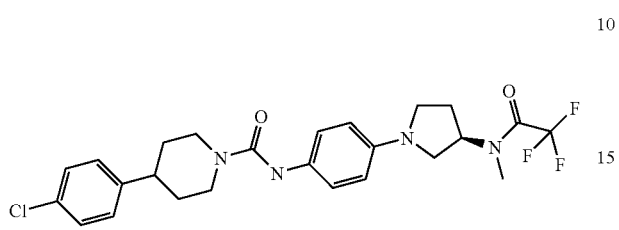

(R)-[N-[1-(4-aminophenyl)pyrrolidin-3-yl]-2,2,2-trifluoro-N-methylacetamide was reacted with carbonyldiimidazole and then with 4-(4-chlorophenyl)-piperidine by method A. This resulted in the product with the molecular weight of 508.98 (C25H28ClF3N4O2); MS (ESI): 509 (M+H+).

(R)-[N-[1-(4-Aminophenyl)pyrrolidin-3-yl]-2,2,2-trifluoro-N-methylacetamide (R)-2,2,2-Trifluoro-N-methyl-N-[1-(4-nitrophenyl)pyrrolidin-3-yl]acetamide was hydrogenated by method B. This resulted in the product with the molecular weight of 287.29 (C13H16F3N3O); MS (ESI): 288 (M+H+).

(R)-2,2,2-Trifluoro-N-methyl-N-[1-(4-nitrophenyl)pyrrolidin-3-yl]acetamide

Trifluoroacetic anhydride (0.5 ml) was added dropwise to a solution of (R)-methyl-[1-(4-nitrophenyl)pyrrolidin-3-yl]amine (0.48 g) in pyridine (2 ml). After 3 hours, the reaction mixture was diluted with water and extracted with ethyl acetate. The organic phase was washed with citric acid solution, dried over magnesium sulfate and concentrated. This resulted in the product with the molecular weight of 317.27 (C13H14F3N3O3); MS (ESI): 318 (M+H+).

(R)-Methyl-[1-(4-nitrophenyl)pyrrolidin-3-yl]amine

A solution of tert-butyl (R)-methyl-[1-(4-nitrophenyl)pyrrolidin-3-yl]-carbamate (0.7 g) in dichloromethane (5 ml) was treated with trifluoroacetic acid (3 ml) for 1 hour. The reaction solution was concentrated and the residue was taken up in dichloromethane. After washing with sodium carbonate solution, the organic phase was dried over magnesium sulfate and concentrated. This resulted in the product with the molecular weight of 221.26 (C11H15N3O2); MS (ESI): 222 (M+H+).

Example 20

4-(4-Chlorophenyl)piperidine-1-carboxylic acid {4-[3-(acetylmethylamino)-pyrrolidin-1-yl]phenyl}methylamide

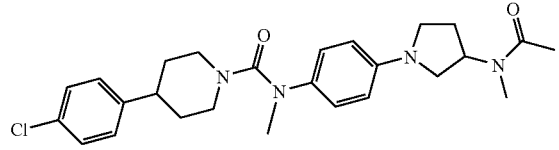

4-(4-Chlorophenyl)piperidine-1-carboxylic acid {4-[3-(acetylmethylamino)-pyrrolidin-1-yl]phenyl}amide was reacted with iodomethane by method F. This resulted in the product with the molecular weight of 469.03 (C26H33ClN4O2); MS (ESI): 469 (M+H+).

Example 21

(R)-4-(4-Chlorophenyl)piperidine-1-carboxylic acid (4-{3-[acetyl-(2-diethylaminoethyl)amino]pyrrolidin-1-yl}phenyl)amide

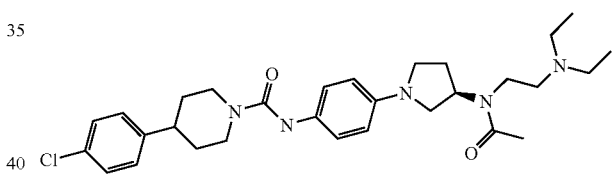

(R)-N-[1-(4-Aminophenyl)pyrrolidin-3-yl]-N-(2-diethylaminoethyl)acetamide was reacted with 4-(4-chlorophenyl)piperidine by method A. This resulted in the product with the molecular weight of 540.15 (C30H42ClN5O2); MS (ESI): 540 (M+H+).

(R)-N-[1-(4-Aminophenyl)pyrrolidin-3-yl]-N-(2-diethylaminoethyl)acetamide (R)-N-(2-Diethylaminoethyl)-N-[1-(4-nitrophenyl)pyrrolidin-3-yl]acetamide was hydrogenated by method B. This resulted in the product with the molecular weight of 318.47 (C18H30N4O); MS (ESI): 319 (M+H+).

(R)-N-(2-Diethylaminoethyl)-N-[1-(4-nitrophenyl)pyrrolidin-3-yl]acetamide (R)-N-[1-(4-nitrophenyl)pyrrolidin-3-yl]acetamide was reacted with 2-chloroethyldiethylamine by method F. This resulted in the product with the molecular weight of 348.45 (C18H28N4O3); MS (ESI): 349 (M+H+).

Example 22

1-[4-(3-Dimethylaminopyrrolidin-1-yl)phenyl]-3-(4-phenoxyphenyl)urea

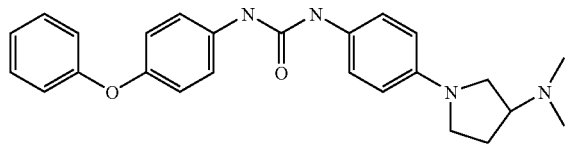

Dimethylpyrrolidin-3-ylamine was reacted with 4-fluoronitrobenzene, the resulting nitro compound was reduced with hydrogen and finally the aniline was reacted with CDI and 4-phenoxyaniline by method A, B and C. This resulted in the product with the molecular weight of 416.53 (C25H28N4O2); MS (ESI): 417 (M+H+).

Example 23

N-{4-[3-(Acetylmethylamino)pyrrolidin-1-yl]phenyl}-2-(4-isobutoxyphenyl)propionamide

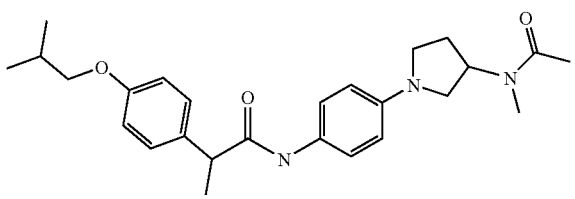

N-[1-(4-aminophenyl)pyrrolidin-3-yl]-N-methylacetamide was reacted with 2-(4-isobutoxyphenyl)propionic acid by method E. This resulted in the product with the molecular weight of 437.59 (C26H35N3O3); MS (ESI): 438 (M+H+).

Example 24

N-(1-{4-[3-(4-Cyclopentyloxyphenyl)ureido]phenyl}pyrrolidin-3-yl)acetamide

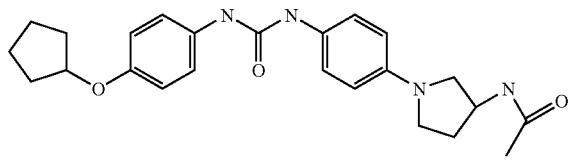

N-Pyrrolidin-3-ylacetamide was reacted with 4-fluoronitrobenzene, the resulting nitro compound was reduced with hydrogen and finally the aniline was reacted with CDI and 4-cyclopentyloxyaniline by method A, B and C. This resulted in the product with the molecular weight of 422.53 (C24H30N4O3); MS (ESI): 423 (M+H+).

(R)- and (S)-N-(1-{4-[3-(4-cyclopentyloxyphenyl)ureido]phenyl}pyrrolidin-3-yl)acetamide were obtained in an analogous manner starting from (R)- and (S)-N-pyrrolidin-3-ylacetamide.

Example 25

N-(1-{4-[3-(4-Cyclopentyloxyphenyl)ureido]phenyl}pyrrolidin-3-yl)-N-ethylacetamide

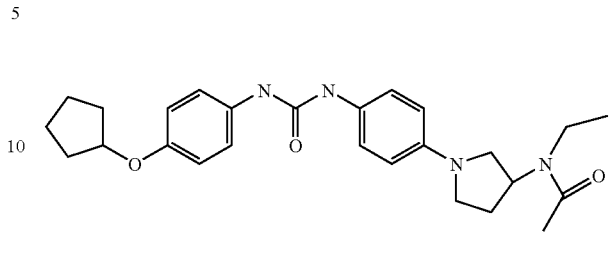

N-Ethyl-N-pyrrolidin-3-ylacetamide was reacted with 4-fluoronitrobenzene, the resulting nitro compound was reduced with hydrogen and finally the aniline was reacted with CDI and 4-cyclopentyloxyaniline by method A, B and C. This resulted in the product with the molecular weight of 450.59 (C26H34N4O3); MS (ESI): 451 (M+H+).

Example 26

4-(4-Chlorophenyl)piperidin-1-carboxylic acid {4-[3-(acetylmethylamino)pyrrolidin-1-yl]-3-methylphenyl}amide

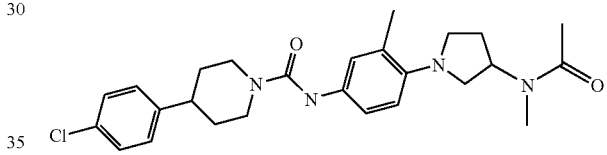

N-Methyl-N-pyrrolidin-3-ylacetamide was reacted with 1-fluoro-2-methyl-4-nitrobenzene, the resulting nitro compound was reduced with hydrogen and finally the aniline was reacted with CDI and 4-(4-chlorophenyl)piperidine by method A, B and C. This resulted in the product with the molecular weight of 469.03 (C26H33ClN4O2); MS (ESI): 469 (M+H+).

Example 27

4-(4-Chlorophenyl)piperidine-1-carboxylic acid {4-[3-(acetylmethylamino)-pyrrolidin-1-yl)-3-fluorophenyl}amide

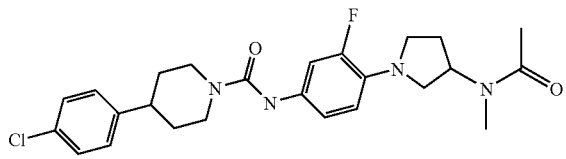

N-Methyl-N-pyrrolidin-3-ylacetamide was reacted with 1,2-difluoro-4-nitrobenzene, the resulting nitro compound was reduced with hydrogen and finally the aniline was reacted with CDI and 4-(4-chlorophenyl)piperidine by method A, B and C. This resulted in the product with the molecular weight of 472.99 (C25H30ClFN4O2); MS (ESI): 473 (M+H+).

Example 28

4-(4-Chlorophenyl)piperidine-1-carboxylic acid {4-[3-(acetylmethylamino)-pyrrolidin-1-yl]-2,6-difluorophenyl}amide

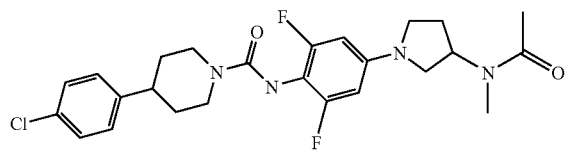

N-Methyl-N-pyrrolidin-3-ylacetamide was reacted with 1,3,5-trifluoro-2-nitrobenzene, the resulting nitro compound was reduced with hydrogen and finally the aniline was reacted with CDI and 4-(4-chlorophenyl)piperidine by method A, B and C. This resulted in the product with the molecular weight of 490.99 (C25H29ClF2N4O2); MS (ESI): 491 (M+H+).

Example 29

4-(4-Chlorophenyl)piperidine-1-carboxylic acid {4-[3-(acetylmethylamino)-pyrrolidin-1-yl]-2-methylphenyl}amide

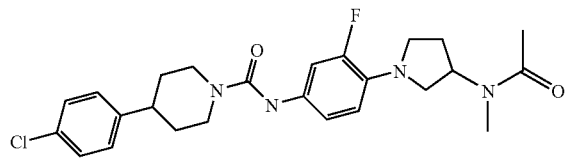

N-Methyl-N-pyrrolidin-3-ylacetamide was reacted with 4-fluoro-2-methyl-1-nitrobenzene, the resulting nitro compound was reduced with hydrogen and finally the aniline was reacted with CDI and 4-(4-chlorophenyl)piperidine by method A, B and C. This resulted in the product with the molecular weight of 469.03 (C26H33ClN4O2); MS (ESI): 469 (M+H+).

Example 30

4-(4-Chlorophenyl)piperidine-1-carboxylic acid {4-[3-(acetylmethylamino)-pyrrolidin-1-yl]-2-fluorophenyl}amide

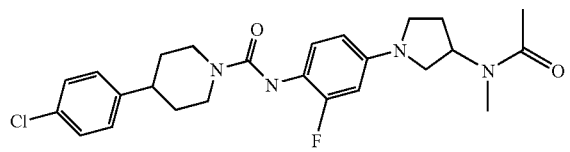

N-Methyl-N-pyrrolidin-3-ylacetamide was reacted with 2,4-difluoro-1-nitrobenzene, the resulting nitro compound was reduced with hydrogen and finally the aniline was reacted with CDI and 4-(4-chlorophenyl)piperidine by method A, B and C. This resulted in the product with the molecular weight of 472.99 (C25H30ClFN4O2); MS (ESI): 473 (M+H+).

Example 31 tert-Butyl (R)-[1-(5-{[4-(4-Chlorophenyl)piperidin-1-carbonyl]amino}pyridin-2-yl)pyrrolidin-3yl]methylcarbamate

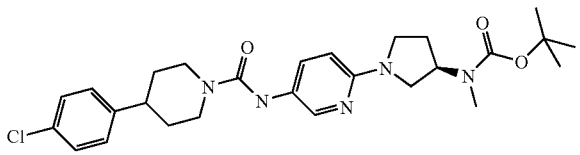

The synthetic sequence for preparing tert-butyl (R)-[1-(4-{[4-(4-chlorophenyl)piperidin-1-carbonyl]amino}phenyl)pyrrolidin-3-yl]methylcarbamate was carried out starting from 2-chloro-5-nitropyridine instead of 4-fluoronitrobenzene. This resulted in the product with the molecular weight of 514.07 (C27H36ClN5O3); MS (ESI): 514 (M+H+).

Example 32

(R)-[4-(4-Chlorophenyl)piperidine-1-carboxylic acid [6-(3-methylamino-pyrrolidin-1-yl)pyridin-3-yl]amide

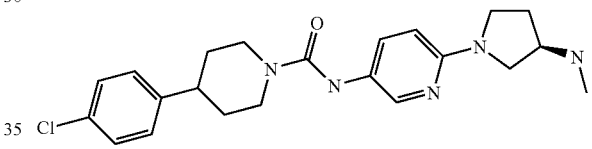

tert-Butyl (R)-[1-(5-{[4-(4-chlorophenyl)piperidine-1-carbonyl]amino}pyridin-2-yl)pyrrolidin-3yl]methylcarbamate was treated with trifluoroacetic acid by method G. This resulted in the product with the molecular weight of 413.95 (C22H28ClN5O); MS (ESI): 414 (M+H+).

It was possible to obtain racemic [4-(4-chlorophenyl)piperidine-1-carboxylic acid [6-(3-methylaminopyrrolidin-yl)pyridin-3-yl]amide in a similar manner.

Example 33

4-(4-Chlorophenyl)piperidine-1-carboxylic acid {6-[3-(acetylmethylamino)-pyrrolidin-1-yl]pyridin-3-yl}amide

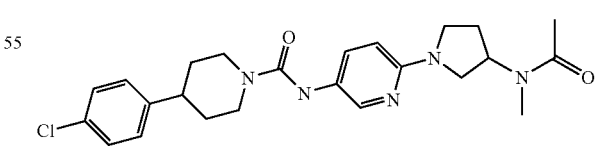

N-Methyl-N-pyrrolidin-3-ylacetamide was reacted with 2-chloro-5-nitro-pyridine, the resulting nitro compound was reduced with hydrogen and finally the aniline was reacted with CDI and 4-(4-chlorophenyl)piperidine by method A, B and C. This resulted in the product with the molecular weight of 490.99 (C25H29ClF2N4O2); MS (ESI): 491 (M+H+).

Example 34

1-[4-(4-Dimethylaminopiperidin-1-yl)phenyl]-3-(4-phenoxyphenyl)urea

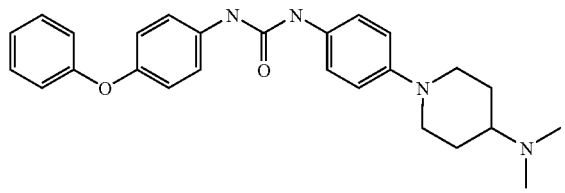

Dimethylpiperidin-4-ylamine was reacted with 4-fluoronitrobenzene, the resulting nitro compound was reduced with hydrogen and finally the aniline ([1-(4-aminophenyl)piperidin-4-yl]dimethylamine) was reacted with CDI and 4-phenoxyaniline by method A, B and C. This resulted in the product with the molecular weight of 430.55 (C26H30N4O2); MS (ESI): 431 (M+H+).

Example 35

1-(4-Cyclopentyloxyphenyl)-3-[4-(4-morpholin-4-ylpiperidin-1-yl)phenyl]urea

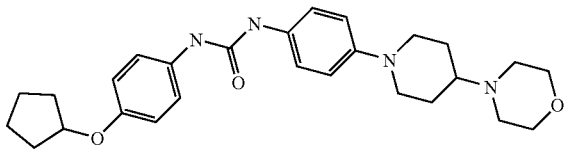

4-Piperidin-4-ylmorpholine was reacted with 4-fluoronitrobenzene, the resulting nitro compound was reduced with hydrogen and finally the aniline was reacted with CDI and 4-cyclopentyloxyaniline by method A, B and C. This resulted in the product with the molecular weight of 464.61 (C27H36N4O3); MS (ESI): 465 (M+H+).

Example 36

4-Butoxy-N-[4-(4-dimethylaminopiperidin-1-yl)phenyl]benzamide

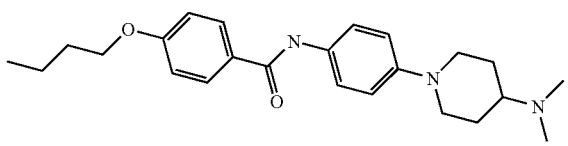

([1-(4-Aminophenyl)piperidin-4-yl]dimethylamine) was reacted with 4-4-butoxybenzoic acid by method E. This resulted in the product with the molecular weight of 395.55 (C24H33N3O2); MS (ESI): 396 (M+H+).

Example 37

4-(4-Chlorophenyl)piperidin-1-carboxylic acid {4-[3-(acetylmethylamino)-azetidin-1-yl]phenyl}amide

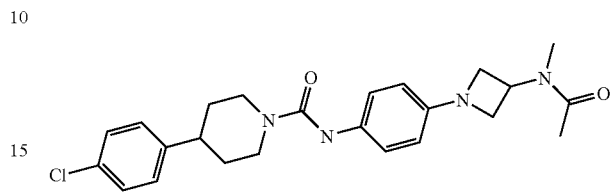

N-[1-(4-aminophenyl)azetidin-3-yl]-N-methylacetamide was reacted with carbonyldiimidazole and 4-(4-chlorophenyl)piperidine by method A. This resulted in the product with the molecular weight of 440.98 (C24H29ClN4O2); MS (ESI): 441 (M+H+).

N-[1-(4-Aminophenyl)azetidin-3-yl]-N-methylacetamide

N-Methyl-N-[1-(4-nitrophenyl)azetidin-3-yl]acetamide was hydrogenated by method B. This resulted in the product with the molecular weight of 219.29 (C12H17N3O); MS (ESI): 220 (M+H+).

N-Methyl-N-[1-(4-nitrophenyl)azetidin-3-yl]acetamide

N-[1-(4-nitrophenyl)azetidin-3-yl]acetamide was alkylated with iodomethane by method F. This resulted in the product with the molecular weight of 249.27 (C12H15N3O3); MS (ESI): 250 (M+H+).

N-[1-(4-Nitrophenyl)azetidin-3-yl]acetamide

Acetic anhydride (0.6 ml) was added to a solution of 1-(4-nitrophenyl)-azetidin-3-ylamine (0.5 g) in pyridine (1.2 ml). After one hour, volatile fractions were removed. This resulted in the product with the molecular weight of 235.24 (C11H13N3O3); MS (ESI): 236 (M+H+).

1-(4-Nitrophenyl)azetidin-3-ylamine tert-Butyl [1-(4-nitrophenyl)azetidin-3-yl]carbamate was treated with trifluoroacetic acid by method G. This resulted in the product with the molecular weight of 193.21 (C9H11N3O2); MS (ESI): 194 (M+H+).

tert-Butyl [1-(4-nitrophenyl)azetidin-3-yl]carbamate tert-Butyl azetidin-3-ylcarbamate was reacted with 4-fluoronitrobenzene by method C. This resulted in the product with the molecular weight of 293.33 (C14H19N3O4); MS (ESI): 294 (M+H+).

Example 38 tert-Butyl [1-(4-{[4-(4-Chlorophenyl)piperidin-1-carbonyl]amino}-phenyl)azetidin-3-yl]methylcarbamate

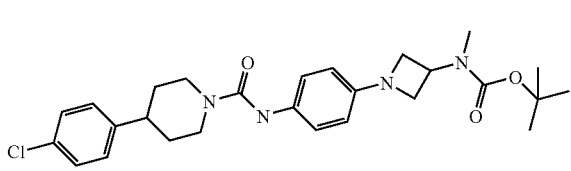

tert-Butyl [1-(4-aminophenyl)azetidin-3-yl]methylcarbamate was reacted with carbonyldiimidazole and 4-(4-chlorophenyl)piperidine by method A. This resulted in the product with the molecular weight of 499.06 (C27H35ClN4O3; MS (ESI): 499 (M+H+).

tert-Butyl [1-(4-aminophenyl)azetidin-3-yl]methylcarbamate tert-Butyl methyl-[1-(4-nitrophenyl)azetidin-3-yl]carbamate was hydrogenated by method B. This resulted in the product with the molecular weight of 277.37 (C15H23N3O2); MS (ESI): 278 (M+H+).

tert-Butyl methyl-[1-(4-nitrophenyl)azetidin-3-yl]carbamate tert-Butyl [1-(4-nitrophenyl)azetidin-3-yl]carbamate was alkylated with iodomethane by method F. This resulted in the product with the molecular weight of 307.35 (C15H21N3O4); MS (ESI): 308 (M+H+).

Example 39

4-(4-Chlorophenyl)piperidin-1-carboxylic acid [4-(3-methylaminoazetidin-1-yl)phenyl]amide

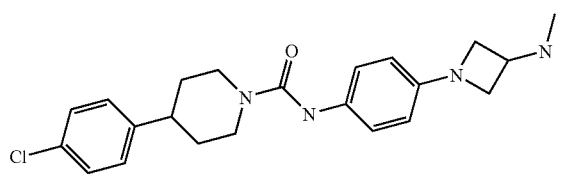

tert-Butyl [1-(4-{[4-(4-chlorophenyl)piperidin-1-carbonyl]amino}-phenyl)azetidin-3-yl]methylcarbamate was reacted with trifluoroacetic acid by method G. This resulted in the product with the molecular weight of 398.94 (C22H27ClN4O); MS (ESI): 399 (M+H+).

Example 40

N-Methyl-N-[1-(4-{3-[4-(pyridin-3-yloxy)phenyl]ureido}phenyl)pyrrolidin-3-yl]acetamide

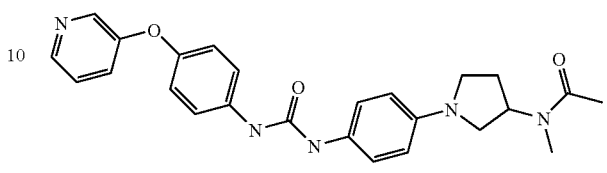

N-[1-(4-Aminophenyl)pyrrolidin-3-yl]-N-methylacetamide was reacted with carbonyldiimidazole and then with 4-(pyridin-3-yloxy)phenylamine by method A. This resulted in the product with the molecular weight of 445.53 (C25H27N5O3); MS (ESI): 446 (M+H+).

Example 41

N-Methyl-N-(1-{4-[3-(4-piperidin-1-ylphenyl)ureido]phenyl}pyrrolidin-3-yl)acetamide

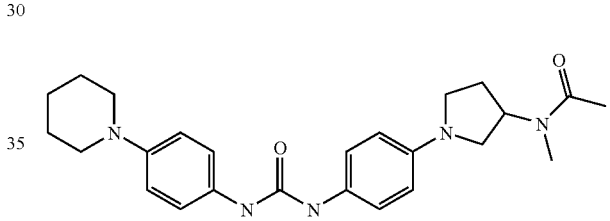

N-[1-(4-Aminophenyl)pyrrolidin-3-yl]-N-methylacetamide was reacted with carbonyldiimidazole and then with 4-piperidin-1-ylphenylamine by method A. This resulted in the product with the molecular weight of 435.57 (C25H33N5O2); MS (ESI): 436 (M+H+).

Example 42

N-{4-[3-(Acetylmethylamino)pyrrolidin-1-yl]phenyl}-4-phenoxybenzamide

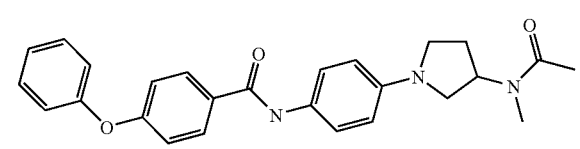

N-[1-(4-Aminophenyl)pyrrolidin-3-yl]-N-methylacetamide was reacted with 4-phenoxybenzoic acid by method E. This resulted in the product with the molecular weight of 429.52 (C26H27N3O3); MS (ESI): 430 (M+H+).

Example 43

N-{4-[3-(Acetylmethylamino)pyrrolidin-1-yl]phenyl}-4-butoxybenzamide

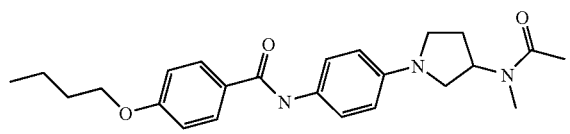

N-[1-(4-Aminophenyl)pyrrolidin-3-yl]-N-methylacetamide was reacted with 4-butoxybenzoic acid by method E. This resulted in the product with the molecular weight of 409.53 (C24H31N3O3); MS (ESI): 410 (M+H+).

Example 44

4-(4-Chlorophenyl)cyclohexanecarboxylic acid {4-[3-(acetylmethylamino)-pyrrolidin-1-yl]phenyl}amide

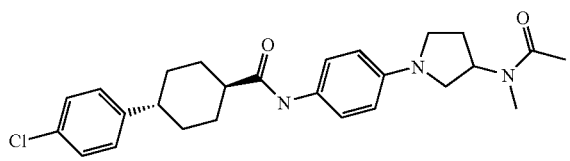

N-[1-(4-Aminophenyl)pyrrolidin-3-yl]-N-methylacetamide was reacted with 4-(4-chlorophenyl)cyclohexanecarboxylic acid by method E. This resulted in the product with the molecular weight of 454.02 (C26H32ClN3O2); MS (ESI): 454 (M+H+).

Example 45

N-{4-[3-(Acetylmethylamino)pyrrolidin-1-yl]phenyl}-3-(4-isopropylphenyl)-acrylamide

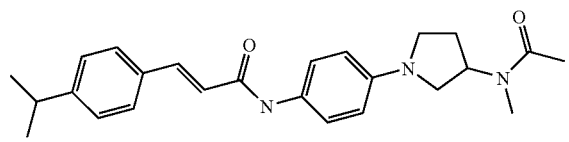

N-[1-(4-Aminophenyl)pyrrolidin-3-yl]-N-methylacetamide was reacted with 3-(4-isopropylphenyl)acrylic acid by method E. This resulted in the product with the molecular weight of 405.54 (C25H31N3O2); MS (ESI): 406 (M+H+).

Example 46

Tetrahydrofuran-2-carboxylic acid (1-{4-[3-(4-cyclopentyloxyphenyl)-ureido]phenyl}pyrrolidin-3-yl)methylamide

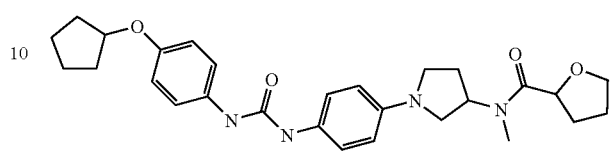

1-(4-Cyclopentyloxyphenyl)-3-[4-(3-methylaminopyrrolidin-1-yl)phenyl]urea was reacted with tetrahydrofuran-2-carboxylic acid by method E. This resulted in the product with the molecular weight of 492.62 (C28H36N4O4); MS (ESI): 493 (M+H+).

Example 47

1-Acetylpyrrolidin-2-carboxylic acid (1-{4-[3-(4-cyclopentyloxyphenyl)-ureido]phenyl}pyrrolidin-3-yl)methylamide

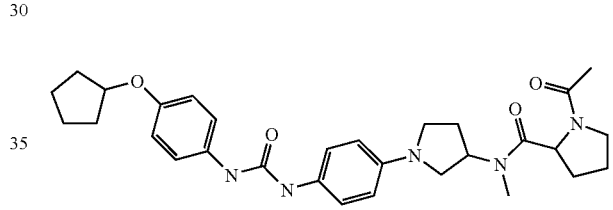

1-(4-Cyclopentyloxyphenyl)-3-[4-(3-methylaminopyrrolidin-1-yl)phenyl]urea was reacted with 1-acetylpyrrolidine-2-carboxylic acid by method E. This resulted in the product with the molecular weight of 533.68 (C30H39N5O4); MS (ESI): 534 (M+H+).

Example 48

5-Oxopyrrolidine-2-carboxylic acid (1-{4-[3-(4-cyclopentyloxyphenyl)-ureido]phenyl}pyrrolidin-3-yl)methylamide

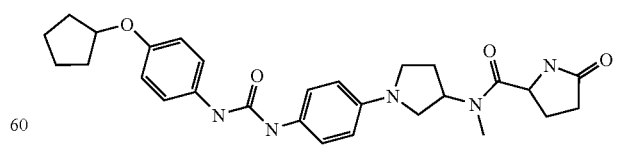

1-(4-Cyclopentyloxyphenyl)-3-[4-(3-methylaminopyrrolidin-1-yl)phenyl]urea was reacted with 5-oxo-pyrrolidine-2-carboxylic acid by method E. This resulted in the product with the molecular weight of 505.62 (C28H35N5O4); MS (ESI): 506 (M+H+).

Example 49

2-Oxothiazolidine-4-carboxylic acid (1-{4-[3-(4-cyclopentyloxyphenyl)-ureido]phenyl}pyrrolidin-3-yl)methylamide

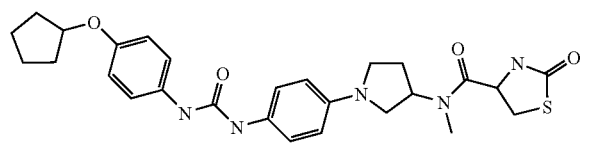

1-(4-Cyclopentyloxyphenyl)-3-[4-(3-methylaminopyrrolidin-1-yl)phenyl]urea was reacted with 2-oxothiazolidine-4-carboxylic acid by method E. This resulted in the product with the molecular weight of 523.66 (C27H33N5O4S); MS (ESI): 524 (M+H+).

Example 50

(R)-1-Methylpiperidine-3-carboxylic acid {1-[4-(4-cyclohexylbenzoyl-amino)phenyl]pyrrolidin-3-yl}methylamide

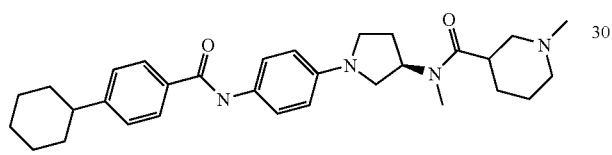

(R)4-Cyclohexyl-N-[4-(3-methylaminopyrrolidin-1-yl)phenyl]benzamide was reacted with 1-methylpiperidine-3-carboxylic acid by method E. This resulted in the product with the molecular weight of 502.71 (C31H42N4O2); MS (ESI): 503 (M+H+).

Example 51

N-(1-{4-[3-(6-Cyclopentyloxypyridin-3-yl)ureido]phenyl}pyrrolidin-3-yl)-N-methylacetamide

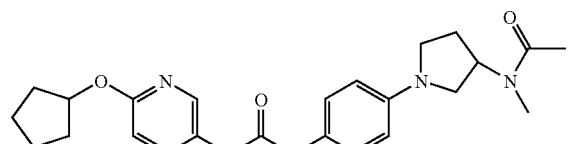

N-[1-(4-aminophenyl)pyrrolidin-3-yl]-N-methylacetamide was reacted with carbonyldiimidazole and then 6-cyclopentyloxypyridin-3-ylamine by method A. This resulted in the product with the molecular weight of 437.55 (C24H31N5O3); MS (ESI): 438 (M+H+).

6-Cyclopentyloxypyridin-3-ylamine

A mixture of 5-nitropyridin-2-ol (14.0 g), bromocyclopentane (8.0 g), potassium carbonate (14 g) and DMF (200 ml) was heated at 80° C. for 6 hours. After cooling, the reaction mixture was diluted with water and extracted with ethyl acetate. The organic phase was washed with water, dried over magnesium sulfate and concentrated. The residue was purified by chromatography on silica gel. The resulting product (2-cyclopentyloxy-5-nitropyridine) was hydrogenated by method B. This resulted in the product with the molecular weight of 178.24 (C10H14N2O); MS (ESI): 179 (M+H+).

Example 52

1-(6-Cyclopentyloxypyridin-3-yl)-3-[4-(3-methylaminopyrrolidin-1-yl)-phenyl]urea

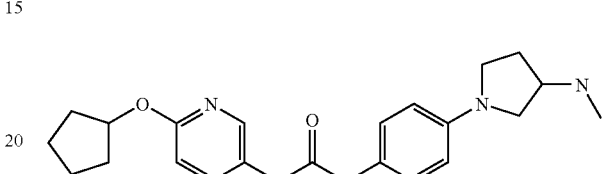

N-(1-{4-[3-(6-Cyclopentyloxypyridin-3-yl)ureido]phenyl}pyrrolidin-3-yl)-N-methylacetamide was treated with sodium hydroxide solution by method D. This resulted in the product with the molecular weight of 395.51 (C22H29N5O2); MS (ESI): 395 (M+H+).

Example 53

4'-Fluorobiphenyl-4-carboxylic acid {4-[3-(acetylmethylamino)pyrrolidin-1-yl]phenyl}amide

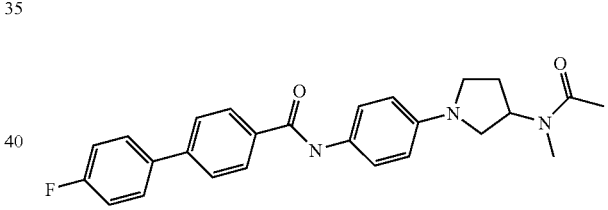

N-[1-(4-Aminophenyl)pyrrolidin-3-yl]-N-methylacetamide was reacted with 4'-fluorobiphenyl-4-carboxylic acid by method E. This resulted in the product with the molecular weight of 431.51 (C26H26FN3O2); MS (ESI): 432 (M+H+).

Example 54

4'-Trifluoromethylbiphenyl-4-carboxylic acid {4-[3-(acetylmethylamino)-pyrrolidin-1-yl]phenyl}amide

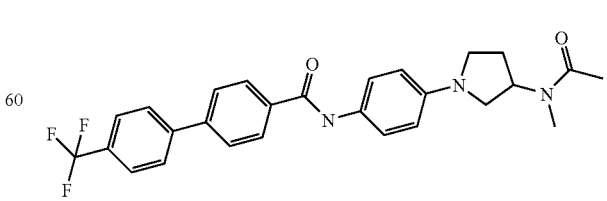

N-[1-(4-Aminophenyl)pyrrolidin-3-yl]-N-methylacetamide was reacted with 4'-trifluoromethylbiphenyl-4-carboxylic acid by method E. This resulted in the product with the molecular weight of 481.52 (C27H26F3N3O2); MS (ESI): 482 (M+H+).

Examples 55-103

1-(4-Phenoxyphenyl)-3-[4-(3-methylaminopyrrolidin-1-yl)phenyl]urea was reacted with various carboxylic acids by method E. The products are compiled in table 2.

Examples 104-144

1-(4-Cyclopentyloxyphenyl)-3-[4-(3-methylaminopyrrolidin-1-yl)phenyl]urea was reacted with various carboxylic acids by method E. The products are compiled in table 3.

Examples 145-185

N-[1-(4-Aminophenyl)pyrrolidin-3-yl]-N-methylacetamide was reacted with various carboxylic acids by method E. The products are compiled in table 4.

Examples 186-234

N-[1-(4-Aminophenyl)pyrrolidin-3-yl]-N-methylacetamide was reacted with carbonyldiimidazole and then with various amines by method A. The products are compiled in table 5.

TABLE 2

| Ex. No. | Structure | Name | Molecular formula | Molecular weight | M + H+ |
|---|---|---|---|---|---|
| 55 | 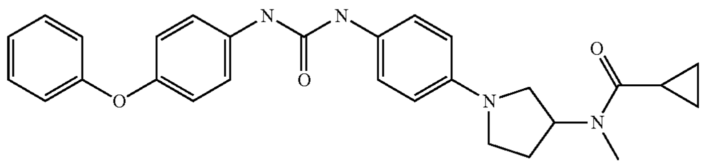 | Cyclopropanecarboxylic acid methyl-(1-{4-[3-(4-phenoxyphenyl)ureido]phenyl}pyrrolidin-3-yl)amide | C28H30N4O3 | 470.58 | 471 |
| 56 | 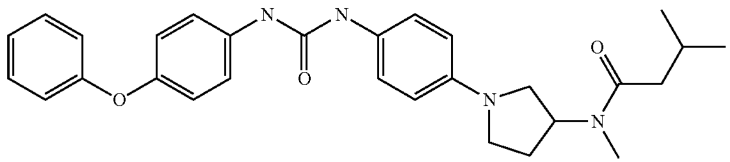 | 3,N-Dimethyl-N-(1-{4-[3-(4-phenoxyphenyl)ureido]-phenyl}pyrrolidin-3-yl)butyramide | C29H34N4O3 | 486.62 | 487 |
| 57 | 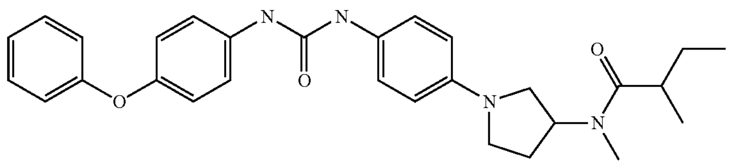 | 2,N-Dimethyl-N-(1-{4-[3-(4-phenoxyphenyl)ureido]-phenyl}pyrrolidin-3-yl)butyramide | C29H34N4O3 | 486.62 | 487 |
| 58 | 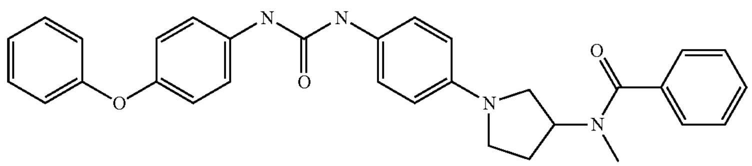 | N-Methyl-N-(1-{4-[3-(4-phenoxyphenyl)ureido]-phenyl}pyrrolidin-3-yl)benzamide | C31H30N4O3 | 506.61 | 507 |
| 59 | 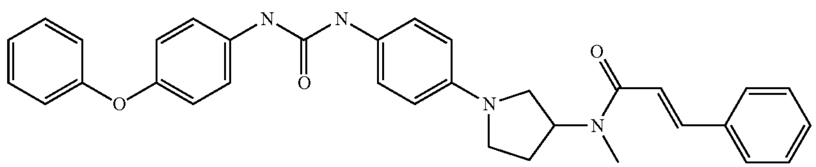 | (E)-N-Methyl-N-(1-{4-[3-(4-phenoxyphenyl)ureido]-phenyl}pyrrolidin-3-yl)-3-phenylacrylamide | C33H32N4O3 | 532.65 | 533 |

TABLE 2-continued

| Ex. No. | Structure | Name | Molecular formula | Molecular weight | M + H+ |
|---|---|---|---|---|---|
| 60 | 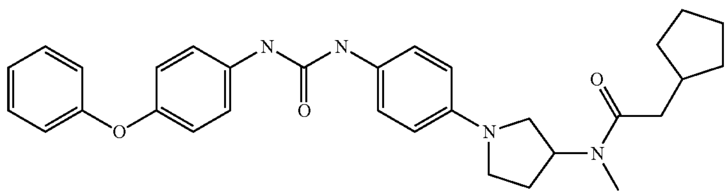 | 2-Cyclopentyl-N-methyl-N-(1-{4-[3-(4-phenoxyphenyl)ureido]phenyl}pyrrolidin-3-yl)acetamide | C31H36N4O3 | 512.66 | 513 |
| 61 | 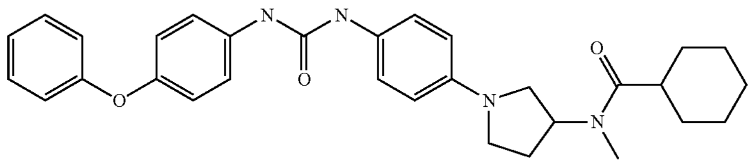 | Cyclohexanecarboxylic acid methyl-(1-{4-[3-(4-phenoxyphenyl)ureido]phenyl}pyrrolidin-3-yl)amide | C31H36N4O3 | 512.66 | 513 |
| 62 | 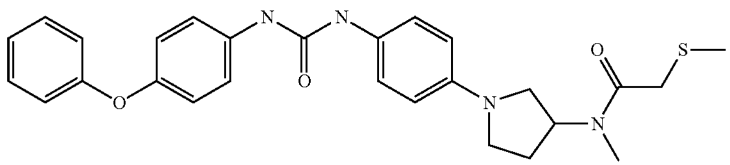 | N-Methyl-2-methylsulfanyl-N-(1-{4-[3-(4-phenoxyphenyl)ureido]phenyl}pyrrolidin-3-yl)acetamide | C27H30N4O3S | 490.63 | 491 |
| 63 | 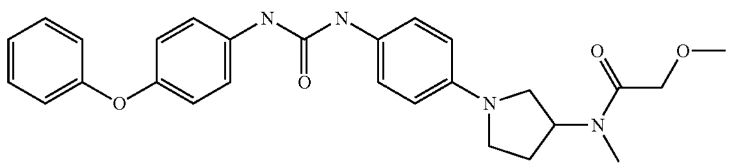 | N-Methoxy-N-methyl-N-(1-{4-[3-(4-phenoxyphenyl)ureido]phenyl}pyrrolidin-3-yl)acetamide | C27H30N4O4 | 474.56 | 475 |
| 64 | 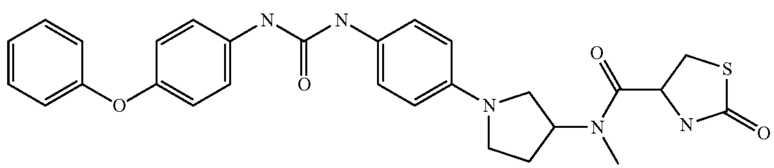 | 2-Oxothiazolidine-4-carboxylic acid methyl-(1-{4-[3-(4-phenoxyphenyl)ureido]phenyl}pyrrolidin-3-yl)amide | C28H29N5O4S | 531.64 | 532 |

TABLE 2-continued

| Ex. No. | Structure | Name | Molecular formula | Molecular weight | M + H+ |
|---|---|---|---|---|---|
| 65 | 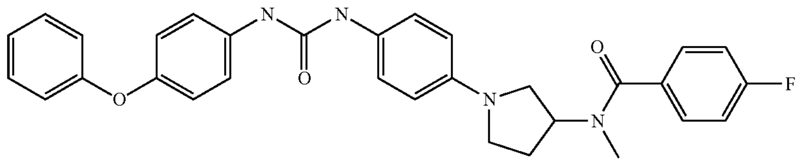 | 4-Fluoro-N-methyl-N-(1-{4-[3-(4-phenoxyphenyl)-ureido]phenyl}pyrrolidin-3-yl)benzamide | C31H29FN4O3 | 524.60 | 525 |
| 66 | 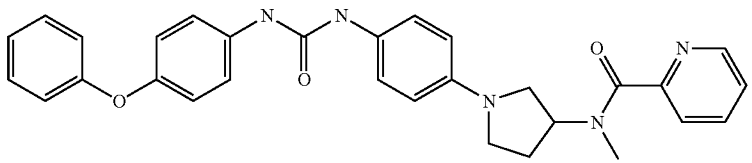 | Pyridine-2-carboxylic acid methyl-(1-{4-[3-(4-phenoxyphenyl)ureido]phenyl}pyrrolidin-3-yl)amide | C30H29N5O3 | 507.60 | 508 |
| 67 | 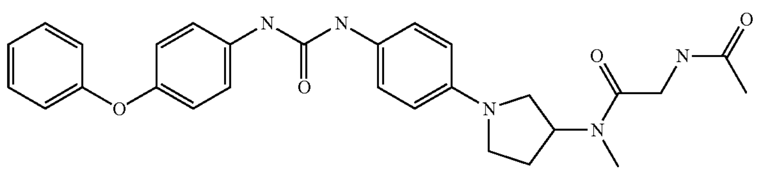 | 2-Acetylamino-N-methyl-N-(1-{4-[3-(4-phenoxyphenyl)ureido]phenyl}pyrrolidin-3-yl)acetamide | C28H31N5O4 | 501.59 | 502 |
| 68 | 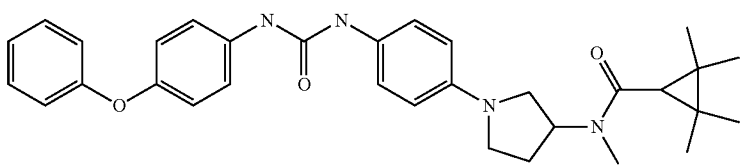 | 2,2,3,3-Tetramethylcyclopropanecarboxylic acid methyl-(1-{4-[3-(4-phenoxyphenyl)ureido]phenyl}pyrrolidin-3-yl)amide | C32H38N4O3 | 526.68 | 527 |
| 69 | 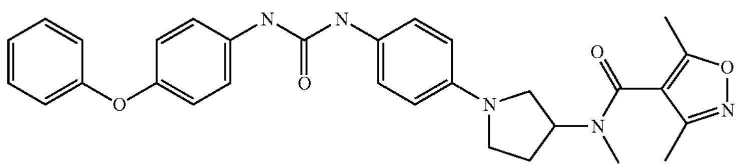 | 3,5-Dimethylisoxazole-4-carboxylic acid methyl-(1-{4-[3-(4-phenoxyphenyl)ureido]phenyl}pyrrolidin-3-yl)amide | C30H31N5O4 | 525.61 | 526 |

TABLE 2-continued

| Ex. No. | Structure | Name | Molecular formula | Molecular weight | M + H+ |
|---|---|---|---|---|---|
| 70 | 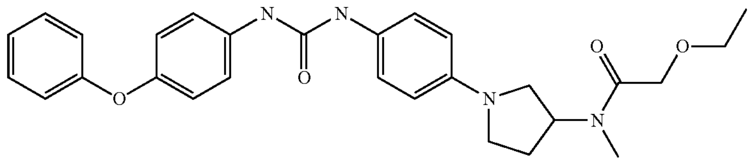 | 2-Ethoxy-N-methyl-N-(1-{4-[3-(4-phenoxyphenyl)-ureido]phenyl}pyrrolidin-3-yl)acetamide | C28H32N4O4 | 488.59 | 489 |
| 71 | 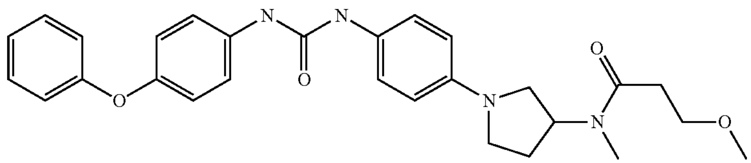 | 3-Methoxy-N-methyl-N-(1-{4-[3-(4-phenoxyphenyl)-ureido]phenyl}pyrrolidin-3-yl)propionamide | C28H32N4O4 | 488.59 | 489 |
| 72 | 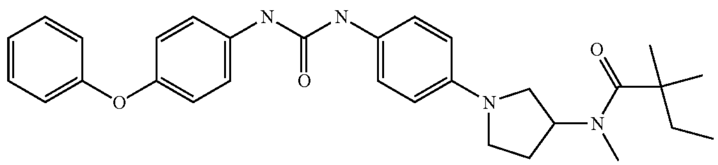 | 2,2,N-Trimethyl-N-(1-{4-[3-(4-phenoxyphenyl)-ureido]phenyl}pyrrolidin-3-yl)butyramide | C30H36N4O3 | 500.65 | 501 |
| 73 | 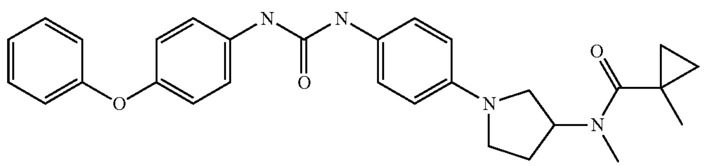 | 1-Methylcyclopropanecarboxylic acid methyl-(1-{4-[3-(4-phenoxyphenyl)ureido]phenyl}-pyrrolidin-3-yl)amide | C29H32N4O3 | 484.60 | 485 |
| 74 | 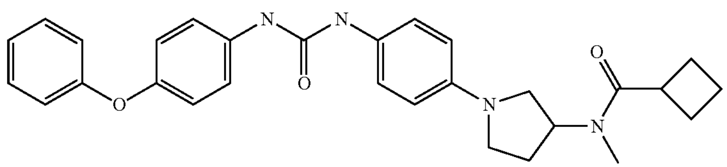 | Cyclobutanecarboxylic acid methyl-(1-{4-[3-(4-phenoxyphenyl)ureido]phenyl}pyrrolidin-3-yl)amide | C29H32N4O3 | 484.60 | 485 |

TABLE 2-continued

| Ex. No. | Structure | Name | Molecular formula | Molecular weight | M + H+ |
|---|---|---|---|---|---|
| 75 | 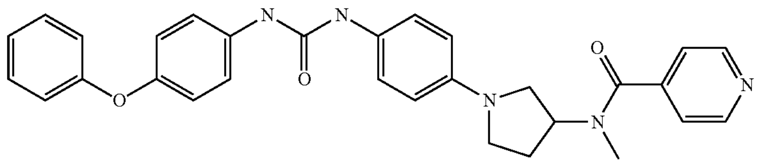 | N-Methyl-N-(1-{4-[3-(4-phenoxyphenyl)ureido]-phenyl}pyrrolidin-3-yl)isonicotinamide | C30H29N5O3 | 507.60 | 508 |
| 76 | 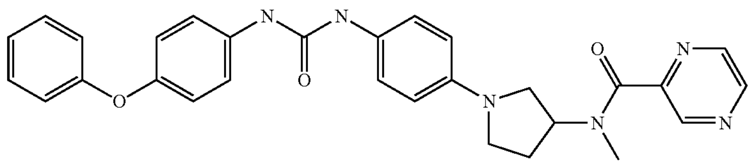 | Pyrazine-2-carboxylic acid methyl-(1-{4-[3-(4-phenoxyphenyl)ureido]phenyl}pyrrolidin-3-yl)amide | C29H28N6O3 | 508.58 | 509 |
| 77 | 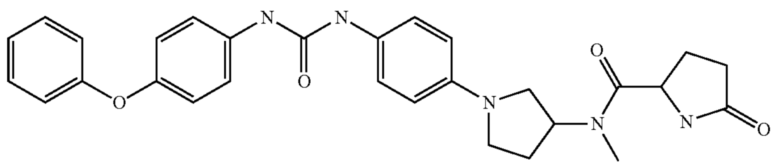 | 5-Oxopyrrolidine-2-carboxylic acid methyl-(1-{4-[3-(4-phenoxyphenyl)ureido]phenyl}pyrrolidin-3-yl)amide | C29H31N5O4 | 513.60 | 514 |
| 78 | 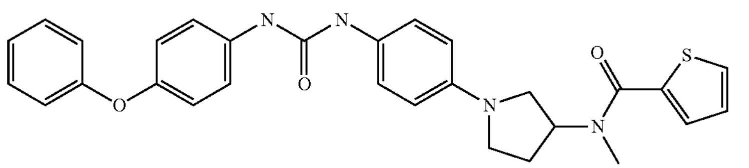 | Thiophene-2-carboxylic acid methyl-(1-{4-[3-(4-phenoxyphenyl)ureido]phenyl}pyrrolidin-3-yl)amide | C29H28N4O3S | 512.64 | 513 |
| 79 | 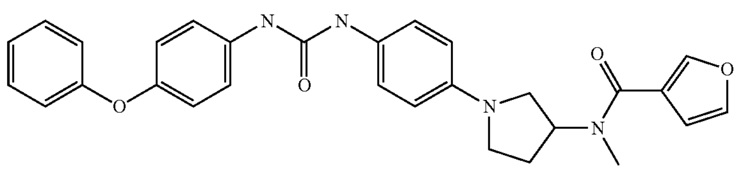 | Furan-3-carboxylic acid methyl-(1-{4-[3-(4-phenoxyphenyl)ureido]phenyl}pyrrolidin-3-yl)amide | C29H28N4O4 | 496.57 | 497 |

TABLE 2-continued

| Ex. No. | Structure | Name | Molecular formula | Molecular weight | M + H+ |
|---|---|---|---|---|---|
| 80 | 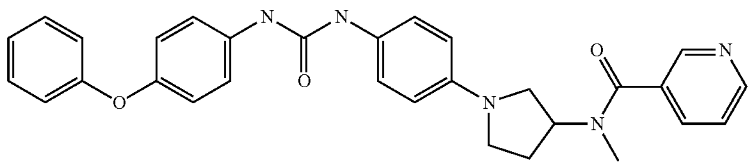 | N-Methyl-N-(1-{4-[3-(4-phenoxyphenyl)ureido]-phenyl}pyrrolidin-3-yl)nicotinamide | C30H29N5O3 | 507.60 | 508 |
| 81 | 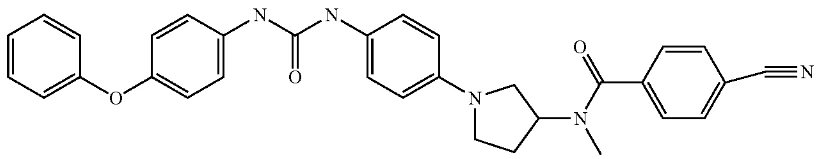 | 4-Cyano-N-methyl-(1-{4-[3-(4-phenoxyphenyl)ureido]phenyl}pyrrolidin-3-yl)benzamide | C32H29N5O3 | 531.62 | 532 |
| 82 | 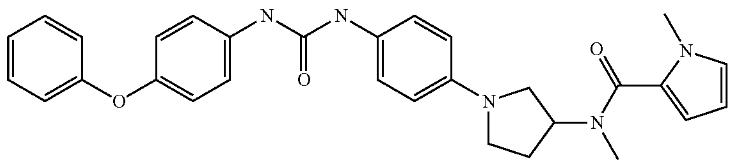 | 1-Methyl-1H-pyrrole-2-carboxylic acid methyl-(1-{4-[3-(4-phenoxyphenyl)ureido]phenyl}pyrrolidin-3-yl)amide | C30H31N5O3 | 509.61 | 510 |
| 83 | 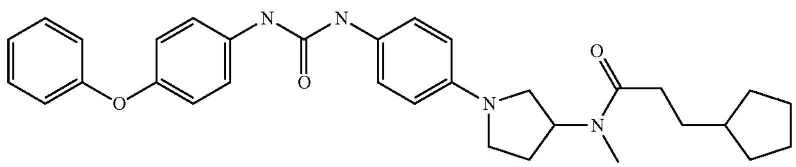 | 3-Cyclopentyl-N-methyl-N-(1-{4-[3-(4-phenoxyphenyl)ureido]phenyl}pyrrolidin-3-yl)propionamide | C32H38N4O3 | 526.68 | 527 |
| 84 | 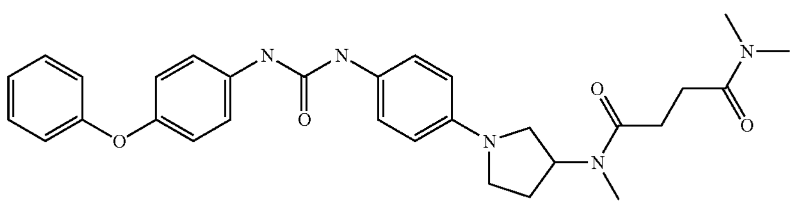 | N,N,N'-Trimethyl-N'-(1-{4-[3-(4-phenoxyphenyl)ureido]phenyl}pyrrolidin-3-yl)succinamide | C30H35N5O4 | 529.64 | 530 |

TABLE 2-continued

| Ex. No. | Structure | Name | Molecular formula | Molecular weight | M + H+ |
|---|---|---|---|---|---|
| 85 | 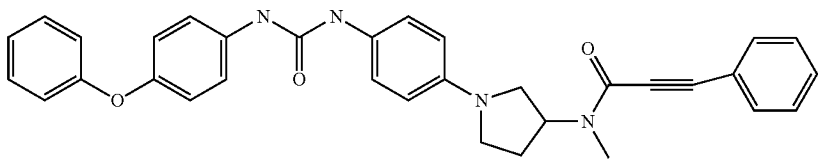 | 3-Phenylpropynoic acid methyl-(1-{4-[3-(4-phenoxyphenyl)ureido]phenyl}pyrrolidin-3-yl)amide | C33H30N4O3 | 530.63 | 531 |
| 86 | 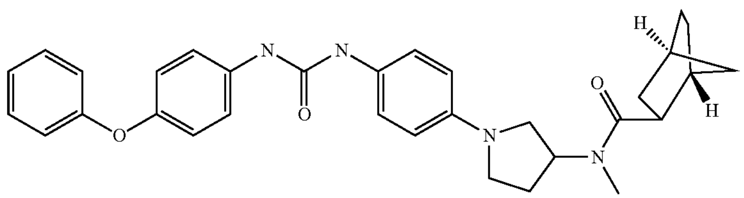 | (1R,4S)-Bicyclo[2.2.1]heptane-2-carboxylic acid methyl-(1-{4-[3-(4-phenoxyphenyl)ureido]phenyl}-pyrrolidin-3-yl)amide | C32H36N4O3 | 524.67 | 525 |
| 87 | 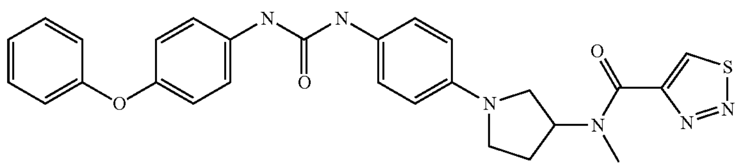 | [1,2,3]Thiadiazol-4-carboxylic acid methyl-(1-{4-[3-(4-phenoxyphenyl)ureido]phenyl}pyrrolidin-3-yl)amide | C27H26N6O3S | 514.61 | 515 |
| 88 | 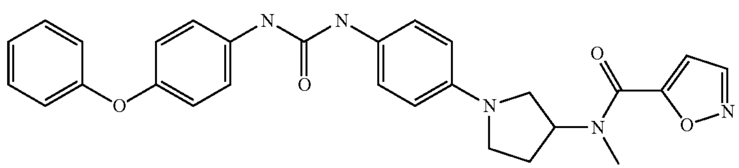 | Isoxazole-5-carboxylic acid methyl-(1-{4-[3-(4-phenoxyphenyl)ureido]phenyl}pyrrolidin-3-yl)amide | C28H27N5O4 | 497.56 | 498 |
| 89 | 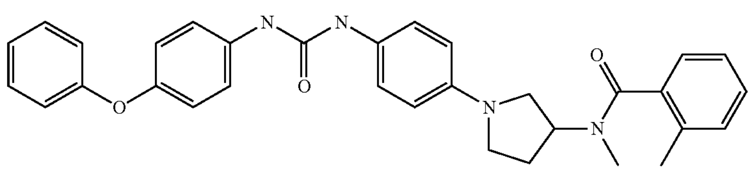 | 2,N-Dimethyl-N-(1-{4-[3-(4-phenoxyphenyl)ureido]-phenyl}pyrrolidin-3-yl)benzamide | C32H32N4O3 | 520.64 | 521 |

TABLE 2-continued

| Ex. No. | Structure | Name | Molecular formula | Molecular weight | M + H+ |
|---|---|---|---|---|---|
| 90 | 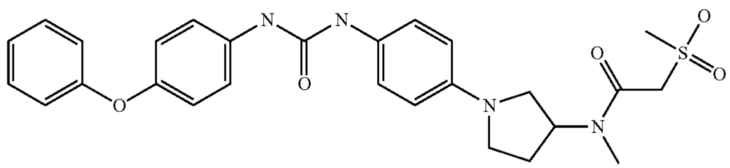 | 2-Methanesulfonyl-N-methyl-N-(1-{4-[3-(4-phenoxyphenyl)ureido]phenyl}pyrrolidin-3-yl)-acetamide | C27H30N4O5S | 522.63 | 523 |
| 91 | 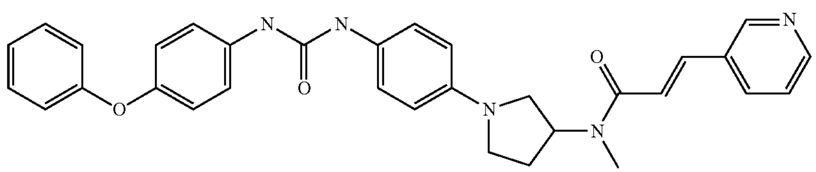 | (E)-N-Methyl-N-(1-{4-[3-(4-phenoxyphenyl)ureido]-phenyl}pyrrolidin-3-yl)-3-pyridin-3-ylacrylamide | C32H31N5O3 | 533.64 | 534 |
| 92 | 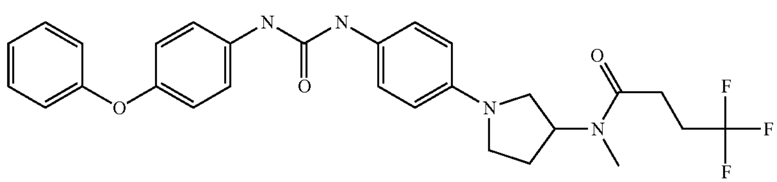 | 4,4,4-Trifluoro-N-methyl-N-(1-{4-[3-(4-phenoxyphenyl)ureido]phenyl}pyrrolidin-3-yl)butyramide | C28H29F3N4O3 | 526.56 | 527 |
| 93 | 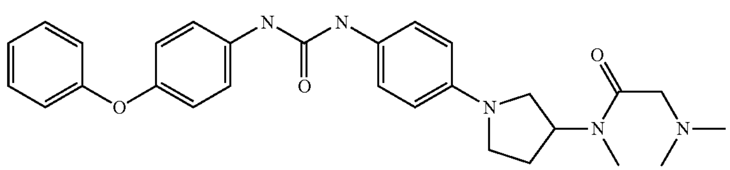 | 2-Dimethylamino-N-methyl-N-(1-{4-[3-(4-phenoxyphenyl)ureido]phenyl}pyrrolidin-3-yl)acetamide | C28H33N5O3 | 487.61 | 488 |
| 94 | 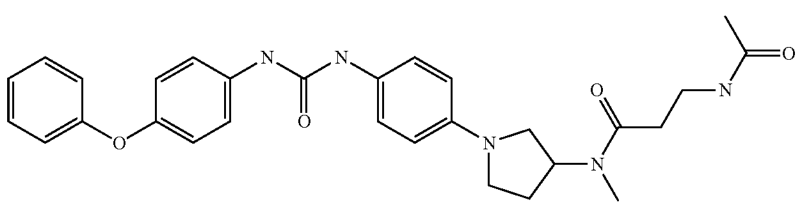 | 3-Acetylamino-N-methyl-N-(1-{4-[3-(4-phenoxyphenyl)ureido]phenyl}pyrrolidin-3-yl)propionamide | C29H33N5O4 | 515.62 | 516 |

TABLE 2-continued

| Ex. No. | Structure | Name | Molecular formula | Molecular weight | M + H+ |
|---|---|---|---|---|---|
| 95 | 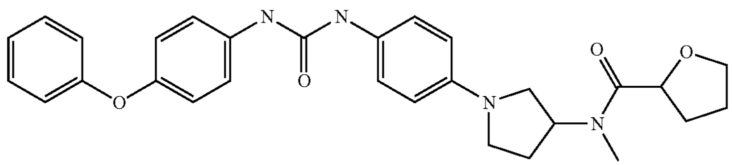 | Tetrahydrofuran-2-carboxylic acid methyl-(1-{4-[3-(4-phenoxyphenyl)ureido]phenyl}pyrrolidin-3-yl)-amide | C29H32N4O4 | 500.60 | 501 |
| 96 | 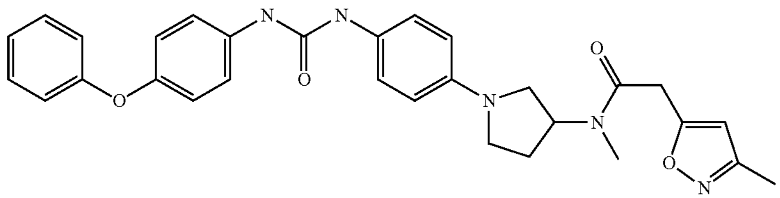 | N-Methyl-2-(3-methylisoxazol-5-yl)-N-(1-{4-[3-(4-phenoxyphenyl)ureido]phenyl}pyrrolidin-3-yl)-acetamide | C30H31N5O4 | 525.61 | 526 |
| 97 | Chiral | (S)-1-Acetylpyrrolidine-2-carboxylic acid methyl-(1-{4-[3-(4-phenoxyphenyl)ureido]phenyl}pyrrolidin-3-yl)amide | C31H35N5O4 | 541.66 | 542 |
| 98 | 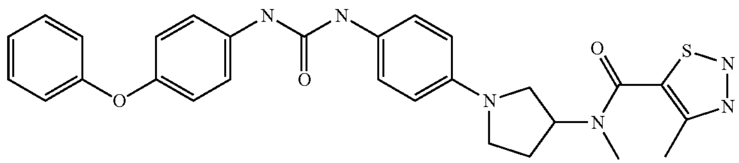 | 4-Methyl-[1,2,3]thiadiazole-5-carboxylic acid methyl-(1-{4-[3-(4-phenoxyphenyl)ureido]phenyl}pyrrolidin-3-yl)amide | C28H28N6O3S | 528.64 | 529 |
| 99 | 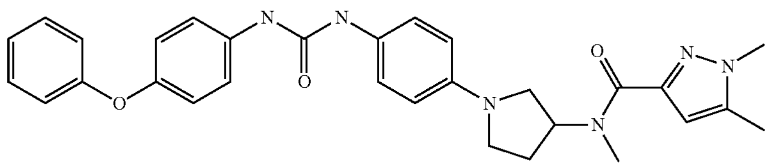 | 1,5-Dimethyl-1H-pyrazole-3-carboxylic acid methyl-(1-{4-[3-(4-phenoxyphenyl)ureido]phenyl}-pyrrolidin-3-yl)amide | C30H32N6O3 | 524.63 | 525 |

TABLE 2-continued

| Ex. No. | Structure | Name | Molecular formula | Molecular weight | M + H+ |
|---|---|---|---|---|---|
| 100 | 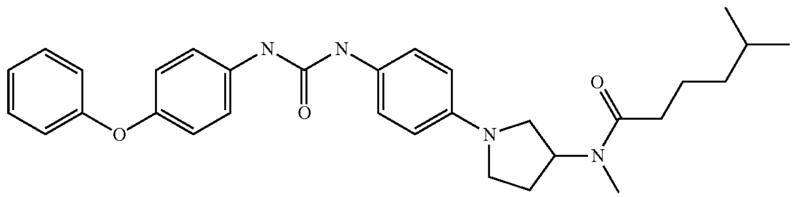 | 5-Methylhexanoic acid methyl-(1-{4-[3-(4-phenoxyphenyl)ureido]phenyl}pyrrolidin-3-yl)amide | C31H38N4O3 | 514.67 | 515 |
| 101 | 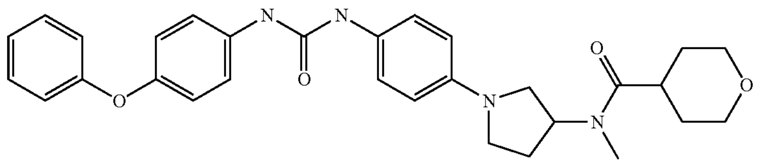 | Tetrahydropyran-4-carboxylic acid methyl-(1-{4-[3-(4-phenoxyphenyl)ureido]phenyl}pyrrolidin-3-yl)-amide | C30H34N4O4 | 514.63 | 515 |
| 102 | 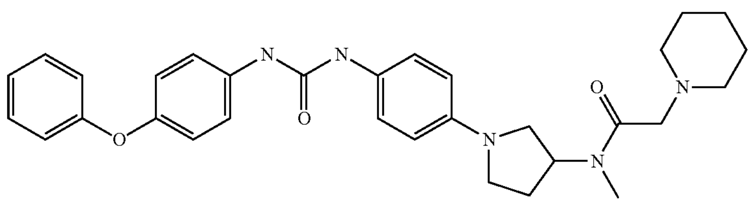 | N-Methyl-N-(1-{4-[3-(4-phenoxyphenyl)-ureido]phenyl}pyrrolidin-3-yl)-2-piperidin-1ylacetamide | C31H37N5O3 | 527.67 | 528 |
| 103 | 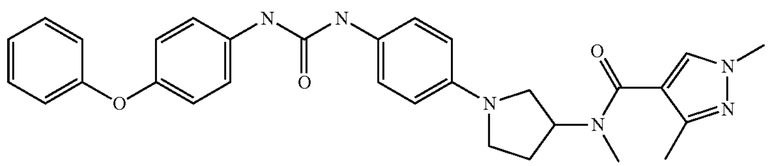 | 1,3-Dimethyl-1H-pyrazole-4-carboxylic acid methyl-(1-{4-[3-(4-phenoxyphenyl)ureido]-phenyl}pyrrolidin-3-yl)amide | C30H32N6O3 | 524.63 | 525 |

TABLE 3

| Ex. No. | Structure | Name | Molecular formula | Molecular weight | M + H+ |
|---|---|---|---|---|---|
| 104 | Chiral | Benzyl(S)-5-[(1-{4-[3-(4-cyclopentyloxyphenyl)-ureido]phenyl}pyrrolidin-3-yl)methylcarbamoyl]-2-oxoimidazolidine-1-carboxylate | C35H40N6O6 | 640.75 | 641 |
| 105 | Chiral | Benzyl(R)-2-[(1-{4-[3-(4-cyclopentyloxyphenyl)-ureido]phenyl}pyrrolidin-3-yl)methylcarbamoyl]-pyrrolidine-1-carboxylate | C36H43N5O5 | 625.77 | 626 |
| 106 | 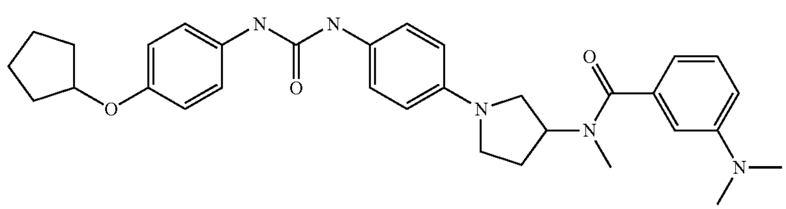 | N-(1-{4-[3-(4-cyclopentyloxyphenyl)ureido]-phenyl}pyrrolidin-3-yl)-3-dimethylamino-N-methyl-benzamide | C32H39N5O3 | 541.70 | 542 |

TABLE 3-continued

| Ex. No. | Structure | Name | Molecular formula | Molecular weight | M + H+ |
|---|---|---|---|---|---|
| 107 | Chiral | Benzyl(S)-2-[(1-{4-[3-(4-cyclopentyloxyphenyl)-ureido]phenyl}pyrrolidin-3-yl)methylcarbamoyl]-5-oxo-pyrrolidine-1-carboxylate | C36H41N5O6 | 639.76 | 640 |
| 108 | 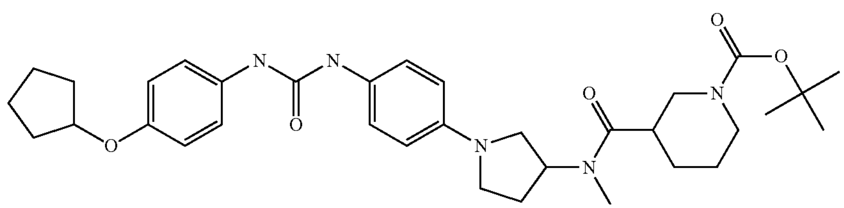 | tert-Butyl 3-[(1-{4-[3-(4-cyclopentyloxyphenyl)-ureido]phenyl}pyrrolidin-3-yl)methyl-carbamoyl]piperidine-1-carboxylate | C34H47N5O5 | 605.78 | 606 |
| 109 | 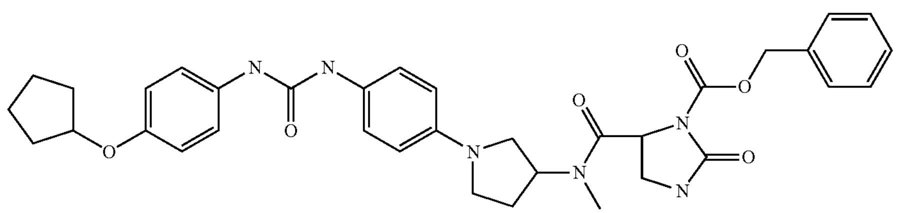 | Benzyl 5-[(1-{4-[3-(4-cyclopentyloxyphenyl)-ureido]phenyl}pyrrolidin-3-yl)methylcarbamoyl]-2-oxo-imidazolidine-1-carboxylate | C35H40N6O6 | 640.75 | 641 |
| 110 | 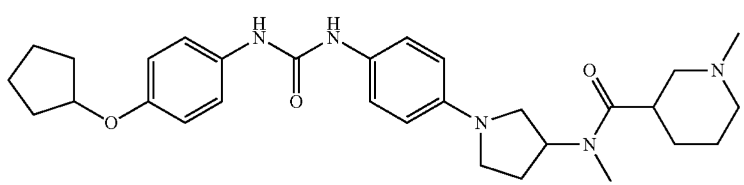 | 1-Methylpiperidine-3-carboxylic acid (1-{4-[3-(4-cyclopentyloxyphenyl)ureido]phenyl}pyrrolidin-3-yl)methyl-amide | C30H41N5O3 | 519.69 | 520 |

TABLE 3-continued

| Ex. No. | Structure | Name | Molecular formula | Molecular weight | M + H+ |
|---|---|---|---|---|---|
| 111 | 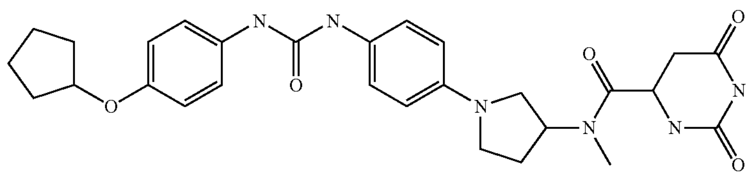 | 2,6-Dioxohexahydropyrimidine-4-carboxylic acid (1-{4-[3-(4-cyclopentyloxyphenyl)-ureido]phenyl}pyrrolidin-3-yl)methylamide | C28H34N6O5 | 534.62 | 535 |
| 112 | 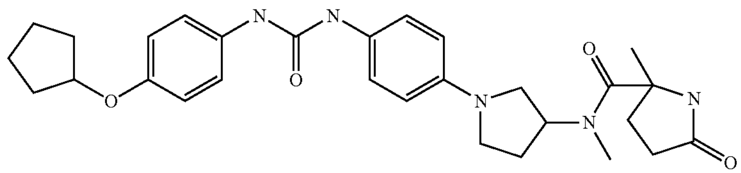 | 2-Methyl-5-oxopyrrolidine-2-carboxylic acid (1-{4-[3-(4-cyclopentyloxyphenyl)ureido]phenyl}-pyrrolidin-3-yl)methylamide | C29H37N5O4 | 519.65 | 520 |
| 113 | 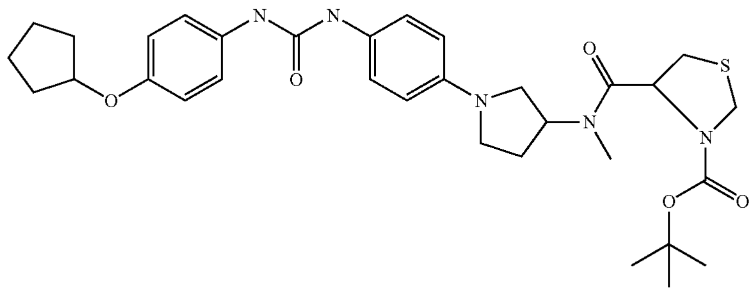 | tert-Butyl 4-[(1-{4-[3-(4-cyclopentyloxyphenyl)-ureido]phenyl}pyrrolidin-3-yl)methylcarbamoyl]-thiazolidine-3-carboxylate | C32H43N5O5S | 609.79 | 610 |
| 114 | Chiral | Benzyl(2S,4R)-4-tert-butoxy-2-[(1-{4-[3-(4-cyclopentyloxyphenyl)ureido]phenyl}pyrrolidin-3-yl)methylcarbamoyl]pyrrolidine-1-carboxylate | C40H51N5O6 | 697.88 | 698 |

TABLE 3-continued

| Ex. No. | Structure | Name | Molecular formula | Molecular weight | M + H+ |
|---|---|---|---|---|---|
| 115 | 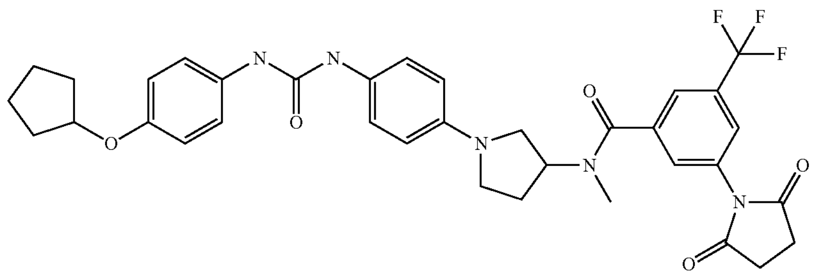 | N-(1-{4-[3-(4-Cyclopentyloxyphenyl)-ureido]phenyl}pyrrolidin-3-yl)-3-(2,5-dioxopyrrolidin-1-yl)-N-methyl-5-trifluoromethylbenzamide | C35H36F3N5O5 | 663.70 | 664 |
| 116 | 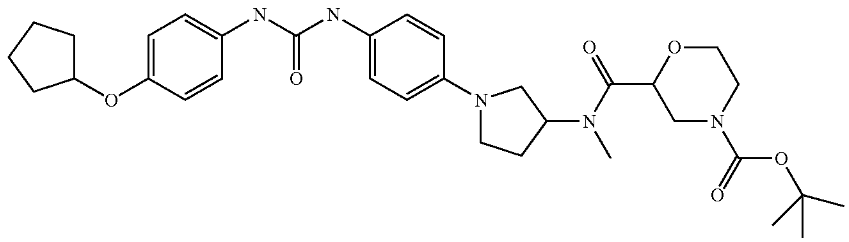 | tert-Butyl-2-[(1-{4-[3-(4-cyclopentyloxyphenyl)-ureido]phenyl}pyrrolidin-3-yl)methylcarbamoyl]-morpholine-4-carboxylate | C33H45N5O6 | 607.76 | 608 |
| 117 | Chiral | (R)-1-(Toluene-4-sulfonyl)pyrrolidine-2-carboxylic acid(1-{4-[3-(4-cyclopentyloxyphenyl)-ureido]phenyl}pyrrolidin-3-yl)methylamide | C35H43N5O5S | 645.83 | 646 |

TABLE 3-continued

| Ex. No. | Structure | Name | Molecular formula | Molecular weight | M + H+ |
|---|---|---|---|---|---|
| 118 | 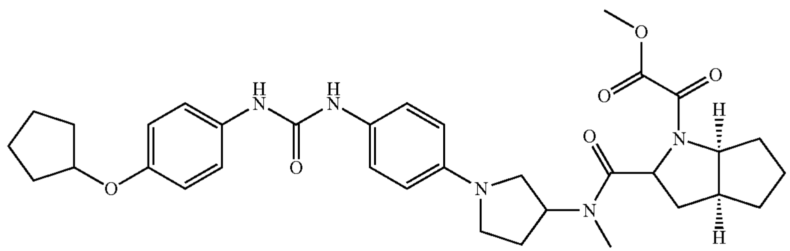 | {(3aS,6aS)-2-[(1-{4-[3-(4-cyclopentyloxyphenyl)-ureido]phenyl}pyrrolidin-3-yl)methylcarbamoyl]-hexahydrocyclopenta[b]pyrrol-1-yl}oxoacetic acid methyl ester | C34H43N5O6 | 617.75 | 618 |
| 119 | 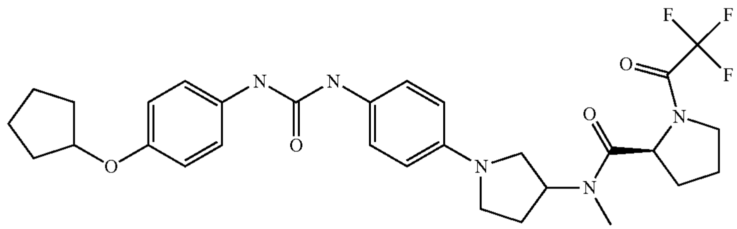 | (S)-1-(2,2,2-Trifluoroacetyl)pyrrolidine-2-carboxylic acid(1-{4-[3-(4-cyclopentyloxyphenyl)ureido]-phenyl}pyrrolidin-3-yl)methylamide | C30H36F3N5O4 | 587.65 | 588 |
| 120 | 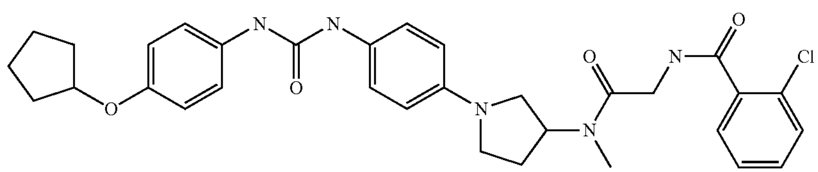 | 2-Chloro-N-{[(1-{4-[3-(4-cyclopentyloxyphenyl)-ureido]phenyl}pyrrolidin-3-yl)methylcarbamoyl]-methyl}benzamide | C32H36ClN5O4 | 590.13 | 590 |
| 121 | 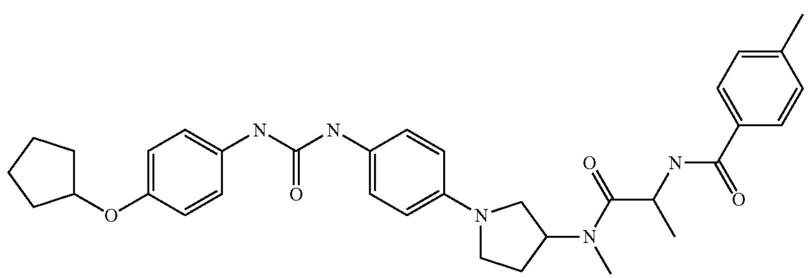 | N-{1-[(1-{4-[3-(4-Cyclopentyloxyphenyl)ureido]-phenyl}pyrrolidin-3-yl)methylcarbamoyl]ethyl}-4-methylbenzamide | C34H41N5O4 | 583.74 | 584 |

TABLE 3-continued

| Ex. No. | Structure | Name | Molecular formula | Molecular weight | M + H+ |
|---|---|---|---|---|---|
| 122 | 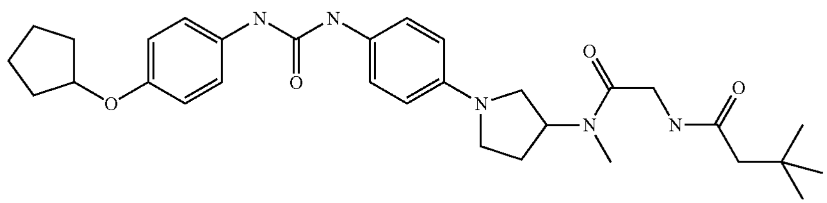 | N-[{(1-{4-[3-(4-Cyclopentyloxyphenyl)ureido]-phenyl}pyrrolidin-3-yl)methylcarbamoyl]methyl}-3,3-dimethylbutyramide | C31H43N5O4 | 549.72 | 550 |
| 123 | 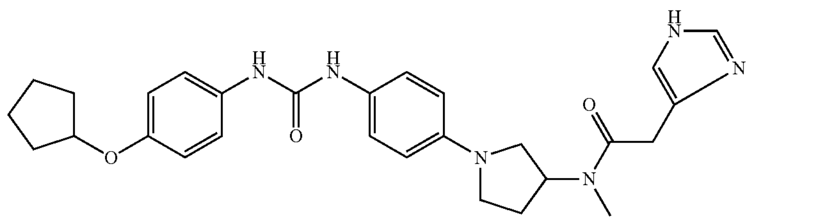 | N-(1-{4-[3-(4-Cyclopentyloxyphenyl)ureido]-phenyl}pyrrolidin-3-yl)-2-(1H-imidazol-4-yl)-N-methylacetamide | C28H34N6O3 | 502.62 | 503 |
| 124 | 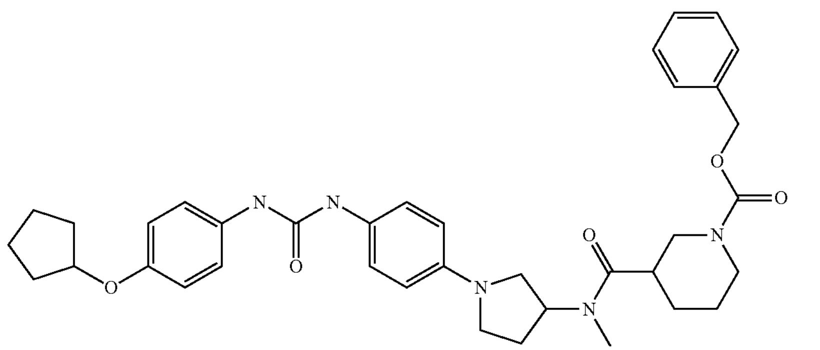 | Benzyl 3-[(1-{4-[3-(4-cyclopentyloxyphenyl)ureido]-phenyl}pyrrolidin-3-yl)methylcarbamoyl]piperidine-1-carboxylate | C37H45N5O5 | 639.80 | 640 |
| 125 | 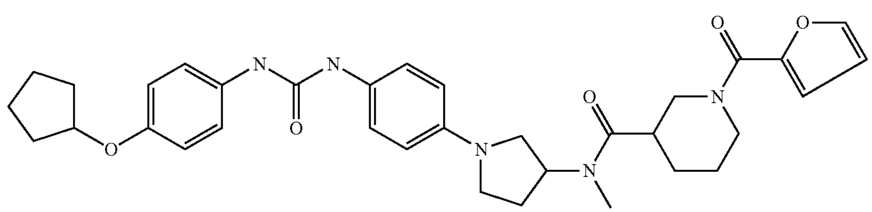 | 1-(Furan-2-carbonyl)piperidine-3-carboxylic acid (1-{4-[3-(4-cyclopentyloxyphenyl)ureido]phenyl}-pyrrolidin-3-yl)methylamide | C34H41N5O5 | 599.74 | 600 |

TABLE 3-continued

| Ex. No. | Structure | Name | Molecular formula | Molecular weight | M + H+ |
|---|---|---|---|---|---|
| 126 | 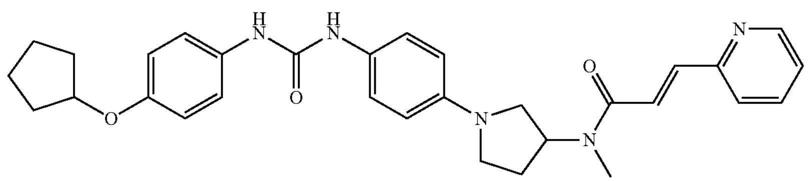 | (E)-N-(1-{4-[3-(4-Cyclopentyloxyphenyl)ureido]-phenyl}pyrrolidin-3-yl)-N-methyl-3-pyridin-2-yl-acrylamide | C31H35N5O3 | 525.66 | 526 |
| 127 | 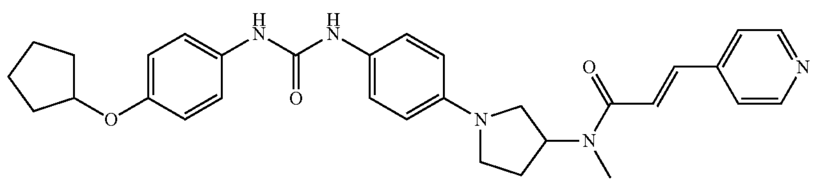 | (E)-N-(1-{4-[3-(4-Cyclopentyloxyphenyl)ureido]-phenyl}pyrrolidin-3-yl)-N-methyl-3-pyridin-4-yl-acrylamide | C31H35N5O3 | 525.66 | 526 |
| 128 | 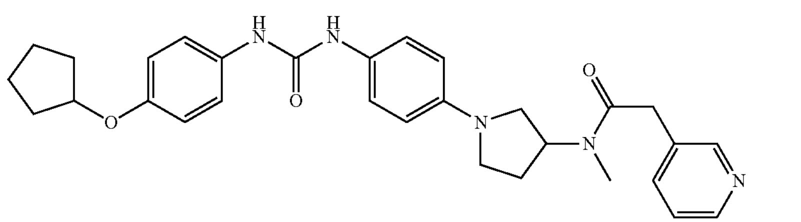 | N-(1-{4-[3-(4-Cyclopentyloxyphenyl)ureido]phenyl}-pyrrolidin-3-yl)-N-methyl-2-pyridin-3-ylacetamide | C30H35N5O3 | 513.65 | 514 |
| 129 | 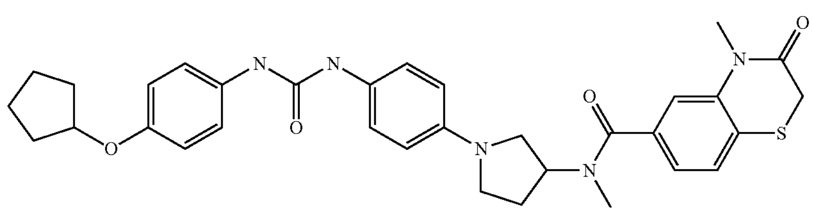 | 4-Methyl-3-oxo-3,4-dihydro-2H-benzo[1,4]thiazine-6-carboxylic acid(1-{4-[3-(4-cyclopentyloxyphenyl)ureido]phenyl}pyrrolidin-3-yl)methylamide | C33H37N5O4S | 599.76 | 600 |

TABLE 3-continued

| Ex. No. | Structure | Name | Molecular formula | Molecular weight | M + H+ |
|---|---|---|---|---|---|
| 130 | 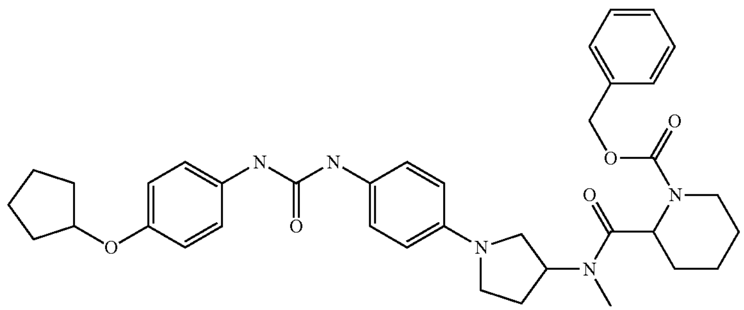 | Benzyl 2-[(1-{4-[3-(4-cyclopentyloxyphenyl)ureido]phenyl}pyrrolidin-3-yl)methylcarbamoyl]piperidin-1-carboxylate | C37H45N5O5 | 639.80 | 640 |
| 131 | Chiral | Benzyl(S)-2-[(1-{4-[3-(4-cyclopentyloxyphenyl)ureido]phenyl}pyrrolidin-3-yl)methylcarbamoyl]-piperidin-1-carboxylate | C36H43N5O5 | 625.77 | 626 |
| 132 | Chiral | (R)-1-Acetylpyrrolidine-2-carboxylic acid(1-{4-[3-(4-cyclopentyloxyphenyl)ureido]phenyl}pyrrolidin-3-yl)methylamide | C30H39N5O4 | 533.68 | 534 |

TABLE 3-continued

| Ex. No. | Structure | Name | Molecular formula | Molecular weight | M + H+ |
|---|---|---|---|---|---|
| 133 | 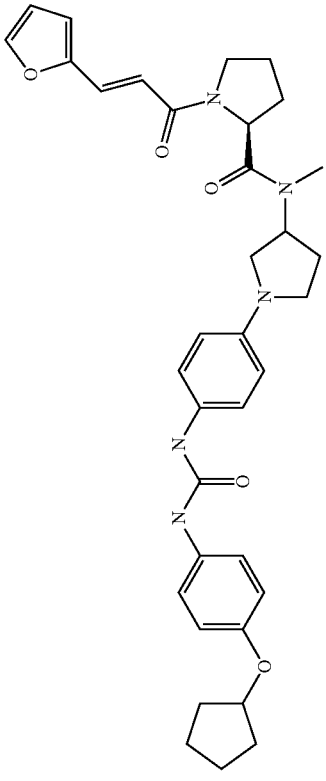 Chiral | (S)-1-((E)-3-Furan-2-ylacryloyl)pyrrolidine-2-carboxylic acid(1-{4-[3-(4-cyclopentyloxyphenyl)-ureido]phenyl}pyrrolidin-3-yl)methylamide | C35H41N5O5 | 611.75 | 612 |
| 134 | 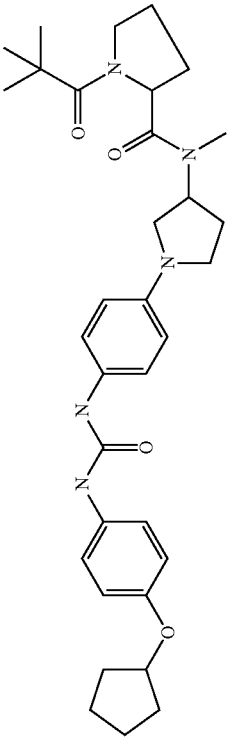 | 1-(2,2-Dimethylpropionyl)pyrrolidine-2-carboxylic acid(1-{4-[3-(4-cyclopentyloxyphenyl)-ureido]phenyl}pyrrolidin-3-yl)methylamide | C33H45N5O4 | 575.76 | 576 |
| 135 | 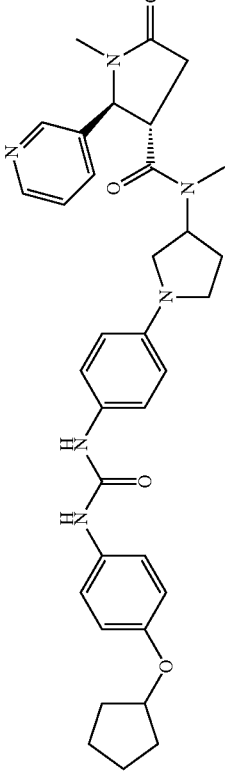 | (trans)-1-Methyl-5-oxo-2-pyridin-3-ylpyrrolidine-3-carboxylic acid(1-{4-[3-(4-cyclopentyloxyphenyl)-ureido]phenyl}pyrrolidin-3-yl)methylamide | C34H40N6O4 | 596.74 | 597 |

TABLE 3-continued

| Ex. No. | Structure | Name | Molecular formula | Molecular weight | M + H+ |
|---|---|---|---|---|---|
| 136 |  Chiral | (S)-1-Benzylpyrrolidine-2-carboxylic acid (1-{4-[3-(4-cyclopentyloxyphenyl)ureido]phenyl}pyrrolidin-3-yl)methyl-amide | C35H43N5O3 | 581.76 | 582 |
| 137 | 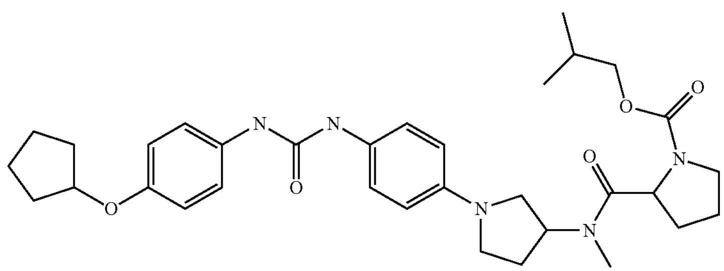 | Isobutyl 2-[(1-{4-[3-(4-cyclopentyloxyphenyl)-ureido]phenyl}pyrrolidin-3-yl)methylcarbamoyl]-pyrrolidine-1-carboxylate | C33H45N5O5 | 591.76 | 592 |
| 138 | 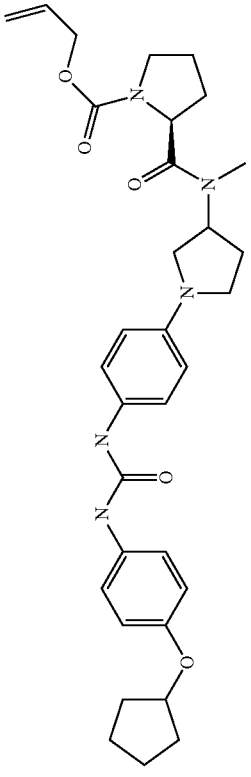 Chiral | Allyl (S)-2-[(1-{4-[3-(4-cyclopentyloxyphenyl)-ureido]phenyl}pyrrolidin-3-yl)methylcarbamoyl]-pyrrolidine-1-carboxylate | C32H41N5O5 | 575.71 | 576 |

TABLE 3-continued

| Ex. No. | Structure | Name | Molecular formula | Molecular weight | M + H+ |
|---|---|---|---|---|---|
| 139 | 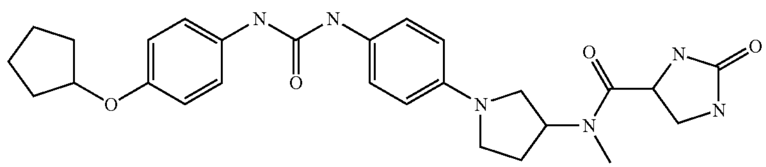 | 2-Oxoimidazolidine-4-carboxylic acid(1-{4-[3-(4-cyclopentyloxyphenyl)ureido]phenyl}pyrrolidin-3-yl)methylamide | C27H34N6O4 | 506.61 | 507 |
| 140 | Chiral | (R)-5-Oxopyrrolidine-2-carboxylic acid(1-{4-[3-(4-cyclopentyloxyphenyl)ureido]phenyl}pyrrolidin-3-yl)methylamide | C28H35N5O4 | 505.62 | 506 |
| 141 | 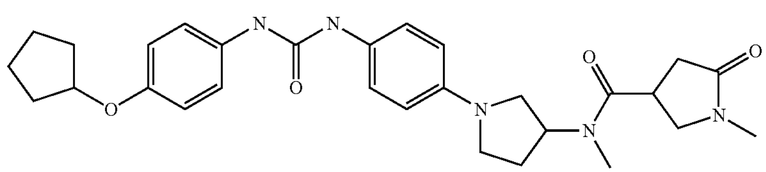 | 1-Methyl-5-oxopyrrolidine-3-carboxylic acid(1-{4-[3-(4-cyclopentyloxyphenyl)ureido]phenyl}pyrrolidin-3-yl)methylamide | C29H37N5O4 | 519.65 | 520 |

TABLE 3-continued

| Ex. No. | Structure | Name | Molecular formula | Molecular weight | M + H+ |
|---|---|---|---|---|---|
| 142 | 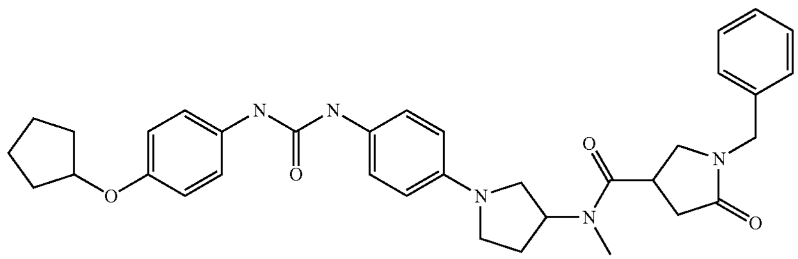 | 1-Benzyl-5-oxopyrrolidine-3-carboxylic acid(1-{4-[3-(4-cyclopentyloxyphenyl)ureido]phenyl}-pyrrolidine-3-yl)methylamide | C35H41N5O4 | 595.75 | 596 |
| 143 | 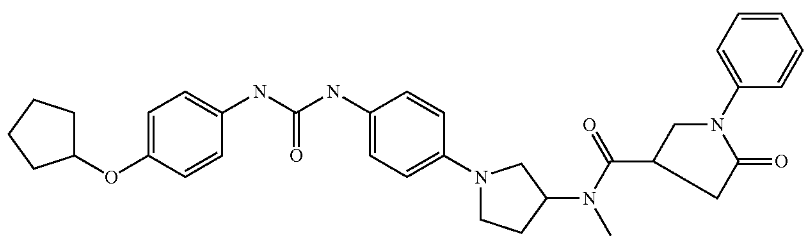 | 5-Oxo-1-phenylpyrrolidine-3-carboxylic acid(1-{4-[3-(4-cyclopentyloxyphenyl)ureido]phenyl}-pyrrolidin-3-yl)methylamide | C34H39N5O4 | 581.72 | 582 |
| 144 | 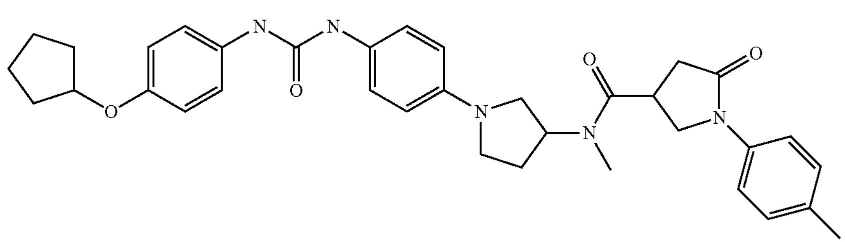 | 5-Oxo-1-p-tolylpyrrolidine-3-carboxylic acid(1-{4-[3-(4-cyclopentyloxyphenyl)ureido]phenyl}-pyrrolidin-3-yl)methylamide | C35H41N5O4 | 595.75 | 596 |

TABLE 4

| Ex. No. | Structure | Name | Molecular formula | Molecular weight | M + H+ |
|---|---|---|---|---|---|
| 145 | 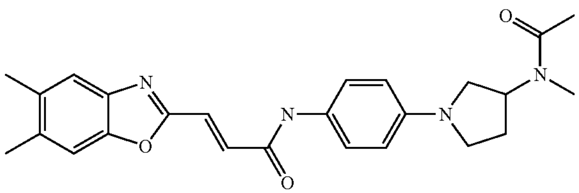 | (E)-N-{4-[3-(Acetylmethylamino)pyrrolidin-1-yl]-phenyl}-3-(5,6-dimethylbenzooxazol-2-yl)-acrylamide | C25H28N4O3 | 432.53 | 433 |
| 146 | 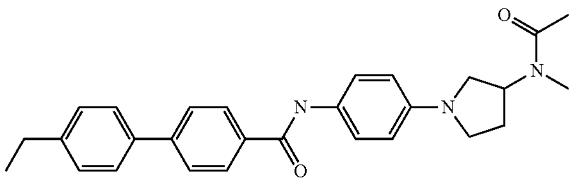 | 4'-Ethylbiphenyl-4-carboxylic acid {4-[3-(acetyl-methylamino)-pyrrolidin-1-yl]phenyl}amide | C28H31N3O2 | 441.58 | 442 |
| 147 | 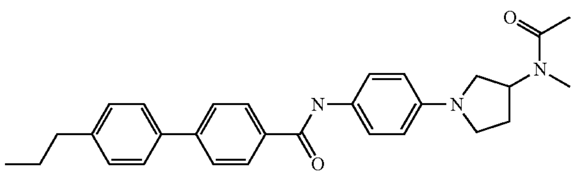 | 4'-Propylbiphenyl-4-carboxylic acid {4-[3-(acetyl-methylamino)-pyrrolidin-1-yl]phenyl}amide | C29H33N3O2 | 455.61 | 456 |
| 148 | 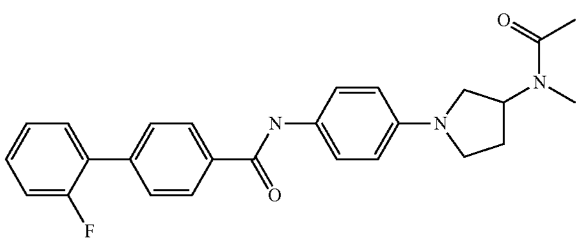 | 2'-Fluorobiphenyl-4-carboxylic acid {4-[3-(acetyl-methylamino)-pyrrolidin-1-yl]phenyl}amide | C26H26FN3O2 | 431.51 | 432 |
| 149 | 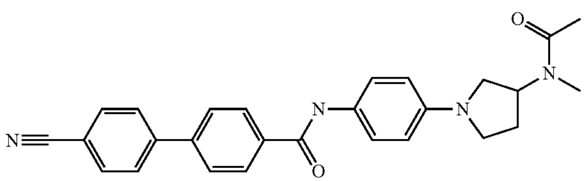 | 4'-Cyanobiphenyl-4-carboxylic acid {4-[3-(acetyl-methylamino)-pyrrolidin-1-yl]phenyl}amide | C27H26N4O2 | 438.53 | 439 |

TABLE 4-continued

| Ex. No. | Structure | Name | Molecular formula | Molecular weight | M + H+ |
|---|---|---|---|---|---|
| 150 | 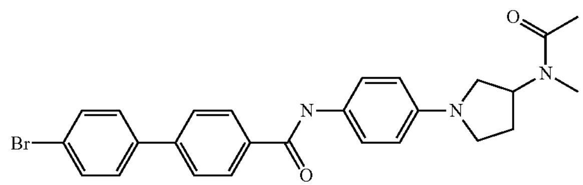 | 4'-Bromobiphenyl-4-carboxylic acid {4-[3-(acetyl-methylamino)-pyrrolidin-1-yl]phenyl}amide | C26H26BrN3O2 | 492.42 | 492 |
| 151 | 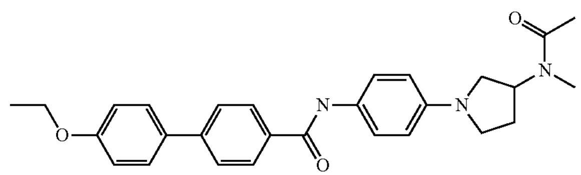 | 4'-Ethoxybiphenyl-4-carboxylic acid {4-[3-(acetyl-methylamino)-pyrrolidin-1-yl]phenyl}amide | C28H31N3O3 | 457.58 | 458 |
| 152 | 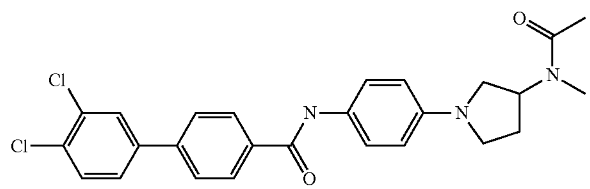 | 3',4'-Dichlorobiphenyl-4-carboxylic acid {4-[3-(acetylmethylamino)pyrrolidin-1-yl]-phenyl}amide | C26H25Cl2N3O2 | 482.41 | 482 |
| 153 | 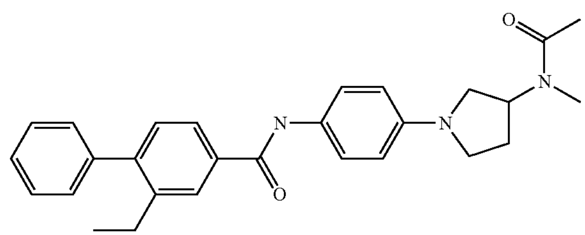 | 2-Ethylbiphenyl-4-carboxylic acid {4-[3-(acetyl-methylamino)-pyrrolidin-1-yl]phenyl}amide | C28H31N3O2 | 441.58 | 442 |
| 154 | 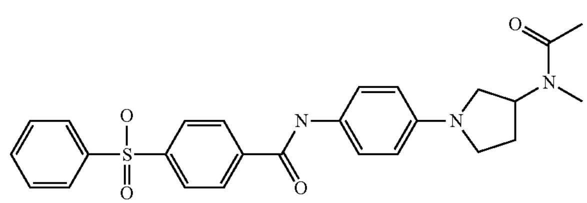 | N-{4-[3-(Acetylmethylamino)pyrrolidin-1-yl]phenyl}-4-benzenesulfonylbenzamide | C26H27N3O4S | 477.59 | 478 |

TABLE 4-continued

| Ex. No. | Structure | Name | Molecular formula | Molecular weight | M + H+ |
|---|---|---|---|---|---|
| 155 | 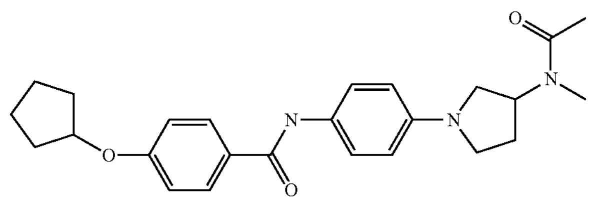 | N-{4-[3-(Acetylmethyl-amino)pyrrolidin-1-yl]phenyl}-4-cyclopentyloxybenzamide | C25H31N3O3 | 421.54 | 422 |
| 156 | 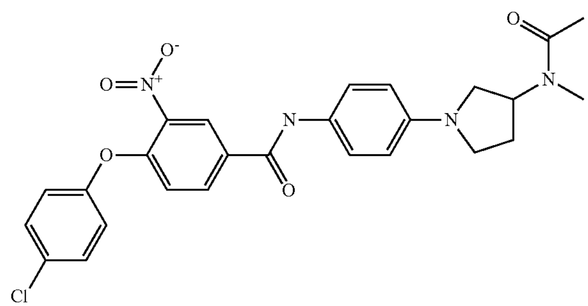 | N-{4-[3-(Acetylmethyl-amino)pyrrolidin-1-yl]phenyl}-4-(4-chlorophenoxy)-3-nitrobenzamide | C26H25ClN4O5 | 508.97 | 509 |
| 157 | 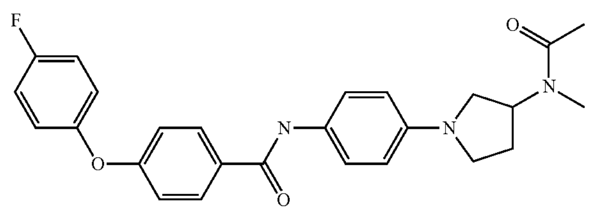 | N-{4-[3-(Acetylmethyl-amino)pyrrolidin-1-yl]phenyl}-4-(4-fluorophenoxy)benzamide | C26H26FN3O3 | 447.51 | 448 |
| 158 | 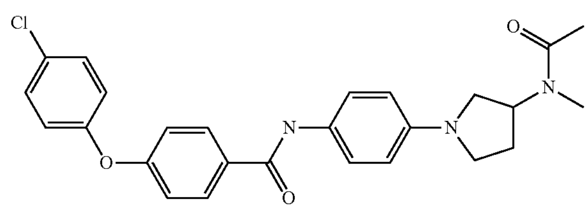 | N-{4-[3-(Acetylmethyl-amino)pyrrolidin-1-yl]phenyl}-4-(4-chlorophenoxy)benzamide | C26H26ClN3O3 | 463.97 | 464 |

TABLE 4-continued

| Ex. No. | Structure | Name | Molecular formula | Molecular weight | M + H+ |
|---|---|---|---|---|---|
| 159 | 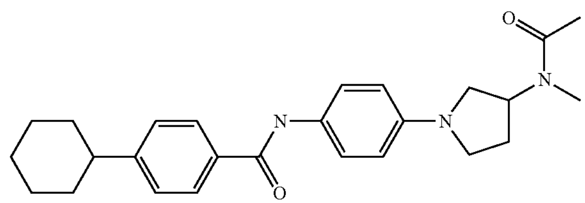 | N-{4-[3-(Acetylmethylamino)pyrrolidin-1-yl]phenyl}-4-cyclohexylbenzamide | C26H33N3O2 | 419.57 | 420 |
| 160 | 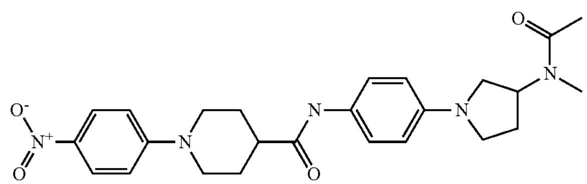 | 1-(4-Nitrophenyl)piperidine-4-carboxylic acid {4-[3-(acetylmethylaminopyrrolidin-1-yl]phenyl}amide | C25H31N5O4 | 465.56 | 466 |
| 161 | 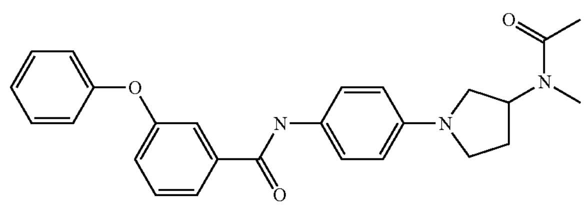 | N-{4-[3-(Acetylmethylamino)pyrrolidin-1-yl]phenyl}-3-phenoxybenzamide | C26H27N3O3 | 429.52 | 430 |
| 162 | 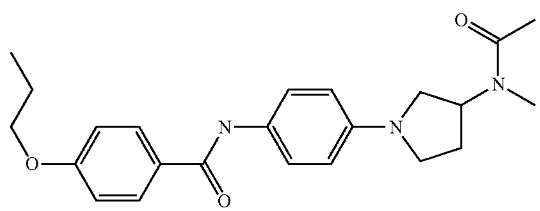 | N-{4-[3-(Acetylmethylamino)pyrrolidin-1-yl]phenyl}-4-propoxybenzamide | C23H29N3O3 | 395.51 | 396 |
| 163 | 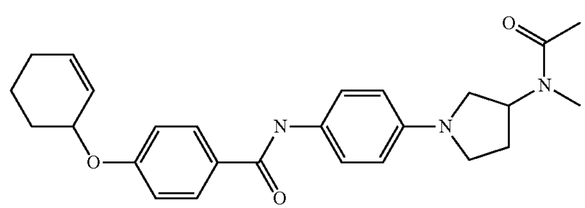 | N-{4-[3-(Acetylmethylamino)pyrrolidin-1-yl]phenyl}-4-(cyclohex-2-enyloxy)benzamide | C26H31N3O3 | 433.56 | 434 |

TABLE 4-continued

| Ex. No. | Structure | Name | Molecular formula | Molecular weight | M + H+ |
|---|---|---|---|---|---|
| 164 | 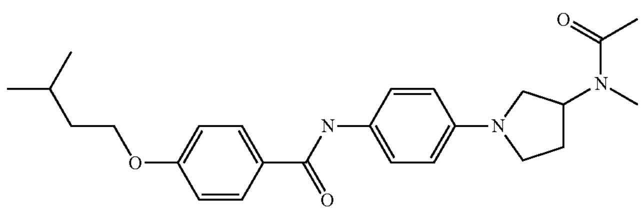 | N-{4-[3-(Acetylmethylamino)pyrrolidin-1-yl]phenyl}-4-(3-methylbutoxy)benzamide | C25H33N3O3 | 423.56 | 424 |
| 165 | 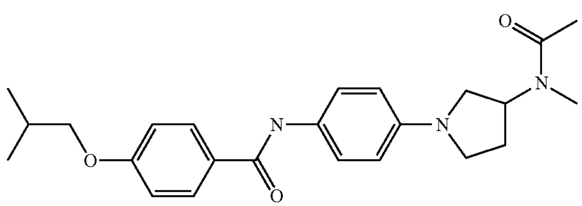 | N-{4-[3-(Acetylmethylamino)pyrrolidin-1-yl]phenyl}-4-isobutoxybenzamide | C24H31N3O3 | 409.53 | 410 |
| 166 | 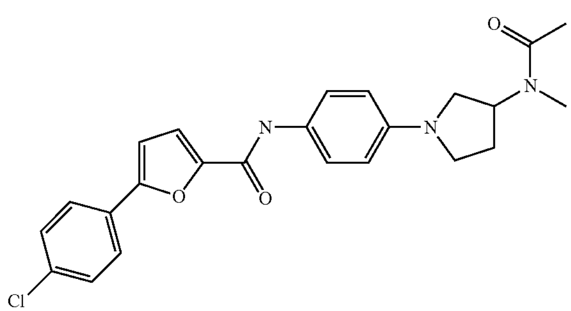 | 5-(4-Chlorophenyl)furan-2-carboxylic acid {4-[3-(acetylmethylamino)pyrrolidin-1-yl]phenyl}amide | C24H24ClN3O3 | 437.93 | 438 |

TABLE 4-continued

| Ex. No. | Structure | Name | Molecular formula | Molecular weight | M + H+ |
|---|---|---|---|---|---|
| 167 | 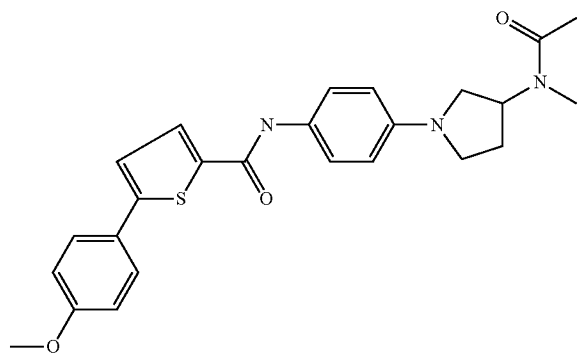 | 5-(4-Methoxyphenyl)thiophene-2-carboxylic acid {4-[3-(acetylmethylamino)pyrrolidin-1-yl]phenyl}amide | C25H27N3O3S | 449.58 | 450 |
| 168 | 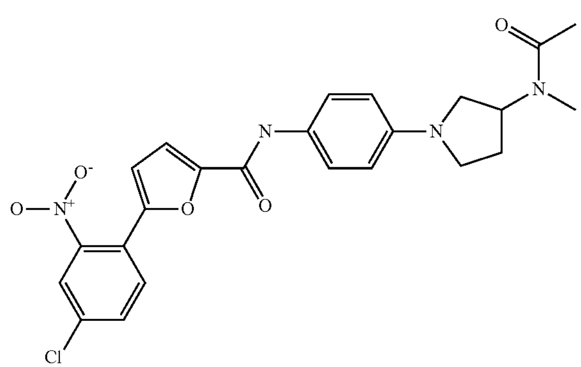 | 5-(4-Chloro-2-nitrophenyl)-furan-2-carboxylic acid {4-[3-(acetylmethylamino)pyrrolidin-1-yl]phenyl}amide | C24H23ClN4O5 | 482.93 | 483 |

TABLE 4-continued

| Ex. No. | Structure | Name | Molecular formula | Molecular weight | M + H+ |
|---|---|---|---|---|---|
| 169 | 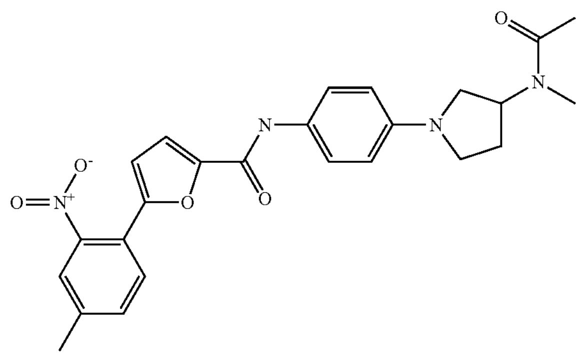 | 5-(4-Methyl-2-nitrophenyl)furan-2-carboxylic acid {4-[3-(acetylmethylamino)pyrrolidin-1-yl]phenyl}-amide | C25H26N4O5 | 462.51 | 463 |
| 170 | 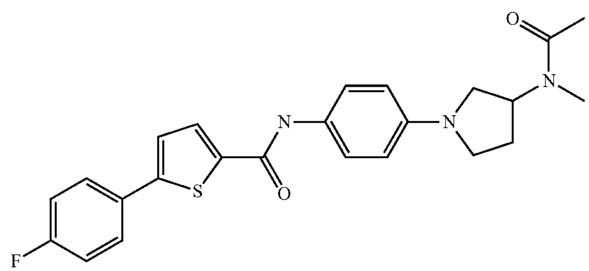 | 5-(4-Fluorophenyl)thiophene-2-carboxylic acid {4-[3-(acetylmethylamino)pyrrolidin-1-yl]phenyl}-amide | C24H24FN3O2S | 437.54 | 438 |
| 171 | 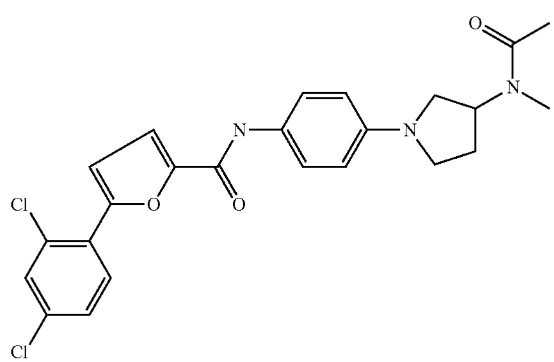 | 5-(2,4-Dichlorophenyl)furan-2-carboxylic acid {4-[3-(acetylmethylamino)pyrrolidin-1-yl]phenyl}-amide | C24H23Cl2N3O3 | 472.38 | 472 |

TABLE 4-continued

| Ex. No. | Structure | Name | Molecular formula | Molecular weight | M + H+ |
|---|---|---|---|---|---|
| 172 | 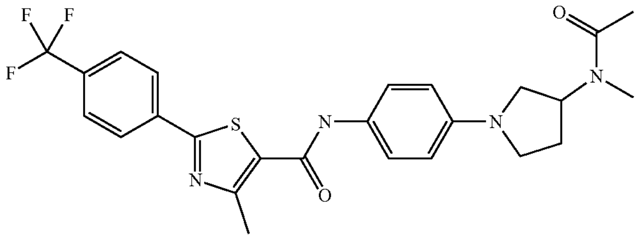 | 4-Methyl-2-(4-trifluoromethyl-phenyl)thiazole-5-carboxylic acid{4-[3-(acetylmethylamino)-pyrrolidin-1-yl]phenyl}amide | C25H25F3N4O2S | 502.56 | 503 |
| 173 | 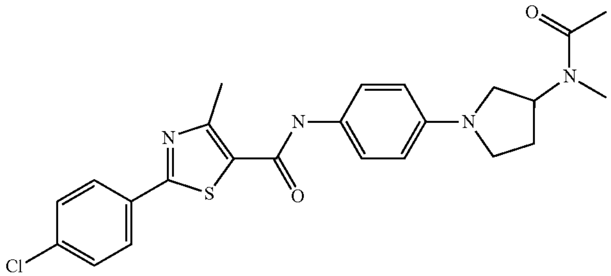 | 2-(4-Chlorophenyl)-4-methyl-thiazole-5-carboxylic acid {4-[3-(acetylmethylamino)-pyrrolidin-1-yl]phenyl}amide | C24H25ClN4O2S | 469.01 | 469 |
| 174 | 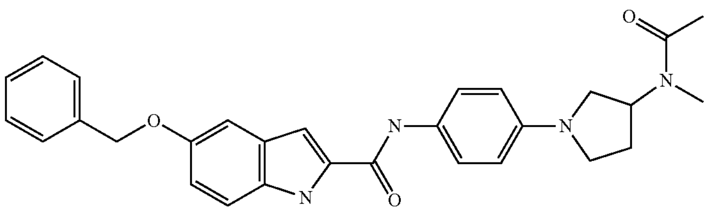 | 5-Benzyloxy-1H-indole-2-carboxylic acid {4-[3-(acetylmethylamino)pyr-rolidin-1-yl]phenyl}amide | C29H30N4O3 | 482.59 | 483 |
| 175 | 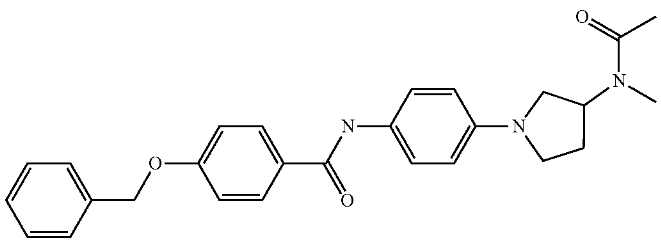 | N-{4-[3-(Acetylmethylamino)-pyrrolidin-1-yl]phenyl}-4-benzyloxybenzamide | C27H29N3O3 | 443.55 | 444 |

TABLE 4-continued

| Ex. No. | Structure | Name | Molecular formula | Molecular weight | M + H+ |
|---|---|---|---|---|---|
| 176 | 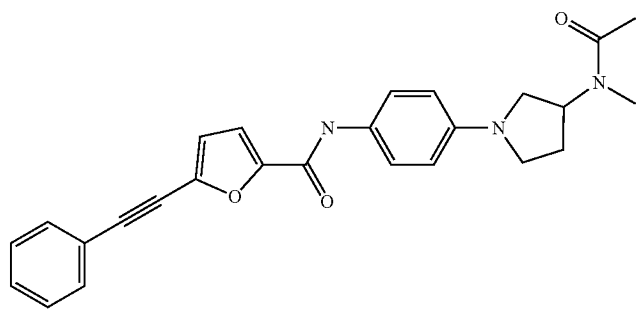 | 5-Phenylethynylfuran-2-carboxylic acid {4-[3-(acetylmethylamino)pyrrolidin-1-yl]phenyl}amide | C26H25N3O3 | 427.51 | 428 |
| 177 | 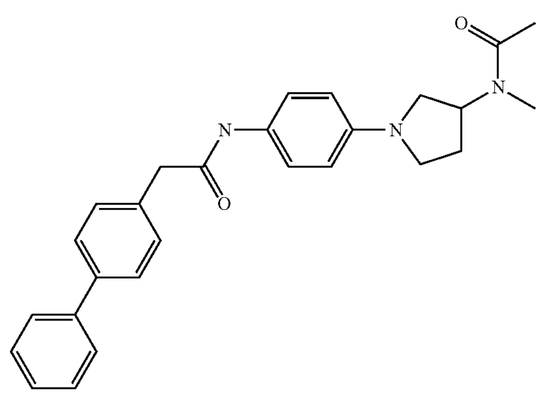 | N-{4-[3-(Acetylmethylamino)pyrrolidin-1-yl]phenyl}-2-biphenyl-4-ylacetamide | C27H29N3O2 | 427.55 | 428 |

TABLE 4-continued

| Ex. No. | Structure | Name | Molecular formula | Molecular weight | M + H+ |
|---|---|---|---|---|---|
| 178 | 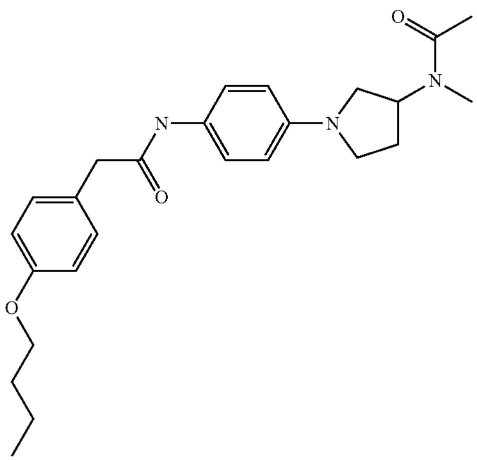 | N-{4-[3-(Acetylmethylamino)-pyrrolidin-1-yl]phenyl}-2-(4-butoxyphenyl)acetamide | C25H33N3O3 | 423.56 | 424 |
| 179 | 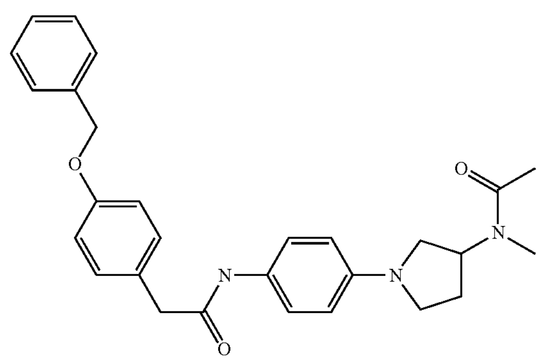 | N-{4-[3-(Acetylmethylamino)-pyrrolidin-1-yl]phenyl}-2-(4-benzyloxyphenyl)acetamide | C28H31N3O3 | 457.58 | 458 |

TABLE 4-continued

| Ex. No. | Structure | Name | Molecular formula | Molecular weight | M + H+ |
|---|---|---|---|---|---|
| 180 | 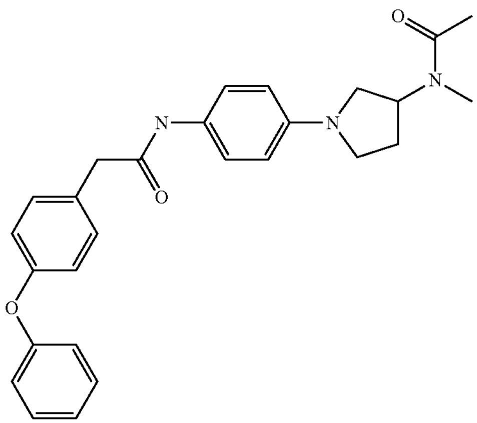 | N-{4-[3-(Acetylmethylamino)-pyrrolidin-1-yl]phenyl}-2-(4-phenoxyphenyl)acetamide | C27H29N3O3 | 443.55 | 444 |
| 181 | 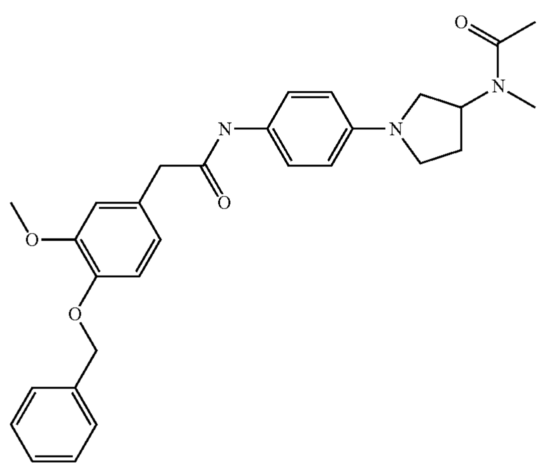 | N-{4-[3-(Acetylmethylamino)-pyrrolidin-1-yl]phenyl}-2-(4-benzyloxy-3-methoxyphenyl)acetamide | C29H33N3O4 | 487.60 | 488 |

TABLE 4-continued
| Ex. No. | Structure | Name | Molecular formula | Molecular weight | M + H+ |
|---|---|---|---|---|---|
| 182 | 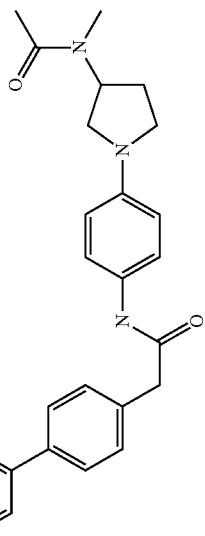 | N-{4-[3-(Acetylmethylamino)-pyrrolidin-1-yl]phenyl}-2-(4'-fluorobiphenyl-4-yl)acetamide | C27H28FN3O2 | 445.54 | 446 |
| 183 | 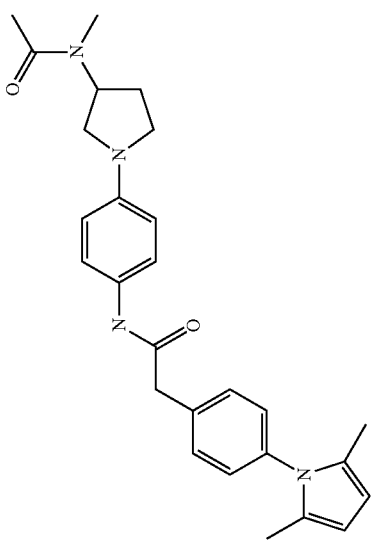 | N-{4-[3-(Acetylmethylamino)-pyrrolidin-1-yl]phenyl}-2-[4-(2,5-dimethylpyrrol-1-yl)phenyl]acetamide | C27H32N4O2 | 444.58 | 445 |

TABLE 4-continued

| Ex. No. | Structure | Name | Molecular formula | Molecular weight | M + H+ |
|---|---|---|---|---|---|
| 184 | 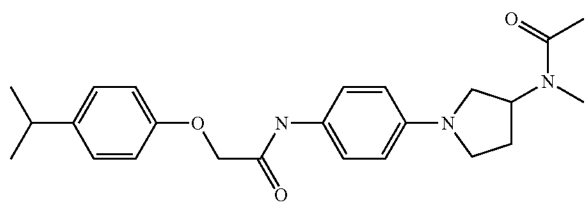 | N-{4-[3-(Acetylmethylamino)-pyrrolidin-1-yl]phenyl}-2-(4-isopropylphenoxy)-acetamide | C24H31N3O3 | 409.53 | 410 |
| 185 | 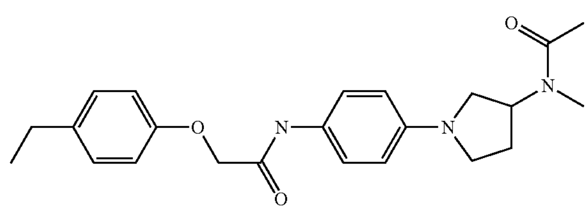 | N-{4-[3-(Acetylmethylamino)-pyrrolidin-1-yl]phenyl}-2-(4-ethylphenoxy)acetamide | C23H29N3O3 | 395.51 | 396 |

TABLE 5

| Ex. No. | Structure | Name | Molecular formula | Molecular weight | M + H+ |
|---|---|---|---|---|---|
| 186 | 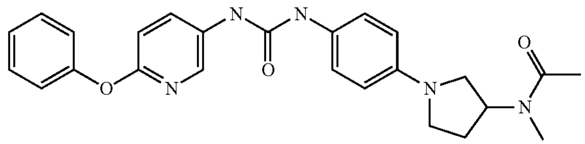 | N-Methyl-N-(1-{4-[3-(6-phenoxypyridin-3-yl)ureido]phenyl}-pyrrolidin-3-yl)acetamide | C25H27N5O3 | 445.53 | 446 |
| 187 | 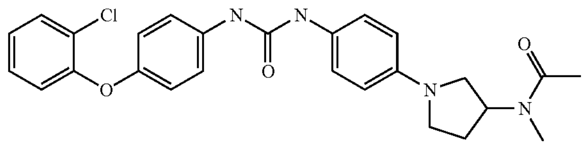 | N-[1-(4-{3-[4-(2-Chlorophenoxy)phenyl]ureido}-phenyl)-pyrrolidin-3-yl]-N-methyl-acetamide | C26H27ClN4O3 | 478.98 | 479 |
| 188 | 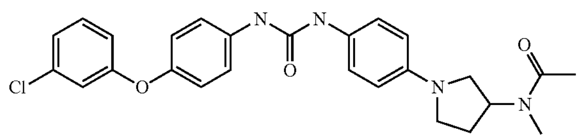 | N-[1-(4-{3-[4-(3-Chlorophenoxy)phenyl]ureido}-phenyl)-pyrrolidin-3-yl]-N-methyl-acetamide | C26H27ClN4O3 | 478.98 | 479 |
| 189 | 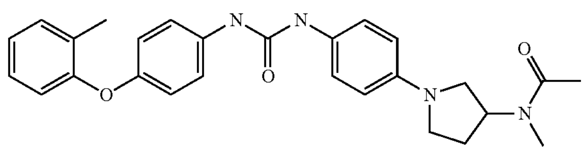 | N-Methyl-N-[1-{4-[3-(4-o-tolyloxyphenyl)ureido]-phenyl}-pyrrolidin-3-yl]acetamide | C27H30N4O3 | 458.57 | 459 |
| 190 | 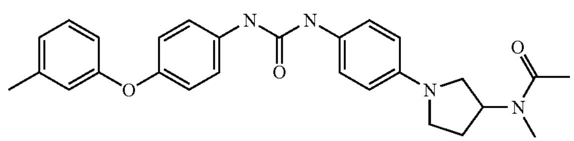 | N-Methyl-N-[1-{4-[3-(4-m-tolyloxyphenyl)ureido]-phenyl}-pyrrolidin-3-yl]acetamide | C27H30N4O3 | 458.57 | 459 |
| 191 | 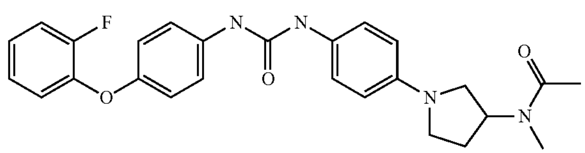 | N-[1-{4-[3-[4-(2-Fluorophenoxy)phenyl]ureido]-phenyl}-pyrrolidin-3-yl]-N-methyl-acetamide | C26H27FN4O3 | 462.53 | 463 |

TABLE 5-continued

| Ex. No. | Structure | Name | Molecular formula | Molecular weight | M + H+ |
|---|---|---|---|---|---|
| 192 | 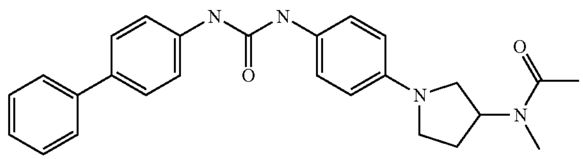 | N-{1-{4-[3-Biphenyl-4-yl-ureido]phenyl]pyrrolidin-3-yl}-N-methylacetamide | C26H28N4O2 | 428.54 | 429 |
| 193 | 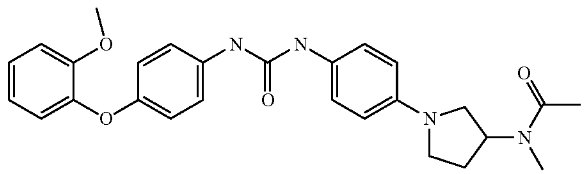 | N-[1-(4-{3-[4-(2-Methoxyphenoxy)phenyl]ureido}-phenyl)-pyrrolidin-3-yl]methyl]-acetamide | C27H30N4O4 | 474.56 | 475 |
| 194 | 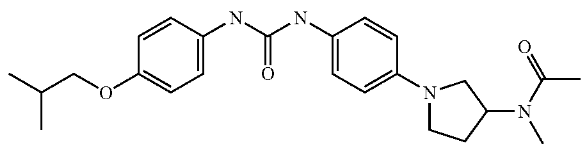 | N-(1-{4-[3-(4-Isobutoxyphenyl)ureido]phenyl}pyrrolidin-3-yl]-N-methylacetamide | C24H32N4O3 | 424.55 | 425 |
| 195 | 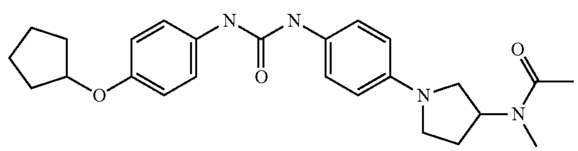 | N-(1-{4-[3-(4-Cyclopentyloxyphenyl)ureido]phenyl}pyrrolidin-3-yl]-N-methylacetamide | C25H32N4O3 | 436.56 | 437 |
| 196 | 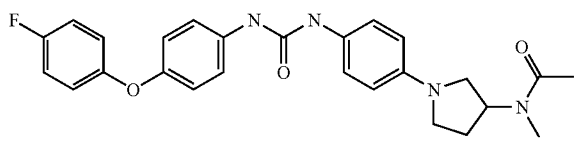 | N-[1-(4-{3-[4-(4-Fluorophenoxy)phenyl]ureido}-phenyl)-pyrrolidin-3-yl]-N-methylacetamide | C26H27FN4O3 | 462.53 | 463 |
| 197 | 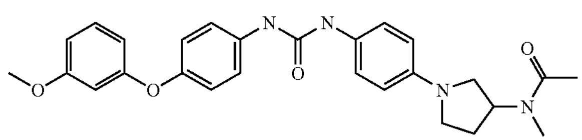 | N-[1-(4-{3-[4-(3-Methoxyphenoxy)phenyl]ureido}-phenyl)-pyrrolidin-3-yl]-N-methylacetamide | C27H30N4O4 | 474.56 | 475 |

TABLE 5-continued

| Ex. No. | Structure | Name | Molecular formula | Molecular weight | M + H+ |
|---|---|---|---|---|---|
| 198 | 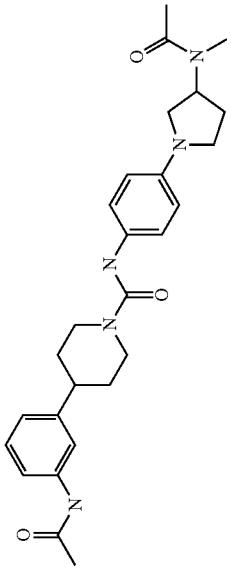 | 4-(3-Acetylaminophenyl)piperidine-1-carboxylic acid {4-[3-(acetylmethylamino)pyrrolidin-1-yl]-phenyl}amide | C27H35N5O3 | 477.61 | 478 |
| 199 | 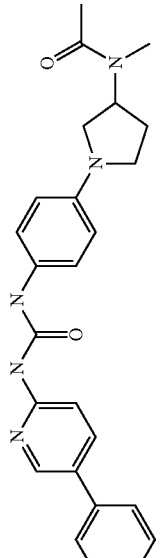 | N-Methyl-N-(1-{4-[3-(5-phenyl-pyridin-2-yl)ureido]-phenyl}-pyrrolidin-3-yl)acetamide | C25H27N5O2 | 429.53 | 430 |
| 200 | 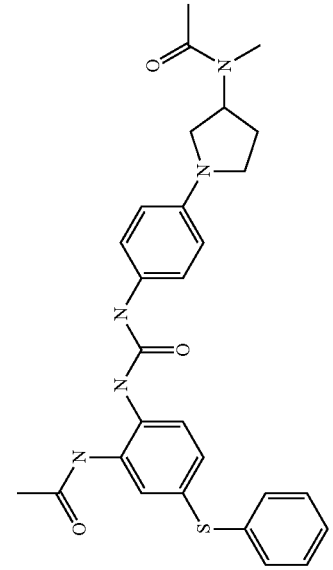 | N-(1-{4-[3-(2-Acetylamino-4-phenylsulfanylphenyl)-ureido]phenyl}pyrrolidin-3-yl)-N-methylacetamide | C28H31N5O3S | 517.65 | 518 |
| 201 | 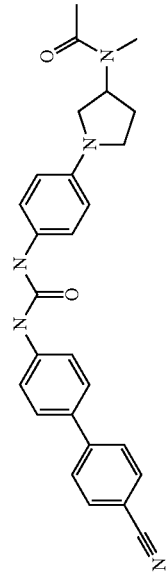 | N-(1-{4-[3-(4'-Cyanobiphenyl-4-yl)ureido]phenyl}pyrrolidin-3-yl)-N-methylacetamide | C27H27N5O2 | 453.55 | 454 |

TABLE 5-continued

| Ex. No. | Structure | Name | Molecular formula | Molecular weight | M + H+ |
|---|---|---|---|---|---|
| 202 | 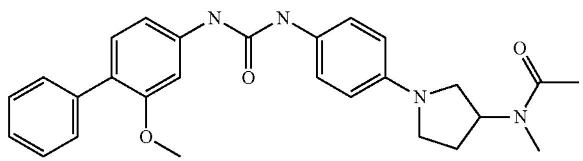 | N-(1-{4-[3-(2-Methoxybiphenyl-4-yl)ureido]phenyl}pyrrolidin-3-yl)-N-methylacetamide | C27H30N4O3 | 458.57 | 459 |
| 203 | 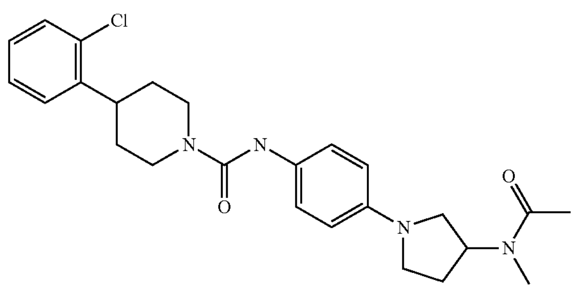 | 4-(2-Chlorophenyl)piperidine-1-carboxylic acid {4-[3-(acetylmethylamino)pyrrolidin-1-yl]phenyl}amide | C25H31ClN4O2 | 455.00 | 455 |
| 204 | 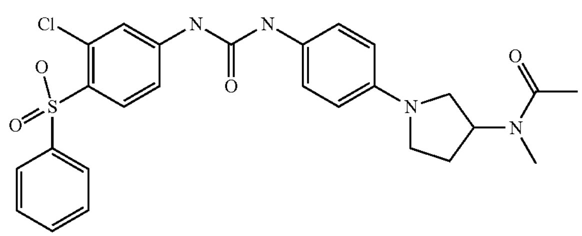 | N-(1-{4-[3-(4-Benzenesulfonyl-3-chlorophenyl)ureido]phenyl}pyrrolidin-3-yl)-N-methylacetamide | C26H27ClN4O4S | 527.05 | 527 |

TABLE 5-continued

| Ex. No. | Structure | Name | Molecular formula | Molecular weight | M + H+ |
|---|---|---|---|---|---|
| 205 | 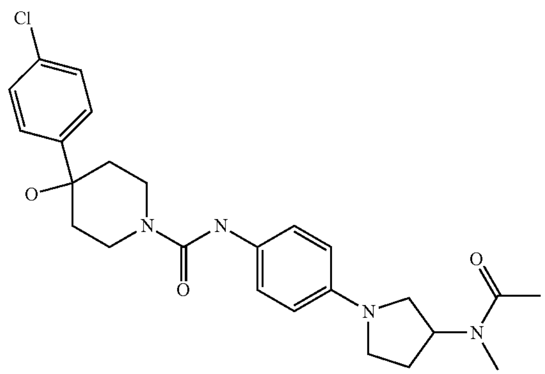 | 4-(4-Chlorophenyl)-4-hydroxy-piperidine-1-carboxylic acid {4-[3-(acetylmethyl-aminopyrrolidin-1-yl]phenyl}amide | C25H31ClN4O3 | 471.00 | 471 |
| 206 | 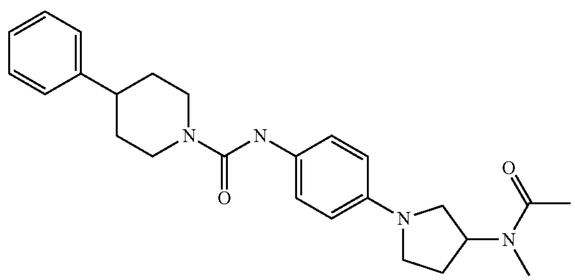 | 4-Phenylpiperidine-1-carboxylic acid {4-[3-(acetylmethylamino)-pyrrolidin-1-yl]phenyl}amide | C25H32N4O2 | 420.56 | 421 |
| 207 | 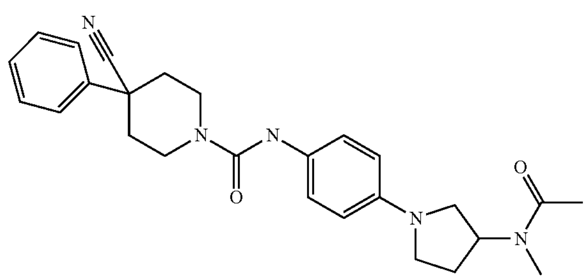 | 4-Cyano-4-phenylpiperidine-1-carboxylic acid {4-[3-(acetylmethylamino)pyrro-lidin-1-yl]phenyl}amide | C26H31N5O2 | 445.57 | 446 |

TABLE 5-continued

| Ex. No. | Structure | Name | Molecular formula | Molecular weight | M + H+ |
|---|---|---|---|---|---|
| 208 | 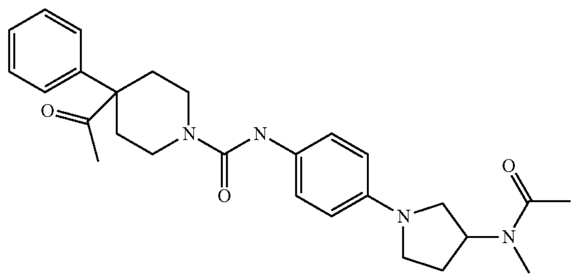 | 4-Acetyl-4-phenylpiperidine-1-carboxylic acid {4-[3-(acetylmethylamino)pyrrolidin-1-yl]phenyl}amide | C27H34N4O3 | 462.60 | 463 |
| 209 | 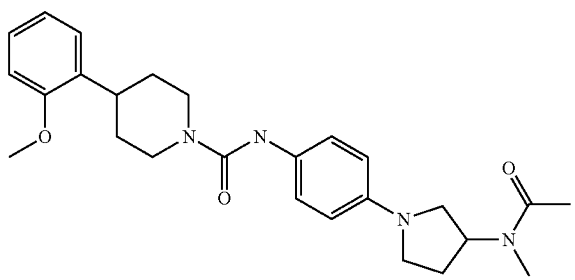 | 4-(2-Methoxyphenyl)piperidine-1-carboxylic acid {4-[3-(acetylmethylamino)pyrrolidin-1-yl]phenyl}amide | C26H34N4O3 | 450.59 | 451 |
| 210 | 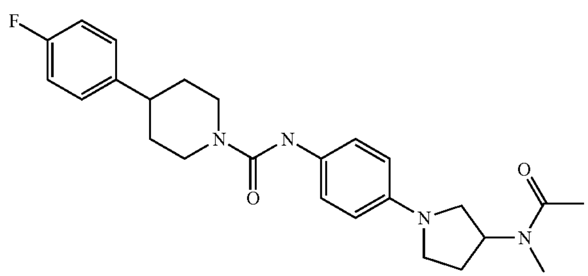 | 4-(4-Fluorophenyl)piperidine-1-carboxylic acid {4-[3-(acetylmethylamino)pyrrolidin-1-yl]phenyl}amide | C25H31FN4O2 | 438.55 | 439 |

TABLE 5-continued

| Ex. No. | Structure | Name | Molecular formula | Molecular weight | M + H+ |
|---|---|---|---|---|---|
| 211 | 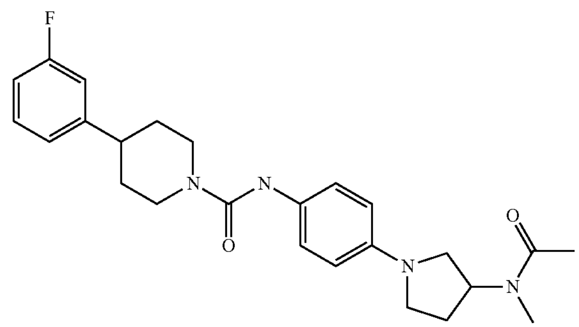 | 4-(3-Fluorophenyl)piperidine-1-carboxylic acid {4-[3-(acetylmethylamino)pyrrolidin-1-yl]phenyl}amide | C25H31FN4O2 | 438.55 | 439 |
| 212 | 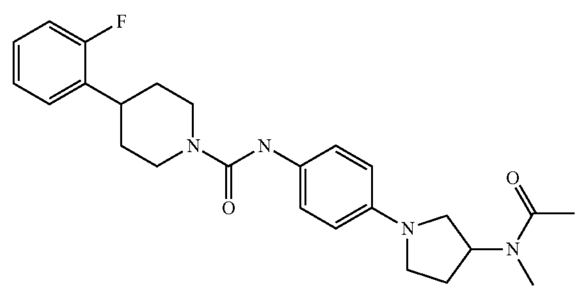 | 4-(2-Fluorophenyl)piperidine-1-carboxylic acid {4-[3-(acetylmethylamino)pyrrolidin-1-yl]phenyl}amide | C25H31FN4O2 | 438.55 | 439 |
| 213 | 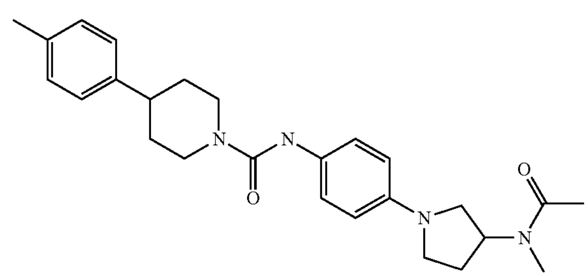 | 4-p-Tolylpiperidine-1-carboxylic acid {4-[3-(acetyl-methylamino)-pyrrolidin-1-yl]phenyl}amide | C26H34N4O2 | 434.59 | 435 |

TABLE 5-continued

| Ex. No. | Structure | Name | Molecular formula | Molecular weight | M + H+ |
|---|---|---|---|---|---|
| 214 | 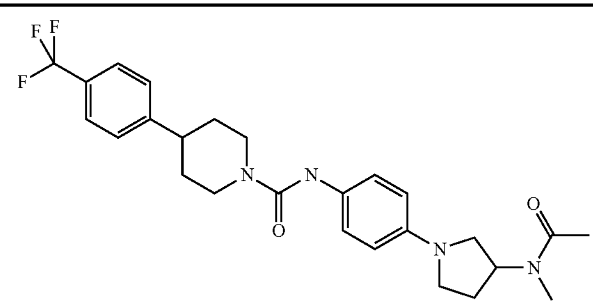 | 4-(4-Trifluoromethylphenyl)piperidine-1-carboxylic acid {4-[3-(acetylmethylamino)pyrrolidin-1-yl]phenyl}amide | C26H31F3N4O2 | 488.56 | 489 |
| 215 | 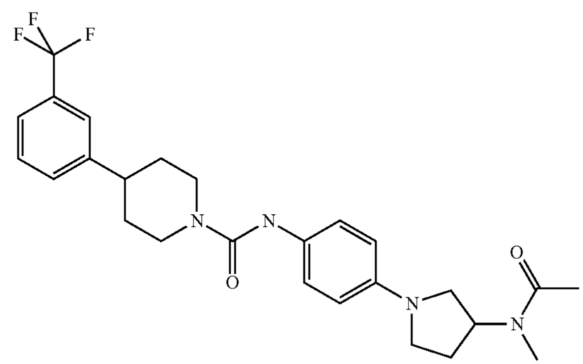 | 4-(3-Trifluoromethylphenyl)piperidine-1-carboxylic acid {4-[3-(acetylmethylamino)pyrrolidin-1-yl]phenyl}amide | C26H31F3N4O2 | 488.56 | 489 |
| 216 | 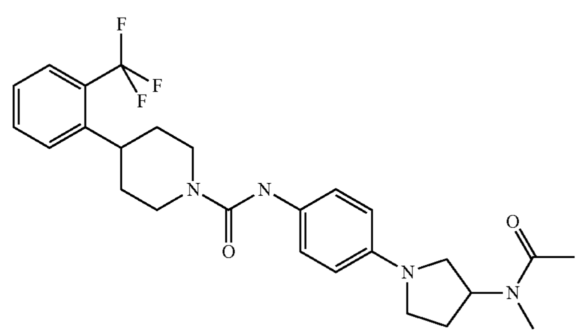 | 4-(2-Trifluoromethylphenyl)piperidine-1-carboxylic acid {4-[3-(acetylmethylaminopyrrolidin-1-yl]phenyl}amide | C26H31F3N4O2 | 488.56 | 489 |

TABLE 5-continued

| Ex. No. | Structure | Name | Molecular formula | Molecular weight | M + H+ |
|---|---|---|---|---|---|
| 217 | 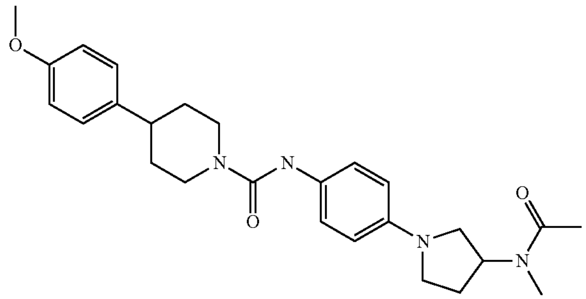 | 4-(4-Methoxyphenyl)piperidine-1-carboxylic acid {4-[3-(acetyl-methylamino)pyrrolidin-1-yl]-phenyl}-amide | C26H34N4O3 | 450.59 | 451 |
| 218 | 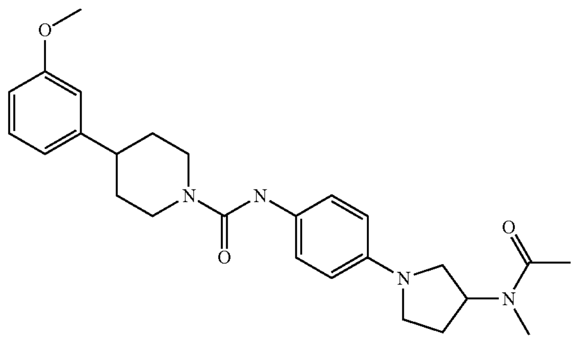 | 4-(3-Methoxyphenyl)piperidine-1-carboxylic acid {4-[3-(acetyl-methylamino)pyrrolidin-1-yl]-phenyl}-amide | C26H34N4O3 | 450.59 | 451 |
| 219 | 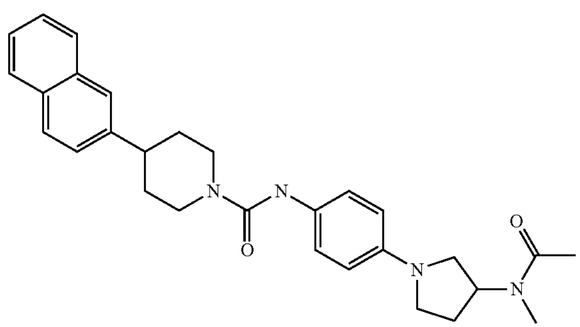 | 4-Naphthalen-2-ylpiperidine-1-carboxylic acid {4-[3-(acetyl-methylamino)pyrrolidin-1-yl]-phenyl}-amide | C29H34N4O2 | 470.62 | 471 |

TABLE 5-continued

| Ex. No. | Structure | Name | Molecular formula | Molecular weight | M + H+ |
|---|---|---|---|---|---|
| 220 | 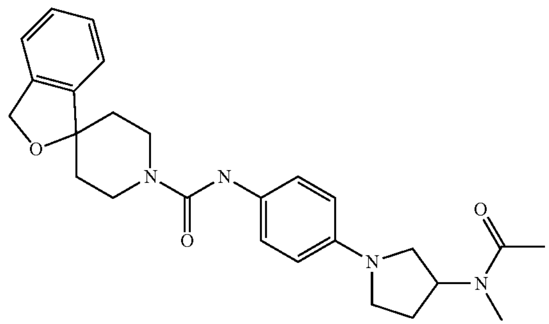 | Benzo[c]-1-oxa-8-aza-spiro-[4,5]decane-8-car-{4-[3-(acetyl-methylamino)pyrrolidin-1-yl]-phenyl-}amide | C26H32N4O3 | 448.57 | 449 |
| 221 | 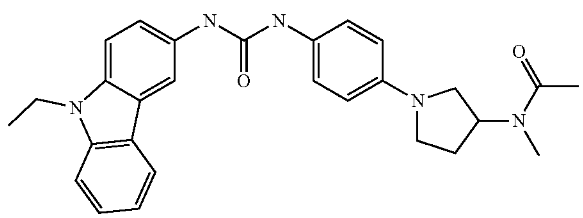 | N-(1-{4-[3-(9-Ethyl-9H-carbazol-3-yl)ureido]-phenyl}-pyrrolidin-3-yl)-N-methyl-acetamide | C28H31N5O2 | 469.59 | 470 |
| 222 | 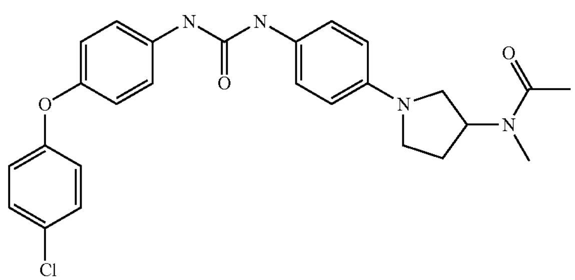 | N-(1-{4-[3-[4-(4-Chloro-phenoxy)phenyl]ureido]-phenyl}pyrrolidin-3-yl)-N-methylacetamide | C26H27ClN4O3 | 478.98 | 479 |

TABLE 5-continued

| Ex. No. | Structure | Name | Molecular formula | Molecular weight | M + H+ |
|---|---|---|---|---|---|
| 223 | 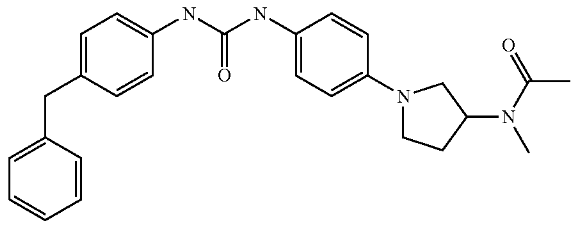 | N-(1-{4-[3-(4-Benzylphenyl)-ureido]phenyl}-pyrrolidin-3-yl)-N-methylacetamide | C27H30N4O2 | 442.57 | 443 |
| 224 | 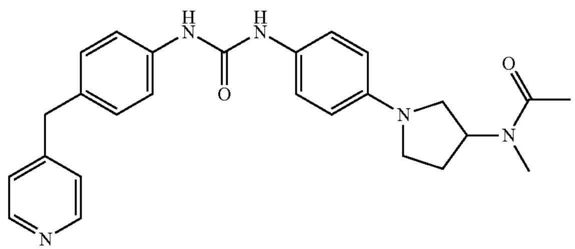 | N-Methyl-N-(1-{4-[3-(4-Pyridin-4-ylmethylphenyl)-ureido]-phenyl}pyrrolidin-3-yl)acetamide | C28H30F3N5O4 | 443.55 | 444 |
| 225 | 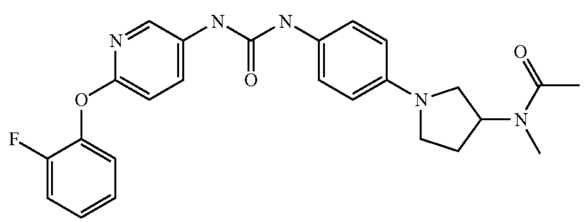 | N-[1-(4-{3-[6-(2-Fluorophenoxy)pyridin-3-yl]ureido}-phenyl)pyrrolidin-3-yl)-N-methylacetamide | C25H26FN5O3 | 463.52 | 464 |

TABLE 5-continued

| Ex. No. | Structure | Name | Molecular formula | Molecular weight | M + H+ |
|---|---|---|---|---|---|
| 226 | 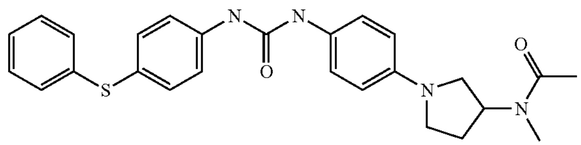 | N-Methyl-N-[1-{4-[3-(4-phenyl-sulfanyl)phenyl]-ureido]phenyl}-pyrrolidin-3-yl)acetamide | C26H28N4O2S | 460.60 | 461 |
| 227 | 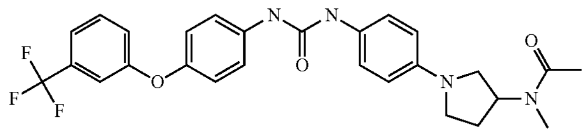 | N-Methyl-N-[1-(4-{3-[4-(3-tri-fluoromethyl)phenoxy)phenyl]-ureido}phenyl)pyrrolidin-3-yl]-acetamide | C27H27F3N4O3 | 512.54 | 513 |
| 228 | 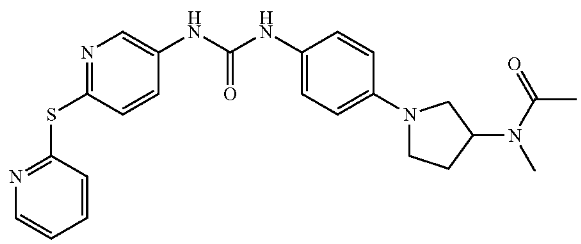 | N-Methyl-N-[1-(4-{3-[6-(pyridin-2-ylsulfanyl)pyridin-3-yl]ureido}phenyl)pyrrolidin-3-yl]acetamide | C26H27F3N6O4S | 462.58 | 463 |
| 229 | 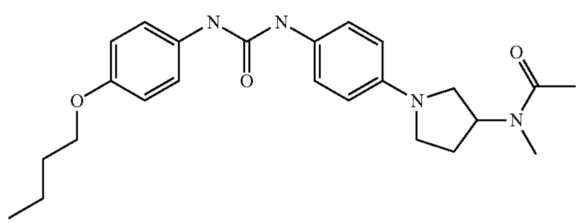 | N-(1-{4-[3-(4-Butoxyphenyl)-ureido]phenyl}-pyrrolidin-3-yl)-N-methylacetamide | C24H32N4O3 | 424.55 | 425 |

TABLE 5-continued

| Ex. No. | Structure | Name | Molecular formula | Molecular weight | M + H+ |
|---|---|---|---|---|---|
| 230 | 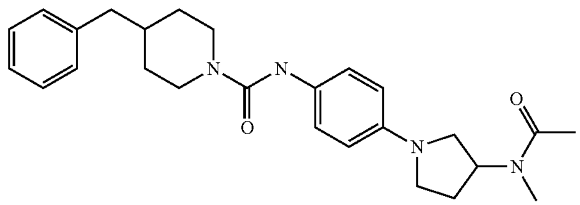 | 4-Benzylpiperidine-1-carboxylic acid {4-[3-(acetylmethylamino)-pyrrolidin-1-yl]phenyl}amide | C26H34N4O2 | 434.59 | 435 |
| 231 | 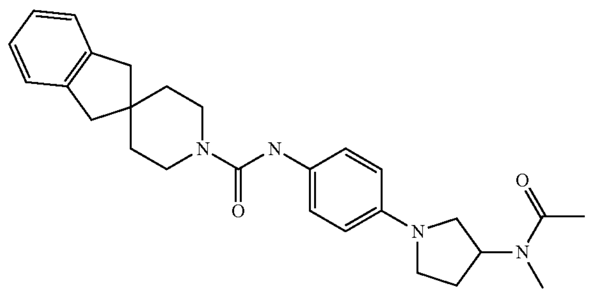 | Benzo-8-azaspiro[4.5]decane-8-carboxylic acid {4-[3-(acetyl-methylamino)pyrrolidin-1-yl]-phenyl}amide | C27H34N4O2 | 446.60 | 447 |
| 232 | 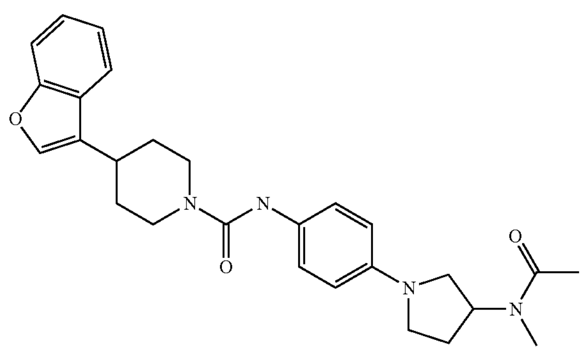 | 4-Benzofuran-3-ylpiperidine-1-carboxylic acid {4-[3-(acetyl-methylamino)pyrrolidin-1-yl]-phenyl}amide | C27H32N4O3 | 460.58 | 461 |

TABLE 5-continued

| Ex. No. | Structure | Name | Molecular formula | Molecular weight | M + H+ |
|---|---|---|---|---|---|
| 233 | 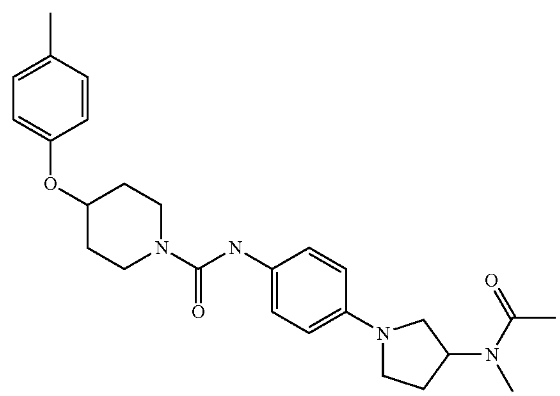 | 4-p-Tolyloxypiperidine-1-carboxylic acid {4-[3-(acetylmethylamino)pyrrolidin-1-yl]phenyl}amide | C26H34N4O3 | 450.59 | 451 |
| 234 | 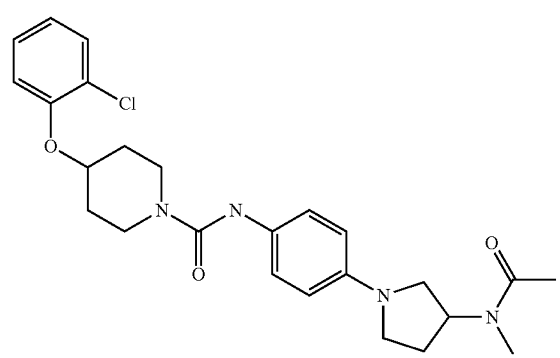 | 4-(2-Chlorophenoxy)piperidine-1-carboxylic acid {4-[3-(acetylmethylamino)pyrrolidin-1-yl]phenyl}-amide | C25H31ClN4O3 | 471.00 | 471 |

Example 235

N-(1-{4-[3-(4-Cyclopentyloxyphenyl)ureido]phenyl}pyrrolidin-3-yl)-N-methyl-2-piperidin-1-yl-acetamide

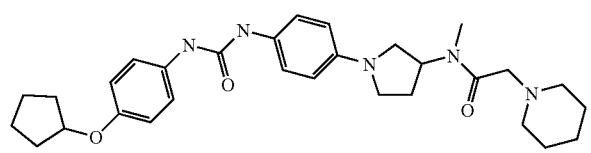

1-(4-Cyclopentyloxyphenyl)-3-[4-(3-methylaminopyrrolidin-1-yl)phenyl]urea was reacted with piperidin-1-ylacetic acid by method E. This resulted in the product with the molecular weight of 519.69 (C30H41N5O3); MS (ESI): 520 (M+H+).

Example 236

1-Methylpiperidine-3-carboxylic acid {(R)-1-[5-(4-cyclohexylbenzoylamino)pyridin-2-yl]pyrrolidin-3-yl}methylamide

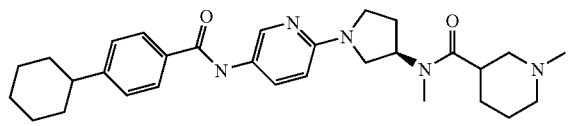

(R)-4-Cyclohexyl-N-[6-(3-methylaminopyrrolidin-1-yl)pyridin-3-yl]benzamide was reacted with 1-methylpiperidin-3-carboxylic acid by method E. This resulted in the product with the molecular weight of 503.69 (C30H41N5O2); MS (ESI): 504 (M+H+).

Example 237

N-{4-[3-(Acetylmethylamino)pyrrolidin-1-yl]phenyl}-2-(4-butoxyphenyl)propionamide

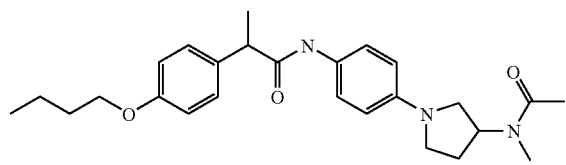

Method H

Caesium carbonate (36 mg) and n-butyl bromide (15 mg) were added to a solution of N-{4-[3-(acetylmethylamino)pyrrolidin-1-yl]phenyl}-2-(4-hydroxyphenyl)propionamide (27 mg) in DMF (1 ml). After a reaction time of 2 hours at room temperature, water was added to the mixture, and it was extracted with ethyl acetate. The organic phase was dried over sodium sulfate and concentrated, and the residue was crystallized from diethyl ether/methanol. This resulted in the product with the molecular weight of 437.59 (C26H35N3O3); MS (ESI): 438 (M+H+).

N-{4-[3-(Acetylmethylamino)pyrrolidin-1-yl]phenyl}-2-(4-hydroxyphenyl)propionamide N-[1-(4-Aminophenyl)pyrrolidin-3-yl]-N-methylacetamide was reacted with 2-(4-hydroxyphenyl)propionic acid by method I. This resulted in the product with the molecular weight of 381.48 (C22H27N3O3); MS (ESI): 382 (M+H+).

Example 238

N-{4-[3-(Acetylmethylamino)pyrrolidin-1-yl]phenyl}-2-(4-isobutoxyphenyl)acetamide

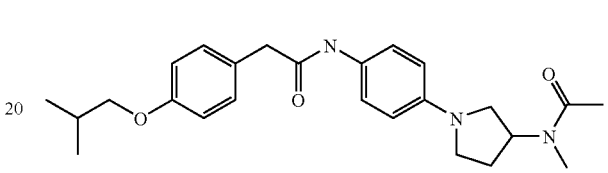

N-{4-[3-(Acetylmethylamino)pyrrolidin-1-yl]phenyl}-2-(4-hydroxyphenyl)acetamide was reacted with isobutyl bromide by method H. This resulted in the product with the molecular weight of 423.56 (C25H33N3O3); MS (ESI): 424 (M+H+).

N-{4-[3-(Acetylmethylamino)pyrrolidin-1-yl]phenyl}-2-(4-hydroxyphenyl)acetamide

Method I

4-Hydroxyphenylacetic acid (305 mg), 1-hydroxybenzotriazole (300 mg) and 1-(3-dimethylaminopropyl)-3-ethylcarbodiimide hydrochloride (480 mg) in DMF (5 ml) were stirred with N-[1-(4-aminophenyl)pyrrolidin-3-yl]-N-methylacetamide (470 mg) at room temperature for 3 hours. Water was then added to the mixture, which was extracted with ethyl acetate. The organic phase was washed with saturated sodium chloride solution, dried over sodium sulfate, concentrated and crystallized from diethyl ether. This resulted in the product with the molecular weight of 367.45 (C21H25N3O3); MS (ESI): 368 (M+H+).

Example 239

(R)-N-{4-[3-(Acetylmethylamino)pyrrolidin-1-yl]phenyl}-2-(4-butoxyphenyl)acetamide

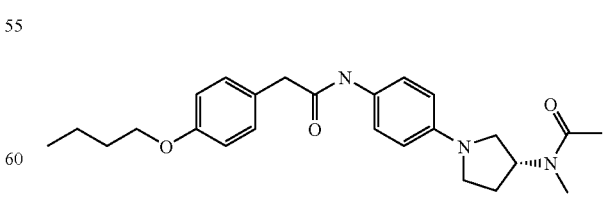

(R)-N-[1-(4-Aminophenyl)pyrrolidin-3-yl]-N-methylacetamide was reacted with 4-butoxyphenylacetic acid by method E. This resulted in the product with the molecular weight of 423.56 (C25H33N3O3); MS (ESI): 424 (M+H+).

Example 240

N-{4-[3-(Acetylmethylamino)pyrrolidin-1-yl]phenyl}-2-(4-cyclopropylmethoxyphenyl)propionamide

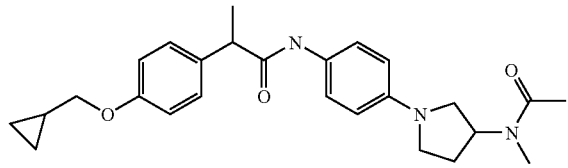

N-{4-[3-(Acetylmethylamino)pyrrolidin-1-yl]phenyl}-2-(4-hydroxyphenyl)propionamide was reacted with bromomethylcyclopropane by method H. This resulted in the product with the molecular weight of 435.57 (C26H33N3O3); MS (ESI): 436 (M+H+).

Example 241

N-{4-[3-(Acetylmethylamino)pyrrolidin-1-yl]phenyl}-2-(4-cyclobutylmethoxyphenyl)propionamide

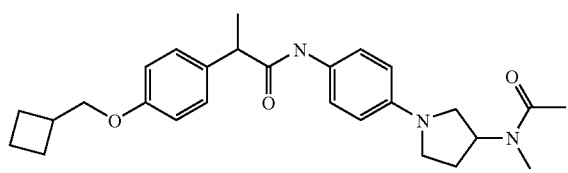

N-{4-[3-(Acetylmethylamino)pyrrolidin-1-yl]phenyl}-2-(4-hydroxyphenyl)propionamide was reacted with bromomethylcyclobutane by method H. This resulted in a product with the molecular weight 449.60 (C27H35N3O3); MS (ESI): 450 (M+H+).

Example 242

1-(4-Methoxyphenyl)cyclopropanecarboxylic acid {4-[3-(acetylmethylamino)pyrrolidin-1-yl]phenyl}amide

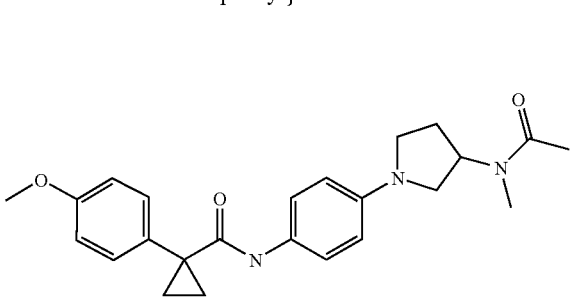

N-[1-(4-Aminophenyl)pyrrolidin-3-yl]-N-methylacetamide was reacted with 1-(4-methoxyphenyl)-1-cyclopropanecarboxylic acid by method E. This resulted in the product with the molecular weight of 407.52 (C24H29N3O3); MS (ESI): 408 (M+H+).

Example 243

1-(4-Butoxyphenyl)cyclopropanecarboxylic acid {4-[3-(acetylmethylamino)-pyrrolidin-1-yl]phenyl}amide

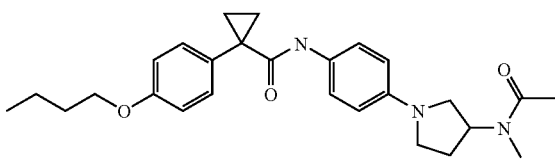

1-(4-Hydroxyphenyl)cyclopropanecarboxylic acid {4-[3-(acetylmethylamino)pyrrolidin-1yl]phenyl}amide was reacted with n-butyl bromide by method H. This resulted in the product with the molecular weight of 449.60, (C27H35N3O3); MS(ESI): 450 (M+H+).

1-(4-Hydroxyphenyl)cyclopropanecarboxylic acid {4-[3-(acetylmethylamino)pyrrolidin-1-yl]phenyl}amide Boron tribromide-dimethyl sulfide (460 mg) was added to a solution of 1-(4-methoxyphenyl)cyclopropanecarboxylic acid {4-[3-(acetylmethylamino)pyrrolidin-1-yl]phenyl}amide (540 mg) in dichloromethane (5.5 ml) at 0° C. After a reaction time of 12 hours at room temperature, water was added to the mixture, the phases were separated, and the aqueous phase was extracted with dichloromethane. The combined organic phases were dried over sodium sulfate, concentrated and purified by chromatography (silica gel, toluene/ethanol/ethyl acetate 8:1:1 with addition of 0.1% triethylamine). This resulted in the product with the molecular weight of 393.49 (C23H27N3O3); MS(ESI): 394 (M+H+).

Example 244

(R)-4-(4-Fluorophenyl)piperidine-1-carboxylic acid {4-[3-(acetylmethylamino)pyrrolidin-1-yl]phenyl}-N-methylamide

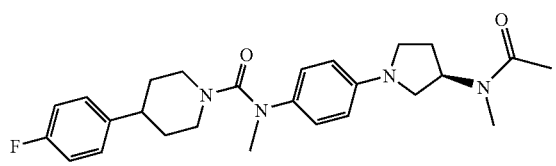

(R)-4-(4-Fluorophenyl)piperidine-1-carboxylic acid {4-[3-(acetylmethylamino)pyrrolidin-1-yl]phenyl}amide (22 mg) was added to a suspension of sodium hydride (95% in oil; 0.005 g) in DMF (1 ml). After evolution of gas ceased, iodomethane (0.02 ml) was added. After two hours, the reaction mixture was cautiously hydrolyzed with water and extracted with dichloromethane. The organic phase was dried over magnesium sulfate and concentrated, and the residue was crystallized from pentane. This resulted in the product with the molecular weight of 452.58 (C26H33FN4O2); MS (ESI): 453 (M+H+).

Example 245

5-2-[(2-Fluorophenyl)ethynyl]furan-2-carboxylic acid {4-[3-(acetylmethylamino)pyrrolidin-1-yl]phenyl}amide

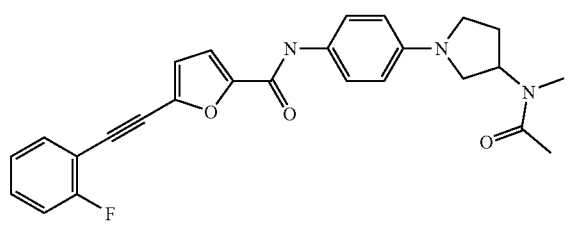

Method J

Firstly diisopropylamine (14.9 mg) and then a solution of 5-bromofuran-2-carboxylic acid {4-[3-(acetylmethylamino)pyrrolidin-1-yl]phenyl}amide (50.0 mg) and 1-ethynyl-2-fluorobenzene (17.7 mg) in dioxane (0.5 ml) and DMF (0.2 ml) were added under inert conditions to a suspension of palladium bis(tri-tert-butylphosphine) dichloride (3.8 mg) and copper(I) iodide (0.9 mg) in DMF (0.5 ml). After a reaction time of 12 hours at room temperature, the mixture was diluted with ethyl acetate and filtered through silica gel, and the filtrate was concentrated and purified by preparative HPLC. This resulted in the product with the molecular weight of 445.18 (C26H24FN3O3); MS(ESI): 446 (M+H+) as hydrotrifluoroacetate.

5-Bromofuran-2-carboxylic acid {4-[3-(acetylmethylamino)pyrrolidin-1-yl]phenyl}amide N-[1-(4-Aminophenyl)pyrrolidin-3-yl]-N-methylacetamide was reacted with 5-bromo-2-furancarboxylic acid by method E. This resulted in the product with the molecular weight of 406.28 (C18H20BrN3O3); MS(ESI): 407 (M+H+).

Example 246

5-2-[(4-Fluorophenyl)ethynyl]furan-2-carboxylic acid {4-[3-(acetylmethylamino)pyrrolidin-1-yl]phenyl}amide

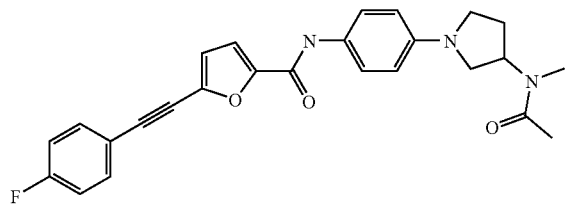

5-Bromofuran-2-carboxylic acid {4-[3-(acetylmethylamino)pyrrolidin-1-yl]phenyl}amide was reacted with 1-ethynyl-4-fluorobenzene by method J. This resulted in the product with the molecular weight of 445.18 (C26H24FN3O3); MS(ESI): 446 (M+H+) as hydrotrifluoroacetate.

Example 247

5-2-[(2-Chlorophenyl)ethynyl]furan-2-carboxylic acid {4-[3-(acetylmethylamino)pyrrolidin-1-yl]phenyl}amide

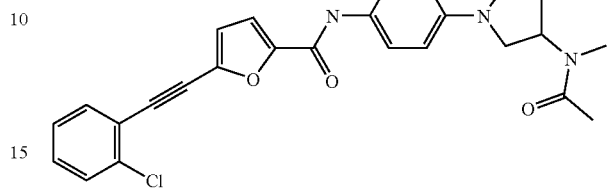

5-Bromofuran-2-carboxylic acid {4-[3-(acetylmethylamino)pyrrolidin-1-yl]phenyl}amide was reacted with 1-ethynyl-2-chlorobenzene by method J. This resulted in the product with the molecular weight of 461.15 (C26H24ClN3O3); MS(ESI): 462 (M+H+) as hydrotrifluoroacetate.

Example 248

R-4-Butoxy-N-(3-fluoro-4-{3-[(2-hydroxy-2-methylpropyl)methylamino]-pyrrolidin-1-yl}-phenyl) benzamide

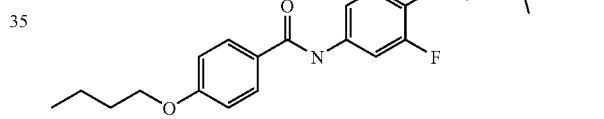

A solution of (R)-4-butoxy-N-[3-fluoro-4-(3-methylaminopyrrolidin-1-yl)phenyl]benzamide (0.03 g) and isobutylene oxide in ethanol (5 ml) were heated under reflux for 3 hours. It was then concentrated in vacuo. This resulted in the product with the molecular weight of 457.59 (C26H36FN3O3); MS (ESI): 458 (M+H+).

Example 249

R-4-Butoxy-N-(3-fluoro-4-{3-[(3-hydroxy-3-methylbutyl)methylamino]pyrrolidin-1-yl}-phenyl)-N-methylbenzamide

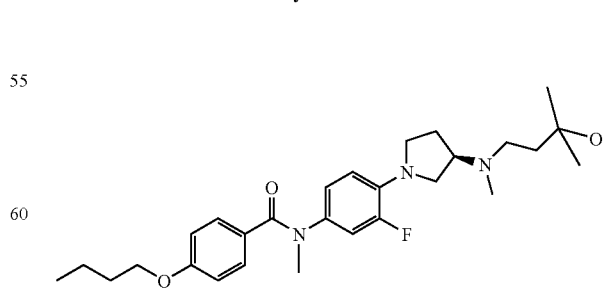

A solution of (R)-4-butoxy-N-[3-fluoro-4-(3-methylaminopyrrolidin-1-yl)phenyl]benzamide (0.03 g), triethylamine (0.02 g) and 4-bromo-2-methylbutan-2-ol (0.03 g) in DMF (2 ml) was heated at 80° C. for 16 hours. After cooling, ethyl acetate (100 ml) was added, the mixture was washed with water (2×50 ml), and the organic phase was dried with sodium sulfate, filtered and concentrated. The residue was purified by preparative HPLC. This resulted in the product with the molecular weight of 471.62 (C27H38FN3O3); MS (ESI): 472 (M+H+).

4-Bromo-2-methylbutan-2-ol

Methylmagnesium bromide (3M in diethyl ether, 46 ml) was added to a solution of ethyl 3-bromopropionate (10 g) in diethyl ether (100 ml) at room temperature under argon. During this, the mixture was kept at above 20° C. and below 35° C. After 2 hours, the mixture was poured into a saturated ammonium chloride solution. This was followed by extraction with diethyl ether, drying with sodium sulfate, filtration and concentration. This resulted in the desired product.

Example 250

R-4-Butoxy-N-[6-(3-dicyclopropylaminopyrrolidin-1-yl)-pyridin-3-yl]benzamide

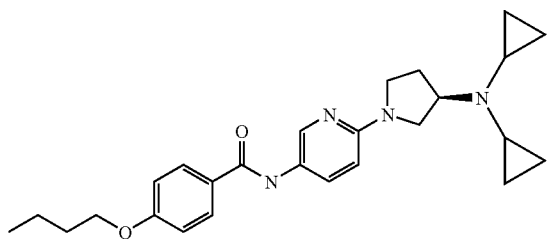

Method K

A solution of (R)-N-[6-(3-aminopyrrolidin-1-yl)pyridin-3-yl]-4-butoxybenzamide (0.065 g) in methanol (2 ml) was mixed with glacial acetic acid (0.11 ml) and [(1-ethoxycyclopropyl)oxy]trimethylsilane (0.19 g). Then sodium cyanoborohydride (0.051 g) was added and the mixture was heated under reflux for 16 hours. The mixture was then filtered, concentrated, taken up in dichloromethane, washed with sodium hydroxide (2N; 20 ml) and sodium chloride solution (20 ml), dried with magnesium sulfate and concentrated. The residue was purified by preparative HPLC. This resulted in the product with the molecular weight of 434.59 (C26H34N4O2); MS (ESI): 435 (M+H+).

Example 251

R-4-Butoxy-N-[6-(3-dicyclopropylaminopyrrolidin-1-yl)pyridin-3-yl]-N-methylbenzamide

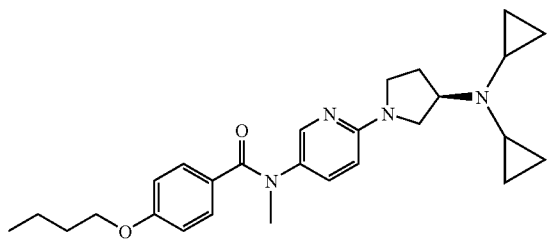

(R)-4-Butoxy-N-[6-(3-dicyclopropylaminopyrrolidin-1-yl)pyridin-3-yl]benzamide was methylated by method F. This resulted in the product with the molecular weight of 448.61 (C27H36N4O2); MS (ESI): 449 (M+H+).

Example 252

R-4-Butoxy-N-{6-[3-(cyclopropylmethylamino)pyrrolidin-1-yl]pyridin-3-yl}benzamide

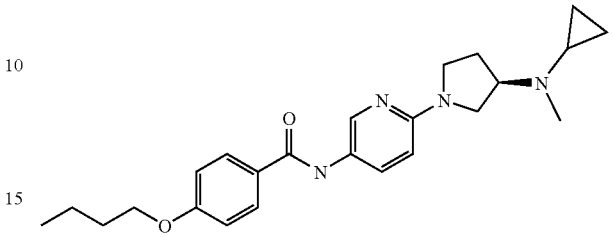

(R)-4-Butoxy-N-[6-(3-methylaminopyrrolidin-1-yl)pyridin-3-yl]benzamide was cyclopropylated by method K. This resulted in the product with the molecular weight of 408.551 (C24H32N4O2); MS (ESI): 409 (M+H+).

Example 253 tert-Butyl {1-[4-(2-amino-4-butoxybenzoylamino)-3-fluorophenyl]pyrrolidin-3-yl}methylcarbamate

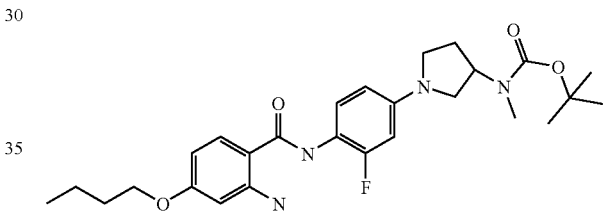

tert-Butyl [1-(4-amino-3-fluorophenyl)pyrrolidin-3-yl]methylcarbamate was reacted with 4-butoxy-2-nitrobenzoic acid by method E, followed by hydrogenation. This resulted in the product with the molecular weight of 500.62 (C27H37FN4O4); MS (ESI): 501 (M+H+).

4-Butoxy-2-nitrobenzoic acid

A solution of 4-fluoro-2-nitrobenzoic acid (1.81 g) in butanol (20 ml) was mixed with sulfuric acid (3 ml) and stirred at 110° C. for 4 hours. Ethyl acetate (100 ml) was added, and the mixture was washed with saturated sodium bicarbonate solution (3×50 ml), dried with sodium sulfate, filtered and concentrated in vacuo. The residue (2.2 g) was added dropwise at −10° C. to a sodium butoxylate solution prepared from butanol (20 ml) and sodium hydride (2.18 g) at −10° C. under argon and then stirred for 20 hours. Ethyl acetate (100 ml) was added, and the mixture was washed with water (2×50 ml), dried over sodium sulfate, filtered and concentrated in vacuo. The residue was purified by preparative HPLC. The butyl 4-butoxy-2-nitrobenzoate was hydrolyzed with sodium hydoxide (5N; 100 ml) in ethanol at room temperature for 3 hours. The mixture was acidified with hydrochloric acid (10N; 100 ml) and extracted with dichloromethane, and the organic phase was dried over sodium sulfate, filtered and concentrated. This resulted in the product with the molecular weight of 239.23 (C11H13NO5); MS (ESI): 240 (M+H+).

Example 254

N-{4-[3-(7-Azabicyclo[2.2.1]hept-7-yl)-2-oxopyrrolidin-1-yl]phenyl}-4-cyclohexyl-N-methylbenzamide

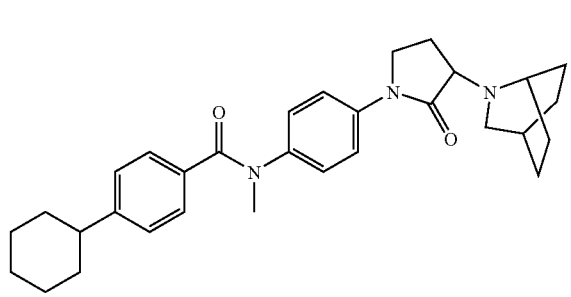

Method L

A mixture of N-[4-(3-bromo-2-oxopyrrolidin-1-yl)phenyl]-4-cyclohexyl-N-methylbenzamide (100 mg), potassium carbonate (60 mg), 7-azabicyclo[2.2.1]heptane (44 mg) and DMF (2 ml) was kept at 50° C. for 6 hours. The mixture was diluted with water and extracted with ethyl acetate.

The organic phase was dried over magnesium sulfate and concentrated. The residue was purified by preparative HPLC. This resulted in the product with the molecular weight of 471.65 (C30H37N3O2); MS (ESI): 472 (M+H+).

N-[4-(3-Bromo-2-oxopyrrolidin-1-yl)phenyl]-4-cyclohexyl-N-methylbenzamide

N-(4-Aminophenyl)-4-cyclohexyl-N-methylbenzamide (3.0 g) in acetonitrile (30 ml) was mixed with trisodium phosphate (0.95 g) and, at 0° C., 2-bromo-4-chlorobutyryl bromide (2.9 g) was added. After one hour, a solution of sodium hydroxide (0.85 g) in water (10 ml) was added and the mixture was stirred vigorously at room temperature for 6 hours. The same amount of sodium hydroxide solution was then added, and stirring was continued for 48 hours. The reaction solution was diluted with water and extracted with ethyl acetate. The organic phase was dried over magnesium sulfate and concentrated. The residue was purified by chromatography on silica gel (mobile phase ethyl acetate/heptane 1:2). This resulted in the product with the molecular weight of 455.40 (C24H27BrN2O2); MS (ESI): 456 (M+H+).

N-(4-Aminophenyl)-4-cyclohexyl-N-methylbenzamide

4-Cyclohexylcarboxylic acid (5.0 g) and 4-nitrophenylisocyanate (4.0 g) were stirred in toluene (150 ml) for 3 hours and then left to stand overnight. The precipitate was filtered off with suction and washed with diethyl ether. The resulting amide was ethylated by method F and hydrogenated by method B. This resulted in the product with the molecular weight of 308.43 (C20H24N2O); MS (ESI): 309 (M+H+).

Example 255

4-Cyclohexyl-N-methyl-N-[4-(3-morpholin-4-yl-2-oxopyrrolidin-1-yl)phenyl]benzamide

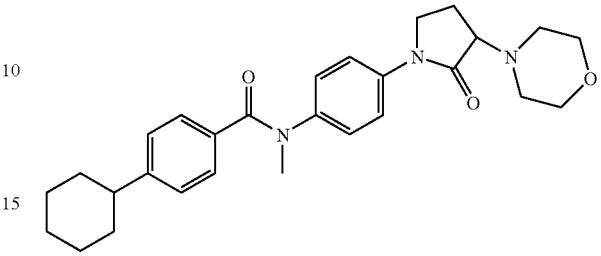

N-[4-(3-Bromo-2-oxopyrrolidin-1-yl)phenyl]-4-cyclohexyl-N-methylbenzamide was reacted with morpholine by method L. This resulted in the product with the molecular weight 461.61 (C28H35N3O3); MS (ESI): 462 (M+H+).

Example 256

4-Cyclohexyl-N-methyl-N-[4-(2-oxo-3-piperidin-1-ylpyrrolidin-1-yl)phenyl]benzamide

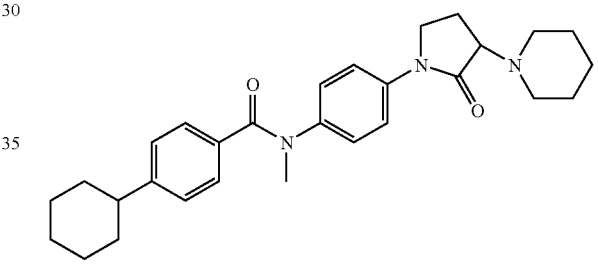

N-[4-(3-Bromo-2-oxopyrrolidin-1-yl)phenyl]-4-cyclohexyl-N-methylbenzamide was reacted with piperidine by method L. This resulted in the product with the molecular weight of 459.64 (C29H37N3O2); MS (ESI): 460 (M+H+).

Example 257

4-Cyclohexyl-N-methyl-N-[4-(2'-oxo[1,3']bipyrrolidinyl-1'-yl)phenyl]benzamide

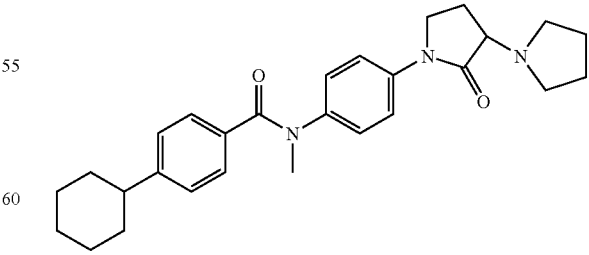

N-[4-(3-Bromo-2-oxopyrrolidin-1-yl)phenyl]-4-cyclohexyl-N-methylbenzamide was reacted with pyrrolidine by method L. This resulted in the product with the molecular weight of 445.61 (C28H35N3O2); MS (ESI): 446 (M+H+).

Example 258

4-Cyclohexyl-N-methyl-N-[4-(3-methylamino-2-oxopyrrolidin-1-yl)phenyl]benzamide

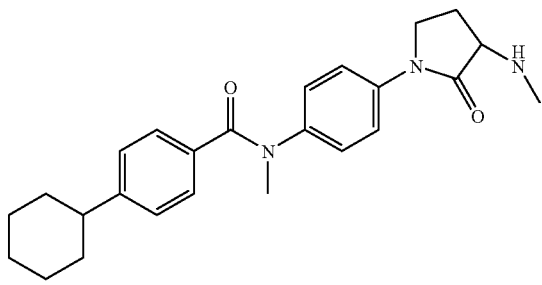

N-[4-(3-Bromo-2-oxopyrrolidin-1-yl)phenyl]-4-cyclohexyl-N-methylbenzamide was reacted with methylamine by method L. This resulted in the product with the molecular weight of 405.54 (C25H31N3O2); MS (ESI): 406 (M+H+).

Example 259

4-Cyclohexyl-N-[4-(3-cyclohexylamino-2-oxopyrrolidin-1-yl)phenyl]-N-methylbenzamide

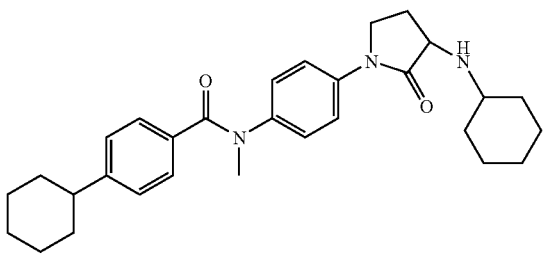

N-[4-(3-Bromo-2-oxopyrrolidin-1-yl)phenyl]-4-cyclohexyl-N-methylbenzamide was reacted with cyclohexylamine by method L. This resulted in the product with the molecular weight of 473.66 (C30H39N3O2); MS (ESI): 474 (M+H+).

Example 260

4-Cyclohexyl-N-{4-[3-(cyclopropylmethylamino)-2-oxopyrrolidin-1-yl]phenyl}-N-methylbenzamide

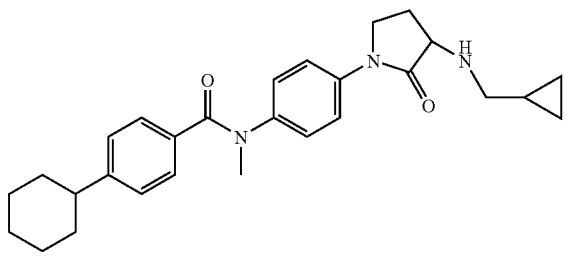

N-[4-(3-Bromo-2-oxopyrrolidin-1-yl)phenyl]-4-cyclohexyl-N-methylbenzamide was reacted with cyclopropylmethylamine by method L. This resulted in the product with the molecular weight of 445.61 (C28H35N3O2); MS (ESI): 446 (M+H+).

Example 261

N-{4-[3-(Acetylmethylamino)-2-oxopyrrolidin-1-yl]phenyl}-4-cyclohexyl-N-methyl-benzamide

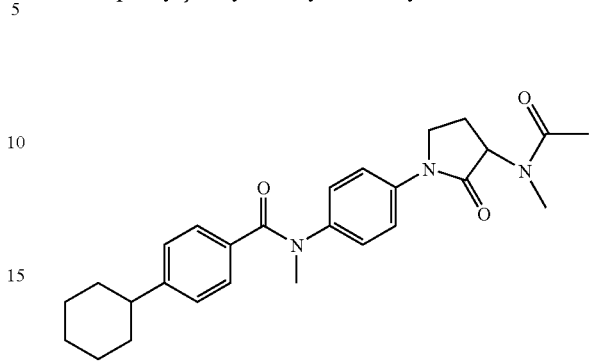

4-Cyclohexyl-N-methyl-N-[4-(3-methylamino-2-oxopyrrolidin-1-yl)phenyl]benzamide (52 mg) was mixed with pyridine (0.5 ml) and acetic anhydride (130 mg) and, after 3 hours, volatile fractions were removed in vacuo. This resulted in the product with the molecular weight of 447.58 (C27H33N3O3); MS (ESI): 448 (M+H+).

Example 262

4-Cyclohexyl-N-methyl-N-[4-(4-methylamino-2-oxopyrrolidin-1-yl)phenyl]benzamide

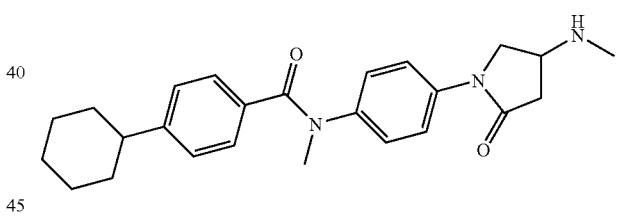

tert-Butanol (8 ml), triethylamine (350 mg) and finally diphenylphosphoryl azide (1.18 g) were added to 1-{4-[(4-cyclohexylbenzoyl)methylamino]phenyl}-5-oxopyrrolidin-3-carboxylic acid (1.5 g), and the mixture was heated at 95° C. for 48 hours. The reaction solution was diluted with ethyl acetate and washed twice with water. The organic phase was dried over magnesium sulfate and concentrated. The crude product was reacted further by method G. This resulted in the product with the molecular weight of 405.54 (C25H31N3O2); MS (ESI): 406 (M+H+).

1-{4-[(4-Cyclohexylbenzoyl)methylamino]phenyl}-5-oxo-pyrrolidine-3-carboxylic acid N-(4-Aminophenyl)-4-cyclohexyl-N-methylbenzamide (3.0 g) was heated with itaconic acid (1.27 g) at 100° C. for 3 hours. Purification took place by filtration through silica gel (mobile phase ethyl acetate/methanol 5:1). This resulted in the product with the molecular weight of 420.51 (C25H28N2O4); MS (ESI): 421 (M+H+).

Example 263

N-{4-[4-(Acetylmethylamino)-2-oxopyrrolidin-1-yl]phenyl}-4-cyclohexyl-N-methylbenzamide

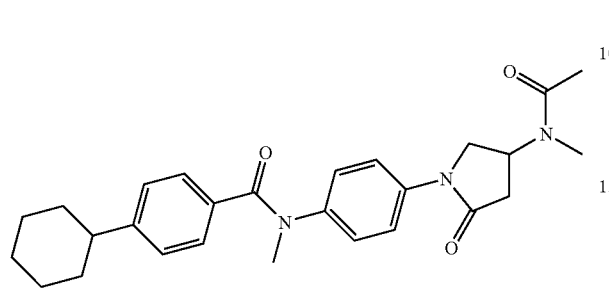

4-Cyclohexyl-N-methyl-N-[4-(4-methylamino-2-oxopyrrolidin-1-yl)phenyl]benzamide (101 mg) was mixed with pyridine (20 mg) and acetic anhydride (25 mg) and, after 3 hours, volatile fractions were removed in vacuo. This resulted in the product with the molecular weight of 447.58 (C27H33N3O3); MS (ESI): 448 (M+H+).

Example 264 tert-Butyl (1-{5-[(4-cyclohexylbenzoyl)propylamino]pyridin-2-yl}pyrrolidin-3-yl)methylcarbamate

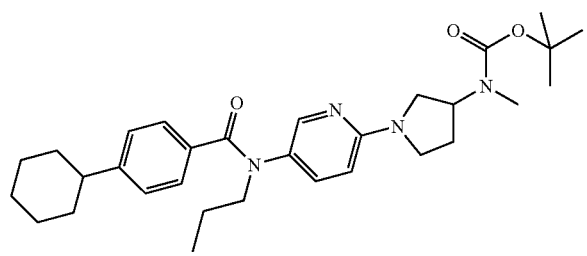

Method F-a tert-Butyl {1-[5-(4-cyclohexylbenzoylamino)pyridin-2-yl]pyrrolidin-3-yl}methylcarbamate (50 mg), cesium carbonate (249 mg), potassium iodide (17 mg), N-methylpyrrolidone (1.5 ml) and propyl iodide (40 mg) were stirred at 60° C. for 5 hours. If conversion was incomplete, the mixture was heated to 100° C. and, after addition of further propyl iodide (40 mg), heated at 140° C. for 12 hours. The reaction mixture was diluted with ethyl acetate, washed with water and sodium bicarbonate solution, dried over Chromabond XTR and concentrated. The residue was purified by preparative HPLC. This resulted in the product with the molecular weight of 520.72 (C31H44N4O3); MS (ESI): 521 (M+H+).

Example 265 tert-Butyl (1-{5-[(4-cyclohexylbenzoyl)-(1-ethylpropyl)amino]pyridin-2-yl}pyrrolidin-3-yl)-methylcarbamate

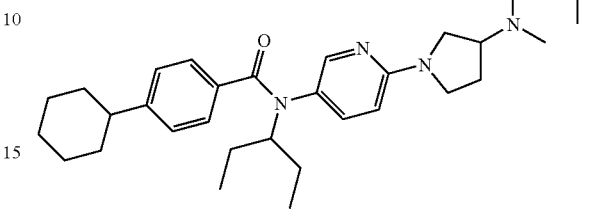

tert-Butyl {1-[5-(4-cyclohexylbenzoylamino)pyridin-2-yl]pyrrolidin-3-yl}methylcarbamate was reacted with 2-ethylbutyl bromide by method F-a. This resulted in the product with the molecular weight of 548.78 (C33H48N4O3); MS (ESI): 549 (M+H+).

Example 266 tert-Butyl (1-{5-[(4-cyclohexylbenzoyl)-(3-methylbut-2-enyl)amino]pyridin-2-yl}pyrrolidin-3-yl)methylcarbamate

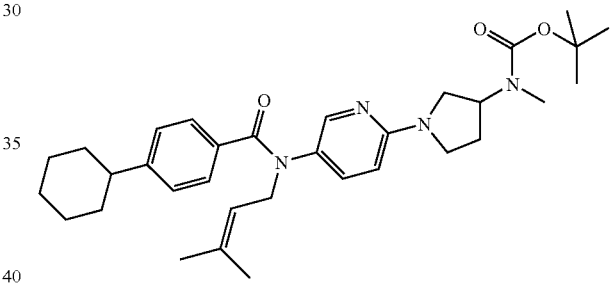

tert-Butyl {1-[5-(4-cyclohexylbenzoylamino)pyridin-2-yl]pyrrolidin-3-yl}methylcarbamate was reacted with 3-methyl-2-butenyl bromide by method F-a. This resulted in the product with the molecular weight of 546.76 (C33H46N4O3); MS (ESI): 547 (M+H+).

Example 267 tert-Butyl (1-{5-[(4-cyclohexylbenzoyl)methylamino]pyridin-2-yl}pyrrolidin-3-yl)methylcarbamate

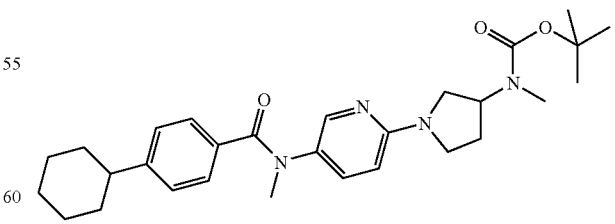

tert-Butyl {1-[5-(4-cyclohexylbenzoylamino)pyridin-2-yl]pyrrolidin-3-yl}methylcarbamate was reacted with methyl iodide by method F-a. This resulted in the product with the molecular weight of 492.67 (C29H40N4O3); MS (ESI): 493 (M+H+).

The following further compounds were obtained by method F-a from tert-butyl {1-[5-(4-cyclohexylbenzoylamino)pyridin-2-yl]pyrrolidin-3-yl}methylcarbamate and the appropriate alkylating agent:

tert-Butyl (1-{5-[sec-butyl-(4-cyclohexylbenzoyl)amino]pyridin-2-yl}pyrrolidin-3-yl)methylcarbamate tert-Butyl (1-{5-[(4-cyclohexylbenzoyl)isopropylamino]pyridin-2-yl}pyrrolidin-3-yl)methylcarbamate tert-Butyl (1-{5-[(4-cyclohexylbenzoyl)prop-2-inylamino]pyridin-2-yl}pyrrolidin-3-yl)-methylcarbamate

Example 268

5-p-Tolylethinylfuran-2-carboxylic acid [4-(3-dimethylaminopyrrolidin-1-yl)phenyl]amide

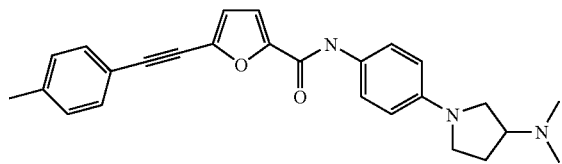

0.042 ml of diisopropylamine was added under argon to 3.8 mg of Pd(tBu)$_2$Cl$_2$ and 0.95 mg of CuI in 0.2 ml of DMF. A solution of 94.6 mg of 5-bromofuran-2-carboxylic acid [4-(3-dimethylaminopyrrolidin-1-yl)phenyl]-amide in 0.3 ml of DMF and a solution of 4-ethynyltoluene in 0.3 ml of DMF were then added dropwise. The solution was stirred at room temperature overnight. The precipitate which had separated out was filtered off with suction and the filtrate purified by preparative HPLC. The desired product with the molecular weight of 413.52; MS (ESI): 414 was obtained as hydrotrifluoroacetate.

5-Bromofuran-2-carboxylic acid [4-(3-dimethylaminopyrrolidin-1-yl)phenyl]amide

[1-(4-Aminophenyl)pyrrolidin-3-yl]dimethylamine was reacted with 5-bromo-2-furancarboxylic acid by method E. The product with a molecular weight of 378.27 (C17H20BrN3O2); MS (ESI): 379 (M+H+) was obtained as hydrotrifluoroacetate.

Examples 269-273 were prepared analogously:

| Ex. No. | Structure | Molecular formula | Molecular weight | M+H+ |
|---|---|---|---|---|
| 269 | 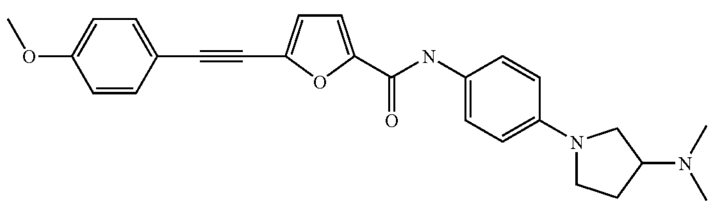 | C26H27N3O3 | 429.21 | 430 |
| 270 | 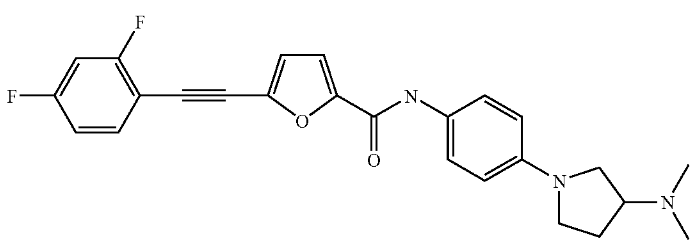 | C25H23F2N3O2 | 435.18 | 436 |
| 271 | 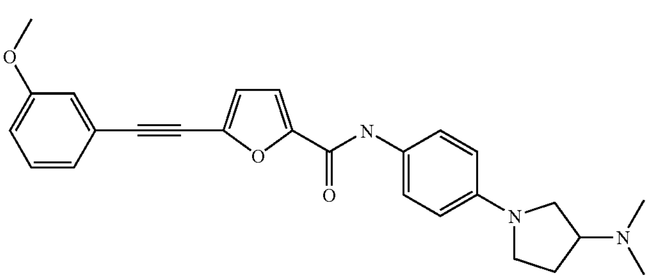 | C26H27N3O3 | 429.21 | 430 |

| Ex. No. | Structure | Molecular formula | Molecular weight | M+H+ |
|---|---|---|---|---|
| 272 | 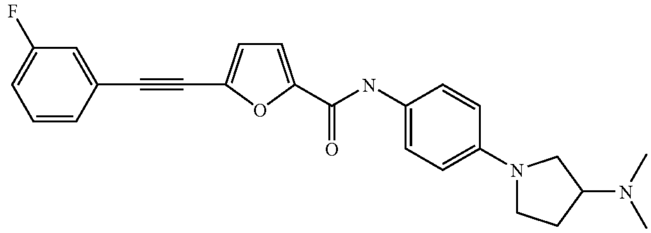 | C25H24FN3O2 | 417.19 | 418 |
| 273 | 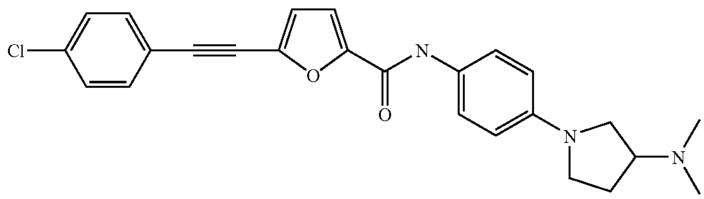 | C25H24ClN3O2 | 433.16 | 434 |

Example 274

(R)-4'-Fluorobiphenyl-4-carboxylic acid [6-(3-dimethylaminopyrrolidin-1-yl)pyridin-3-yl]-amide

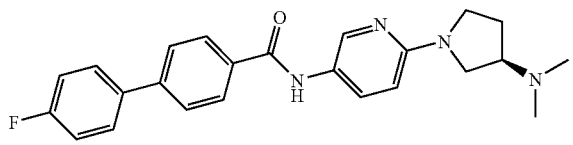

Method M (R)-4'-Fluorobiphenyl-4-carboxylic acid [6-(3-methylaminopyrrolidin-1-yl)pyridin-3-yl]-amide (390 mg) dissolved in formic acid (230 mg) was mixed with formaldehyde solution (37% aq.; 0.4 ml) and the mixture was heated at 80° C. for 3 hours. The cooled reaction solution was concentrated and partitioned between ethyl acetate and a saturated sodium carbonate solution. The organic phase was dried over magnesium sulfate and concentrated. The crude product was purified by preparative HPLC. This resulted in the product with the molecular weight of 404.49 (C24H25FN4O); MS (ESI): 405 (M+H+).

Example 275

1-(4-Fluorophenyl)piperidine-4-carboxylic acid {4-[3-(acetylmethylamino)pyrrolidin-1-yl]phenyl}amide

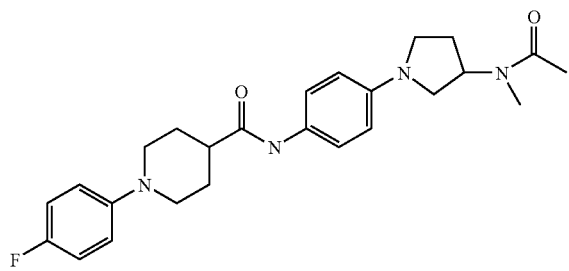

Method E-a

A mixture of 0.048 g of 1-(4-fluorophenyl)piperidine-4-carboxylic acid and 0.5 ml of SOCl$_2$ and one drop of DMF were stirred at room temperature for 2 hours. The excess SOCl$_2$ was then removed in vacuo. The residue was dissolved in 0.4 ml of DMF, and 0.033 ml of triethylamine and 0.048 g of N-[1-(4-aminophenyl)pyrrolidin-3-yl]-N-methylacetamide were added. The solution was stirred at room temperature overnight. The solution was then filtered and purified by preparative HPLC. This resulted in the product with the molecular weight of 438.20 (C25H31FN4O2); MS (ESI): 439 (M+H+) as hydrotrifluoroacetate.

1-(4-Fluorophenyl)piperidine-4-carboxylic acid 0.875 g of 4-bromofluorobenzene, 0.016 g of Pd(dba)3*CHCl3, 0.022 g 2-(dicyclohexylphosphino)biphenyl and 2.28 g of cesium carbonate were put in a heat-dried and argon-flushed flask, and 0.943 g of ethyl 4-piperidinecarboxylate in 5 ml of degassed toluene was added. The solution was heated at 100° C. overnight. The mixture was cooled and then concentrated in vacuo. The residue was taken up in ethyl acetate/water. The organic phase was washed with 10% NaHCO3 solution, dried over sodium sulfate and concentrated in vacuo. The residue was purified by preparative HPLC.

4.4 ml of a 2N potassium hydroxide solution were added to a solution of 1.1 g of ethyl 1-(4-fluorophenyl)piperidine-4-carboxylate in 100 ml of methanol. The mixture was stirred at room temperature overnight. The pH was then adjusted to 6 with 5% hydrochloric acid, and the solution was concentrated in vacuo. The residue was purified by preparative HPLC.

Example 276

4-Phenoxycyclohexanecarboxylic acid {4-[3-(acetylmethylamino)pyrrolidin-1-yl]phenyl}amide

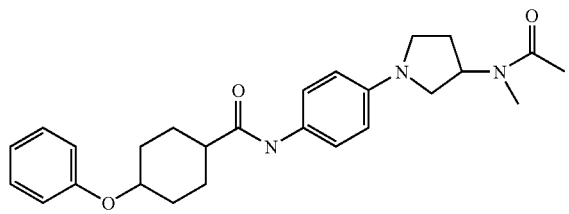

0.251 g of PyBOP and 0.135 ml of triethylamine were added to a solution of 0.106 g of 4-phenoxycyclohexanecarboxylic acid and 0.113 g of N-[1-(4-aminophenyl)pyrrolidin-3-yl]-N-methylacetamide in 9 ml of DMF at 0° C. After 10 minutes, the solution was allowed to reach room temperature and was stirred at this temperature overnight. The solvent was then removed in vacuo, and the residue was taken up in water/ethyl acetate. The ethyl acetate phase was washed with 10% citric acid and 10% NaHCO3 solution and dried over sodium sulfate, and the solvent was removed in vacuo. The residue was purified by preparative HPLC. The desired product was obtained. Molecular weight 435.25 (C26H33N3O3), MS: 436 (M+H+).

4-Phenoxycyclohexanecarboxylic acid 0.63 g of p-toluenesulfonyl chloride was added to a solution of 0.522 g of ethyl 4-hydroxycyclohexanecarboxylate in 5.0 ml of pyridine. The reaction was stirred at room temperature for 3 hours. The reaction mixture was concentrated in vacuo. The resulting solid was taken up in water and ethyl acetate, and the organic phase was washed three times with 2N hydrochloric acid and once with saturated NaCl solution. The organic phase was dried over sodium sulfate and concentrated in vacuo. The resulting product was employed without further purification in the next step. The resulting product (0.55 g) was dissolved in 11.2 ml of DMF, and 0.159 g of phenol and 0.549 g of cesium carbonate were added. The solution was then heated at 80° C. for 6 hours. After cooling, the mixture was concentrated in vacuo and purified by column chromatography on silica gel (eluent: ethyl acetate/n-heptane 1:1). The desired product was obtained. Molecular weight 248.32 (C15H20O3), MS: 249 (M+H+).

0.06 ml of 2N potassium hydroxide solution was added to a solution of 0.12 g of ethyl 4-phenoxycyclohexanecarboxylate in 8 ml of water/THF (1:1). The solution was heated at 60° C. for 3 hours. Ethyl acetate and 10% citric acid were added to the mixture. The aqueous phase was extracted three times with ethyl acetate, dried over sodium sulfate and concentrated in vacuo. The resulting compound was employed without further purification in the next stage.

Example 277

N-[4-(3-Cyclohexylaminopyrrolidin-1-yl)phenyl]-4-isobutoxybenzamide

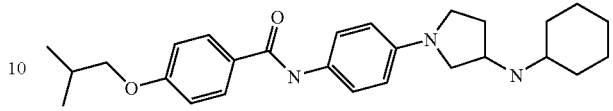

Method N (4-Isobutoxy-N-[4-(3-oxopyrrolidin-1-yl)phenyl]benzamide (50 mg) in methanol (2 ml) was mixed with aminocyclohexane (28 mg) and glacial acetic acid (10 mg), and a solution of sodium cyanoborohydride (1M in toluene; 0.17 ml) was added. After 8 hours, the reaction solution was concentrated and partitioned between ethyl acetate and water. The organic phase was dried over magnesium sulfate and concentrated. The crude product was purified by preparative HPLC. This resulted in the. product with the molecular weight of 435.61 (C27H37N3O2); MS (ESI): 436 (M+H+).

4-Isobutoxy-N-[4-(3-oxopyrrolidin-1-yl)phenyl] benzamide

4-Isobutoxybenzoic acid was reacted with 4-(1,4-dioxa-7-azaspiro[4.4]non-7-yl)phenylamine by method E-a. The resulting amide (0.25 g) in acetone (10 ml) was mixed with para-toluene sulfonic acid (monohydrate, 109 mg), and the mixture was boiled under reflux for 8 hours. After adding triethylamine (0.5 ml), the mixture was diluted with water and extracted with ethyl acetate. The organic phase was dried over magnesium sulfate and concentrated. This resulted in the product with the molecular weight of 352.44 (C21H24N2O3); MS (ESI): 353 (M+H+).

4-Butoxy-N-[4-(3-oxopyrrolidin-1-yl)-phenyl]benzamide was obtained using 4-butoxybenzoic acid in an analogous way. Likewise, 4-butoxybenzoic acid and 4-(1,4-dioxa-7-azaspiro[4.4]non-7-yl)-3-fluorophenylamine initially resulted in 4-butoxy-N-[4-(1,4-dioxa-7-azaspiro[4.4]non-7-yl)-3-fluorophenyl]benzamide which, after methylation by method F and treatment with para-toluenesulfonic acid as described above, afforded 4-butoxy-N-[3-fluoro-4-(3-oxopyrrolidin-1-yl)phenyl]benzamide.

4-(1,4-Dioxa-7-azaspiro[4.4]non-7-yl)phenylamine

Trimethylchlorosilane (9.3 g) was slowly added to a solution of 1-benzyl-3-pyrrolidinone (5.0 g) in dichloromethane (30 ml) and ethylene glycol (2.67 g). After 18 hours, the mixture was poured into sodium hydroxide solution (1N). The organic phase was separated off, dried over magnesium sulfate and concentrated. The residue was dissolved in methanol (30 ml) and ammonium formate (5.2 g) and palladium hydroxide (10% on carbon, 300 mg) were added. The mixture was boiled under reflux for 8 hours, filtered and concentrated. The residue was reacted with 4-fluoronitrobenzene by method C. Hydrogenation was finally carried out by method B. This resulted in the product with the molecular weight of 220.27 (C12H16N2O2); MS (ESI): 221 (M+H+).

4-(1,4-Dioxa-7-azaspiro[4.4]non-7-yl)-3-fluorophenylamine was obtained analogously using 3,4-difluoronitrobenzene.

Example 278

(R)-4-(4-Chlorophenyl)piperidin-1-carboxylic acid {4-[3-(methylpyrimidin-2-yl-amino)pyrrolidin-1-yl]phenyl}amide

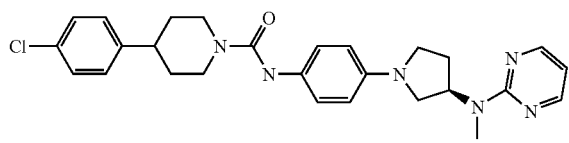

(R)-4-(4-Chlorophenyl)piperidine-1-carboxylic acid [4-(3-methylaminopyrrolidin-1-yl)phenyl]amide (100 mg) was reacted with potassium carbonate (100 mg) and 2-bromopyrimidine (50 mg) in N-methylpyrrolidone (3 ml) at 100° C. for 4 hours. The reaction solution was then partitioned between ethyl acetate and water. The organic phase was dried over magnesium sulfate and concentrated. The crude product was purified by preparative HPLC. This resulted in the product with the molecular weight of 491.04 (C27H31ClN6O); MS (ESI): 491 (M+H+).

Example 279 tert-Butyl [1-(4-{[5-(2-fluorophenyl)furan-2-carbonyl]amino}phenyl)pyrrolidin-3-yl]methylcarbamate

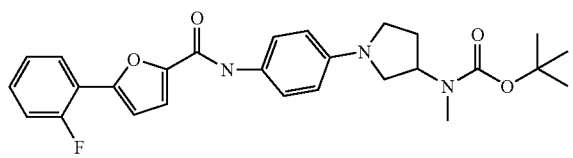

Method O

Tetrakis(triphenylphosphine)palladium(0) (20 mg) was added to a solution of tert-butyl (1-{4-[(5-bromofuran-2-carbonyl)amino]phenyl}pyrrolidin-3-yl)methylcarbamate (252 mg) in degassed toluene (4 ml) under argon in a 10 ml two-necked flask and stirred at room temperature for 10 minutes. Then a solution of 2-fluorobenzeneboronic acid (73 mg in 1 ml of ethanol) and 0.35 ml of 2M sodium carbonate solution were added, and the mixture was stirred at 100° C. for 24 hours.

Then water (5 ml) and ethyl acetate (5 ml) were added to the reaction mixture, the organic phase was separated off, and the aqueous phase was extracted 2× with ethyl acetate (10 ml). The combined organic phases were concentrated and the residue was purified by preparative HPLC. The desired product with the molecular weight of 479.56 (C27H30FN3O4); MS (ESI): 480 (M+H+) was obtained as hydrotrifluoroacetate. It is alternatively possible to use cesium carbonate as base and to heat the reaction at 150° C. in a microwave apparatus for 3 minutes.

tert-Butyl (1-{4-[(5-bromofuran-2-carbonyl)amino]phenyl}pyrrolidin-3-yl)methylcarbamate 5-Bromofuran-2-carboxylic acid was reacted with tert-butyl [1-(4-aminophenyl)pyrrolidin-3-yl]methylcarbamate by method E. This resulted in the product with the molecular weight of 464.36 (C21H26BrN3O4); MS (ESI): 464 (M+H+).

The following compounds were prepared analogously:

5-Bromofuran-2-carboxylic acid [4-(3-dimethylaminopyrrolidin-1-yl)phenyl]amide tert-Butyl (1-{4-[(5-bromothiophene-2-carbonyl)amino]phenyl}pyrrolidin-3-yl)methylcarbamate 2-Bromothiazole-4-carboxylic acid [4-(3-dimethylaminopyrrolidin-1-yl)phenyl]amide 4-Iodo-N-[4-(3-dimethylaminopyrrolidin-1-yl)phenyl]benzamide (R)-N-[4-(3-Dimethylaminopyrrolidin-1-yl)-3-fluorophenyl]-4-iodobenzamide 4-Bromo-N-[4-(3-dimethylaminopyrrolidin-1-yl)phenyl]-3-fluorobenzamide

Example 280

(3R)-3'-Cyanobiphenyl-4-carboxylic acid [4-(3-dimethylaminopyrrolidin-1-yl)-3-fluorophenyl]amide

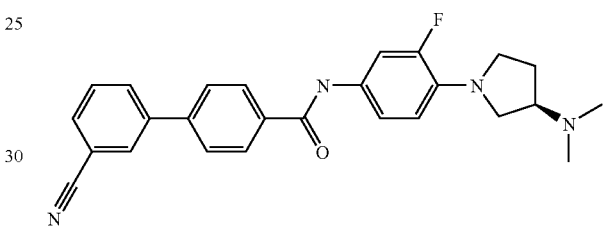

Method O-b 0.002 mg of Pd(PPh3)4 were added to a solution of 0.022 g of (R)-N-[4-(3-dimethylaminopyrrolidin-1-yl)-3-fluorophenyl]-4-iodobenzamide in 0.45 ml of degassed DMF and stirred at room temperature for 10 minutes. 0.035 ml of water, 0.021 g of K3PO4 and 0.008 g of 3-cyanophenylboronic acid were then added to the solution. The reaction solution was heated at 80° C. overnight. The solution was then filtered and purified by preparative HPLC. This resulted in the product with the molecular weight of 428.20 (C26H25FlN4O); MS (ESI): 429 (M+H+) as hydrotrifluoroacetate.

Example 281

3,2',4'-Trifluorobiphenyl-4-carboxylic acid [4-(3-dimethylaminopyrrolidin-1-yl)phenyl]-amide

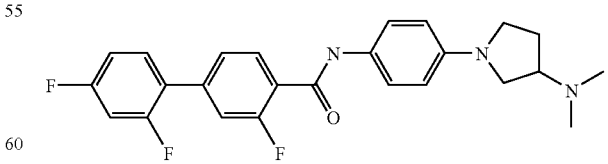

1-Bromo-2,4-difluorobenzene was reacted with N-[4-(3-dimethylaminopyrrolidin-1-yl)phenyl]-2-fluoro-4-boronic acid benzamide by method O-b. This resulted in the product with the molecular weight of 439.19 (C25H24F3N3O); MS (ESI): 440 (M+H+) as hydrotrifluoroacetate.

N-[4-(3-Dimethylaminopyrrolidin-1-yl)phenyl]-2-fluoro-4-boronic acid benzamide

4-Carboxy-3-fluorophenylboronic acid was reacted with [1-(4-aminophenyl)pyrrolidin-3-yl]dimethylamine by method E-b. This resulted in the product with the molecular weight of 371.18 (C19H23BFN3O3); MS (ESI): 372 (M+H+) as hydrotrifluoroacetate.

Example 282

5-(2,4-Difluorophenyl)thiophen-2-carboxylic acid [4-(3-dimethylaminopyrrolidin-1-yl)-phenyl]amide

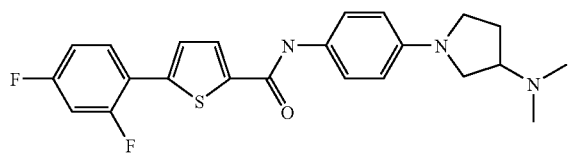

1-Bromo-2,4-difluorobenzene was reacted with 2-boronic acid thiophen-5-carboxylic acid [4-(3-dimethylaminopyrrolidin-1-yl)phenyl]amide by method O-b. This resulted in the product with molecular weight of 427.52 (C23H23F2N3OS); MS (ESI): 428 (M+H+) as hydrotrifluoroacetate.

2-Boronic acid thiophene-5-carboxylic acid [4-(3-dimethylaminopyrrolidin-1-yl)phenyl]amide 5-Carboxy-2-thiopheneboronic acid was reacted with [1-(4-aminophenyl)pyrrolidin-3-yl]-dimethylamine by method E-b. This resulted in the product with the molecular weight of 359.15 (C17H22BN3O3S); MS (ESI): 360 (M+H+) as hydrotrifluoroacetate.

Example 283

N-[4-(3-Dimethylaminopyrrolidin-1-yl)phenyl]-6-(4-fluorophenyl)nicotinamide

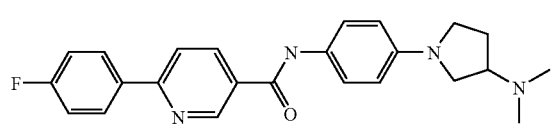

5-[4-(3-Dimethylaminopyrrolidin-1-yl)phenylcarbamoyl]pyridin-2-yl [trifluoro-methanesulfonate was reacted with 4-fluorobenzeneboronic acid under the conditions of method O-b. (Heating at 140° C. in a microwave apparatus for 15 minutes). This resulted in the product with the molecular weight of 404.20 (C24H25FN4O); MS (ESI): 405 (M+H+) as hydrotrifluoroacetate.

5-[4-(3-Dimethylaminopyrrolidin-1-yl)phenylcarbamoyl]pyridin-2-yl [trifluoromethanesulfonate A suspension of 0.05 g of N-[4-(3-dimethylaminopyrrolidin-1-yl)phenyl]-6-hydroxynicotinamide in 0.4 ml of DME was added to a solution of 0.084 ml of LDA solution (2M) in 0.4 ml of DME at 0° C. The mixture was stirred at 0° C. for 2 hours. A solution of 0.055 g of N-phenyltrifluoromethanesulfonimide in 0.2 ml of DME was then added to the mixture. The reaction solution was allowed to reach room temperature and was heated at 80° C. for 3 hours. After cooling, the solution was concentrated in vacuo. The residue was taken up in ethyl acetate/water, and the aqueous phase was extracted three times with ethyl acetate. The combined organic phases were dried over sodium sulfate, concentrated in vacuo and purified by preparative HPLC.

N-[4-(3-Dimethylaminopyrrolidin-1-yl)-phenyl]-6-hydroxynicotinamide

6-Hydroxynicotinic acid was reacted with [1-(4-aminophenyl)pyrrolidin-3-yl]dimethylamine by method E-b. This resulted in the product with the molecular weight of 326.17 (C18H22N4O2); MS (ESI): 327 (M+H+) as hydrotrifluoroacetate.

Example 284

N-[4-(3-Dimethylaminopyrrolidin-1-yl)phenyl]-6-(2,4-difluorophenyl)nicotinamide

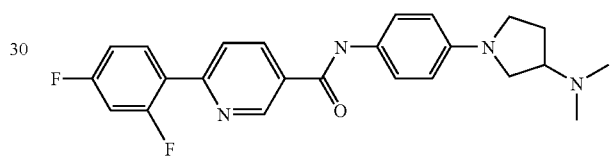

2,4-Difluorophenylboronic acid was reacted with 5-[4-(3-dimethylaminopyrrolidin-1-yl)-phenylcarbamoyl]pyridin-2-yl [trifluoromethanesulfonate by method O-b. This resulted in the product with the molecular weight of 422.00 (C24H24F2N4O); MS (ESI): 423 (M+H+) as hydrotrifluoroacetate.

Example 285

2',4'-Difluorobiphenyl-4-carboxylic acid [4-(3-dimethylaminopyrrolidin-1-yl)phenyl]amide

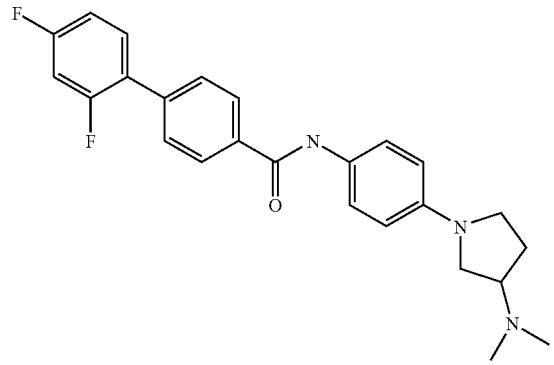

2',4'-Difluorobiphenyl-4-carboxylic acid was reacted with [1-(4-aminophenyl)pyrrolidin-3-yl]dimethylamine by method E-a. This resulted in the product with the molecular weight of 421.20 (C25H25F2N3O); MS (ESI): 422 (M+H+) as hydrotrifluoroacetate.

2',4'-Difluorobiphenyl-4-carboxylic acid

Method P

0.098 ml of 1 N lithium hydroxide solution was added to a solution of 0.051 g of ethyl 2',4'-difluorobiphenyl-4-carboxylate in 1 ml THF/water (1:1), and the mixture was stirred at room temperature overnight. 5% hydrochloric acid was used to neutralize the solution, which was concentrated in vacuo, and the residue was purified by preparative HPLC.

Ethyl 2',4'-difluorobiphenyl-4-carboxylate 0.009 g of Pd(PPh3)4 was added to a solution of 0.091 g of ethyl 4-iodobenzoate in 0.96 ml of degassed toluene and stirred at room temperature for 10 minutes. Then a solution of 0.047 g of 2,4-difluorophenylboronic acid in 0.114 ml of ethanol and 0.201 ml of a 2N Na2CO3 solution was added to the reaction solution. The solution was heated at 100° C. overnight. The reaction mixture was then concentrated in vacuo, and water/ethyl acetate were added to the residue. The aqueous phase was extracted three times with ethyl acetate and dried over sodium sulfate, and the solvent was removed in vacuo and purified by preparative HPLC.

Example 286

2',4'-Difluorobiphenyl-4-carboxylic acid {4-[3-(acetylmethylamino)pyrrolidin-1-yl]phenyl}-amide

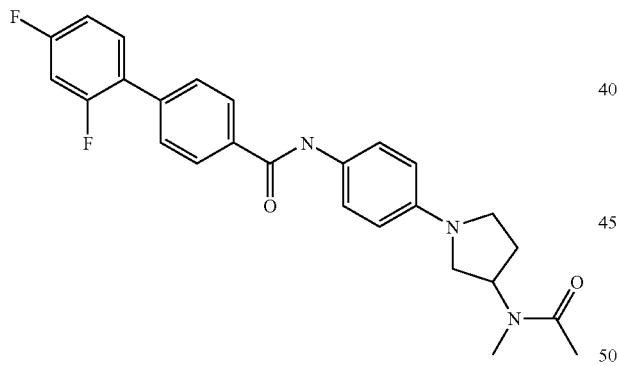

Method E-b

0.095 g of HATU, 0.068 g of HOBT and 0.035 ml of triethylamine were added to a solution of 0.047 g of 2',4'-difluorobiphenyl-4-carboxylic acid and 0.058 g of N-[1-(4-aminophenyl)pyrrolidin-3-yl]-N-methylacetamide in 2 ml of DMF at 0° C. After 10 minutes, the solution was allowed to reach room temperature and was stirred at this temperature overnight. The solvent was then removed in vacuo, and the residue was taken up in water/ethyl acetate. The ethyl acetate phase was washed with 10% NaHCO3 solution and water. The ethyl acetate phase was dried over sodium sulfate, and the solvent was removed in vacuo. The residue was purified by preparative HPLC. The desired product was obtained. Molecular weight 449.19 (C26H25F2N3O2), MS: 450 (M+H+).

Example 287

N-[4-(3-Dimethylaminopyrrolidin-1-yl)phenyl]-3-fluoro-4-(4-methylpiperidin-1-yl)-benzamide

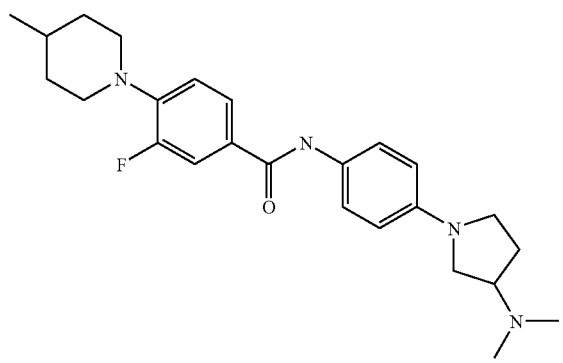

3-Fluoro-4-(4-methylpiperidin-1-yl)benzoic acid was reacted with [1-(4-aminophenyl)-pyrrolidin-3-yl]dimethylamine by method E-a. This resulted in the product with the molecular weight of 424.00 (C25H33FN4O); MS (ESI): 425 (M+H+) as hydrotrifluoroacetate.

3-Fluoro-4-(4-methylpiperidin-1-yl)benzoic acid

Methyl 3-fluoro-4-(4-methylpiperidin-1-yl)benzoate was treated with lithium hydroxide by method P. This resulted in the product with the molecular weight of 237.28 (C13H16FNO2); MS (ESI): 238 (M+H+).

Methyl 3-fluoro-4-(4-methylpiperidin-1-yl)benzoate 0.076 g of potassium carbonate was added to a solution of 0.086 g of methyl 3,4-difluorobenzoate and 0.050 g of 4-methylpiperidine in 0.5 ml of DMF. The reaction was heated at 60° C. for 2 days, filtered and purified by preparative HPLC. This resulted in the product with the molecular weight of 251.3 (C14H18FNO2); MS (ESI): 252 (M+H+) as hydrotrifluoroacetate.

Example 288

4-Butoxy-N-(4-{3-[(2-dimethylaminoacetyl)methylamino]pyrrolidin-1-yl}phenyl)-N-methylbenzamide

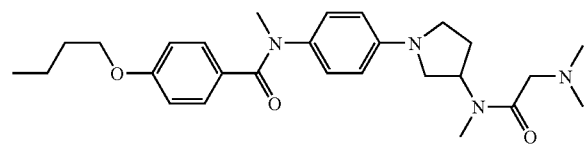

4-Butoxy-N-methyl-N-[4-(3-methylaminopyrrolidin-1-yl)phenyl]benzamide was reacted with N,N-dimethylglycine by method E. This resulted in the product with the molecular weight of 466.63 (C27H38N4O3); MS (ESI): 467 (M+H+).

(R)-4-Butoxy-N-(4-{3-[(2-dimethylaminoacetyl)methylamino]pyrrolidin-1-yl}phenyl)-N-methylbenzamide was obtained analogously.

Example 289

N-{4-[3-(Acetylmethylamino)pyrrolidin-1-yl]phenyl}-4-butoxy-N-methylbenzamide

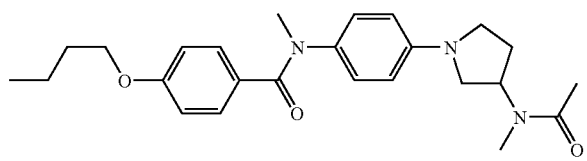

4-Butoxy-N-methyl-N-[4-(3-methylaminopyrrolidin-1-yl)phenyl]benzamide was mixed with pyridine and acetic anhydride. Volatile fractions were removed after 2 hours. This resulted in the product with the molecular weight of 423.56 (C25H33N3O3); MS (ESI): 424 (M+H+).

Example 290

4-Butyrylamino-N-[4-(3-dimethylaminopyrrolidin-1-yl)phenyl]benzamide

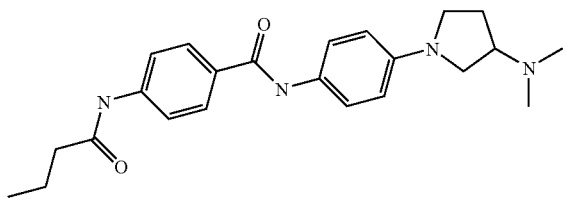

Method Q

4-Amino-N-[4-(3-dimethylaminopyrrolidin-1-yl)phenyl]benzamide (32 mg) in dichloromethane (2 ml) was mixed with potassium carbonate (50 mg) and butyryl chloride (11 mg). The mixture was filtered and concentrated after 12 hours. The residue was purified by preparative HPLC. This resulted in the product with the molecular weight of 394.52 (C23H30N4O3); MS (ESI): 395 (M+H+).

An alternative possibility is to react 4-amino-N-[4-(3-dimethylaminopyrrolidin-1-yl)-phenyl]benzamide with butyric acid by method E.

4-Amino-N-[4-(3-dimethylaminopyrrolidin-1-yl)phenyl]benzamide 4-tert-Butoxycarbonylaminobenzoic acid was reacted with 1-(4-aminophenyl)pyrrolidin-3-yl]dimethylamine by method E, and the product was treated by method G. This resulted in the product with the molecular weight of 324.43 (C19H24N4O); MS (ESI): 325 (M+H+).

Example 291

2-Phenylethynylthiazole-4-carboxylic acid [4-(3-dimethylaminopyrrolidin-1-yl)phenyl]-amide

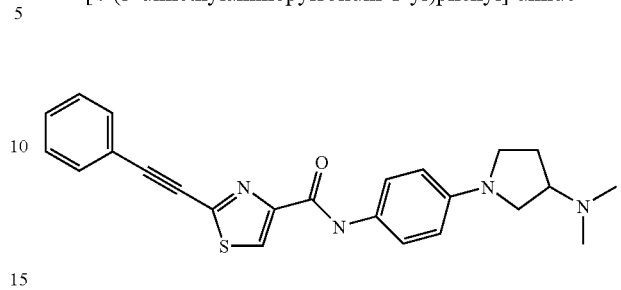

2-Bromothiazole-4-carboxylic acid [4-(3-dimethylaminopyrrolidin-1-yl)phenyl]amide (100 mg) was dissolved in tetrahydrofuran (2 ml), and phenylacetylene (52 mg), triethylamine (52 mg), triphenylphosphine (17 mg), bis(triphenylphosphine)palladium dichloride (89 mg) and copper (I) iodide (9.6 mg) were added. The reaction mixture was heated at 150° C. in a microwave apparatus for 3 minutes and then concentrated. The residue was purified by preparative HPLC. This resulted in the product with the molecular weight of 416.55 (C24H24N4OS); MS (ESI): 417 (M+H+).

Example 292

5-(4-Fluorophenyl)pyridine-2-carboxylic acid [4-(3-dimethylaminopyrrolidin-1-yl)phenyl]-amide

Method O-a

5-Chloropyridine-2-carboxylic acid [4-(3-dimethylaminopyrrolidin-1-yl)phenyl]amide (100 mg) dissolved in toluene was mixed with 4-fluorophenylboronic acid (81 mg), POPD (15 mg) and cesium carbonate (2M aq.; 0.5 ml). The reaction was heated at 150° C. in a microwave apparatus for 10 minutes and then concentrated. The residue was purified by preparative HPLC. This resulted in the product with the molecular weight of 404.49 (C24H25FN4O); MS (ESI): 405 (M+H+).

5-Chloropyridine-2-carboxylic acid [4-(3-dimethylaminopyrrolidin-1-yl)phenyl]amide

[1-(4-Aminophenyl)pyrrolidin-3-yl]dimethylamine was reacted with 5-chloropyridine-2-carboxylic acid by method E. This resulted in the product with the molecular weight of 344.85 (C18H21 ClN4O); MS (ESI): 345 (M+H+).

Example 293

5-(4-Fluorophenyl)pyridine-2-carboxylic acid [4-(3-dimethylaminopyrrolidin-1-yl)phenyl]-amide

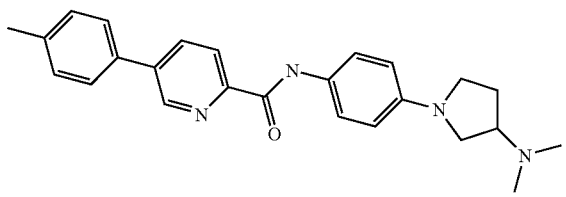

5-Chloropyridine-2-carboxylic acid [4-(3-dimethylaminopyrrolidin-1-yl)phenyl]amide was reacted with 4-methylphenylboronic acid by method O-a. This resulted in the product with the molecular weight of 400.53 (C25H28N4O); MS (ESI): 401 (M+H+).

Example 294

1-Benzenesulfonylpiperidine-4-carboxylic acid [4-(3-dimethylaminopyrrolidin-1-yl)-phenyl]amide

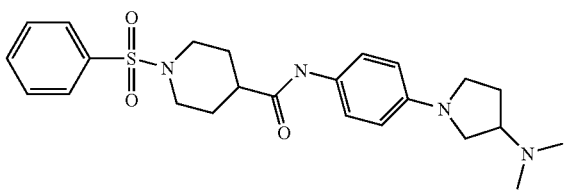

Piperidine-4-carboxylic acid [4-(3-dimethylaminopyrrolidin-1-yl)phenyl]amide (70 mg) dissolved in N-methylpyrrolidone (2 ml) was mixed with potassium carbonate (45 mg) and benzenesulfonyl chloride (35 mg). After 12 hours, the mixture was filtered and the filtrate was purified by preparative HPLC. This resulted in the product with the molecular weight of 456.61 (C24H32N4O3S); MS (ESI): 457 (M+H+).

Example 295

1-(4-Fluorobenzenesulfonyl)piperidine-4-carboxylic acid [4-(3-dimethylaminopyrrolidin-1-yl)phenyl]amide

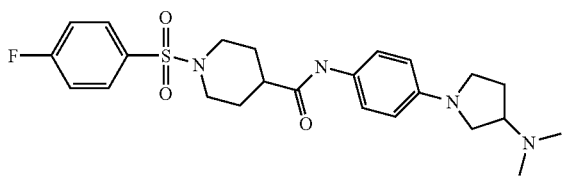

Piperidine-4-carboxylic acid [4-(3-dimethylaminopyrrolidin-1-yl)phenyl]amide (70 mg) dissolved in N-methylpyrrolidone (2 ml) was mixed with potassium carbonate (45 mg) and 4-fluorobenzenesulfonyl chloride (40 mg). After 12 hours, the mixture was filtered and the filtrate was purified by preparative HPLC. This resulted in the product with the molecular weight of 474.60 (C24H31FN4O3S); MS (ESI): 475 (M+H+).

Example 296

1-(Butane-1-sulfonyl)piperidine-4-carboxylic acid [4-(3-dimethylaminopyrrolidin-1-yl)-phenyl]amide

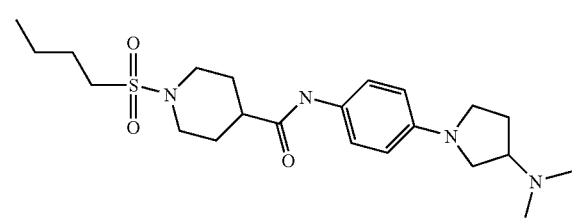

Piperidine-4-carboxylic acid [4-(3-dimethylaminopyrrolidin-1-yl)phenyl]amide (70 mg) dissolved in N-methylpyrrolidone (2 ml) was mixed with potassium carbonate (45 mg) and butylsulfonyl chloride (30 mg). After 12 hours, the mixture was filtered and the filtrate was purified by preparative HPLC. This resulted in the product with the molecular weight of 436.62 (C22H36N4O3S); MS (ESI): 437 (M+H+).

Example 297

5-(4-Butoxyphenylethynyl)furan-2-carboxylic acid [4-(3-dimethylaminopyrrolidin-1-yl)-phenyl]amide

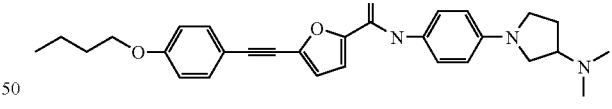

Method J-a

5-Bromofuran-2-carboxylic acid [4-(3-dimethylaminopyrrolidin-1-yl)phenyl]amide (75 mg) was dissolved together with 1-butoxy-4-ethynylbenzene (35 mg) in N,N-dimethylformamide (1 ml) and, under argon, added dropwise to a suspension of Pd(tBu3P)2Cl2 (4 mg), copper (I) iodide (75 mg) and N,N-diisopropylamine (20 mg) in anhydrous tetrahydrofuran (3 ml). The mixture was stirred at room temperature for 8 hours. The reaction was worked up by filtration through a syringe filter and concentrated, and the crude product was purified by preparative HPLC. This resulted in the product with the molecular weight of 471.6 (C29H33N3O3); MS (ESI): 472 (M+H+) as hydrotrifluoroacetate.

Example 298

6-Butoxy-N-[4-(3-dimethylaminopyrrolidin-1-yl)phenyl]nicotinamide

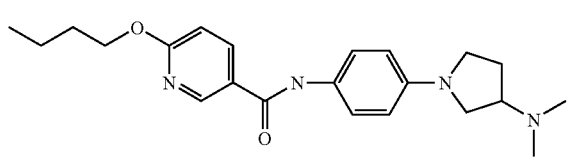

Method H-a

A solution of 0.1 g of potassium hydroxide in 1 ml of DMSO was stirred at room temperature for 10 minutes and then 0.1 g of N-[4-(3-dimethylaminopyrrolidin-1-yl)-phenyl]-6-hydroxynicotinamide was added. The reaction solution was stirred for 10 minutes and then 0.084 g of 1-bromobutane was added. The mixture was stirred at room temperature overnight. After addition of water and ethyl acetate, the aqueous phase was extracted three times with ethyl acetate. The combined organic phases were dried over sodium sulfate, concentrated in vacuo and purified by preparative HPLC. This resulted in the product with the molecular weight of 382.24 (C22H30N4O2); MS (ESI): 383 (M+H+) as hydrotrifluoroacetate.

Example 299

6-Cyclopropylmethoxy-N-[4-(3-dimethylaminopyrrolidin-1-yl)phenyl]nicotinamide

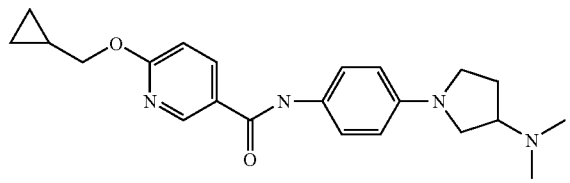

(Bromomethyl)cyclopropane was reacted with N-[4-(3-dimethylaminopyrrolidin-1-yl)-phenyl]-6-hydroxynicotinamide by method H-a. This resulted in the product with the molecular weight of 380.22 (C22H28N4O2); MS (ESI): 381 (M+H+) as hydrotrifluoroacetate.

Example 300

N-[4-(3-Dimethylaminopyrrolidin-1-yl)phenyl]-6-isobutoxynicotinamide

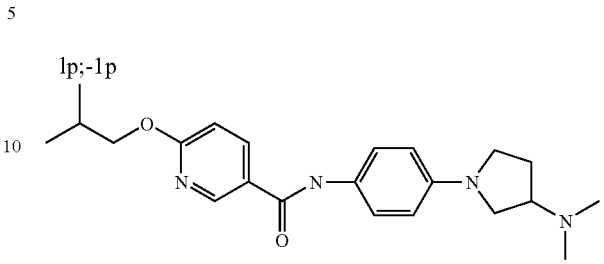

1-Bromo-2-methylpropane was reacted with N-[4-(3-dimethylaminopyrrolidin-1-yl)-phenyl]-6-hydroxynicotinamide by method H-a. This resulted in the product with the molecular weight of 382.24 (C22H30N4O2); MS (ESI): 383 (M+H+) as hydrotrifluoroacetate.

Example 301

N-[4-(3-Dimethylaminopyrrolidin-1-yl)phenyl]-6-(4-fluorophenoxy)nicotinamide 49 mg of potassium carbonate were added to a solution of 0.041 g of 6-chloro-N-[4-(3-dimethylaminopyrrolidin-1-yl)phenyl]nicotinamide and 4-fluorophenol (30 mg) in 0.8 ml of DMF, and the reaction was heated at 140° C. in a microwave apparatus for 90 minutes. After addition of water and ethyl acetate, the aqueous phase was extracted three times with ethyl acetate. The combined organic phases were dried over sodium sulfate, concentrated in vacuo and purified by preparative HPLC. This resulted in the product with the molecular weight of 420.2 (C24H25FN4O2); MS (ESI): 421 (M+H+) as hydrotrifluoroacetate.

6-Chloro-N-[4-(3-dimethylaminopyrrolidin-1-yl)phenyl]nicotinamide

6-Chloronicotinic acid was reacted with [1-(4-aminophenyl)pyrrolidin-3-yl]dimethylamine by method E-b. This resulted in the product with the molecular weight of 344.14 (C18H21ClN4O); MS (ESI): 345 (M+H+) as hydrotrifluoroacetate.

The following examples were prepared analogously.

| Ex. No. | Structure | Molecular formula | Molecular weight | M+H+ |
|---|---|---|---|---|
| 302 | 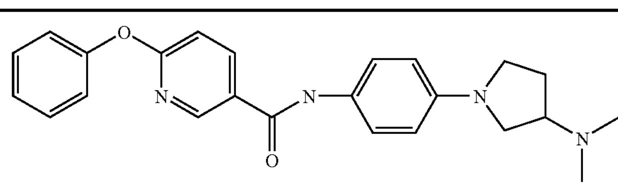 | C24H26N4O2 | 402.21 | 403 |

| Ex. No. | Structure | Molecular formula | Molecular weight | M+H+ |
|---|---|---|---|---|
| 303 | 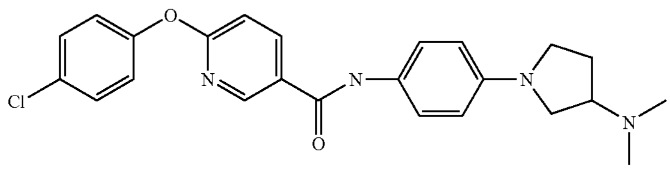 | C24H25ClN4O2 | 436.17 | 437 |
| 304 | 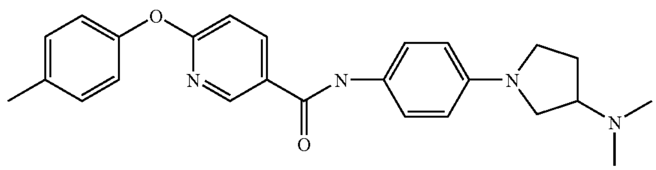 | C25H28N4O2 | 416.22 | 417 |

Example 305

N-[4-(3-Dimethylaminopyrrolidin-1-yl)phenyl]-2-fluoro-4-phenoxybenzamide

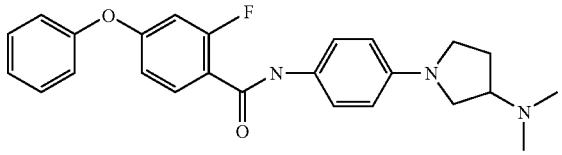

Powdered molecular sieves (4 A), 0.01 g of copper acetate and 0.02 g of N-[4-(3-dimethylaminopyrrolidin-1-yl)phenyl]-2-fluoro-4-boronic acid benzamide were added to a solution of 0.008 g of phenol in 0.5 ml of methylene chloride and stirred at 40° C. for 24 hours. The solvent was then removed in vacuo, the residue was taken up in water/ethyl acetate, and the aqueous phase was extracted three times with ethyl acetate. The combined organic phases were dried over sodium sulfate, concentrated in vacuo and purified by preparative HPLC. This resulted in the product with the molecular weight of 419.2 (C25H26FN3O2); MS (ESI): 420 (M+H+) as hydrotrifluoroacetate.

N-[4-(3-Dimethylaminopyrrolidin-1-yl)phenyl]-2-fluoro-4-boronic acid benzamide

4-Carboxy-3-fluorophenylboronic acid was reacted with [1-(4-aminophenyl)pyrrolidin-3-yl]dimethylamine by method E-b. This resulted in the product with the molecular weight of 371.18 (C19H23BFN3O3); MS (ESI): 372 (M+H+) as hydrotrifluoroacetate.

Example 306

4-(3-Cyanophenyl)-3,6-dihydro-2H-pyridine-1-carboxylic acid [4-(3-dimethylaminopyrrolidin-1-yl)phenyl]amide

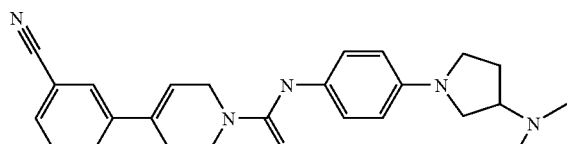

4-(4,4,5,5-Tetramethyl-[1,3,2]dioxaborolan-2-yl)-3,6-dihydro-2H-pyridine-1-carboxylic acid [4-(3-dimethylaminopyrrolidin-1-yl)phenyl]amide was reacted with 3-bromobenzonitrile by method O-a. This resulted in the product with the molecular weight of 415.54 (C25H29N5O); MS (ESI): 416 (M+H+)

4-(4,4,5,5-Tetramethyl-[1,3,2]dioxaborolan-2-yl)-3,6-dihydro-2H-pyridine-1-carboxylic acid [4-(3-dimethylaminopyrrolidin-1-yl)phenyl]amide 4-(4,4,5,5-Tetramethyl-[1,3,2]dioxaborolan-2-yl)-1,2,3,6-tetrahydropyridine was reacted with [1-(4-aminophenyl)pyrrolidin-3-yl]dimethylamine by method A. This resulted in the product with the molecular weight of 440.40 (C24H37BN4O3); MS (ESI): 441 (M+H+)

Example 307

4-(2-Cyanophenyl)-3,6-dihydro-2H-pyridine-1-carboxylic acid [4-(3-dimethylamino-pyrrolidin-1-yl)phenyl]amide

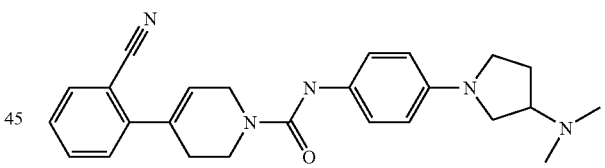

4-(4,4,5,5-Tetramethyl-[1,3,2]dioxaborolan-2-yl)-3,6-dihydro-2H-pyridine-1-carboxylic acid [4-(3-dimethylaminopyrrolidin-1-yl)phenyl]amide was reacted with 2-bromobenzonitrile by method O-a. This resulted in the product with the molecular weight of 415.54 (C25H29N5O); MS (ESI): 416 (M+H+)

Example 308

4-(3-Methylsulfanylphenyl)-3,6-dihydro-2H-pyridine-1-carboxylic acid [4-(3-dimethylaminopyrrolidin-1-yl)phenyl]amide

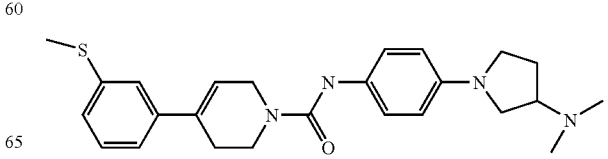

4-(4,4,5,5-Tetramethyl-[1,3,2]dioxaborolan-2-yl)-3,6-dihydro-2H-pyridine-1-carboxylic acid [4-(3-dimethylaminopyrrolidin-1-yl)phenyl]amide was reacted with 3-bromothioanisole by method O-a. This resulted in the product with the molecular weight of 436.62 (C25H32N4OS); MS (ESI): 437 (M+H+)

Example 309

4-(5-Chloropyridin-2-yloxy)-N-[4-(3-dimethylaminopyrrolidin-1-yl)phenyl]benzamide

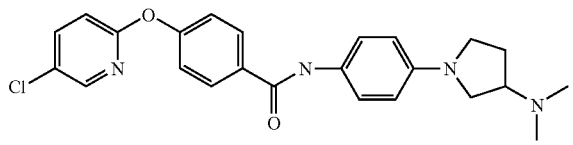

0.143 g of potassium carbonate was added to a solution of 0.19 g of 4-[4-(3-dimethylaminopyrrolidin-1-yl)phenylcarbamoyl]phenyl acetate in 2 ml of DMF, and the solution was heated at 130° C. in a microwave apparatus for 15 minutes. The solution was then mixed with water and ethyl acetate, the aqueous phase was freeze-dried, and the residue was employed without further purification in the next stage.

Method R

A solution of 0.05 g of N-[4-(3-dimethylaminopyrrolidin-1-yl)phenyl]-4-hydroxybenzamide, 0.017 g of 2,5-dichloropyridine and 0.064 g of potassium carbonate in 0.8 ml of DMF was heated at 230° C. in a microwave apparatus for 30 minutes. The solution was filtered and purified by preparative HPLC. This resulted in the product with the molecular weight of 436.17 (C24H25ClN4O2); MS (ESI): 437 (M+H+) as hydrotrifluoroacetate.

4-[4-(3-Dimethylaminopyrrolidin-1-yl)phenylcarbamoyl]phenyl Acetate

4-Acetoxybenzoic acid was reacted with [1-(4-aminophenyl)pyrrolidin-3-yl]dimethylamine by method E-b. This resulted in the product with the molecular weight of 367.19 (C21H25N3O3); MS (ESI): 368 (M+H+) as hydrotrifluoroacetate.

Example 310

N-[4-(3-Dimethylaminopyrrolidin-1-yl)phenyl]-4-(5-fluoropyridin-2-yloxy)benzamide

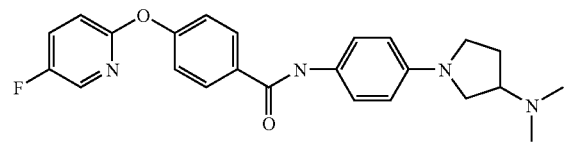

2-Chloro-5-fluoropyridine was reacted with N-[4-(3-dimethylaminopyrrolidin-1-yl)phenyl]-4-hydroxybenzamide by method R. This resulted in the product with the molecular weight of 420.2 (C24H25FN4O2); MS (ESI): 421 (M+H+) as hydrotrifluoroacetate.

Example 311

4-(6-Chloropyridin-3-yloxy)-N-[4-(3-dimethylaminopyrrolidin-1-yl)phenyl]benzamide

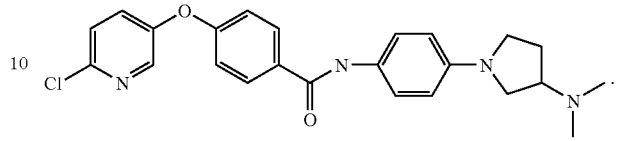

was obtained as by-product of the reaction in example 310. This resulted in the product with the molecular weight of 436.95 (C24H25ClN4O2); MS (ESI): 437 (M+H+) as hydrotrifluoroacetate.

Example 312

5-Chloro-3',6'-dihydro-2'H-[2,4']bipyridinyl-1'-carboxylic acid [4-(3-dimethylamino-pyrrolidin-1-yl)phenyl]amide

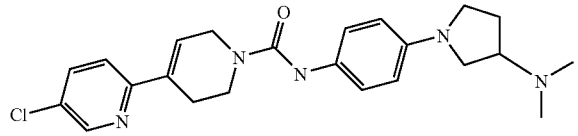

[1-(4-Aminophenyl)pyrrolidin-3-yl]dimethylamine (32 mg) and carbonyldiimidazole (27.1 mg) were dissolved in acetonitrile (1.5 ml), and the mixture was stirred for 3 hours. Triethylamine (63.4 µl) was added to a solution of 5-chloro-1',2',3',6'-tetrahydro-[2,4']bipyridine (40.7 mg) in THF (1 ml) and chloroform (0.5 ml). After 15 minutes, the mixture was added dropwise to the first solution and stirred overnight. The mixture was concentrated and the residue was partitioned between dichloromethane and water. The organic phase was dried over sodium sulfate, filtered and concentrated. Contamination by the primary and/or secondary amine was removed by dissolving the residue in dichloromethane (1.5 ml) and adding the solution to a stirred suspension of polymer-bound p-toluenesulfonyl chloride (0.5 g) in dichloromethane (6 ml) and triethylamine (128 µl). After 3 hours, the resin was filtered off and washed several times with dichloromethane. The combined organic phases were concentrated. The residue was purified by chromatography (silica gel, mobile phase: ethyl acetate/dichloromethane (5%), ammonia (7N in methanol, 2%), later ethyl acetate/dichloromethane (5%), ammonia (7N in methanol, 3%). This resulted in the product with the molecular weight of 425.97 (C23H28ClN5O); MS (ESI): 426 (M+H+).

5-Chloro-1',2',3',6'-tetrahydro-[2,4']bipyridine

A solution of tert-butyl 5-chloro-3',6'-dihydro-2'H-[2,4']bipyridine-1'-carboxylate (50 mg) in chloroform (2.4 ml) was mixed with hydrogen chloride (4N in dioxane; 0.8 ml) and the mixture was concentrated after 13 hours. This resulted in the product with the molecular weight of 194.67 (C10H11ClN2); MS (ESI): 195 (M+H+).- tert-Butyl 5-chloro-3',6'-dihydro-2'H-[2,4']bipyridine-1'-carbamate

A solution of 2-bromo-5-chloropyridine (131 mg) in DMF (degassed with nitrogen; 4.5 ml) was added to a mixture of tert-butyl 4-(4,4,5,5-tetramethyl-[1,3,2]dioxaborolan-2-yl)-3,6-dihydro-2H-pyridin-1-carbamate (Eastwood, Paul R., *Tetrahedron Lett*, 41, 19, 2000, 3705-3708; 200 mg), potassium carbonate (0.265 g) and Pd(dppf)Cl₂ (50 mg). The mixture was heated at 80° C. for 8 hours. After cooling, the mixture was diluted with dichloromethane and washed with sodium carbonate solution and water. The organic phase was dried over sodium sulfate, filtered and concentrated. The residue was purified by chromatography (silica gel, mobile phase: heptane/ethyl acetate (2%)/dichloromethane (5%), later heptane/ethyl acetate (5%)/dichloromethane (5%)).

Example 313

5-(2-Amino-4-methylphenyl)furan-2-carboxylic acid [4-(3-dimethylamino-pyrrolidin-1-yl)-phenyl]amide

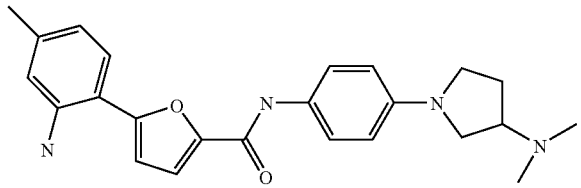

5-(2-Nitro-4-methylphenyl)furan-2-carboxylic acid [4-(3-dimethylamino-pyrrolidin-1-yl)-phenyl]amide was hydrogenated by method B. This resulted in the product with the molecular weight of 404.22 (C24H28N4O2); MS (ESI): 405 (M+H+).

Example 314

5-(2-Acetylamino-4-methylphenyl)furan-2-carboxylic acid [4-(3-dimethylaminopyrrolidin-1-yl)phenyl]amide

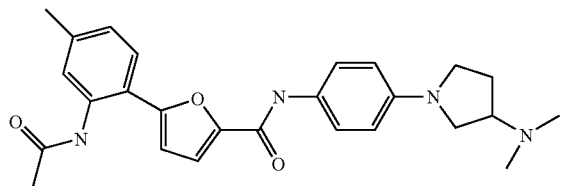

5-(2-Amino-4-methylphenyl)furan-2-carboxylic acid [4-(3-dimethylamino-pyrrolidin-1-yl)-phenyl]amide was reacted with acetyl chloride by method Q. This resulted in the product with the molecular weight of 446.23 (C26H30N4O3); MS (ESI): 447 (M+H+).

Example 315

5-(2-Isobutyrylamino-4-methylphenyl)furan-2-carboxylic acid [4-(3-dimethylamino-pyrrolidin-1-yl)phenyl]amide

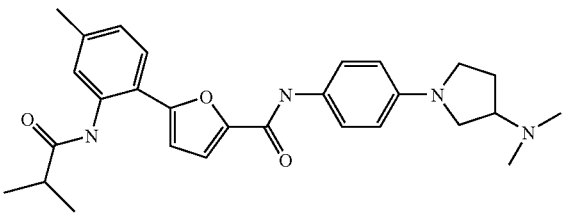

5-(2-Amino-4-methylphenyl)furan-2-carboxylic acid [4-(3-dimethylamino-pyrrolidin-1-yl)-phenyl]amide was reacted with isobutyryl chloride by method Q. This resulted in the product with the molecular weight of 474.26 (C28H34N4O3); MS (ESI): 475 (M+H+).

Example 316

5'-Chloro-3,4,5,6-tetrahydro-2H-[1,2']bipyridinyl-4-carboxylic acid [4-(3-dimethylamino-pyrrolidin-1-yl)phenyl]methylamide

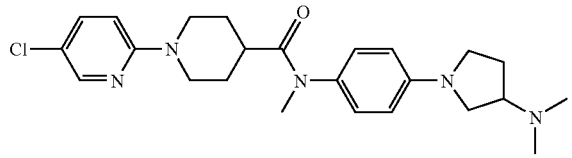

Piperidine-4-carboxylic acid [4-(3-dimethylaminopyrrolidin-1-yl)phenyl]-methylamide (44.4 mg) and 2,5-dichloropyridine (60 mg) were heated at 160° C. for 15 minutes. o-Xylene (0.5 ml) was added and heating at 160° C. was continued for 2 hours. The cooled crude mixture was purified by chromatography (silica gel, eluent: ethyl acetate/ammonia (7N in methanol)). This resulted in the product with the molecular weight of 442.01 (C24H32ClN5O); MS (ESI): 442 (M+H+).

Piperidine-4-carboxylic acid [4-(3-dimethylaminopyrrolidin-1-yl)phenyl]methylamide tert-Butyl 4-{[4-(3-dimethylaminopyrrolidin-1-yl)phenyl]methylcarbamoyl}-piperidine-1-carboxylate was treated with trifluoroacetic acid by method G. This resulted in the product with the molecular weight of 330.48 (C19H30N4O); MS (ESI): 331 (M+H+).

Piperidine-4-carboxylic acid [4-(3-dimethylamino-pyrrolidin-1-yl)phenyl]-amide can be prepared analogously.

tert-Butyl 4-{[4-(3-dimethylaminopyrrolidin-1-yl)phenyl]methylcarbamoyl}-piperidine-1-carboxylate A solution of N-Boc-piperidine-4-carboxylic acid (550 mg) and pyridine (0.47 ml) in dichloromethane (15 ml) was mixed with thionyl chloride (0.21 ml) and, after 30 minutes, a solution of dimethyl[1-(4-methylaminophenyl)pyrrolidin-3-yl]amine (0.5 g), triethylamine (1.17 ml), DMAP (0.44 g) and dichloromethane (10 ml) was added dropwise. After 16 hours, the mixture was diluted with dichloromethane, washed with water and saturated brine, dried over sodium tert-Butyl 4-{[4-(3-dimethylaminopyrrolidin-1-yl)phenyl]carbamoyl}piperidin-1-carboxylate can be prepared analogously.

The following examples were prepared analogously.

| Ex. No. | Structure | Molecular formula | Molecular weight | M+H+ |
|---|---|---|---|---|
| 317 | 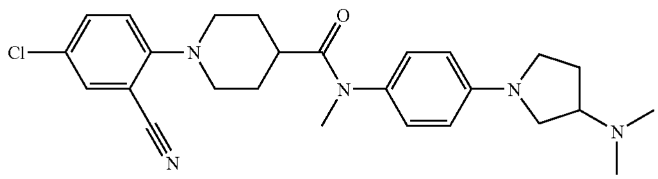 | C25H30ClN5O | 466.03 | 466 |
| 318 | 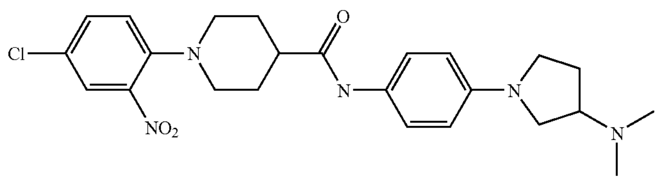 | C24H30ClN5O3 | 471.99 | 472 |
| 319 | 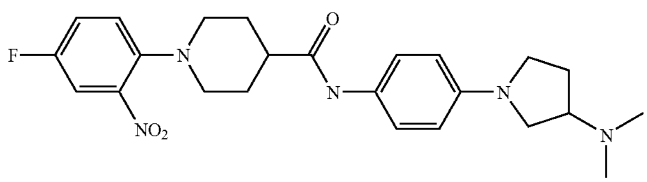 | C24H30FN5O3 | 455.54 | 456 |

Example 320

3,4,5,6-Tetrahydro-2H-[1,2']bipyridinyl-4-carboxylic acid [4-(3-dimethylaminopyrrolidin-1-yl)phenyl]amide

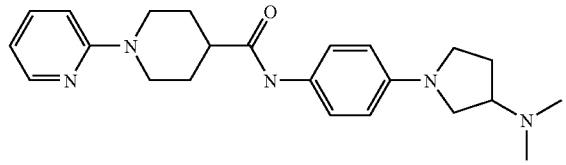

Piperidine-4-carboxylic acid [4-(3-dimethylaminopyrrolidin-1-yl)phenyl]-amide (30 mg) and 2-chloropyridine (90 mg) were heated at 160° C. for 2 hours. 2-Chloropyridine (0.2 ml) was added and the mixture was again heated at 160° C. for 4 hours. The cooled crude mixture was purified by chromatography (silica gel, eluent: ethyl acetate/ammonia (3N in methanol)). This resulted in the product with the molecular weight of 393.54(C23H31N5O); MS (ESI): 394 (M+H+).

The following examples were prepared analogously.

| Ex. No. | Structure | Molecular formula | Molecular weight | M+H+ |
|---|---|---|---|---|
| 321 | 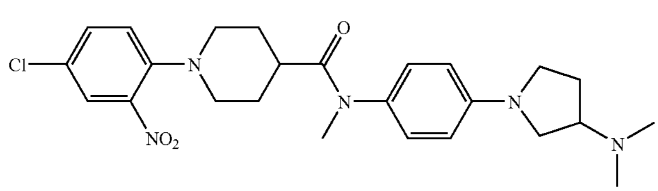 | C25H32ClN5O3 | 486.02 | 486 |
| 322 | 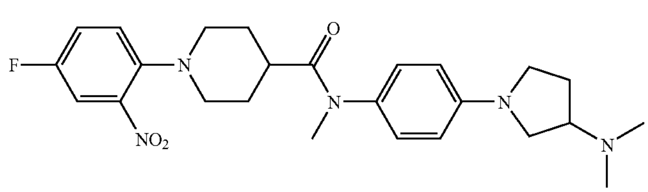 | C24H30FN5O3 | 469.56 | 470 |

Example 323

5'-Chloro-3,4,5,6-tetrahydro-2H-[1,2']bipyridinyl-4-carboxylic acid [4-(3-dimethylamino-pyrrolidin-1-yl)phenyl]amid

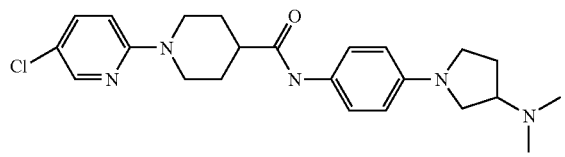

Piperidine-4-carboxylic acid [4-(3-dimethylaminopyrrolidin-1-yl)phenyl]amide (30 mg), 2,5-dichloropyridine (30 mg) and tributylamine (0.2 ml) were heated at 160° C. for 2 hours. The cooled crude mixture was washed with heptane and purified by chromatography (silica gel, eluent: ethyl acetate/ammonia (3N in methanol)). This resulted in the product with the molecular weight of 427.98 (C23H30ClN5O); MS (ESI): 428 (M+H+).

Example 324

1-(4-Chloro-2-cyanophenyl)piperidine-4-carboxylic acid [4-(3-dimethylaminopyrrolidin-1-yl)phenyl]amide

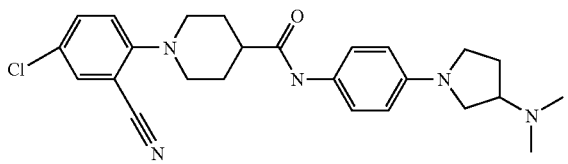

Piperidine-4-carboxylic acid [4-(3-dimethylaminopyrrolidin-1-yl)phenyl]amide was reacted with 2,5-dichlorobenzonitrile as described in example 323. This resulted in the product with the molecular weight of 452.00 (C25H30ClN5O); MS (ESI): 452 (M+H+).

Example 325

1-(2-Acetylamino-4-chlorophenyl)piperidine-4-carboxylic acid [4-(3-dimethylamino-pyrrolidin-1-yl)phenyl]methylamide

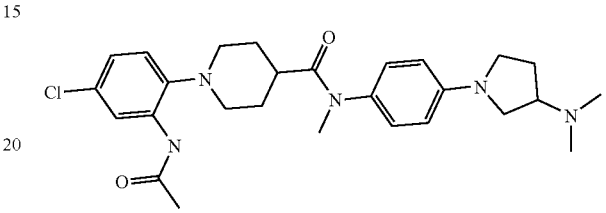

Palladium on carbon (10%; 10 mg) was added to a solution of 1-(4-chloro-2-nitro-phenyl)piperidine-4-carboxylic acid [4-(3-dimethylaminopyrrolidin-1-yl)phenyl]methylamide (50 mg) in glacial acetic acid (5 ml). The solution was stirred under a hydrogen atmosphere (1 bar), and acetic anhydride (14 μl) was added. After one hour, further acetic anhydride (6 μl) were added and the mixture was stirred for 15 minutes. The suspension was filtered and the filtrate was concentrated. The residue was purified by chromatography (silica gel, eluent: ethyl acetate/ammonia (7N in methanol)). This resulted in the product with the molecular weight of 498.07 (C27H36ClN5O2); MS (ESI): 498 (M+H+).

The following examples were prepared analogously.

| Ex. No. | Structure | Molecular formula | Molecular weight | M+H+ |
|---|---|---|---|---|
| 326 | 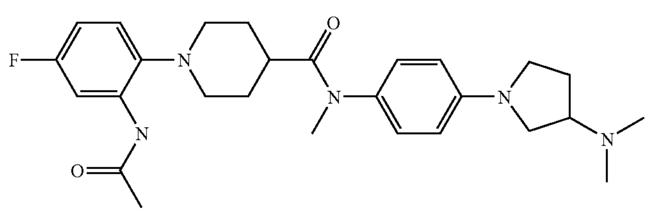 | C27H36FN5O2 | 481.62 | 482 |
| 327 | 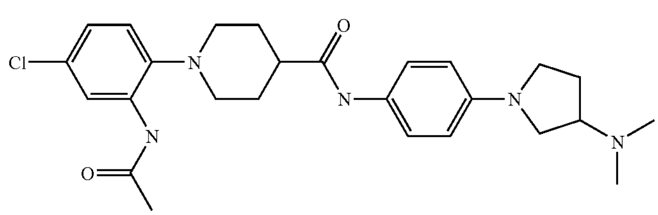 | C26H34ClN5O2 | 484.05 | 484 |

| Ex. No. | Structure | Molecular formula | Molecular weight | M+H+ |
|---|---|---|---|---|
| 328 | 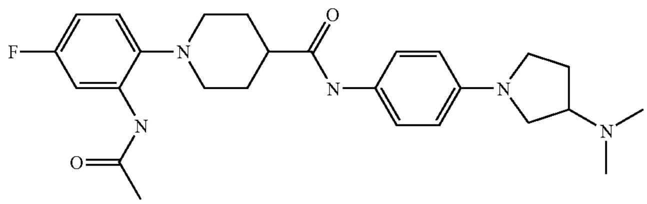 | C26H34FN5O3 | 467.59 | 468 |

Example 329

(R)-N-[4-(3-Dimethylaminopyrrolidin-1-yl)phenyl]-2-(4-phenylpiperidin-1-yl)acetamide

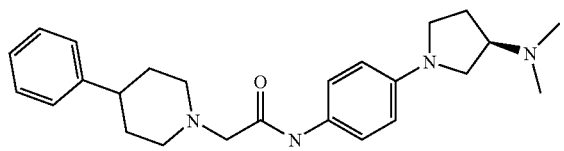

Cesium carbonate (100 mg) and 4-phenylpiperidine (48 mg) were added to a solution of (R)-2-chloro-N-[4-(3-dimethylaminopyrrolidin-1-yl)phenyl]acetamide (80 mg) in acetonitrile (5 ml) and DMF (1 ml), and the mixture was kept at 65° C. for 12 hours. The mixture was freed of volatile fractions and the residue was partitioned between water and dichloromethane. The organic phase was dried over sodium sulfate, filtered and concentrated. The residue was purified by chromatography (silica gel, eluent: methanol/dichloromethane). This resulted in the product with the molecular weight of 406.58 (C25H34N4O); MS (ESI): 407 (M+H+).

It is alternatively possible to use potassium carbonate or pyridine as auxiliary bases, to add potassium iodide as catalyst, or to carry out the reaction at 150° C. in a microwave apparatus.

(R)-2-Chloro-N-[4-(3-dimethylaminopyrrolidin-1-yl) phenyl]acetamide

Triethylamine (2.03 g) was added to a solution of (R)-[1-(4-aminophenyl)pyrrolidin-3-yl]-dimethylamine (3.15 g) in dichloromethane (120 ml), and then chloroacetyl chloride (2.26 g) was added dropwise. After 3 hours, the mixture was diluted with dichloromethane and washed with water and brine. The organic phase was dried over sodium sulfate, filtered and concentrated. The residue was purified by chromatography (silica gel, eluent: methanol/dichloromethane). This resulted in the product with the molecular weight of 281.79 (C14H20ClN3O); MS (ESI): 282 (M+H+).

The following were obtained analogously:

N-{4-[3-(Acetylmethylamino)pyrrolidin-1-yl]phenyl}-2-chloroacetamide

2-Chloro-N-[4-(3-dimethylaminopyrrolidin-1-yl)phenyl]acetamide (R)-2-Chloro-N-[6-(3-dimethylaminopyrrolidin-1-yl)pyridin-3-yl]acetamide The following examples were prepared in analogy to the method given in example 329:

| Ex. No. | Structure | Molecular formula | Molecular weight | M+H+ |
|---|---|---|---|---|
| 330 | 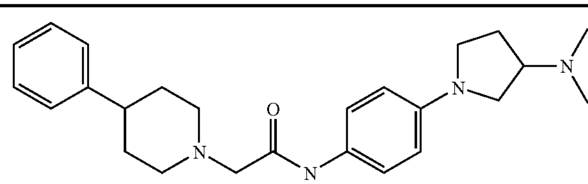 | C25H34N4O | 406.58 | 407 |
| 331 | 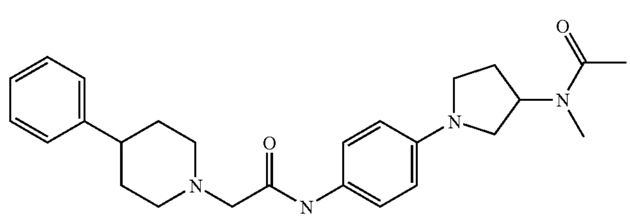 | C26H34N4O2 | 434.59 | 435 |

-continued

| Ex. No. | Structure | Molecular formula | Molecular weight | M+H+ |
|---|---|---|---|---|
| 332 | 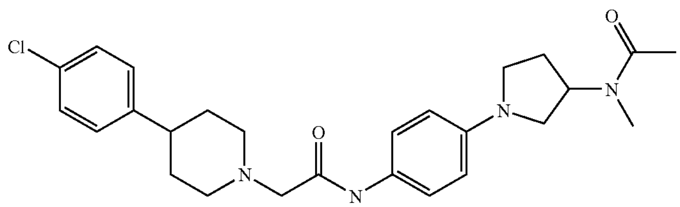 | C26H33ClN4O2 | 469.03 | 469 |
| 333 | 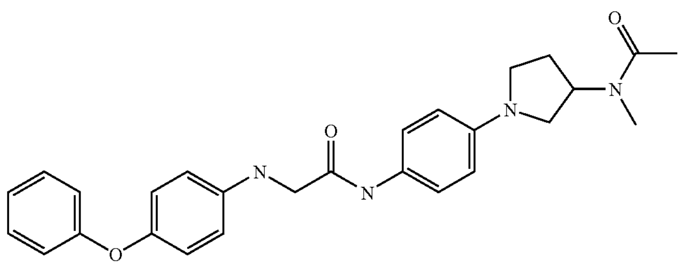 | C27H30N4O3 | 458.57 | 459 |
| 334 | 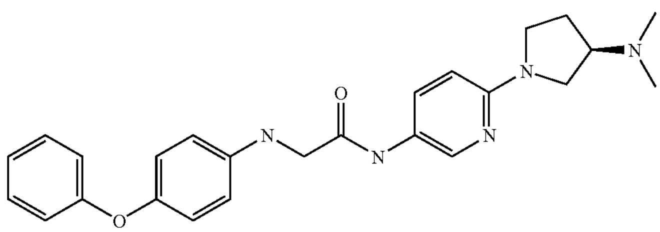 | C25H29N5O2 | 431.54 | 432 |
| 335 | 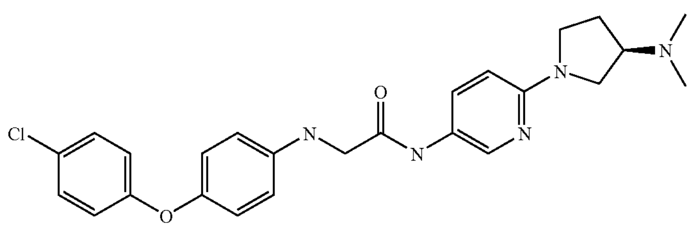 | C25H28ClN5O2 | 465.99 | 466 |
| 336 | 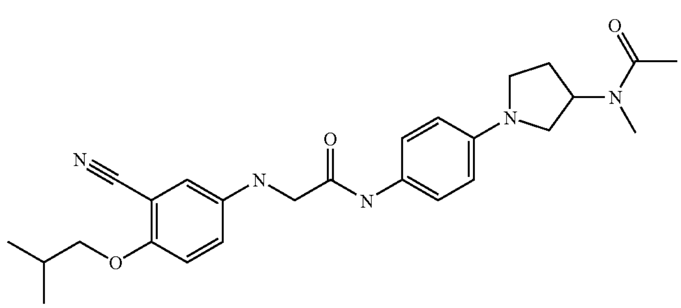 | C26H33N5O3 | 463.59 | 464 |
| 337 | 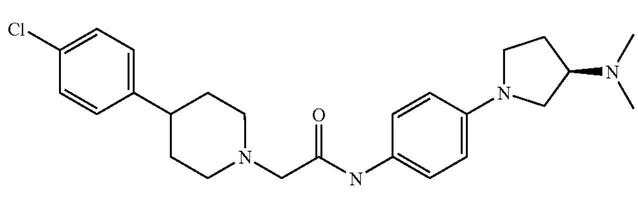 | C25H33ClN4O2 | 441.02 | 441 |

-continued

| Ex. No. | Structure | Molecular formula | Molecular weight | M+H+ |
|---|---|---|---|---|
| 338 | 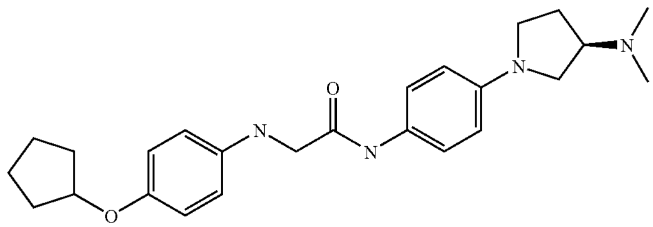 | C25H34N4O2 | 422.58 | 423 |
| 339 | 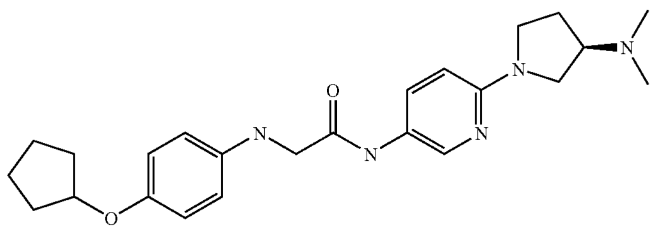 | C24H33N5O2 | 423.56 | 424 |

Example 340

(R)-4-Benzylpiperidine-1-carboxylic acid [6-(3-dimethylaminopyrrolidin-1-yl)pyridin-3-yl]-amide

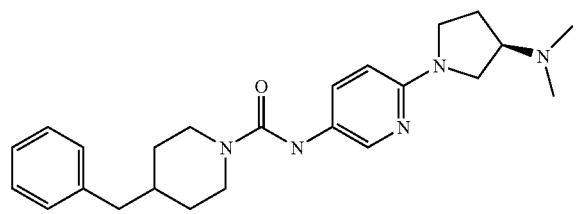

(R)-6-(3-Dimethylaminopyrrolidin-1-yl)pyridin-3-ylamine was added to a solution of carbonyldiimidazole (53 mg) in DMF (0.5 ml) at 0° C. After 15 minutes, 4-benzylpiperidine (57 mg) was added and the mixture was heated at 90° C. for one hour. The cooled mixture was freed of volatile fractions. The residue was purified by chromatography (silica gel, eluent: methanol/dichloromethane). This resulted in the product with the molecular weight of 407.56 (C24H33N5O); MS (ESI): 408 (M+H+).

The following examples were prepared analogously:

| Ex. No. | Structure | Molecular formula | Molecular weight | M+H+ |
|---|---|---|---|---|
| 341 | 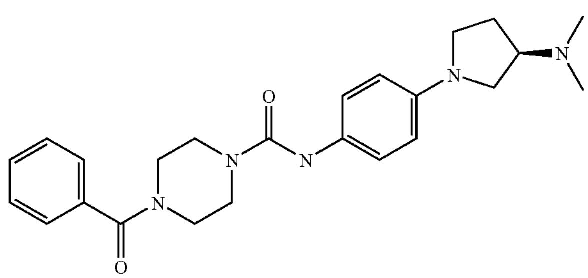 | C24H31N5O2 | 421.55 | 422 |

-continued
| Ex. No. | Structure | Molecular formula | Molecular weight | M+H+ |
|---|---|---|---|---|
| 342 | 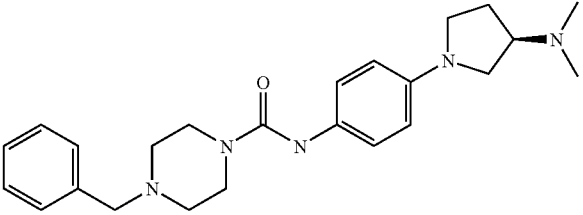 | C24H33N5O | 407.56 | 408 |
| 343 | 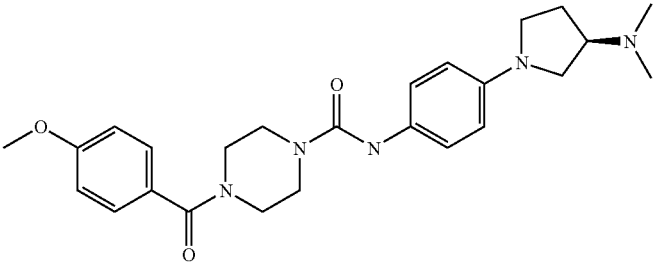 | C26H34N4O3 | 450.59 | 451 |
| 344 | 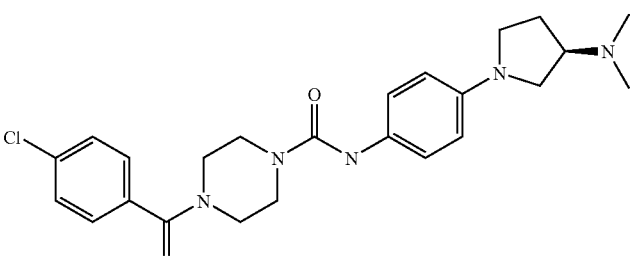 | C25H31ClN4O2 | 455.00 | 455 |
| 345 | 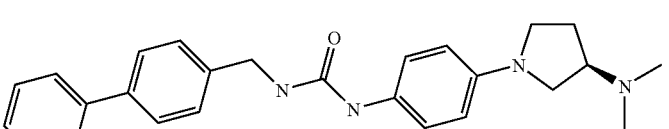 | C26H30N4O | 414.56 | 415 |
| 346 | 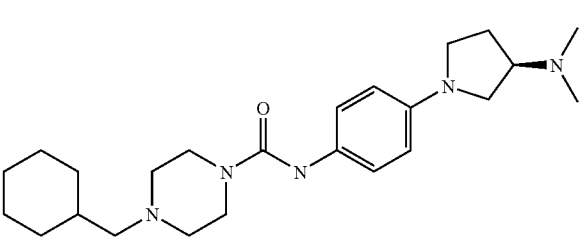 | C24H39N5O | 413.61 | 414 |
| 347 | 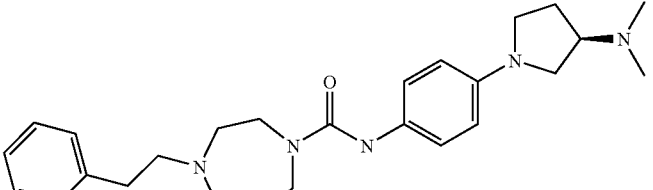 | C26H37N5O | 435.62 | 436 |

Example 348

(R)-4-Cyclopropylmethoxy-N-[4-(3-dimethylaminopyrrolidin-1-yl)-3-fluorophenyl]-benzamide

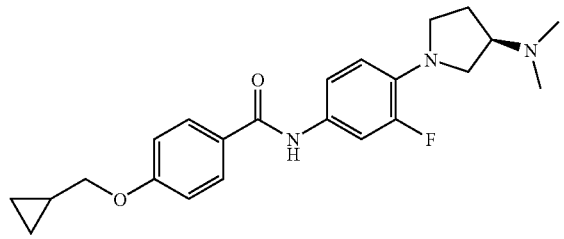

(R)-4-Benzyloxy-N-[4-(3-dimethylaminopyrrolidin-1-yl)-3-fluorophenyl]benzamide underwent debenzylating hydrogenation by method B. The resulting (R)-N-[4-(3-dimethylaminopyrrolidin-1-yl)-3-fluorophenyl]-4-hydroxybenzamide was alkylated with cyclopropylmethyl bromide by method H. This resulted in the product with the molecular weight of 397.50 (C23H28N3O2); MS (ESI): 398 (M+H+).

The following examples were likewise obtained by method H:

| Ex. No. | Structure | Molecular formula | Molecular weight | M+H+ |
|---|---|---|---|---|
| 349 | 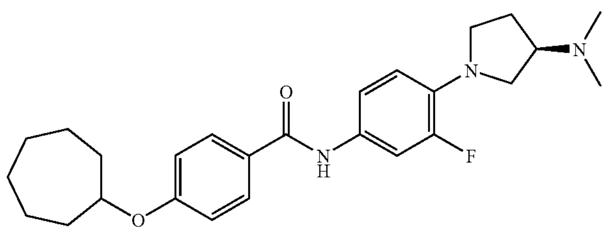 | C26H34FN3O2 | 439.58 | 440 |
| 350 | 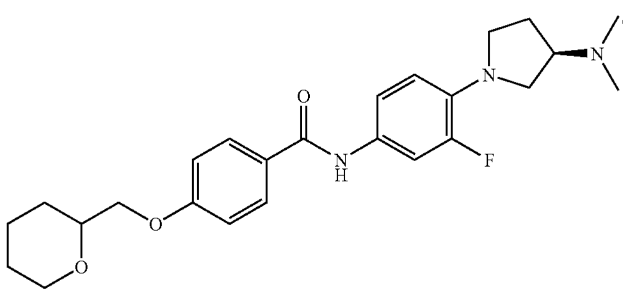 | C25H32FN3O3 | 441.55 | 442 |
| 351 | 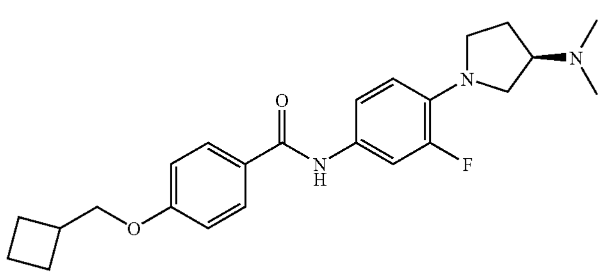 | C24H30FN3O2 | 411.52 | 412 |

Example 352

(R)-N-[4-(3-Dimethylaminopyrrolidin-1-yl)-3-fluorophenyl]-4-(pyridin-2-yloxy)benzamide

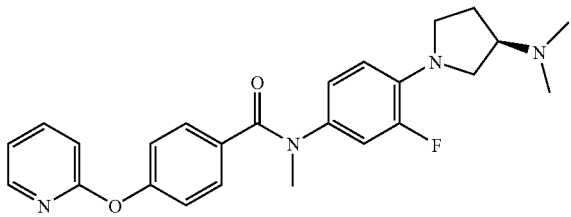

(R)-N-[4-(3-Dimethylaminopyrrolidin-1-yl)-3-fluorophenyl]-4-hydroxybenzamide was reacted with 2-chloropyridine by method R. This resulted in the product with the molecular weight of 434.52 (C25H27N4O2); MS (ESI): 435 (M+H+).

Example 353-Example 507

Various pyrrolidinylanilines were reacted with diverse amines by method A. The resulting products are summarized in table 6.

Example 508-Example 1130

Various pyrrolidinylanilines were reacted with diverse acids by methods E. The resulting products are summarized in table 7.

Example 1131-Example 1232

Various (hetero)aryl halides were reacted with diverse boronic acids by methods O. The resulting products are summarized in table 8.

Example 1233-Example 1237

Various aryl halides were reacted with diverse acetylenes by methods J. The resulting products are summarized in table 9.

Example 1238-Example 1403

Various aminopyrrolidines and N-arylpyrrolidinones were reacted with diverse aldehydes, ketones and amines by method N. The resulting products are summarized in table 10.

Example 1404-Example 1423

Various aminopyrrolidines were reductively methylated with formaldehyde by method E. The resulting products are summarized in table 11.

Example 1424-Example 1443

Various amides were alkylated by method F. The resulting products are summarized in table 12.

Example 1444-Example 1618

Various tert-butyl carbamates were cleaved by method G. The resulting products were summarized in table 13.

TABLE 6

| Ex. No. | Structure | Molecular formula | Monoisotopic molecular wt. | M+H+ |
|---|---|---|---|---|
| 353 | 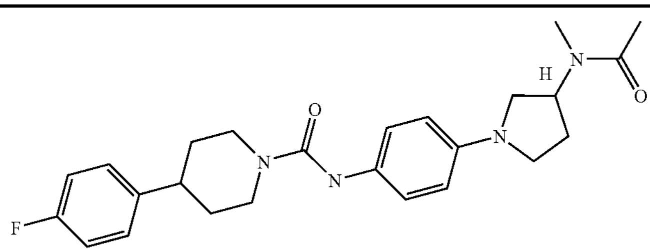 | C25H31FN4O2 | 438.24 | 439 |
| 354 | 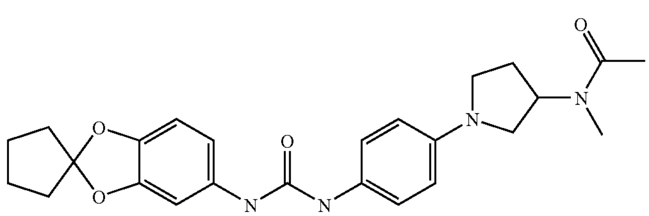 | C25H30N4O4 | 450.23 | 451 |
| 355 | 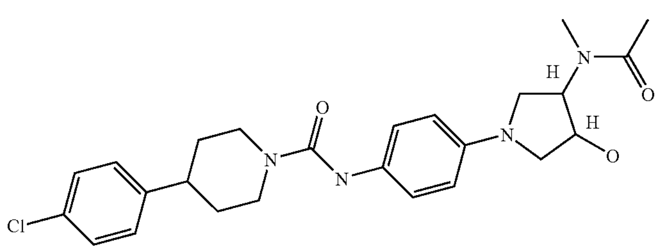 | C25H31ClN4O3 | 470.21 | 471 |

TABLE 6-continued

| Ex. No. | Structure | Molecular formula | Monoisotopic molecular wt. | M+H+ |
|---|---|---|---|---|
| 356 | 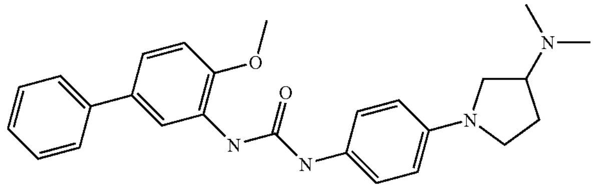 | C26H30N4O2 | 430.24 | 431 |
| 357 | 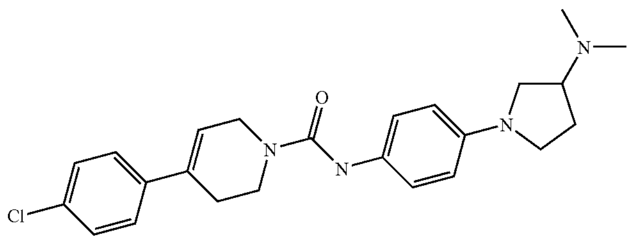 | C24H29ClN4O | 424.20 | 425 |
| 358 | 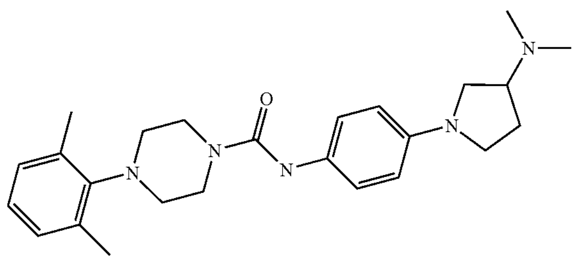 | C25H35N5O | 421.28 | 422 |
| 359 | 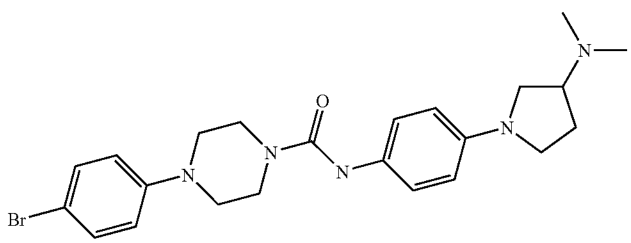 | C23H30BrN5O | 471.16 | 472 |
| 360 | 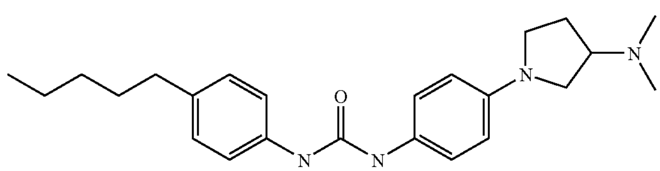 | C24H34N4O | 394.27 | 395 |
| 361 | 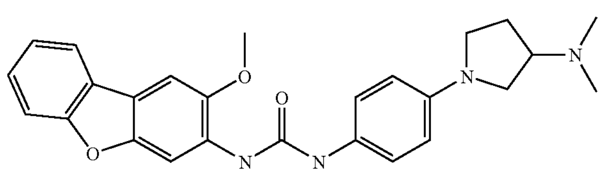 | C26H28N4O3 | 444.22 | 445 |
| 362 | 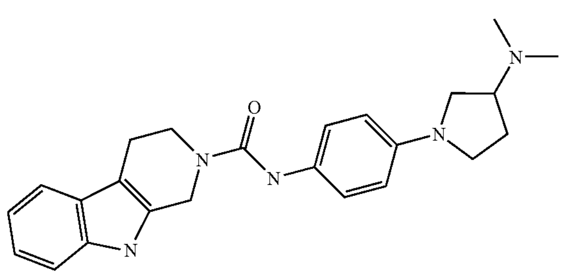 | C24H29N5O | 403.24 | 404 |

TABLE 6-continued

| Ex. No. | Structure | Molecular formula | Monoisotopic molecular wt. | M+H+ |
| --- | --- | --- | --- | --- |
| 363 | 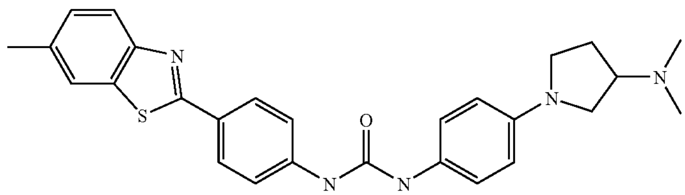 | C27H29N5OS | 471.21 | 472 |
| 364 | 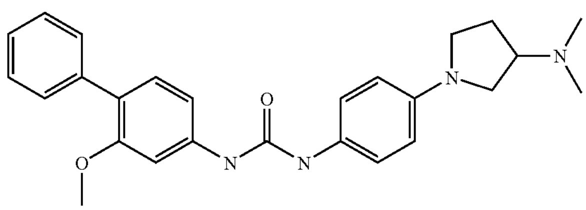 | C26H30N4O2 | 430.24 | 431 |
| 365 | 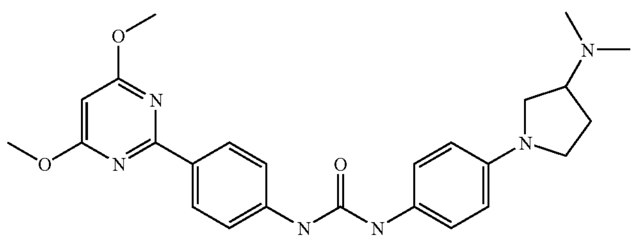 | C25H30N6O3 | 462.24 | 463 |
| 366 | 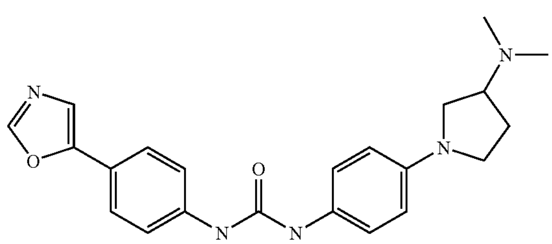 | C22H25N5O2 | 391.20 | 392 |
| 367 | 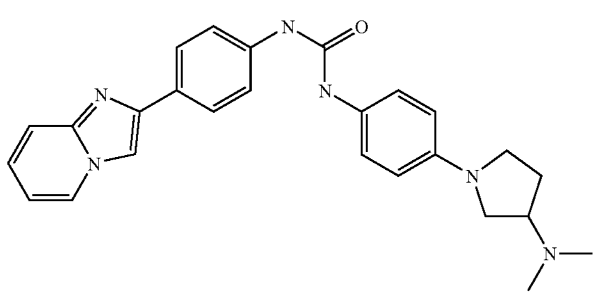 | C26H28N6O | 440.23 | 441 |
| 368 | 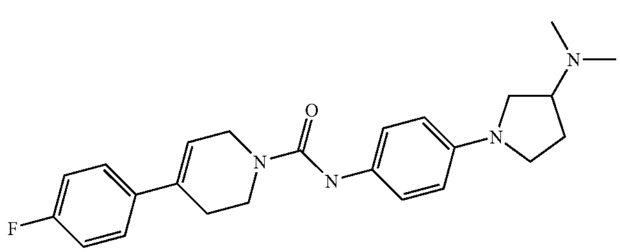 | C24H29FN4O | 408.23 | 409 |

TABLE 6-continued

| Ex. No. | Structure | Molecular formula | Monoisotopic molecular wt. | M+H+ |
|---|---|---|---|---|
| 369 | 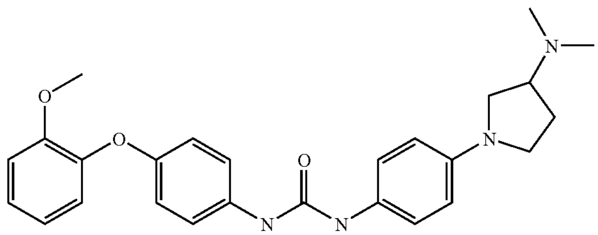 | C26H30N4O3 | 446.23 | 447 |
| 370 | 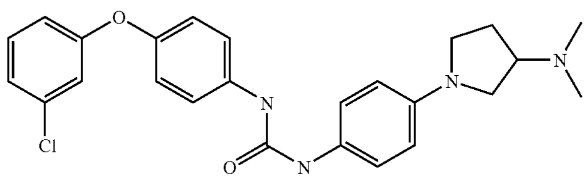 | C25H27ClN4O2 | 450.18 | 451 |
| 371 | 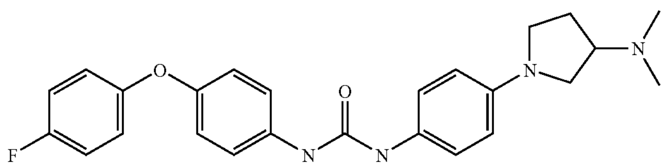 | C25H27FN4O2 | 434.21 | 435 |
| 372 | 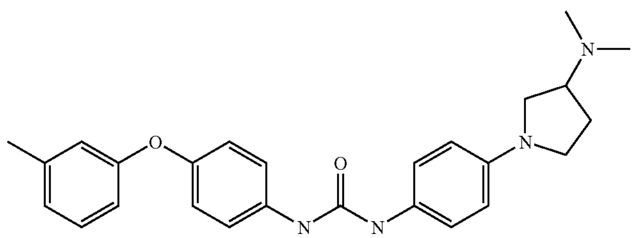 | C26H30N4O2 | 430.24 | 431 |
| 373 | 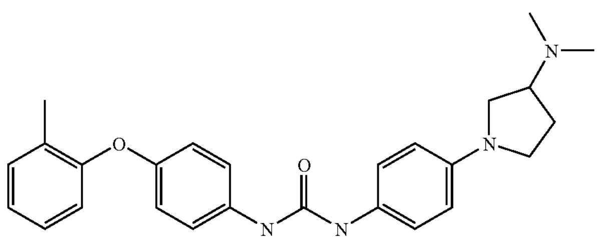 | C26H30N4O2 | 430.24 | 431 |
| 374 | 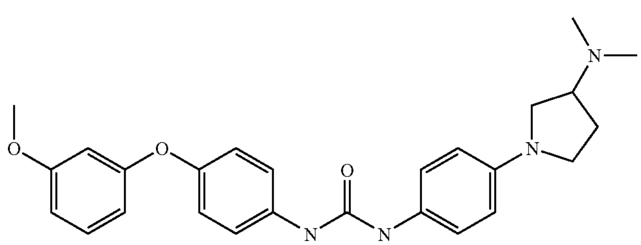 | C26H30N4O3 | 446.23 | 447 |
| 375 | 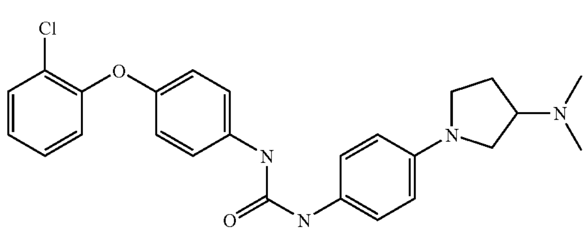 | C25H27ClN4O2 | 450.18 | 451 |

TABLE 6-continued

| Ex. No. | Structure | Molecular formula | Monoisotopic molecular wt. | M+H+ |
|---|---|---|---|---|
| 376 | 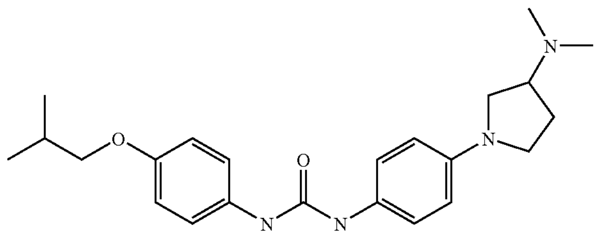 | C23H32N4O2 | 396.25 | 397 |
| 377 | 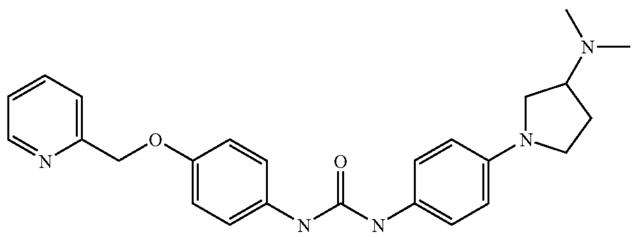 | C25H29N5O2 | 431.23 | 432 |
| 378 | 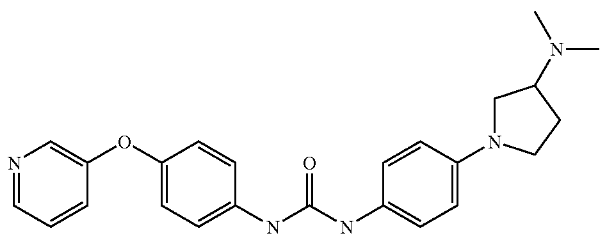 | C24H27N5O2 | 417.22 | 418 |
| 379 | 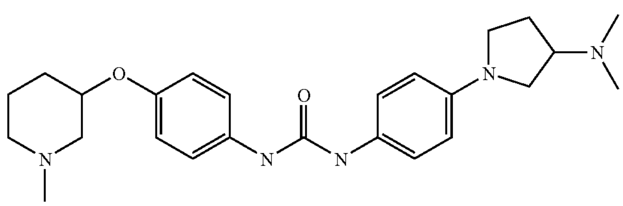 | C25H35N5O2 | 437.28 | 438 |
| 380 | 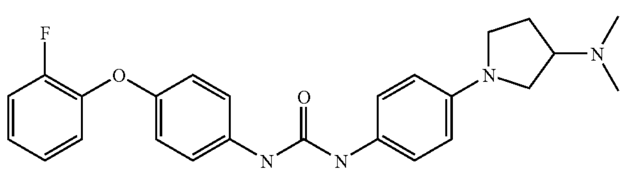 | C25H27FN4O2 | 434.21 | 435 |
| 381 | 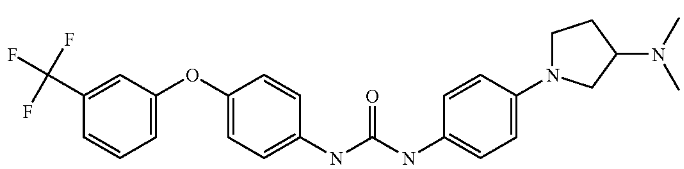 | C26H27F3N4O2 | 484.21 | 485 |
| 382 | 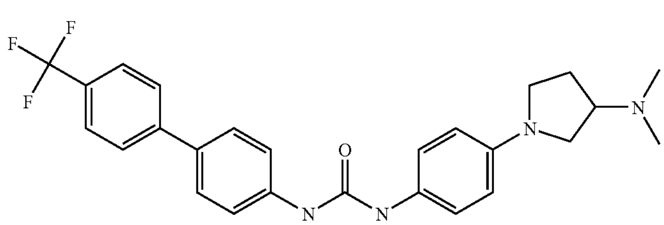 | C26H27F3N4O | 468.21 | 469 |

TABLE 6-continued
| Ex. No. | Structure | Molecular formula | Monoisotopic molecular wt. | M+H+ |
|---|---|---|---|---|
| 383 | 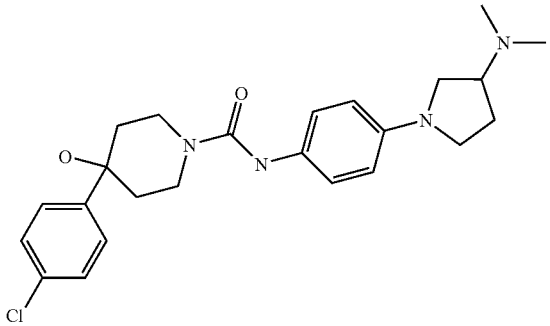 | C24H31ClN4O2 | 442.21 | 443 |
| 384 | 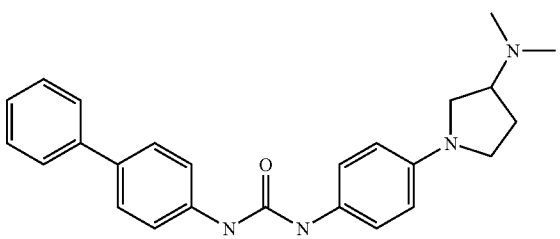 | C25H28N4O | 400.23 | 401 |
| 385 | 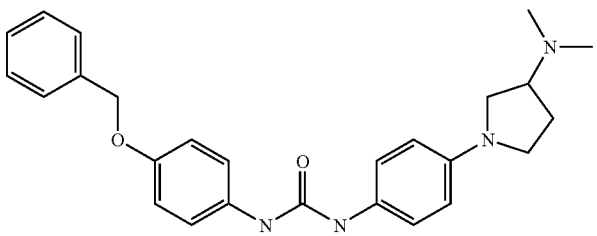 | C26H30N4O2 | 430.24 | 431 |
| 386 | 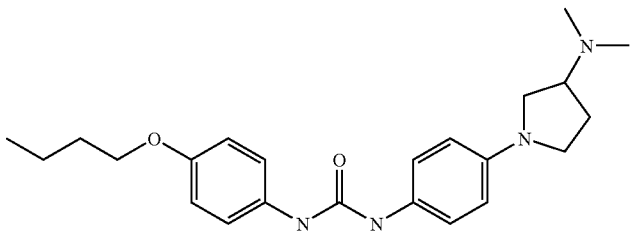 | C23H32N4O2 | 396.25 | 397 |
| 387 | 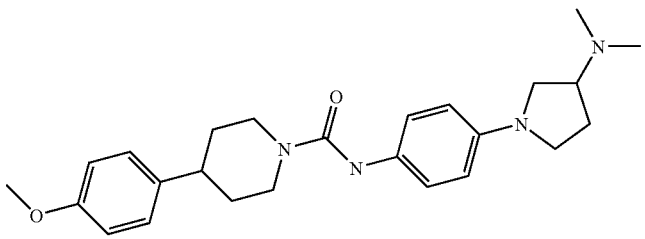 | C25H34N4O2 | 422.27 | 423 |
| 388 | 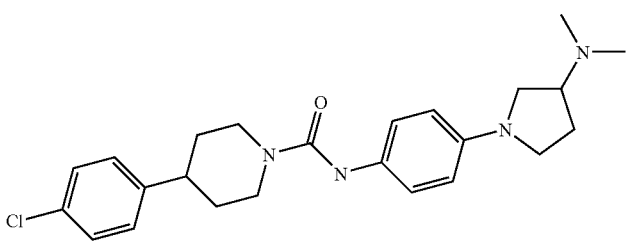 | C24H31ClN4O | 426.22 | 427 |

TABLE 6-continued
| Ex. No. | Structure | Molecular formula | Monoisotopic molecular wt. | M+H+ |
|---|---|---|---|---|
| 389 | 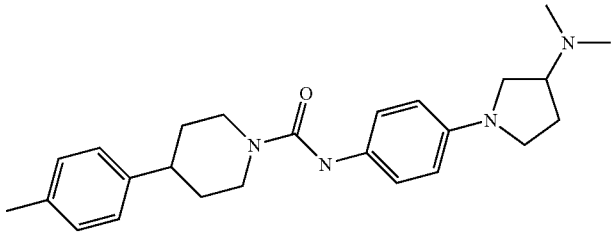 | C25H34N4O | 406.27 | 407 |
| 390 | 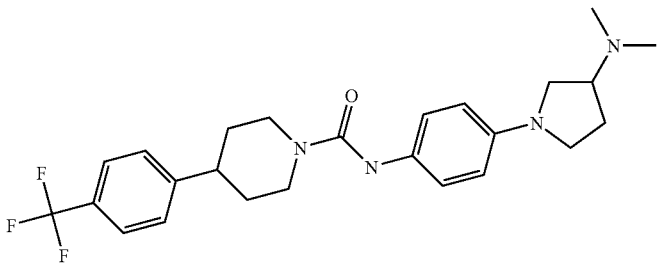 | C25H31F3N4O | 460.24 | 461 |
| 391 | 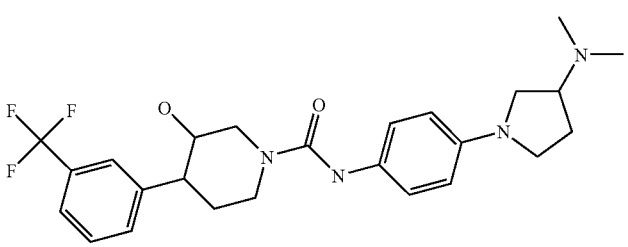 | C25H31F3N4O2 | 476.24 | 477 |
| 392 | 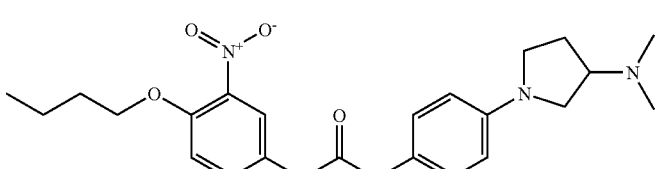 | C23H31N5O4 | 441.24 | 442 |
| 393 | 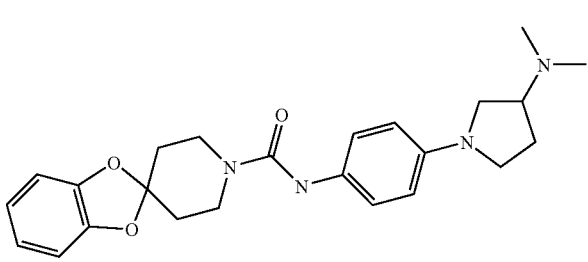 | C24H30N4O3 | 422.23 | 423 |
| 394 | 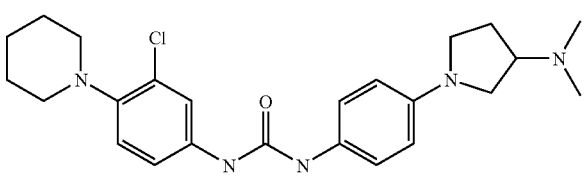 | C24H32ClN5O | 441.23 | 442 |
| 395 | 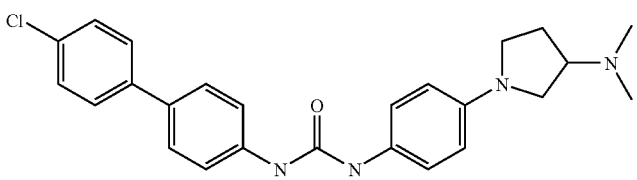 | C25H27ClN4O | 434.19 | 435 |

TABLE 6-continued

| Ex. No. | Structure | Molecular formula | Monoisotopic molecular wt. | M+H+ |
|---|---|---|---|---|
| 396 | 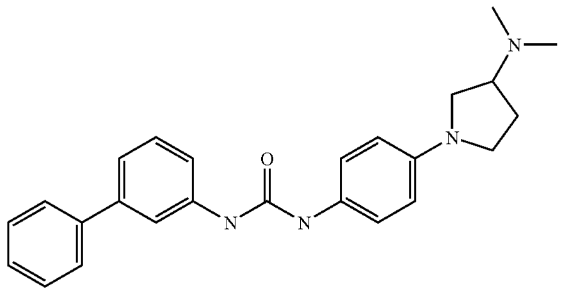 | C25H28N4O | 400.23 | 401 |
| 397 | 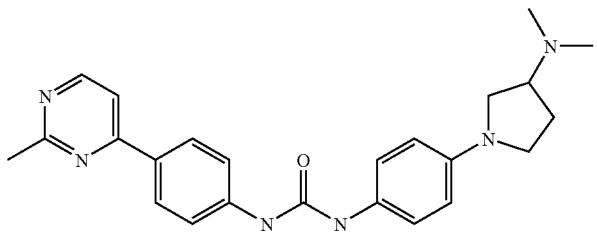 | C24H28N6O | 416.23 | 417 |
| 398 | 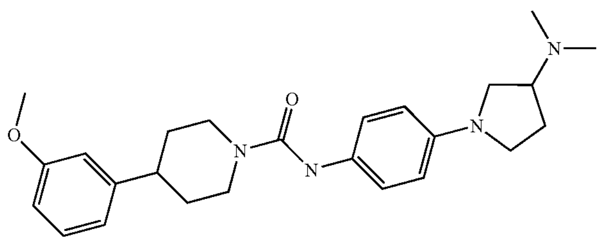 | C25H34N4O2 | 422.27 | 423 |
| 399 | 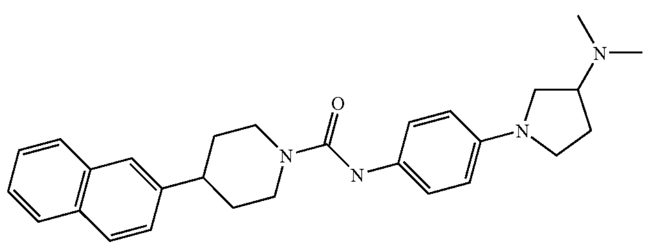 | C28H34N4O | 442.27 | 443 |
| 400 | 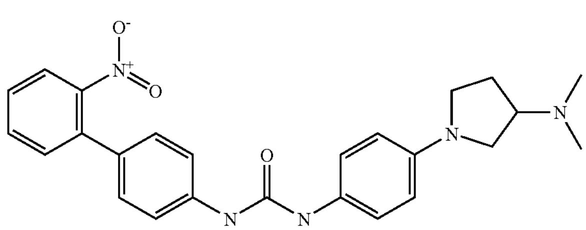 | C25H27N5O3 | 445.21 | 446 |
| 401 | 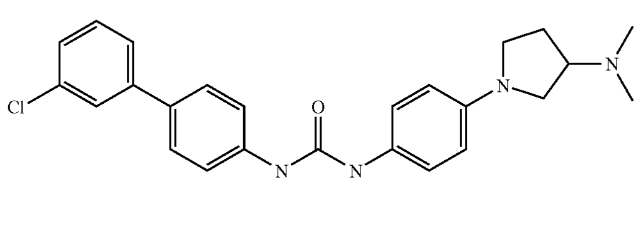 | C25H27ClN4O | 434.19 | 435 |

TABLE 6-continued

| Ex. No. | Structure | Molecular formula | Monoisotopic molecular wt. | M+H+ |
|---|---|---|---|---|
| 402 | 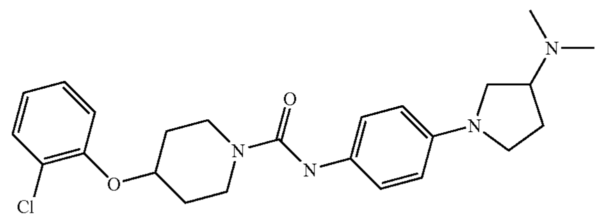 | C24H31ClN4O2 | 442.21 | 443 |
| 403 | 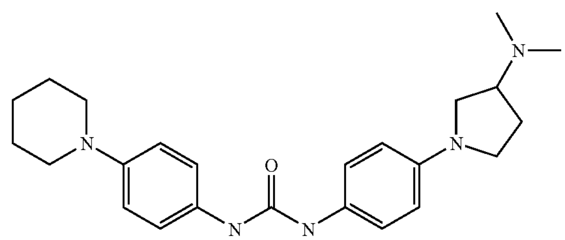 | C24H33N5O | 407.27 | 408 |
| 404 | 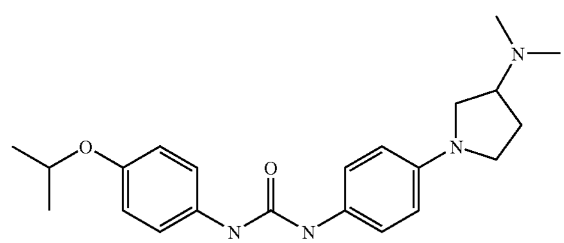 | C22H30N4O2 | 382.24 | 383 |
| 405 | 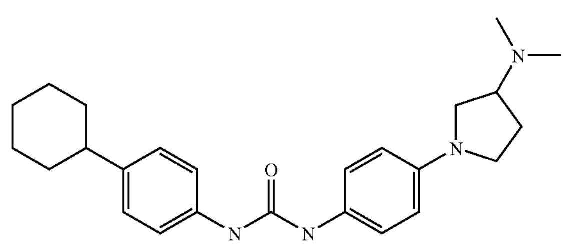 | C25H34N4O | 406.27 | 407 |
| 406 | 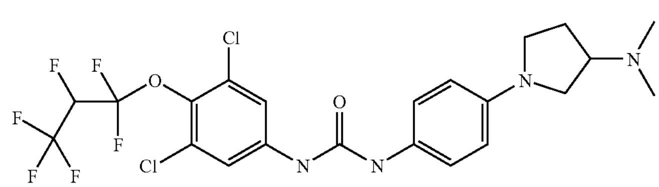 | C22H22Cl2F6N4O2 | 558.10 | 559 |
| 407 | 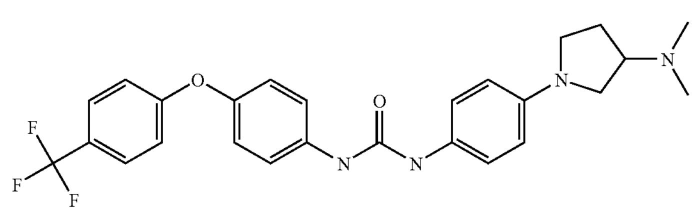 | C26H27F3N4O2 | 484.21 | 485 |

TABLE 6-continued

| Ex. No. | Structure | Molecular formula | Monoisotopic molecular wt. | M+H⁺ |
|---|---|---|---|---|
| 408 | 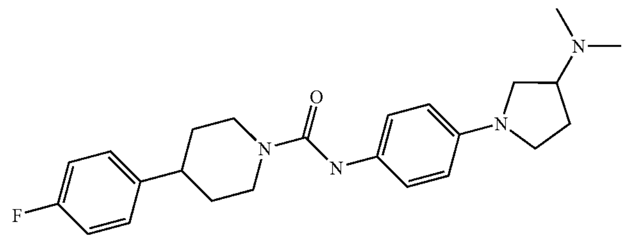 | C24H31FN4O | 410.25 | 411 |
| 409 | 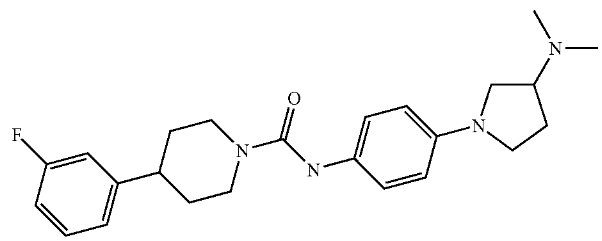 | C24H31FN4O | 410.25 | 411 |
| 410 | 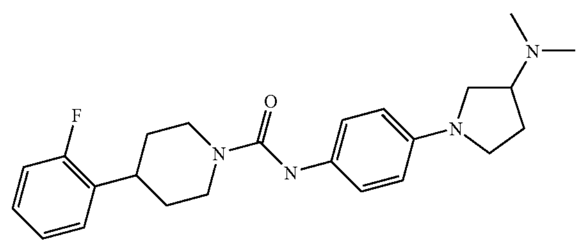 | C24H31FN4O | 410.25 | 411 |
| 411 | 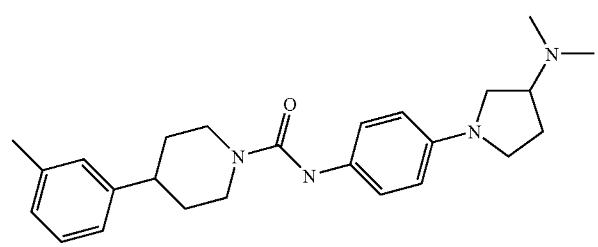 | C25H34N4O | 406.27 | 407 |
| 412 | 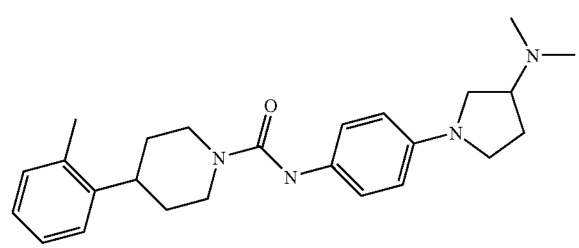 | C25H34N4O | 406.27 | 407 |
| 413 | 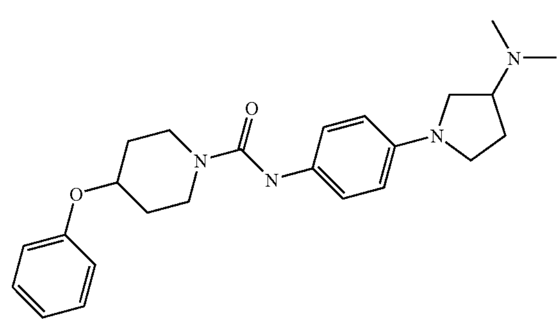 | C24H32N4O2 | 408.25 | 409 |

TABLE 6-continued

| Ex. No. | Structure | Molecular formula | Monoisotopic molecular wt. | M+H+ |
|---|---|---|---|---|
| 414 | 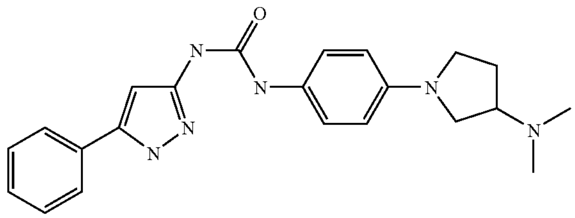 | C22H26N6O | 390.22 | 391 |
| 415 | 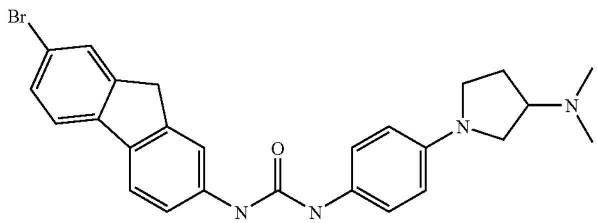 | C26H27BrN4O | 490.14 | 491 |
| 416 | 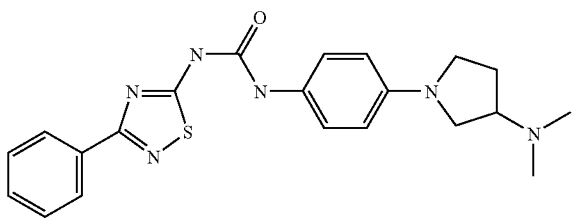 | C21H24N6OS | 408.17 | 409 |
| 417 | 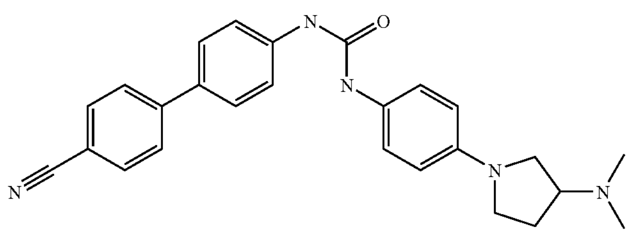 | C26H27N5O | 425.22 | 426 |
| 418 | 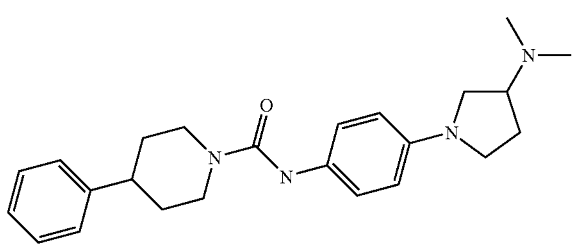 | C24H32N4O | 392.26 | 393 |
| 419 | 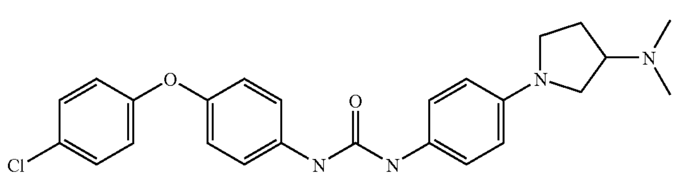 | C25H27ClN4O2 | 450.18 | 451 |

TABLE 6-continued
| Ex. No. | Structure | Molecular formula | Monoisotopic molecular wt. | M+H+ |
|---|---|---|---|---|
| 420 | 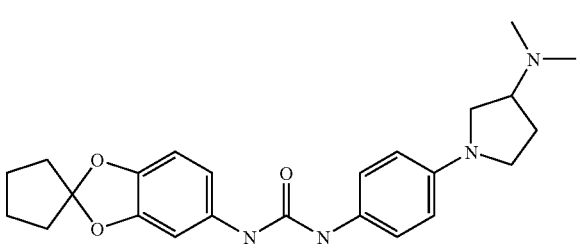 | C24H30N4O3 | 422.23 | 423 |
| 421 | 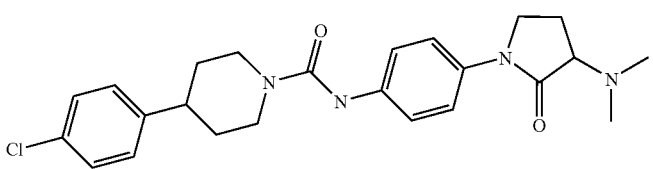 | C24H29ClN4O2 | 440.20 | 441 |
| 422 | 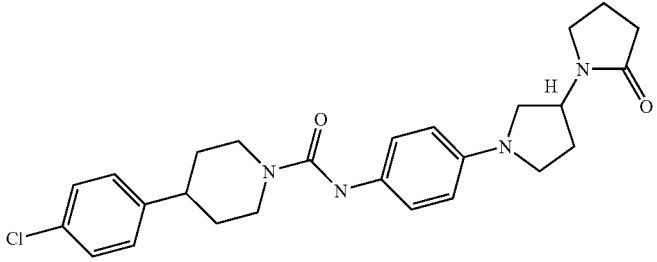 | C26H31ClN4O2 | 466.21 | 467 |
| 423 | 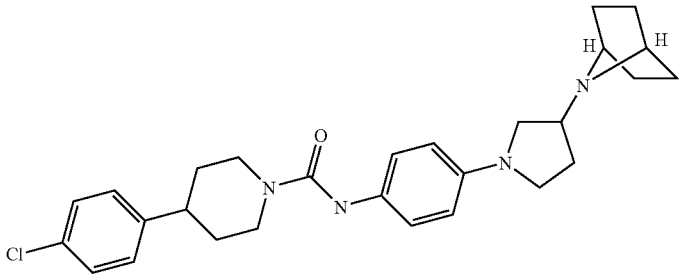 | C28H35ClN4O | 478.25 | 479 |
| 424 | 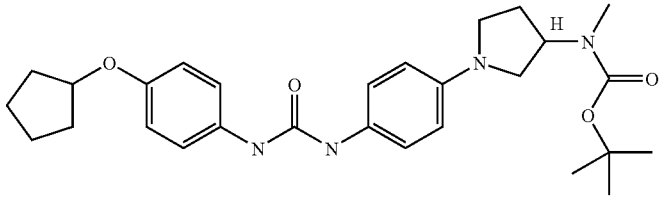 | C28H38N4O4 | 494.29 | 495 |
| 425 | 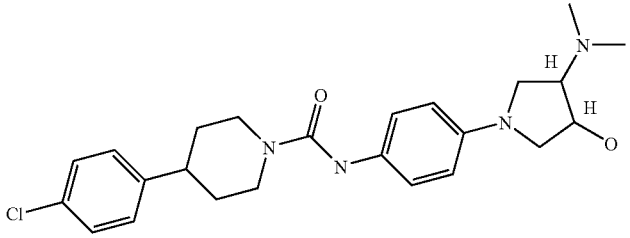 | C24H31ClN4O2 | 442.21 | 443 |

TABLE 6-continued

| Ex. No. | Structure | Molecular formula | Monoisotopic molecular wt. | M+H⁺ |
|---|---|---|---|---|
| 426 | 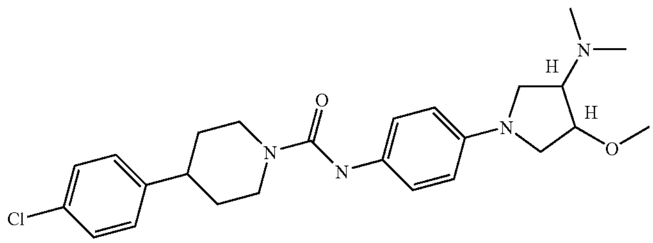 | C25H33ClN4O2 | 456.23 | 457 |
| 427 | 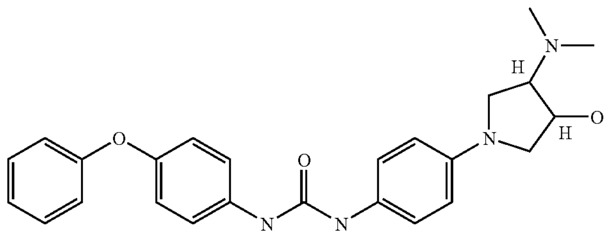 | C25H28N4O3 | 432.22 | 433 |
| 428 | 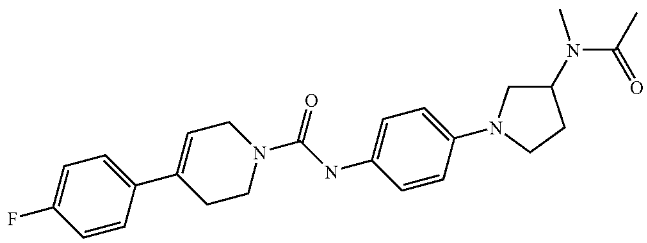 | C25H29FN4O2 | 436.23 | 437 |
| 429 | 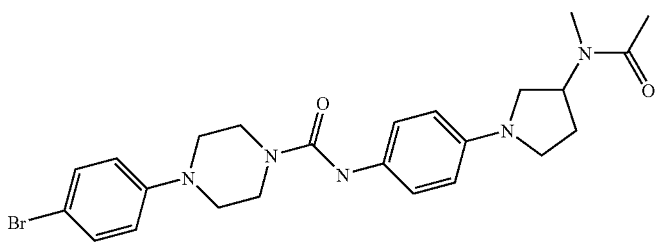 | C24H30BrN5O2 | 499.16 | 500 |
| 430 | 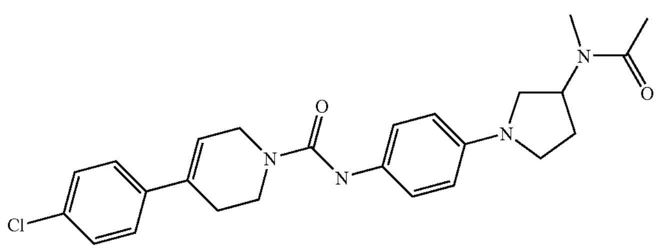 | C25H29ClN4O2 | 452.20 | 453 |
| 431 | 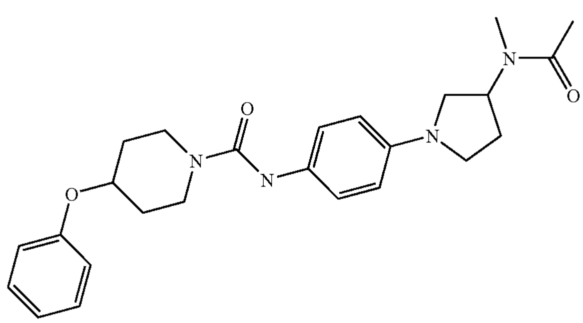 | C25H32N4O3 | 436.25 | 437 |

TABLE 6-continued

| Ex. No. | Structure | Molecular formula | Monoisotopic molecular wt. | M+H+ |
|---|---|---|---|---|
| 432 | 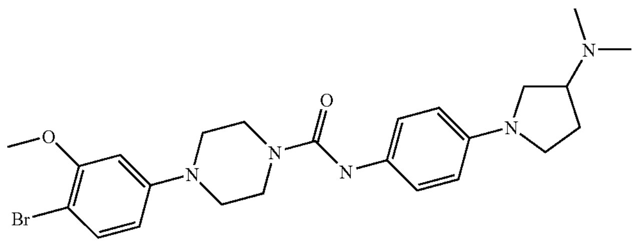 | C24H32BrN5O2 | 501.17 | 502 |
| 433 | 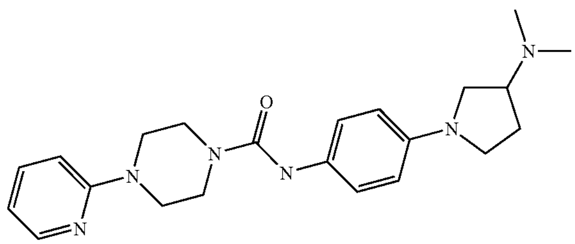 | C22H30N6O | 394.25 | 395 |
| 434 | 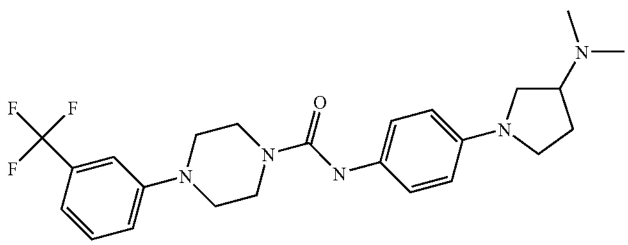 | C24H30F3N5O | 461.24 | 462 |
| 435 | 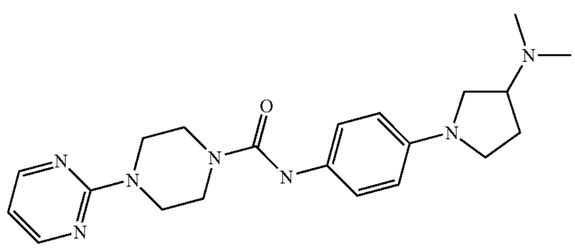 | C21H29N7O | 395.24 | 396 |
| 436 | 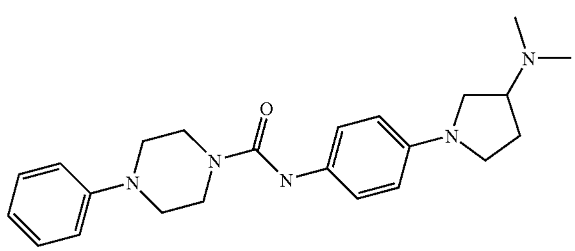 | C23H31N5O | 393.25 | 394 |
| 437 | 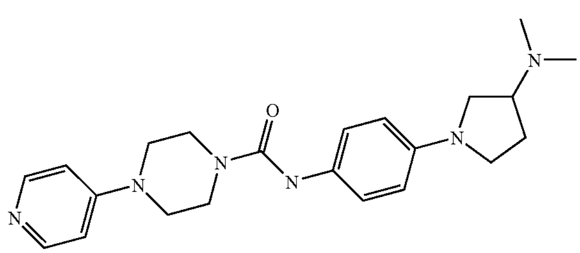 | C22H30N6O | 394.25 | 395 |

TABLE 6-continued

| Ex. No. | Structure | Molecular formula | Monoisotopic molecular wt. | M+H+ |
|---|---|---|---|---|
| 438 | 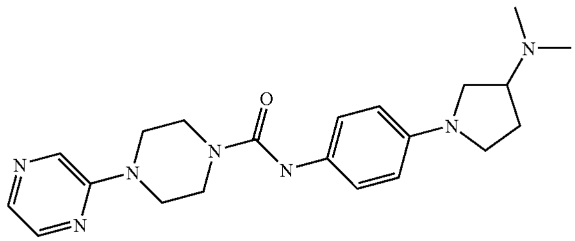 | C21H29N7O | 395.24 | 396 |
| 439 | 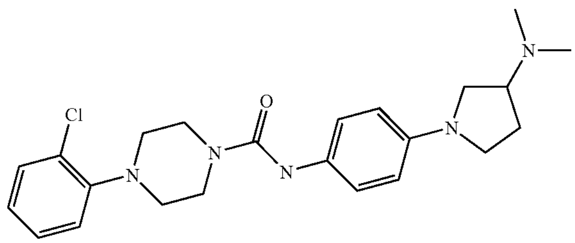 | C23H30ClN5O | 427.21 | 428 |
| 440 | 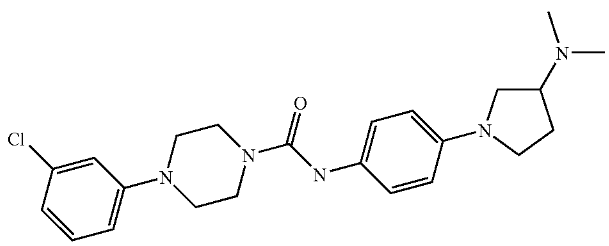 | C23H30ClN5O | 427.21 | 428 |
| 441 | 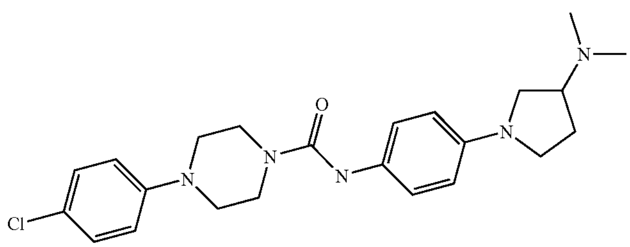 | C23H30ClN5O | 427.21 | 428 |
| 442 | 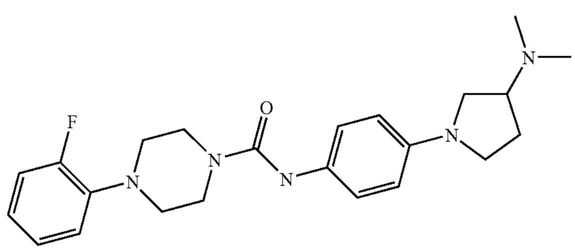 | C23H30FN5O | 411.24 | 412 |
| 443 | 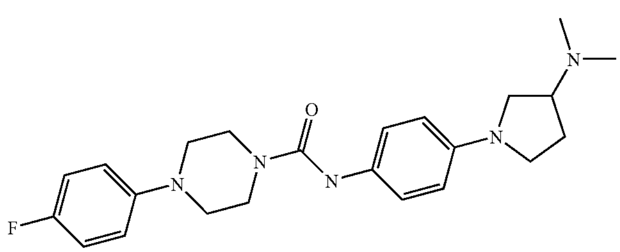 | C23H30FN5O | 411.24 | 412 |

TABLE 6-continued

| Ex. No. | Structure | Molecular formula | Monoisotopic molecular wt. | M+H+ |
|---|---|---|---|---|
| 444 | 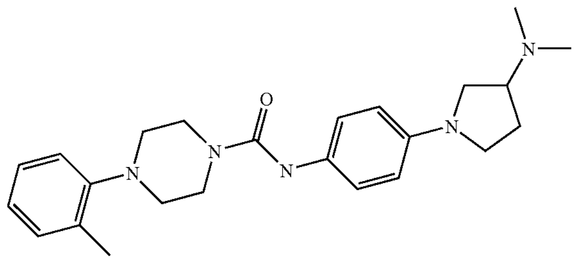 | C24H33N5O | 407.27 | 408 |
| 445 | 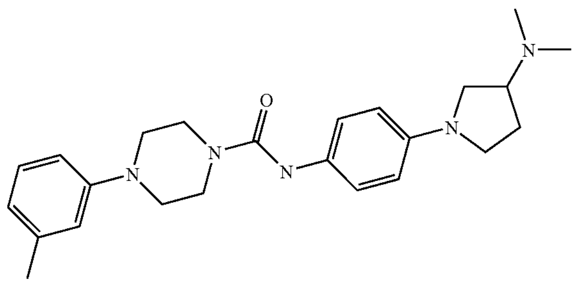 | C24H33N5O | 407.27 | 408 |
| 446 | 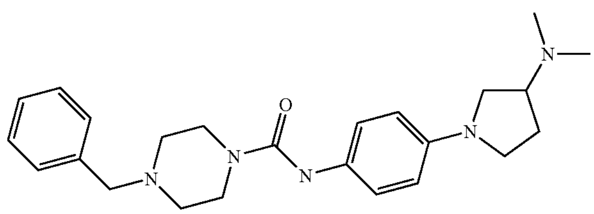 | C24H33N5O | 407.27 | 408 |
| 447 | 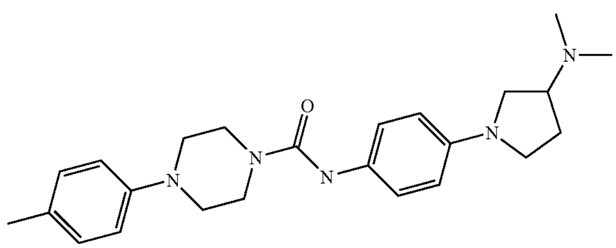 | C24H33N5O | 407.27 | 408 |
| 448 | 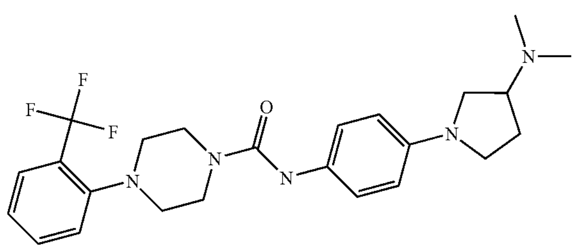 | C24H30F3N5O | 461.24 | 462 |
| 449 | 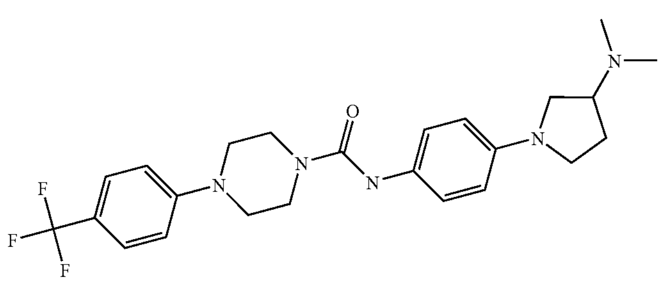 | C24H30F3N5O | 461.24 | 462 |

TABLE 6-continued

| Ex. No. | Structure | Molecular formula | Monoisotopic molecular wt. | M+H+ |
|---|---|---|---|---|
| 450 | 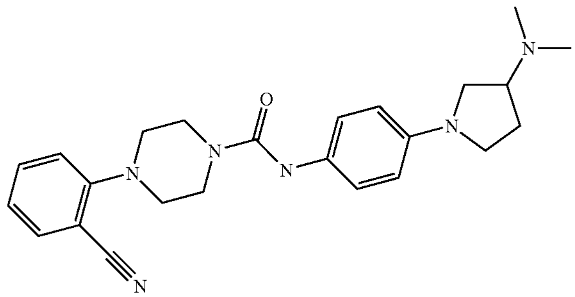 | C24H30N6O | 418.25 | 419 |
| 451 | 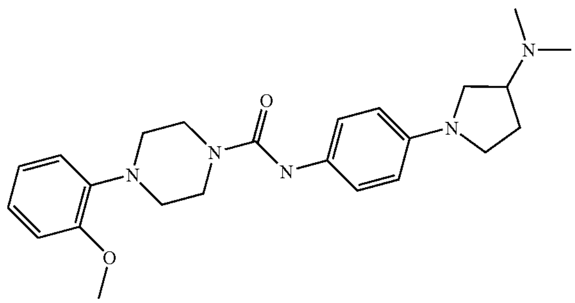 | C24H33N5O2 | 423.26 | 424 |
| 452 | 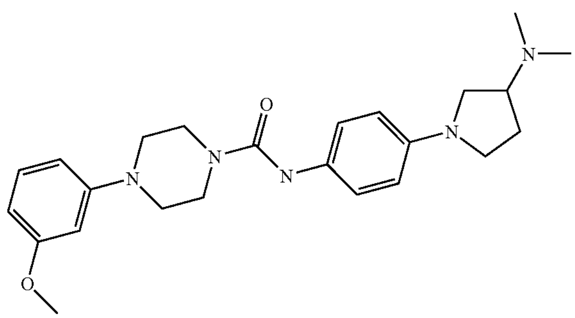 | C24H33N5O2 | 423.26 | 424 |
| 453 | 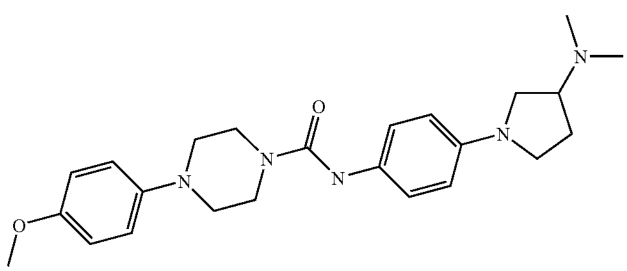 | C24H33N5O2 | 423.26 | 424 |
| 454 | 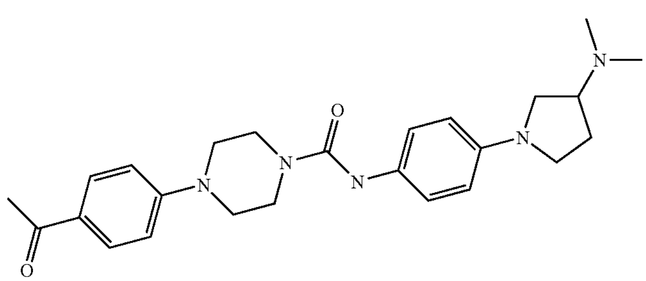 | C25H33N5O2 | 435.26 | 436 |

TABLE 6-continued

| Ex. No. | Structure | Molecular formula | Monoisotopic molecular wt. | M+H+ |
|---|---|---|---|---|
| 455 | 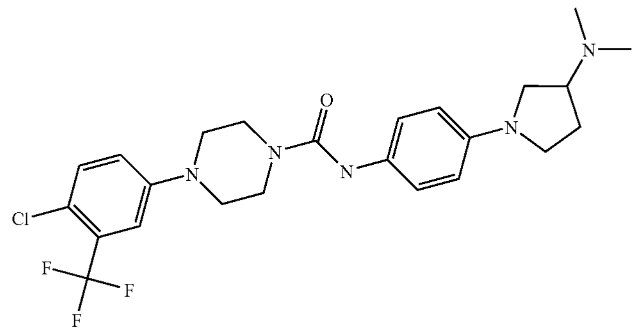 | C24H29ClF3N5O | 495.20 | 496 |
| 456 | 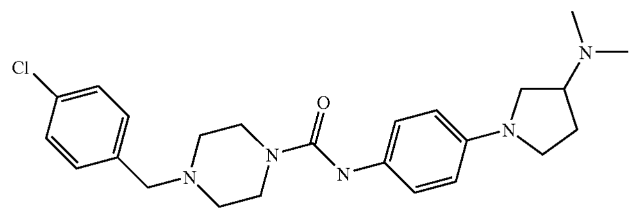 | C24H32ClN5O | 441.23 | 442 |
| 457 | 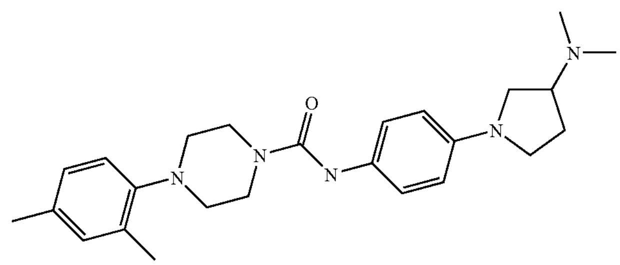 | C25H35N5O | 421.28 | 422 |
| 458 | 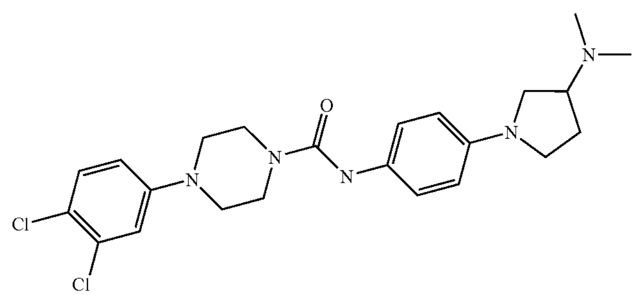 | C23H29Cl2N5O | 461.17 | 462 |
| 459 | 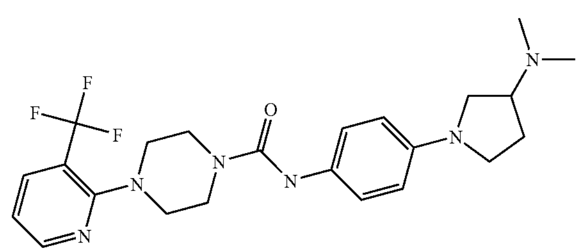 | C23H29F3N6O | 462.24 | 463 |

TABLE 6-continued
| Ex. No. | Structure | Molecular formula | Monoisotopic molecular wt. | M+H⁺ |
|---|---|---|---|---|
| 460 | 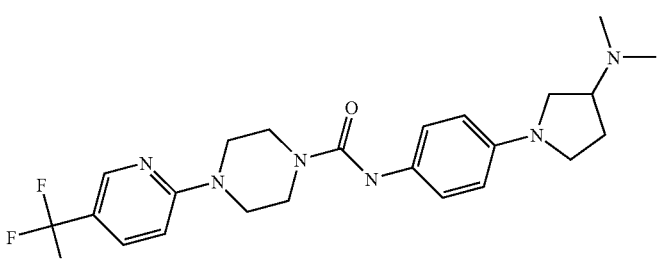 | C23H29F3N6O | 462.24 | 463 |
| 461 | 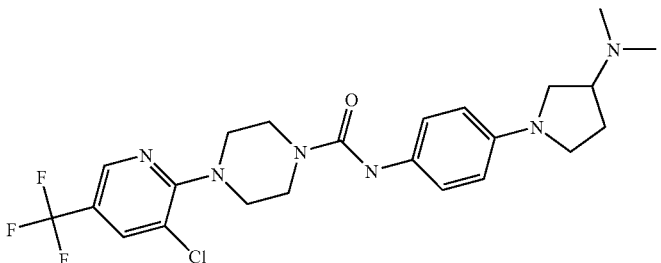 | C23H28ClF3N6O | 496.20 | 497 |
| 462 | 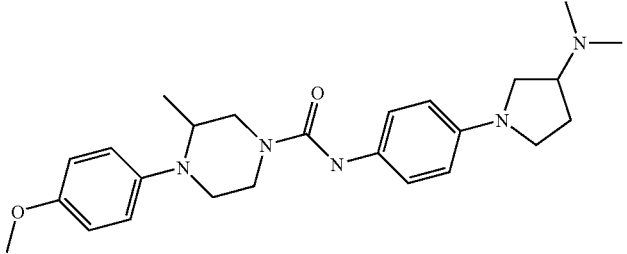 | C25H35N5O2 | 437.28 | 438 |
| 463 | 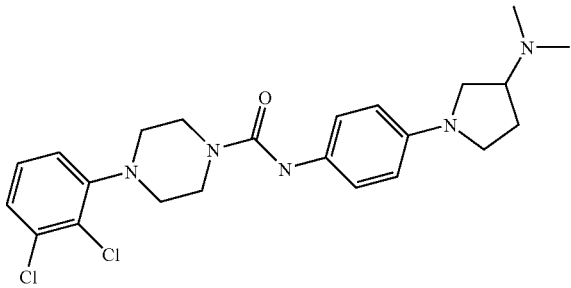 | C23H29Cl2N5O | 461.17 | 462 |
| 464 | 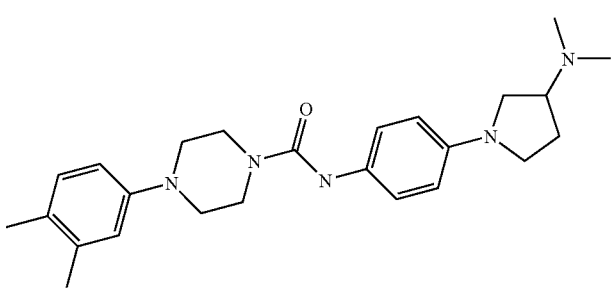 | C25H35N5O | 421.28 | 422 |

TABLE 6-continued

| Ex. No. | Structure | Molecular formula | Monoisotopic molecular wt. | M+H+ |
|---|---|---|---|---|
| 465 | 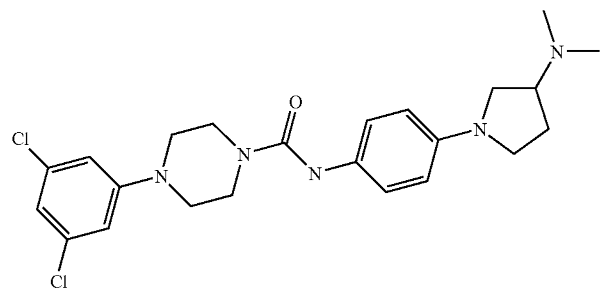 | C23H29Cl2N5O | 461.17 | 462 |
| 466 | 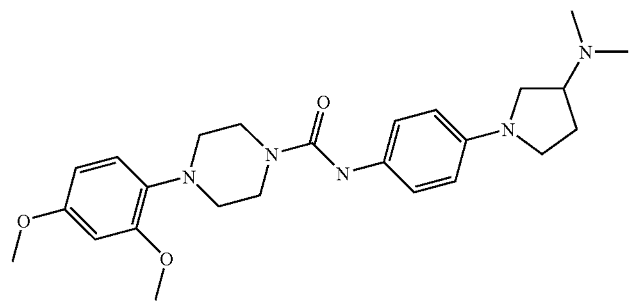 | C25H35N5O3 | 453.27 | 454 |
| 467 | 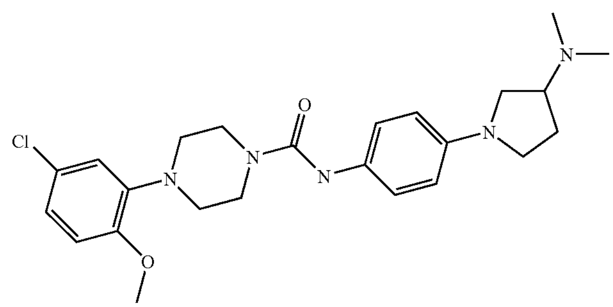 | C24H32ClN5O2 | 457.22 | 458 |
| 468 | 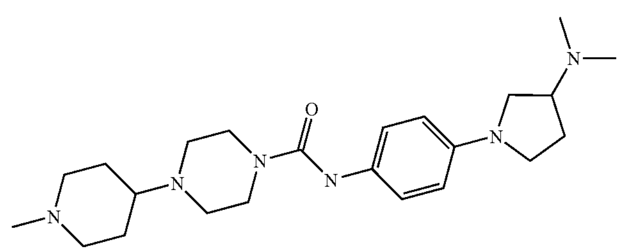 | C23H38N6O | 414.31 | 415 |
| 469 | 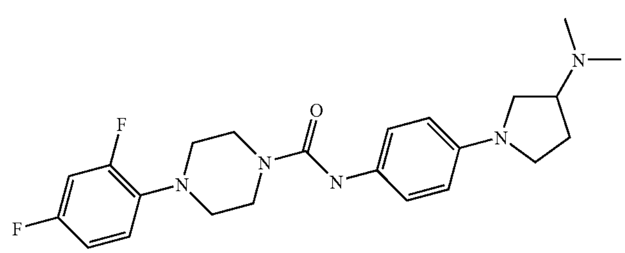 | C23H29F2N5O | 429.23 | 430 |

TABLE 6-continued
| Ex. No. | Structure | Molecular formula | Monoisotopic molecular wt. | M+H+ |
|---|---|---|---|---|
| 470 | 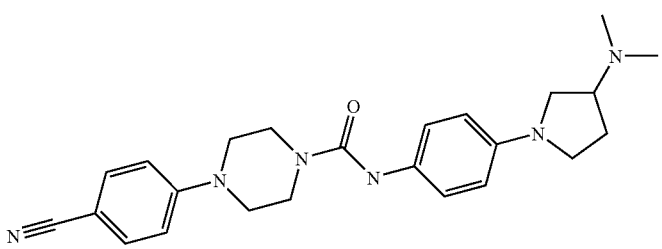 | C24H30N6O | 418.25 | 419 |
| 471 | 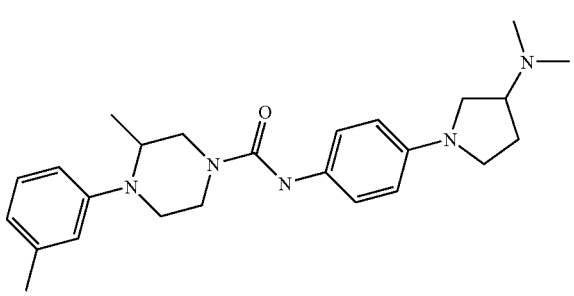 | C25H35N5O | 421.28 | 422 |
| 472 | 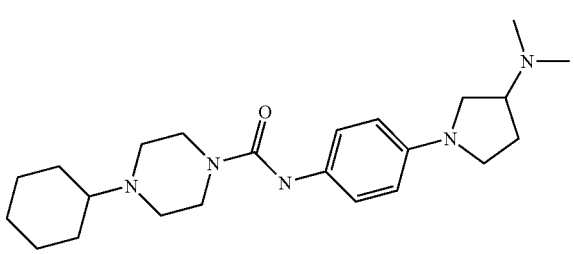 | C23H37N5O | 399.30 | 400 |
| 473 | 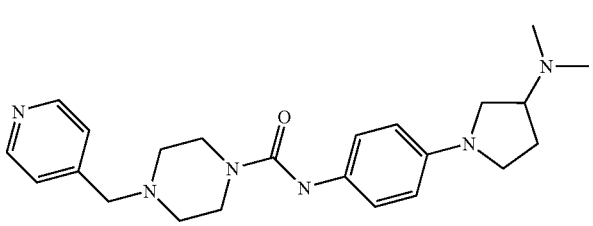 | C23H32N6O | 408.26 | 409 |
| 474 | 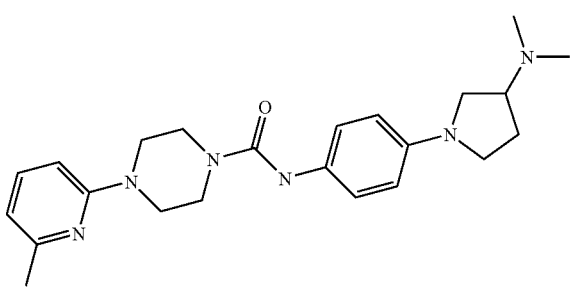 | C23H32N6O | 408.26 | 409 |

TABLE 6-continued

| Ex. No. | Structure | Molecular formula | Monoisotopic molecular wt. | M+H[+] |
|---|---|---|---|---|
| 475 | 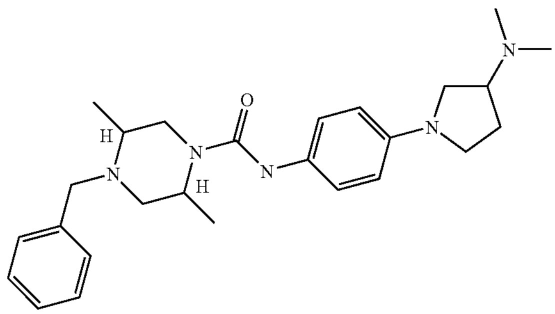 | C26H37N5O | 435.30 | 436 |
| 476 | 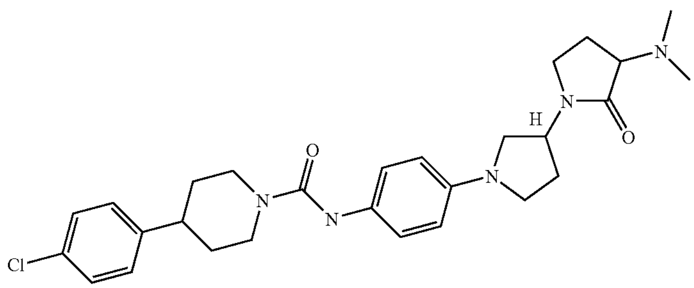 | C28H36ClN5O2 | 509.26 | 510 |
| 477 | 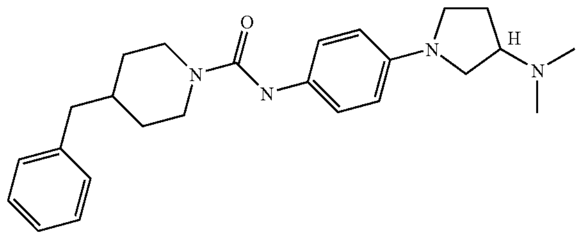 | C25H34N4O | 406.27 | 407 |
| 478 | 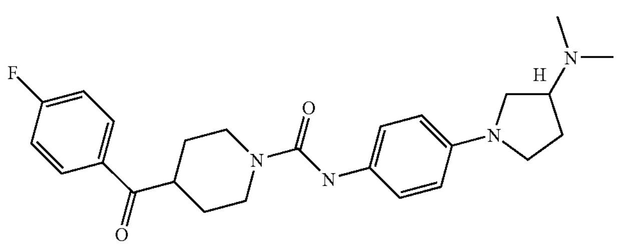 | C25H31FN4O2 | 438.24 | 439 |
| 479 | 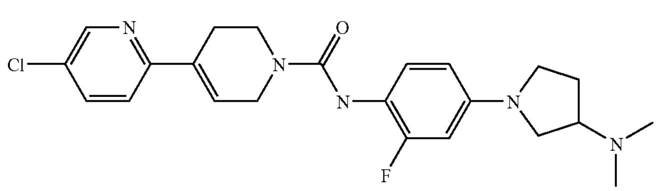 | C23H27ClFN5O | 443.96 | 444 |
| 480 | 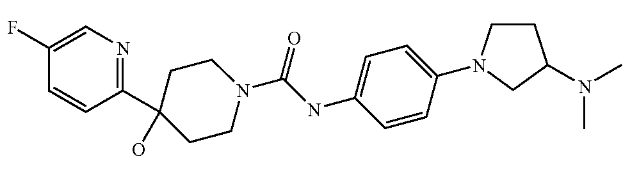 | C23H30FN5O2 | 427.53 | 428 |

TABLE 6-continued

| Ex. No. | Structure | Molecular formula | Monoisotopic molecular wt. | M+H⁺ |
|---|---|---|---|---|
| 481 | 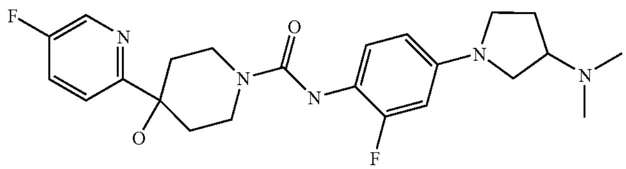 | C23H29F2N5O2 | 445.52 | 446 |
| 482 | 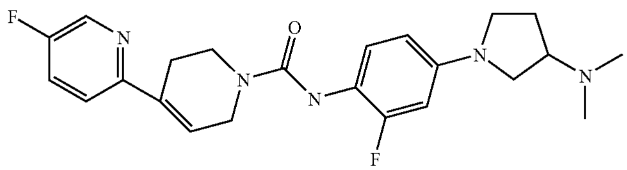 | C23H27F2N5O | 427.50 | 428 |
| 483 | 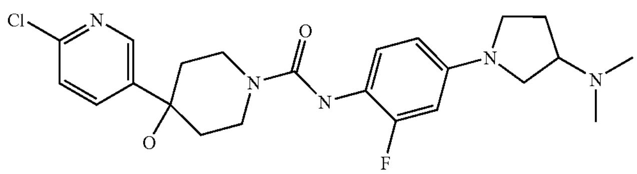 | C23H29ClFN5O2 | 461.97 | 462 |
| 484 | 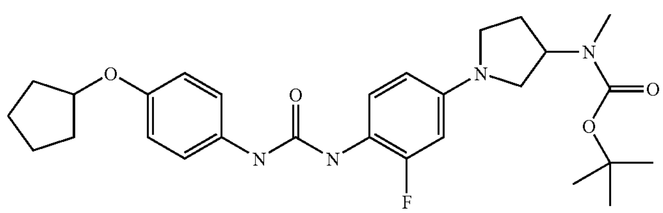 | C28H37FN4O4 | 512.28 | 513 |
| 485 | 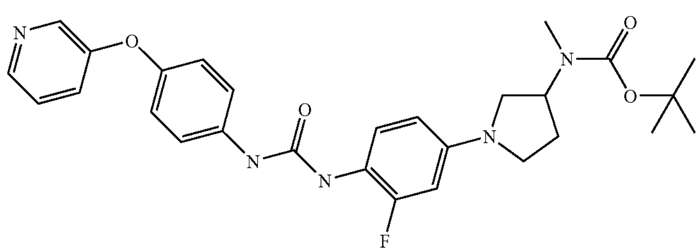 | C28H32FN5O4 | 521.24 | 522 |
| 486 | 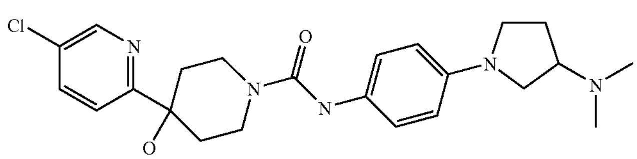 | C23H30ClN5O2 | 443.98 | 444 |
| 487 | 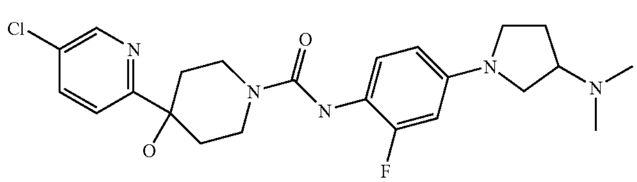 | C23H29ClFN5O2 | 461.97 | 462 |

TABLE 6-continued

| Ex. No. | Structure | Molecular formula | Monoisotopic molecular wt. | M+H[+] |
|---|---|---|---|---|
| 488 | 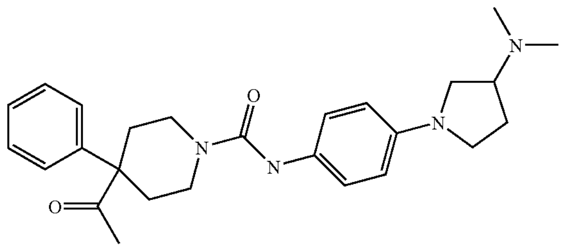 | C26H34N4O2 | 434.27 | 435 |
| 489 | 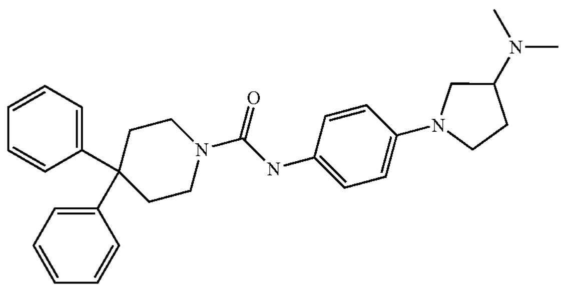 | C30H36N4O | 468.29 | 469 |
| 490 | 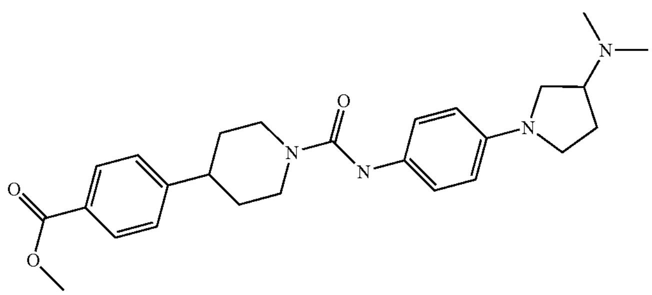 | C26H34N4O3 | 450.26 | 451 |
| 491 | 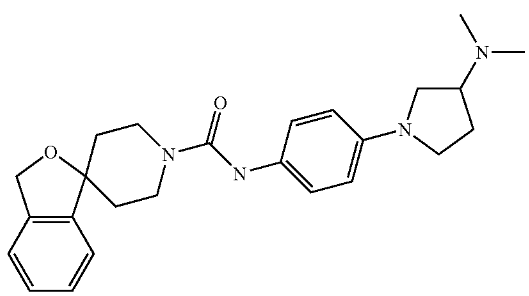 | C25H32N4O2 | 420.25 | 421 |
| 492 | 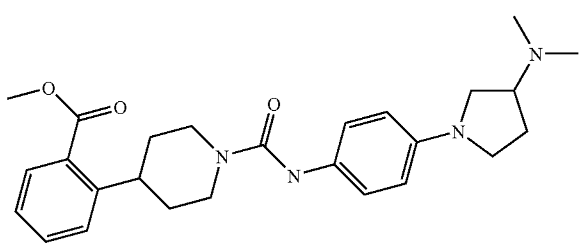 | C26H34N4O3 | 450.26 | 451 |

TABLE 6-continued

| Ex. No. | Structure | Molecular formula | Monoisotopic molecular wt. | M+H[+] |
|---|---|---|---|---|
| 493 | 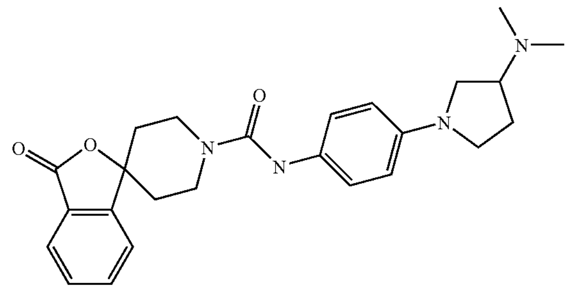 | C25H30N4O3 | 434.23 | 435 |
| 494 | 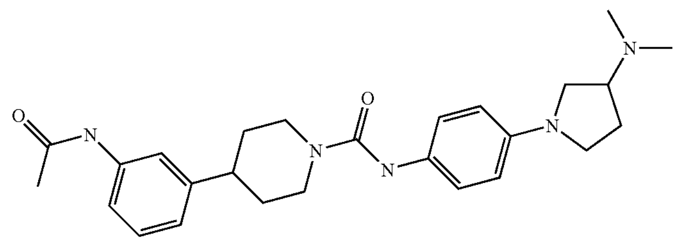 | C26H35N5O2 | 449.28 | 450 |
| 495 | 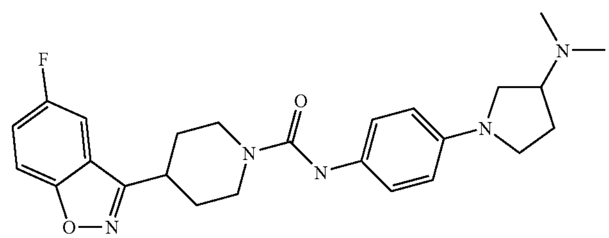 | C25H30FN5O2 | 451.24 | 452 |
| 496 | 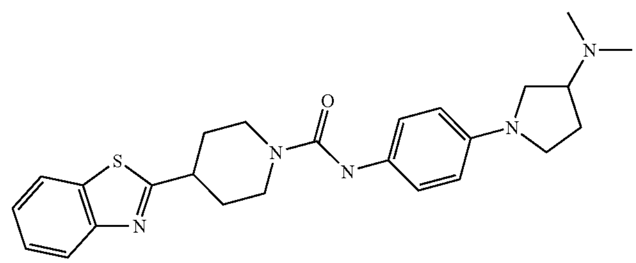 | C25H31N5OS | 449.23 | 450 |
| 497 | 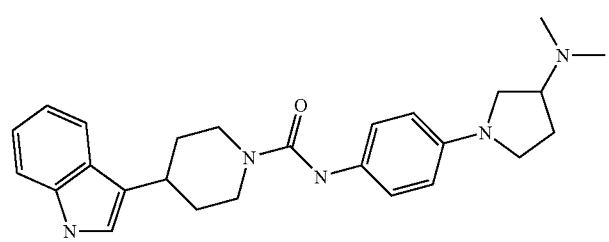 | C26H33N5O | 431.27 | 432 |
| 498 | 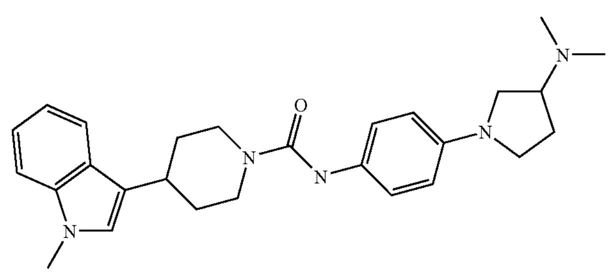 | C27H35N5O | 445.28 | 446 |

TABLE 6-continued

| Ex. No. | Structure | Molecular formula | Monoisotopic molecular wt. | M+H+ |
|---|---|---|---|---|
| 499 | 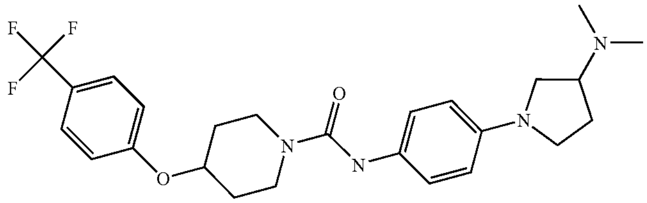 | C25H31F3N4O2 | 476.24 | 477 |
| 500 | 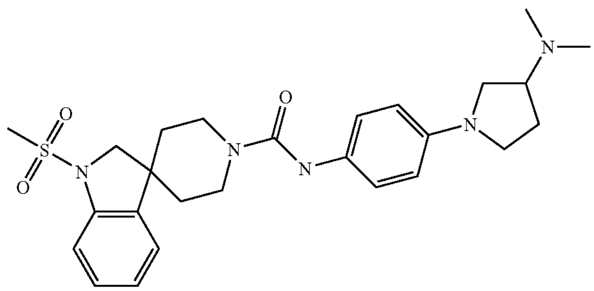 | C26H35N5O3S | 497.25 | 498 |
| 501 | 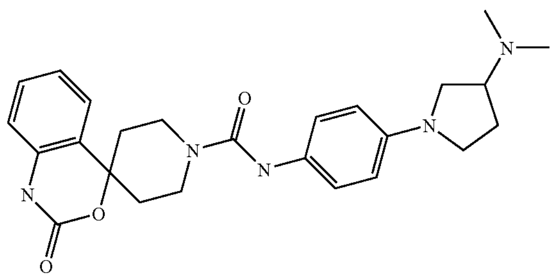 | C25H31N5O3 | 449.24 | 450 |
| 502 | 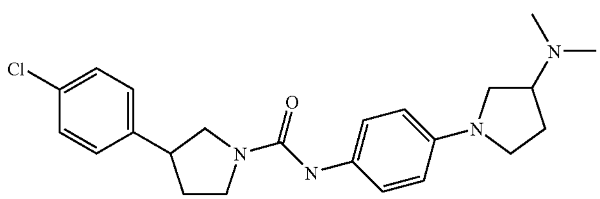 | C23H29ClN4O | 412.20 | 413 |
| 503 | 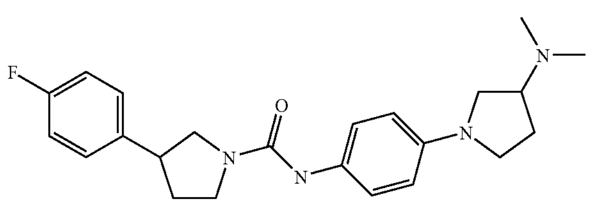 | C23H29FN4O | 396.23 | 397 |
| 504 | 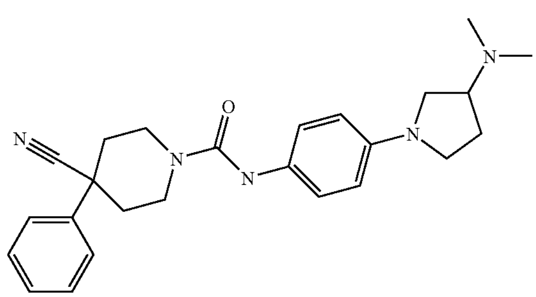 | C25H31N5O | 417.25 | 418 |

TABLE 6-continued

| Ex. No. | Structure | Molecular formula | Monoisotopic molecular wt. | M+H+ |
|---|---|---|---|---|
| 505 | 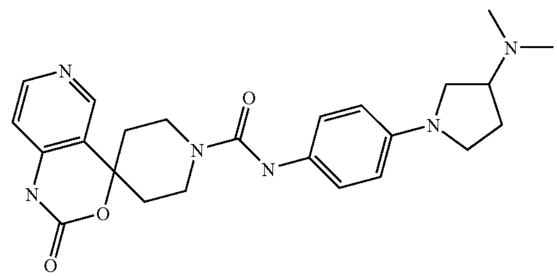 | C24H30N6O3 | 450.24 | 451 |
| 506 | 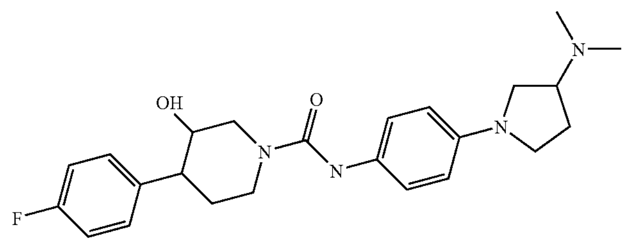 | C24H31FN4O2 | 426.24 | 427 |
| 507 | 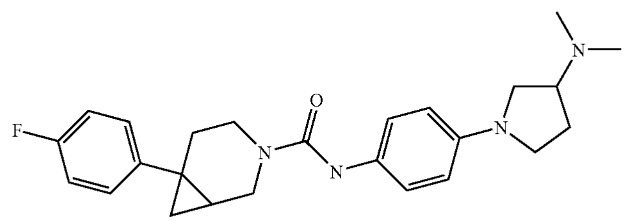 | C25H31FN4O | 422.25 | 423 |

TABLE 7

| Ex. No. | Structure | Molecular formula | Monoisotopic molecular wt. | M + H+ |
|---|---|---|---|---|
| 508 | 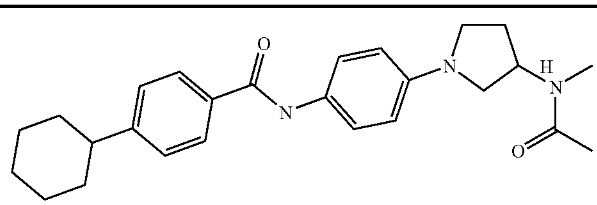 | C26H33N3O2 | 419.26 | 420 |
| 509 | 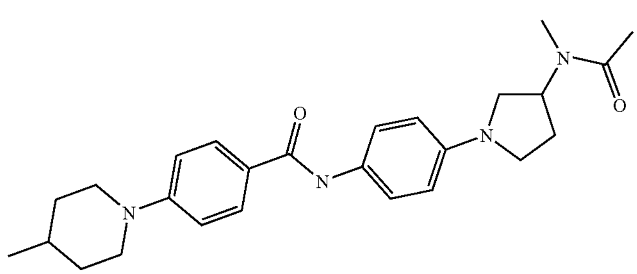 | C26H34N4O2 | 434.27 | 435 |

TABLE 7-continued

| Ex. No. | Structure | Molecular formula | Monoisotopic molecular wt. | M + H+ |
|---|---|---|---|---|
| 510 | 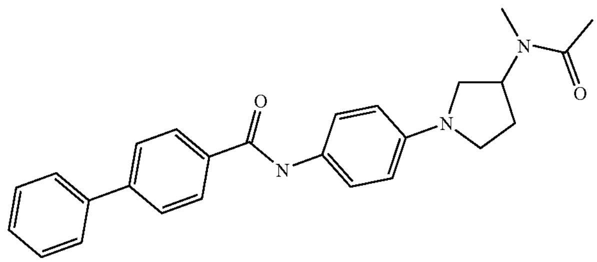 | C26H27N3O2 | 413.21 | 414 |
| 511 | 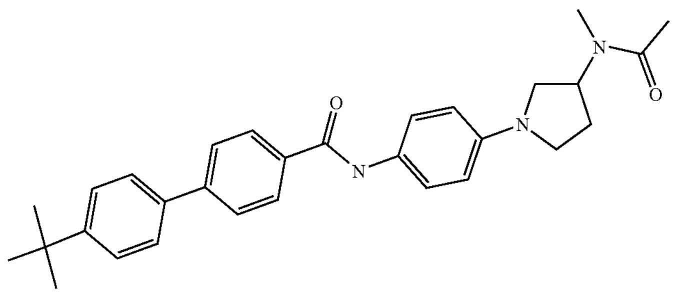 | C30H35N3O2 | 469.27 | 470 |
| 512 | 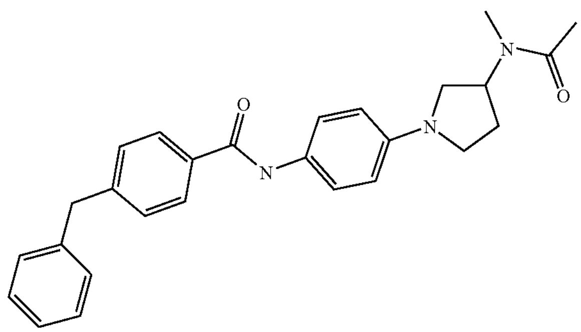 | C27H29N3O2 | 427.23 | 428 |
| 513 | 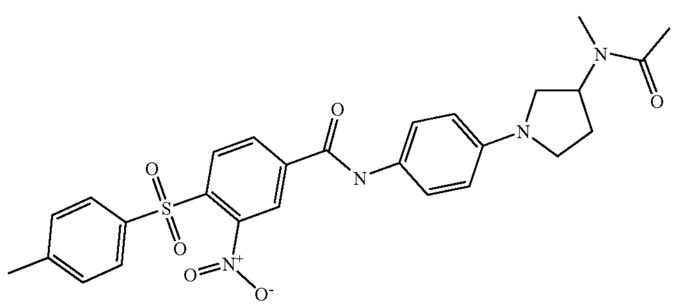 | C27H28N4O6S | 536.17 | 537 |
| 514 | 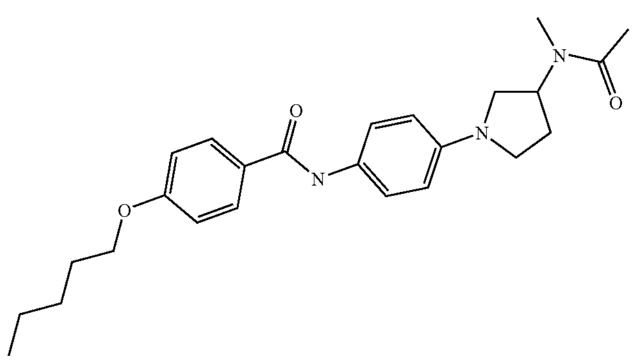 | C25H33N3O3 | 423.25 | 424 |

TABLE 7-continued

| Ex. No. | Structure | Molecular formula | Monoisotopic molecular wt. | M + H⁺ |
|---|---|---|---|---|
| 515 | 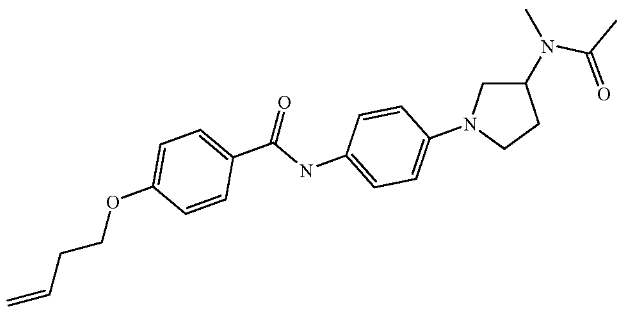 | C24H29N3O3 | 407.22 | 408 |
| 516 | 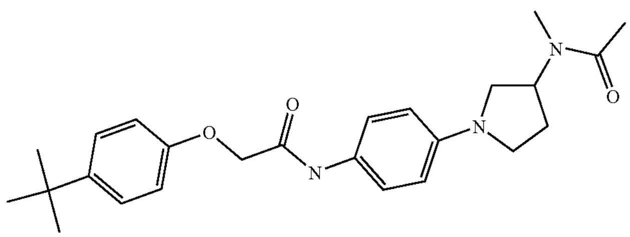 | C25H33N3O3 | 423.25 | 424 |
| 517 | 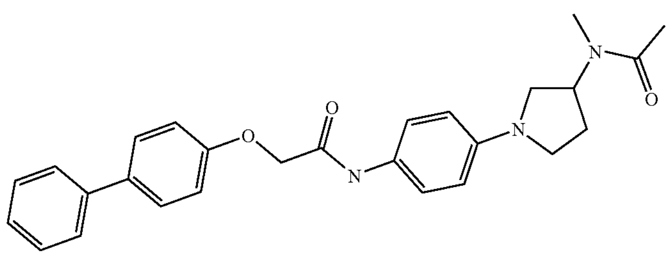 | C27H29N3O3 | 443.22 | 444 |
| 518 | 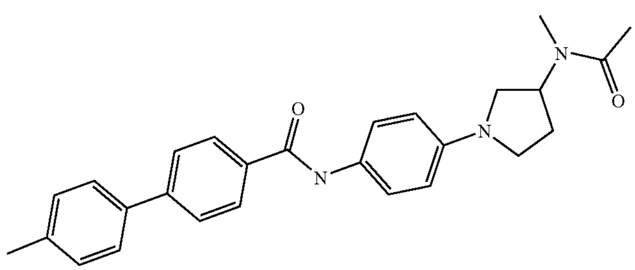 | C27H29N3O2 | 427.23 | 428 |
| 519 | 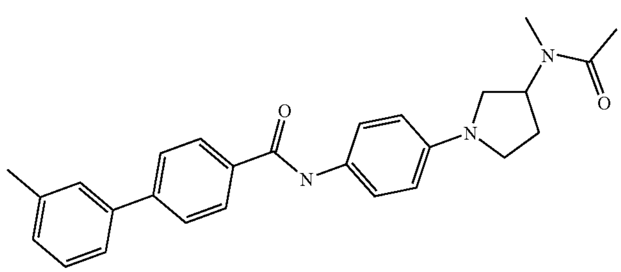 | C27H29N3O2 | 427.23 | 428 |

TABLE 7-continued

| Ex. No. | Structure | Molecular formula | Monoisotopic molecular wt. | M + H+ |
|---|---|---|---|---|
| 520 | 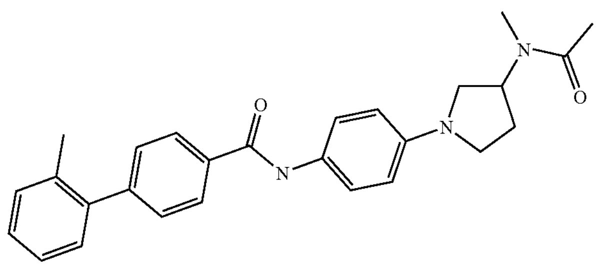 | C27H29N3O2 | 427.23 | 428 |
| 521 | 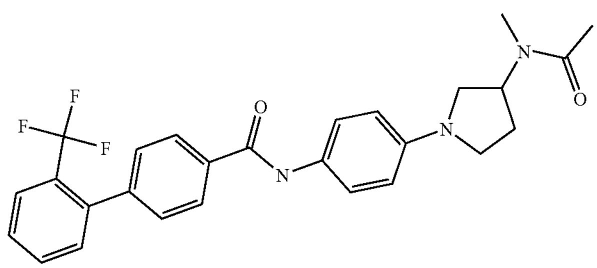 | C27H26F3N3O2 | 481.20 | 482 |
| 522 | 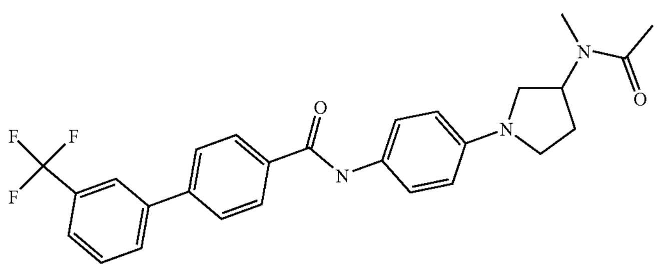 | C27H26F3N3O2 | 481.20 | 482 |
| 523 | 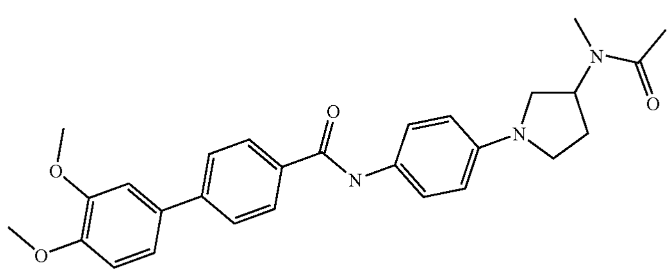 | C28H31N3O4 | 473.23 | 474 |
| 524 | 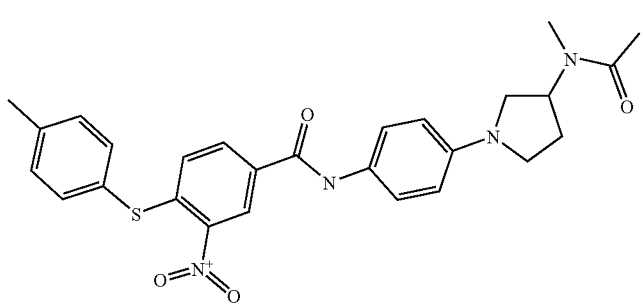 | C27H28N4O4S | 504.18 | 505 |

TABLE 7-continued

| Ex. No. | Structure | Molecular formula | Monoisotopic molecular wt. | M + H+ |
|---|---|---|---|---|
| 525 | 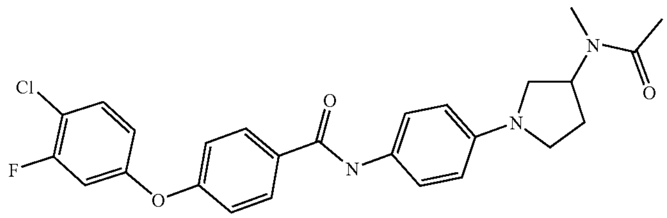 | C26H25ClFN3O3 | 481.16 | 482 |
| 526 | 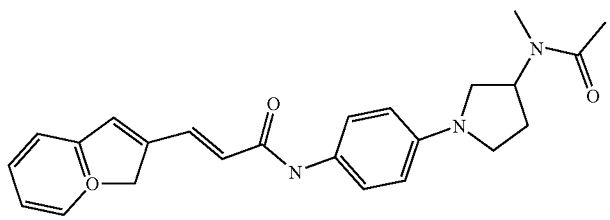 | C24H25N3O3 | 403.19 | 404 |
| 527 | 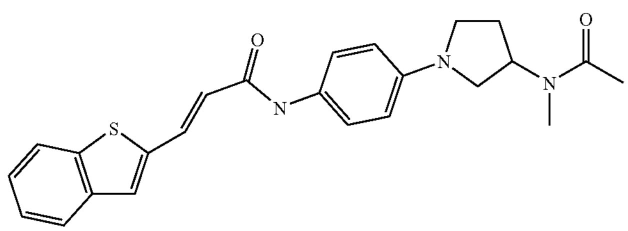 | C24H25N3O2S | 419.17 | 420 |
| 528 | 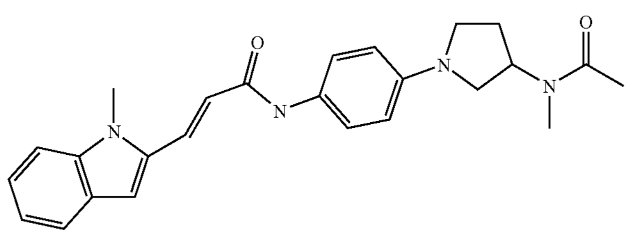 | C25H28N4O2 | 416.22 | 417 |
| 529 | 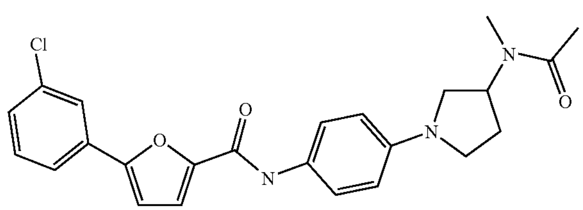 | C24H24ClN3O3 | 437.15 | 438 |
| 530 | 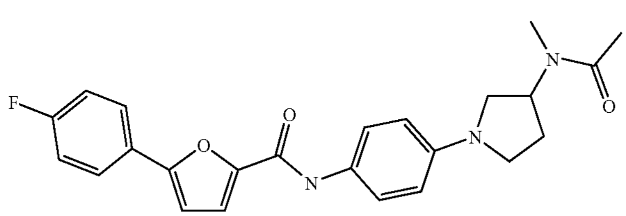 | C24H24FN3O3 | 421.18 | 422 |

TABLE 7-continued

| Ex. No. | Structure | Molecular formula | Monoisotopic molecular wt. | M + H⁺ |
|---|---|---|---|---|
| 531 | 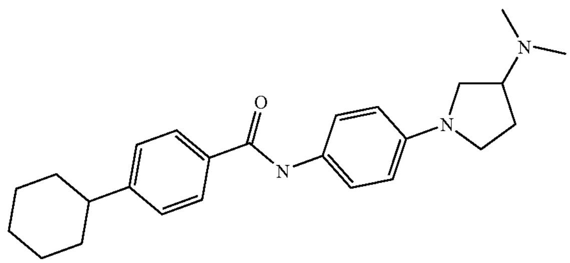 | C25H33N3O | 391.26 | 392 |
| 532 | 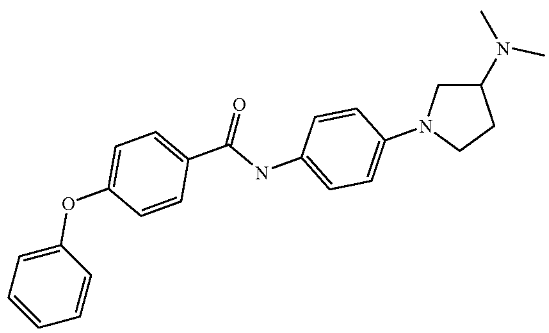 | C25H27N3O2 | 401.21 | 402 |
| 533 | 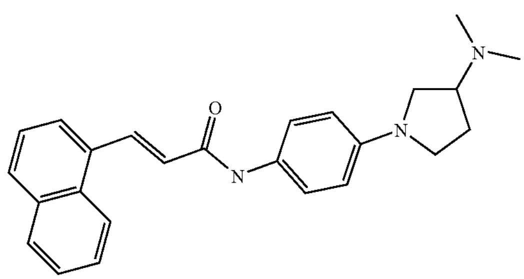 | C25H27N3O | 385.21 | 386 |
| 534 | 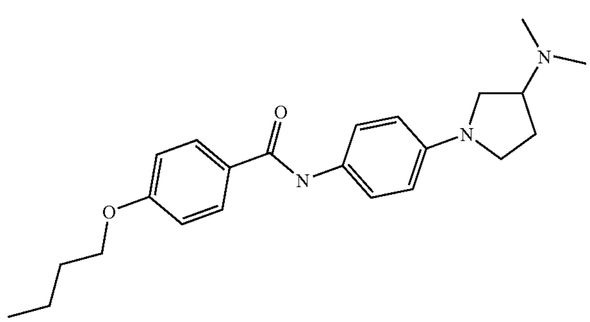 | C23H31N3O2 | 381.24 | 382 |
| 535 | 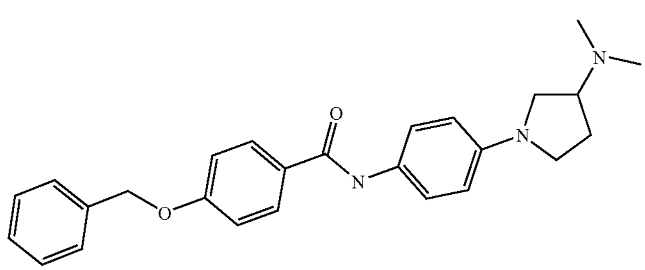 | C26H29N3O2 | 415.23 | 416 |

TABLE 7-continued

| Ex. No. | Structure | Molecular formula | Monoisotopic molecular wt. | M + H+ |
|---|---|---|---|---|
| 536 | 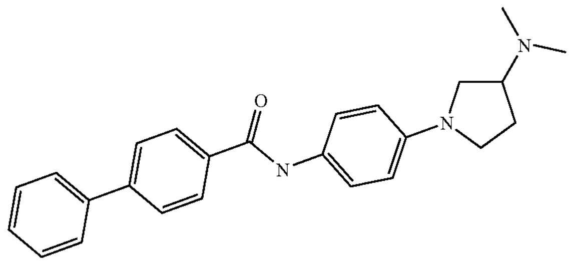 | C25H27N3O | 385.21 | 386 |
| 537 | 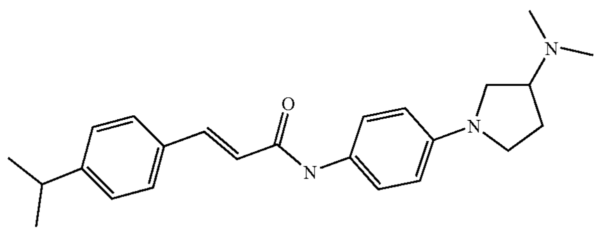 | C24H31N3O | 377.25 | 378 |
| 538 | 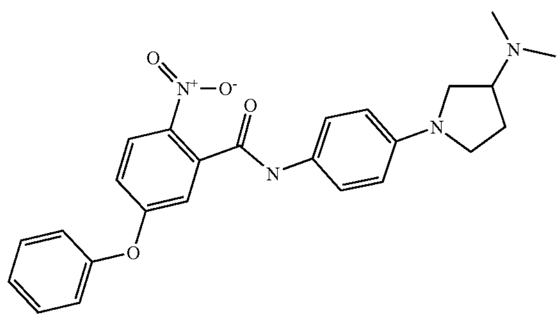 | C25H26N4O4 | 446.20 | 447 |
| 539 | 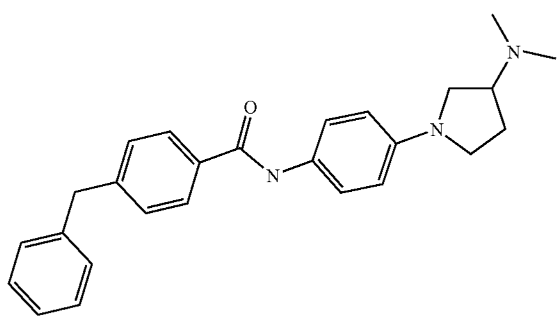 | C26H29N3O | 399.23 | 400 |
| 540 | 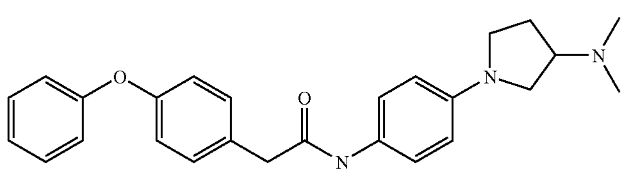 | C26H29N3O2 | 415.23 | 416 |
| 541 | 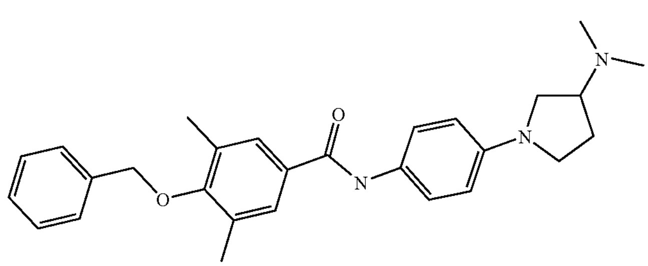 | C28H33N3O2 | 443.26 | 444 |

TABLE 7-continued

| Ex. No. | Structure | Molecular formula | Monoisotopic molecular wt. | M + H+ |
|---|---|---|---|---|
| 542 | 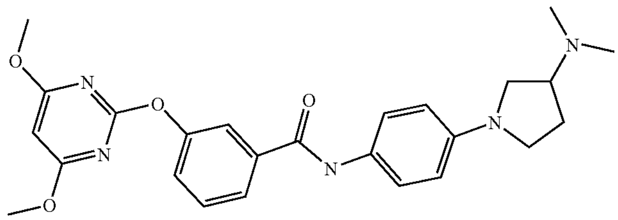 | C25H29N5O4 | 463.22 | 464 |
| 543 | 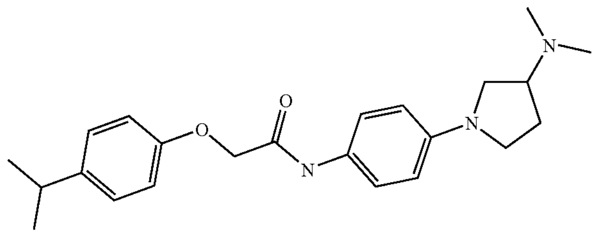 | C23H31N3O2 | 381.24 | 382 |
| 544 | 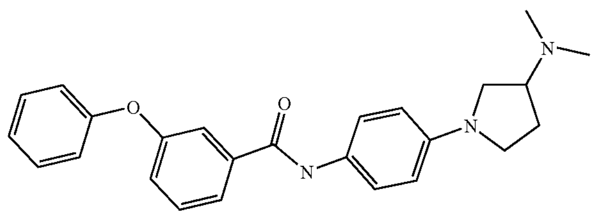 | C25H27N3O2 | 401.21 | 402 |
| 545 | 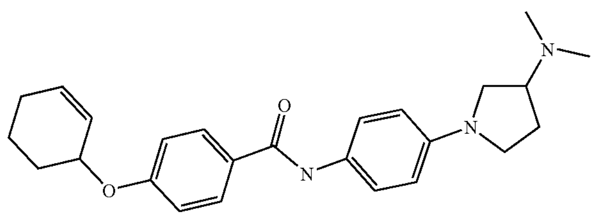 | C25H31N3O2 | 405.24 | 406 |
| 546 | 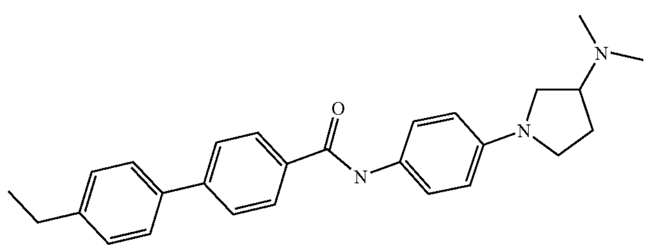 | C27H31N3O | 413.25 | 414 |
| 547 | 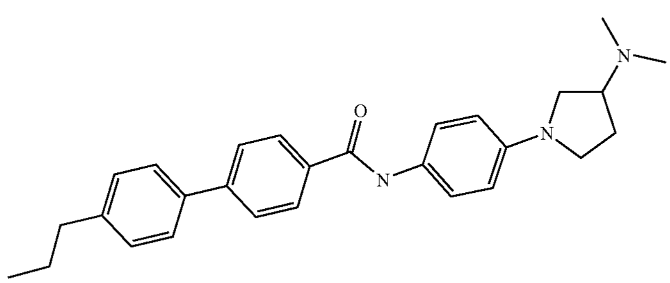 | C28H33N3O | 427.26 | 428 |

TABLE 7-continued

| Ex. No. | Structure | Molecular formula | Monoisotopic molecular wt. | M + H+ |
|---|---|---|---|---|
| 548 | 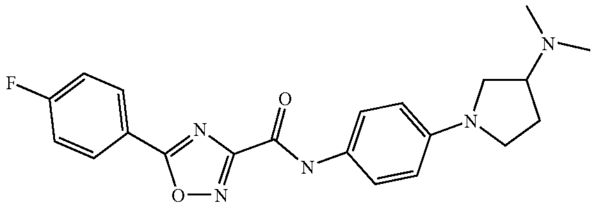 | C21H22FN5O2 | 395.18 | 396 |
| 549 | 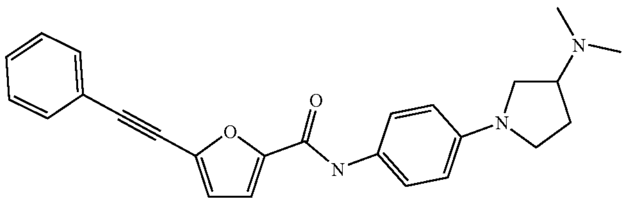 | C25H25N3O2 | 399.20 | 400 |
| 550 | 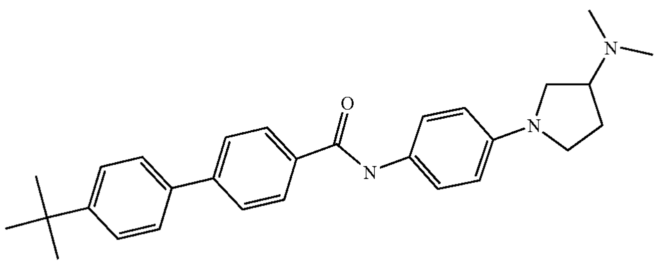 | C29H35N3O | 441.28 | 442 |
| 551 | 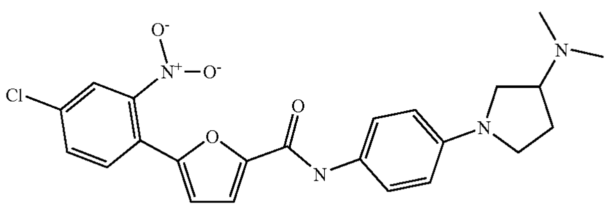 | C23H23ClN4O4 | 454.14 | 455 |
| 552 | 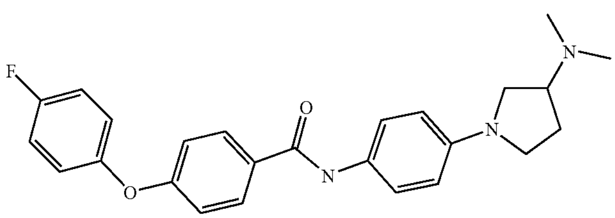 | C25H26FN3O2 | 419.20 | 420 |
| 553 | 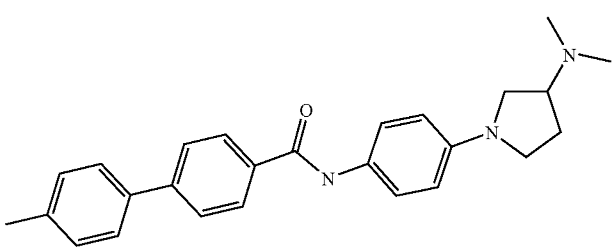 | C26H29N3O | 399.23 | 400 |

TABLE 7-continued

| Ex. No. | Structure | Molecular formula | Monoisotopic molecular wt. | M + H⁺ |
|---|---|---|---|---|
| 554 | 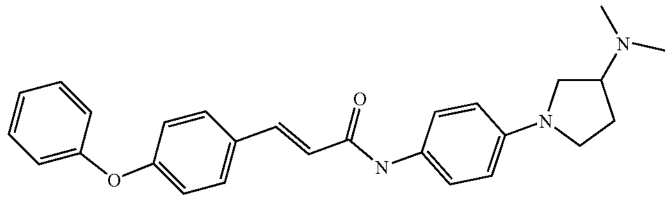 | C27H29N3O2 | 427.23 | 428 |
| 555 | 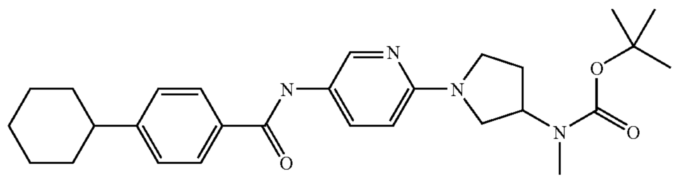 | C28H38N4O3 | 478.29 | 479 |
| 556 | 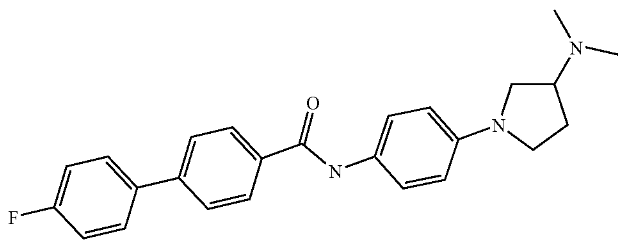 | C25H26FN3O | 403.21 | 404 |
| 557 | 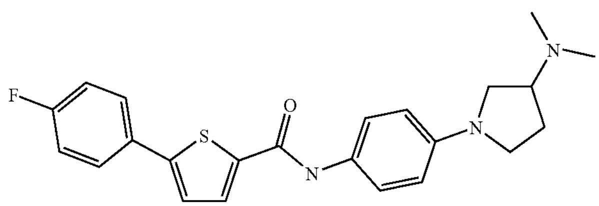 | C23H24FN3OS | 409.16 | 410 |
| 558 | 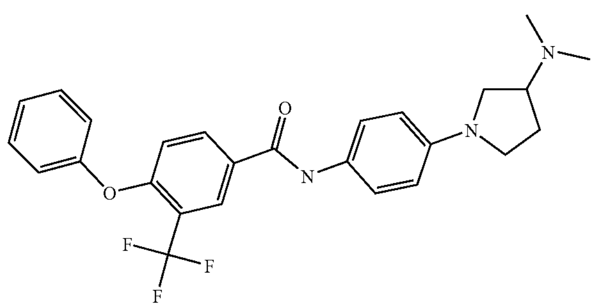 | C26H26F3N3O2 | 469.20 | 470 |
| 559 | 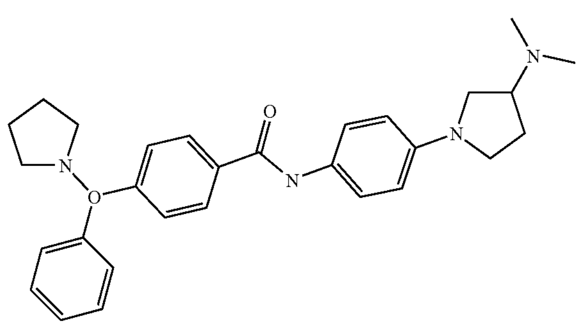 | C29H34N4O2 | 470.27 | 471 |

TABLE 7-continued

| Ex. No. | Structure | Molecular formula | Monoisotopic molecular wt. | M + H⁺ |
|---|---|---|---|---|
| 560 | 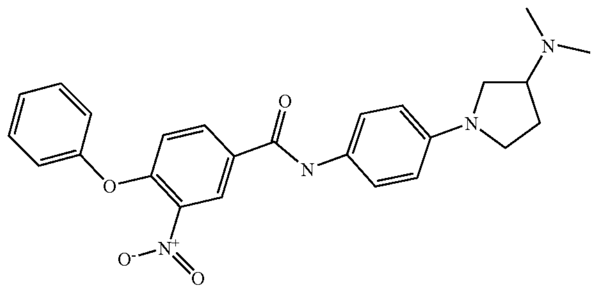 | C25H26N4O4 | 446.20 | 447 |
| 561 | 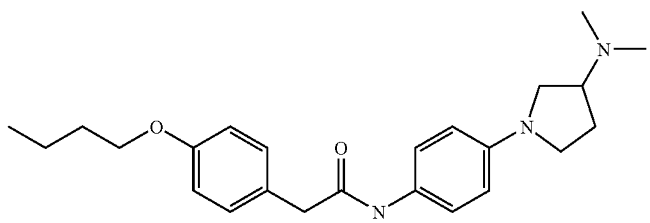 | C24H33N3O2 | 395.26 | 396 |
| 562 | 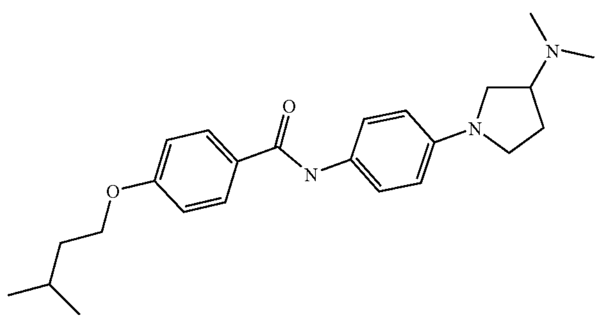 | C24H33N3O2 | 395.26 | 396 |
| 563 | 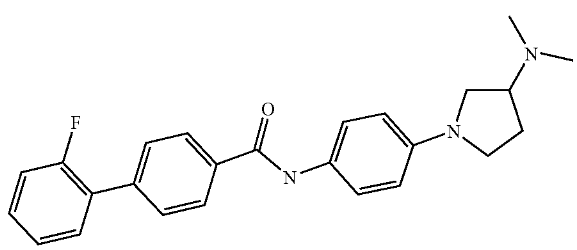 | C25H26FN3O | 403.21 | 404 |
| 564 | 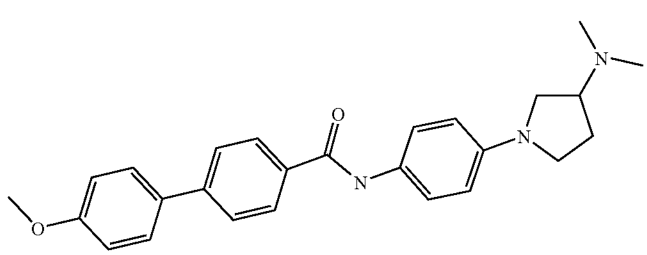 | C26H29N3O2 | 415.23 | 416 |

TABLE 7-continued

| Ex. No. | Structure | Molecular formula | Monoisotopic molecular wt. | M + H+ |
|---|---|---|---|---|
| 565 | 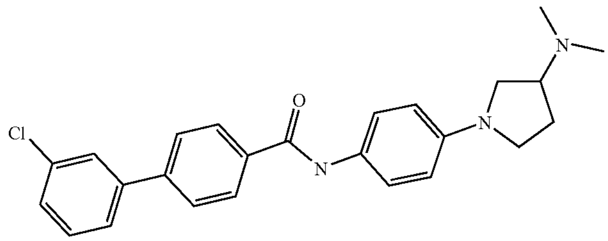 | C25H26ClN3O | 419.18 | 420 |
| 566 | 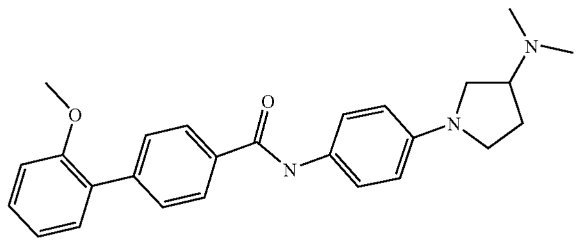 | C26H29N3O2 | 415.23 | 416 |
| 567 | 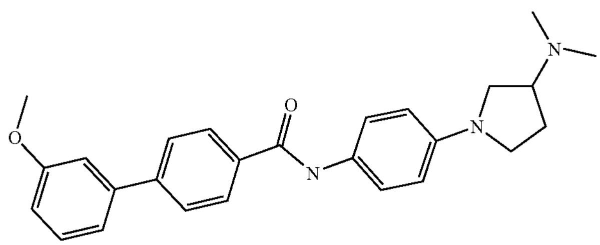 | C26H29N3O2 | 415.23 | 416 |
| 568 | 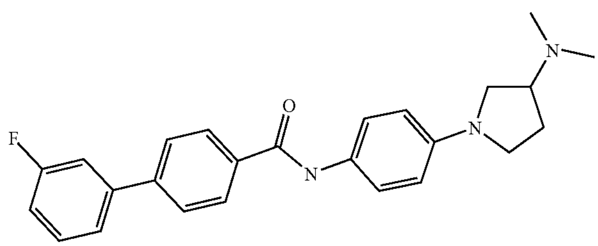 | C25H26FN3O | 403.21 | 404 |
| 569 | 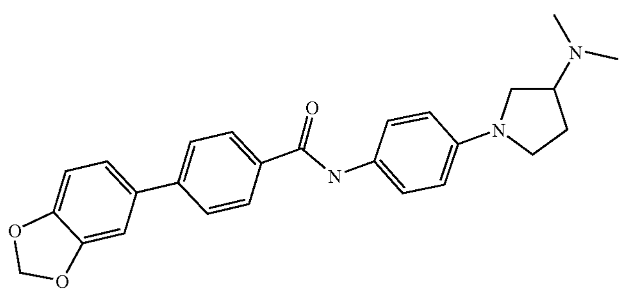 | C26H27N3O3 | 429.20 | 430 |
| 570 | 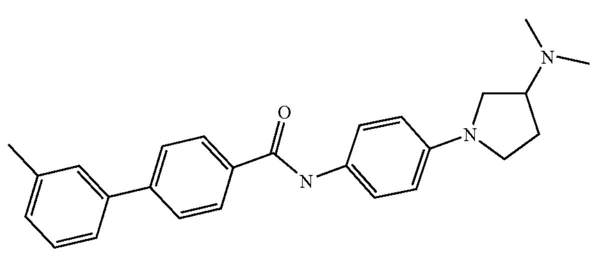 | C26H29N3O | 399.23 | 400 |

TABLE 7-continued
| Ex. No. | Structure | Molecular formula | Monoisotopic molecular wt. | M + H+ |
|---|---|---|---|---|
| 571 | 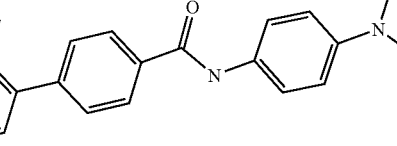 | C26H29N3O | 399.23 | 400 |
| 572 | 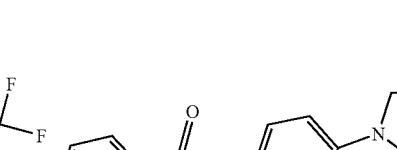 | C26H26F3N3O | 453.20 | 454 |
| 573 | 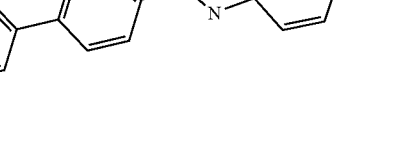 | C26H26F3N3O | 453.20 | 454 |
| 574 | 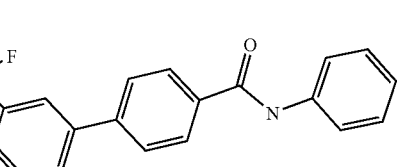 | C26H35N3O2 | 421.27 | 422 |
| 575 | 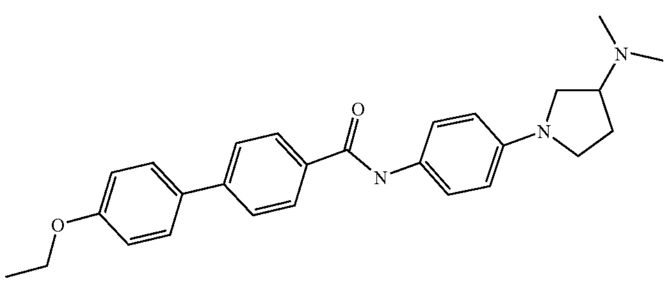 | C27H31N3O2 | 429.24 | 430 |
| 576 | 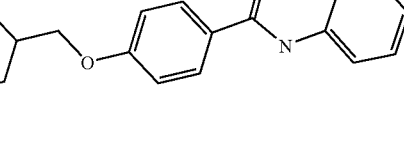 | C25H26ClN3O | 419.18 | 420 |

TABLE 7-continued

| Ex. No. | Structure | Molecular formula | Monoisotopic molecular wt. | M + H⁺ |
|---|---|---|---|---|
| 577 | 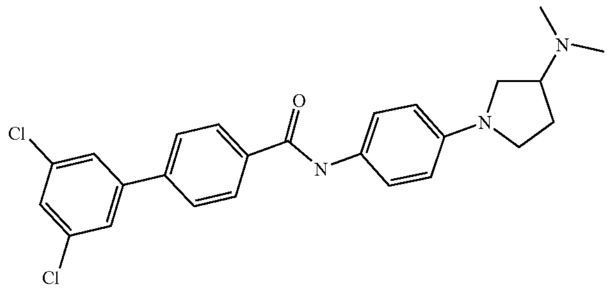 | C25H25Cl2N3O | 453.14 | 454 |
| 578 | 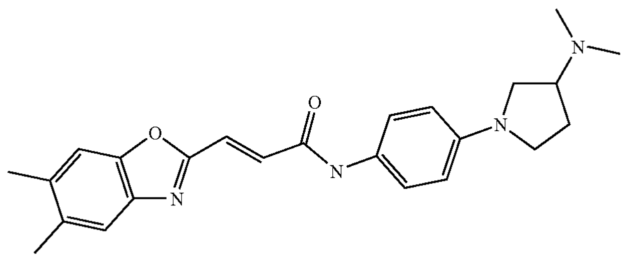 | C24H28N4O2 | 404.22 | 405 |
| 579 | 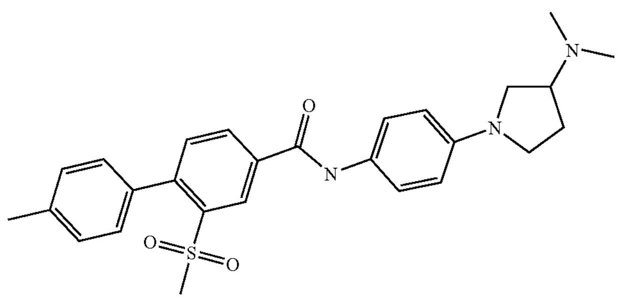 | C27H31N3O3S | 477.21 | 478 |
| 580 | 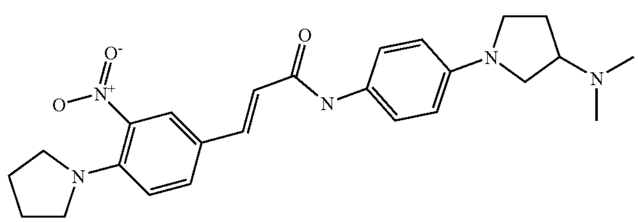 | C25H31N5O3 | 449.24 | 450 |
| 581 | 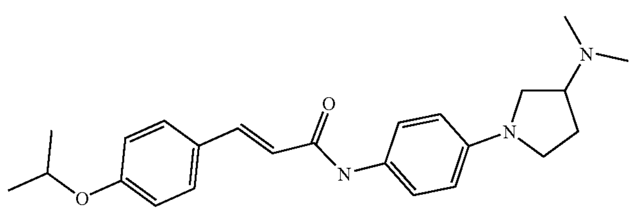 | C24H31N3O2 | 393.24 | 394 |
| 582 | 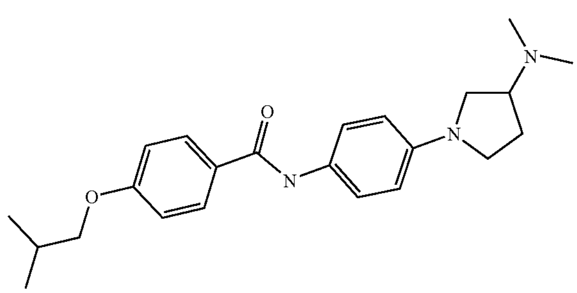 | C23H31N3O2 | 381.24 | 382 |

TABLE 7-continued

| Ex. No. | Structure | Molecular formula | Monoisotopic molecular wt. | M + H+ |
|---|---|---|---|---|
| 583 | 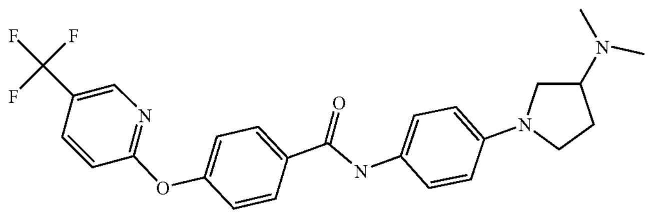 | C25H25F3N4O2 | 470.19 | 471 |
| 584 | 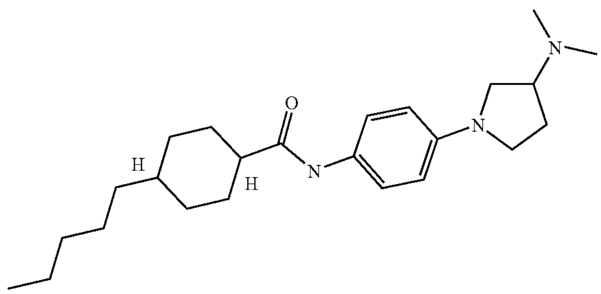 | C24H39N3O | 385.31 | 386 |
| 585 | 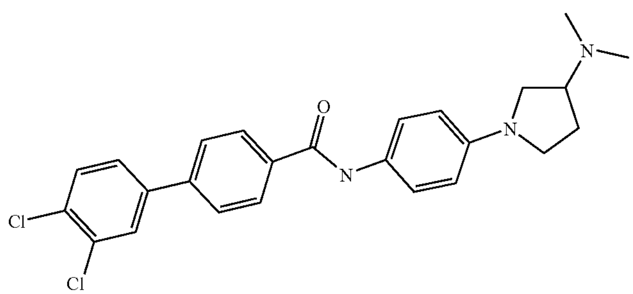 | C25H25Cl2N3O | 453.14 | 454 |
| 586 | 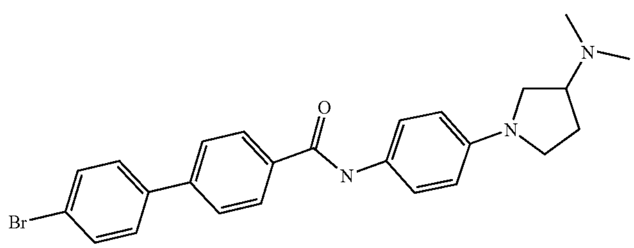 | C25H26BrN3O | 463.13 | 464 |
| 587 | 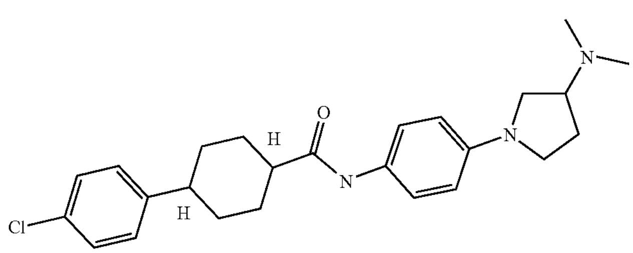 | C25H32ClN3O | 425.22 | 426 |
| 588 | 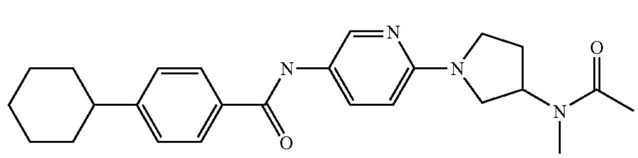 | C25H32N4O2 | 420.25 | 421 |

TABLE 7-continued

| Ex. No. | Structure | Molecular formula | Monoisotopic molecular wt. | M + H⁺ |
|---|---|---|---|---|
| 589 | 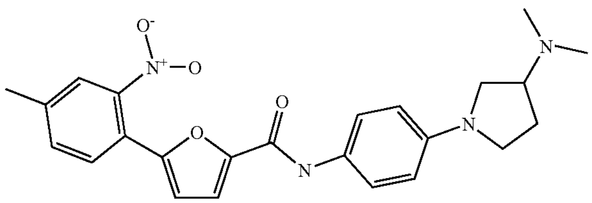 | C24H26N4O4 | 434.20 | 435 |
| 590 | 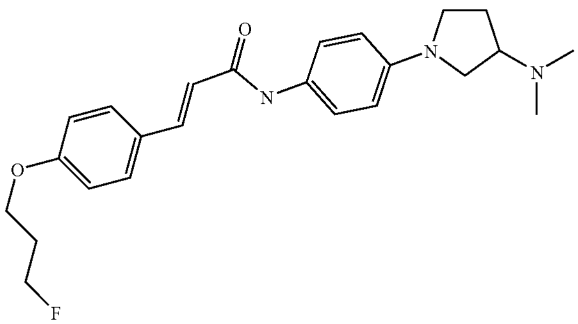 | C24H30FN3O2 | 411.23 | 412 |
| 591 | 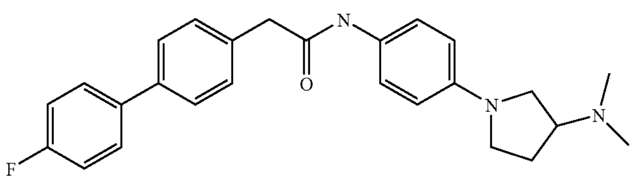 | C26H28FN3O | 417.22 | 418 |
| 592 | 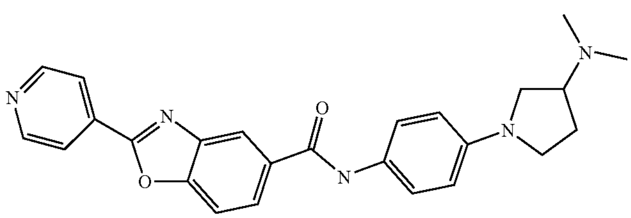 | C25H25N5O2 | 427.20 | 428 |
| 593 | 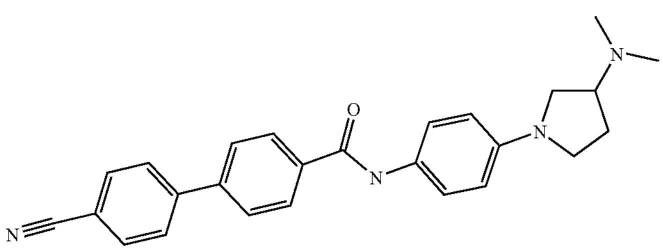 | C26H26N4O | 410.21 | 411 |
| 594 | 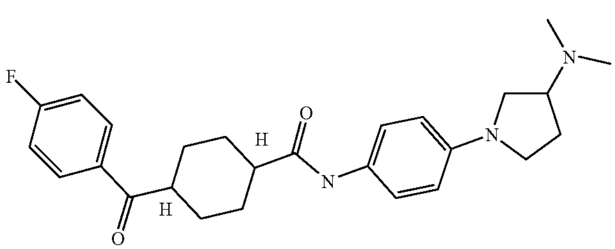 | C26H32FN3O2 | 437.25 | 438 |

TABLE 7-continued

| Ex. No. | Structure | Molecular formula | Monoisotopic molecular wt. | M + H+ |
|---|---|---|---|---|
| 595 | 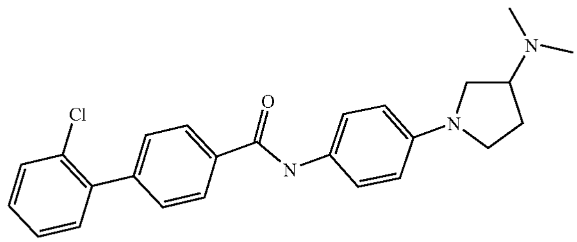 | C25H26ClN3O | 419.18 | 420 |
| 596 | 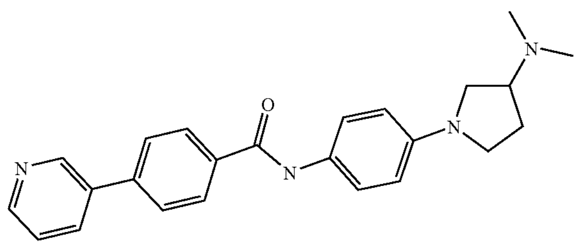 | C24H26N4O | 386.21 | 387 |
| 597 | 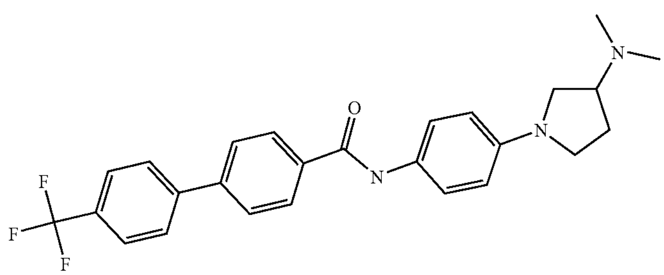 | C26H26F3N3O | 453.20 | 454 |
| 598 | 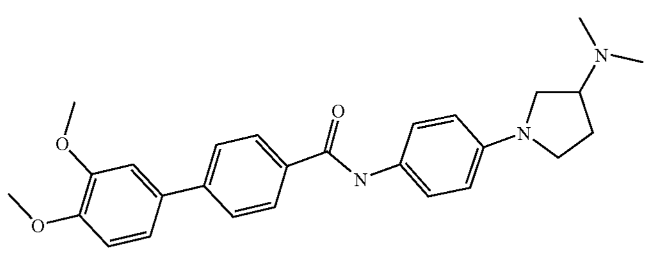 | C27H31N3O3 | 445.24 | 446 |
| 599 | 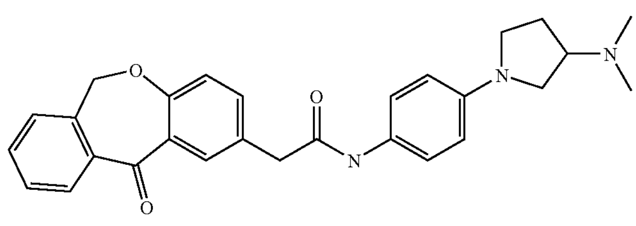 | C28H29N3O3 | 455.22 | 456 |
| 600 | 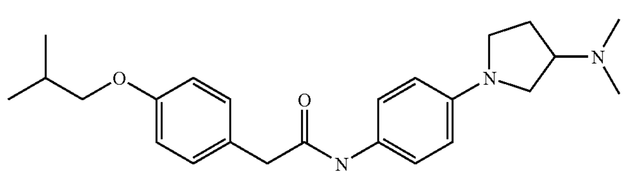 | C24H33N3O2 | 395.26 | 396 |

TABLE 7-continued

| Ex. No. | Structure | Molecular formula | Monoisotopic molecular wt. | M + H+ |
|---|---|---|---|---|
| 601 | 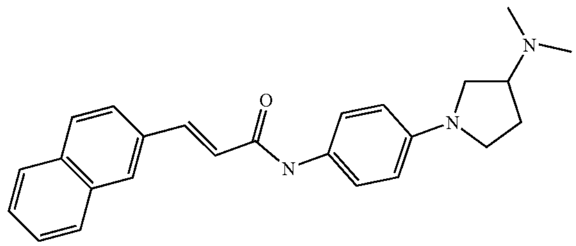 | C25H27N3O | 385.21 | 386 |
| 602 | 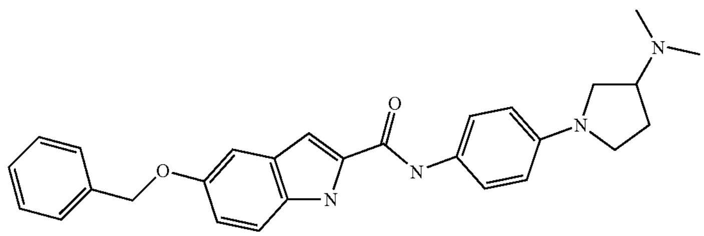 | C28H30N4O2 | 454.24 | 455 |
| 603 | 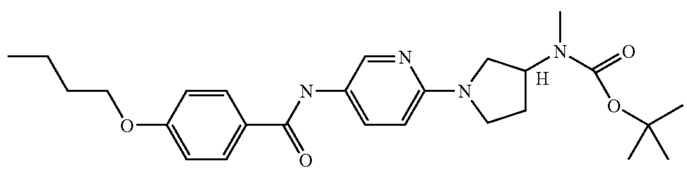 | C26H36N4O4 | 468.27 | 469 |
| 604 | 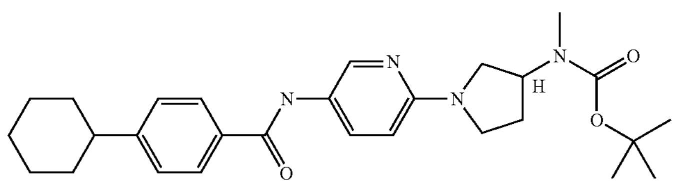 | C28H38N4O3 | 478.29 | 479 |
| 605 | 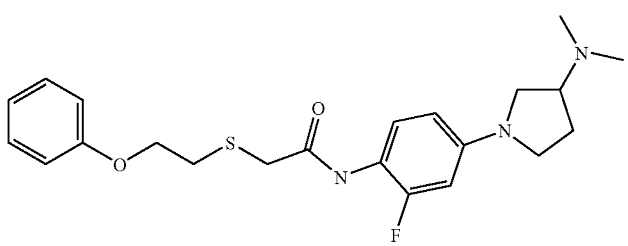 | C22H28FN3O2S | 417.55 | 418 |
| 606 | 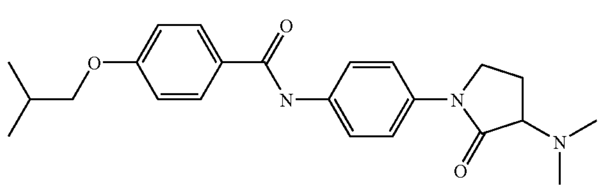 | C23H29N3O3 | 395.22 | 396 |
| 607 | 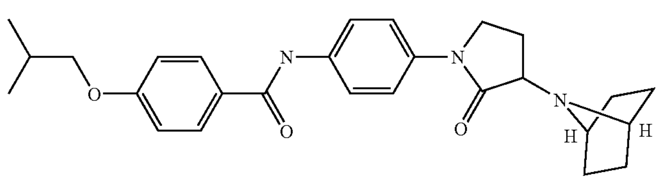 | C27H33N3O3 | 447.25 | 448 |

TABLE 7-continued
| Ex. No. | Structure | Molecular formula | Monoisotopic molecular wt. | M + H⁺ |
|---|---|---|---|---|
| 608 | 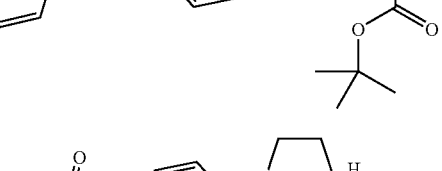 | C27H37N3O4 | 467.28 | 468 |
| 609 | 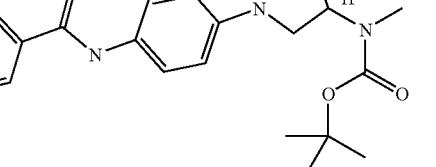 | C29H39N3O3 | 477.30 | 478 |
| 610 | 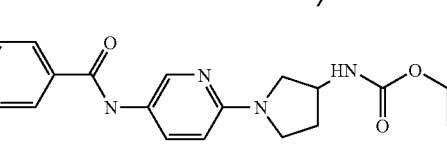 | C27H29FN4O3 | 476.22 | 477 |
| 611 | 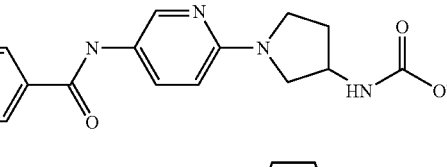 | C25H34N4O4 | 454.26 | 455 |
| 612 | 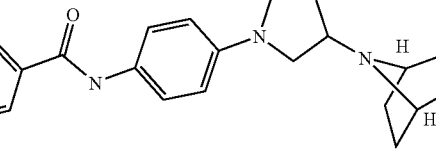 | C27H35N3O2 | 433.27 | 434 |
| 613 | 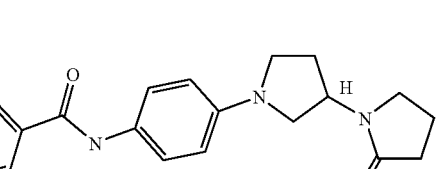 | C25H31N3O3 | 421.24 | 422 |
| 614 | 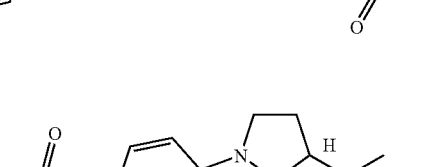 | C28H32N4O4 | 488.24 | 489 |
| 615 | 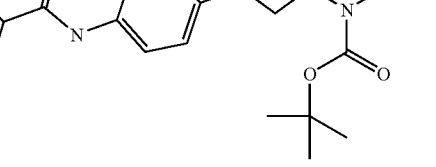 | C27H35ClN4O3 | 498.24 | 499 |

TABLE 7-continued

| Ex. No. | Structure | Molecular formula | Monoisotopic molecular wt. | M + H+ |
|---|---|---|---|---|
| 616 | 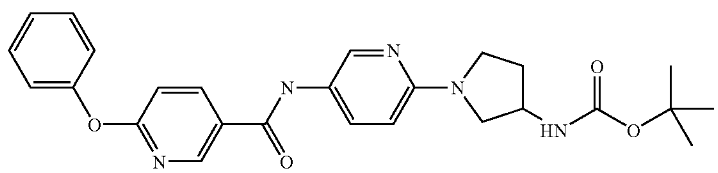 | C26H29N5O4 | 475.22 | 476 |
| 617 | 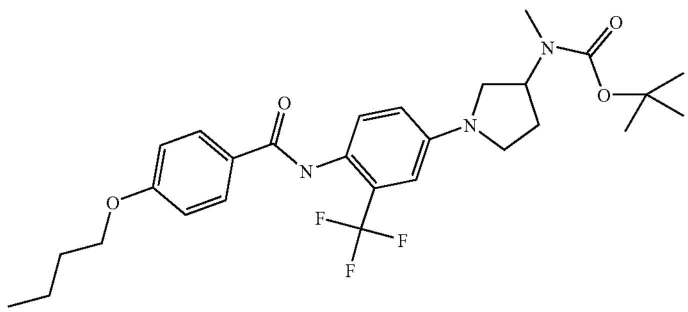 | C28H36F3N3O4 | 535.27 | 536 |
| 618 | 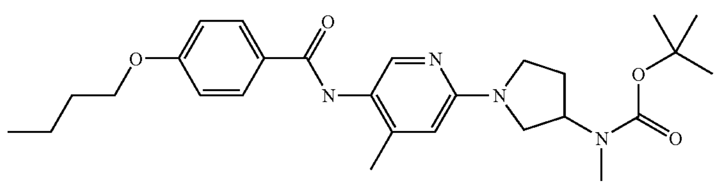 | C27H38N4O4 | 482.29 | 483 |
| 619 | 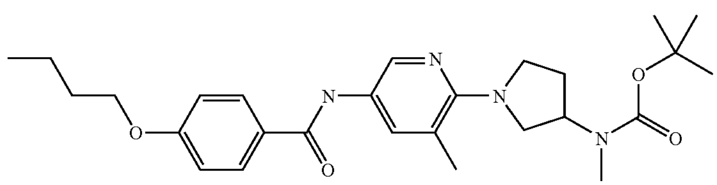 | C27H38N4O4 | 482.29 | 483 |
| 620 | 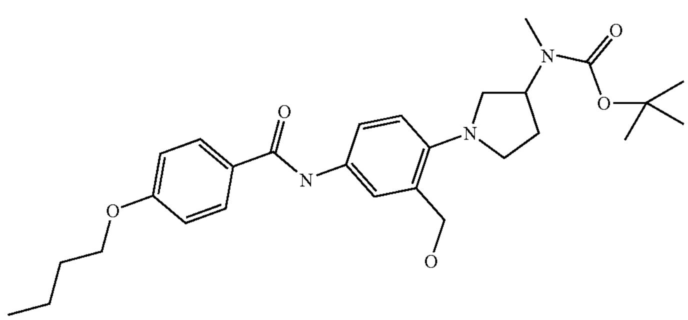 | C28H39N3O5 | 497.29 | 498 |
| 621 | 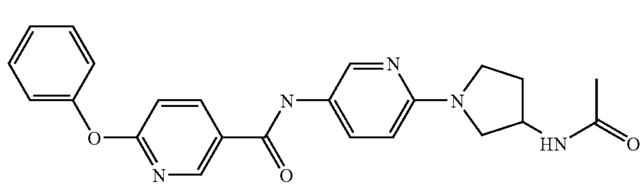 | C23H23N5O3 | 417.18 | 418 |

TABLE 7-continued

| Ex. No. | Structure | Molecular formula | Monoisotopic molecular wt. | M + H+ |
|---|---|---|---|---|
| 622 | 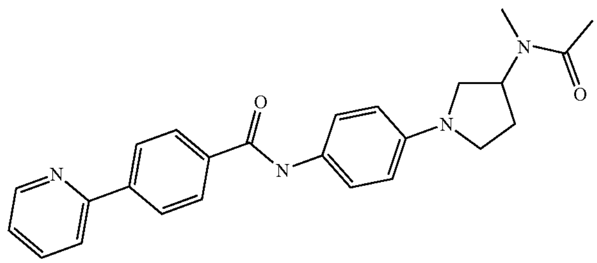 | C25H26N4O2 | 414.21 | 415 |
| 623 | 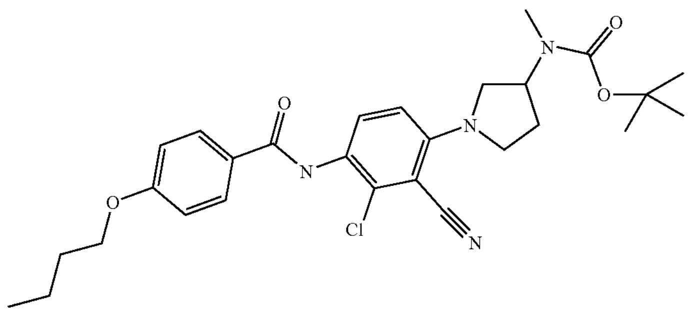 | C28H35ClN4O4 | 526.23 | 527 |
| 624 | 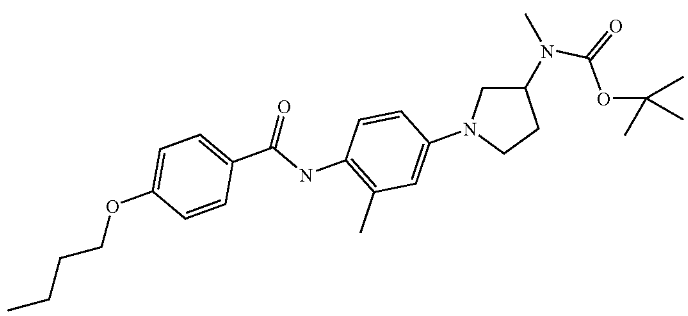 | C28H39N3O4 | 481.29 | 482 |
| 625 | 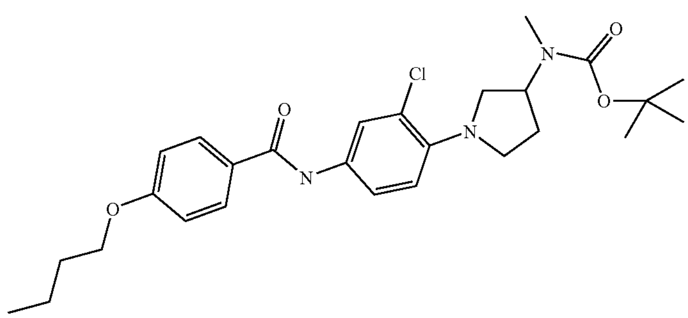 | C27H36ClN3O4 | 501.24 | 502 |
| 626 | 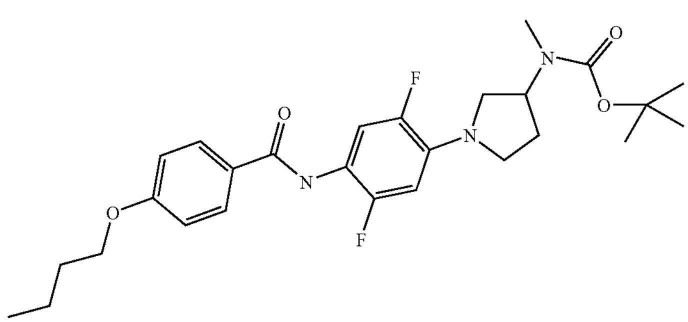 | C27H35F2N3O4 | 503.26 | 504 |

TABLE 7-continued

| Ex. No. | Structure | Molecular formula | Monoisotopic molecular wt. | M + H⁺ |
|---|---|---|---|---|
| 627 | 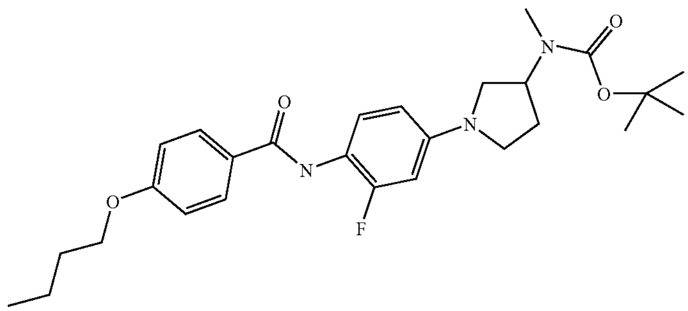 | C27H36FN3O4 | 485.27 | 486 |
| 628 | 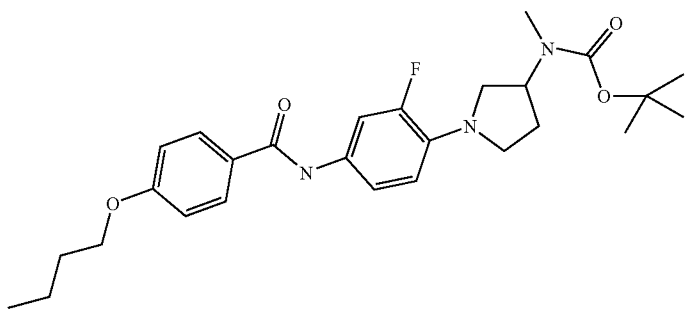 | C27H36FN3O4 | 485.27 | 486 |
| 629 | 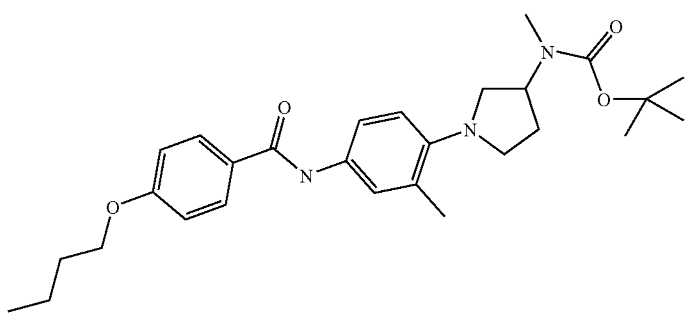 | C28H39N3O4 | 481.29 | 482 |
| 630 | 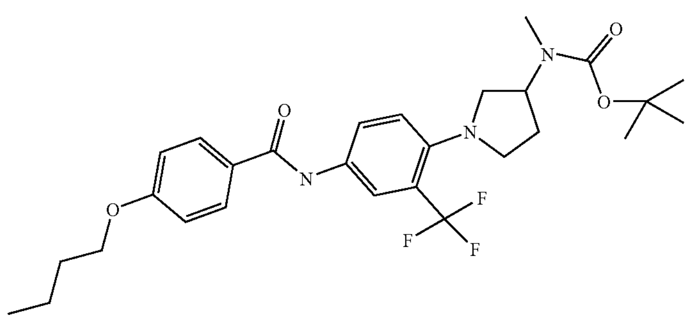 | C28H36F3N3O4 | 535.27 | 536 |
| 631 | 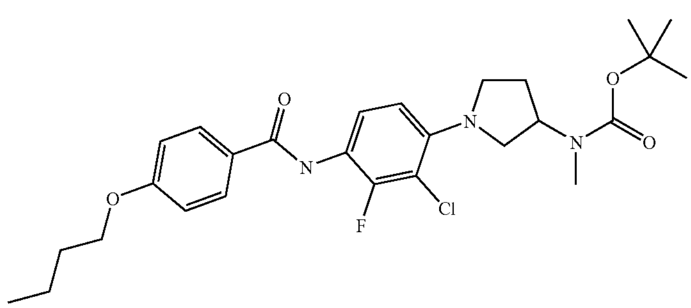 | C27H35ClFN3O4 | 519.23 | 520 |

TABLE 7-continued

| Ex. No. | Structure | Molecular formula | Monoisotopic molecular wt. | M + H+ |
|---|---|---|---|---|
| 632 | 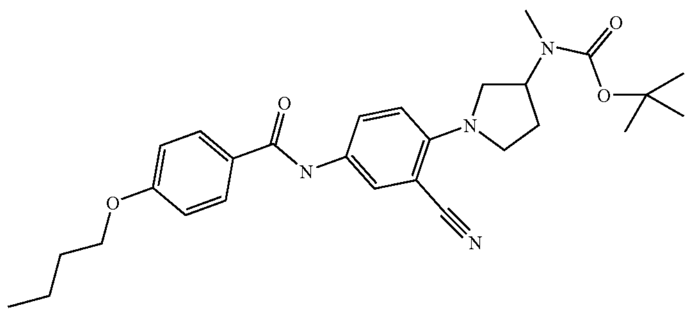 | C28H36N4O4 | 492.27 | 493 |
| 633 | 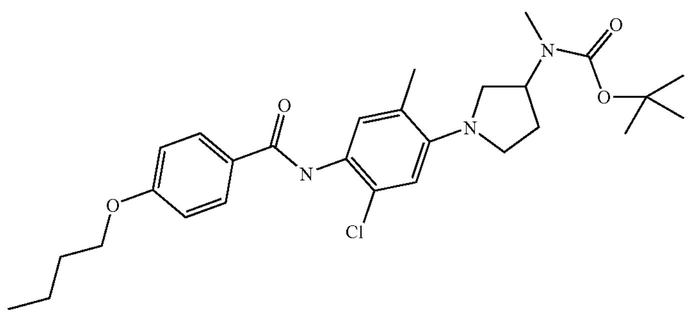 | C28H38ClN3O4 | 515.26 | 516 |
| 634 | 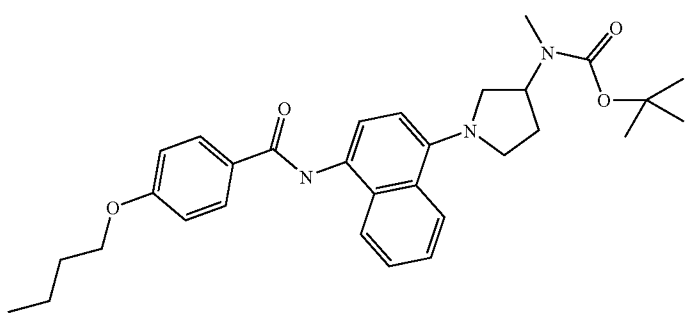 | C31H39N3O4 | 517.29 | 518 |
| 635 | 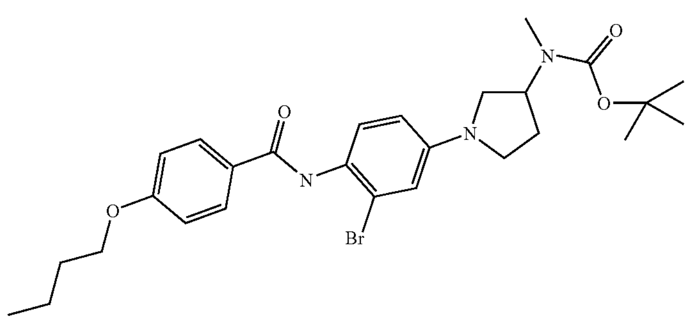 | C27H36BrN3O4 | 545.19 | 546 |

TABLE 7-continued
| Ex. No. | Structure | Molecular formula | Monoisotopic molecular wt. | M + H+ |
|---|---|---|---|---|
| 636 | 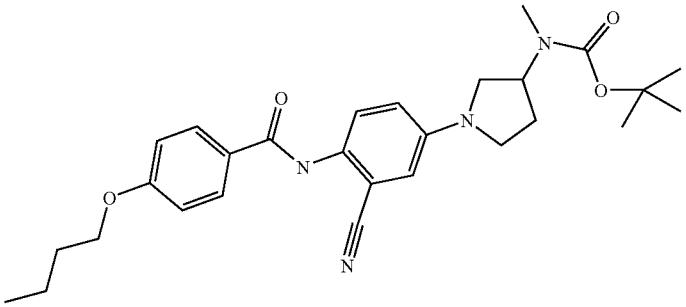 | C28H36N4O4 | 492.27 | 493 |
| 637 | 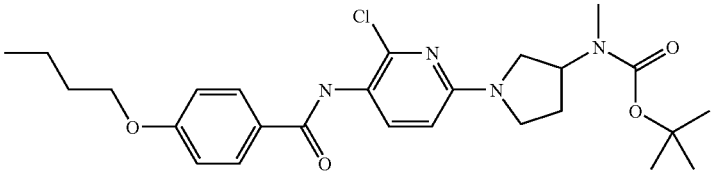 | C26H35ClN4O4 | 502.23 | 503 |
| 638 | 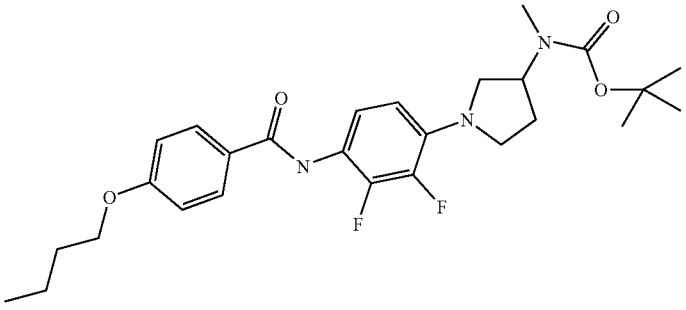 | C27H35F2N3O4 | 503.26 | 504 |
| 639 | 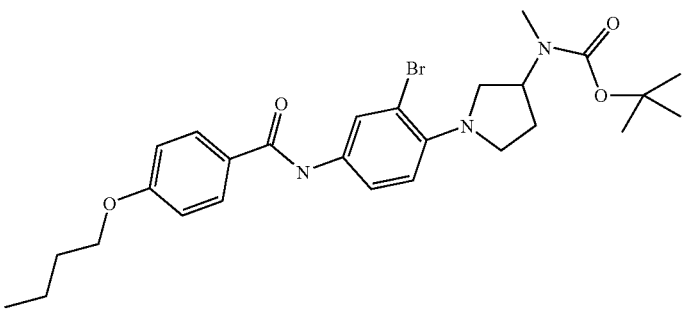 | C27H36BrN3O4 | 545.19 | 546 |
| 640 | 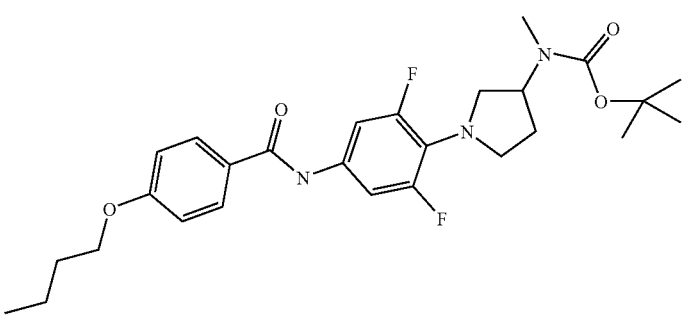 | C27H35F2N3O4 | 503.26 | 504 |

TABLE 7-continued

| Ex. No. | Structure | Molecular formula | Monoisotopic molecular wt. | M + H+ |
|---|---|---|---|---|
| 641 | 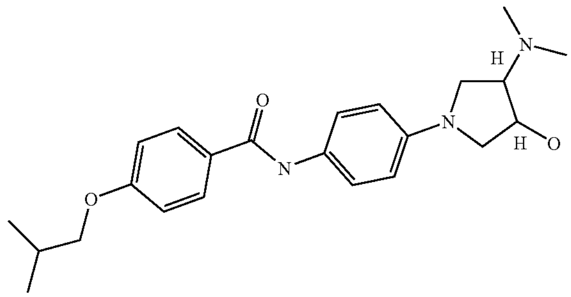 | C23H31N3O3 | 397.24 | 398 |
| 642 | 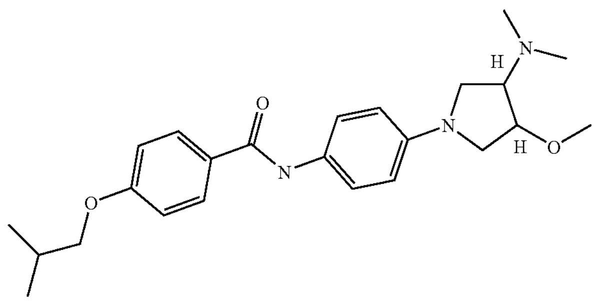 | C24H33N3O3 | 411.25 | 412 |
| 643 | 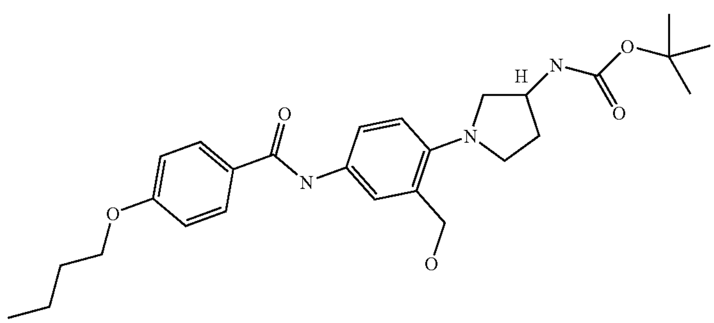 | C27H37N3O5 | 483.27 | 484 |
| 644 | 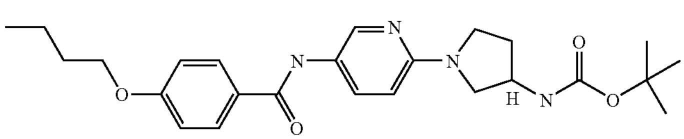 | C25H34N4O4 | 454.26 | 455 |
| 645 | 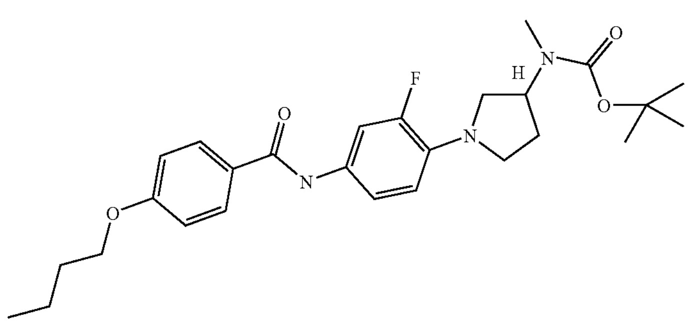 | C27H36FN3O4 | 485.27 | 486 |

TABLE 7-continued

| Ex. No. | Structure | Molecular formula | Monoisotopic molecular wt. | M + H⁺ |
|---|---|---|---|---|
| 646 | 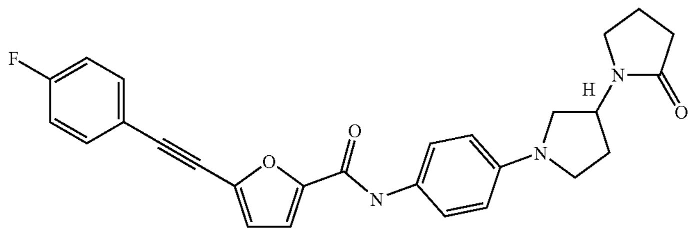 | C27H24FN3O3 | 457.18 | 458 |
| 647 | 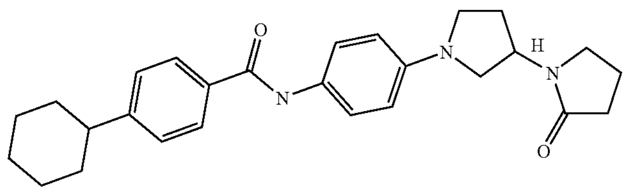 | C27H33N3O2 | 431.26 | 432 |
| 648 | 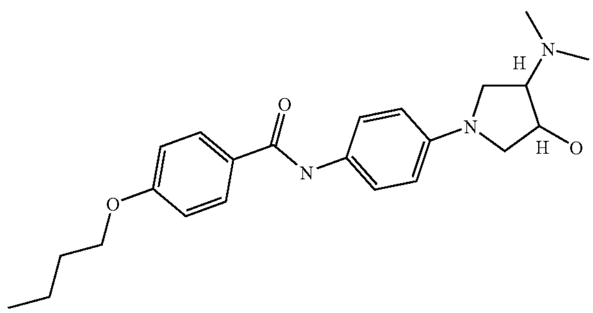 | C23H31N3O3 | 397.24 | 398 |
| 649 | 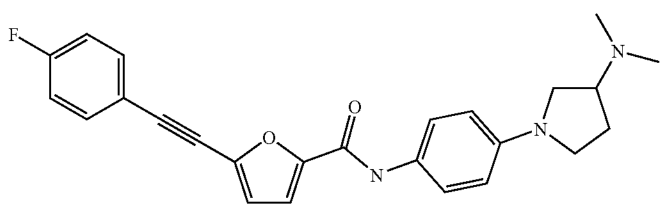 | C25H24FN3O2 | 417.18 | 418 |
| 650 | 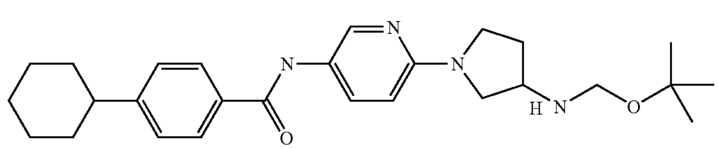 | C27H36N4O3 | 464.28 | 465 |
| 651 | 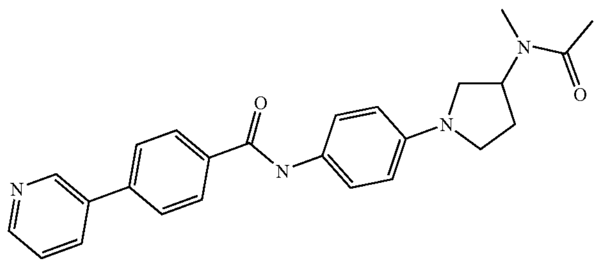 | C25H26N4O2 | 414.21 | 415 |

TABLE 7-continued
| Ex. No. | Structure | Molecular formula | Monoisotopic molecular wt. | M + H⁺ |
|---|---|---|---|---|
| 652 | 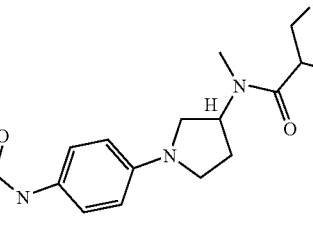 | C31H33FN4O3 | 528.25 | 529 |
| 653 | 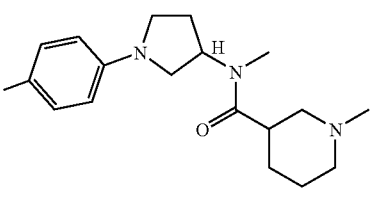 | C32H38N4O2 | 510.30 | 511 |
| 654 | 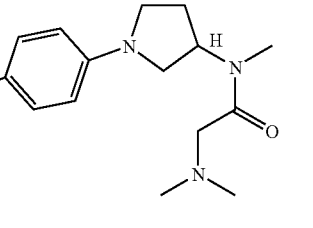 | C28H38N4O2 | 462.30 | 463 |
| 655 | 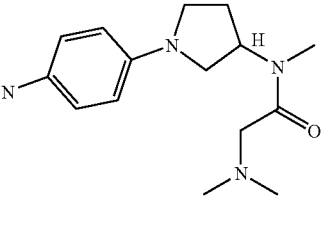 | C29H34N4O2 | 470.27 | 471 |
| 656 | 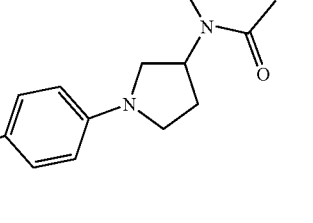 | C26H26ClN3O2 | 447.17 | 448 |
| 657 | 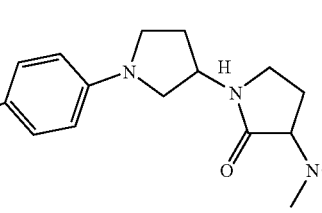 | C29H38N4O2 | 474.30 | 475 |

TABLE 7-continued

| Ex. No. | Structure | Molecular formula | Monoisotopic molecular wt. | M + H+ |
|---|---|---|---|---|
| 658 | 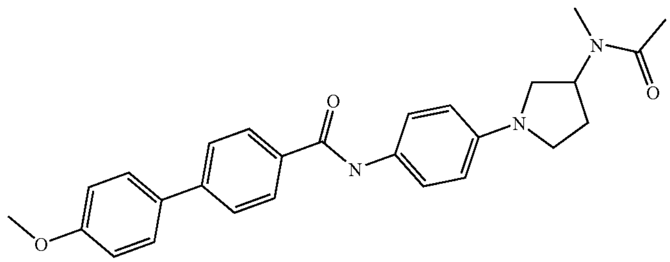 | C27H29N3O3 | 443.22 | 444 |
| 659 | 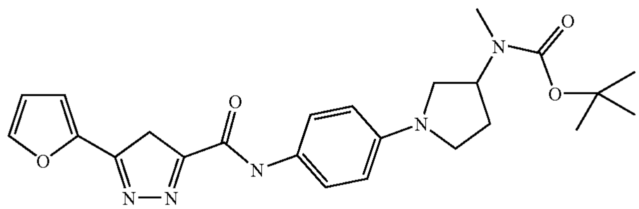 | C24H29N5O4 | 451.22 | 452 |
| 660 | 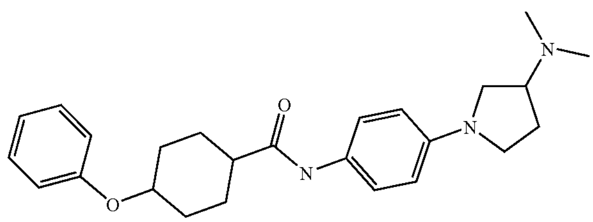 | C25H33N3O2 | 407.26 | 408 |
| 661 | 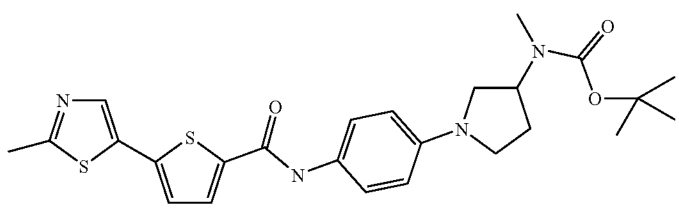 | C25H30N4O3S2 | 498.18 | 499 |
| 662 | 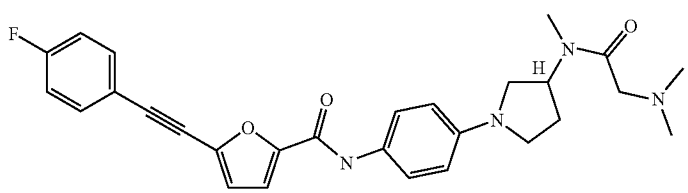 | C28H29FN4O3 | 488.22 | 489 |
| 663 | 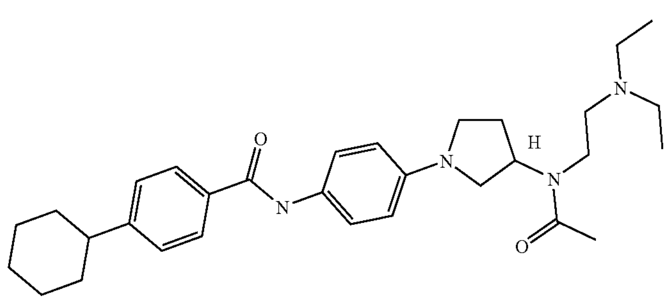 | C31H44N4O2 | 504.35 | 505 |

TABLE 7-continued
| Ex. No. | Structure | Molecular formula | Monoisotopic molecular wt. | M + H+ |
|---|---|---|---|---|
| 664 | 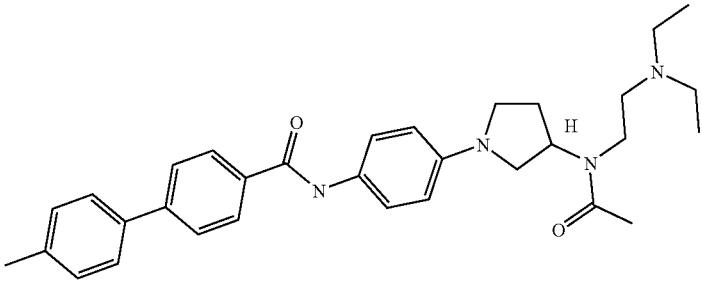 | C32H40N4O2 | 512.32 | 513 |
| 665 | 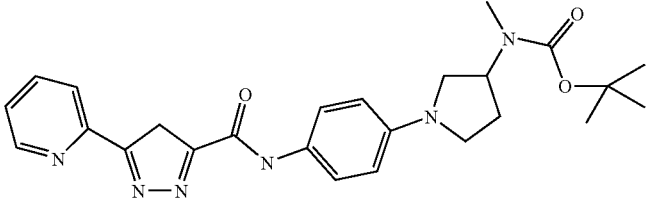 | C25H30N6O3 | 462.24 | 463 |
| 666 | 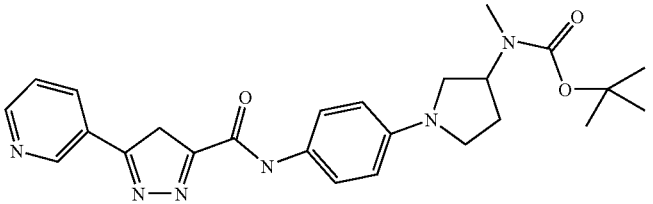 | C25H30N6O3 | 462.24 | 463 |
| 667 | 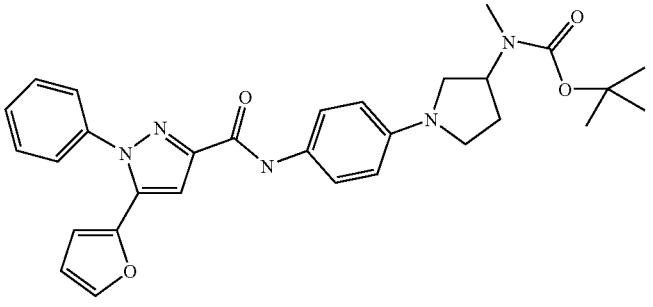 | C30H33N5O4 | 527.25 | 528 |
| 668 | 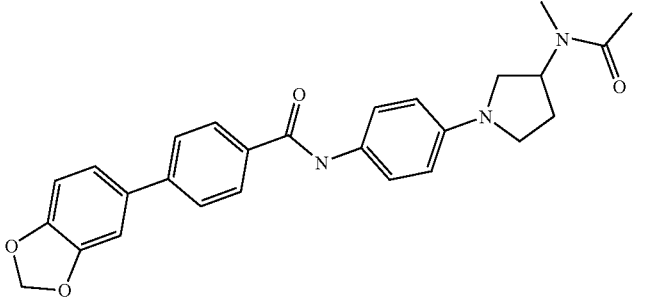 | C27H27N3O4 | 457.20 | 458 |
| 669 | 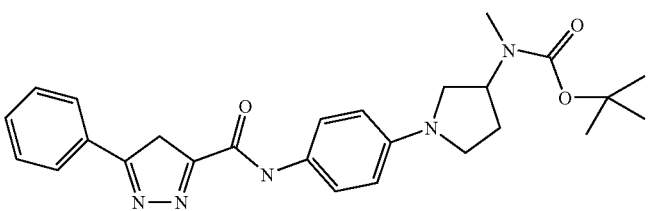 | C26H31N5O3 | 461.24 | 462 |

TABLE 7-continued

| Ex. No. | Structure | Molecular formula | Monoisotopic molecular wt. | M + H⁺ |
|---|---|---|---|---|
| 670 | 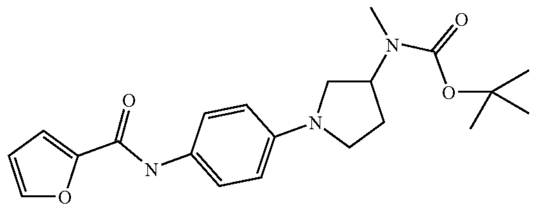 | C21H27N3O4 | 385.20 | 386 |
| 671 | 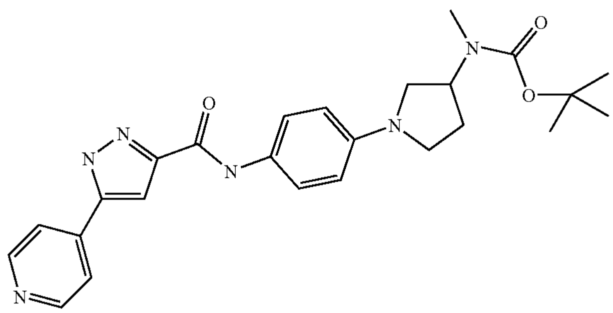 | C25H30N6O3 | 462.24 | 463 |
| 672 | 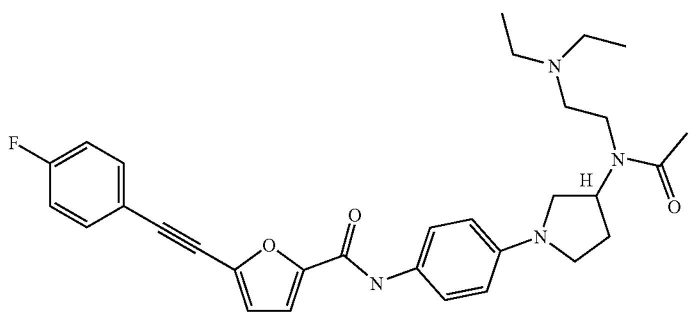 | C31H35FN4O3 | 530.27 | 531 |
| 673 | 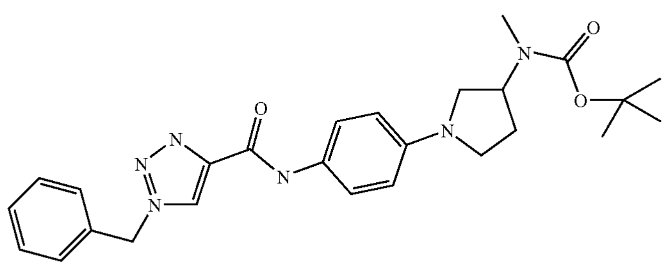 | C26H32N6O3 | 476.25 | 477 |
| 674 | 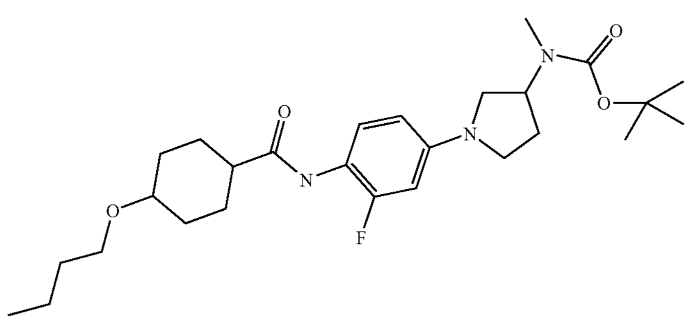 | C27H42FN3O4 | 491.32 | 492 |

TABLE 7-continued

| Ex. No. | Structure | Molecular formula | Monoisotopic molecular wt. | M + H⁺ |
|---|---|---|---|---|
| 675 | 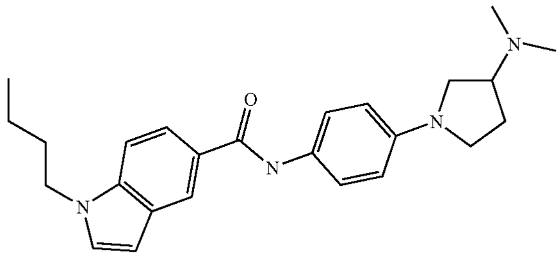 | C25H32N4O | 404.26 | 405 |
| 676 | 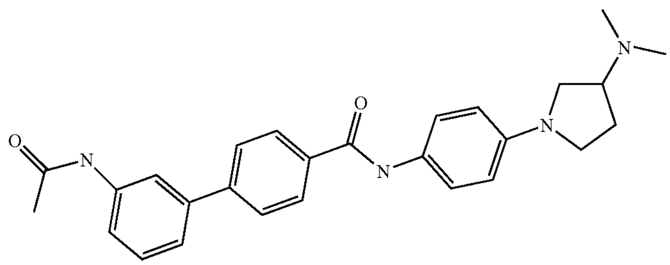 | C27H30N4O2 | 442.24 | 443 |
| 677 | 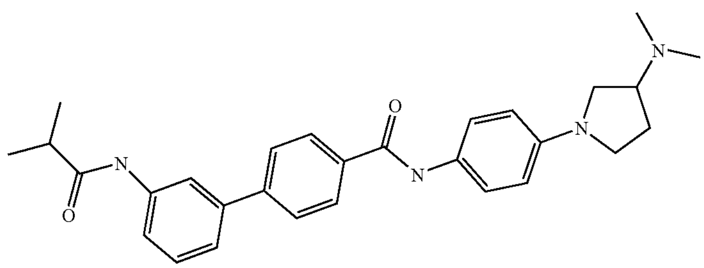 | C29H34N4O2 | 470.27 | 471 |
| 678 | 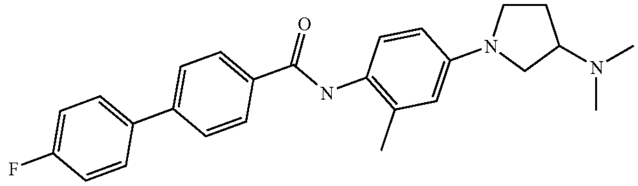 | C26H28FN3O | 417.22 | 418 |
| 679 | 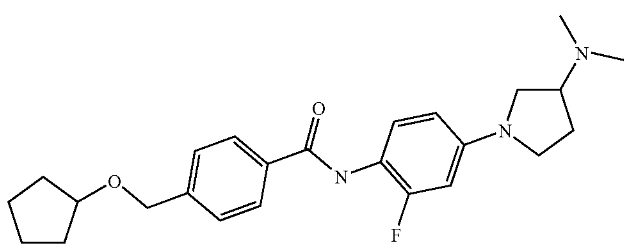 | C25H32FN3O2 | 425.55 | 426 |
| 680 | 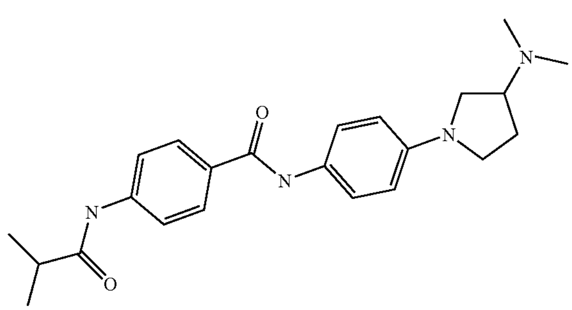 | C23H30N4O2 | 394.24 | 395 |

TABLE 7-continued

| Ex. No. | Structure | Molecular formula | Monoisotopic molecular wt. | M + H+ |
|---|---|---|---|---|
| 681 | 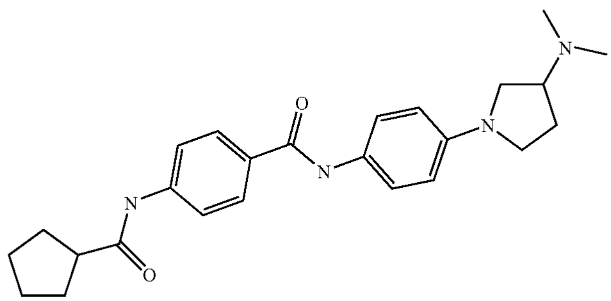 | C25H32N4O2 | 420.25 | 421 |
| 682 | 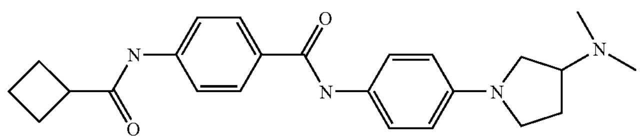 | C24H30N4O2 | 406.24 | 407 |
| 683 | 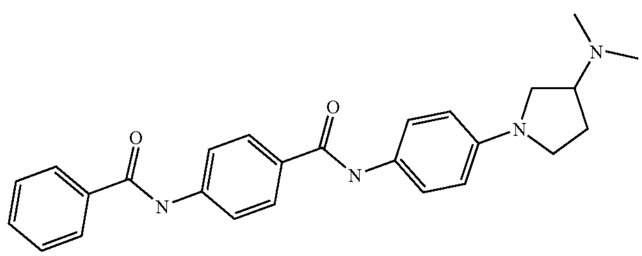 | C26H28N4O2 | 428.22 | 429 |
| 684 | 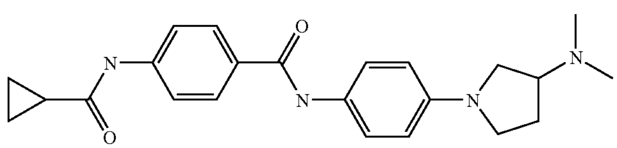 | C23H28N4O2 | 392.22 | 393 |
| 685 | 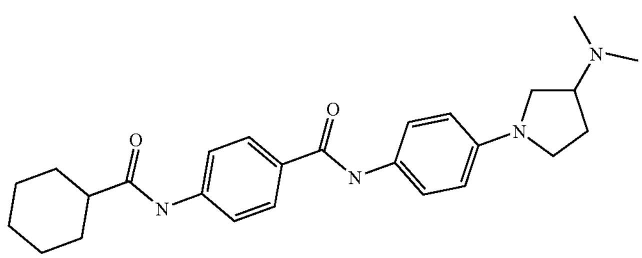 | C26H34N4O2 | 434.27 | 435 |
| 686 | 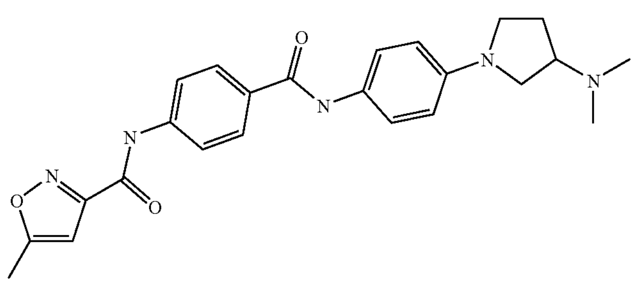 | C24H27N5O3 | 433.21 | 434 |

TABLE 7-continued

| Ex. No. | Structure | Molecular formula | Monoisotopic molecular wt. | M + H+ |
|---|---|---|---|---|
| 687 | 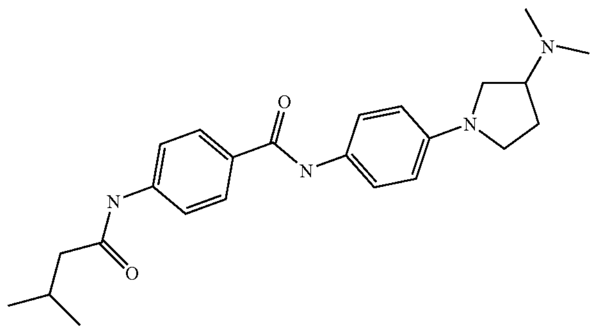 | C24H32N4O2 | 408.25 | 409 |
| 688 | 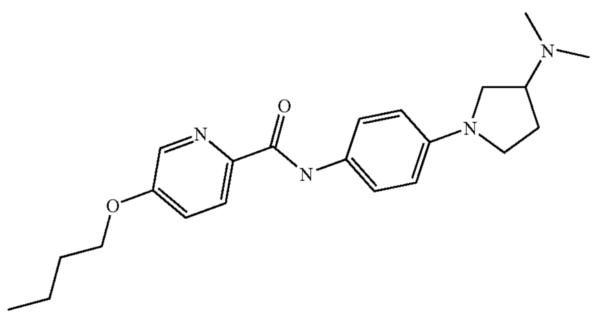 | C22H30N4O2 | 382.24 | 383 |
| 689 | 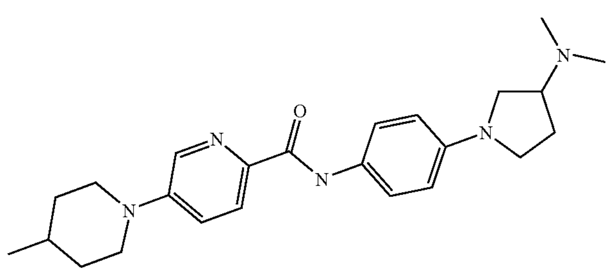 | C24H33N5O | 407.27 | 408 |
| 690 | 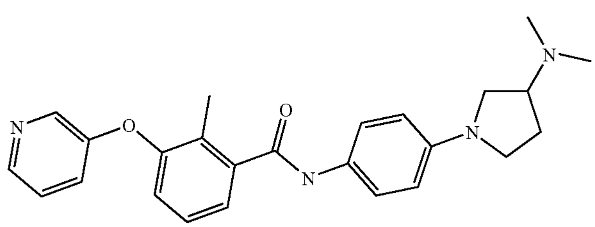 | C25H28N4O2 | 416.22 | 417 |
| 691 | 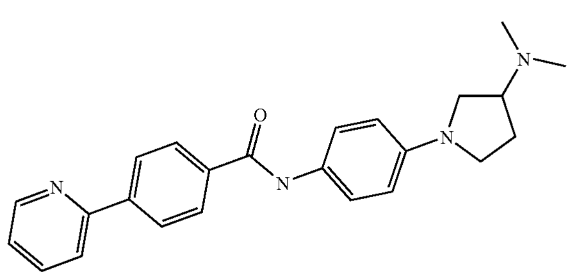 | C24H26N4O | 386.21 | 387 |

TABLE 7-continued

| Ex. No. | Structure | Molecular formula | Monoisotopic molecular wt. | M + H⁺ |
|---|---|---|---|---|
| 692 | 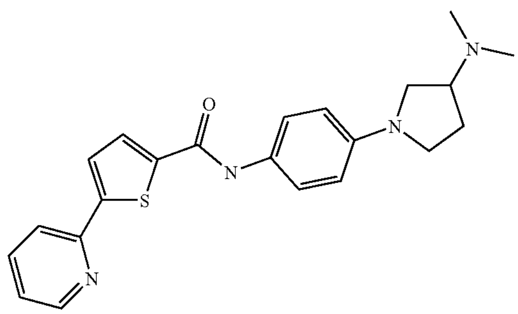 | C22H24N4OS | 392.17 | 393 |
| 693 | 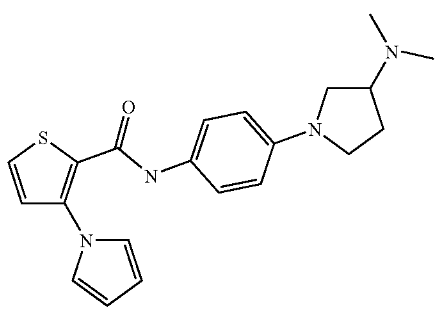 | C21H24N4OS | 380.17 | 381 |
| 694 | 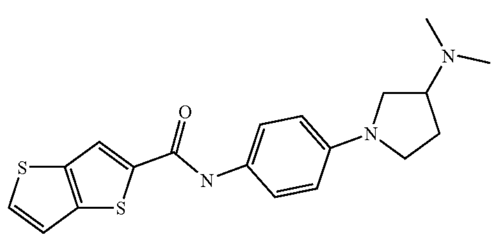 | C19H21N3OS2 | 371.11 | 372 |
| 695 | 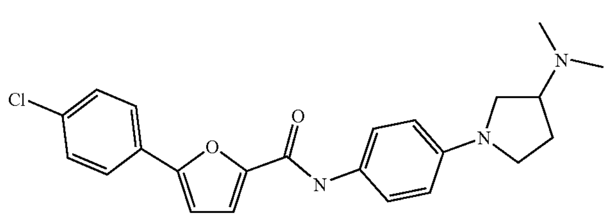 | C23H24ClN3O2 | 409.16 | 410 |
| 696 | 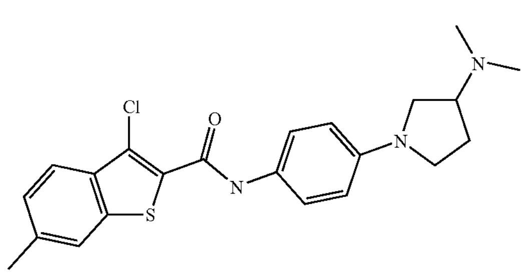 | C22H24ClN3OS | 413.13 | 414 |

TABLE 7-continued

| Ex. No. | Structure | Molecular formula | Monoisotopic molecular wt. | M + H⁺ |
|---|---|---|---|---|
| 697 | 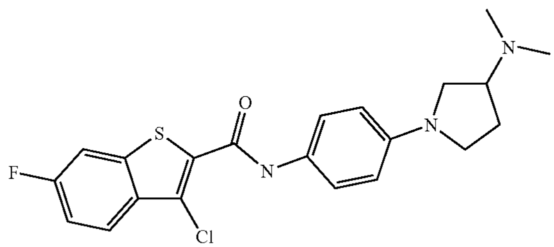 | C21H21ClFN3OS | 417.11 | 418 |
| 698 | 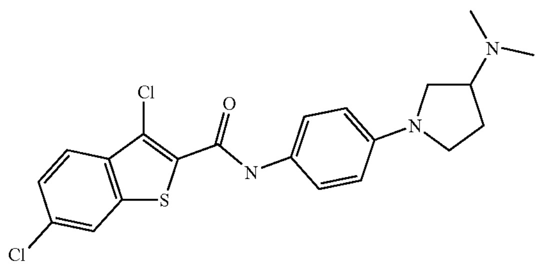 | C21H21Cl2N3OS | 433.08 | 434 |
| 699 | 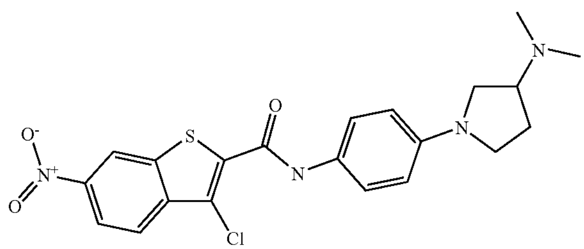 | C21H21ClN4O3S | 444.10 | 445 |
| 700 | 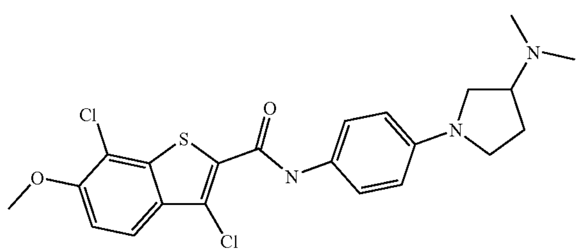 | C22H23Cl2N3O2S | 463.09 | 464 |
| 701 | 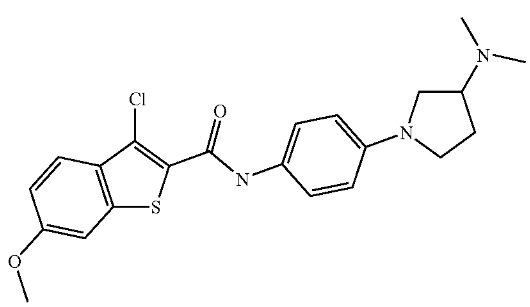 | C22H24ClN3O2S | 429.13 | 430 |

TABLE 7-continued

| Ex. No. | Structure | Molecular formula | Monoisotopic molecular wt. | M + H⁺ |
|---|---|---|---|---|
| 702 | 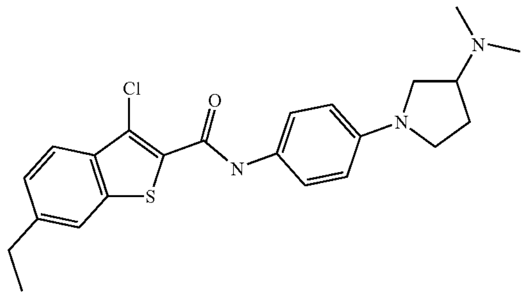 | C23H26ClN3OS | 427.15 | 428 |
| 703 | 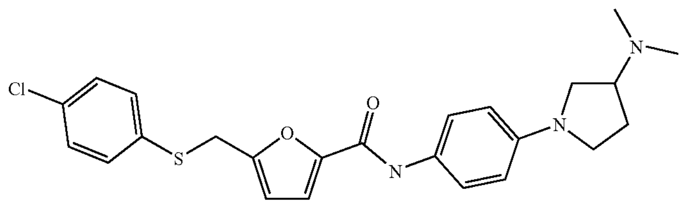 | C24H26ClN3O2S | 455.14 | 456 |
| 704 | 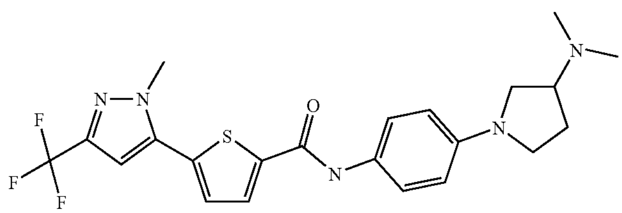 | C22H24F3N5OS | 463.17 | 464 |
| 705 | 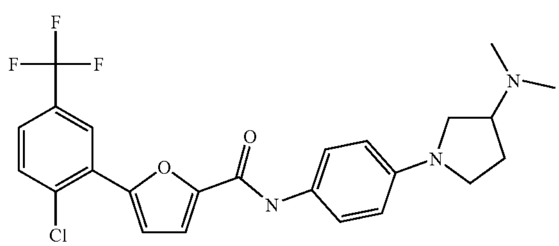 | C24H23ClF3N3O2 | 477.14 | 478 |
| 706 | 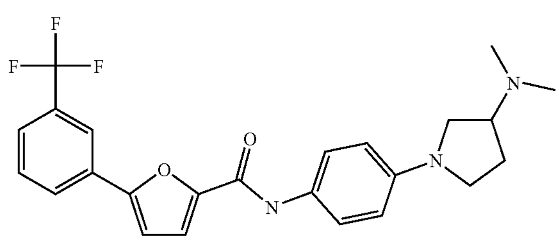 | C24H24F3N3O2 | 443.18 | 444 |
| 707 | 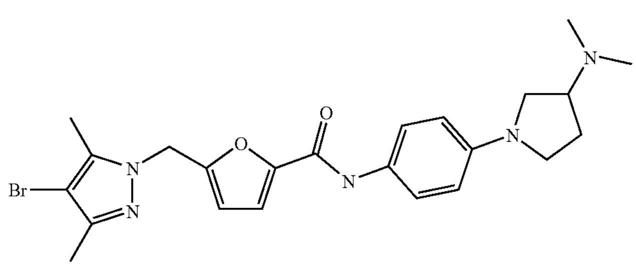 | C23H28BrN5O2 | 485.14 | 486 |

TABLE 7-continued

| Ex. No. | Structure | Molecular formula | Monoisotopic molecular wt. | M + H+ |
|---|---|---|---|---|
| 708 | 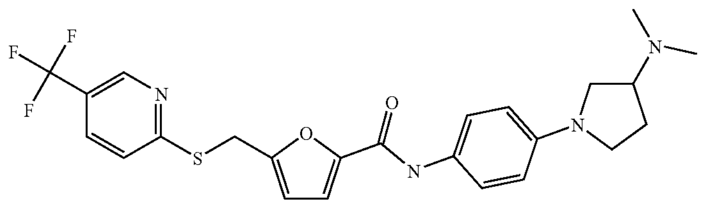 | C24H25F3N4O2S | 490.17 | 491 |
| 709 | 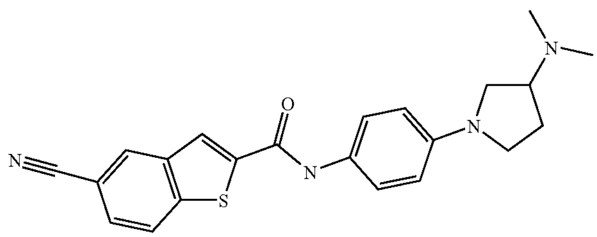 | C22H22N4OS | 390.15 | 391 |
| 710 | 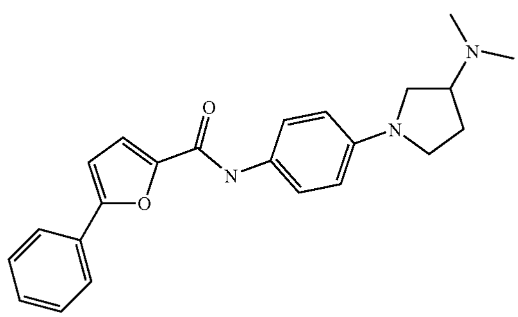 | C23H25N3O2 | 375.20 | 376 |
| 711 | 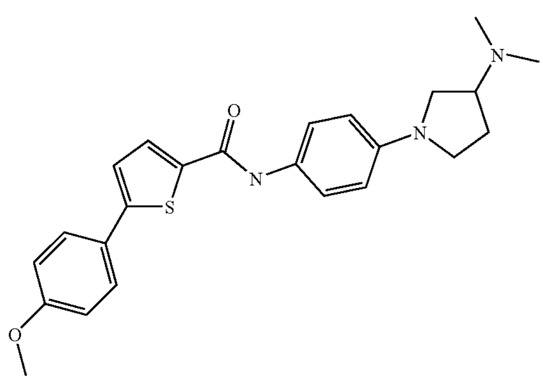 | C24H27N3O2S | 421.18 | 422 |
| 712 | 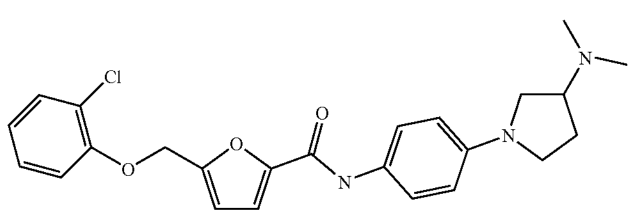 | C24H26ClN3O3 | 439.17 | 440 |

TABLE 7-continued

| Ex. No. | Structure | Molecular formula | Monoisotopic molecular wt. | M + H⁺ |
|---|---|---|---|---|
| 713 | 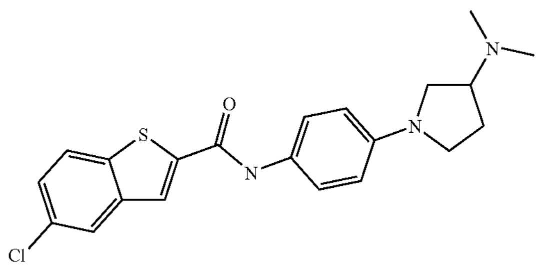 | C21H22ClN3OS | 399.12 | 400 |
| 714 | 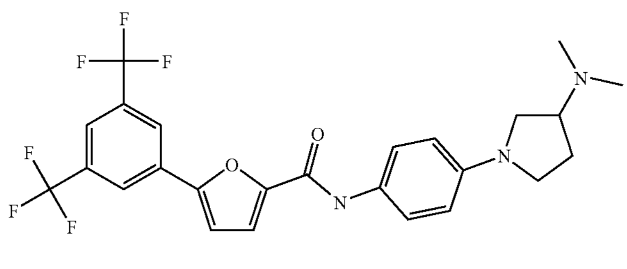 | C25H23F6N3O2 | 511.17 | 512 |
| 715 | 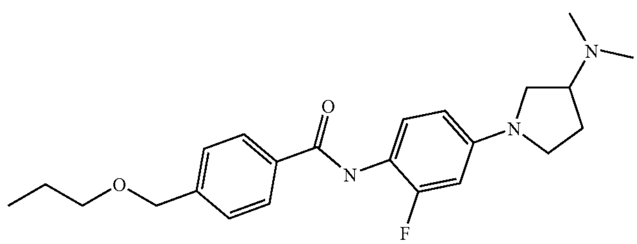 | C23H30FN3O2 | 399.51 | 400 |
| 716 | 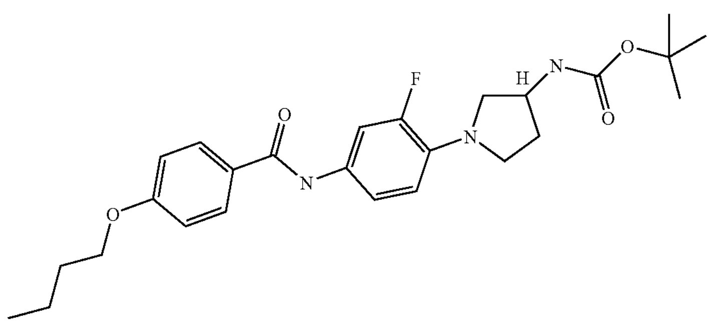 | C26H34FN3O4 | 471.25 | 472 |
| 717 | 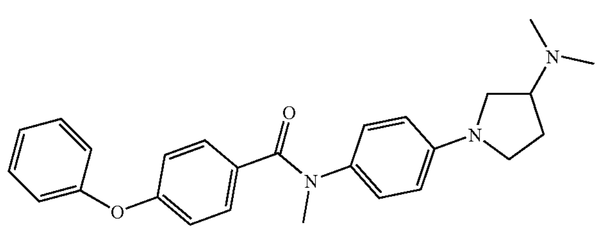 | C26H29N3O2 | 415.23 | 416 |

TABLE 7-continued

| Ex. No. | Structure | Molecular formula | Monoisotopic molecular wt. | M + H+ |
|---|---|---|---|---|
| 718 | 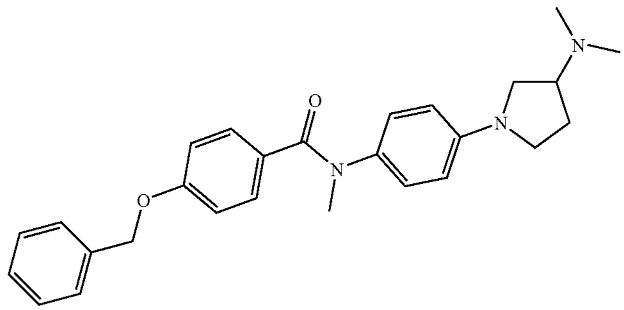 | C27H31N3O2 | 429.24 | 430 |
| 719 | 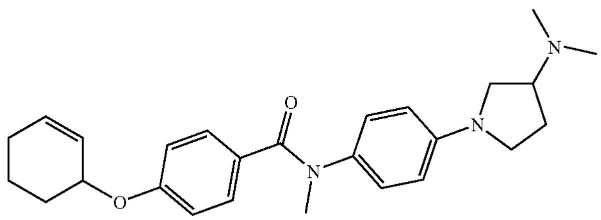 | C26H33N3O2 | 419.26 | 420 |
| 720 | 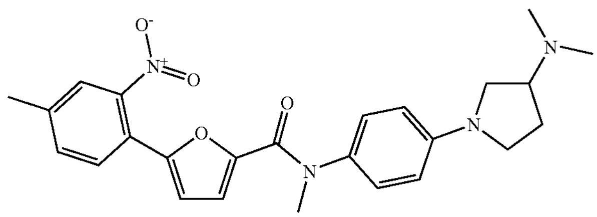 | C25H28N4O4 | 448.21 | 449 |
| 721 | 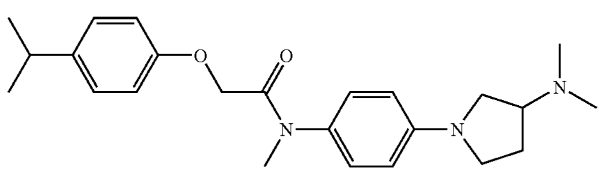 | C24H33N3O2 | 395.26 | 396 |
| 722 | 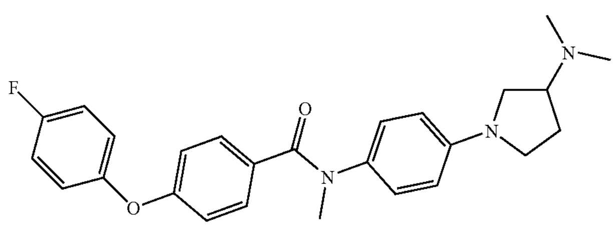 | C26H28FN3O2 | 433.22 | 434 |
| 723 | 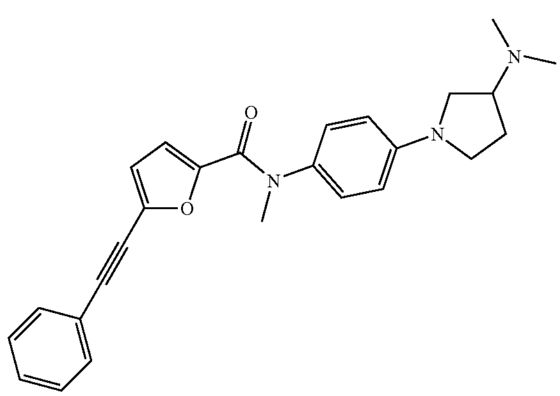 | C26H27N3O2 | 413.21 | 414 |

TABLE 7-continued

| Ex. No. | Structure | Molecular formula | Monoisotopic molecular wt. | M + H+ |
|---|---|---|---|---|
| 724 | 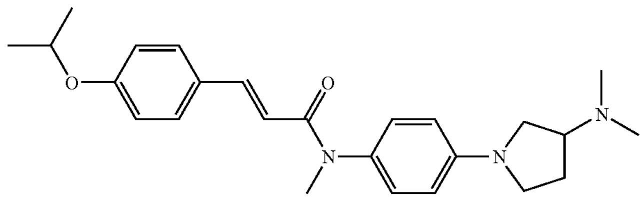 | C25H33N3O2 | 407.26 | 408 |
| 725 | 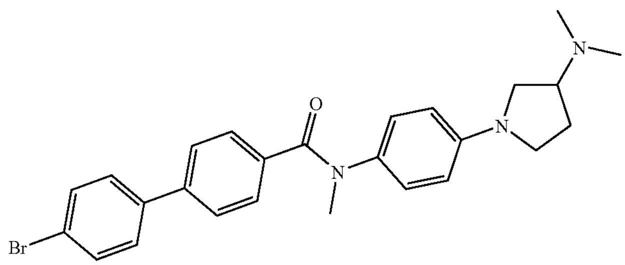 | C26H28BrN3O | 477.14 | 478 |
| 726 | 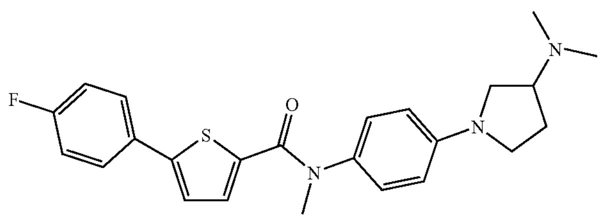 | C24H26FN3OS | 423.18 | 424 |
| 727 | 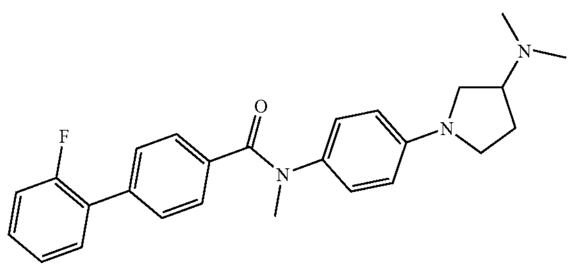 | C26H28FN3O | 417.22 | 418 |
| 728 | 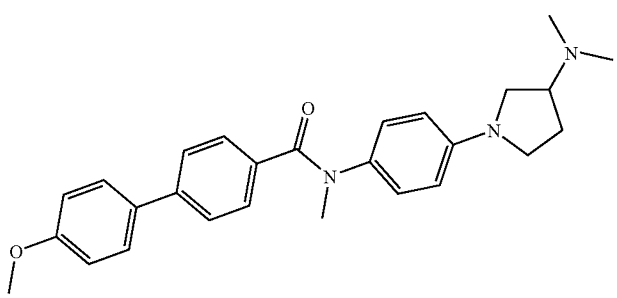 | C27H31N3O2 | 429.24 | 430 |
| 729 | 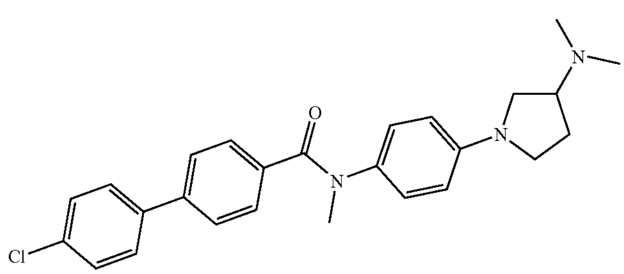 | C26H28ClN3O | 433.19 | 434 |

TABLE 7-continued
| Ex. No. | Structure | Molecular formula | Monoisotopic molecular wt. | M + H+ |
|---|---|---|---|---|
| 730 | 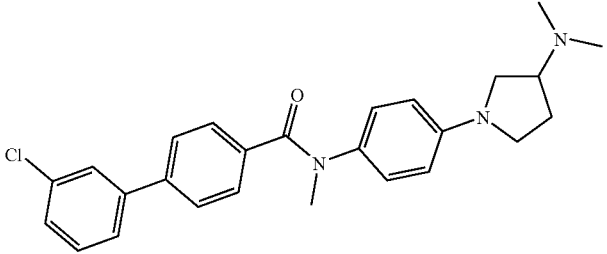 | C26H28ClN3O | 433.19 | 434 |
| 731 | 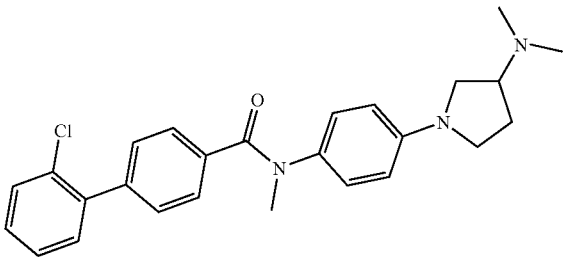 | C26H28ClN3O | 433.19 | 434 |
| 732 | 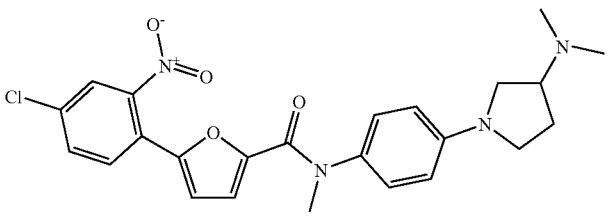 | C24H25ClN4O4 | 468.16 | 469 |
| 733 | 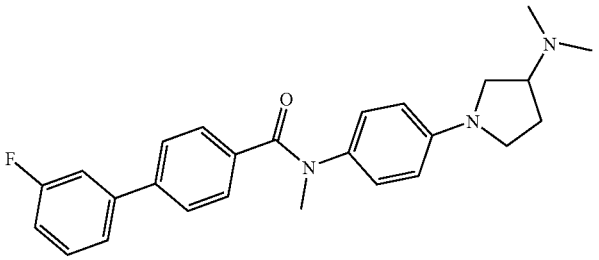 | C26H28FN3O | 417.22 | 418 |
| 734 | 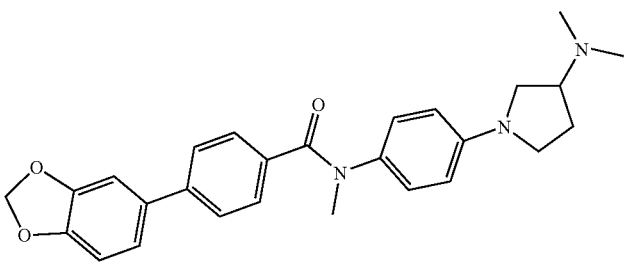 | C27H29N3O3 | 443.22 | 444 |

TABLE 7-continued

| Ex. No. | Structure | Molecular formula | Monoisotopic molecular wt. | M + H⁺ |
|---|---|---|---|---|
| 735 | 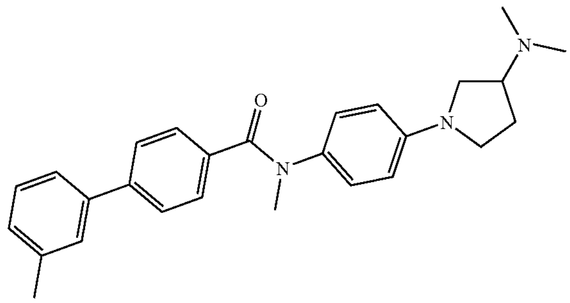 | C27H31N3O | 413.25 | 414 |
| 736 | 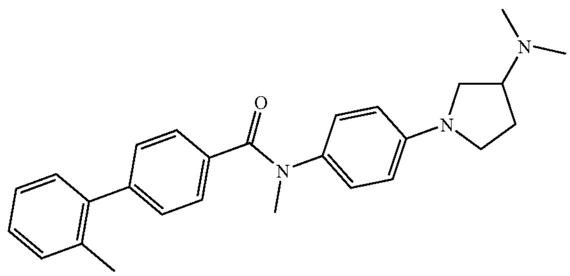 | C27H31N3O | 413.25 | 414 |
| 737 | 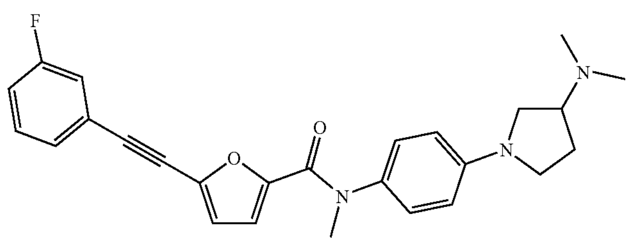 | C26H26FN3O2 | 431.20 | 432 |
| 738 | 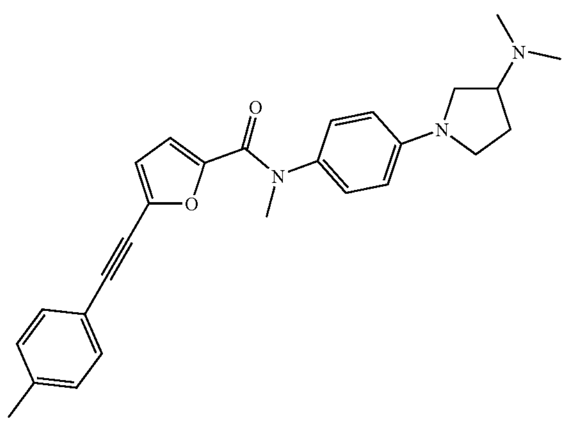 | C27H29N3O2 | 427.23 | 428 |
| 739 | 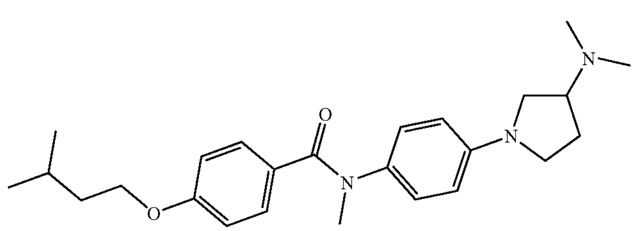 | C25H35N3O2 | 409.27 | 410 |

TABLE 7-continued

| Ex. No. | Structure | Molecular formula | Monoisotopic molecular wt. | M + H+ |
|---|---|---|---|---|
| 740 | 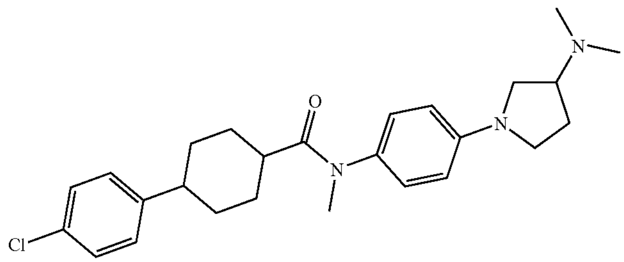 | C26H34ClN3O | 439.24 | 440 |
| 741 | 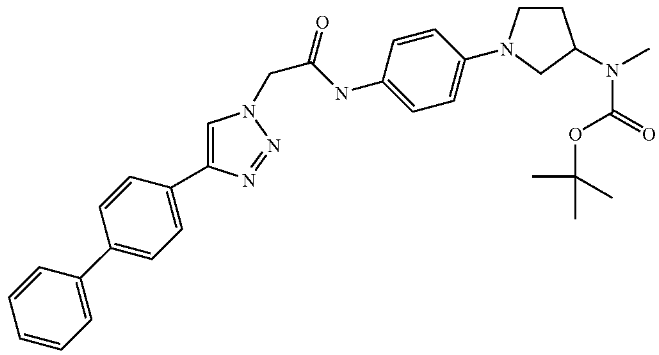 | C32H36N6O3 | 552.28 | 553 |
| 742 | 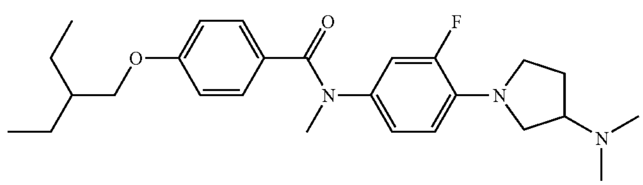 | C26H36FN3O2 | 411.59 | 412 |
| 743 | 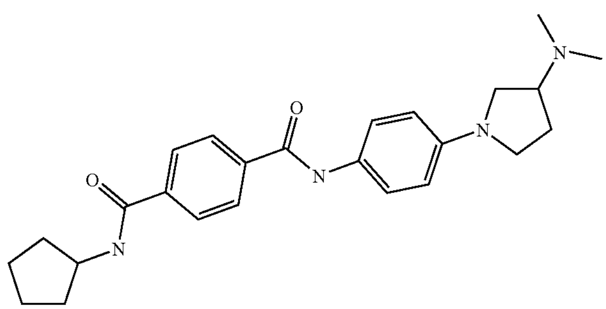 | C25H32N4O2 | 420.25 | 421 |
| 744 | 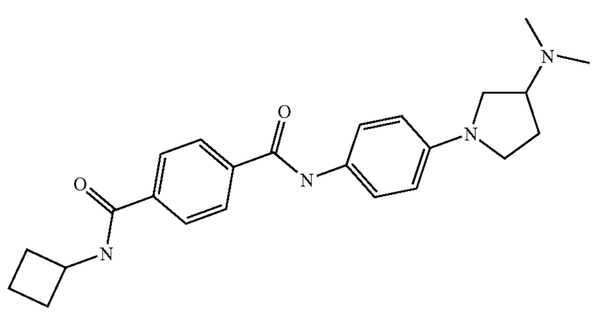 | C24H30N4O2 | 406.24 | 407 |

TABLE 7-continued

| Ex. No. | Structure | Molecular formula | Monoisotopic molecular wt. | M + H⁺ |
|---|---|---|---|---|
| 745 | 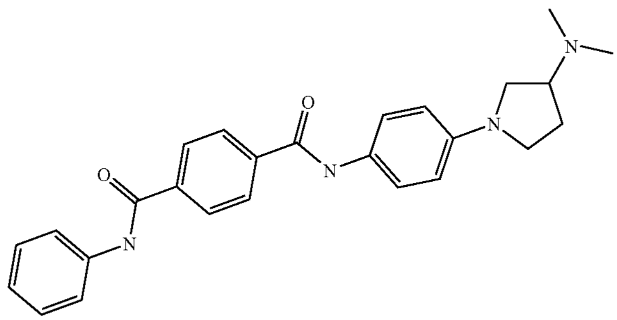 | C26H28N4O2 | 428.22 | 429 |
| 746 | 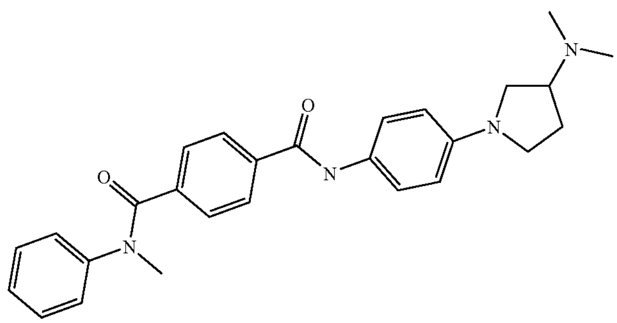 | C27H30N4O2 | 442.24 | 443 |
| 747 | 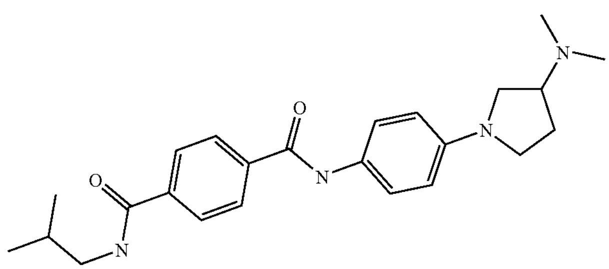 | C24H32N4O2 | 408.25 | 409 |
| 748 | 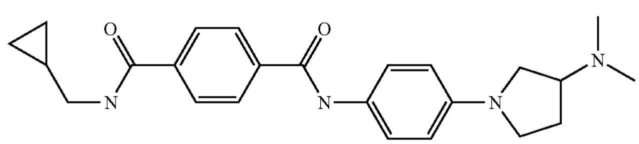 | C24H30N4O2 | 406.24 | 407 |
| 749 | 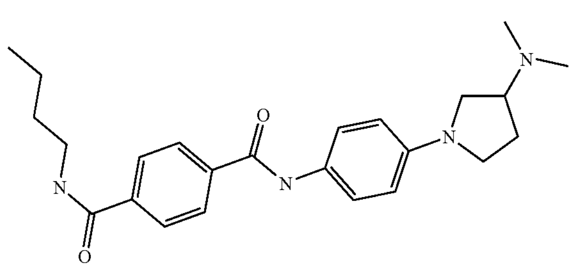 | C24H32N4O2 | 408.25 | 409 |

TABLE 7-continued

| Ex. No. | Structure | Molecular formula | Monoisotopic molecular wt. | M + H+ |
|---|---|---|---|---|
| 750 | 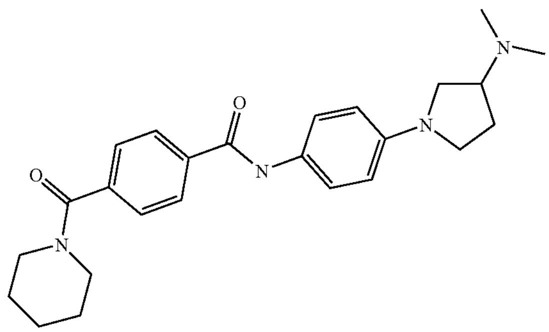 | C25H32N4O2 | 420.25 | 421 |
| 751 | 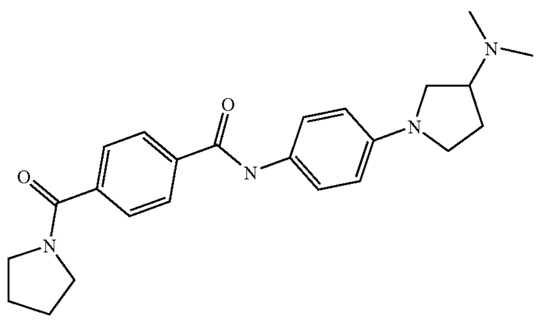 | C24H30N4O2 | 406.24 | 407 |
| 752 | 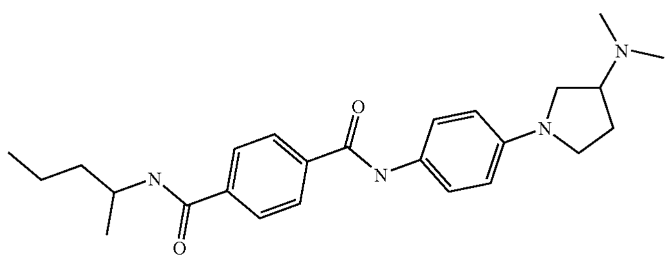 | C25H34N4O2 | 422.27 | 423 |
| 753 | 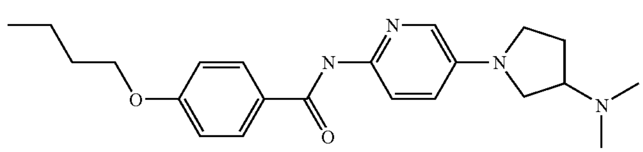 | C22H30N4O2 | 382.24 | 383 |
| 754 | 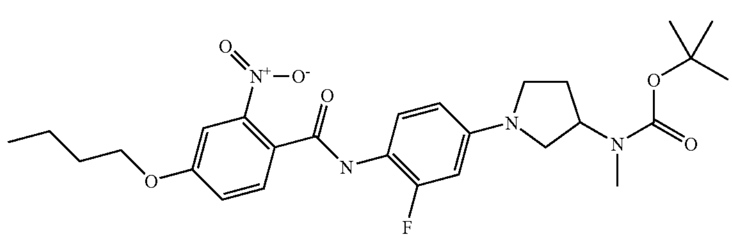 | C27H35FN4O6 | 530.25 | 531 |

TABLE 7-continued

| Ex. No. | Structure | Molecular formula | Monoisotopic molecular wt. | M + H+ |
|---|---|---|---|---|
| 755 | 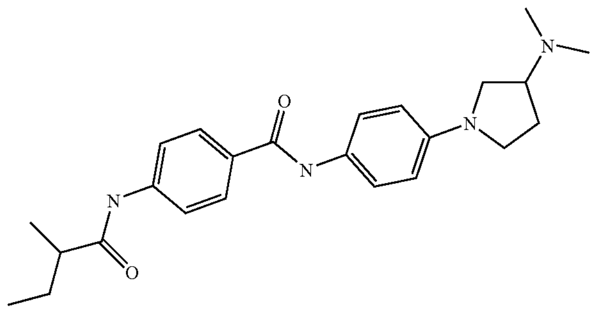 | C24H32N4O2 | 408.25 | 409 |
| 756 | 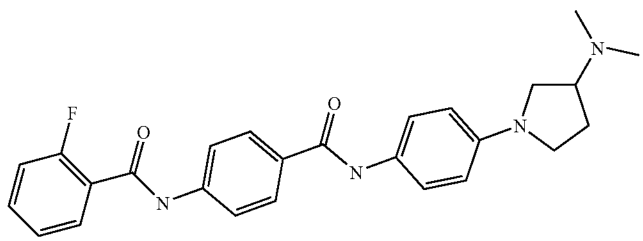 | C26H27FN4O2 | 446.21 | 447 |
| 757 | 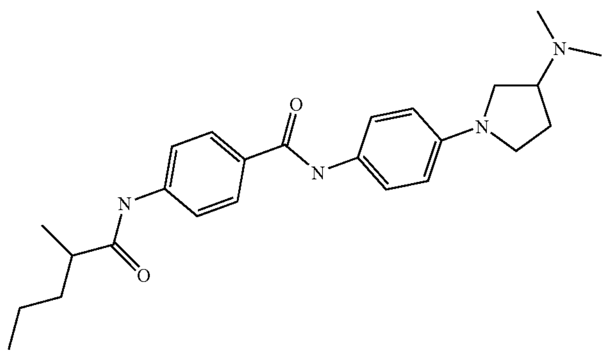 | C25H34N4O2 | 422.27 | 423 |
| 758 | 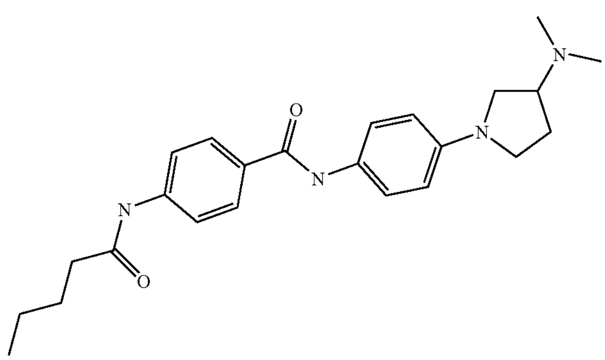 | C24H32N4O2 | 408.25 | 409 |
| 759 | 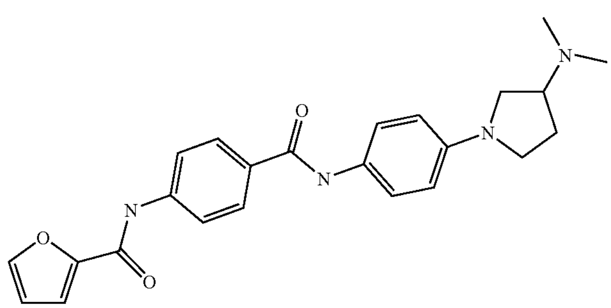 | C24H26N4O3 | 418.20 | 419 |

TABLE 7-continued
| Ex. No. | Structure | Molecular formula | Monoisotopic molecular wt. | M + H+ |
|---|---|---|---|---|
| 760 | 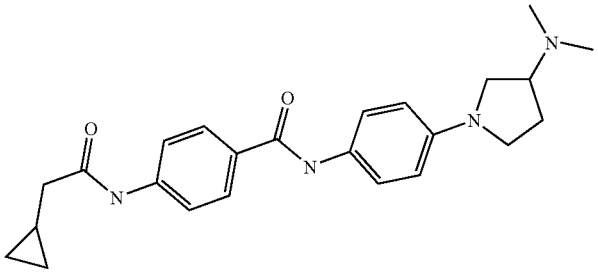 | C24H30N4O2 | 406.24 | 407 |
| 761 | 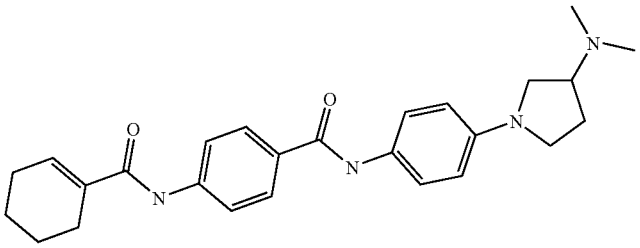 | C26H32N4O2 | 432.25 | 433 |
| 762 | 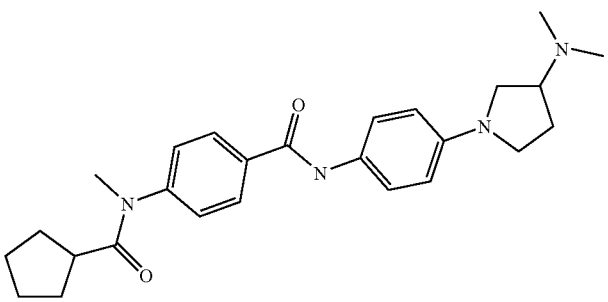 | C26H34N4O2 | 434.27 | 435 |
| 763 | 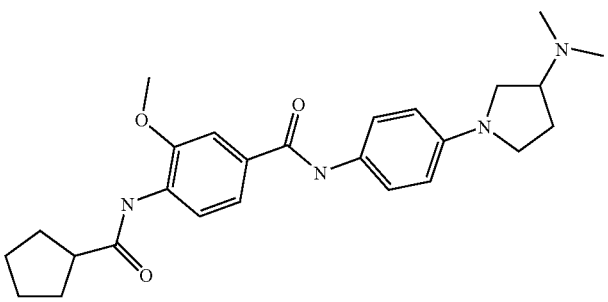 | C26H34N4O3 | 450.26 | 451 |
| 764 | 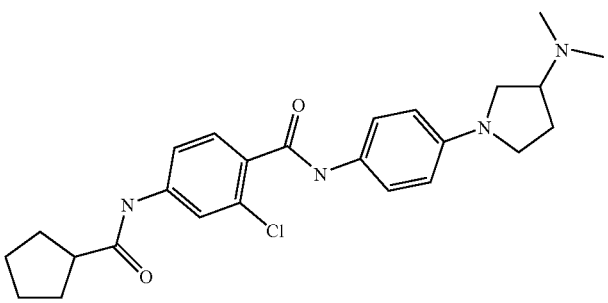 | C25H31ClN4O2 | 454.21 | 455 |

TABLE 7-continued

| Ex. No. | Structure | Molecular formula | Monoisotopic molecular wt. | M + H⁺ |
|---|---|---|---|---|
| 765 | 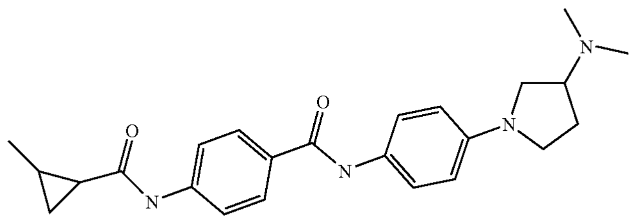 | C24H30N4O2 | 406.24 | 407 |
| 766 | 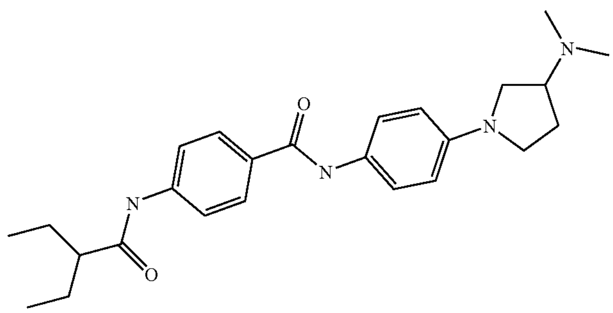 | C25H34N4O2 | 422.27 | 423 |
| 767 | 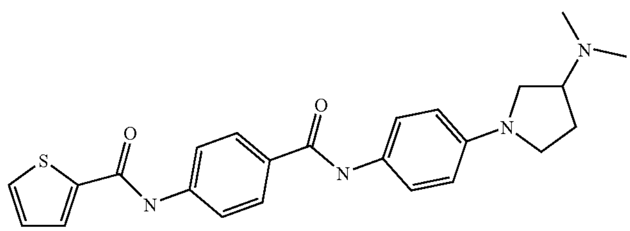 | C24H26N4O2S | 434.18 | 435 |
| 768 | 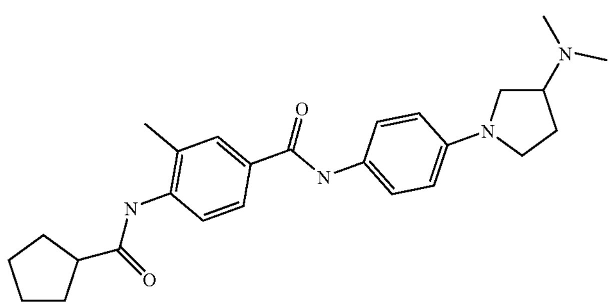 | C26H34N4O2 | 434.27 | 435 |
| 769 | 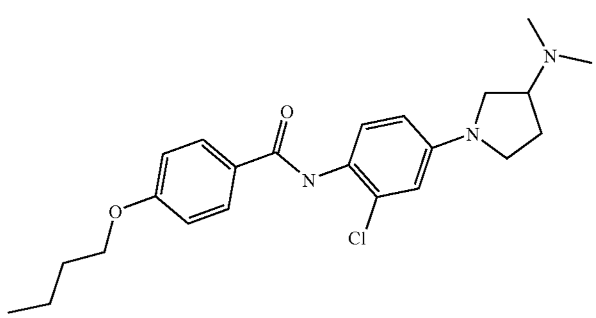 | C23H30ClN3O2 | 415.20 | 416 |

TABLE 7-continued

| Ex. No. | Structure | Molecular formula | Monoisotopic molecular wt. | M + H+ |
|---|---|---|---|---|
| 770 | 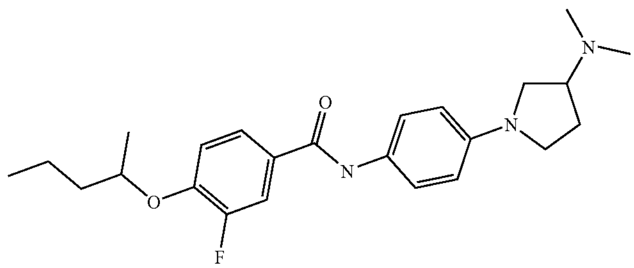 | C24H32FN3O2 | 413.25 | 414 |
| 771 | 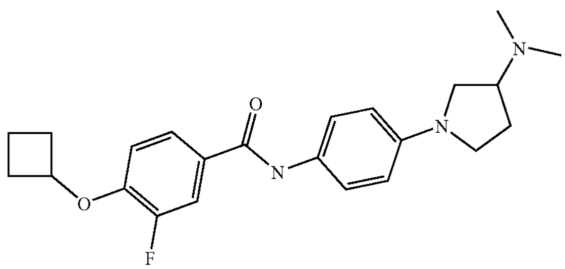 | C23H28FN3O2 | 397.22 | 398 |
| 772 | 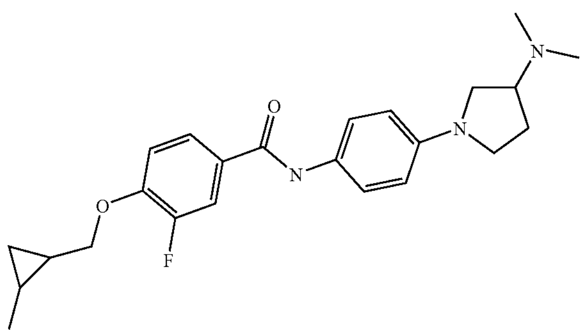 | C24H30FN3O2 | 411.23 | 412 |
| 773 | 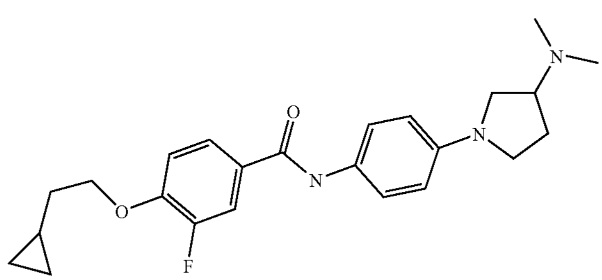 | C24H30FN3O2 | 411.23 | 412 |
| 774 | 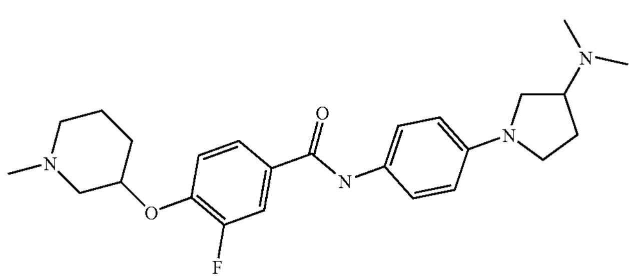 | C25H33FN4O2 | 440.26 | 441 |

TABLE 7-continued

| Ex. No. | Structure | Molecular formula | Monoisotopic molecular wt. | M + H⁺ |
|---|---|---|---|---|
| 775 | 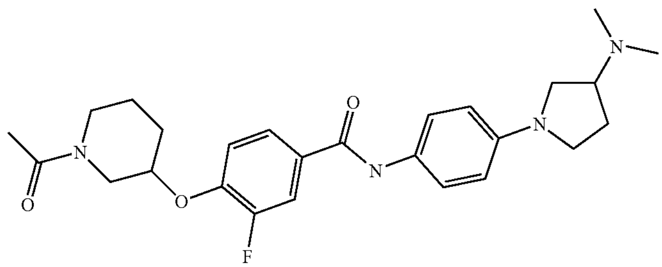 | C26H33FN4O3 | 468.25 | 469 |
| 776 | 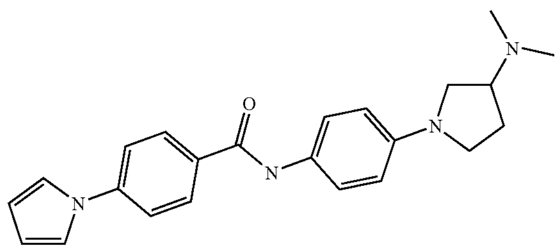 | C23H26N4O | 374.21 | 375 |
| 777 | 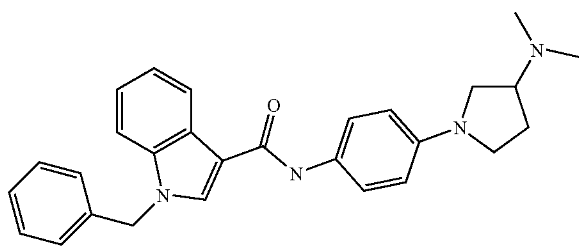 | C28H30N4O | 438.24 | 439 |
| 778 | 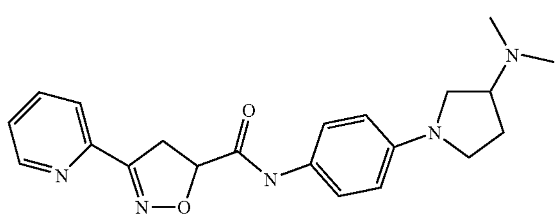 | C21H25N5O2 | 379.20 | 380 |
| 779 | 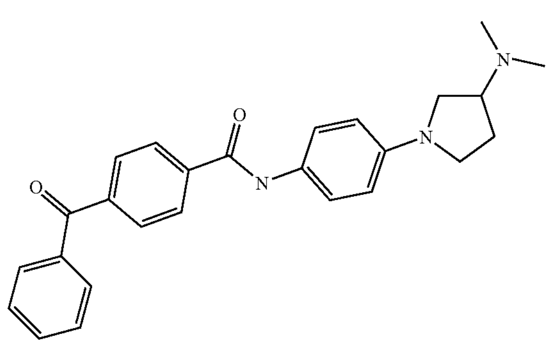 | C26H27N3O2 | 413.21 | 414 |

TABLE 7-continued
| Ex. No. | Structure | Molecular formula | Monoisotopic molecular wt. | M + H+ |
|---|---|---|---|---|
| 780 | 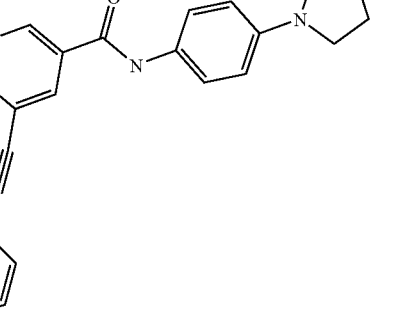 | C26H26N4O | 410.21 | 411 |
| 781 | 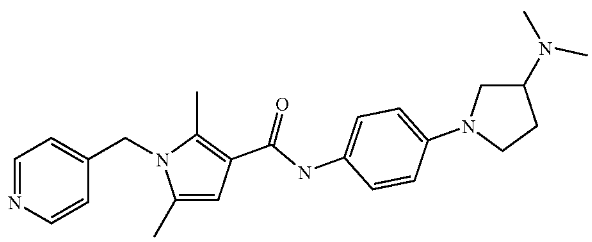 | C25H31N5O | 417.25 | 418 |
| 782 | 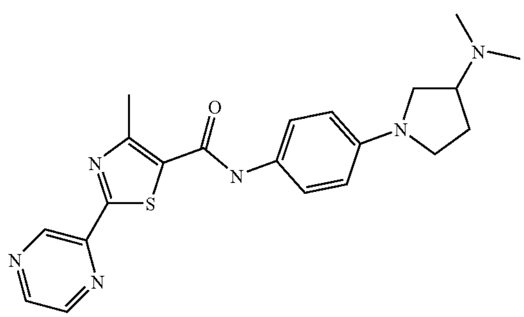 | C21H24N6OS | 408.17 | 409 |
| 783 | 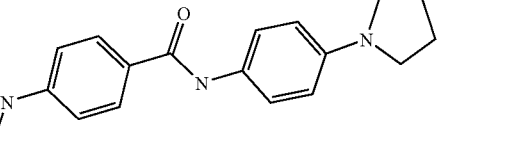 | C22H25N5O | 375.21 | 376 |
| 784 | 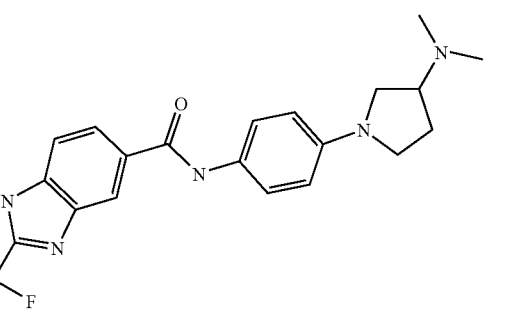 | C24H28F3N5O | 459.23 | 460 |

TABLE 7-continued

| Ex. No. | Structure | Molecular formula | Monoisotopic molecular wt. | M + H+ |
|---|---|---|---|---|
| 785 | 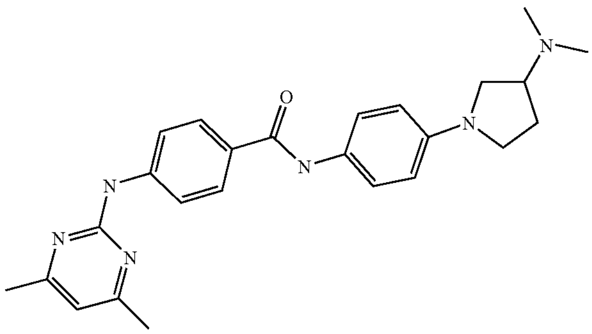 | C25H30N6O | 430.25 | 431 |
| 786 | 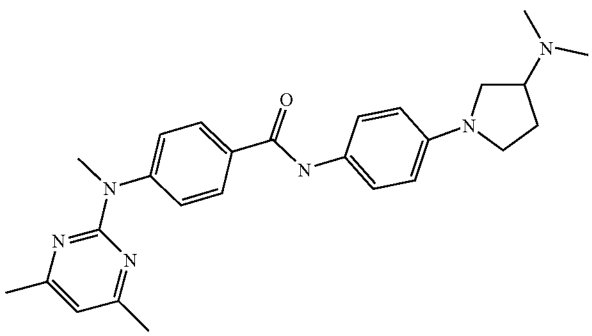 | C26H32N6O | 444.26 | 445 |
| 787 | 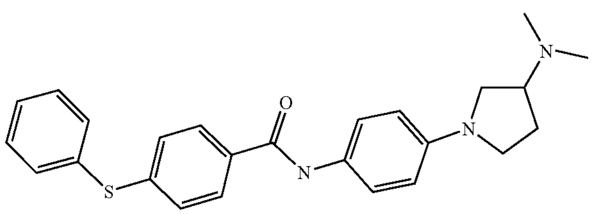 | C25H27N3OS | 417.19 | 418 |
| 788 | 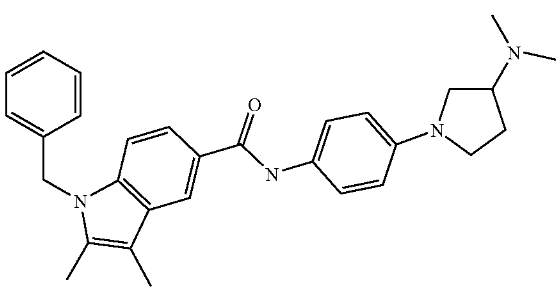 | C30H34N4O | 466.27 | 467 |
| 789 | 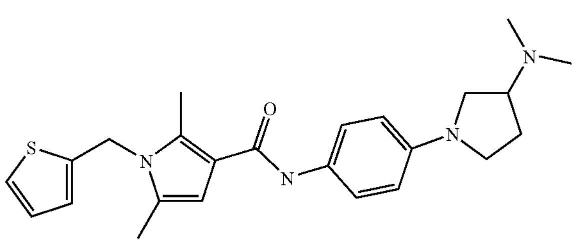 | C24H30N4OS | 422.21 | 423 |

TABLE 7-continued

| Ex. No. | Structure | Molecular formula | Monoisotopic molecular wt. | M + H+ |
|---|---|---|---|---|
| 790 | 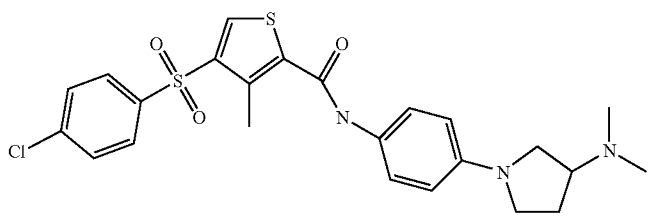 | C24H26ClN3O3S2 | 503.11 | 504 |
| 791 | 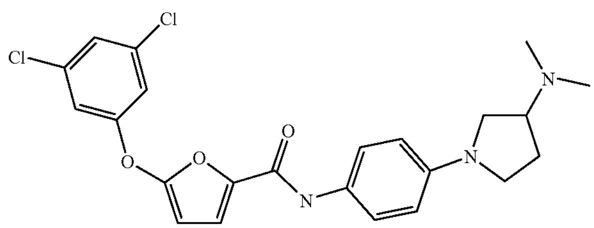 | C23H23Cl2N3O3 | 459.11 | 460 |
| 792 | 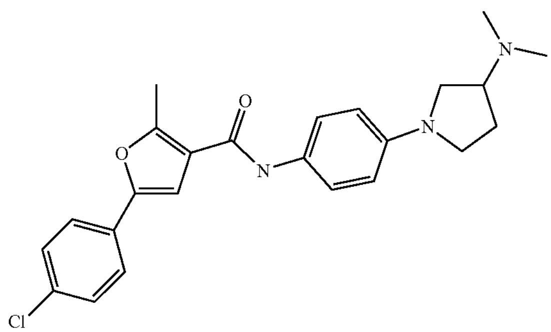 | C24H26ClN3O2 | 423.17 | 424 |
| 793 | 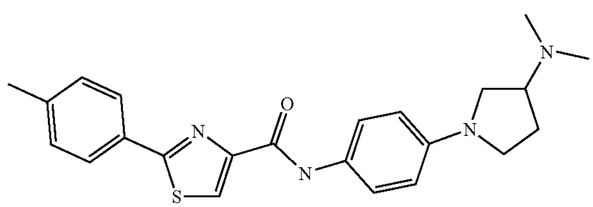 | C23H26N4OS | 406.18 | 407 |
| 794 | 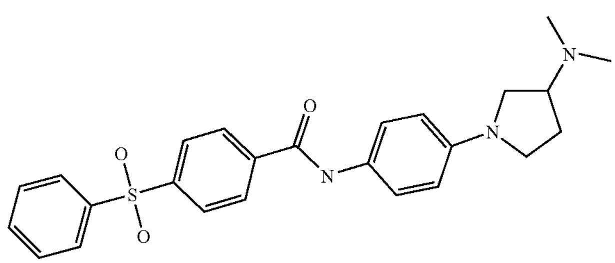 | C25H27N3O3S | 449.18 | 450 |
| 795 | 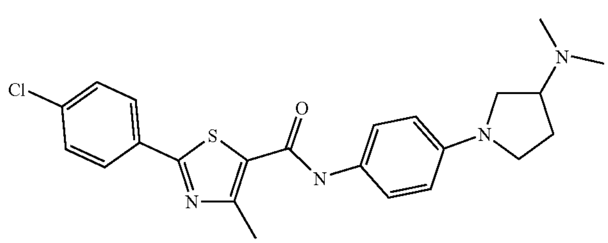 | C23H25ClN4OS | 440.14 | 441 |

TABLE 7-continued

| Ex. No. | Structure | Molecular formula | Monoisotopic molecular wt. | M + H+ |
|---|---|---|---|---|
| 796 | 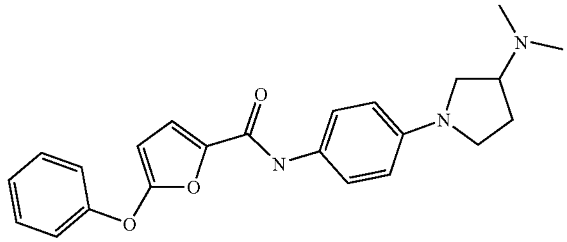 | C23H25N3O3 | 391.19 | 392 |
| 797 | 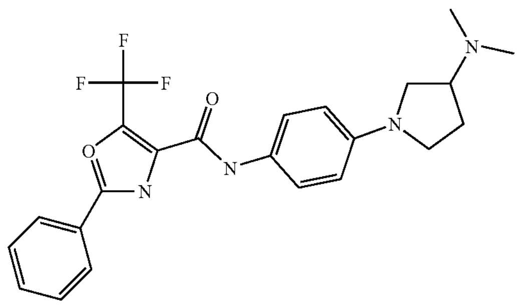 | C23H23F3N4O2 | 444.18 | 445 |
| 798 | 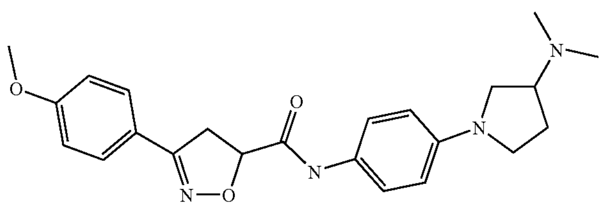 | C23H28N4O3 | 408.22 | 409 |
| 799 | 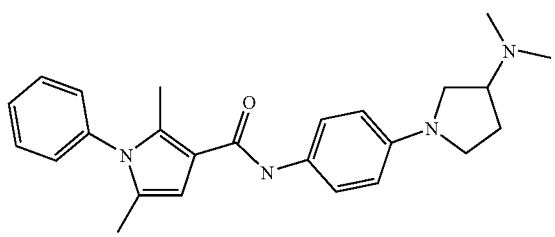 | C25H30N4O | 402.24 | 403 |
| 800 | 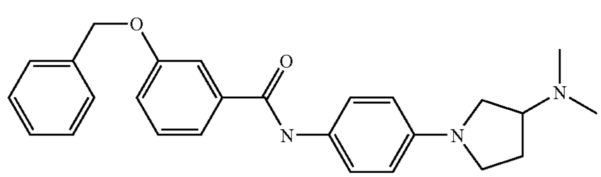 | C26H29N3O2 | 415.23 | 416 |
| 801 | 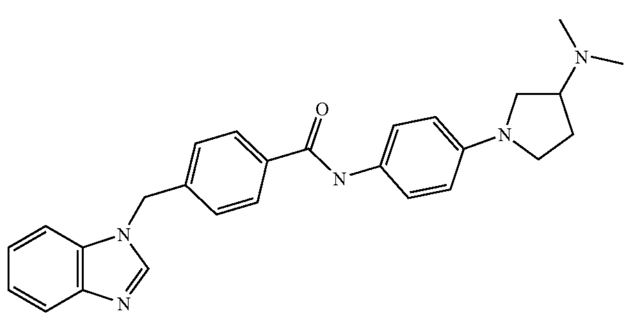 | C27H29N5O | 439.24 | 440 |

TABLE 7-continued

| Ex. No. | Structure | Molecular formula | Monoisotopic molecular wt. | M + H⁺ |
|---|---|---|---|---|
| 802 | 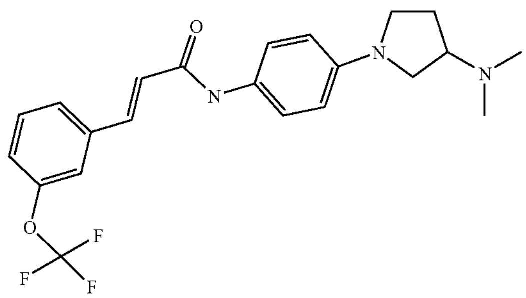 | C22H24F3N3O2 | 419.18 | 420 |
| 803 | 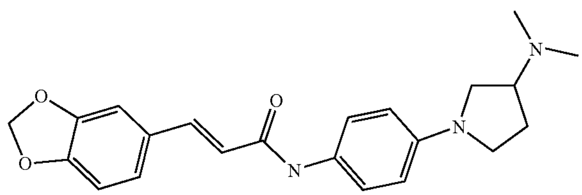 | C22H25N3O3 | 379.19 | 380 |
| 804 | 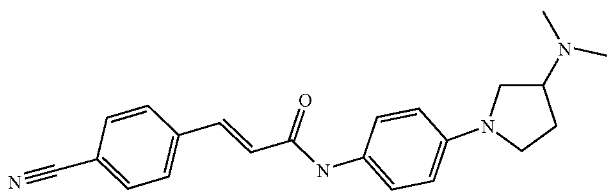 | C22H24N4O | 360.20 | 361 |
| 805 | 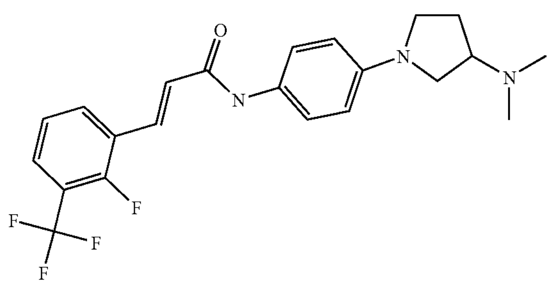 | C22H23F4N3O | 421.18 | 422 |
| 806 | 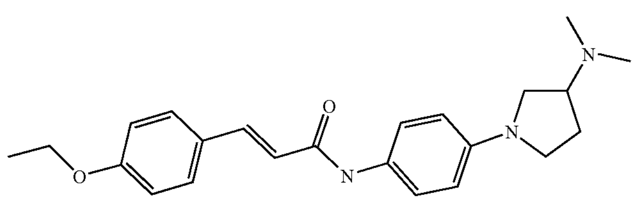 | C23H29N3O2 | 379.23 | 380 |
| 807 | 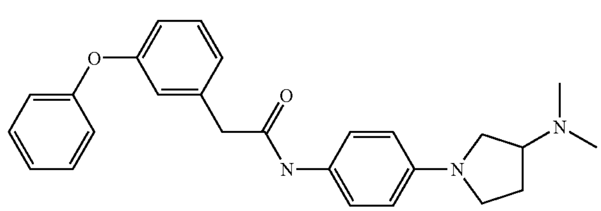 | C26H29N3O2 | 415.23 | 416 |

TABLE 7-continued

| Ex. No. | Structure | Molecular formula | Monoisotopic molecular wt. | M + H+ |
|---|---|---|---|---|
| 808 | 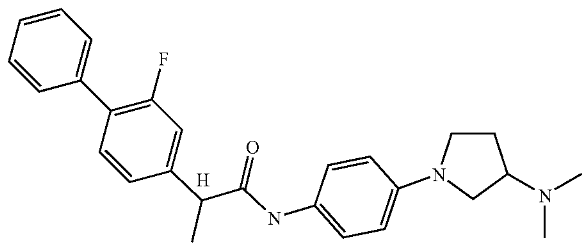 | C27H30FN3O | 431.24 | 432 |
| 809 | 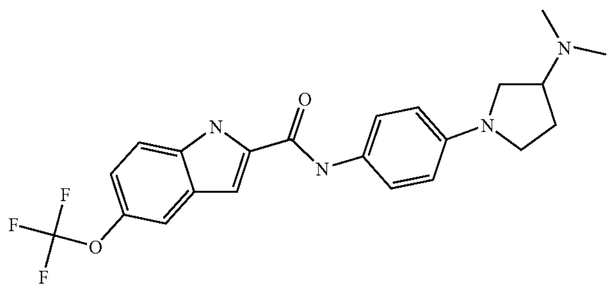 | C22H23F3N4O2 | 432.18 | 433 |
| 810 | 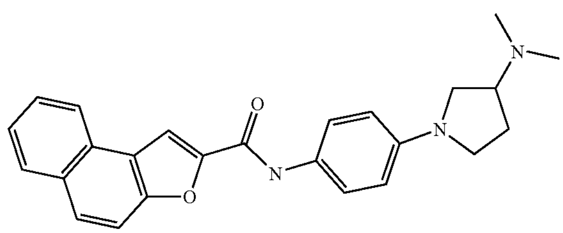 | C25H25N3O2 | 399.20 | 400 |
| 811 | 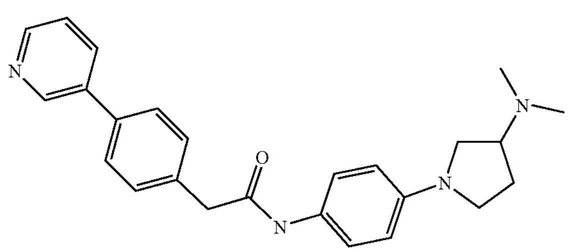 | C25H28N4O | 400.23 | 401 |
| 812 | 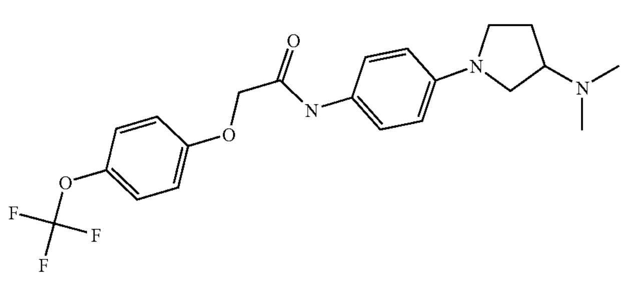 | C21H24F3N3O3 | 423.18 | 424 |

TABLE 7-continued

| Ex. No. | Structure | Molecular formula | Monoisotopic molecular wt. | M + H+ |
|---|---|---|---|---|
| 813 | 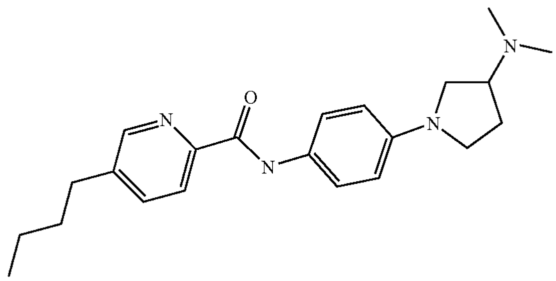 | C22H30N4O | 366.24 | 367 |
| 814 | 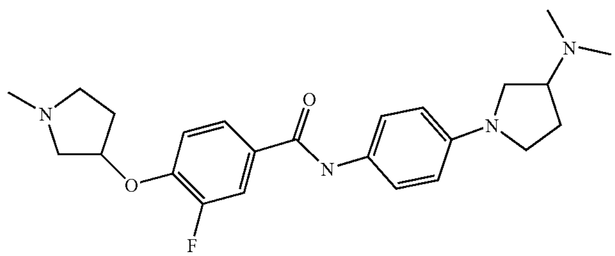 | C24H31FN4O2 | 426.24 | 427 |
| 815 | 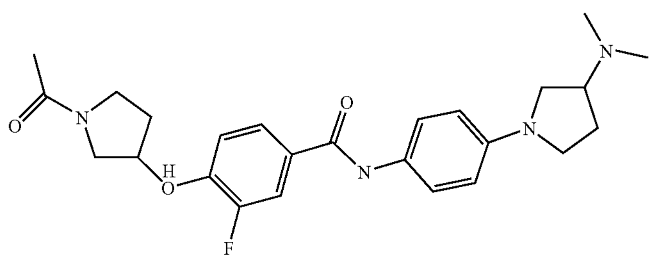 | C25H31FN4O3 | 454.24 | 455 |
| 816 | 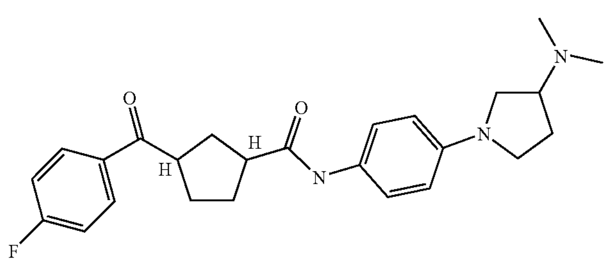 | C25H30FN3O2 | 423.23 | 424 |
| 817 | 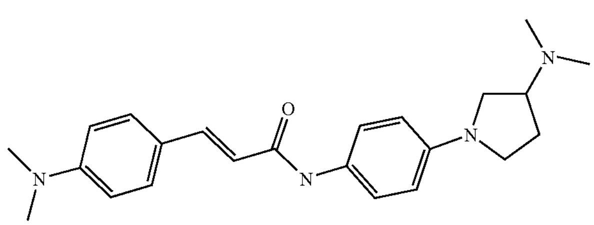 | C23H30N4O | 378.24 | 379 |

TABLE 7-continued

| Ex. No. | Structure | Molecular formula | Monoisotopic molecular wt. | M + H⁺ |
|---|---|---|---|---|
| 818 | 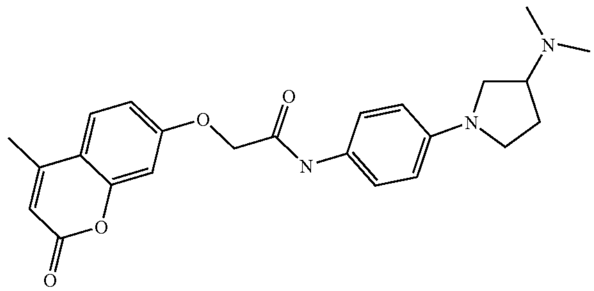 | C24H27N3O4 | 421.20 | 422 |
| 819 | 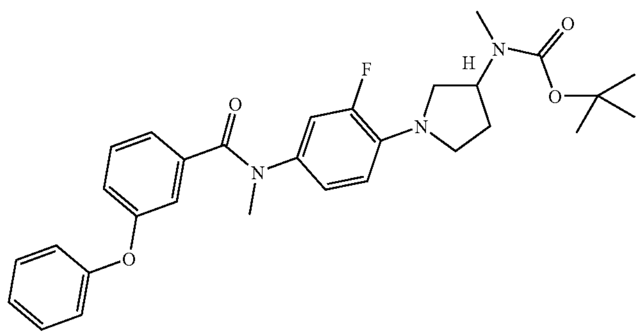 | C30H34FN3O4 | 519.25 | 520 |
| 820 | 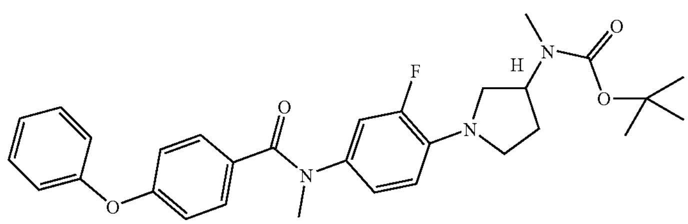 | C30H34FN3O4 | 519.25 | 520 |
| 821 | 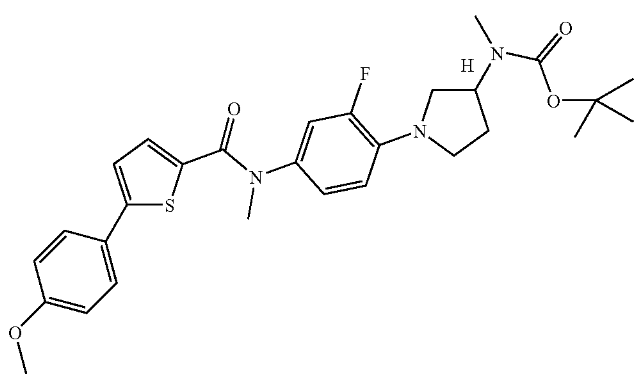 | C29H34FN3O4S | 539.22 | 540 |
| 822 | 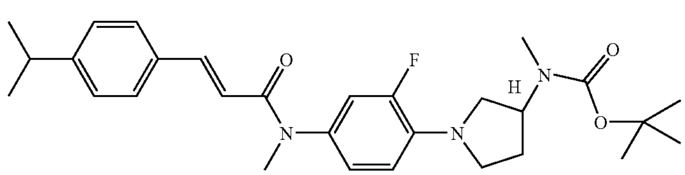 | C29H38FN3O3 | 495.29 | 496 |

TABLE 7-continued

| Ex. No. | Structure | Molecular formula | Monoisotopic molecular wt. | M + H⁺ |
|---|---|---|---|---|
| 823 | 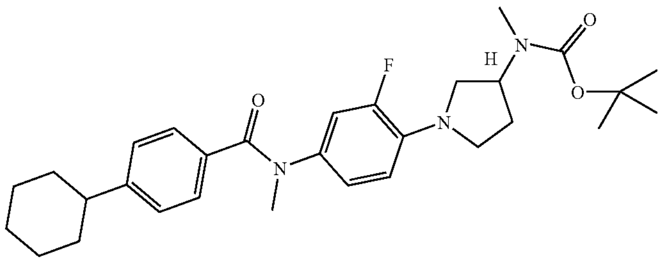 | C30H40FN3O3 | 509.30 | 510 |
| 824 | 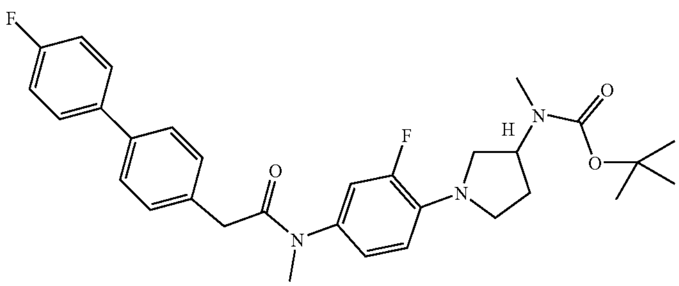 | C31H35F2N3O3 | 535.27 | 536 |
| 825 | 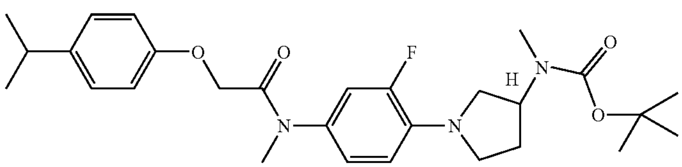 | C28H38FN3O4 | 499.29 | 500 |
| 826 | 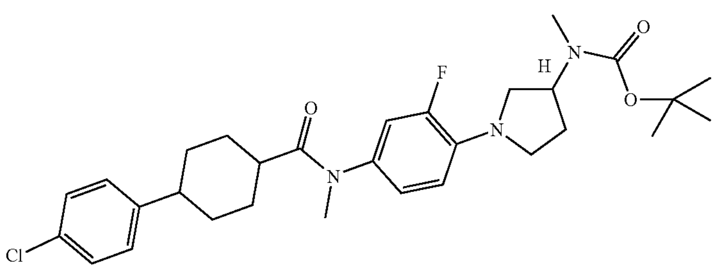 | C30H39ClFN3O3 | 543.27 | 544 |
| 827 | 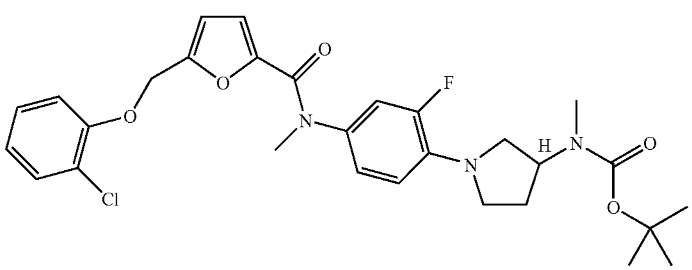 | C29H33ClFN3O5 | 557.21 | 558 |
| 828 | 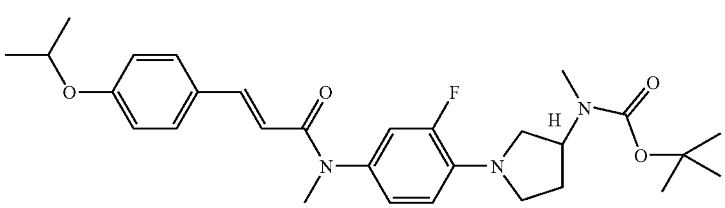 | C29H38FN3O4 | 511.29 | 512 |

TABLE 7-continued

| Ex. No. | Structure | Molecular formula | Monoisotopic molecular wt. | M + H⁺ |
|---|---|---|---|---|
| 829 | 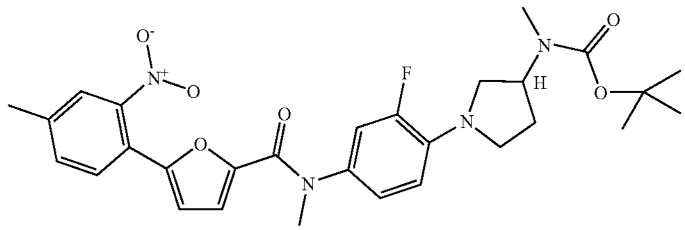 | C29H33FN4O6 | 552.24 | 553 |
| 830 | 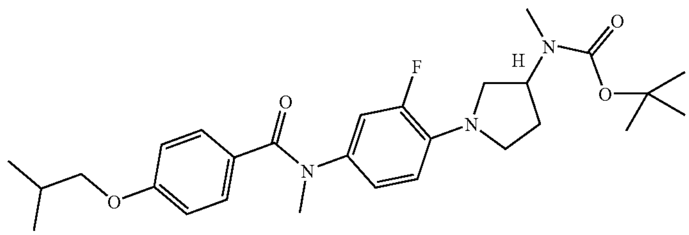 | C28H38FN3O4 | 499.29 | 500 |
| 831 | 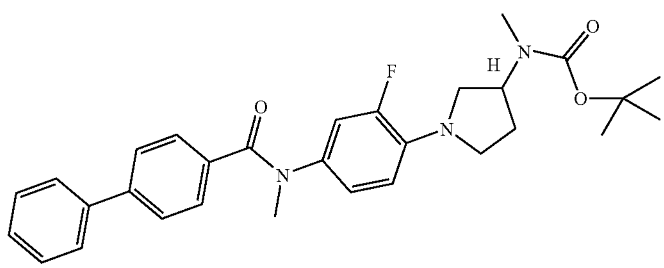 | C30H34FN3O3 | 503.26 | 504 |
| 832 | 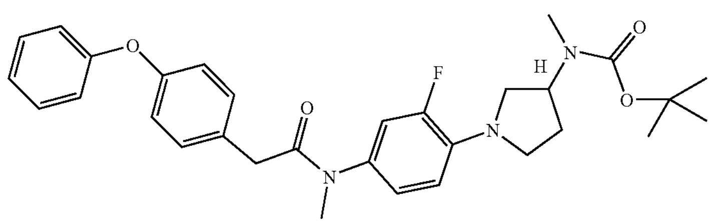 | C31H36FN3O4 | 533.27 | 534 |
| 833 | 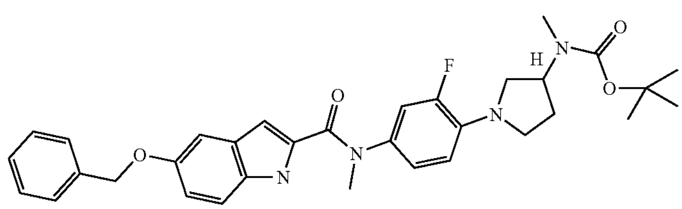 | C33H37FN4O4 | 572.28 | 573 |
| 834 | 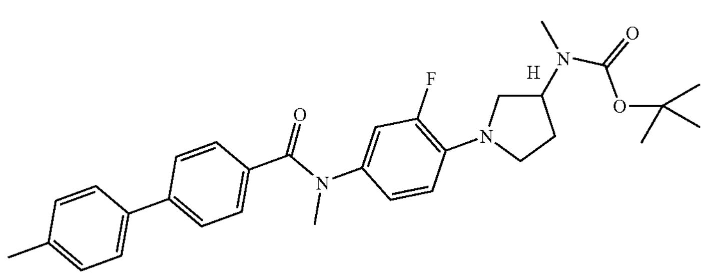 | C31H36FN3O3 | 517.27 | 518 |

TABLE 7-continued

| Ex. No. | Structure | Molecular formula | Monoisotopic molecular wt. | M + H+ |
|---|---|---|---|---|
| 835 | 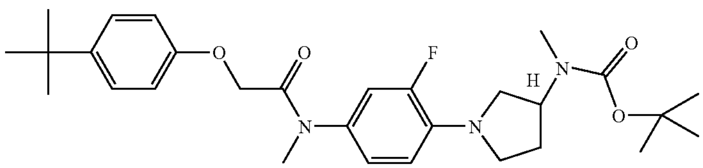 | C29H40FN3O4 | 513.30 | 514 |
| 836 | 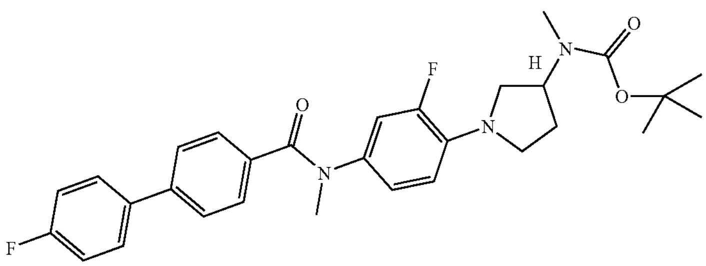 | C30H33F2N3O3 | 521.25 | 522 |
| 837 | 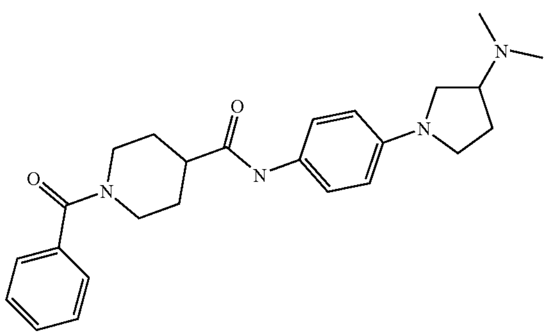 | C25H32N4O2 | 420.25 | 421 |
| 838 | 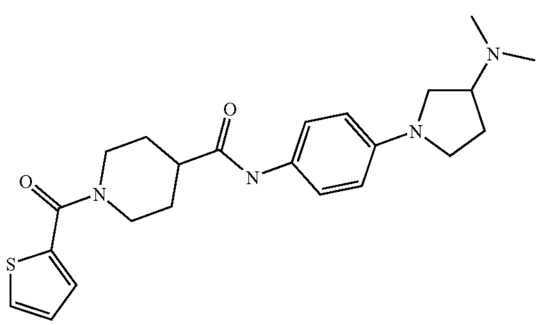 | C23H30N4O2S | 426.21 | 427 |
| 839 | 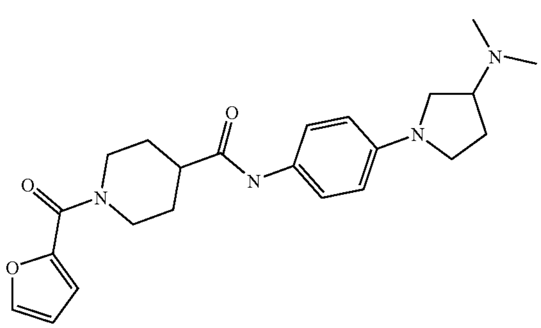 | C23H30N4O3 | 410.23 | 411 |

TABLE 7-continued

| Ex. No. | Structure | Molecular formula | Monoisotopic molecular wt. | M + H+ |
|---|---|---|---|---|
| 840 | 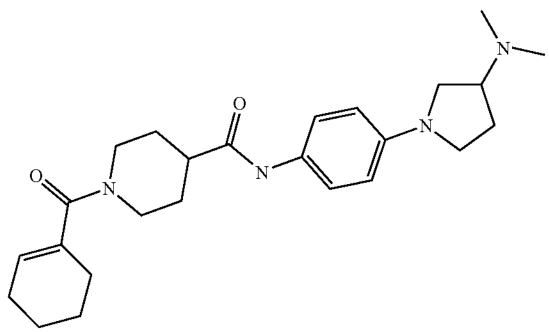 | C25H36N4O2 | 424.28 | 425 |
| 841 | 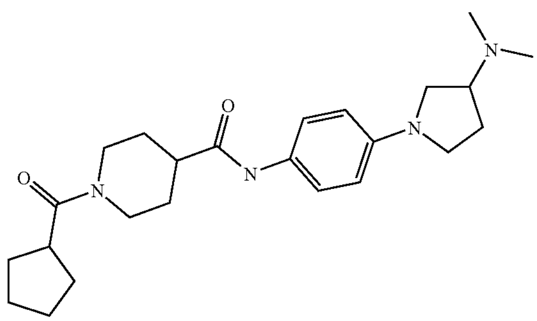 | C24H36N4O2 | 412.28 | 413 |
| 842 | 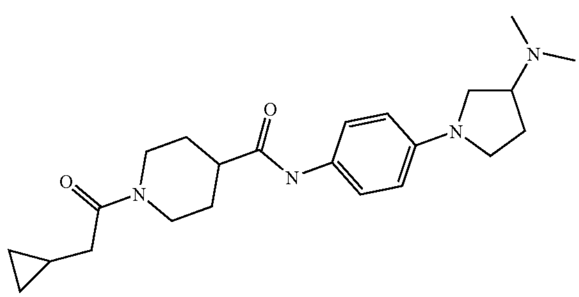 | C23H34N4O2 | 398.27 | 399 |
| 843 | 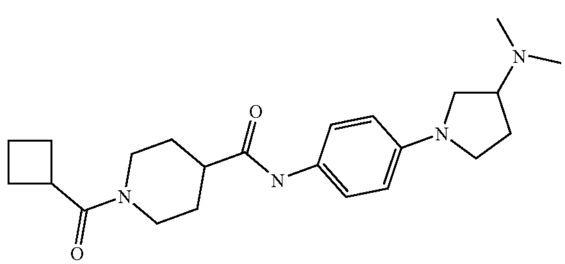 | C23H34N4O2 | 398.27 | 399 |
| 844 | 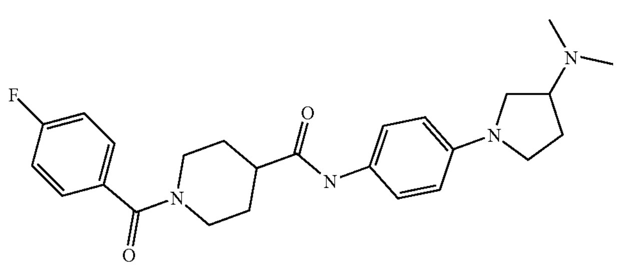 | C25H31FN4O2 | 438.24 | 439 |

TABLE 7-continued

| Ex. No. | Structure | Molecular formula | Monoisotopic molecular wt. | M + H+ |
|---|---|---|---|---|
| 845 | 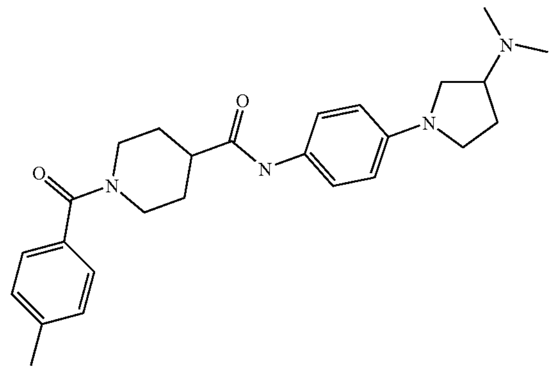 | C26H34N4O2 | 434.27 | 435 |
| 846 | 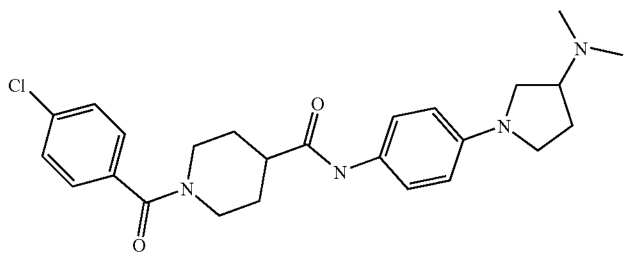 | C25H31ClN4O2 | 454.21 | 455 |
| 847 | 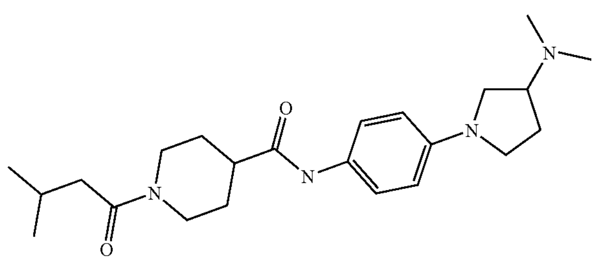 | C23H36N4O2 | 400.28 | 401 |
| 848 | 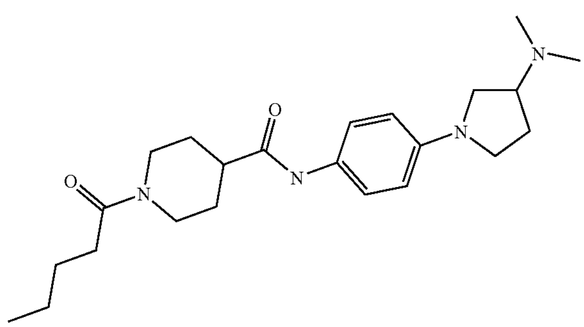 | C23H36N4O2 | 400.28 | 401 |
| 849 | 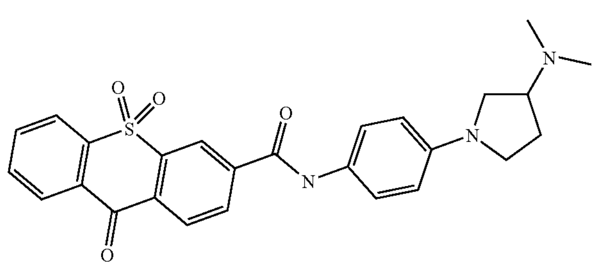 | C26H25N3O4S | 475.16 | 476 |

TABLE 7-continued
| Ex. No. | Structure | Molecular formula | Monoisotopic molecular wt. | M + H+ |
|---|---|---|---|---|
| 850 | 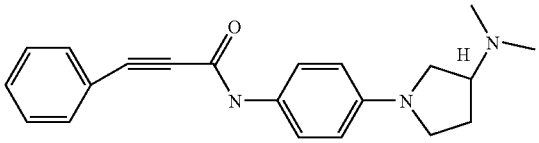 | C21H23N3O | 333.18 | 334 |
| 851 | 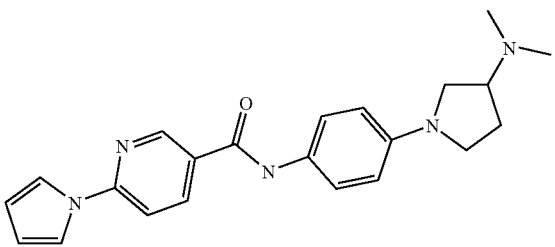 | C22H25N5O | 375.21 | 376 |
| 852 | 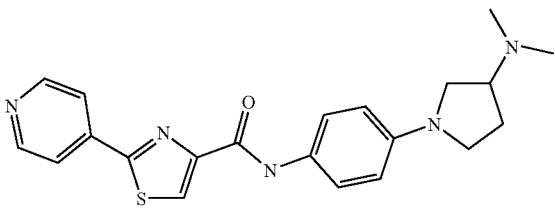 | C21H23N5OS | 393.16 | 394 |
| 853 | 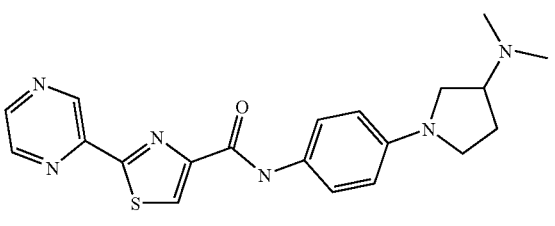 | C20H22N6OS | 394.16 | 395 |
| 854 | 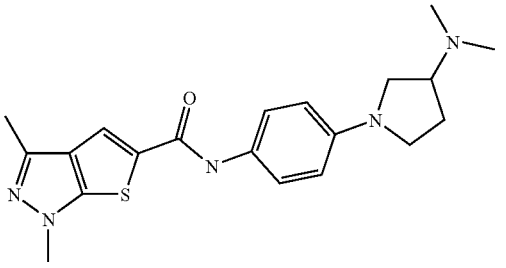 | C20H25N5OS | 383.18 | 384 |
| 855 | 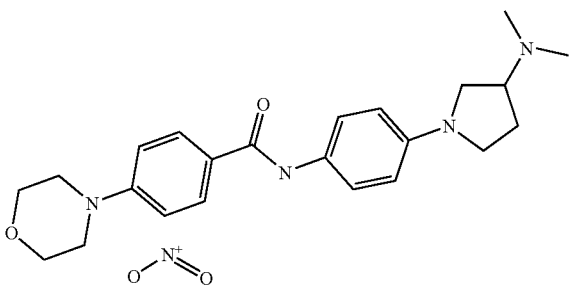 | C23H29N5O4 | 439.22 | 440 |

TABLE 7-continued

| Ex. No. | Structure | Molecular formula | Monoisotopic molecular wt. | M + H+ |
|---|---|---|---|---|
| 856 | 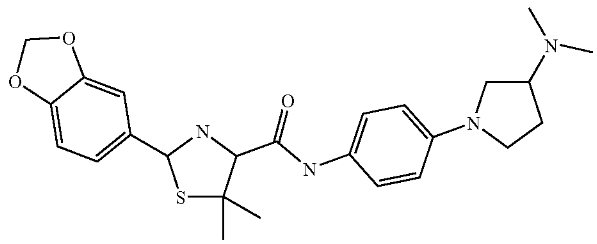 | C25H32N4O3S | 468.22 | 469 |
| 857 | 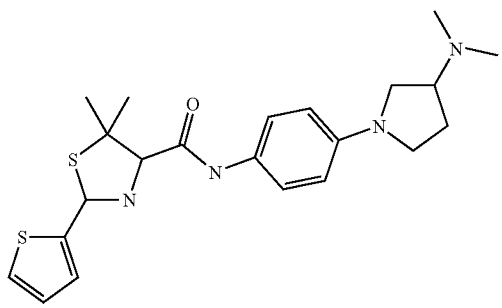 | C22H30N4OS2 | 430.19 | 431 |
| 858 | 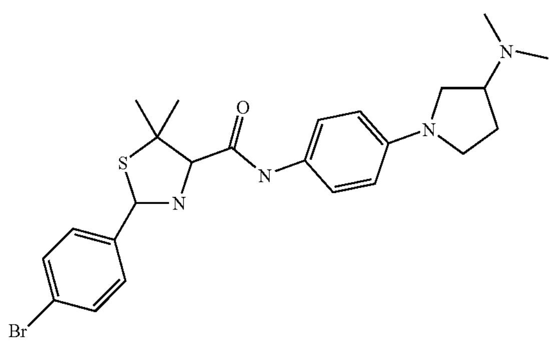 | C24H31BrN4OS | 502.14 | 503 |
| 859 | 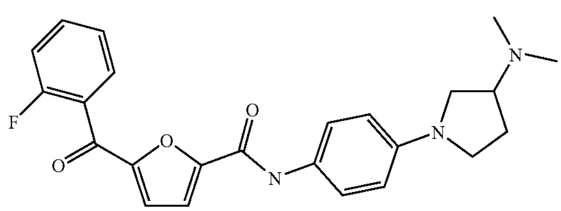 | C24H24FN3O3 | 421.18 | 422 |
| 860 | 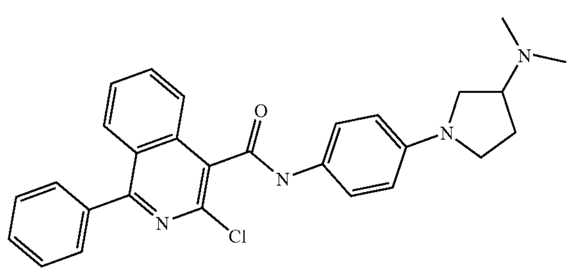 | C28H27ClN4O | 470.19 | 471 |

TABLE 7-continued
| Ex. No. | Structure | Molecular formula | Monoisotopic molecular wt. | M + H+ |
|---|---|---|---|---|
| 861 | 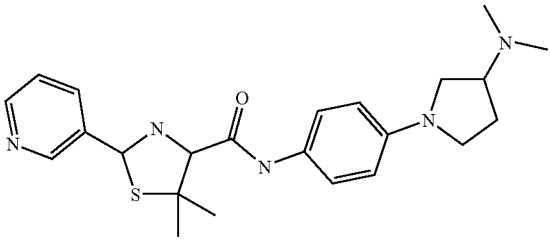 | C23H31N5OS | 425.23 | 426 |
| 862 | 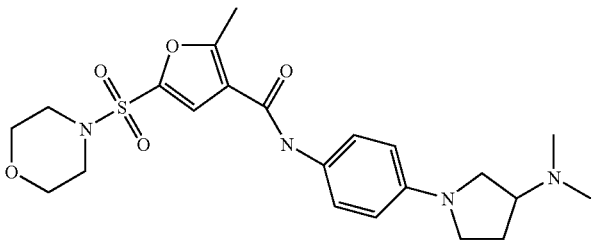 | C22H30N4O5S | 462.19 | 463 |
| 863 | 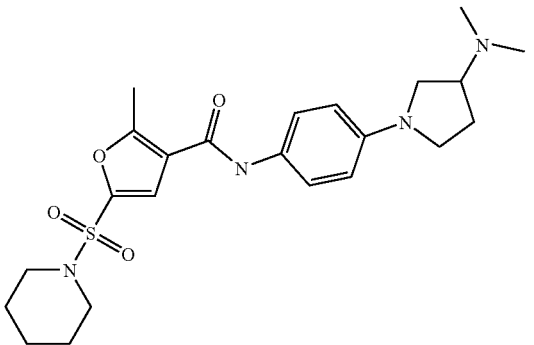 | C23H32N4O4S | 460.21 | 461 |
| 864 | 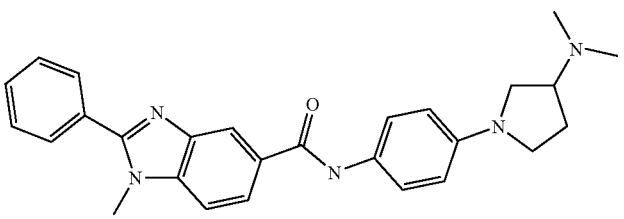 | C27H29N5O | 439.24 | 440 |
| 865 | 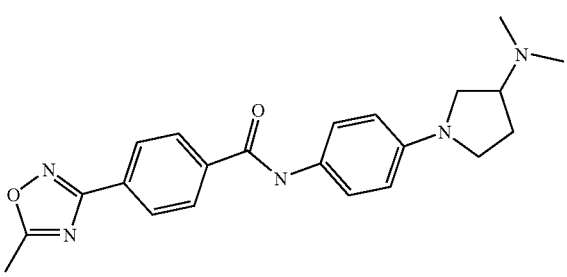 | C22H25N5O2 | 391.20 | 392 |

TABLE 7-continued

| Ex. No. | Structure | Molecular formula | Monoisotopic molecular wt. | M + H⁺ |
|---|---|---|---|---|
| 866 | 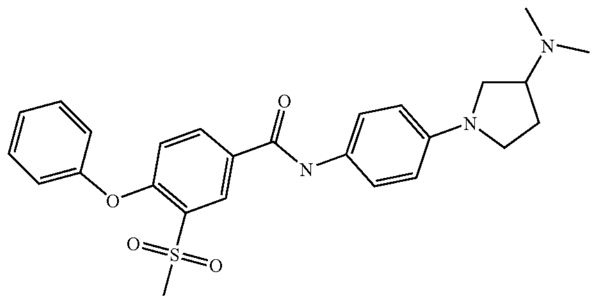 | C26H29N3O4S | 479.19 | 480 |
| 867 | 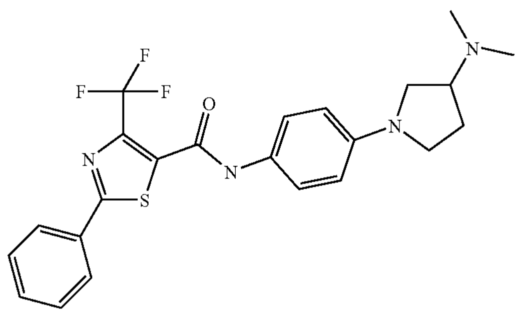 | C23H23F3N4OS | 460.15 | 461 |
| 868 | 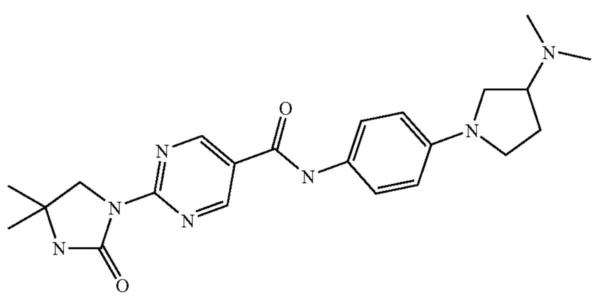 | C22H29N7O2 | 423.24 | 424 |
| 869 | 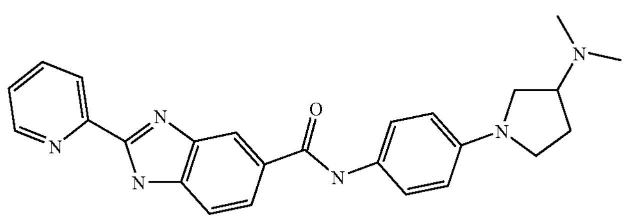 | C25H26N6O | 426.22 | 427 |
| 870 | 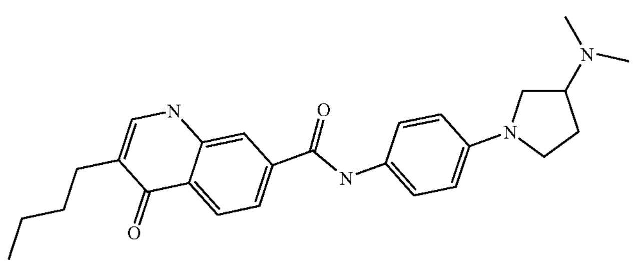 | C26H32N4O2 | 432.25 | 433 |

TABLE 7-continued
| Ex. No. | Structure | Molecular formula | Monoisotopic molecular wt. | M + H+ |
|---|---|---|---|---|
| 871 | 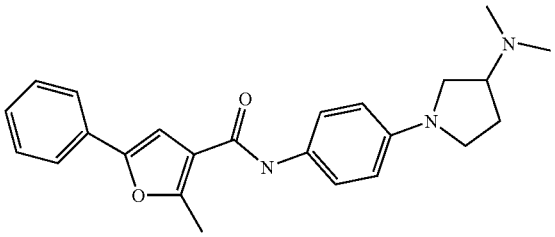 | C24H27N3O2 | 389.21 | 390 |
| 872 | 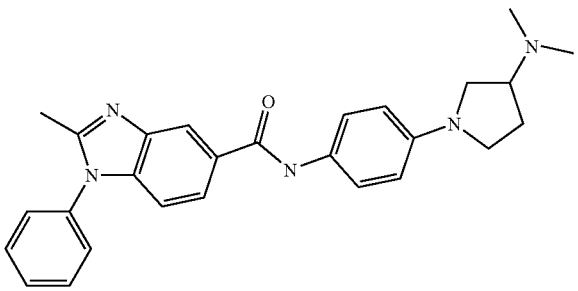 | C27H29N5O | 439.24 | 440 |
| 873 | 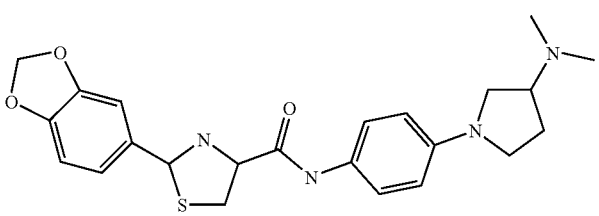 | C23H28N4O3S | 440.19 | 441 |
| 874 | 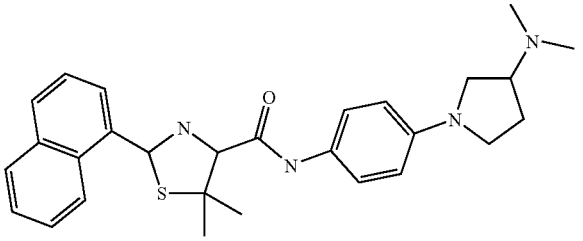 | C28H34N4OS | 474.24 | 475 |
| 875 | 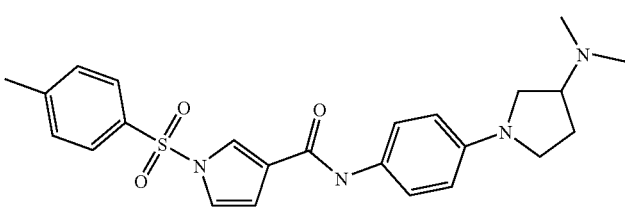 | C24H28N4O3S | 452.19 | 453 |
| 876 | 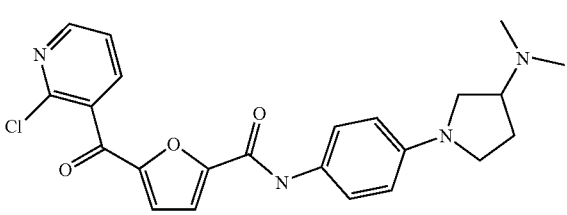 | C23H23ClN4O3 | 438.15 | 439 |

TABLE 7-continued

| Ex. No. | Structure | Molecular formula | Monoisotopic molecular wt. | M + H⁺ |
|---|---|---|---|---|
| 877 | 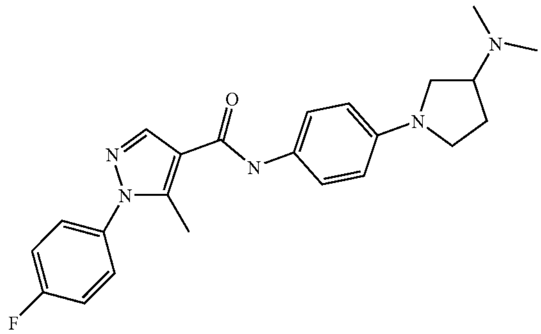 | C23H26FN5O | 407.21 | 408 |
| 878 | 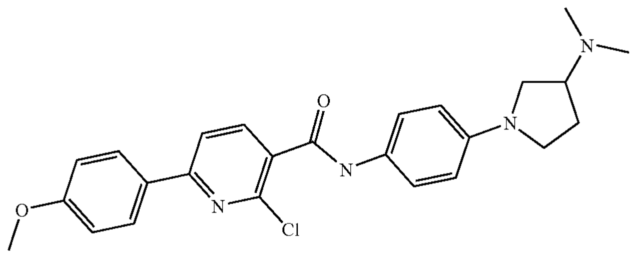 | C25H27ClN4O2 | 450.18 | 451 |
| 879 | 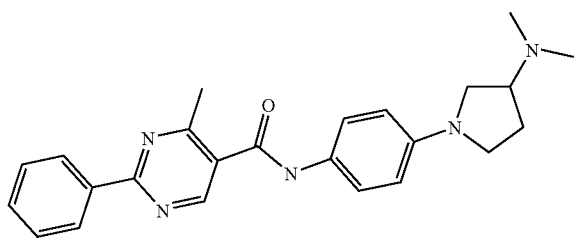 | C24H27N5O | 401.22 | 402 |
| 880 | 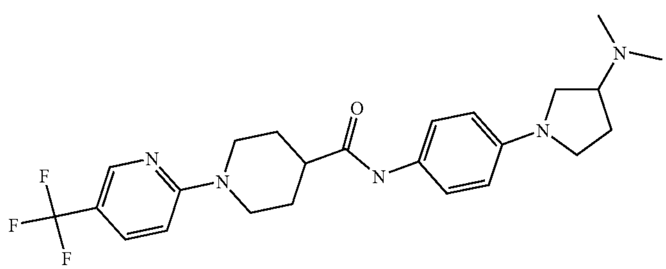 | C24H30F3N5O | 461.24 | 462 |
| 881 | 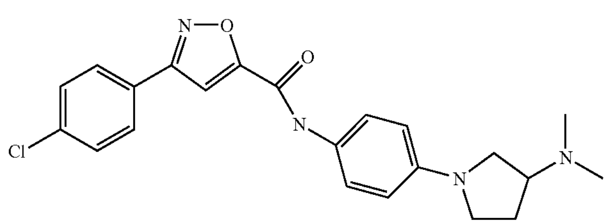 | C22H23ClN4O2 | 410.15 | 411 |
| 882 | 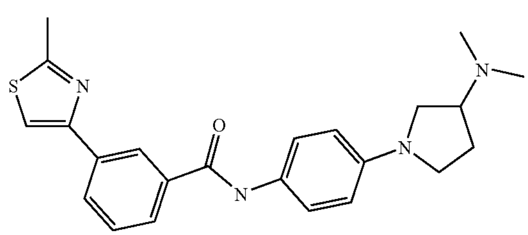 | C23H26N4OS | 406.18 | 407 |

TABLE 7-continued

| Ex. No. | Structure | Molecular formula | Monoisotopic molecular wt. | M + H+ |
|---|---|---|---|---|
| 883 | 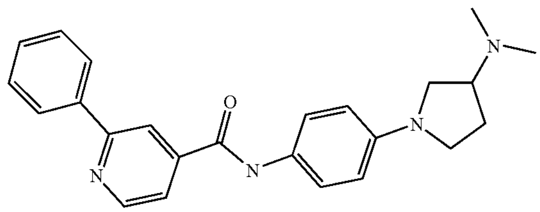 | C24H26N4O | 386.21 | 387 |
| 884 | 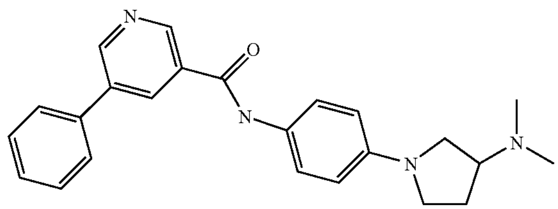 | C24H26N4O | 386.21 | 387 |
| 885 | 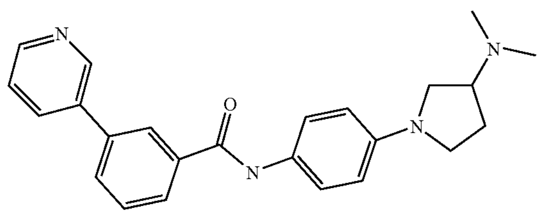 | C24H26N4O | 386.21 | 387 |
| 886 | 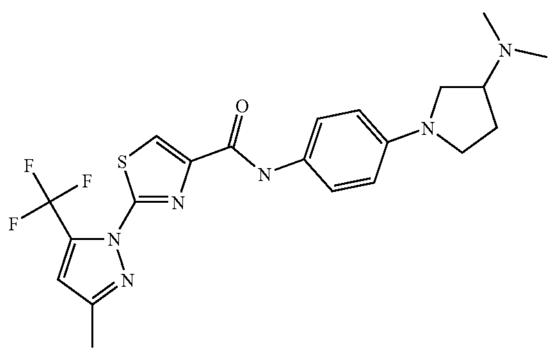 | C21H23F3N6OS | 464.16 | 465 |
| 887 | 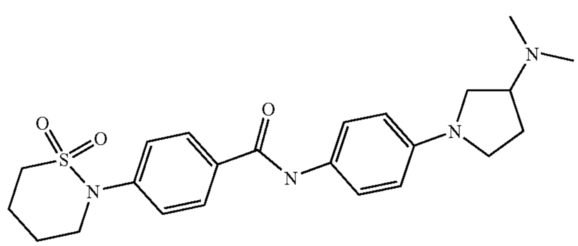 | C23H30N4O3S | 442.20 | 443 |
| 888 | 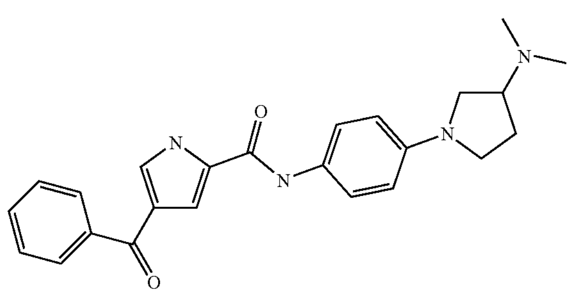 | C24H26N4O2 | 402.21 | 403 |

TABLE 7-continued

| Ex. No. | Structure | Molecular formula | Monoisotopic molecular wt. | M + H+ |
|---|---|---|---|---|
| 889 | 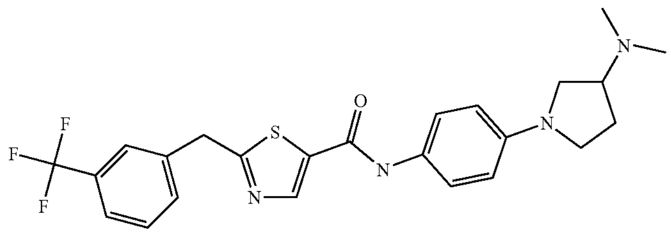 | C24H25F3N4OS | 474.17 | 475 |
| 890 | 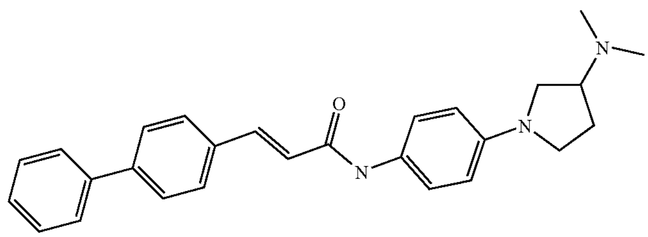 | C27H29N3O | 411.23 | 412 |
| 891 | 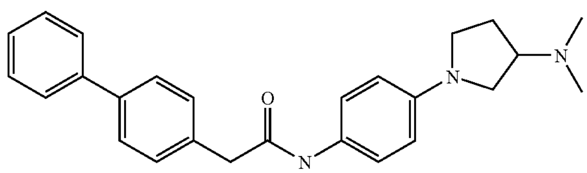 | C26H29N3O | 399.23 | 400 |
| 892 | 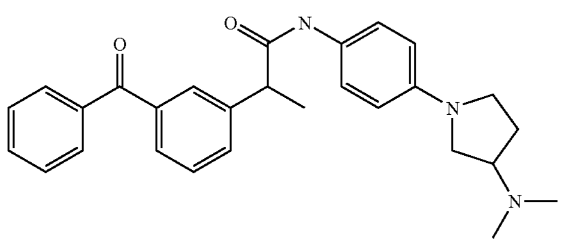 | C28H31N3O2 | 441.24 | 442 |
| 893 | 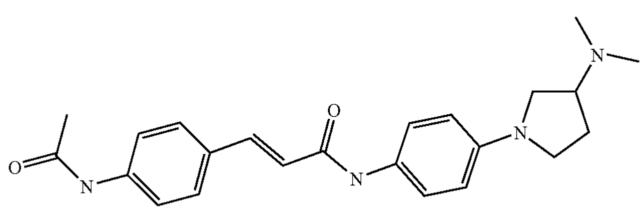 | C23H28N4O2 | 392.22 | 393 |
| 894 | 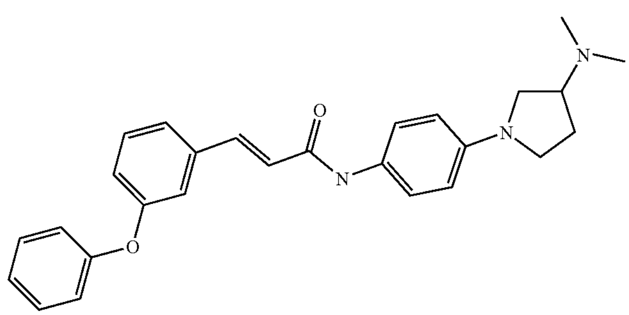 | C27H29N3O2 | 427.23 | 428 |

TABLE 7-continued

| Ex. No. | Structure | Molecular formula | Monoisotopic molecular wt. | M + H⁺ |
|---|---|---|---|---|
| 895 | 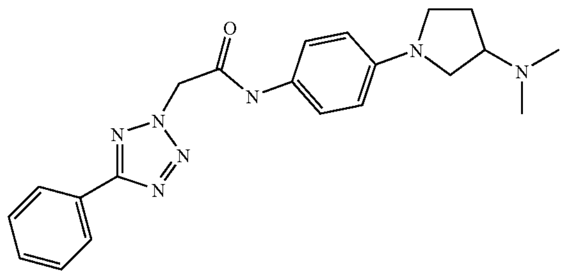 | C21H25N7O | 391.21 | 392 |
| 896 | 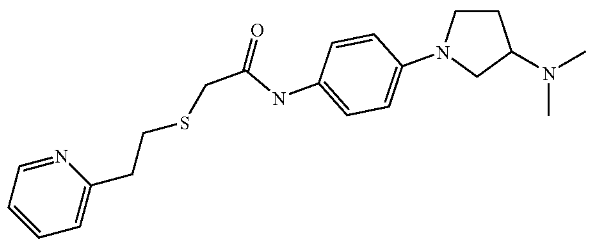 | C21H28N4OS | 384.20 | 385 |
| 897 | 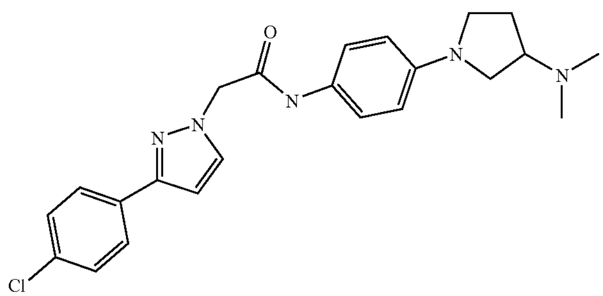 | C23H26ClN5O | 423.18 | 424 |
| 898 | 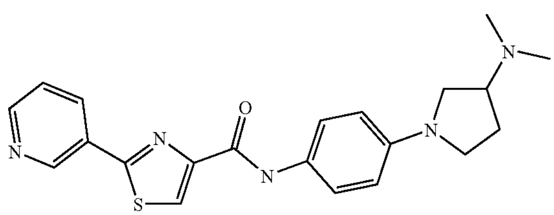 | C21H23N5OS | 393.16 | 394 |
| 899 | 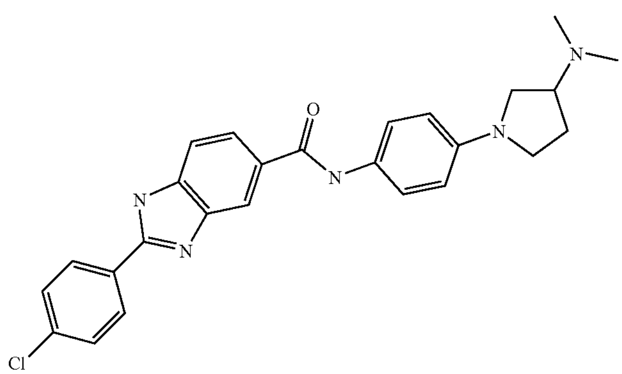 | C26H26ClN5O | 459.18 | 460 |

TABLE 7-continued

| Ex. No. | Structure | Molecular formula | Monoisotopic molecular wt. | M + H+ |
|---|---|---|---|---|
| 900 | 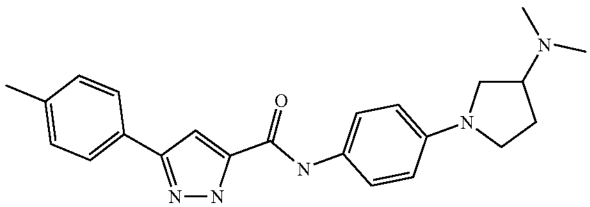 | C23H27N5O | 389.22 | 390 |
| 901 | 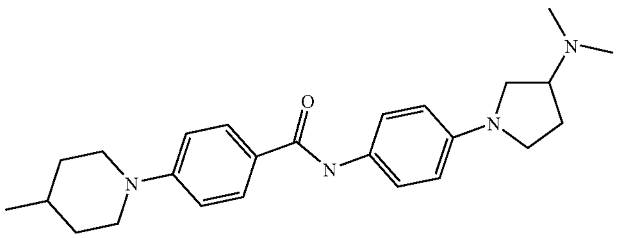 | C25H34N4O | 406.27 | 407 |
| 902 | 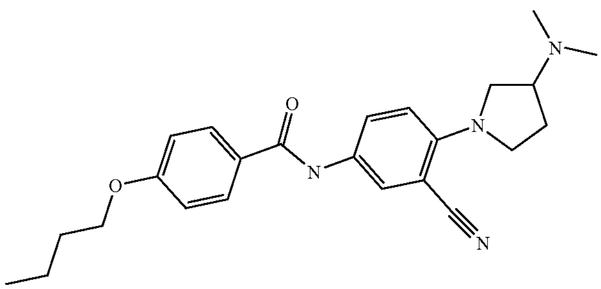 | C24H30N4O2 | 406.24 | 407 |
| 903 | 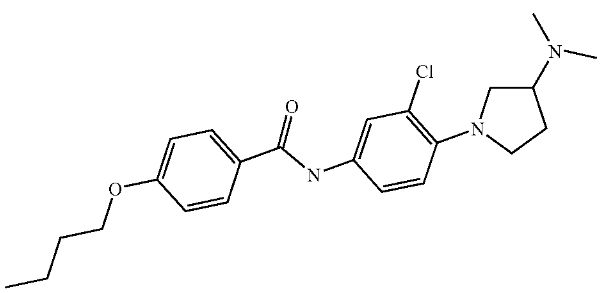 | C23H30ClN3O2 | 415.20 | 416 |
| 904 | 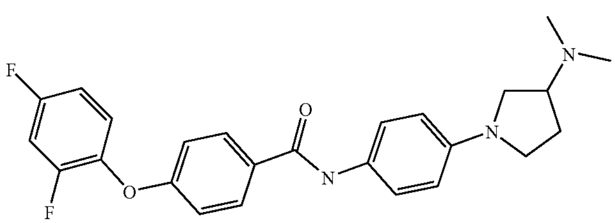 | C25H25F2N3O2 | 437.19 | 438 |
| 905 | 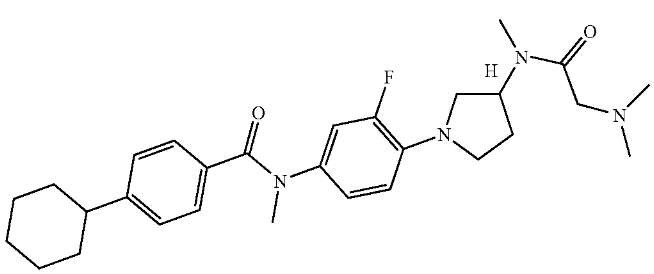 | C29H39FN4O2 | 494.31 | 495 |

TABLE 7-continued

| Ex. No. | Structure | Molecular formula | Monoisotopic molecular wt. | M + H+ |
|---|---|---|---|---|
| 906 | 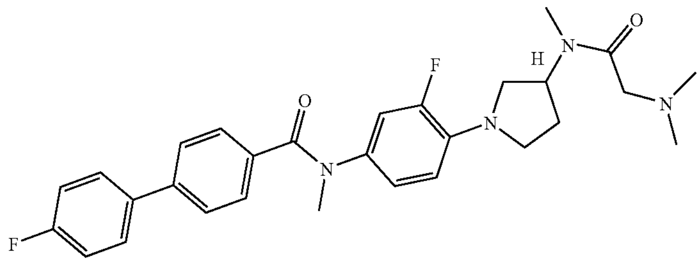 | C29H32F2N4O2 | 506.25 | 507 |
| 907 | 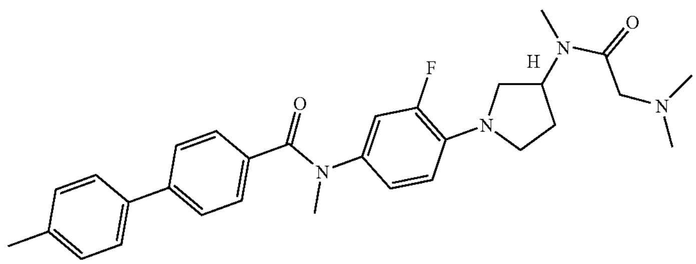 | C30H35FN4O2 | 502.27 | 503 |
| 908 | 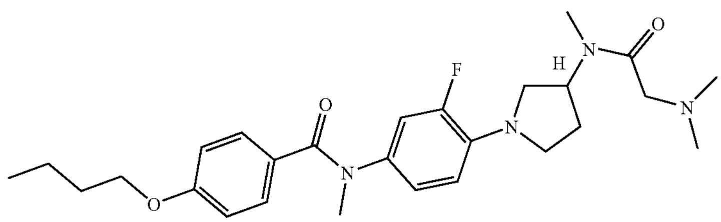 | C27H37FN4O3 | 484.29 | 485 |
| 909 | 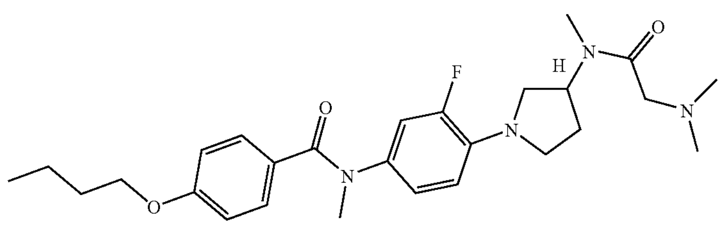 | C27H37FN4O3 | 484.29 | 485 |
| 910 | 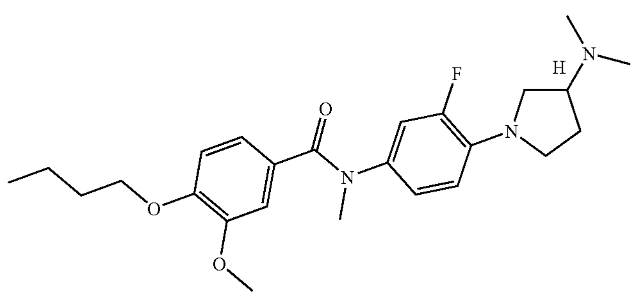 | C25H34FN3O3 | 443.26 | 444 |
| 911 | 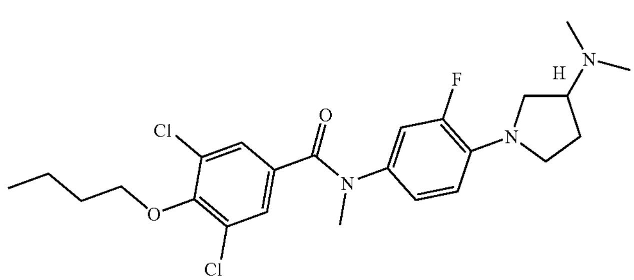 | C24H30Cl2FN3O2 | 481.17 | 482 |

TABLE 7-continued

| Ex. No. | Structure | Molecular formula | Monoisotopic molecular wt. | M + H⁺ |
|---|---|---|---|---|
| 912 | 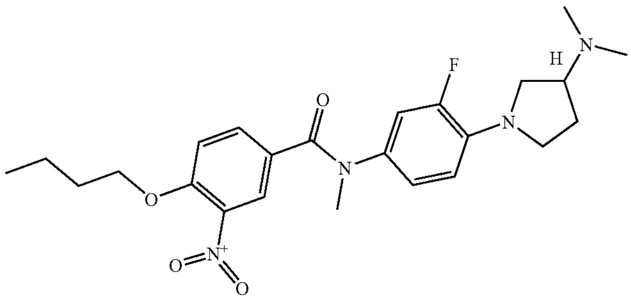 | C24H31FN4O4 | 458.23 | 459 |
| 913 | 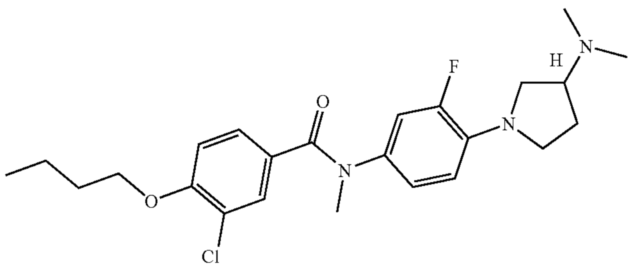 | C24H31ClFN3O2 | 447.21 | 448 |
| 914 | 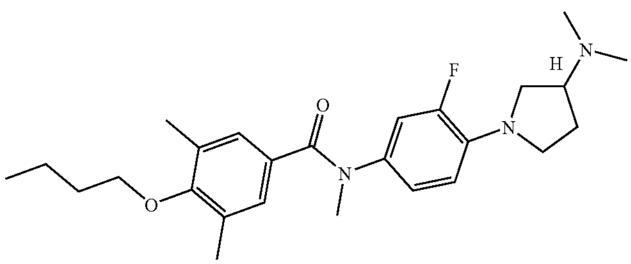 | C26H36FN3O2 | 441.28 | 442 |
| 915 | 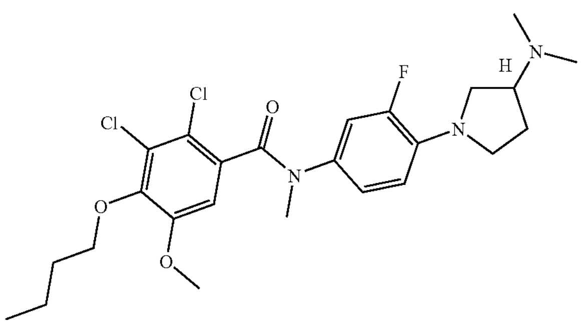 | C25H32Cl2FN3O3 | 511.18 | 512 |
| 916 | 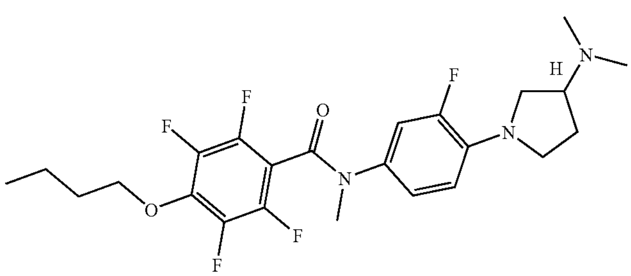 | C24H28F5N3O2 | 485.21 | 486 |

TABLE 7-continued

| Ex. No. | Structure | Molecular formula | Monoisotopic molecular wt. | M + H+ |
|---|---|---|---|---|
| 917 | 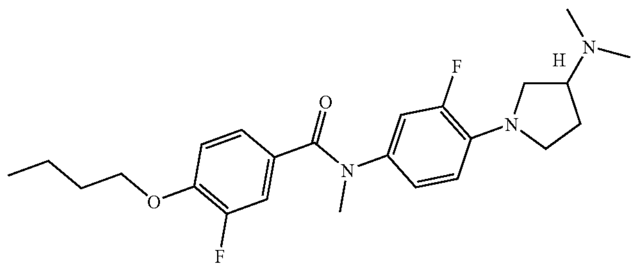 | C24H31F2N3O2 | 431.24 | 432 |
| 918 | 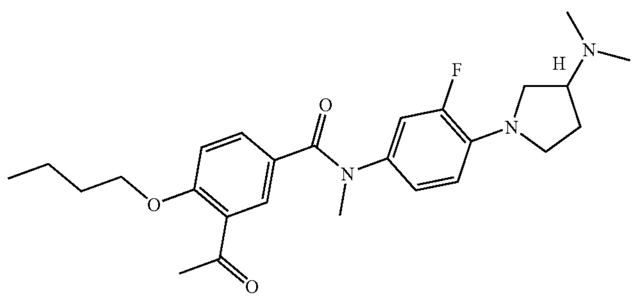 | C26H34FN3O3 | 455.26 | 456 |
| 919 | 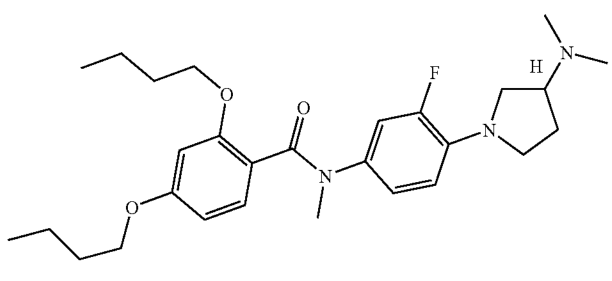 | C28H40FN3O3 | 485.30 | 486 |
| 920 | 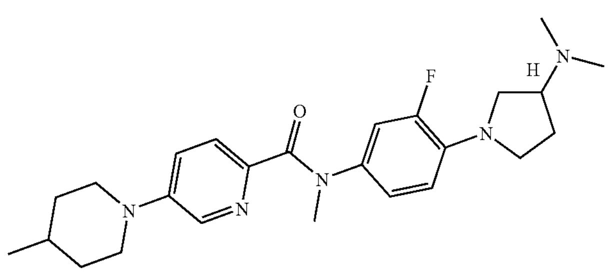 | C25H34FN5O | 439.27 | 440 |
| 921 | 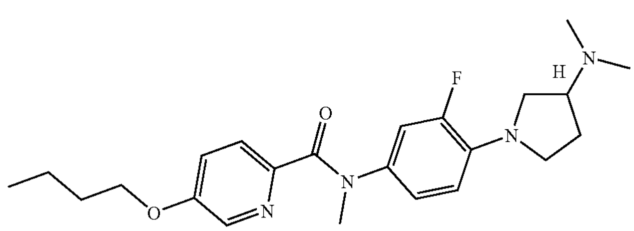 | C23H31FN4O2 | 414.24 | 415 |

TABLE 7-continued

| Ex. No. | Structure | Molecular formula | Monoisotopic molecular wt. | M + H⁺ |
|---|---|---|---|---|
| 922 | 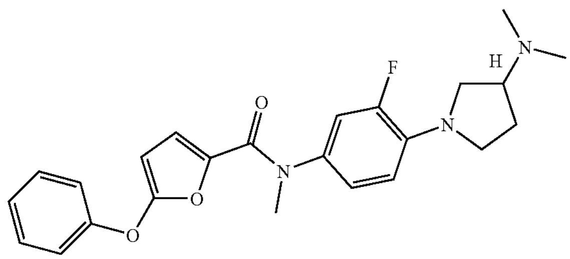 | C24H26FN3O3 | 423.20 | 424 |
| 923 | 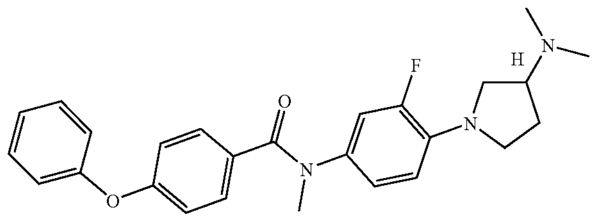 | C26H28FN3O2 | 433.22 | 434 |
| 924 | 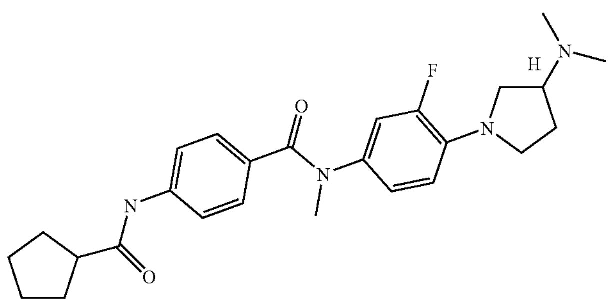 | C26H33FN4O2 | 452.26 | 453 |
| 925 | 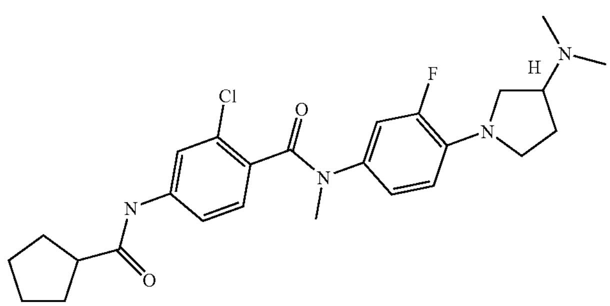 | C26H32ClFN4O2 | 486.22 | 487 |
| 926 | 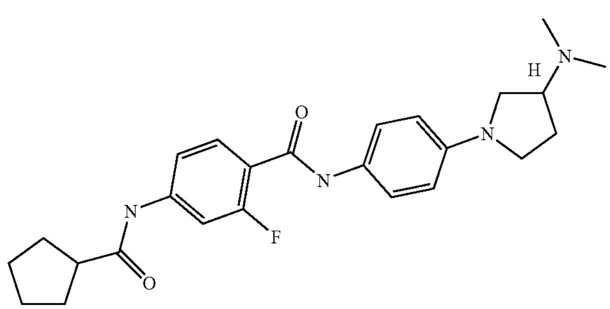 | C25H31FN4O2 | 438.24 | 439 |

TABLE 7-continued
| Ex. No. | Structure | Molecular formula | Monoisotopic molecular wt. | M + H+ |
|---|---|---|---|---|
| 927 | 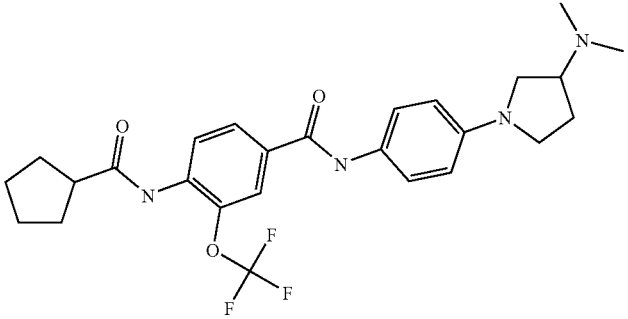 | C26H31F3N4O3 | 504.23 | 505 |
| 928 | 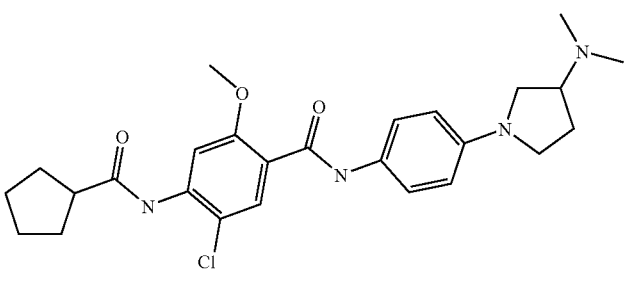 | C26H33ClN4O3 | 484.22 | 485 |
| 929 | 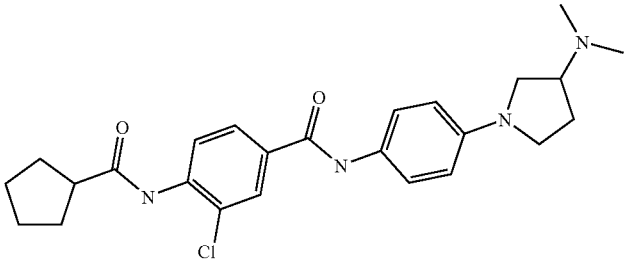 | C25H31ClN4O2 | 454.21 | 455 |
| 930 | 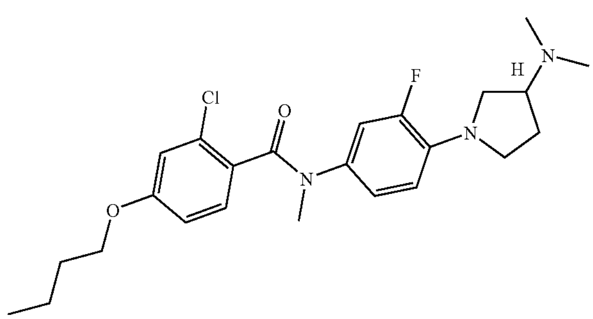 | C24H31ClFN3O2 | 447.21 | 448 |
| 931 | 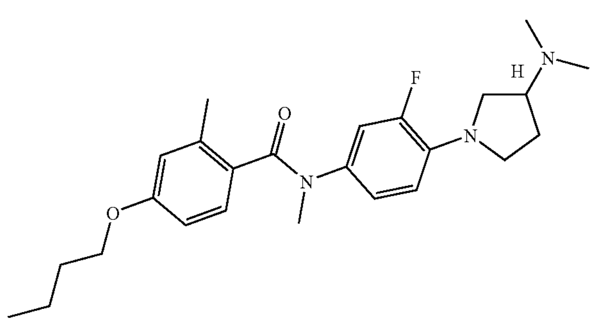 | C25H34FN3O2 | 427.26 | 428 |

TABLE 7-continued

| Ex. No. | Structure | Molecular formula | Monoisotopic molecular wt. | M + H+ |
|---|---|---|---|---|
| 932 | 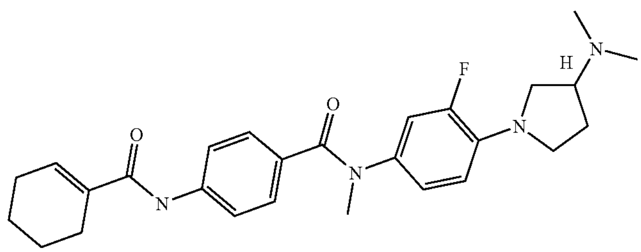 | C27H33FN4O2 | 464.26 | 465 |
| 933 | 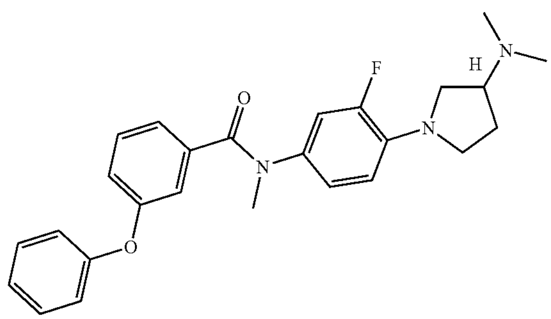 | C26H28FN3O2 | 433.22 | 434 |
| 934 | 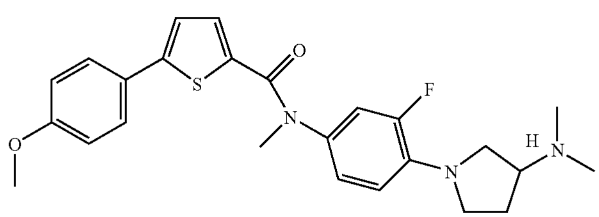 | C25H28FN3O2S | 453.19 | 454 |
| 935 | 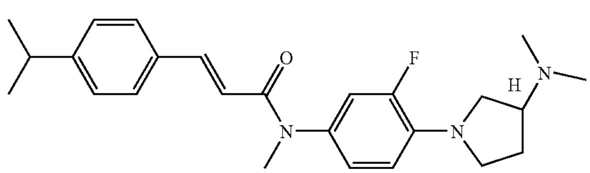 | C25H32FN3O | 409.25 | 410 |
| 936 | 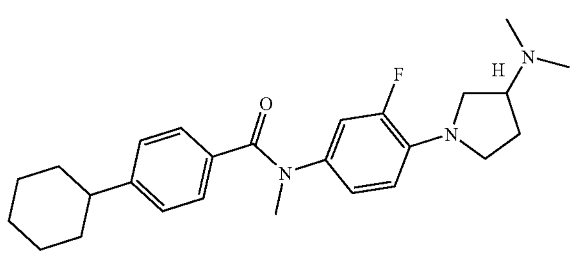 | C26H34FN3O | 423.27 | 424 |
| 937 | 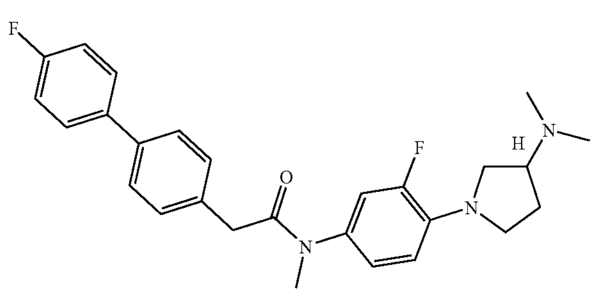 | C27H29F2N3O | 449.23 | 450 |

TABLE 7-continued

| Ex. No. | Structure | Molecular formula | Monoisotopic molecular wt. | M + H⁺ |
|---|---|---|---|---|
| 938 | 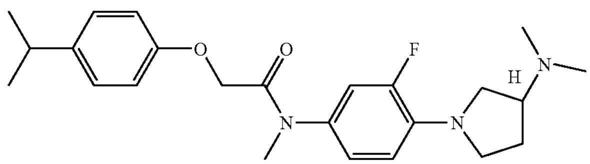 | C24H32FN3O2 | 413.25 | 414 |
| 939 | 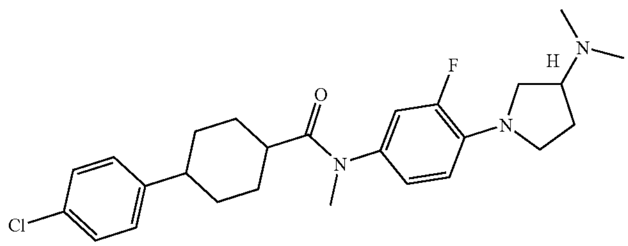 | C26H33ClFN3O | 457.23 | 458 |
| 940 | 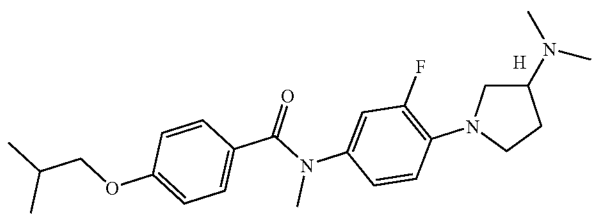 | C24H32FN3O2 | 413.25 | 414 |
| 941 | 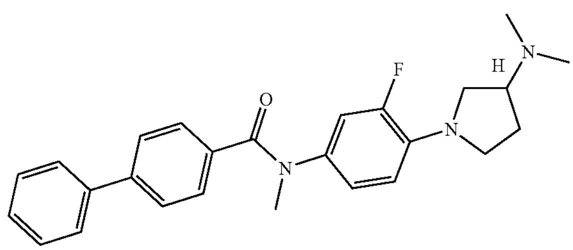 | C26H28FN3O | 417.22 | 418 |
| 942 | 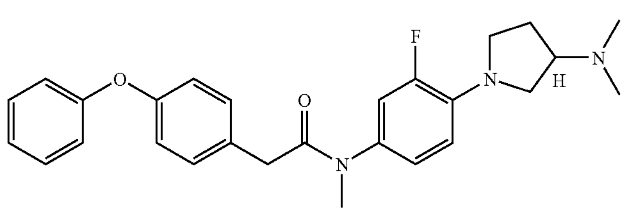 | C27H30FN3O2 | 447.23 | 448 |
| 943 | 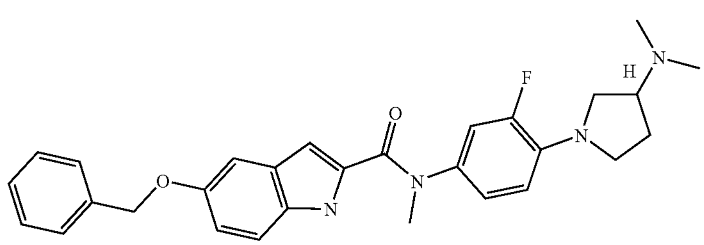 | C29H31FN4O2 | 486.24 | 487 |

TABLE 7-continued

| Ex. No. | Structure | Molecular formula | Monoisotopic molecular wt. | M + H⁺ |
|---|---|---|---|---|
| 944 | 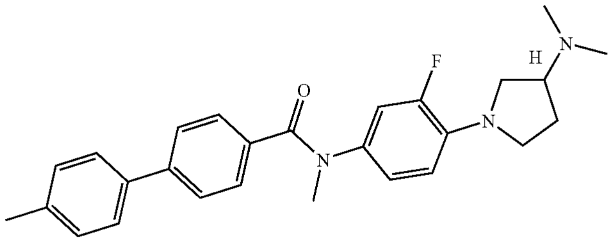 | C27H30FN3O | 431.24 | 432 |
| 945 | 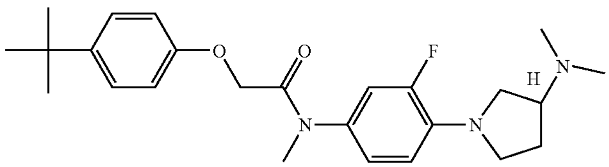 | C25H34FN3O2 | 427.26 | 428 |
| 946 | 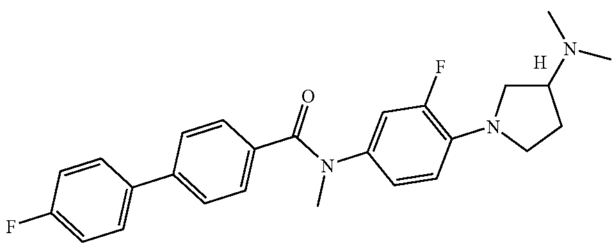 | C26H27F2N3O | 435.21 | 436 |
| 947 | 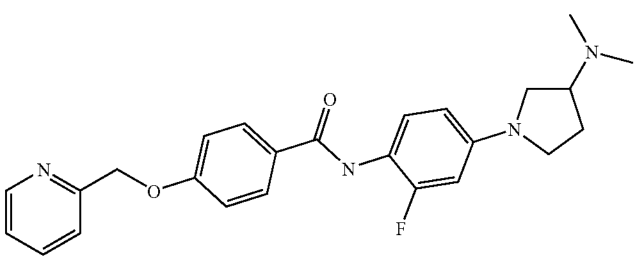 | C25H27FN4O2 | 434.52 | 435 |
| 948 | 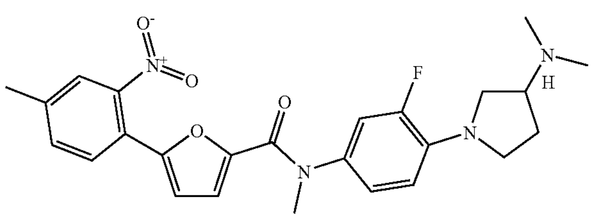 | C25H27FN4O4 | 466.20 | 467 |
| 949 | 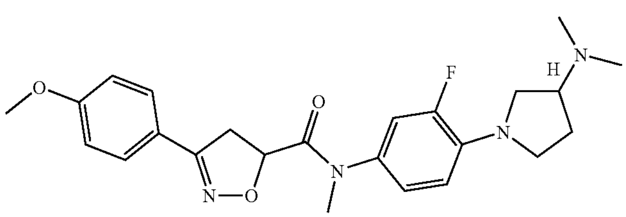 | C24H29FN4O3 | 440.22 | 441 |
| 950 | 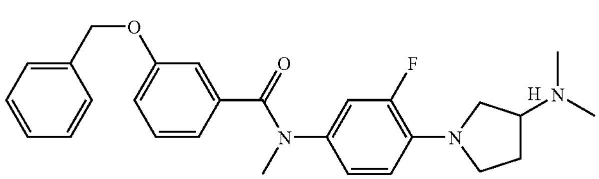 | C27H30FN3O2 | 447.23 | 448 |

TABLE 7-continued

| Ex. No. | Structure | Molecular formula | Monoisotopic molecular wt. | M + H+ |
|---|---|---|---|---|
| 951 | 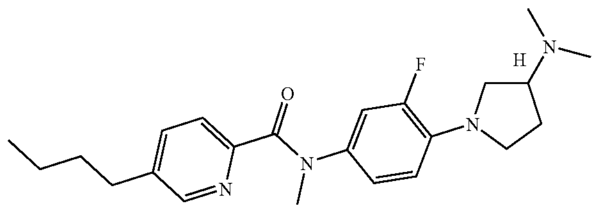 | C23H31FN4O | 398.25 | 399 |
| 952 | 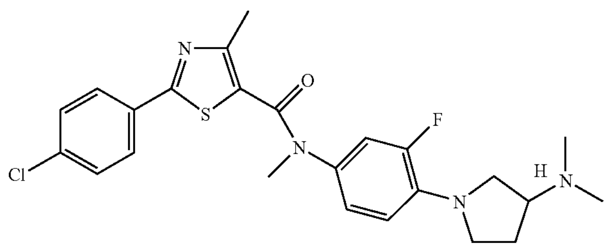 | C24H26ClFN4OS | 472.15 | 473 |
| 953 | 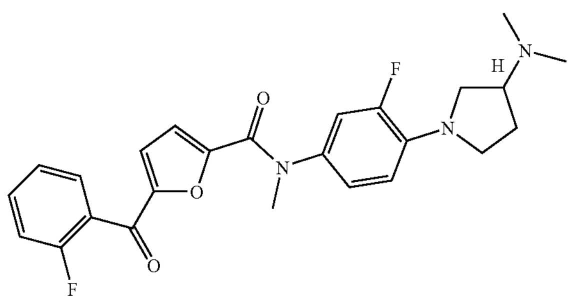 | C25H25F2N3O3 | 453.19 | 454 |
| 954 | 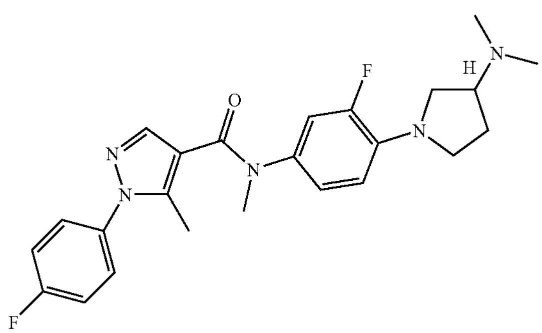 | C24H27F2N5O | 439.22 | 440 |
| 955 | 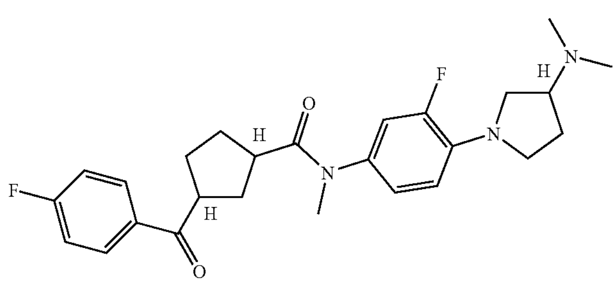 | C26H31F2N3O2 | 455.24 | 456 |

TABLE 7-continued

| Ex. No. | Structure | Molecular formula | Monoisotopic molecular wt. | M + H+ |
|---|---|---|---|---|
| 956 | 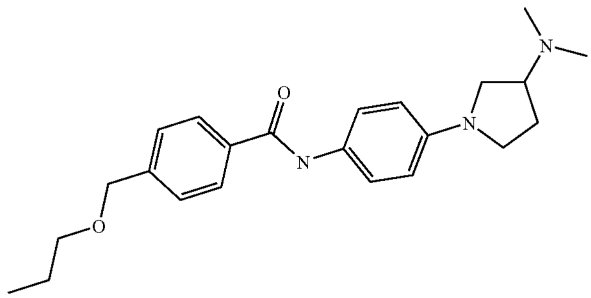 | C23H31N3O2 | 381.24 | 382 |
| 957 | 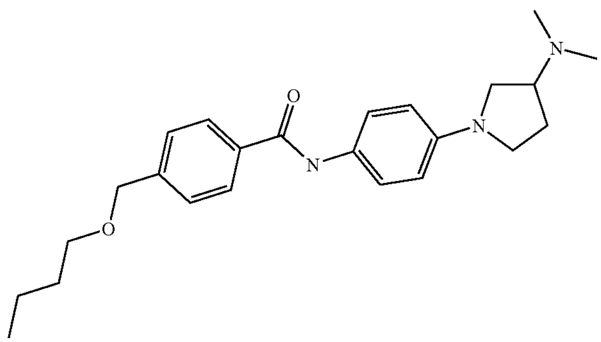 | C24H33N3O2 | 395.26 | 396 |
| 958 | 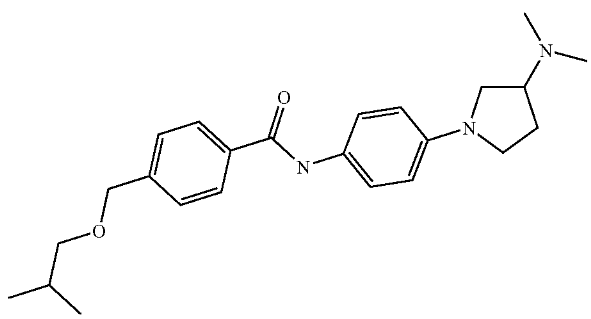 | C24H33N3O2 | 395.26 | 396 |
| 959 | 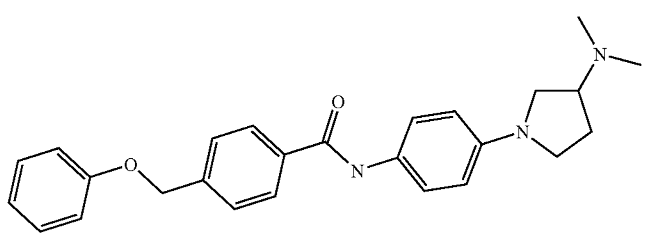 | C26H29N3O2 | 415.23 | 416 |
| 960 | 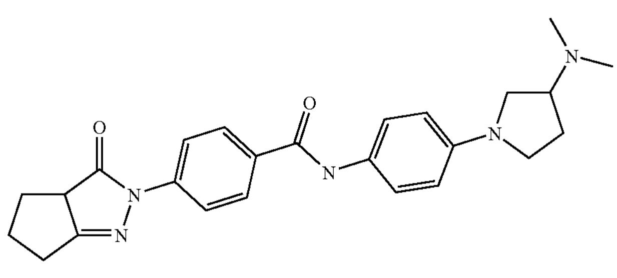 | C25H29N5O2 | 431.23 | 432 |

TABLE 7-continued

| Ex. No. | Structure | Molecular formula | Monoisotopic molecular wt. | M + H+ |
|---|---|---|---|---|
| 961 | 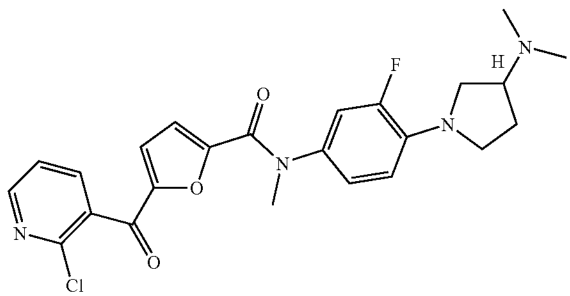 | C24H24ClFN4O3 | 470.15 | 471 |
| 962 | 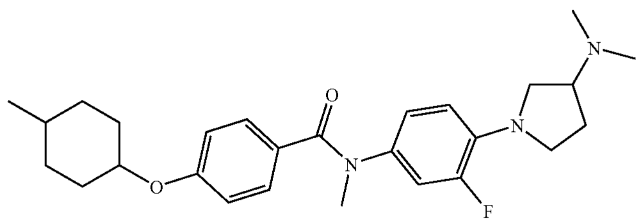 | C27H36FN3O2 | 453.61 | 454 |
| 963 | 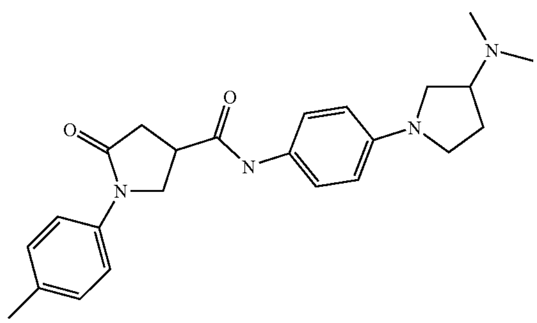 | C24H30N4O2 | 406.24 | 407 |
| 964 | 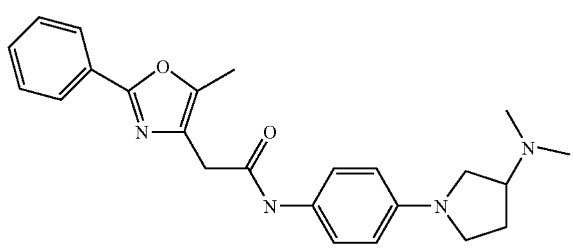 | C24H28N4O2 | 404.22 | 405 |
| 965 | 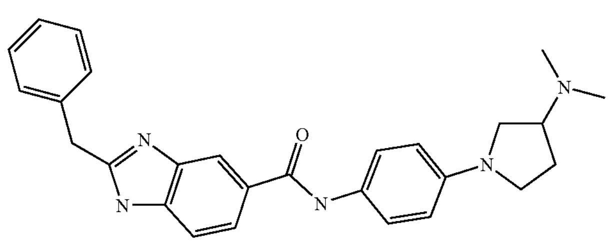 | C27H29N5O | 439.24 | 440 |

TABLE 7-continued

| Ex. No. | Structure | Molecular formula | Monoisotopic molecular wt. | M + H+ |
|---|---|---|---|---|
| 966 | 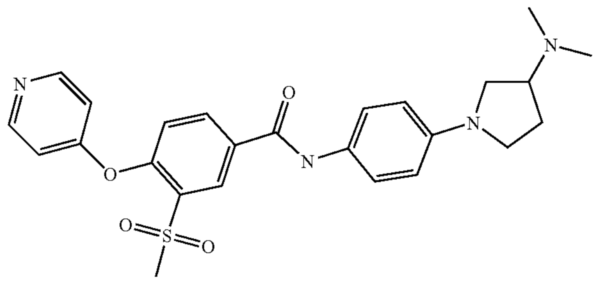 | C25H28N4O4S | 480.18 | 481 |
| 967 | 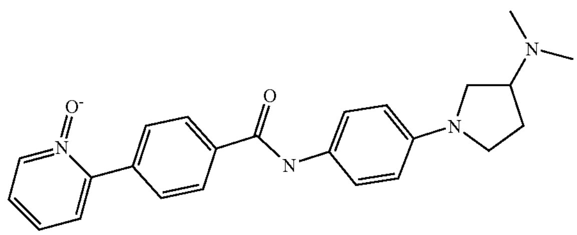 | C24H26N4O2 | 402.21 | 403 |
| 968 | 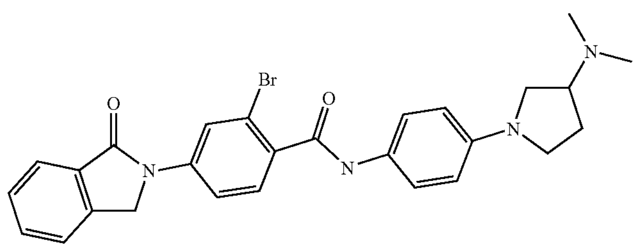 | C27H27BrN4O2 | 518.13 | 519 |
| 969 | 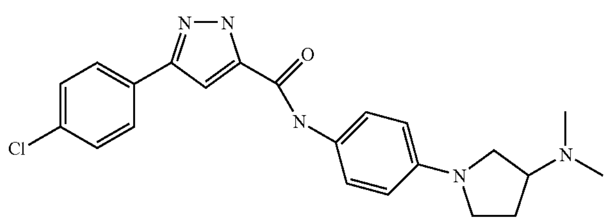 | C22H24ClN5O | 409.17 | 410 |
| 970 | 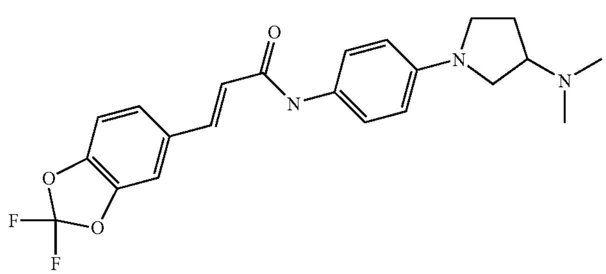 | C22H23F2N3O3 | 415.17 | 416 |
| 971 | 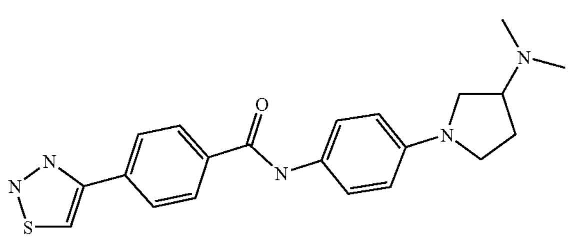 | C21H23N5OS | 393.16 | 394 |

TABLE 7-continued

| Ex. No. | Structure | Molecular formula | Monoisotopic molecular wt. | M + H⁺ |
|---|---|---|---|---|
| 972 | 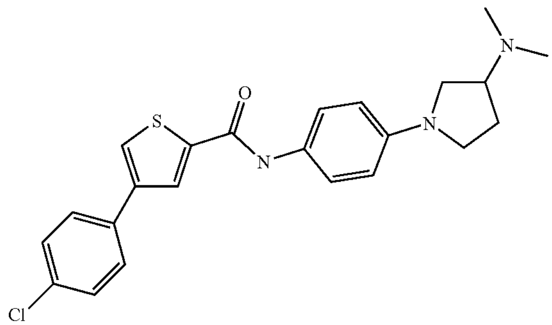 | C23H24ClN3OS | 425.13 | 426 |
| 973 | 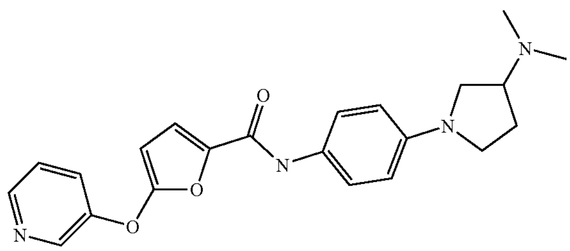 | C22H24N4O3 | 392.18 | 393 |
| 974 | 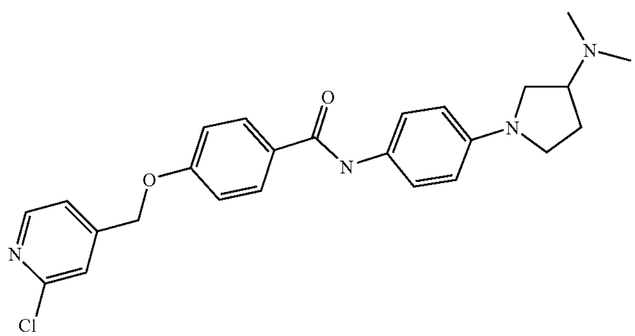 | C25H27ClN4O2 | 450.18 | 451 |
| 975 | 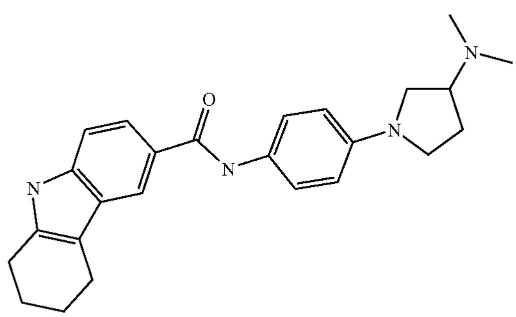 | C25H30N4O | 402.24 | 403 |
| 976 | 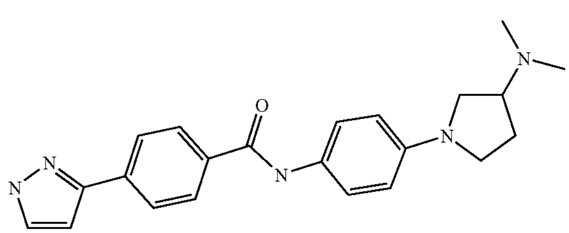 | C22H25N5O | 375.21 | 376 |

TABLE 7-continued

| Ex. No. | Structure | Molecular formula | Monoisotopic molecular wt. | M + H⁺ |
|---|---|---|---|---|
| 977 | 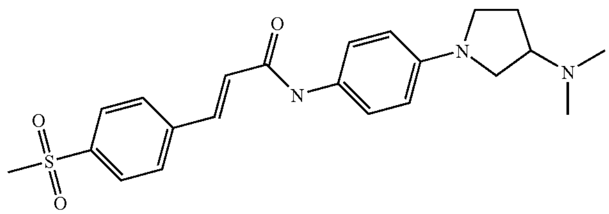 | C22H27N3O3S | 413.18 | 414 |
| 978 | 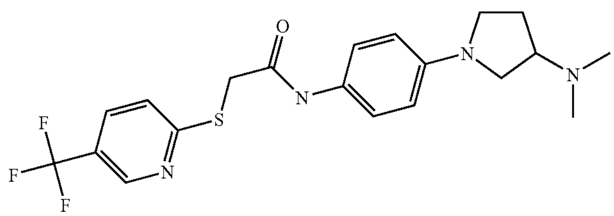 | C20H23F3N4OS | 424.15 | 425 |
| 979 | 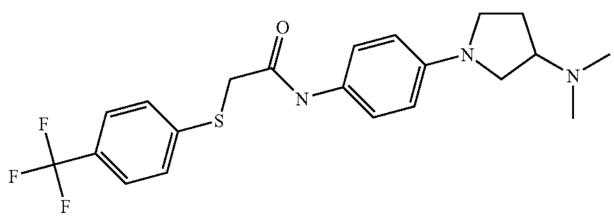 | C21H24F3N3OS | 423.16 | 424 |
| 980 | 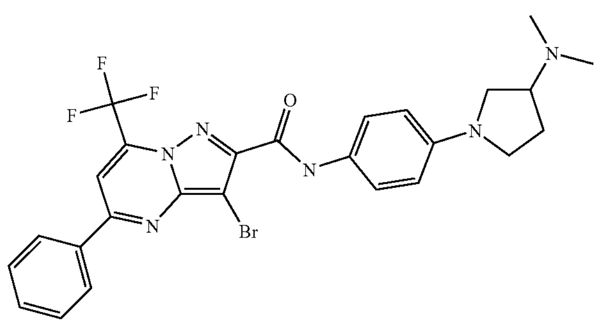 | C26H24BrF3N6O | 572.11 | 573 |
| 981 | 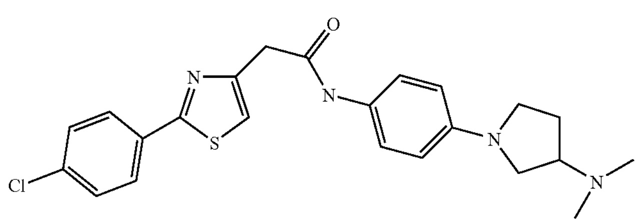 | C23H25ClN4OS | 440.14 | 441 |
| 982 | 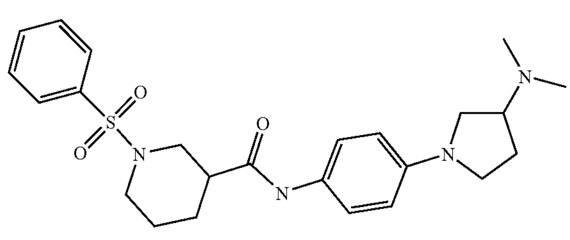 | C24H32N4O3S | 456.22 | 457 |

TABLE 7-continued

| Ex. No. | Structure | Molecular formula | Monoisotopic molecular wt. | M + H+ |
|---|---|---|---|---|
| 983 | 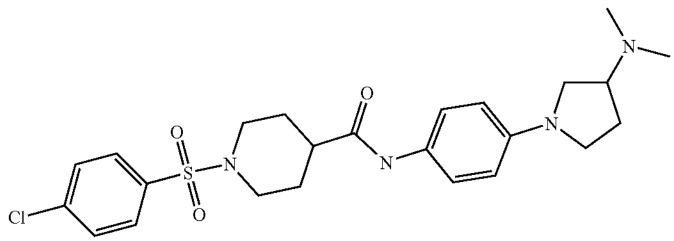 | C24H31ClN4O3S | 490.18 | 491 |
| 984 | 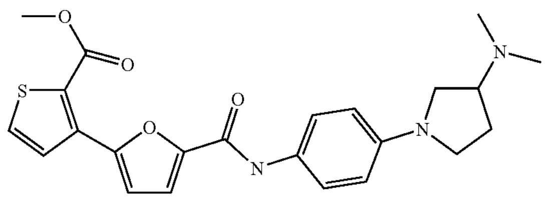 | C23H25N3O4S | 439.16 | 440 |
| 985 | 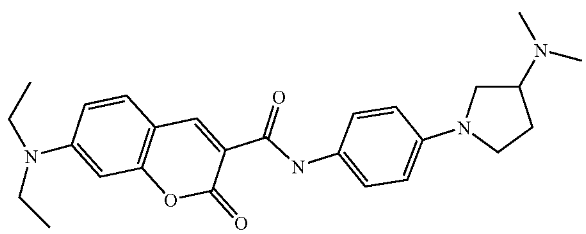 | C26H32N4O3 | 448.25 | 449 |
| 986 | 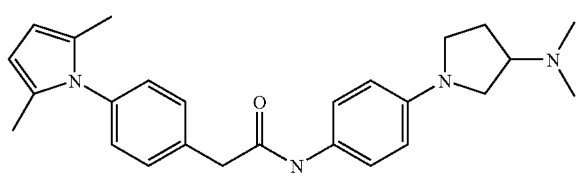 | C26H32N4O | 416.26 | 417 |
| 987 | 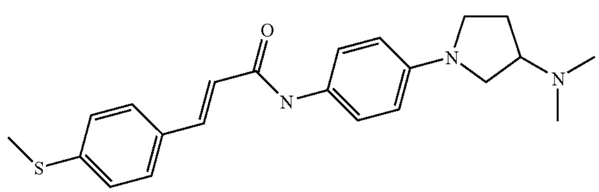 | C22H27N3OS | 381.19 | 382 |
| 988 | 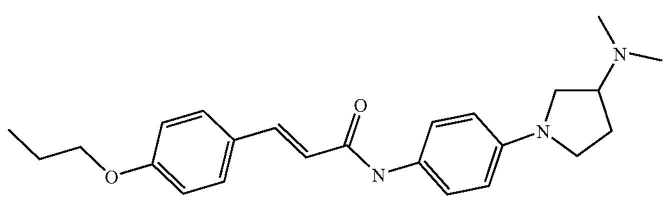 | C24H31N3O2 | 393.24 | 394 |
| 989 | 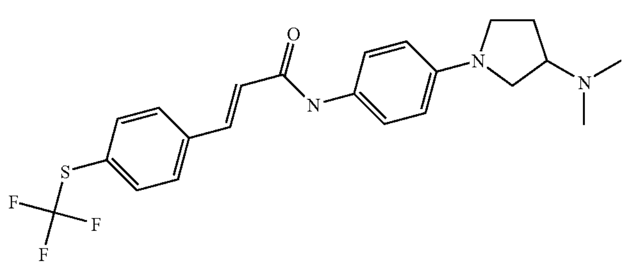 | C22H24F3N3OS | 435.16 | 436 |

TABLE 7-continued

| Ex. No. | Structure | Molecular formula | Monoisotopic molecular wt. | M + H⁺ |
|---|---|---|---|---|
| 990 | 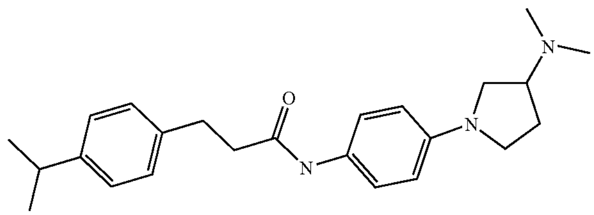 | C24H33N3O | 379.26 | 380 |
| 991 | 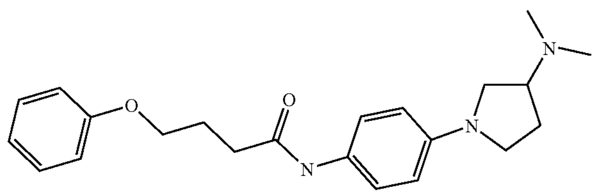 | C22H29N3O2 | 367.23 | 368 |
| 992 | 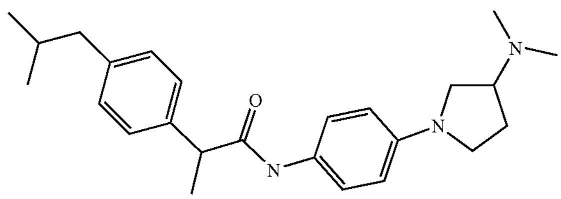 | C25H35N3O | 393.28 | 394 |
| 993 | 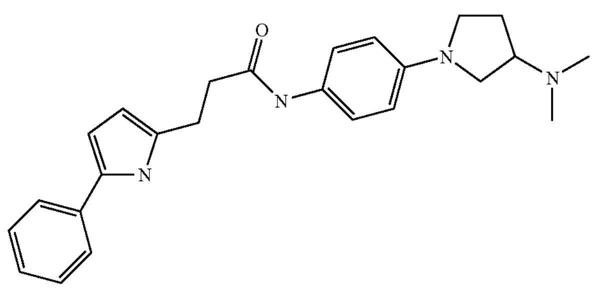 | C25H30N4O | 402.24 | 403 |
| 994 | 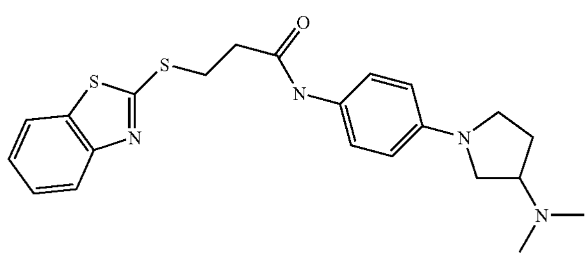 | C22H26N4OS2 | 426.15 | 427 |
| 995 | 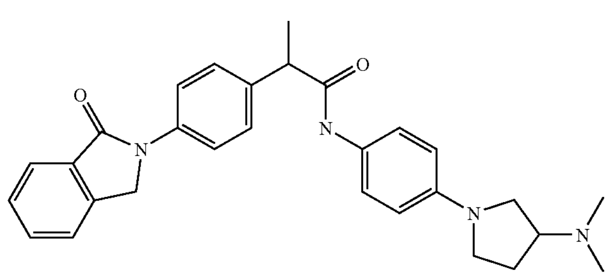 | C29H32N4O2 | 468.25 | 469 |

TABLE 7-continued

| Ex. No. | Structure | Molecular formula | Monoisotopic molecular wt. | M + H⁺ |
|---|---|---|---|---|
| 996 | 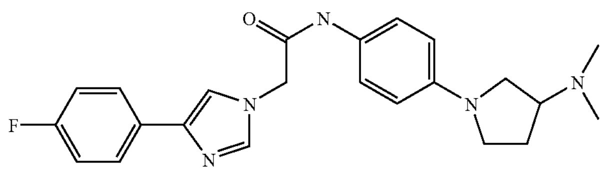 | C23H26FN5O | 407.21 | 408 |
| 997 | 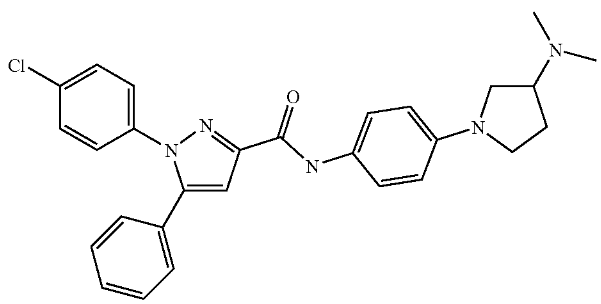 | C28H28ClN5O | 485.20 | 486 |
| 998 | 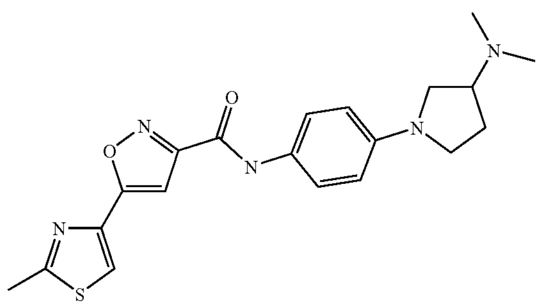 | C20H23N5O2S | 397.16 | 398 |
| 999 | 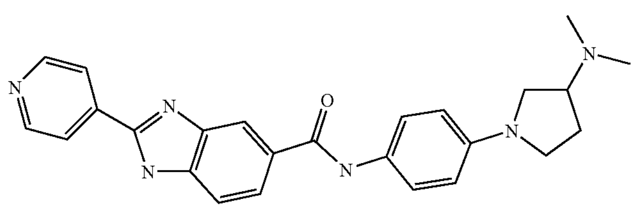 | C25H26N6O | 426.22 | 427 |
| 1000 | 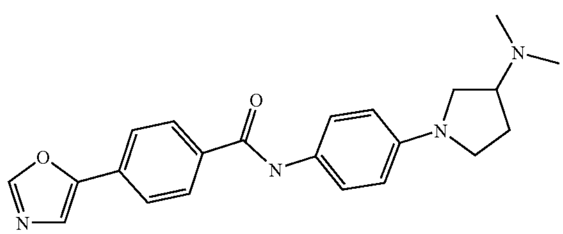 | C22H24N4O2 | 376.19 | 377 |
| 1001 | 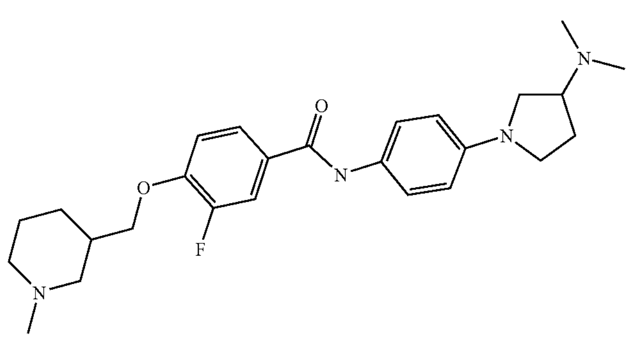 | C26H35FN4O2 | 454.27 | 455 |

TABLE 7-continued

| Ex. No. | Structure | Molecular formula | Monoisotopic molecular wt. | M + H⁺ |
|---|---|---|---|---|
| 1002 | 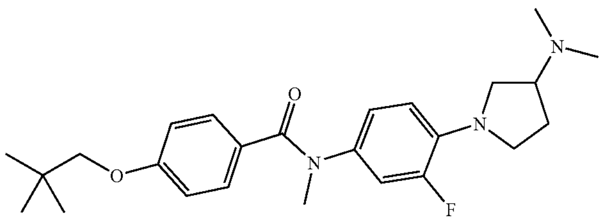 | C25H34FN3O2 | 427.57 | 428 |
| 1003 | 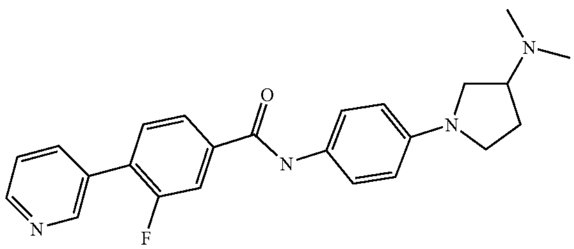 | C24H25FN4O | 404.20 | 405 |
| 1004 | 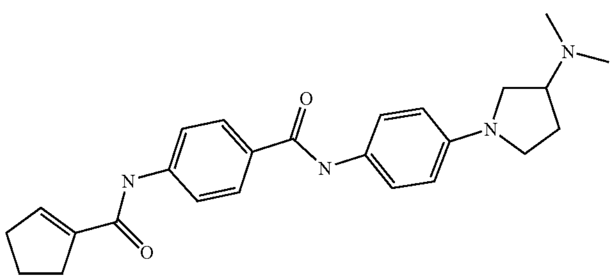 | C25H30N4O2 | 418.24 | 419 |
| 1005 | 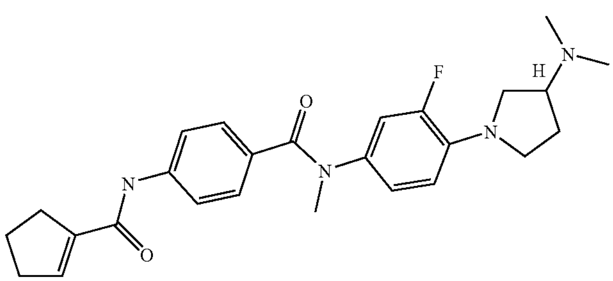 | C26H31FN4O2 | 450.24 | 451 |
| 1006 | 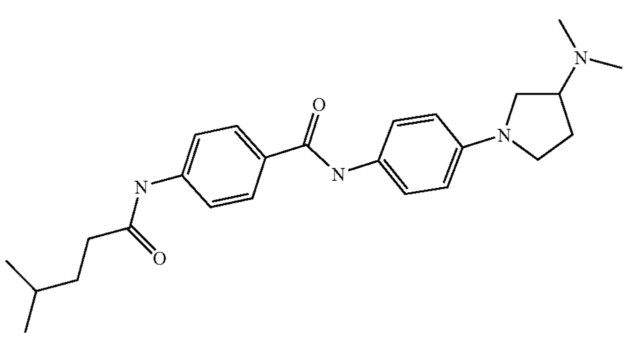 | C25H34N4O2 | 422.27 | 423 |

TABLE 7-continued
| Ex. No. | Structure | Molecular formula | Monoisotopic molecular wt. | M + H⁺ |
|---|---|---|---|---|
| 1007 | 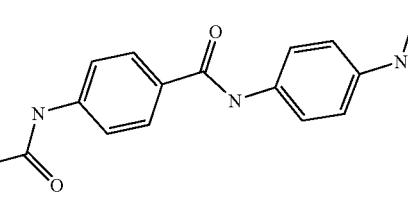 | C24H30N4O2 | 406.24 | 407 |
| 1008 | 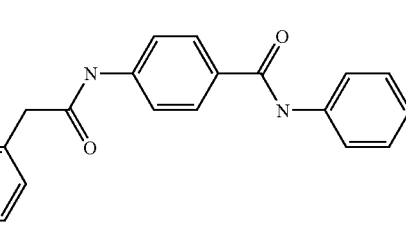 | C27H30N4O2 | 442.24 | 443 |
| 1009 | 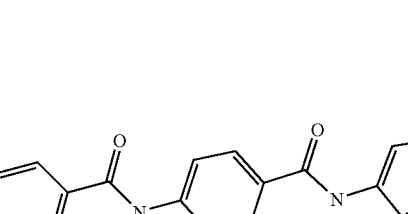 | C27H29FN4O2 | 460.23 | 461 |
| 1010 | 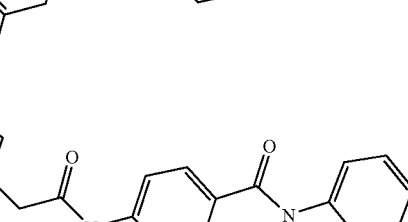 | C26H34N4O2 | 434.27 | 435 |
| 1011 | 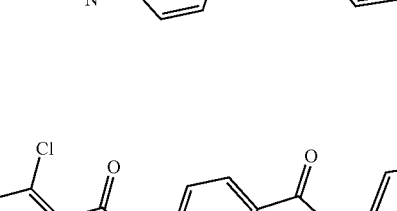 | C26H26ClFN4O2 | 480.17 | 481 |
| 1012 | 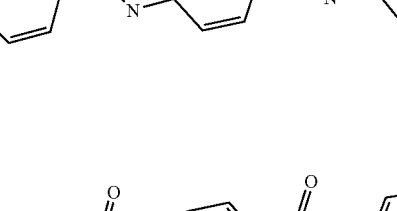 | C26H27FN4O2 | 446.21 | 447 |

TABLE 7-continued

| Ex. No. | Structure | Molecular formula | Monoisotopic molecular wt. | M + H+ |
|---|---|---|---|---|
| 1013 | 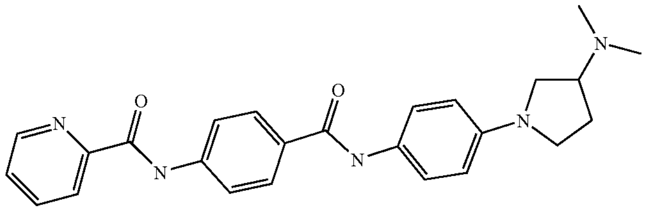 | C25H27N5O2 | 429.22 | 430 |
| 1014 | 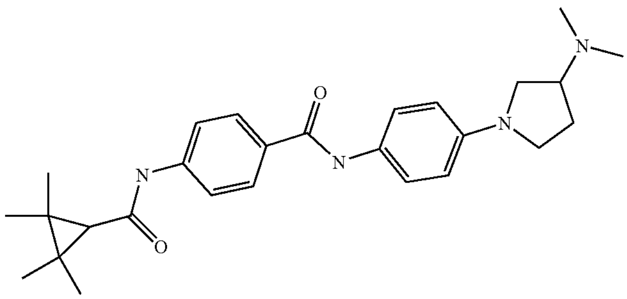 | C27H36N4O2 | 448.28 | 449 |
| 1015 | 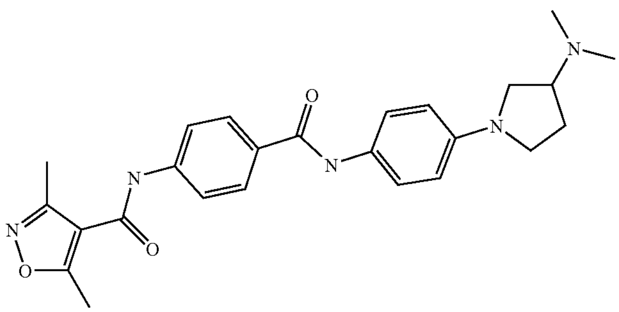 | C25H29N5O3 | 447.23 | 448 |
| 1016 | 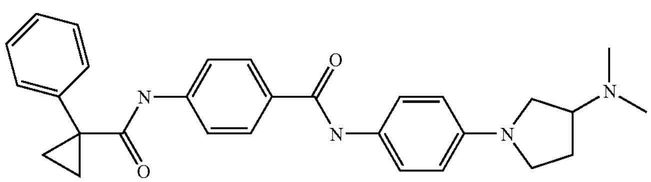 | C29H32N4O2 | 468.25 | 469 |
| 1017 | 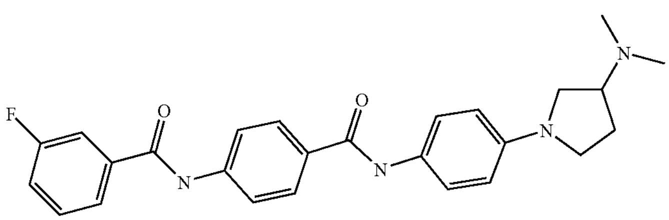 | C26H27FN4O2 | 446.21 | 447 |
| 1018 | 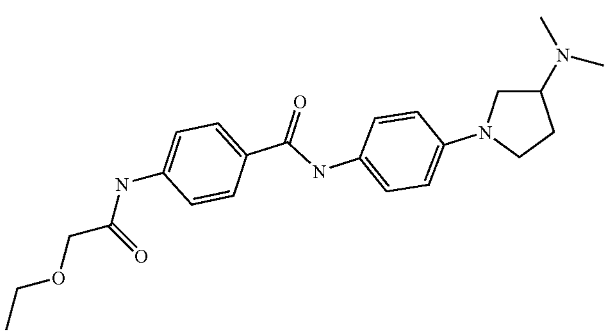 | C23H30N4O3 | 410.23 | 411 |

TABLE 7-continued
| Ex. No. | Structure | Molecular formula | Monoisotopic molecular wt. | M + H+ |
|---|---|---|---|---|
| 1019 | 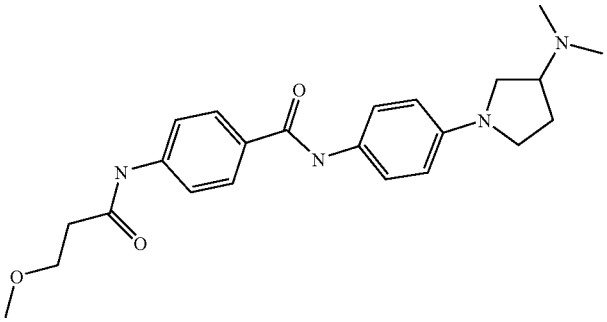 | C23H30N4O3 | 410.23 | 411 |
| 1020 | 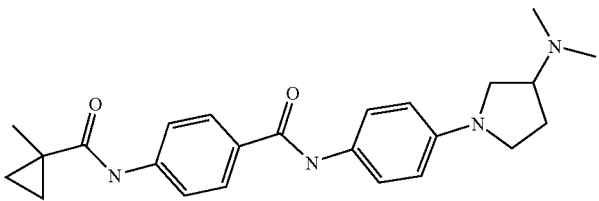 | C24H30N4O2 | 406.24 | 407 |
| 1021 | 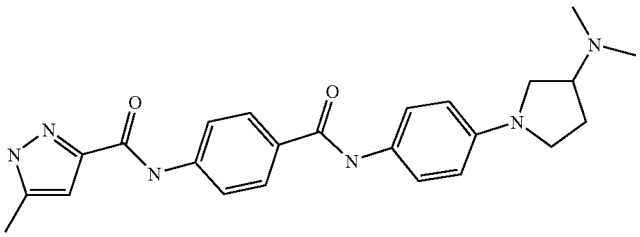 | C24H28N6O2 | 432.23 | 433 |
| 1022 | 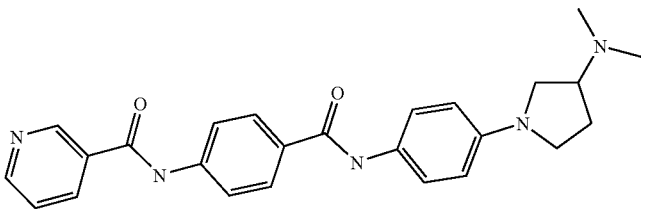 | C25H27N5O2 | 429.22 | 430 |
| 1023 | 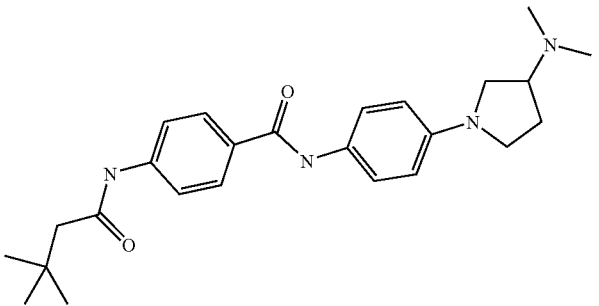 | C25H34N4O2 | 422.27 | 423 |

TABLE 7-continued
| Ex. No. | Structure | Molecular formula | Monoisotopic molecular wt. | M + H⁺ |
|---|---|---|---|---|
| 1024 | 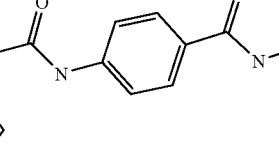 | C25H28N4O2S | 448.19 | 449 |
| 1025 | 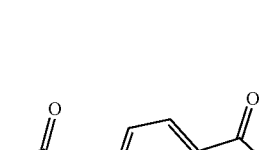 | C25H29N5O2 | 431.23 | 432 |
| 1026 | 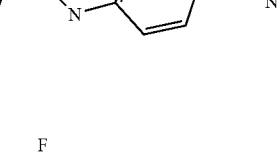 | C26H26F2N4O2 | 464.20 | 465 |
| 1027 | 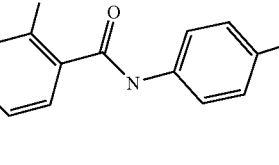 | C24H27N5O2 | 417.22 | 418 |
| 1028 | 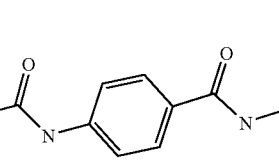 | C29H38N4O2 | 474.30 | 475 |
| 1029 | 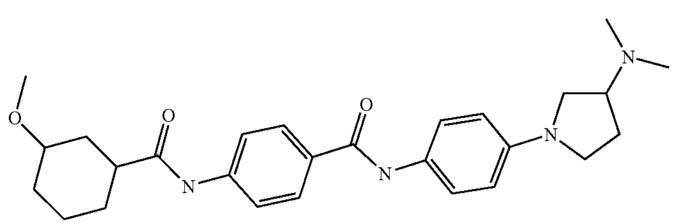 | C27H36N4O3 | 464.28 | 465 |

TABLE 7-continued

| Ex. No. | Structure | Molecular formula | Monoisotopic molecular wt. | M + H+ |
|---|---|---|---|---|
| 1030 | 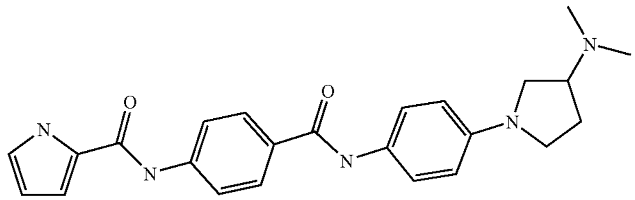 | C24H27N5O2 | 417.22 | 418 |
| 1031 | 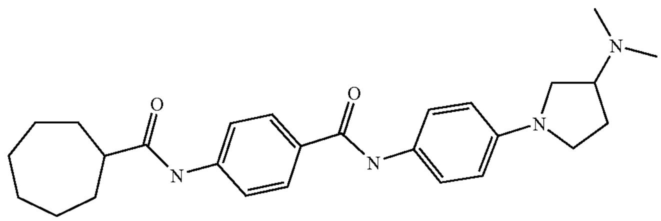 | C27H36N4O2 | 448.28 | 449 |
| 1032 | 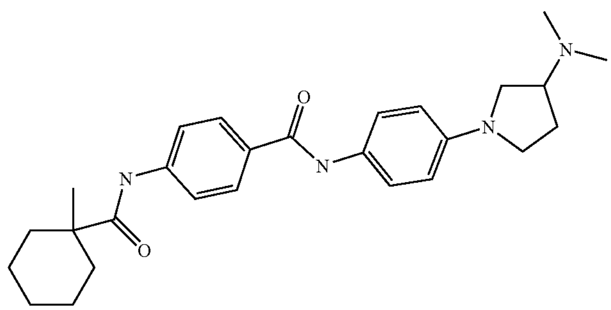 | C27H36N4O2 | 448.28 | 449 |
| 1033 | 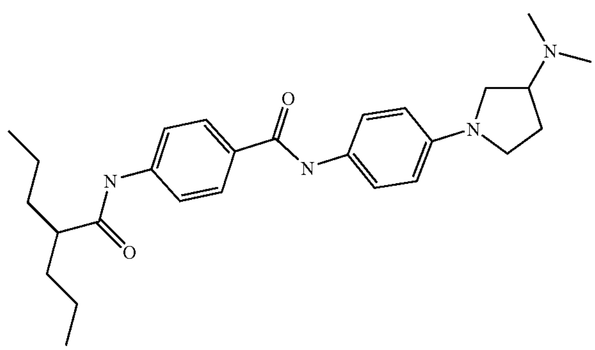 | C27H38N4O2 | 450.30 | 451 |
| 1034 | 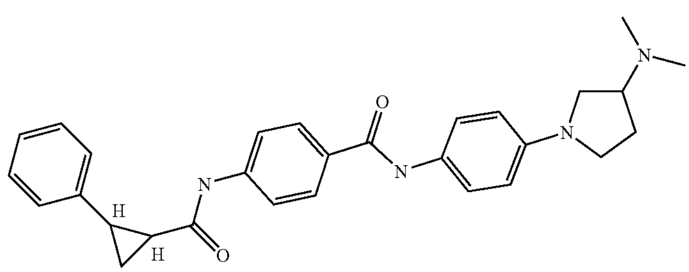 | C29H32N4O2 | 468.25 | 469 |
| 1035 | 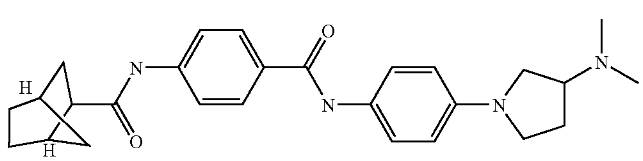 | C27H34N4O2 | 446.27 | 447 |

TABLE 7-continued
| Ex. No. | Structure | Molecular formula | Monoisotopic molecular wt. | M + H+ |
|---|---|---|---|---|
| 1036 | 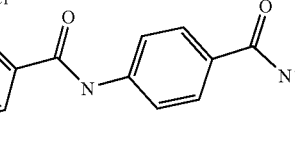 | C26H27ClN4O2 | 462.18 | 463 |
| 1037 | 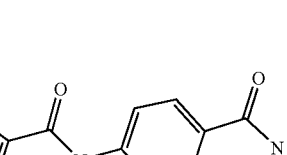 | C22H24N6O2S | 436.17 | 437 |
| 1038 | 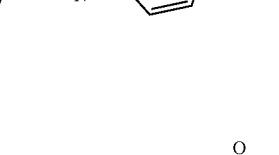 | C23H25N5O3 | 419.20 | 420 |
| 1039 | 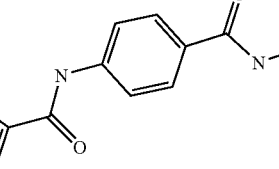 | C25H32N4O2 | 420.25 | 421 |
| 1040 | 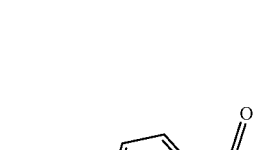 | C26H27ClN4O2 | 462.18 | 463 |
| 1041 | 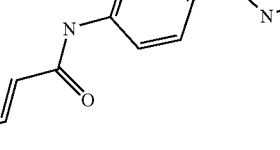 | C27H30N4O2 | 442.24 | 443 |

TABLE 7-continued

| Ex. No. | Structure | Molecular formula | Monoisotopic molecular wt. | M + H+ |
|---|---|---|---|---|
| 1042 | 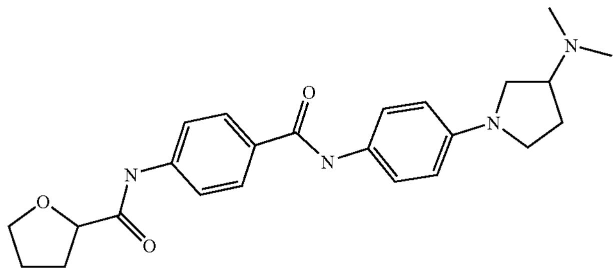 | C24H30N4O3 | 422.23 | 423 |
| 1043 | 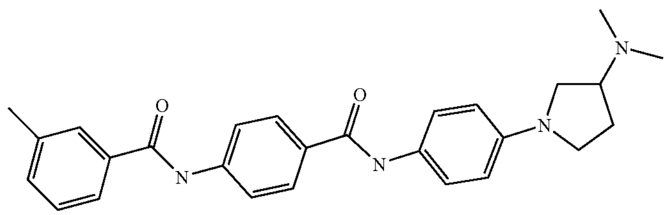 | C27H30N4O2 | 442.24 | 443 |
| 1044 | 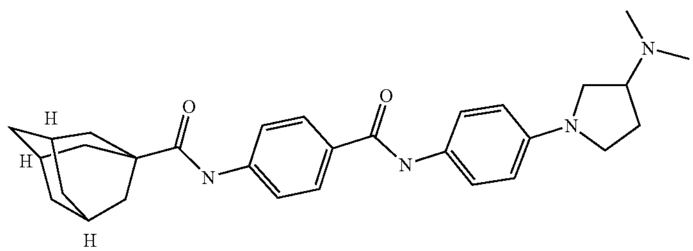 | C30H38N4O2 | 486.30 | 487 |
| 1045 | 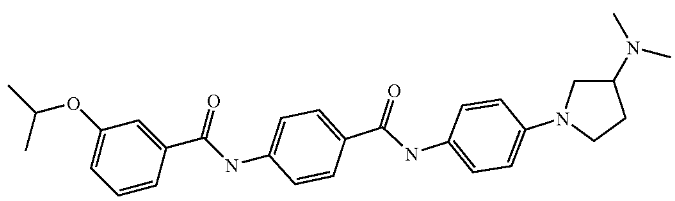 | C29H34N4O3 | 486.26 | 487 |
| 1046 | 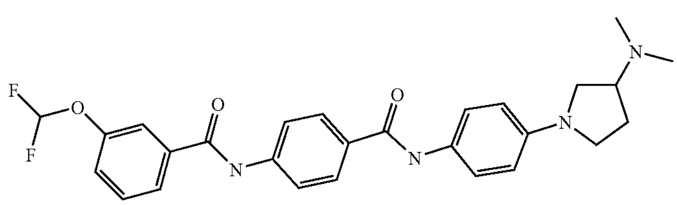 | C27H28F2N4O3 | 494.21 | 495 |
| 1047 | 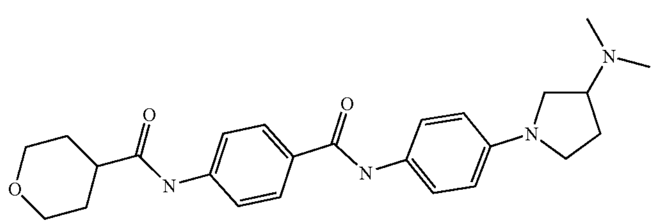 | C25H32N4O3 | 436.25 | 437 |

TABLE 7-continued

| Ex. No. | Structure | Molecular formula | Monoisotopic molecular wt. | M + H⁺ |
|---|---|---|---|---|
| 1048 | 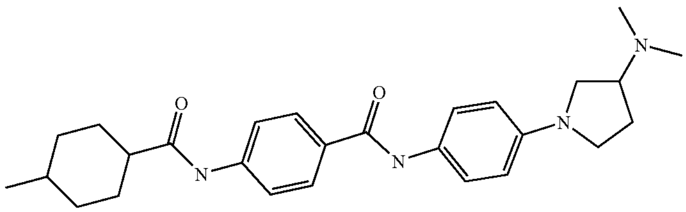 | C27H36N4O2 | 448.28 | 449 |
| 1049 | 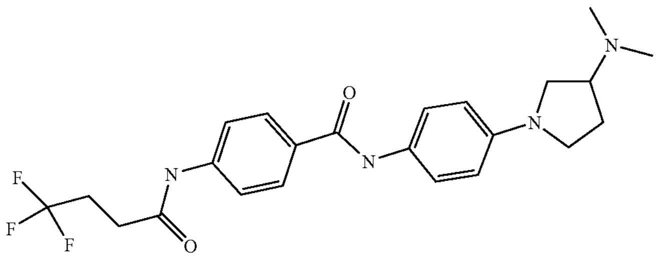 | C23H27F3N4O2 | 448.21 | 449 |
| 1050 | 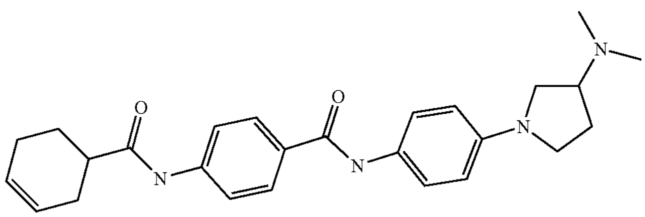 | C26H32N4O2 | 432.25 | 433 |
| 1051 | 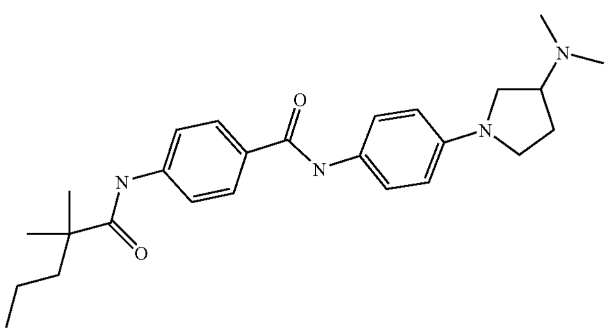 | C26H36N4O2 | 436.28 | 437 |
| 1052 | 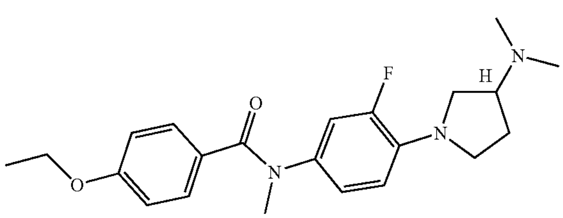 | C22H28FN3O2 | 385.22 | 386 |
| 1053 | 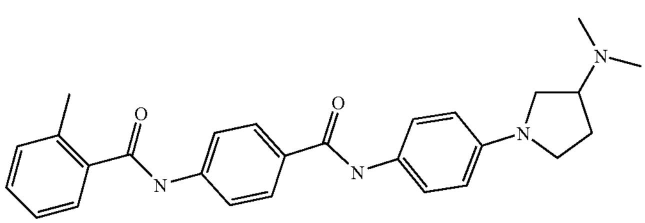 | C27H30N4O2 | 442.24 | 443 |

TABLE 7-continued

| Ex. No. | Structure | Molecular formula | Monoisotopic molecular wt. | M + H⁺ |
|---|---|---|---|---|
| 1054 | 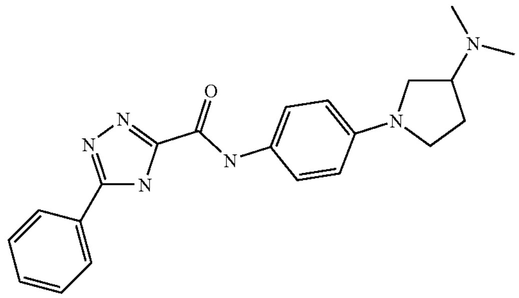 | C21H24N6O | 376.20 | 377 |
| 1055 | 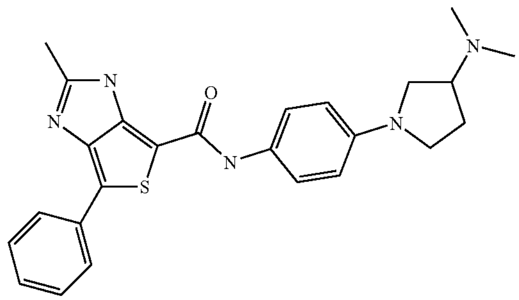 | C25H27N5OS | 445.19 | 446 |
| 1056 | 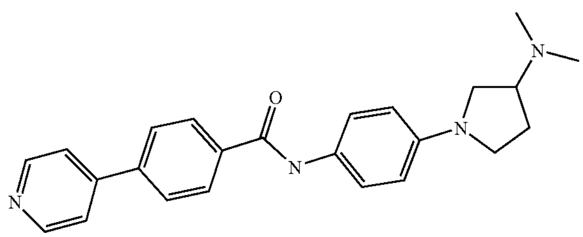 | C24H26N4O | 386.21 | 387 |
| 1057 | 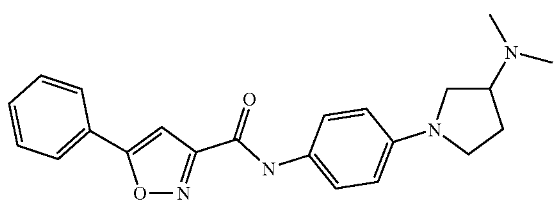 | C22H24N4O2 | 376.19 | 377 |
| 1058 | 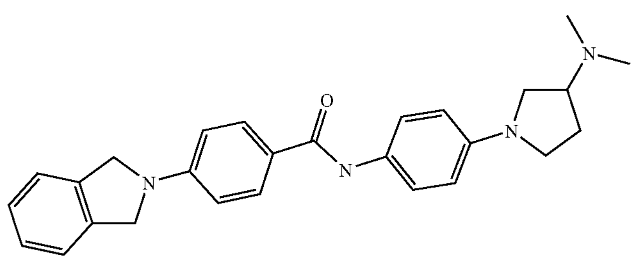 | C27H30N4O | 426.24 | 427 |
| 1059 | 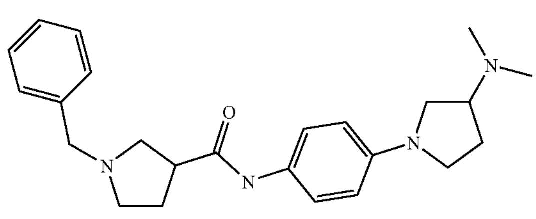 | C24H32N4O | 392.26 | 393 |

TABLE 7-continued

| Ex. No. | Structure | Molecular formula | Monoisotopic molecular wt. | M + H⁺ |
|---|---|---|---|---|
| 1060 | 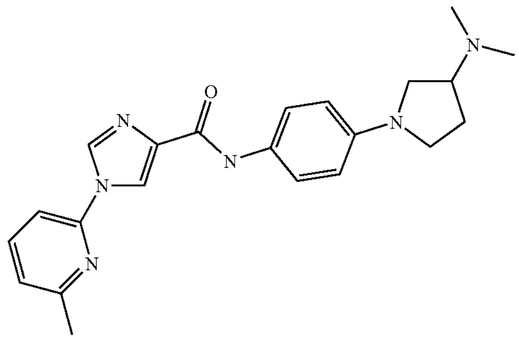 | C22H26N6O | 390.22 | 391 |
| 1061 | 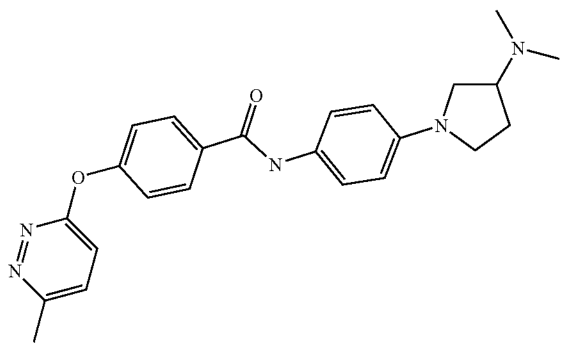 | C24H27N5O2 | 417.22 | 418 |
| 1062 | 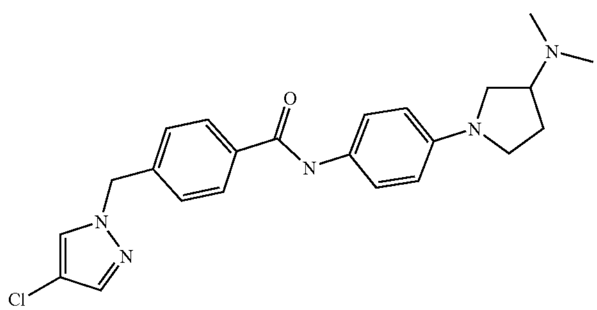 | C23H26ClN5O | 423.18 | 424 |
| 1063 | 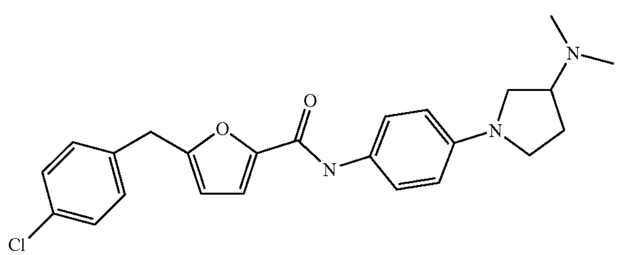 | C24H26ClN3O2 | 423.17 | 424 |
| 1064 | 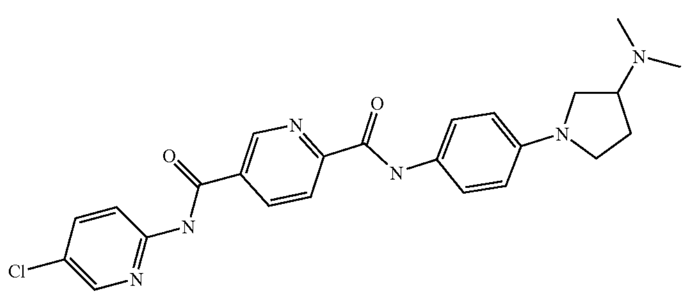 | C24H25ClN6O2 | 464.17 | 465 |

TABLE 7-continued
| Ex. No. | Structure | Molecular formula | Monoisotopic molecular wt. | M + H+ |
|---|---|---|---|---|
| 1065 | 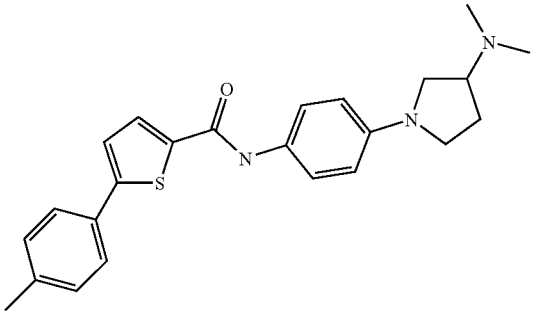 | C24H27N3OS | 405.19 | 406 |
| 1066 | 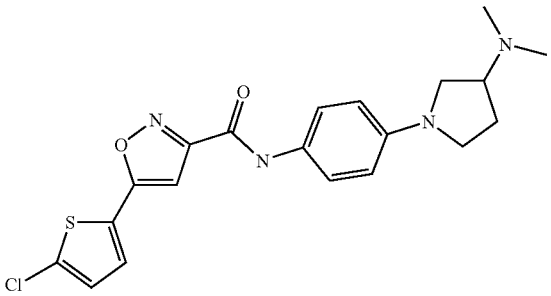 | C20H21ClN4O2S | 416.11 | 417 |
| 1067 | 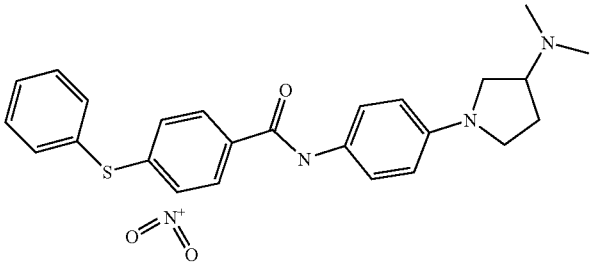 | C25H26N4O3S | 462.17 | 463 |
| 1068 | 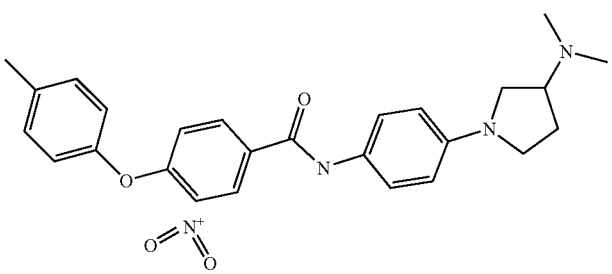 | C26H28N4O4 | 460.21 | 461 |
| 1069 | 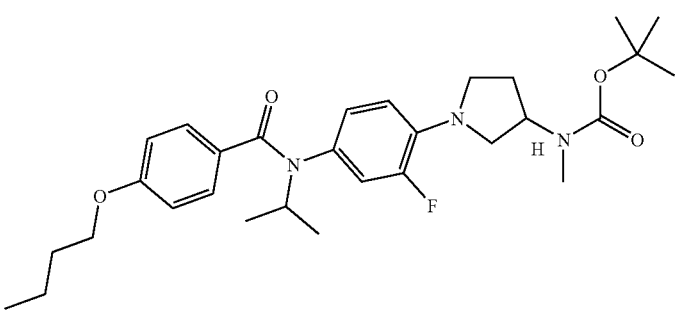 | C30H42FN3O4 | 527.32 | 528 |

TABLE 7-continued

| Ex. No. | Structure | Molecular formula | Monoisotopic molecular wt. | M + H⁺ |
|---|---|---|---|---|
| 1070 | 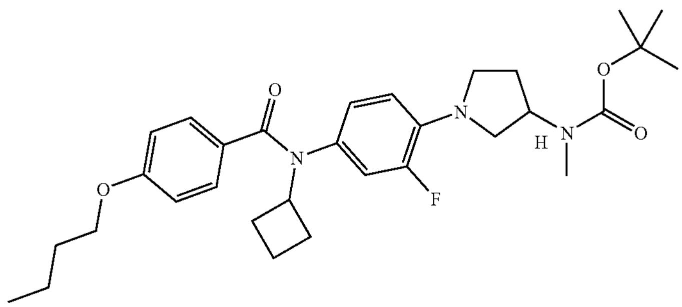 | C31H42FN3O4 | 539.32 | 540 |
| 1071 | 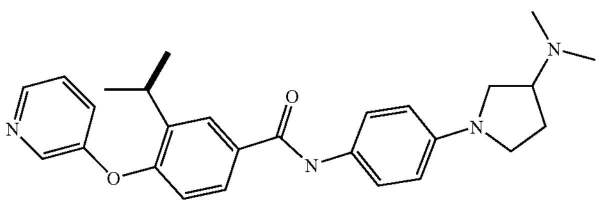 | C27H30N4O2 | 442.24 | 443 |
| 1072 | 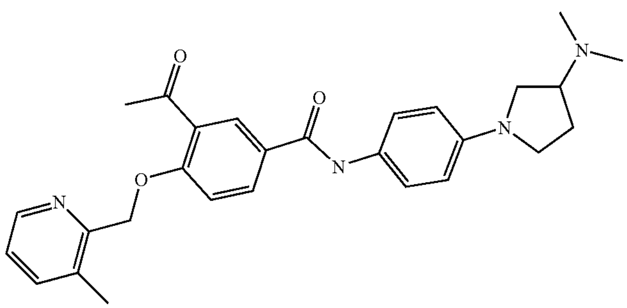 | C28H32N4O3 | 472.25 | 473 |
| 1073 | 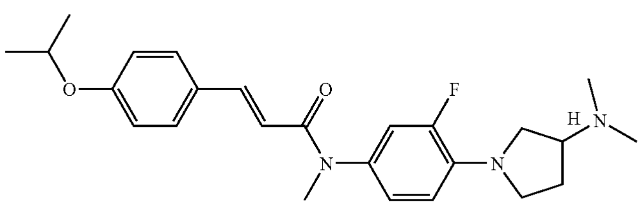 | C25H32FN3O2 | 425.25 | 426 |
| 1074 | 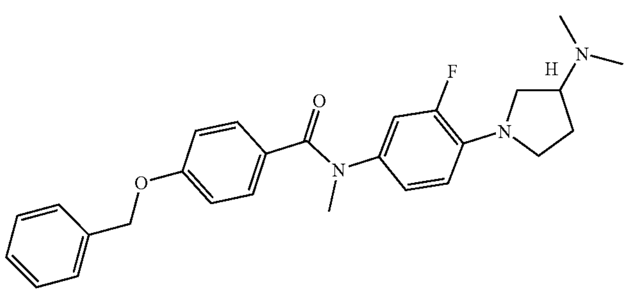 | C27H30FN3O2 | 447.23 | 448 |
| 1075 | 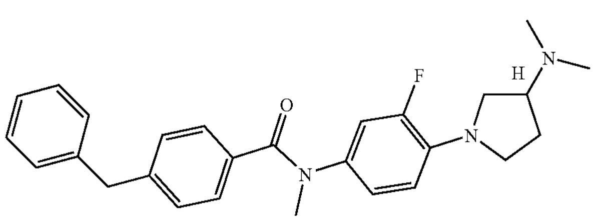 | C27H30FN3O | 431.24 | 432 |

TABLE 7-continued
| Ex. No. | Structure | Molecular formula | Monoisotopic molecular wt. | M + H+ |
|---|---|---|---|---|
| 1076 | 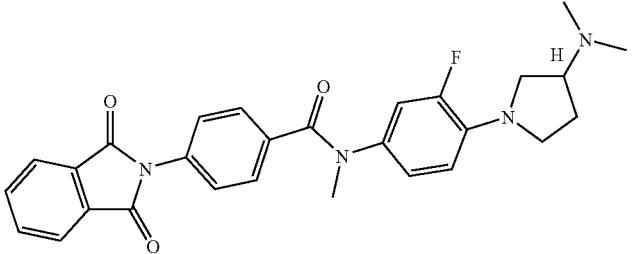 | C28H27FN4O3 | 486.21 | 487 |
| 1077 | 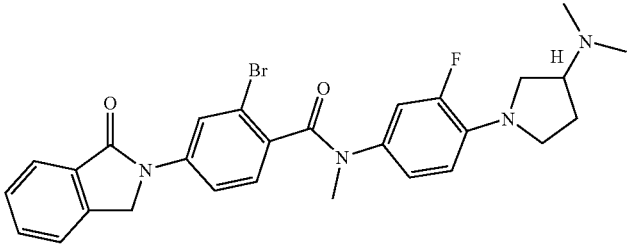 | C28H28BrFN4O2 | 550.14 | 551 |
| 1078 | 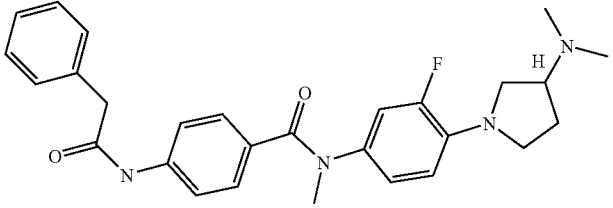 | C28H31FN4O2 | 474.24 | 475 |
| 1079 | 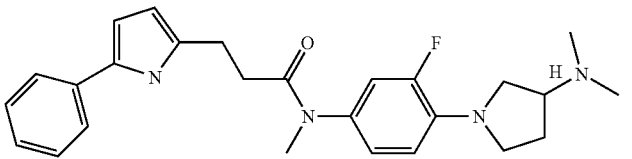 | C26H31FN4O | 434.25 | 435 |
| 1080 | 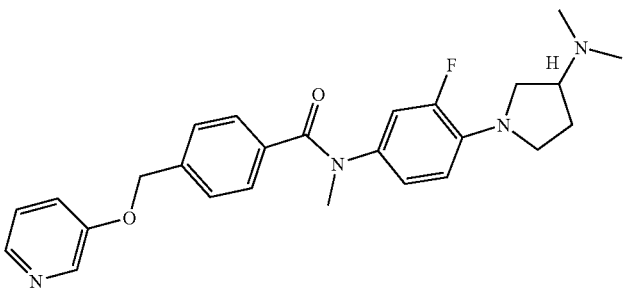 | C26H29FN4O2 | 448.23 | 449 |
| 1081 | 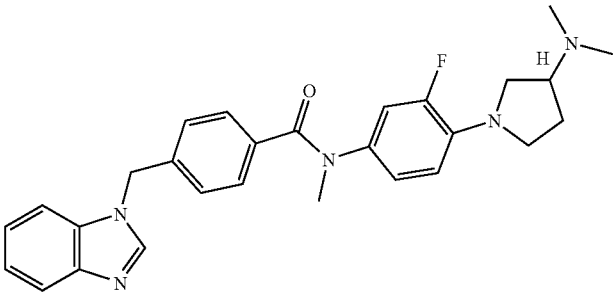 | C28H30FN5O | 471.24 | 472 |

TABLE 7-continued

| Ex. No. | Structure | Molecular formula | Monoisotopic molecular wt. | M + H+ |
|---|---|---|---|---|
| 1082 | 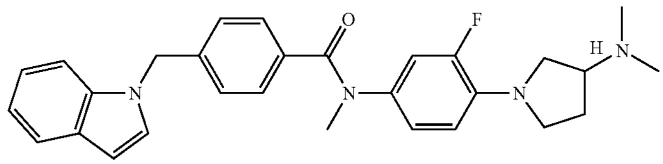 | C29H31FN4O | 470.25 | 471 |
| 1083 | 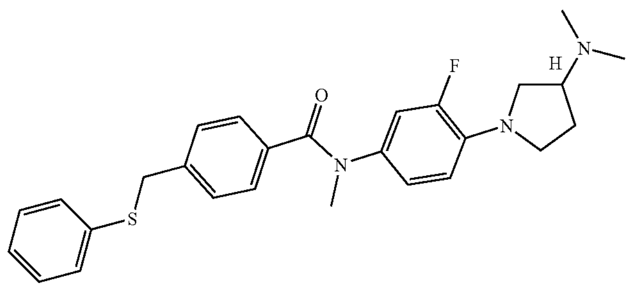 | C27H30FN3OS | 463.21 | 464 |
| 1084 | 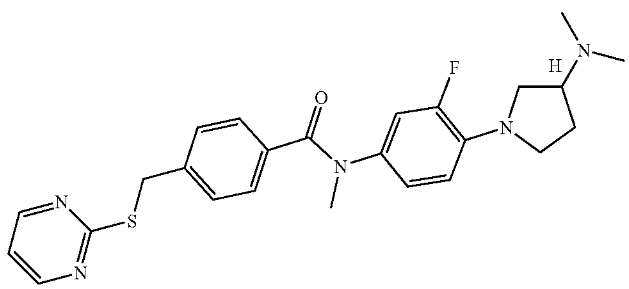 | C25H28FN5OS | 465.20 | 466 |
| 1085 | 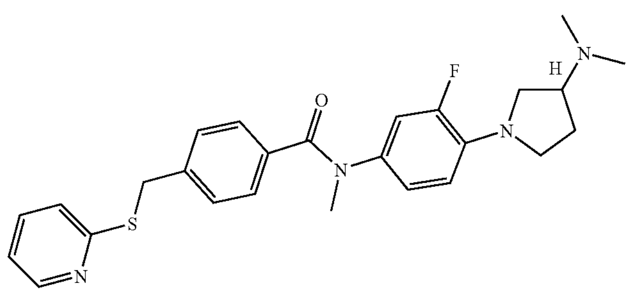 | C26H29FN4OS | 464.20 | 465 |
| 1086 | 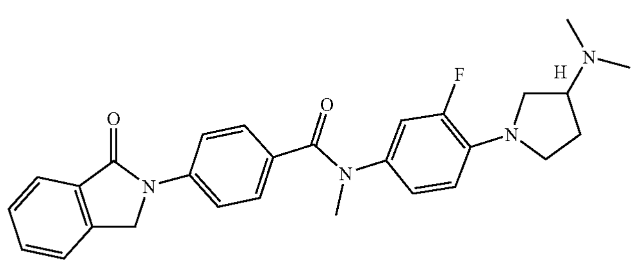 | C28H29FN4O2 | 472.23 | 473 |

TABLE 7-continued

| Ex. No. | Structure | Molecular formula | Monoisotopic molecular wt. | M + H⁺ |
|---|---|---|---|---|
| 1087 | 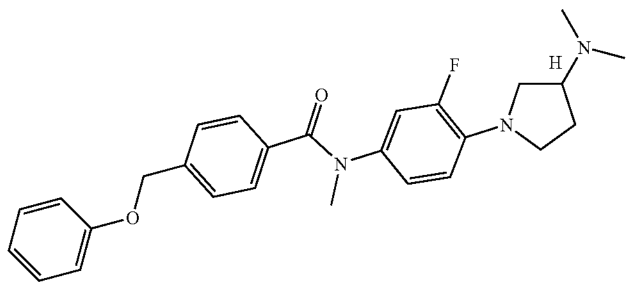 | C27H30FN3O2 | 447.23 | 448 |
| 1088 | 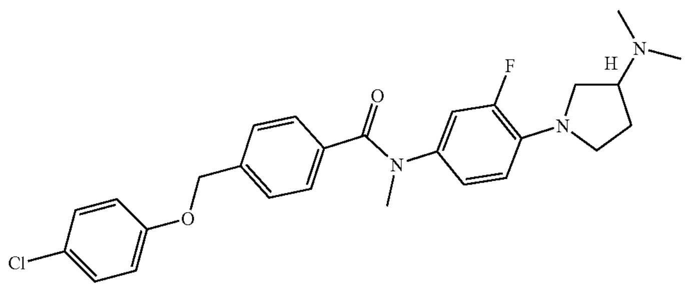 | C27H29ClFN3O2 | 481.19 | 482 |
| 1089 | 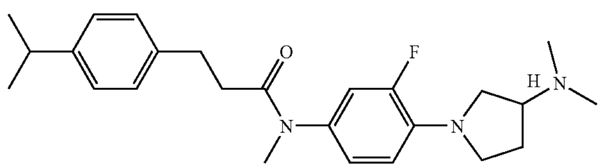 | C25H34FN3O | 411.27 | 412 |
| 1090 | 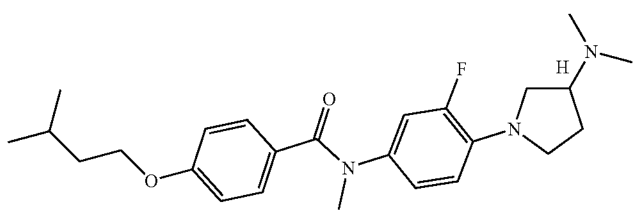 | C25H34FN3O2 | 427.26 | 428 |
| 1091 | 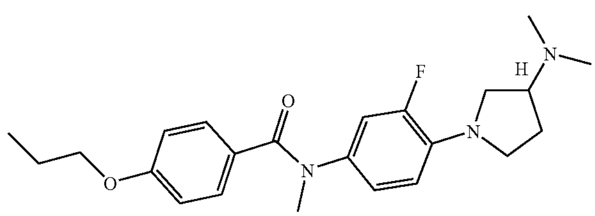 | C23H30FN3O2 | 399.23 | 400 |
| 1092 | 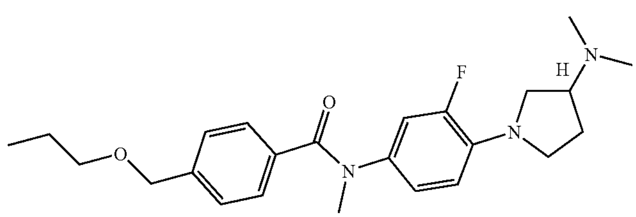 | C24H32FN3O2 | 413.25 | 414 |
| 1093 | — | C26H32FN3O2 | 437.25 | 438 |
| 1094 | — | C30H36N4O4 | 516.27 | 517 |

TABLE 7-continued

| Ex. No. | Structure | Molecular formula | Monoisotopic molecular wt. | M + H+ |
|---|---|---|---|---|
| 1095 | 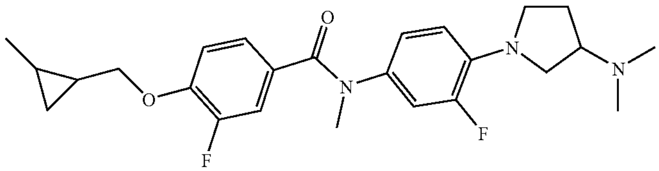 | C25H31F2N3O2 | 443.24 | 444 |
| 1096 | 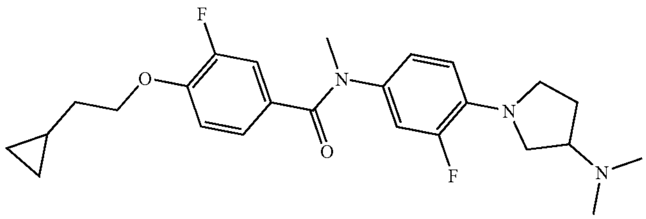 | C25H31F2N3O2 | 443.24 | 444 |
| 1097 | 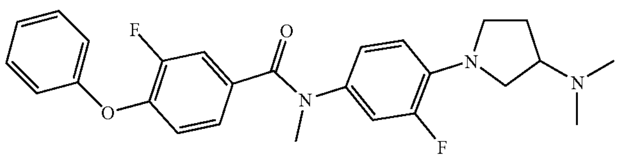 | C26H27F2N3O2 | 451.21 | 452 |
| 1098 | 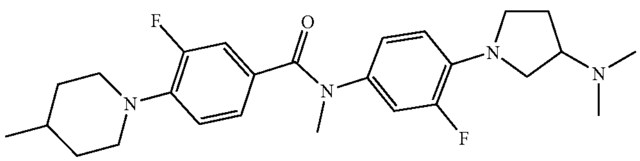 | C26H34F2N4O | 456.27 | 457 |
| 1099 | 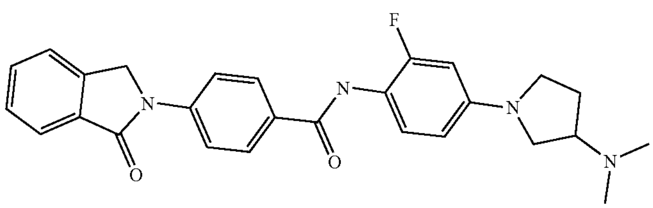 | C27H27FN4O2 | 458.21 | 459 |
| 1100 | 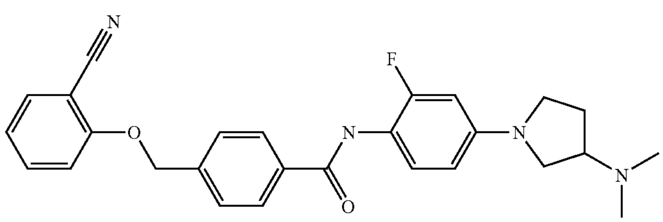 | C27H27FN4O2 | 458.21 | 459 |
| 1101 | 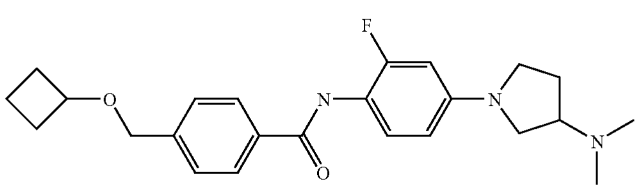 | C24H30FN3O2 | 411.23 | 412 |
| 1102 | 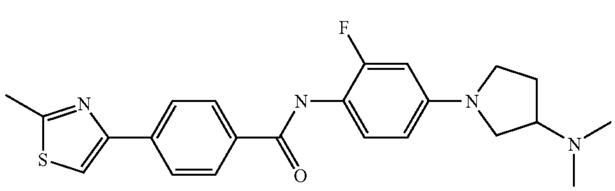 | C23H25FN4OS | 424.17 | 425 |

TABLE 7-continued

| Ex. No. | Structure | Molecular formula | Monoisotopic molecular wt. | M + H+ |
|---|---|---|---|---|
| 1103 | 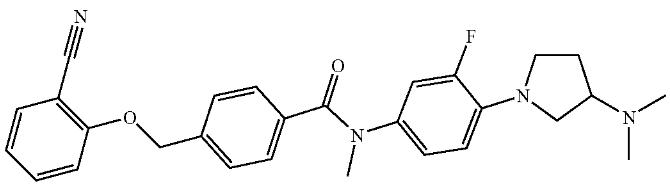 | C28H29FN4O2 | 472.23 | 473 |
| 1104 | 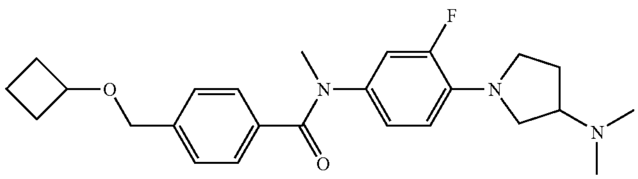 | C25H32FN3O2 | 425.25 | 426 |
| 1105 | 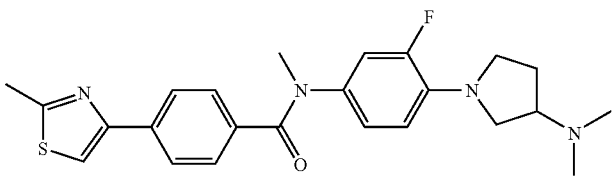 | C24H27FN4OS | 438.19 | 439 |
| 1106 | 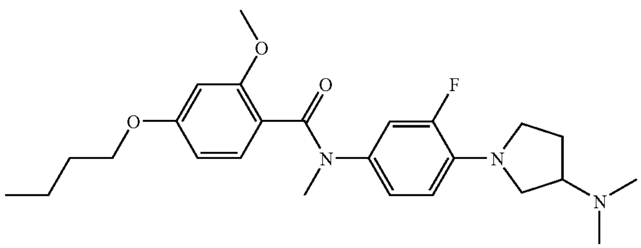 | C25H34FN3O3 | 443.26 | 444 |
| 1107 | 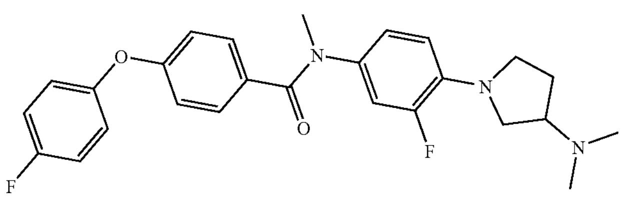 | C26H27F2N3O2 | 451.21 | 452 |
| 1108 | 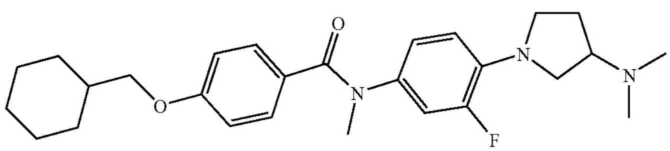 | C27H36FN3O2 | 453.28 | 454 |
| 1109 | 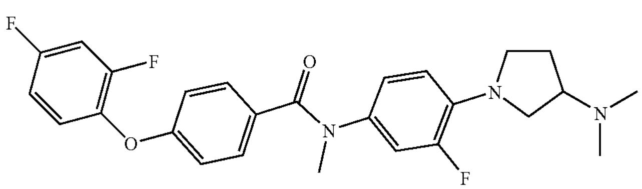 | C26H26F3N3O2 | 469.20 | 470 |
| 1110 | 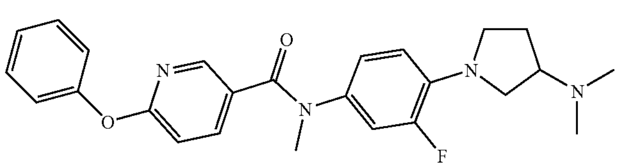 | C25H27FN4O2 | 434.21 | 435 |

TABLE 7-continued

| Ex. No. | Structure | Molecular formula | Monoisotopic molecular wt. | M + H+ |
|---|---|---|---|---|
| 1111 | 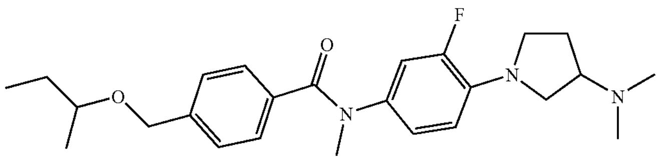 | C25H34FN3O2 | 427.26 | 428 |
| 1112 | 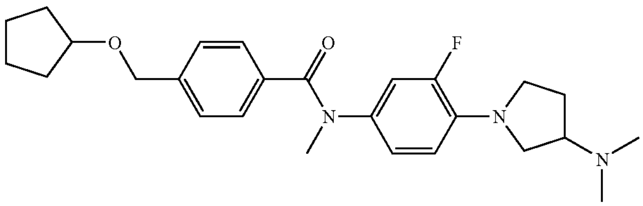 | C26H34FN3O2 | 439.26 | 440 |
| 1113 | 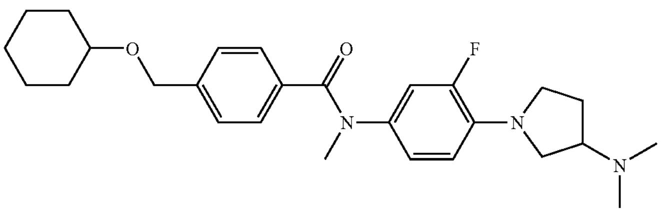 | C27H36FN3O2 | 453.28 | 454 |
| 1114 | 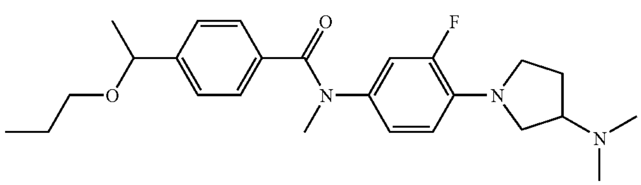 | C25H34FN3O2 | 427.26 | 428 |
| 1115 | 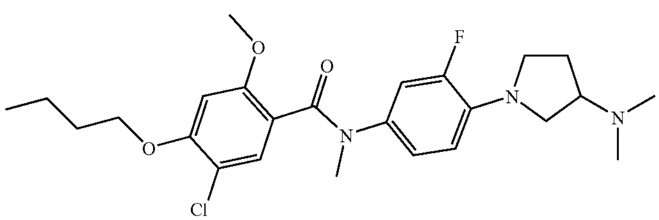 | C25H33ClFN3O3 | 477.22 | 478 |
| 1116 | 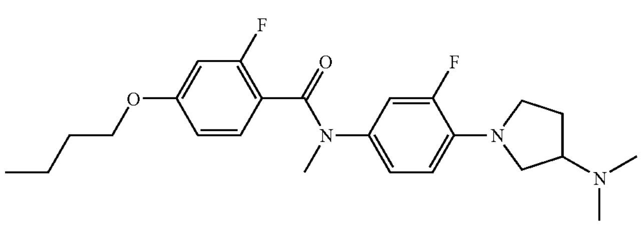 | C24H31F2N3O2 | 431.24 | 432 |
| 1117 | 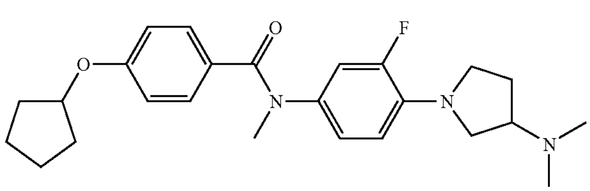 | C25H32FN3O2 | 425.25 | 426 |

TABLE 7-continued

| Ex. No. | Structure | Molecular formula | Monoisotopic molecular wt. | M + H+ |
|---|---|---|---|---|
| 1118 | 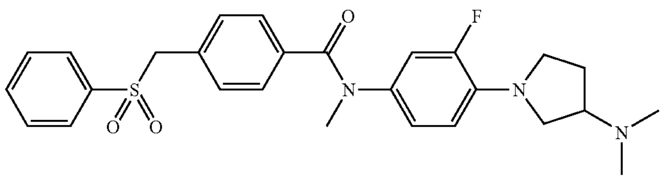 | C27H30FN3O3S | 495.62 | 496 |
| 1119 | 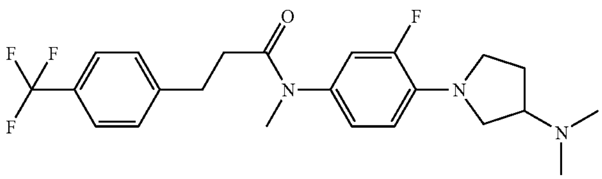 | C23H27F4N3O | 437.21 | 438 |
| 1120 | 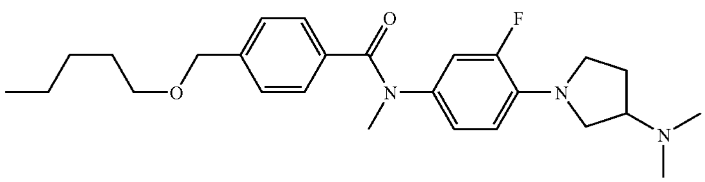 | C26H36FN3O2 | 441.28 | 442 |
| 1121 | 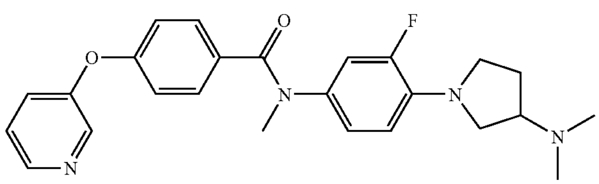 | C25H27FN4O2 | 434.21 | 435 |
| 1122 | 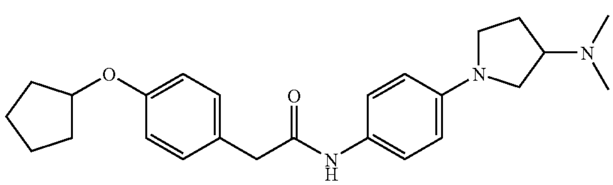 | C25H33N3O2 | 407.26 | 408 |
| 1123 | 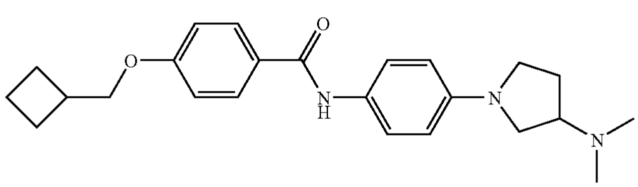 | C24H31N3O2 | 393.24 | 394 |
| 1124 | 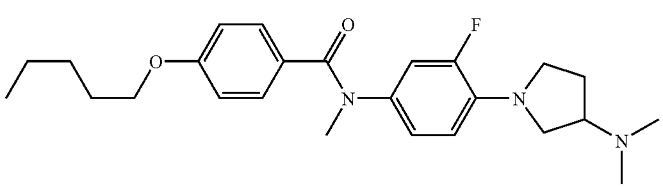 | C25H34FN3O2 | 427.26 | 428 |
| 1125 | 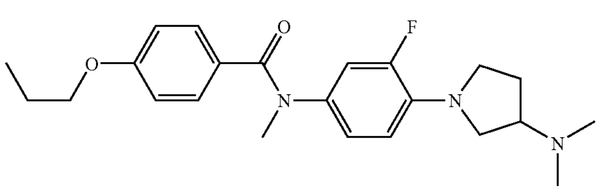 | C23H30FN3O2 | 399.23 | 400 |

TABLE 7-continued

| Ex. No. | Structure | Molecular formula | Monoisotopic molecular wt. | M + H⁺ |
|---|---|---|---|---|
| 1126 | 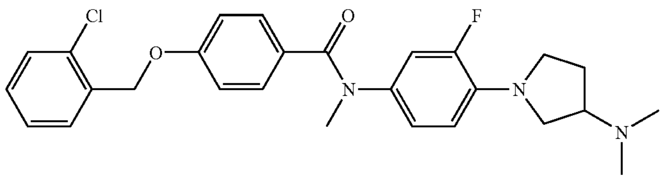 | C27H29ClFN3O2 | 481.19 | 482 |
| 1127 | 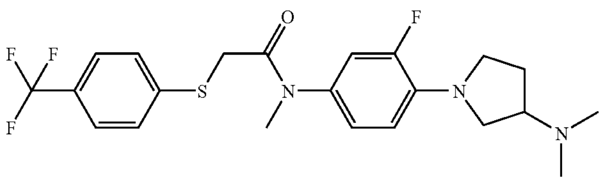 | C22H25F4N3OS | 455.17 | 456 |
| 1128 | 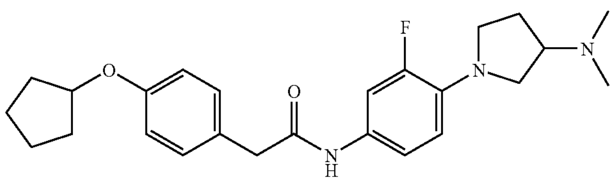 | C25H32FN3O2 | 425.25 | 426 |
| 1129 | 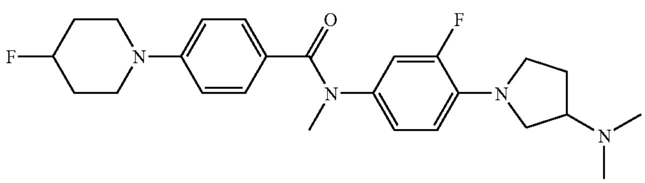 | C25H32F2N4O | 442.25 | 443 |
| 1130 | 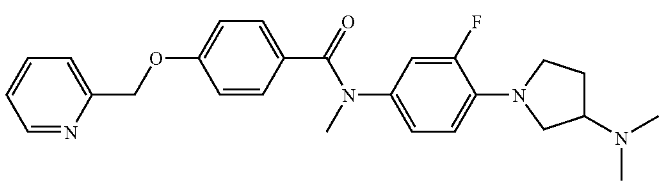 | C26H29FN4O2 | 448.23 | 449 |

TABLE 8

| Ex. No. | Structure | Molecular formula | Monoisotopic molecular wt. | M + H⁺ |
|---|---|---|---|---|
| 1131 | 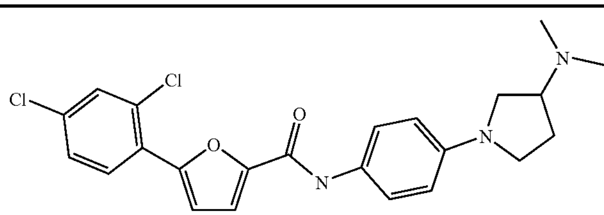 | C23H23Cl2N3O2 | 443.12 | 444 |
| 1132 | 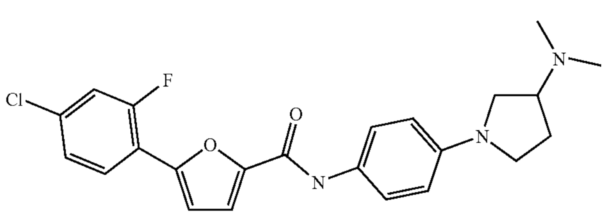 | C23H23ClFN3O2 | 427.15 | 428 |

TABLE 8-continued

| Ex. No. | Structure | Molecular formula | Monoisotopic molecular wt. | M + H+ |
|---|---|---|---|---|
| 1133 | 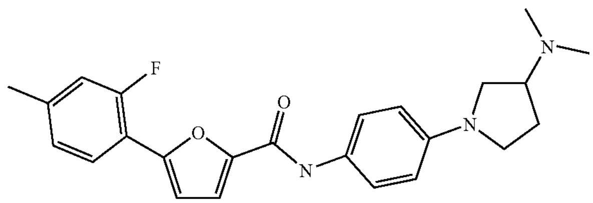 | C24H26FN3O2 | 407.20 | 408 |
| 1134 | 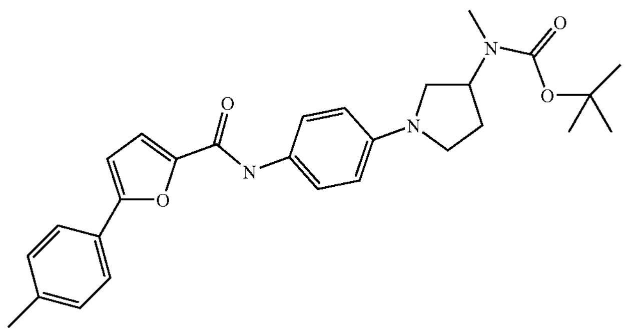 | C28H33N3O4 | 475.25 | 476 |
| 1135 | 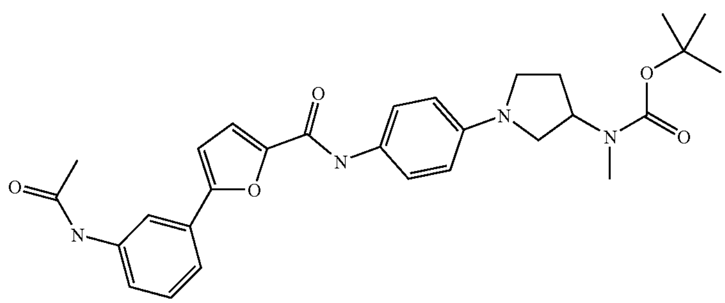 | C29H34N4O5 | 518.25 | 519 |
| 1136 | 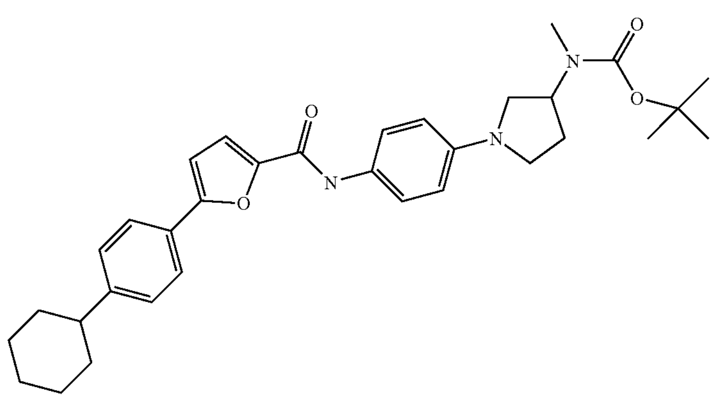 | C33H41N3O4 | 543.31 | 544 |

TABLE 8-continued

| Ex. No. | Structure | Molecular formula | Monoisotopic molecular wt. | M + H+ |
|---|---|---|---|---|
| 1137 | 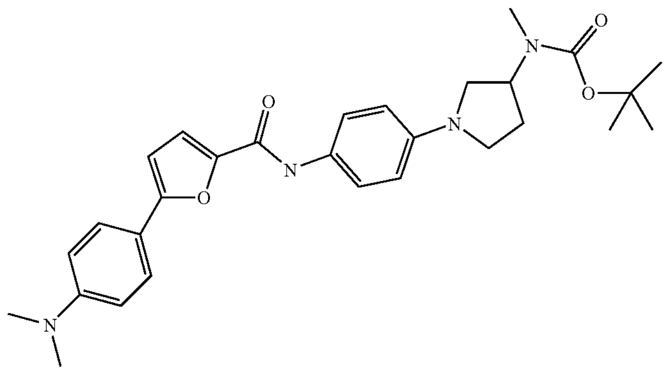 | C29H36N4O4 | 504.27 | 505 |
| 1138 | 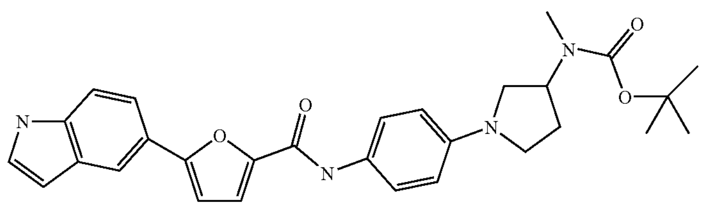 | C29H32N4O4 | 500.24 | 501 |
| 1139 | 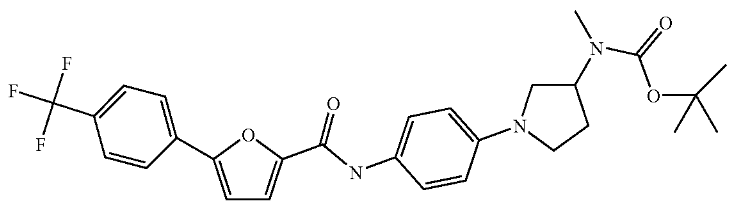 | C28H30F3N3O4 | 529.22 | 530 |
| 1140 | 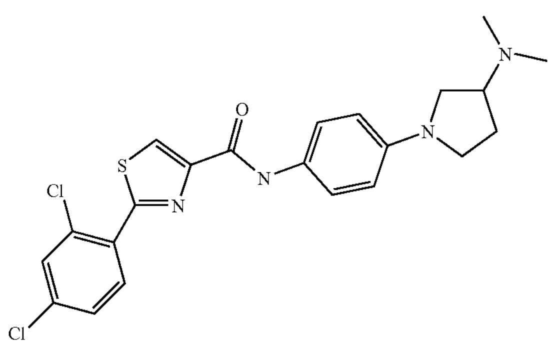 | C22H22Cl2N4OS | 460.09 | 461 |
| 1141 | 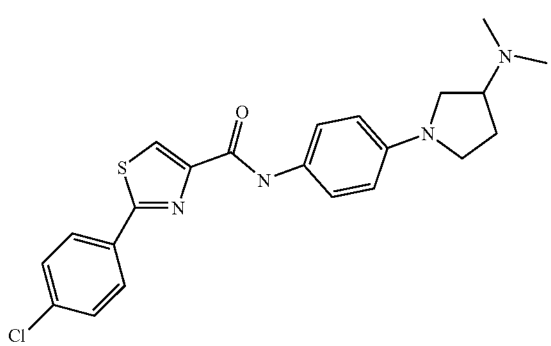 | C22H23ClN4OS | 426.13 | 427 |

TABLE 8-continued

| Ex. No. | Structure | Molecular formula | Monoisotopic molecular wt. | M + H⁺ |
|---|---|---|---|---|
| 1142 | 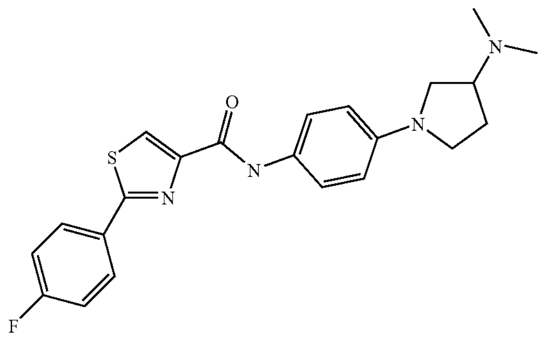 | C22H23FN4OS | 410.16 | 411 |
| 1143 | 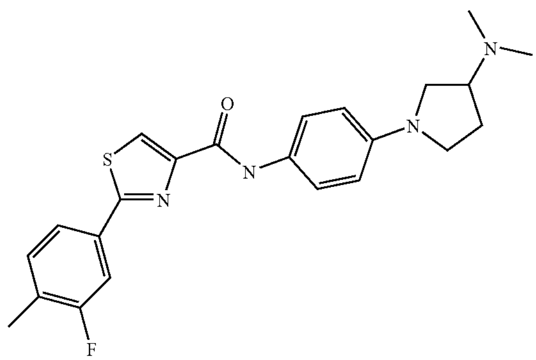 | C23H25FN4OS | 424.17 | 425 |
| 1144 | 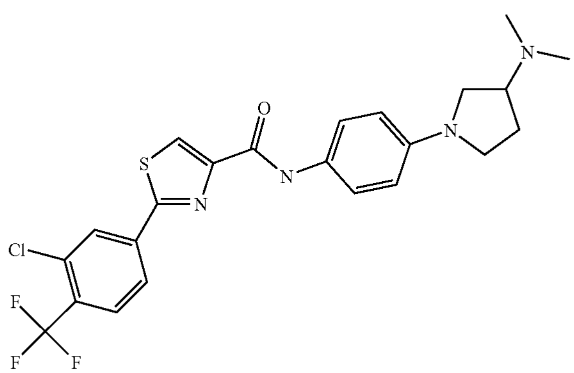 | C23H22ClF3N4OS | 494.12 | 495 |
| 1145 | 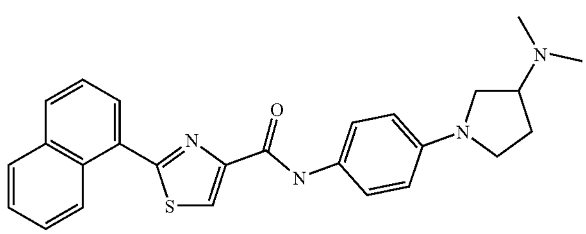 | C26H26N4OS | 442.18 | 443 |
| 1146 | 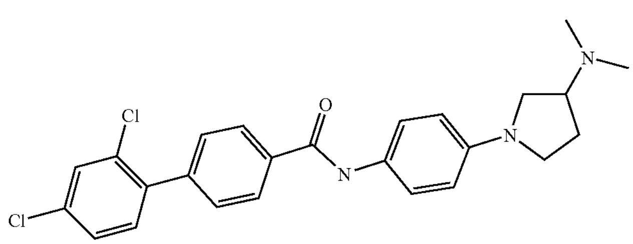 | C25H25Cl2N3O | 453.14 | 454 |

TABLE 8-continued

| Ex. No. | Structure | Molecular formula | Monoisotopic molecular wt. | M + H⁺ |
|---|---|---|---|---|
| 1147 | 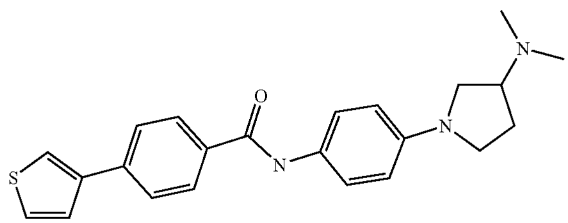 | C23H25N3OS | 391.17 | 392 |
| 1148 | 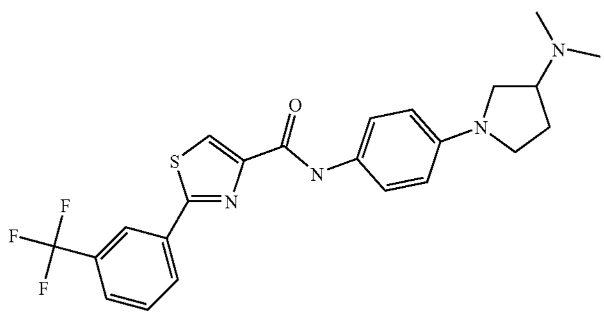 | C23H23F3N4OS | 460.15 | 461 |
| 1149 | 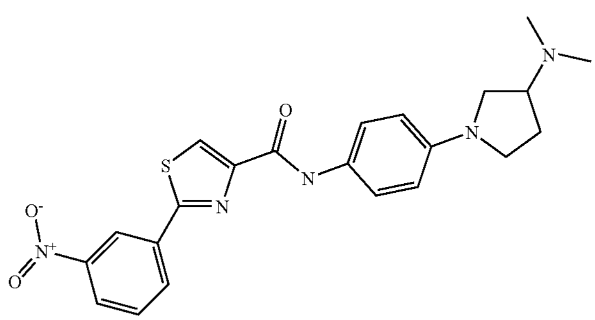 | C22H23N5O3S | 437.15 | 438 |
| 1150 | 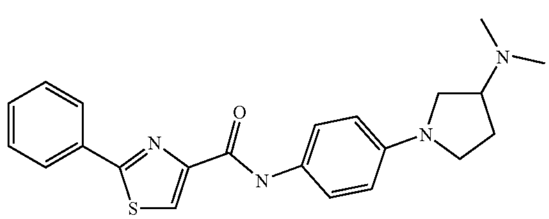 | C22H24N4OS | 392.17 | 393 |
| 1151 | 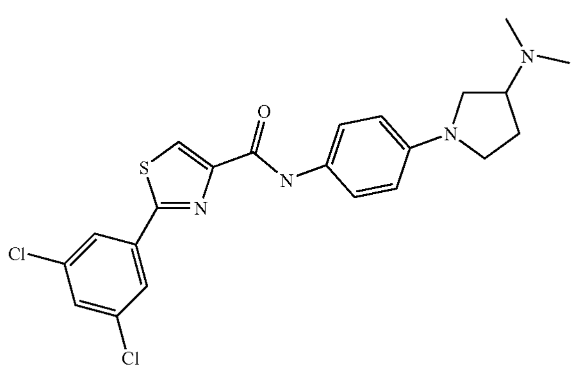 | C22H22Cl2N4OS | 460.09 | 461 |

TABLE 8-continued

| Ex. No. | Structure | Molecular formula | Monoisotopic molecular wt. | M + H+ |
|---|---|---|---|---|
| 1152 | 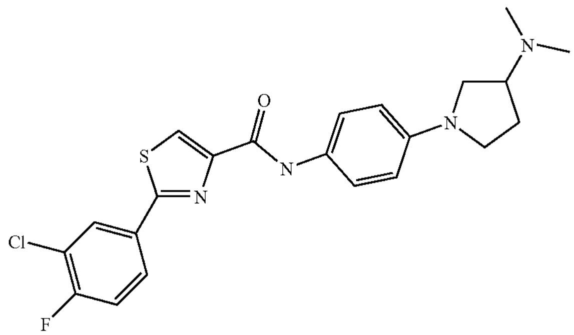 | C22H22ClFN4OS | 444.12 | 445 |
| 1153 | 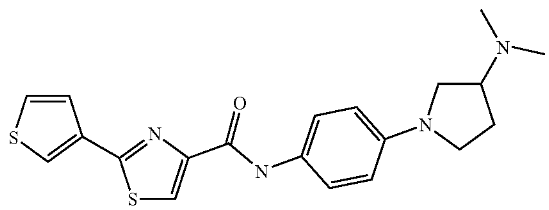 | C20H22N4OS2 | 398.12 | 399 |
| 1154 | 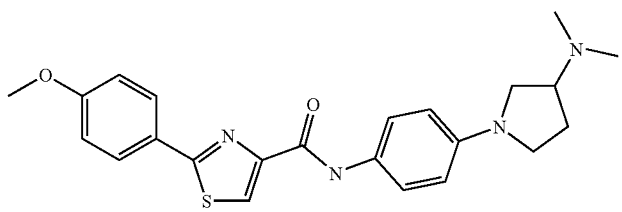 | C23H26N4O2S | 422.18 | 423 |
| 1155 | 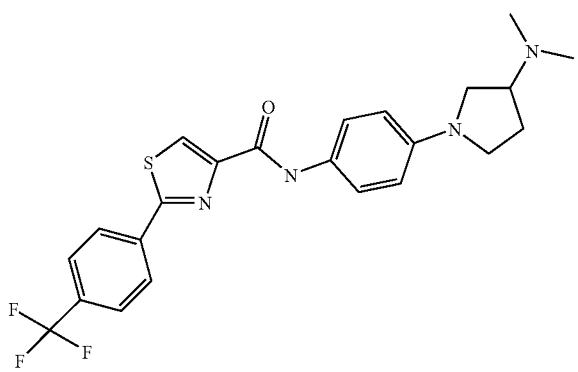 | C23H23F3N4OS | 460.15 | 461 |
| 1156 | 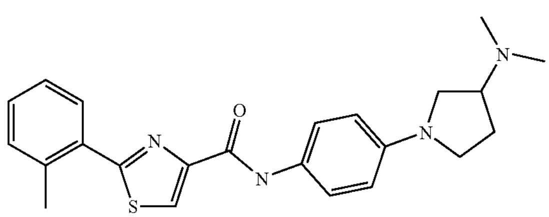 | C23H26N4OS | 406.18 | 407 |
| 1157 | 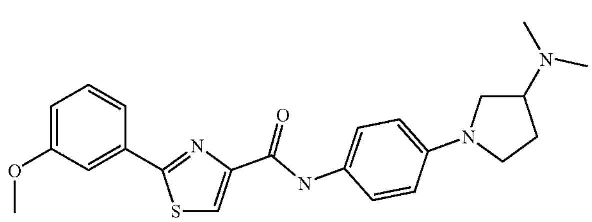 | C23H26N4O2S | 422.18 | 423 |

TABLE 8-continued

| Ex. No. | Structure | Molecular formula | Monoisotopic molecular wt. | M + H⁺ |
|---|---|---|---|---|
| 1158 | 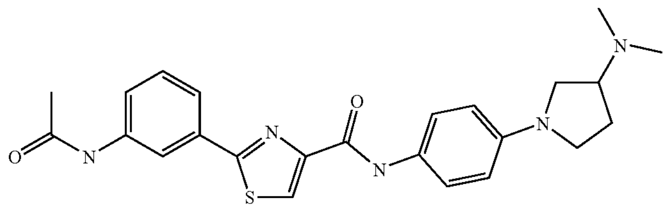 | C24H27N5O2S | 449.19 | 450 |
| 1159 | 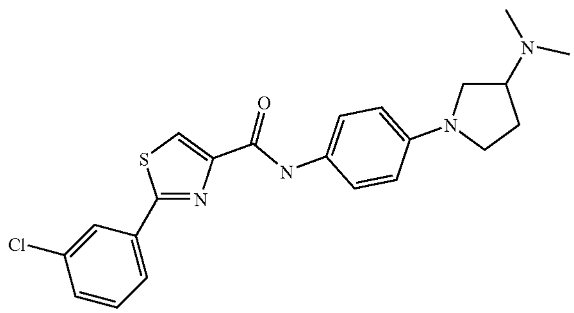 | C22H23ClN4OS | 426.13 | 427 |
| 1160 | 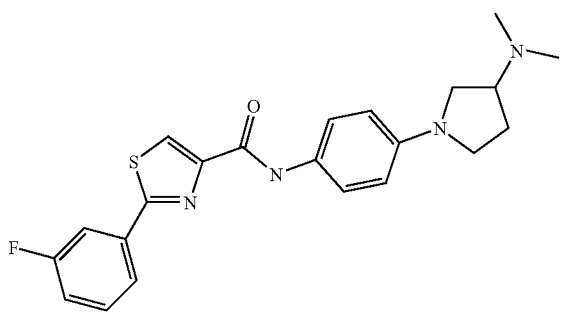 | C22H23FN4OS | 410.16 | 411 |
| 1161 | 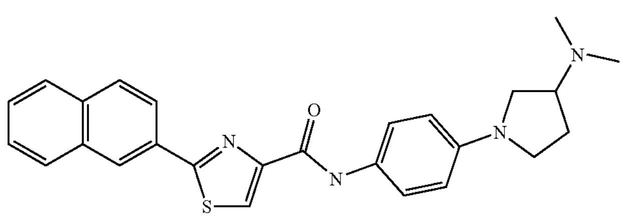 | C26H26N4OS | 442.18 | 443 |
| 1162 | 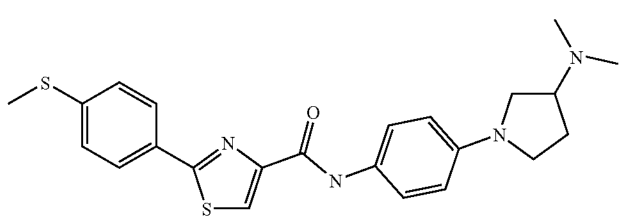 | C23H26N4OS2 | 438.15 | 439 |

TABLE 8-continued

| Ex. No. | Structure | Molecular formula | Monoisotopic molecular wt. | M + H+ |
|---|---|---|---|---|
| 1163 | 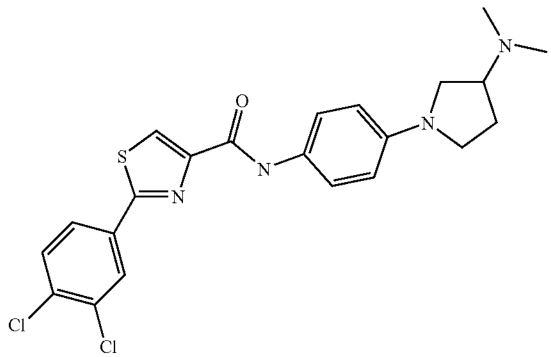 | C22H22Cl2N4OS | 460.09 | 461 |
| 1164 | 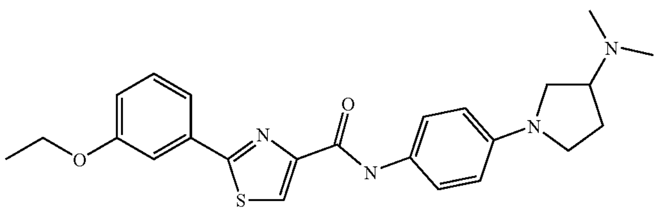 | C24H28N4O2S | 436.19 | 437 |
| 1165 | 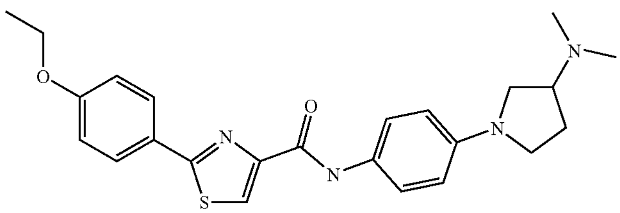 | C24H28N4O2S | 436.19 | 437 |
| 1166 | 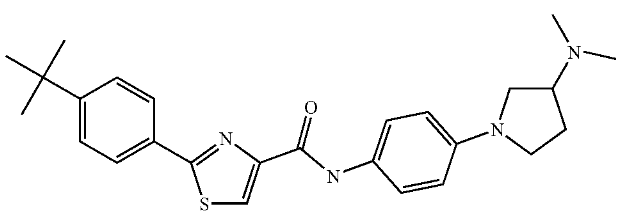 | C26H32N4OS | 448.23 | 449 |
| 1167 | 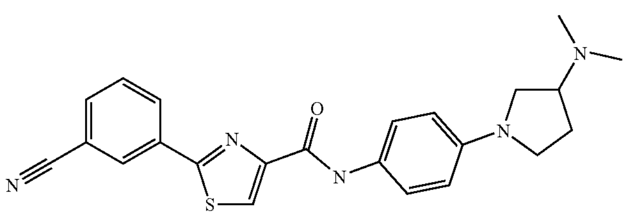 | C23H23N5OS | 417.16 | 418 |
| 1168 | 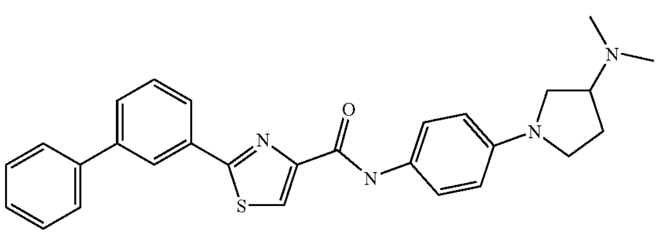 | C28H28N4OS | 468.20 | 469 |

… TABLE 8-continued

| Ex. No. | Structure | Molecular formula | Monoisotopic molecular wt. | M + H⁺ |
|---|---|---|---|---|
| 1169 | 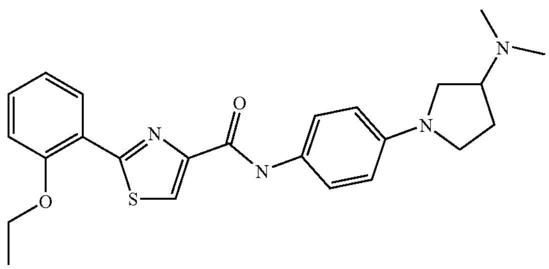 | C24H28N4O2S | 436.19 | 437 |
| 1170 | 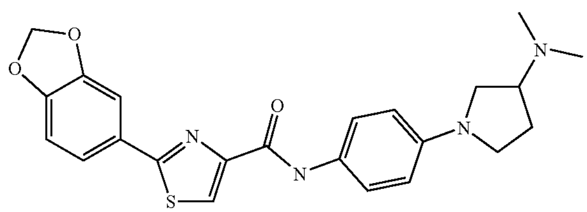 | C23H24N4O3S | 436.16 | 437 |
| 1171 | 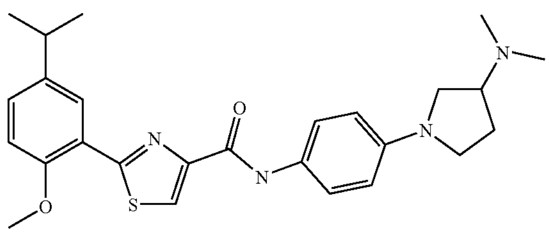 | C26H32N4O2S | 464.23 | 465 |
| 1172 | 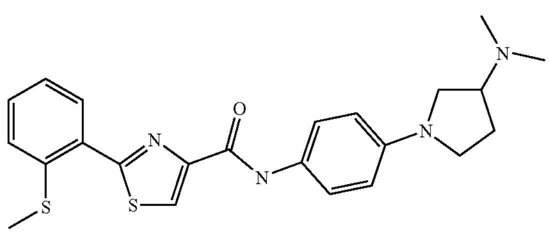 | C23H26N4OS2 | 438.15 | 439 |
| 1173 | 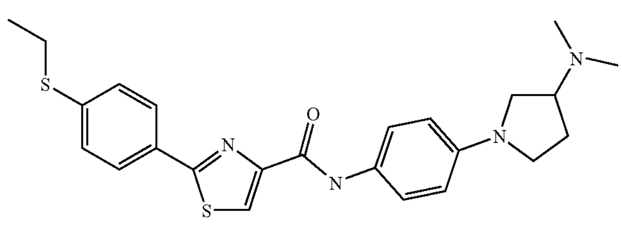 | C24H28N4OS2 | 452.17 | 453 |
| 1174 | 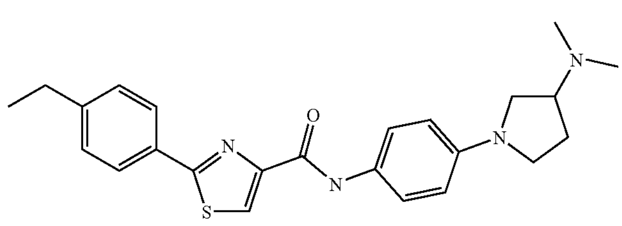 | C24H28N4OS | 420.20 | 421 |

TABLE 8-continued

| Ex. No. | Structure | Molecular formula | Monoisotopic molecular wt. | M + H⁺ |
|---|---|---|---|---|
| 1175 | 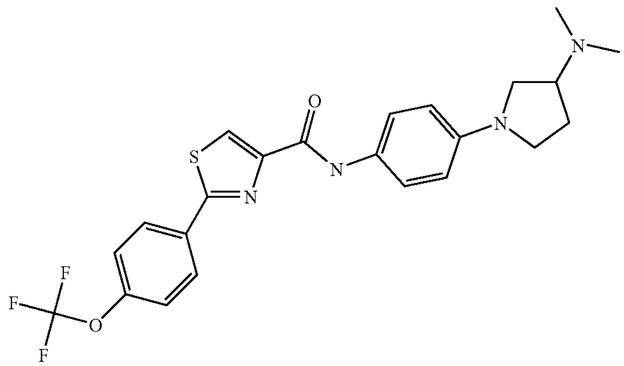 | C23H23F3N4O2S | 476.15 | 477 |
| 1176 | 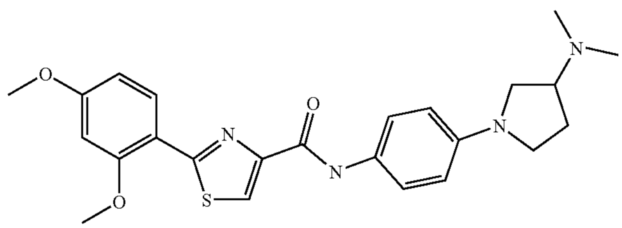 | C24H28N4O3S | 452.19 | 453 |
| 1177 | 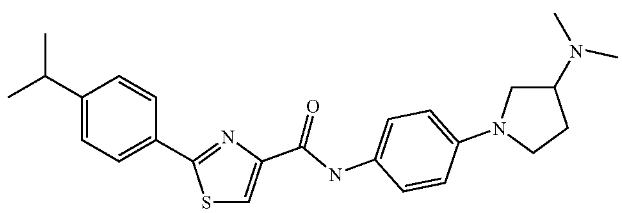 | C25H30N4OS | 434.21 | 435 |
| 1178 | 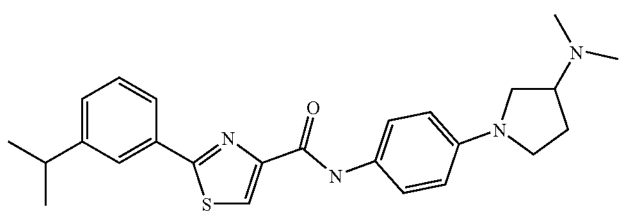 | C25H30N4OS | 434.21 | 435 |
| 1179 | 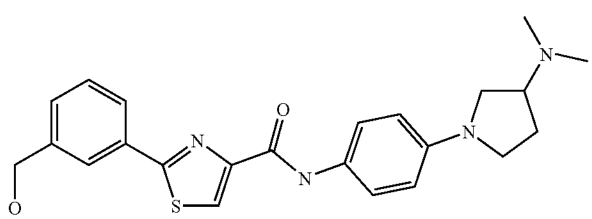 | C23H26N4O2S | 422.18 | 423 |
| 1180 | 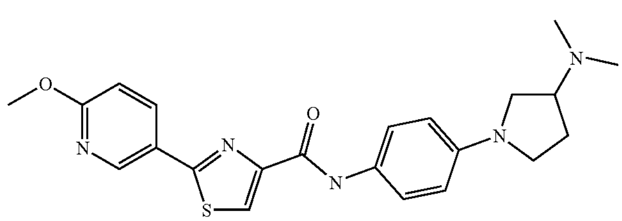 | C22H25N5O2S | 423.17 | 424 |

TABLE 8-continued
| Ex. No. | Structure | Molecular formula | Monoisotopic molecular wt. | M + H+ |
|---|---|---|---|---|
| 1181 | 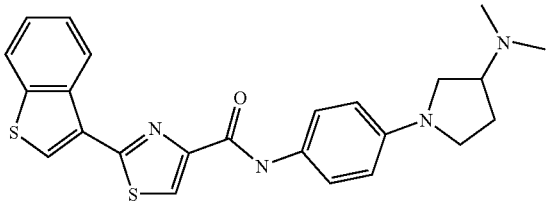 | C24H24N4OS2 | 448.14 | 449 |
| 1182 | 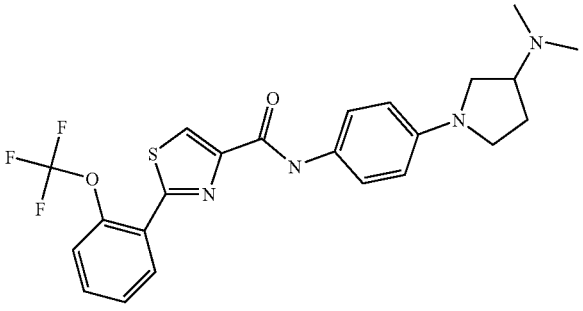 | C23H23F3N4O2S | 476.15 | 477 |
| 1183 | 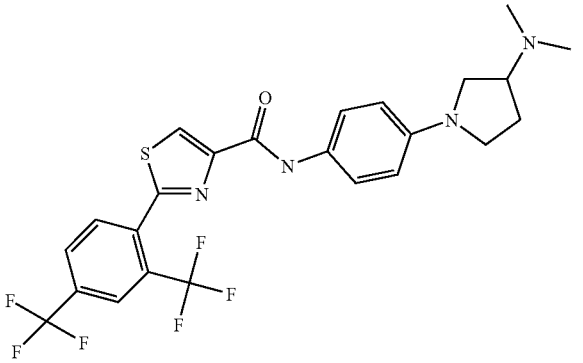 | C24H22F6N4OS | 528.14 | 529 |
| 1184 | 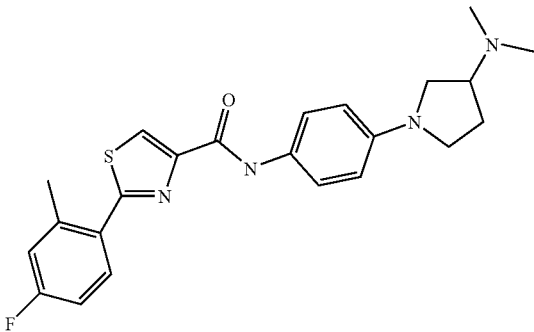 | C23H25FN4OS | 424.17 | 425 |
| 1185 | 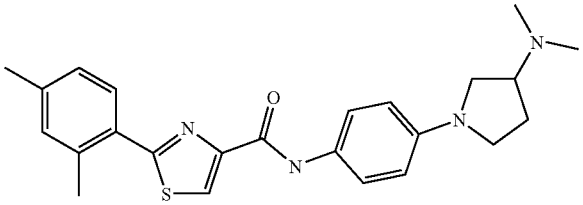 | C24H28N4OS | 420.20 | 421 |

TABLE 8-continued

| Ex. No. | Structure | Molecular formula | Monoisotopic molecular wt. | M + H⁺ |
|---|---|---|---|---|
| 1186 | 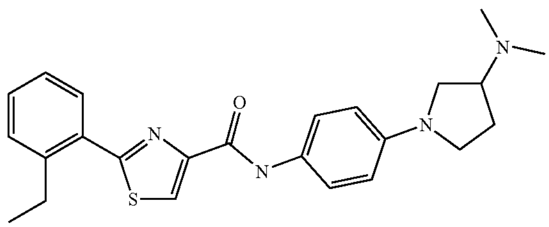 | C24H28N4OS | 420.20 | 421 |
| 1187 | 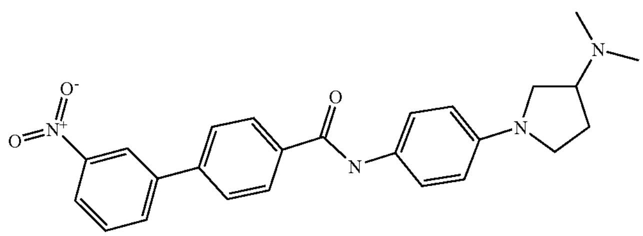 | C25H26N4O3 | 430.20 | 431 |
| 1188 | 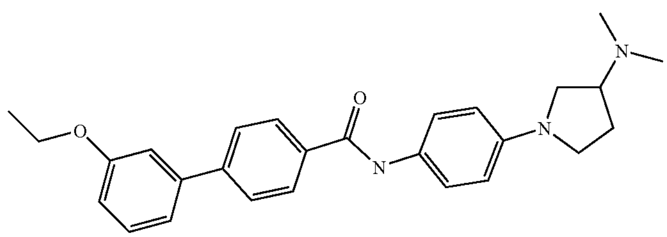 | C27H31N3O2 | 429.24 | 430 |
| 1189 | 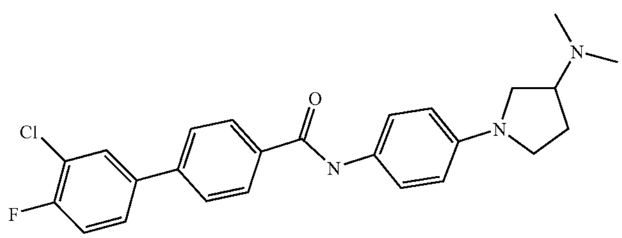 | C25H25ClFN3O | 437.17 | 438 |
| 1190 | 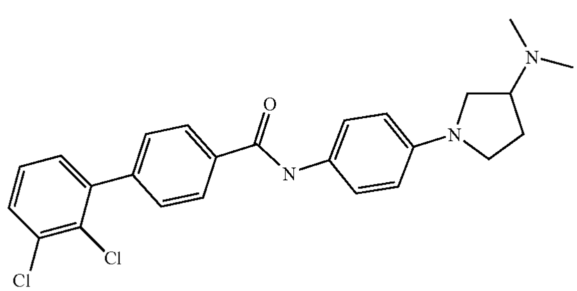 | C25H25Cl2N3O | 453.14 | 454 |
| 1191 | 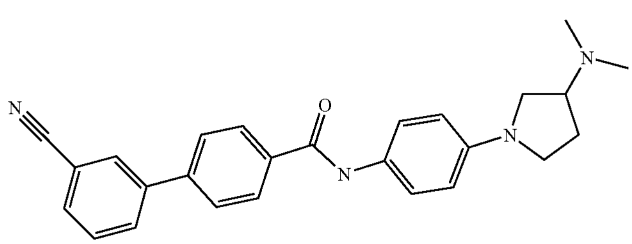 | C26H26N4O | 410.21 | 411 |

TABLE 8-continued
| Ex. No. | Structure | Molecular formula | Monoisotopic molecular wt. | M + H⁺ |
|---|---|---|---|---|
| 1192 | 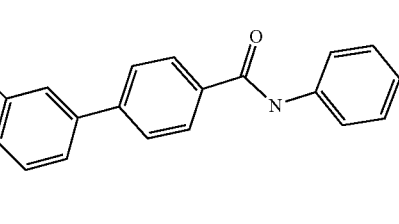 | C27H29N3O2 | 427.23 | 428 |
| 1193 | 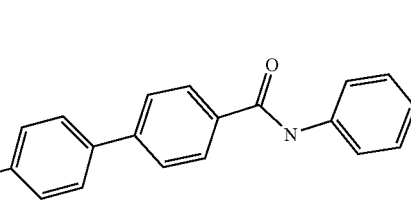 | C27H29N3O2 | 427.23 | 428 |
| 1194 | 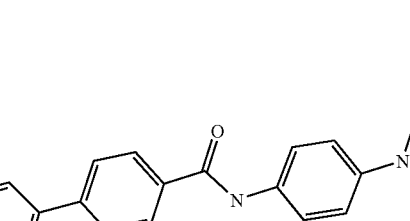 | C25H25F2N3O | 421.20 | 422 |
| 1195 | 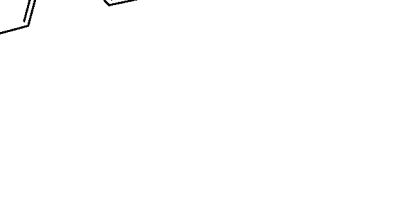 | C25H25F2N3O | 421.20 | 422 |
| 1196 | 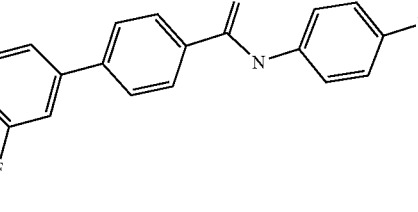 | C26H28N4O3 | 444.22 | 445 |

TABLE 8-continued

| Ex. No. | Structure | Molecular formula | Monoisotopic molecular wt. | M + H⁺ |
|---|---|---|---|---|
| 1197 | 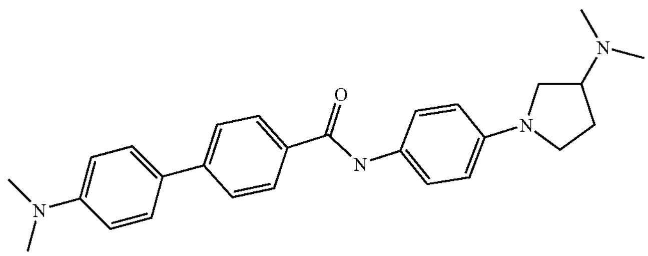 | C27H32N4O | 428.26 | 429 |
| 1198 | 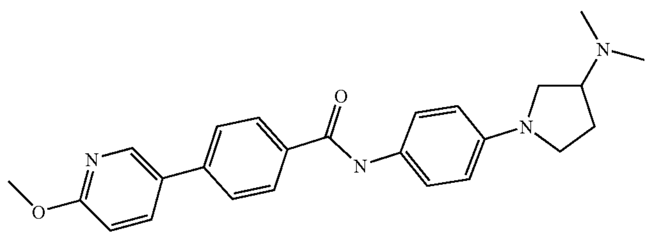 | C25H28N4O2 | 416.22 | 417 |
| 1199 | 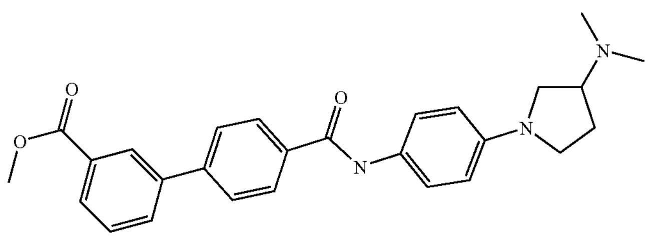 | C27H29N3O3 | 443.22 | 444 |
| 1200 | 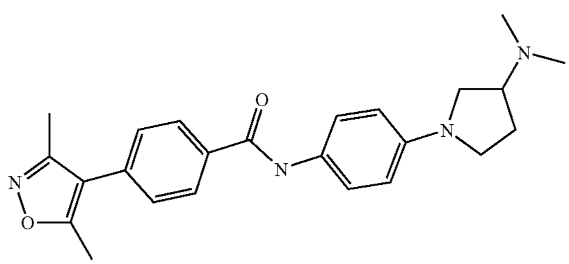 | C24H28N4O2 | 404.22 | 405 |
| 1201 | 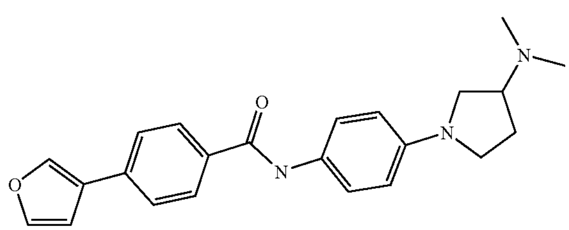 | C23H25N3O2 | 375.20 | 376 |
| 1202 | 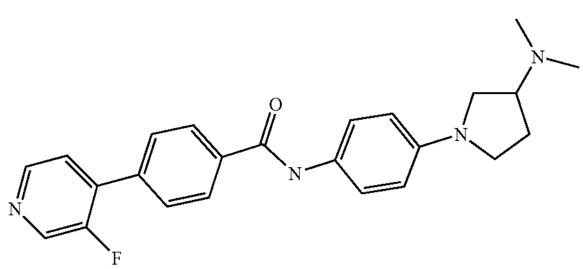 | C24H25FN4O | 404.20 | 405 |

TABLE 8-continued

| Ex. No. | Structure | Molecular formula | Monoisotopic molecular wt. | M + H⁺ |
|---|---|---|---|---|
| 1203 | 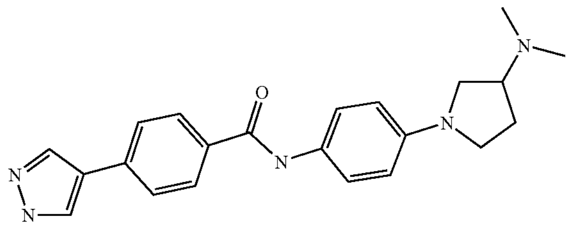 | C22H25N5O | 375.21 | 376 |
| 1204 | 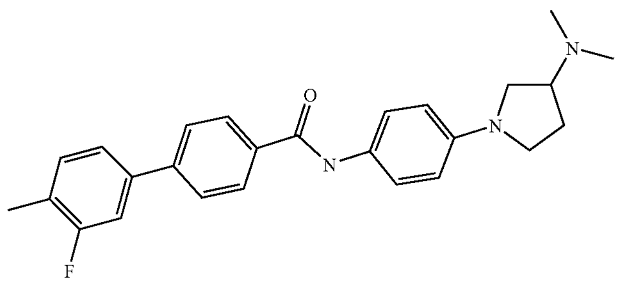 | C26H28FN3O | 417.22 | 418 |
| 1205 | 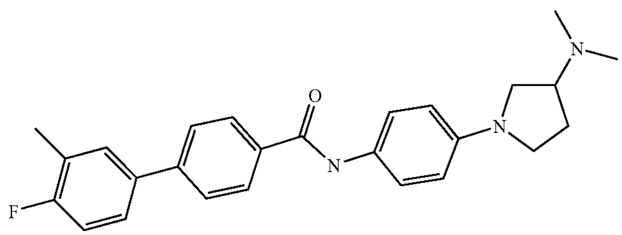 | C26H28FN3O | 417.22 | 418 |
| 1206 | 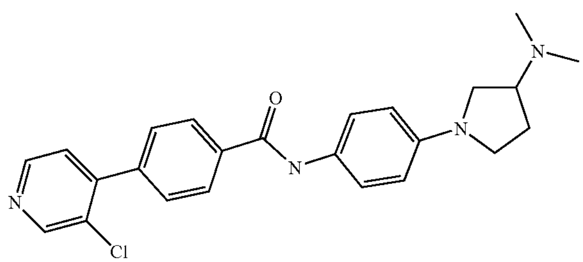 | C24H25ClN4O | 420.17 | 421 |
| 1207 | 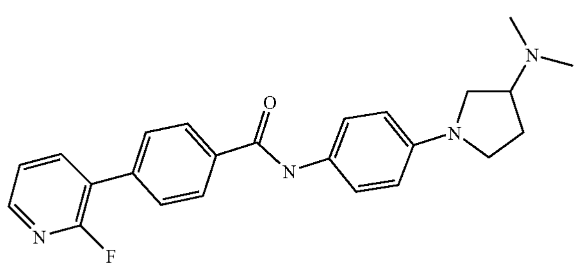 | C24H25FN4O | 404.20 | 405 |
| 1208 | 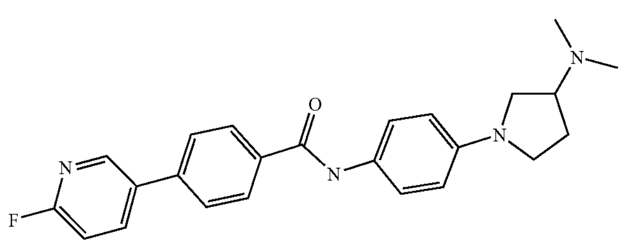 | C24H25FN4O | 404.20 | 405 |

TABLE 8-continued
| Ex. No. | Structure | Molecular formula | Monoisotopic molecular wt. | M + H⁺ |
|---|---|---|---|---|
| 1209 | 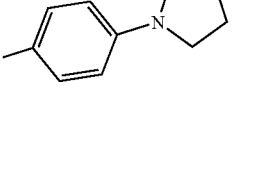 | C26H28FN3O2 | 433.22 | 434 |
| 1210 | 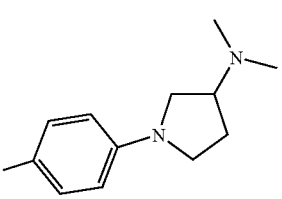 | C27H30N4O2 | 442.24 | 443 |
| 1211 | 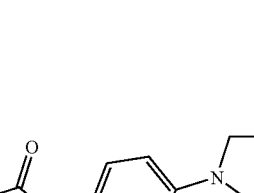 | C25H26N4O3 | 430.20 | 431 |
| 1212 | 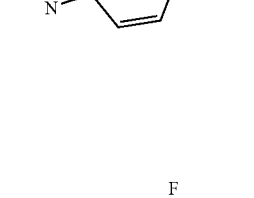 | C26H25FN4O | 428.20 | 429 |
| 1213 | 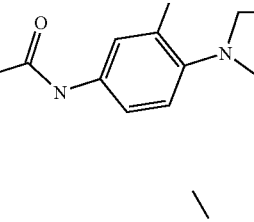 | C24H25FN4O | 404.20 | 405 |
| 1214 | 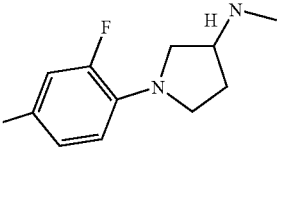 | C24H25FN4O | 404.20 | 405 |

TABLE 8-continued

| Ex. No. | Structure | Molecular formula | Monoisotopic molecular wt. | M + H+ |
|---|---|---|---|---|
| 1215 | 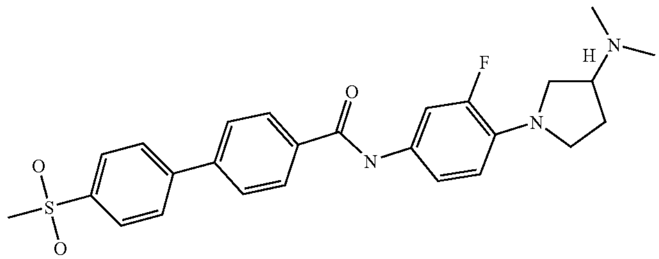 | C26H28FN3O3S | 481.18 | 482 |
| 1216 | 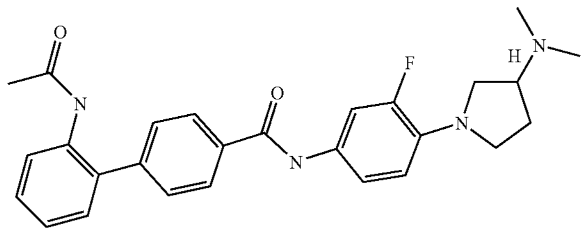 | C27H29FN4O2 | 460.23 | 461 |
| 1217 | 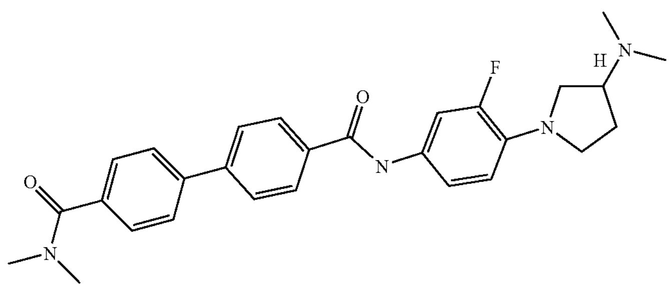 | C28H31FN4O2 | 474.24 | 475 |
| 1218 | 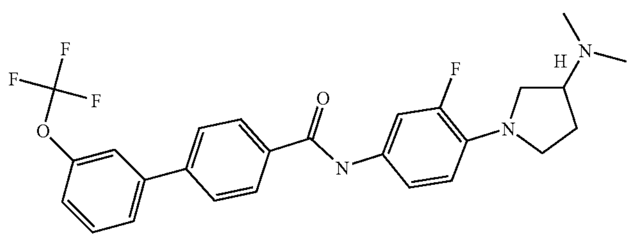 | C26H25F4N3O2 | 487.19 | 488 |
| 1219 | 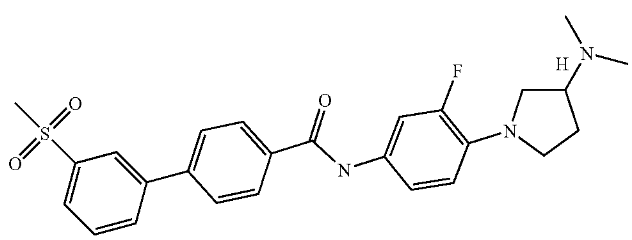 | C26H28FN3O3S | 481.18 | 482 |
| 1220 | 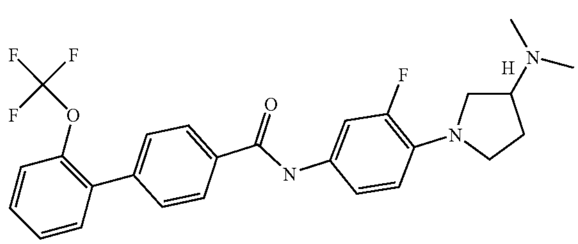 | C26H25F4N3O2 | 487.19 | 488 |

TABLE 8-continued

| Ex. No. | Structure | Molecular formula | Monoisotopic molecular wt. | M + H⁺ |
|---|---|---|---|---|
| 1221 | 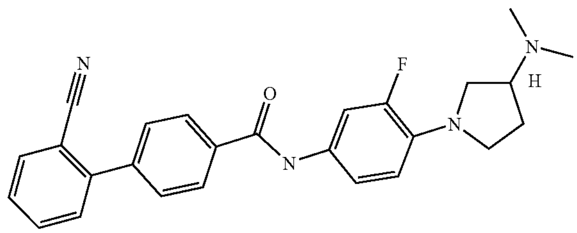 | C26H25FN4O | 428.20 | 429 |
| 1222 | 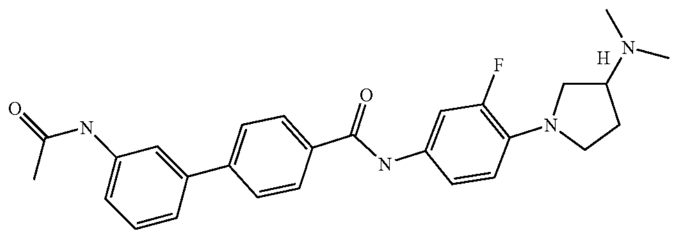 | C27H29FN4O2 | 460.23 | 461 |
| 1223 | 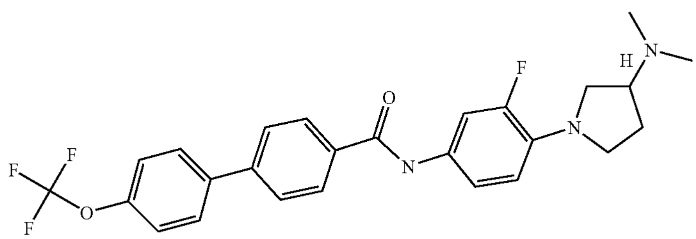 | C26H25F4N3O2 | 487.19 | 488 |
| 1224 | 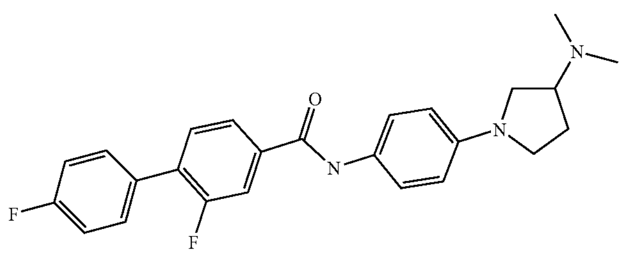 | C25H25F2N3O | 421.20 | 422 |
| 1225 | 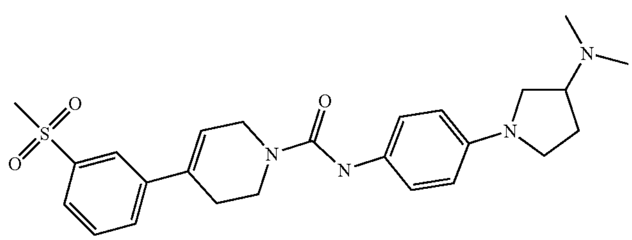 | C25H32N4O3S | 468.22 | 469 |
| 1226 | 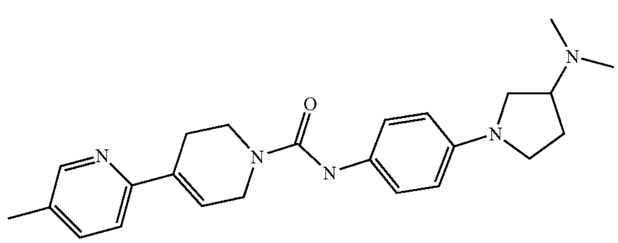 | C24H31N5O | 405.25 | 406 |

TABLE 8-continued

| Ex. No. | Structure | Molecular formula | Monoisotopic molecular wt. | M + H+ |
|---|---|---|---|---|
| 1227 | 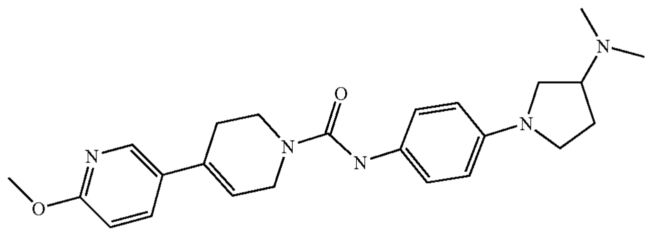 | C24H31N5O2 | 421.25 | 422 |
| 1228 | 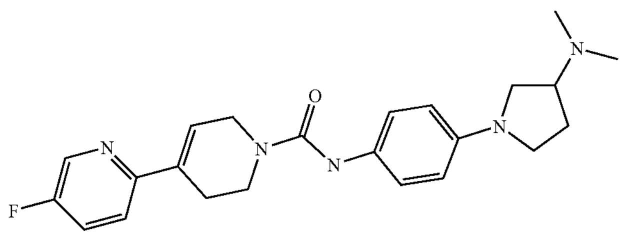 | C23H28FN5O | 409.23 | 410 |
| 1229 | 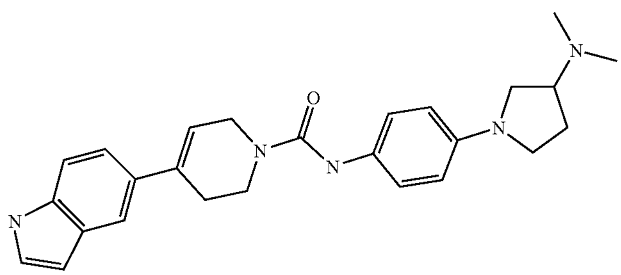 | C26H31N5O | 429.25 | 430 |
| 1230 | 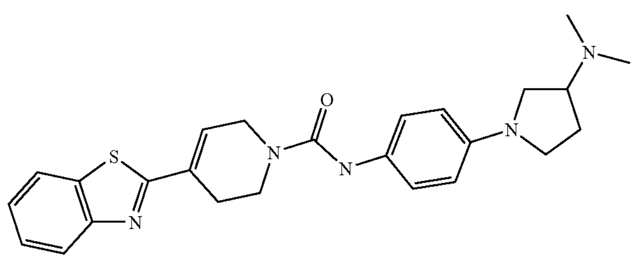 | C25H29N5OS | 447.21 | 448 |
| 1231 | 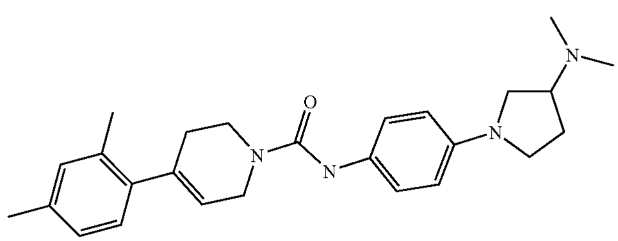 | C26H34N4O | 418.27 | 419 |
| 1232 | 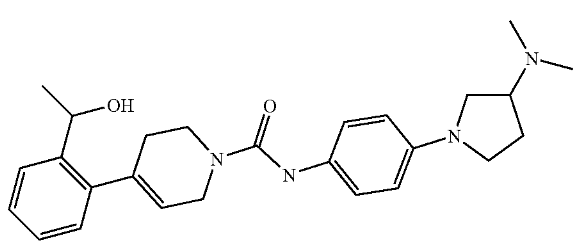 | C26H32N4O2 | 432.25 | 433 |

TABLE 9

| Ex. No. | Structure | Molecular formula | Monoisotopic molecular wt. | M + H⁺ |
| --- | --- | --- | --- | --- |
| 1233 | 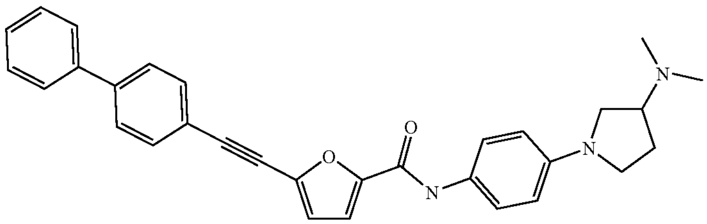 | C31H29N3O2 | 475.23 | 476 |
| 1234 | 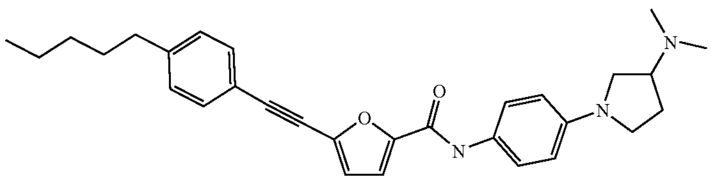 | C30H35N3O2 | 469.27 | 470 |
| 1235 | 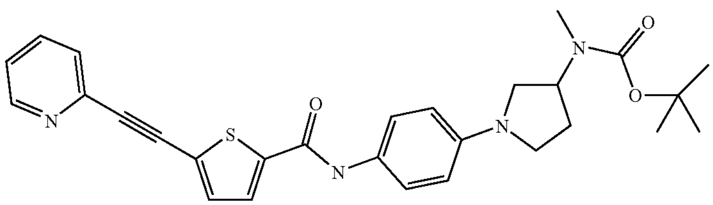 | C28H30N4O3S | 502.20 | 503 |
| 1236 | 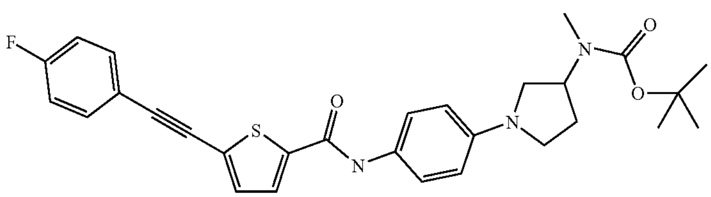 | C29H30FN3O3S | 519.20 | 520 |
| 1237 | 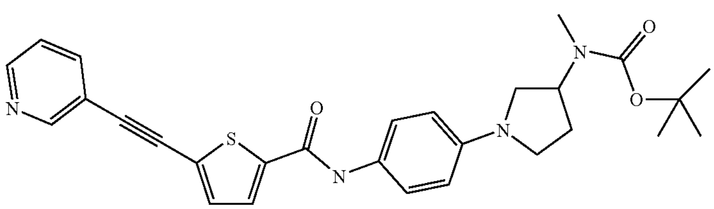 | C28H30N4O3S | 502.20 | 503 |

TABLE 10

| Ex. No. | Structure | Molecular formula | Monoisotopic molecular wt. | M + H⁺ |
| --- | --- | --- | --- | --- |
| 1238 | 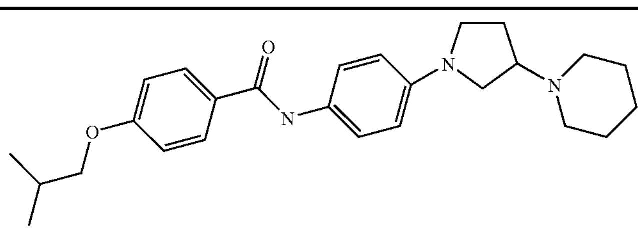 | C26H35N3O2 | 421.27 | 422 |

TABLE 10-continued
| Ex. No. | Structure | Molecular formula | Monoisotopic molecular wt. | M + H⁺ |
|---|---|---|---|---|
| 1239 | 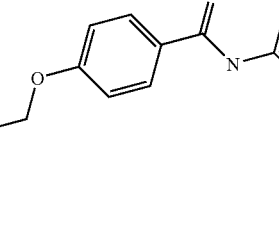 | C26H35N3O2 | 421.27 | 422 |
| 1240 | 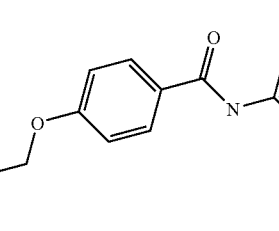 | C25H31F2N3O2 | 443.24 | 444 |
| 1241 | 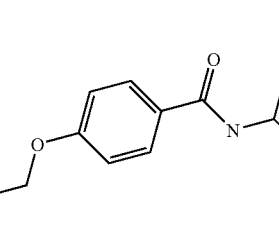 | C27H35N3O2 | 433.27 | 434 |
| 1242 | 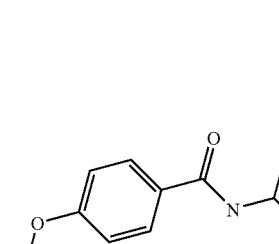 | C26H35N3O2 | 421.27 | 422 |
| 1243 | 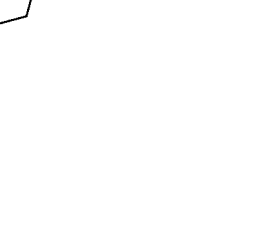 | C25H36N4O2 | 424.28 | 425 |

TABLE 10-continued
| Ex. No. | Structure | Molecular formula | Monoisotopic molecular wt. | M + H+ |
|---|---|---|---|---|
| 1244 | 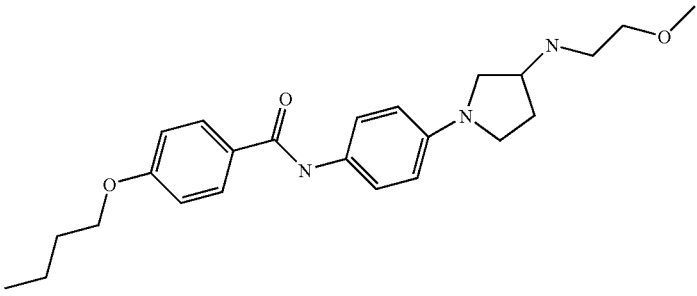 | C24H33N3O3 | 411.25 | 412 |
| 1245 | 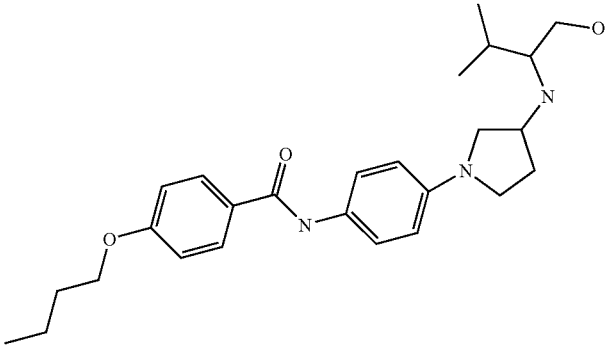 | C26H37N3O3 | 439.28 | 440 |
| 1246 | 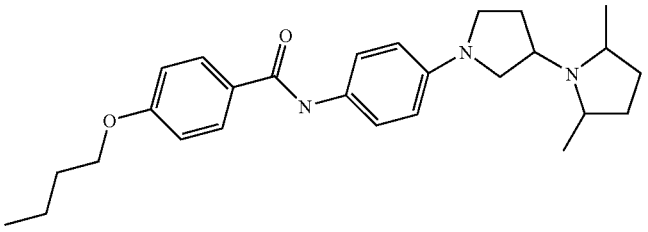 | C27H37N3O2 | 435.29 | 436 |
| 1247 | 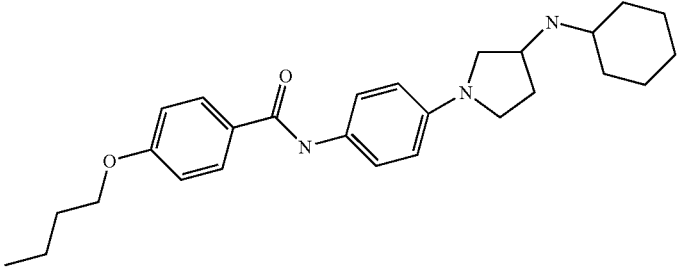 | C27H37N3O2 | 435.29 | 436 |
| 1248 | 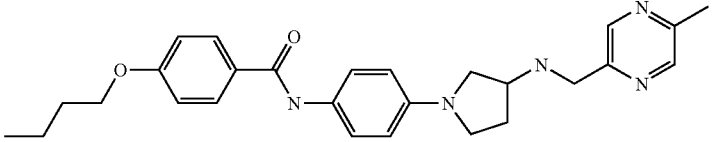 | C27H33N5O2 | 459.26 | 460 |

TABLE 10-continued

| Ex. No. | Structure | Molecular formula | Monoisotopic molecular wt. | M + H+ |
|---|---|---|---|---|
| 1249 | 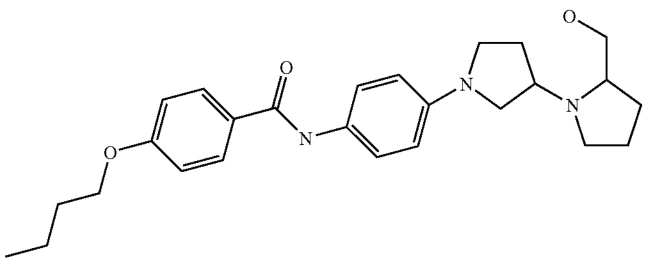 | C26H35N3O3 | 437.27 | 438 |
| 1250 | 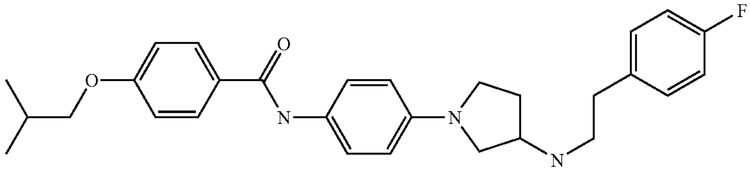 | C29H34FN3O2 | 475.26 | 476 |
| 1251 | 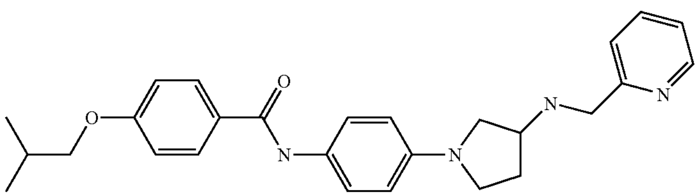 | C27H32N4O2 | 444.25 | 445 |
| 1252 | 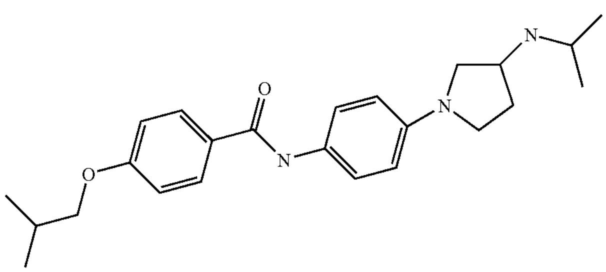 | C24H33N3O2 | 395.26 | 396 |
| 1253 | 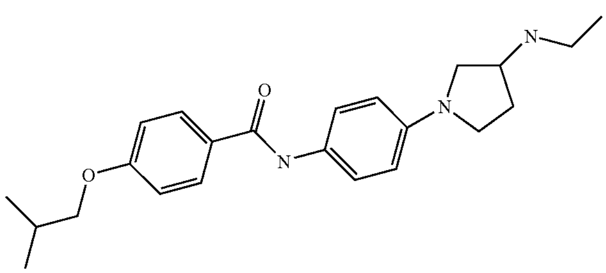 | C23H31N3O2 | 381.24 | 382 |
| 1254 | 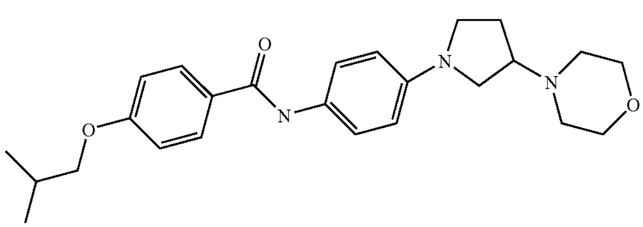 | C25H33N3O3 | 423.25 | 424 |

TABLE 10-continued

| Ex. No. | Structure | Molecular formula | Monoisotopic molecular wt. | M + H⁺ |
|---|---|---|---|---|
| 1255 | 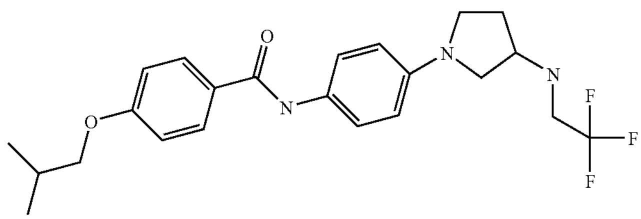 | C23H28F3N3O2 | 435.21 | 436 |
| 1256 | 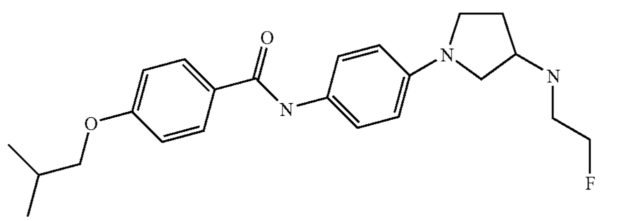 | C23H30FN3O2 | 399.23 | 400 |
| 1257 | 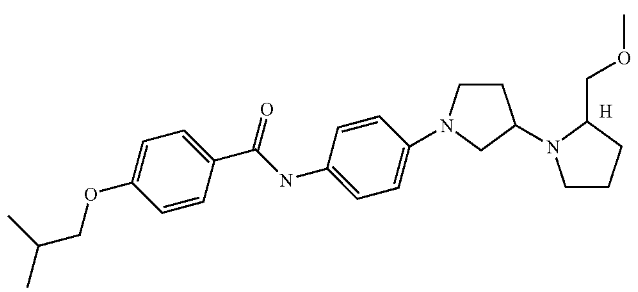 | C27H37N3O3 | 451.28 | 452 |
| 1258 | 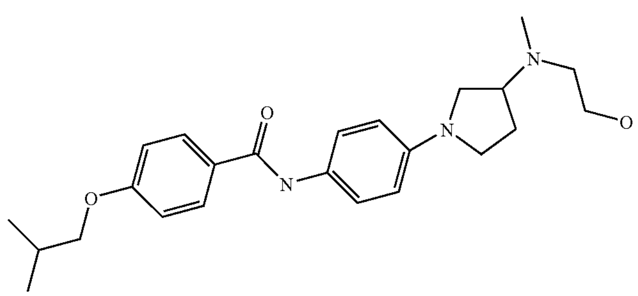 | C24H33N3O3 | 411.25 | 412 |
| 1259 | 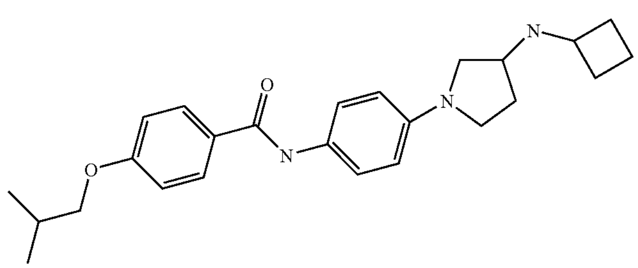 | C25H33N3O2 | 407.26 | 408 |
| 1260 | 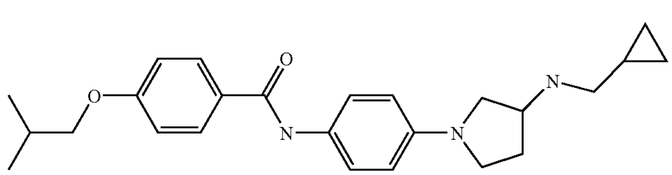 | C25H33N3O2 | 407.26 | 408 |

TABLE 10-continued

| Ex. No. | Structure | Molecular formula | Monoisotopic molecular wt. | M + H+ |
|---|---|---|---|---|
| 1261 | 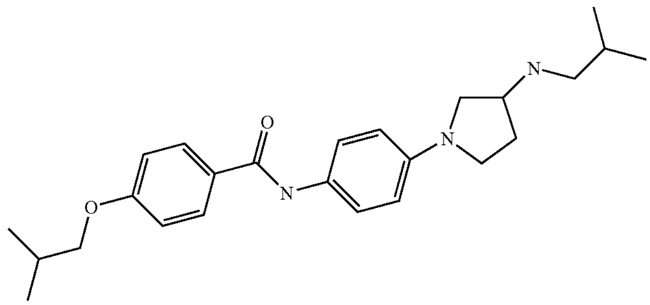 | C25H35N3O2 | 409.27 | 410 |
| 1262 | 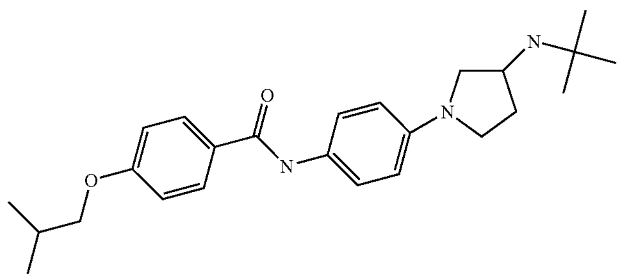 | C25H35N3O2 | 409.27 | 410 |
| 1263 | 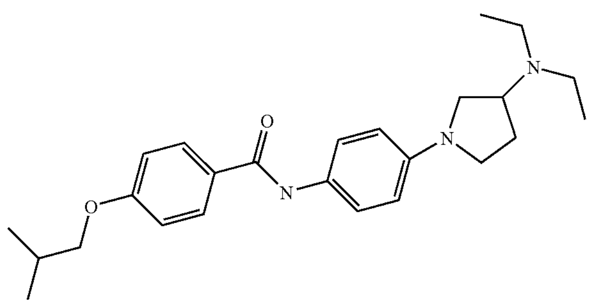 | C25H35N3O2 | 409.27 | 410 |
| 1264 | 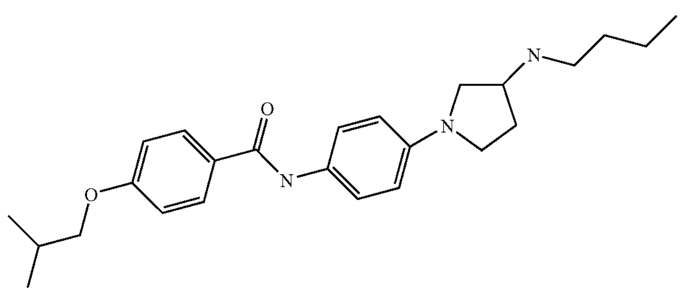 | C25H35N3O2 | 409.27 | 410 |
| 1265 | 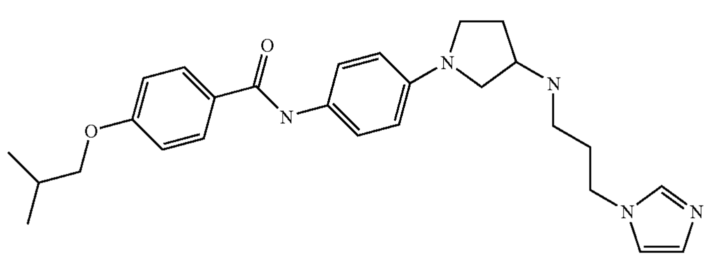 | C27H35N5O2 | 461.28 | 462 |

TABLE 10-continued
| Ex. No. | Structure | Molecular formula | Monoisotopic molecular wt. | M + H+ |
|---|---|---|---|---|
| 1266 | 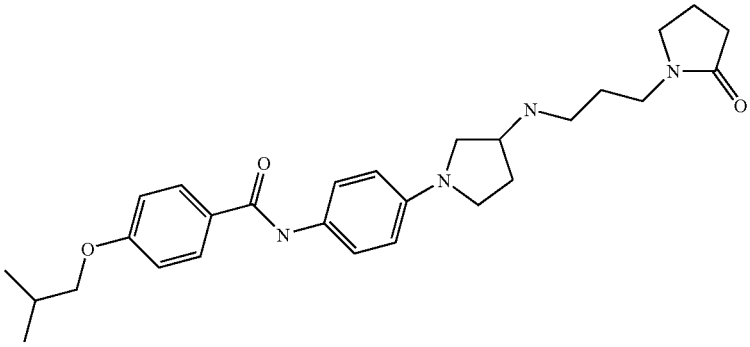 | C28H38N4O3 | 478.29 | 479 |
| 1267 | 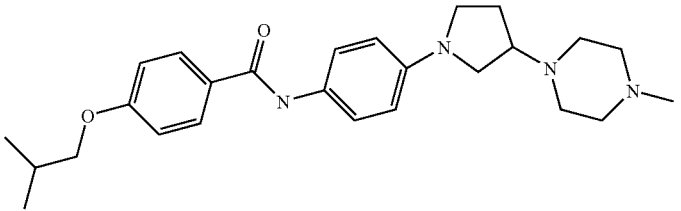 | C26H36N4O2 | 436.28 | 437 |
| 1268 | 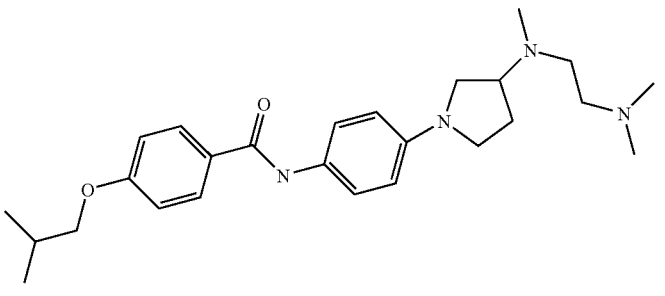 | C26H38N4O2 | 438.30 | 439 |
| 1269 | 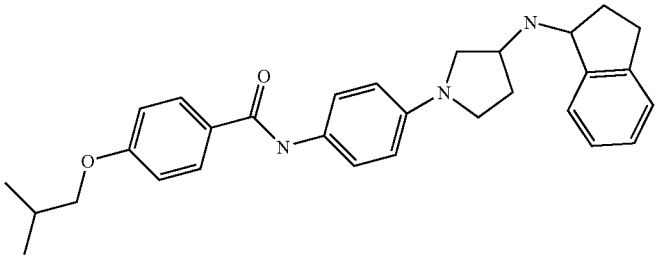 | C30H35N3O2 | 469.27 | 470 |
| 1270 | 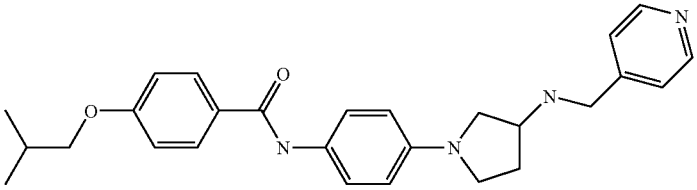 | C27H32N4O2 | 444.25 | 445 |
| 1271 | 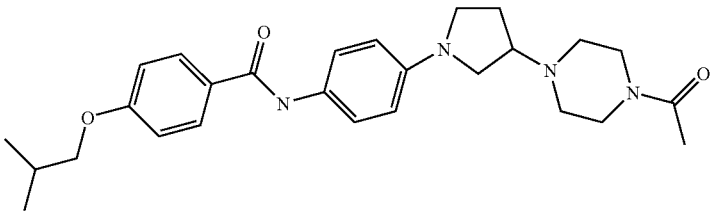 | C27H36N4O3 | 464.28 | 465 |

TABLE 10-continued

| Ex. No. | Structure | Molecular formula | Monoisotopic molecular wt. | M + H+ |
|---|---|---|---|---|
| 1272 | 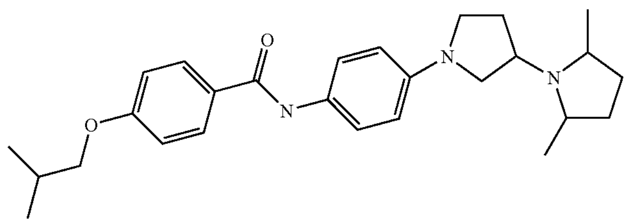 | C27H37N3O2 | 435.29 | 436 |
| 1273 | 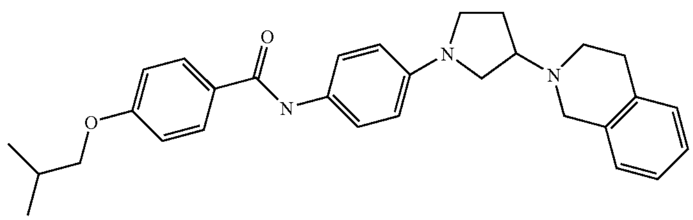 | C30H35N3O2 | 469.27 | 470 |
| 1274 | 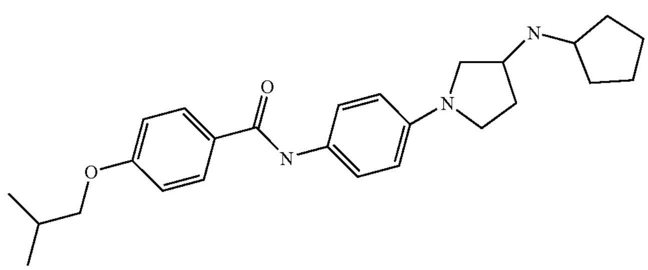 | C26H35N3O2 | 421.27 | 422 |
| 1275 | 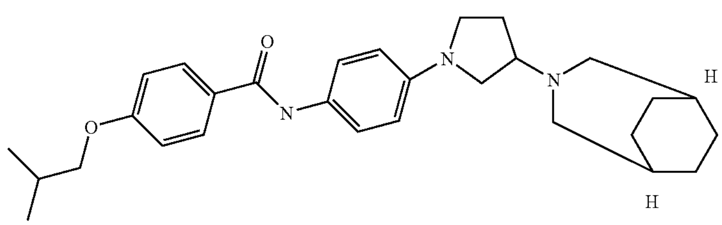 | C29H39N3O2 | 461.30 | 462 |
| 1276 | 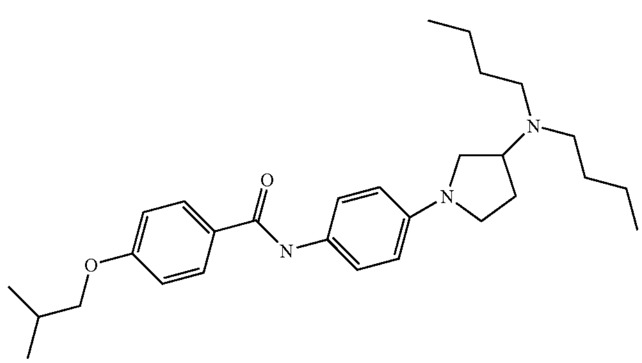 | C29H43N3O2 | 465.34 | 466 |
| 1277 | 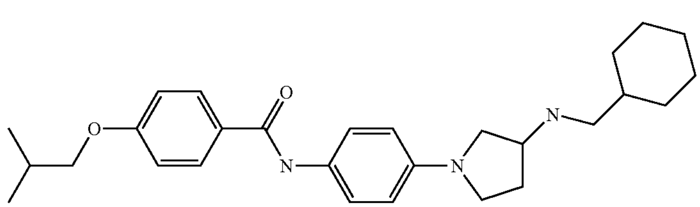 | C28H39N3O2 | 449.30 | 450 |

TABLE 10-continued
| Ex. No. | Structure | Molecular formula | Monoisotopic molecular wt. | M + H+ |
|---|---|---|---|---|
| 1278 | 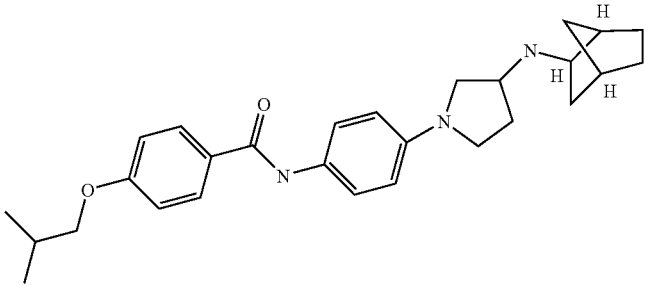 | C28H37N3O2 | 447.29 | 448 |
| 1279 | 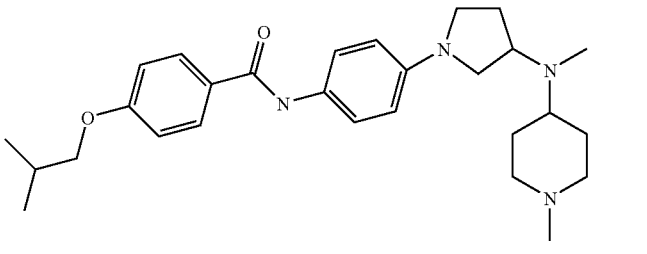 | C28H40N4O2 | 464.32 | 465 |
| 1280 | 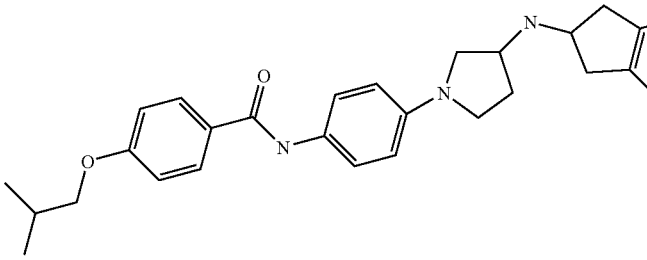 | C30H35N3O2 | 469.27 | 470 |
| 1281 | 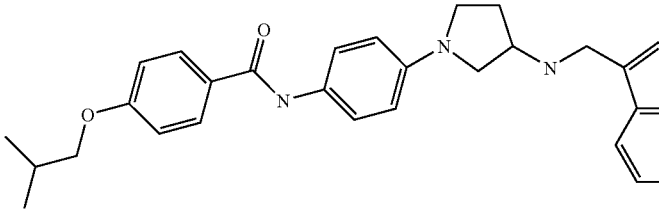 | C30H34N4O2 | 482.27 | 483 |
| 1282 | 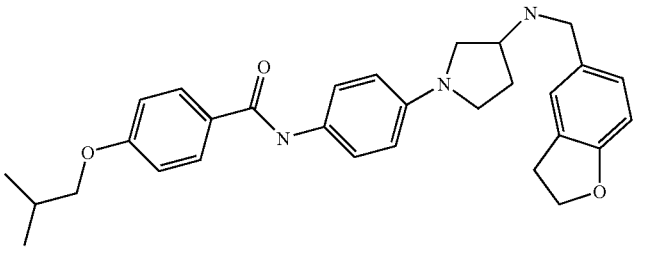 | C30H35N3O3 | 485.27 | 486 |
| 1283 | 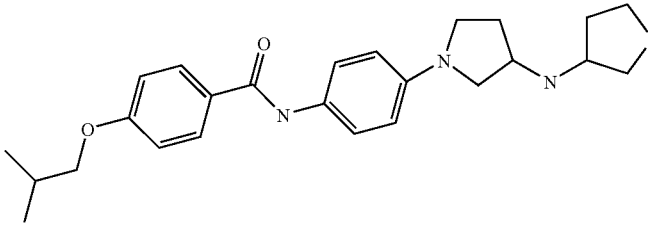 | C25H33N3O4S | 471.22 | 472 |

TABLE 10-continued
| Ex. No. | Structure | Molecular formula | Monoisotopic molecular wt. | M + H+ |
|---|---|---|---|---|
| 1284 | 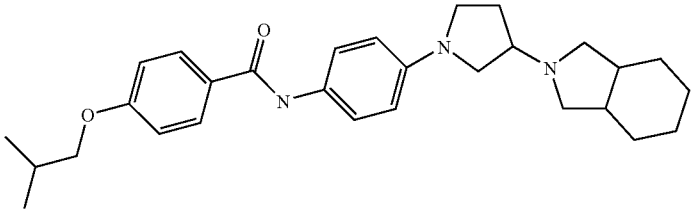 | C29H39N3O2 | 461.30 | 462 |
| 1285 | 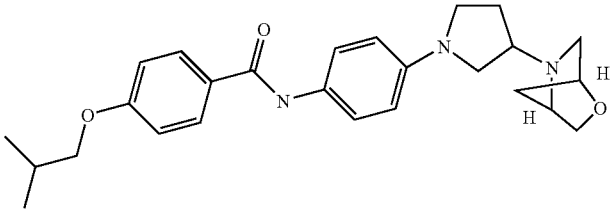 | C26H33N3O3 | 435.25 | 436 |
| 1286 | 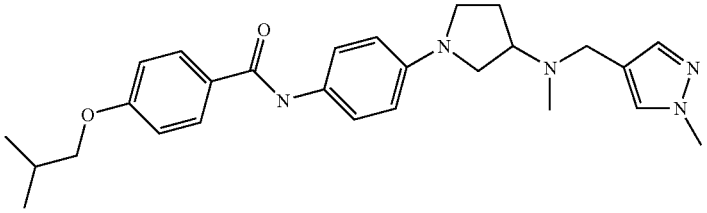 | C27H35N5O2 | 461.28 | 462 |
| 1287 | 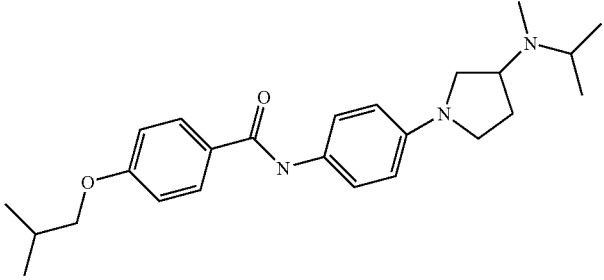 | C25H35N3O2 | 409.27 | 410 |
| 1288 | 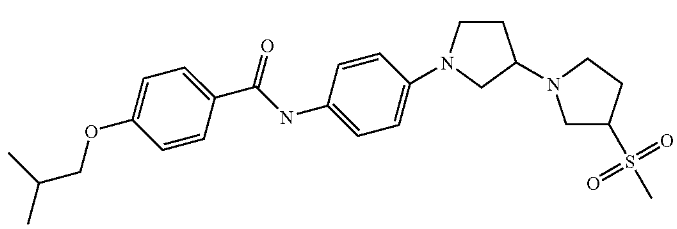 | C26H35N3O4S | 485.23 | 486 |
| 1289 | 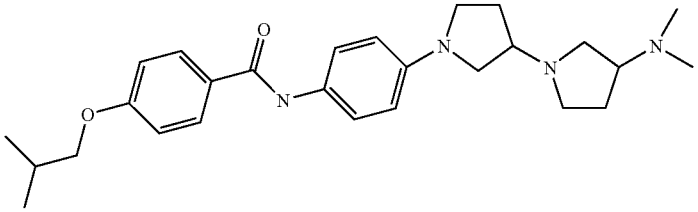 | C27H38N4O2 | 450.30 | 451 |

TABLE 10-continued

| Ex. No. | Structure | Molecular formula | Monoisotopic molecular wt. | M + H+ |
|---|---|---|---|---|
| 1290 | 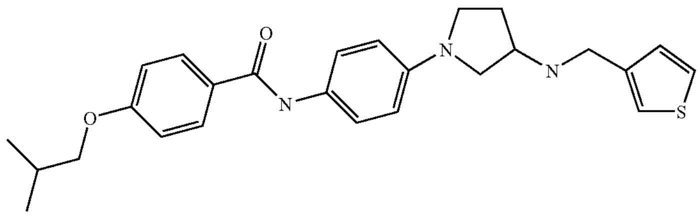 | C26H31N3O2S | 449.21 | 450 |
| 1291 | 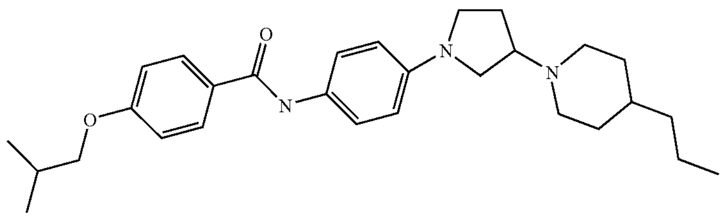 | C29H41N3O2 | 463.32 | 464 |
| 1292 | 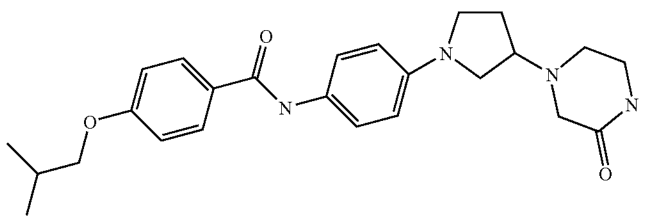 | C25H32N4O3 | 436.25 | 437 |
| 1293 | 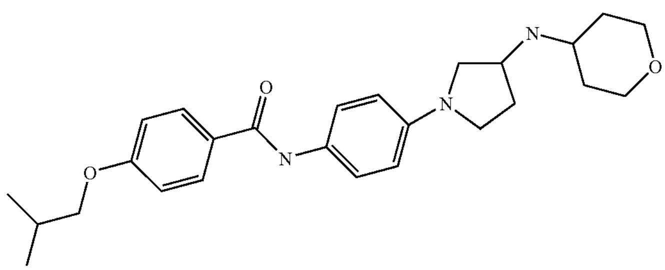 | C26H35N3O3 | 437.27 | 438 |
| 1294 | 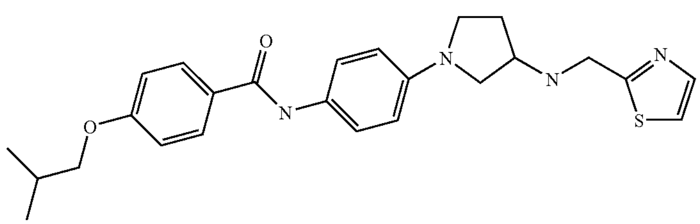 | C25H30N4O2S | 450.21 | 451 |
| 1295 | 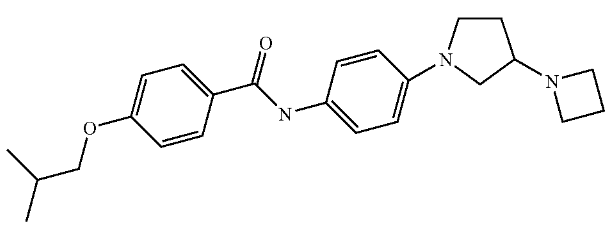 | C24H31N3O2 | 393.24 | 394 |
| 1296 | 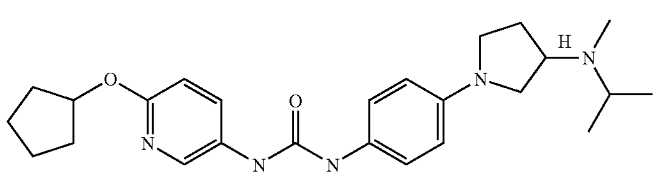 | C25H35N5O2 | 437.28 | 438 |

TABLE 10-continued
| Ex. No. | Structure | Molecular formula | Monoisotopic molecular wt. | M + H+ |
|---|---|---|---|---|
| 1297 | 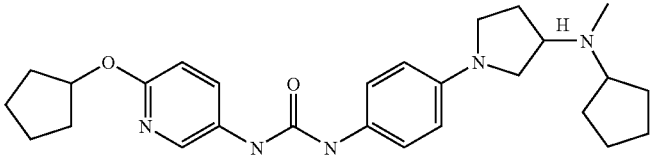 | C27H37N5O2 | 463.30 | 464 |
| 1298 | 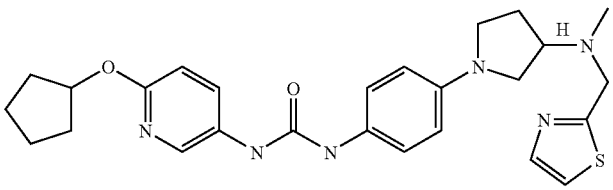 | C26H32N6O2S | 492.23 | 493 |
| 1299 | 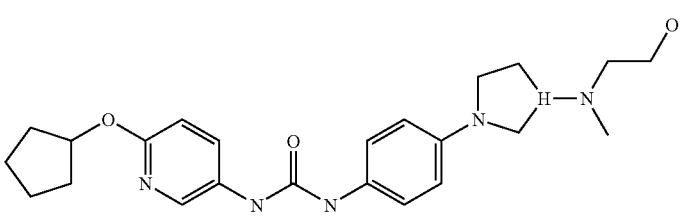 | C24H33N5O3 | 439.26 | 440 |
| 1300 | 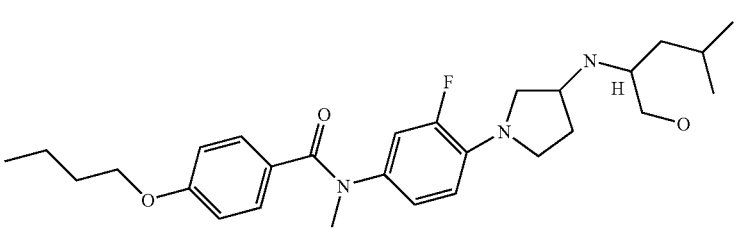 | C28H40FN3O3 | 485.30 | 486 |
| 1301 | 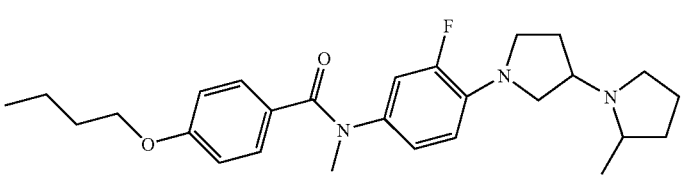 | C27H36FN3O2 | 453.28 | 454 |
| 1302 | 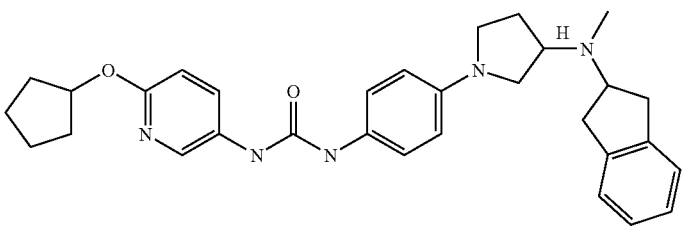 | C31H37N5O2 | 511.30 | 512 |
| 1303 | 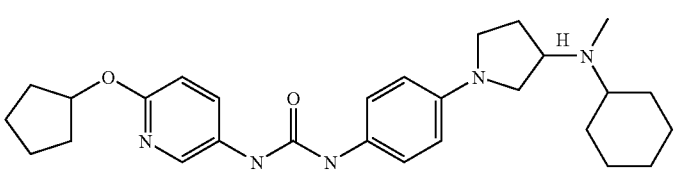 | C28H39N5O2 | 477.31 | 478 |

TABLE 10-continued

| Ex. No. | Structure | Molecular formula | Monoisotopic molecular wt. | M + H+ |
|---|---|---|---|---|
| 1304 | 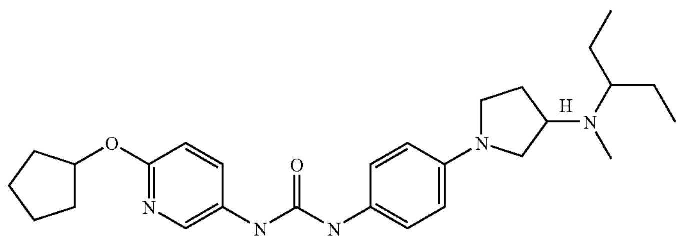 | C27H39N5O2 | 465.31 | 466 |
| 1305 | 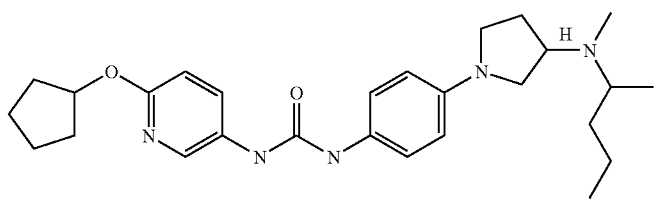 | C27H39N5O2 | 465.31 | 466 |
| 1306 | 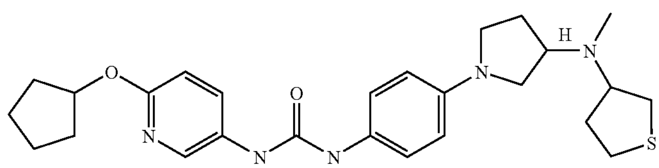 | C26H35N5O2S | 481.25 | 482 |
| 1307 | 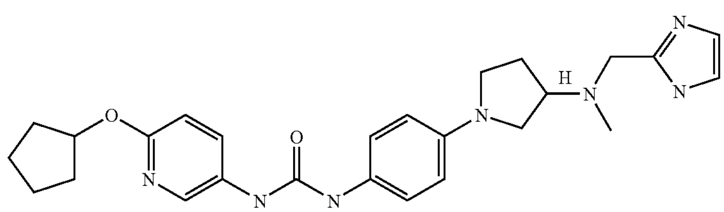 | C26H33N7O2 | 475.27 | 476 |
| 1308 | 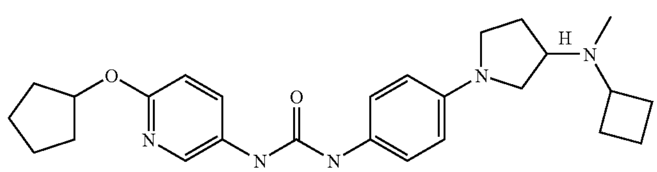 | C26H35N5O2 | 449.28 | 450 |
| 1309 | 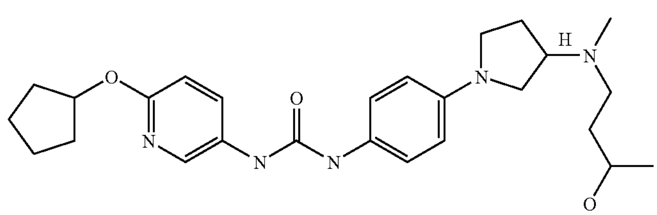 | C26H37N5O3 | 467.29 | 468 |
| 1310 | 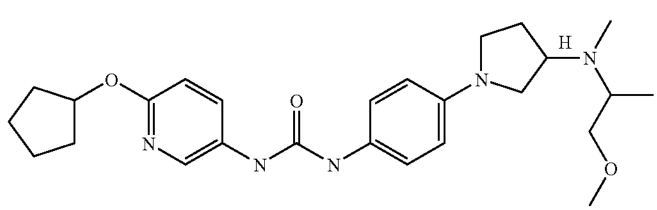 | C26H37N5O3 | 467.29 | 468 |

TABLE 10-continued

| Ex. No. | Structure | Molecular formula | Monoisotopic molecular wt. | M + H⁺ |
|---|---|---|---|---|
| 1311 | 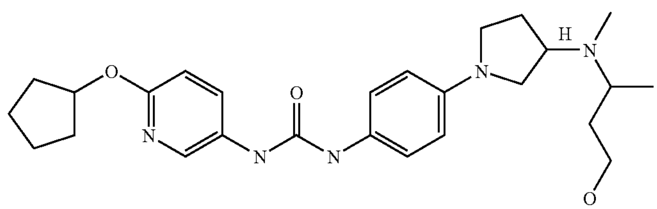 | C26H37N5O3 | 467.29 | 468 |
| 1312 | 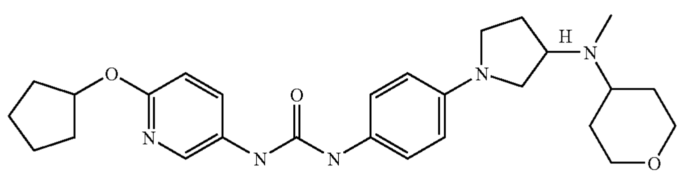 | C27H37N5O3 | 479.29 | 480 |
| 1313 | 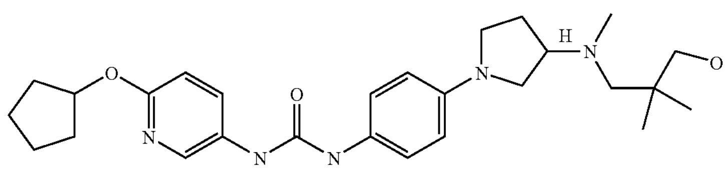 | C27H39N5O3 | 481.30 | 482 |
| 1314 | 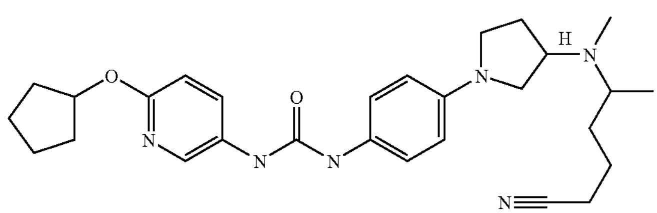 | C28H38N6O2 | 490.31 | 491 |
| 1315 | 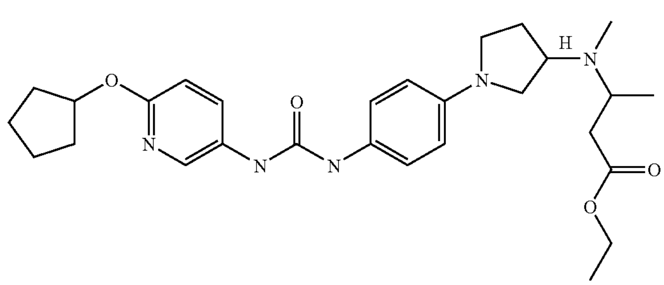 | C28H39N5O4 | 509.30 | 510 |
| 1316 | 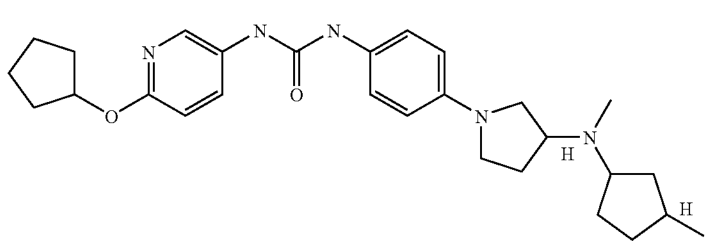 | C28H39N5O2 | 477.31 | 478 |

TABLE 10-continued

| Ex. No. | Structure | Molecular formula | Monoisotopic molecular wt. | M + H+ |
|---|---|---|---|---|
| 1317 | 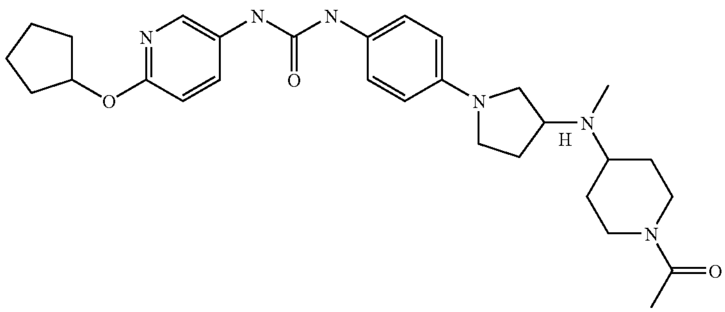 | C29H40N6O3 | 520.32 | 521 |
| 1318 | 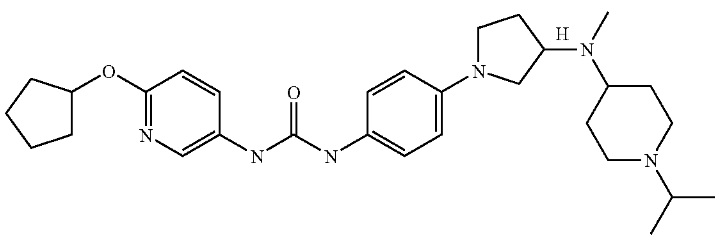 | C30H44N6O2 | 520.35 | 521 |
| 1319 | 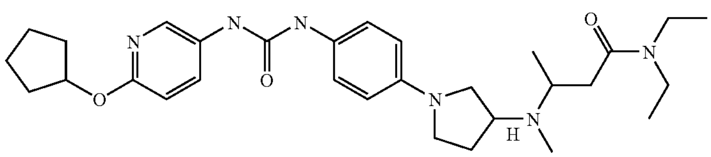 | C30H44N6O3 | 536.35 | 537 |
| 1320 | 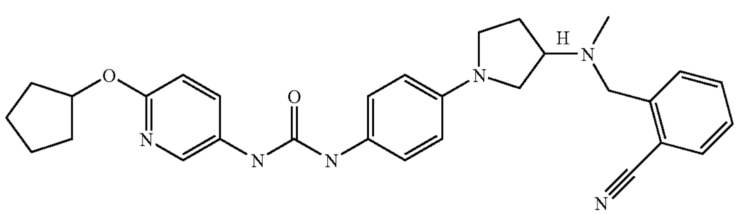 | C30H34N6O2 | 510.27 | 511 |
| 1321 | 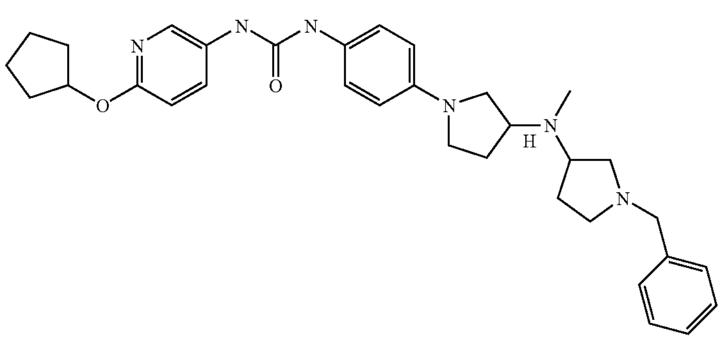 | C33H42N6O2 | 554.34 | 555 |
| 1322 | 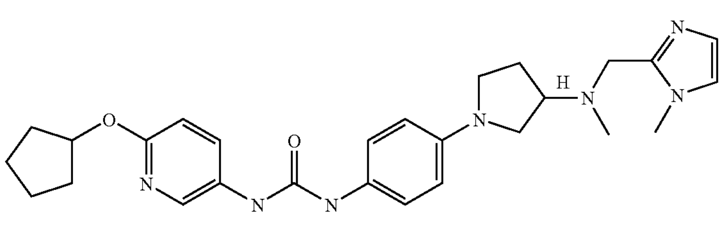 | C27H35N7O2 | 489.29 | 490 |

TABLE 10-continued
| Ex. No. | Structure | Molecular formula | Monoisotopic molecular wt. | M + H+ |
|---|---|---|---|---|
| 1323 | 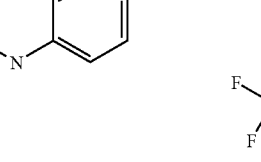 | C29H38F3N5O2 | 545.30 | 546 |
| 1324 | 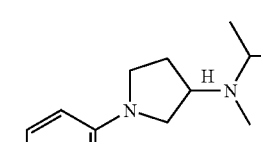 | C29H39N7O2 | 517.32 | 518 |
| 1325 | 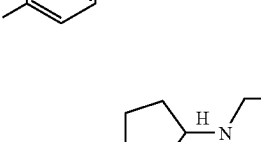 | C31H37N7O2 | 539.30 | 540 |
| 1326 | 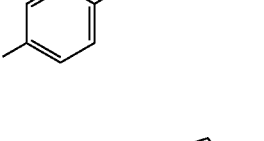 | C26H33N7O2 | 475.27 | 476 |
| 1327 | 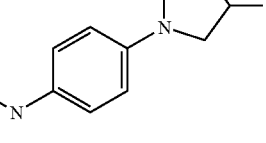 | C26H37N5O2S | 483.27 | 484 |
| 1328 | 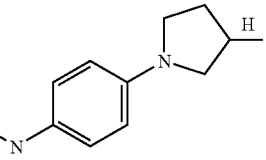 | C26H35N5O2 | 449.28 | 450 |
| 1329 | 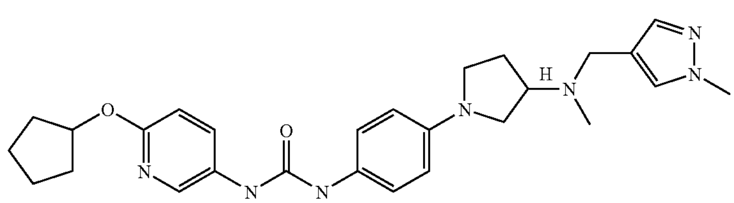 | C27H35N7O2 | 489.29 | 490 |

TABLE 10-continued

| Ex. No. | Structure | Molecular formula | Monoisotopic molecular wt. | M + H+ |
|---|---|---|---|---|
| 1330 | 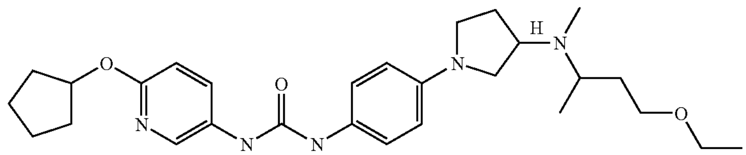 | C28H41N5O3 | 495.32 | 496 |
| 1331 | 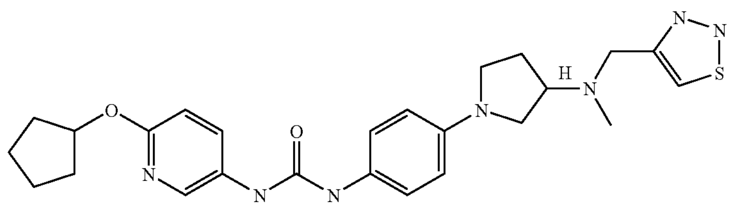 | C25H31N7O2S | 493.23 | 494 |
| 1332 | 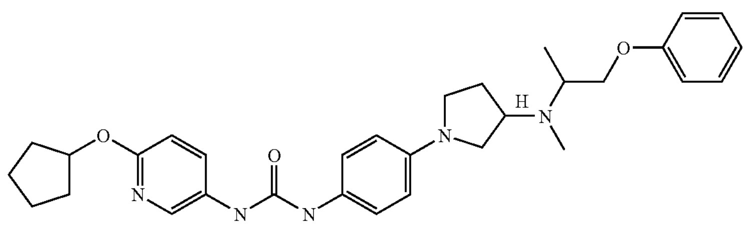 | C31H39N5O3 | 529.30 | 530 |
| 1333 | 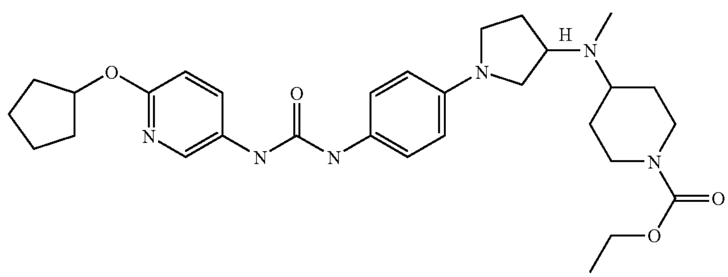 | C30H42N6O4 | 550.33 | 551 |
| 1334 | 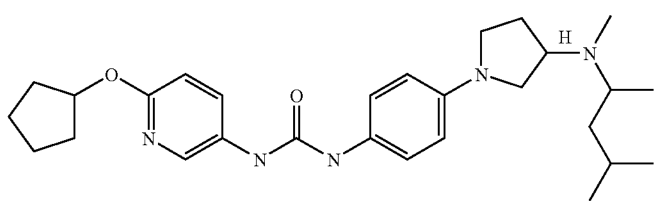 | C28H41N5O2 | 479.33 | 480 |
| 1335 | 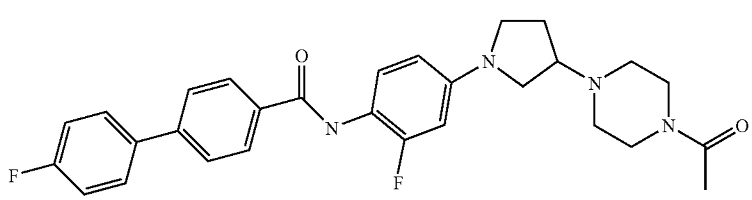 | C29H30F2N4O2 | 504.58 | 505 |
| 1336 | 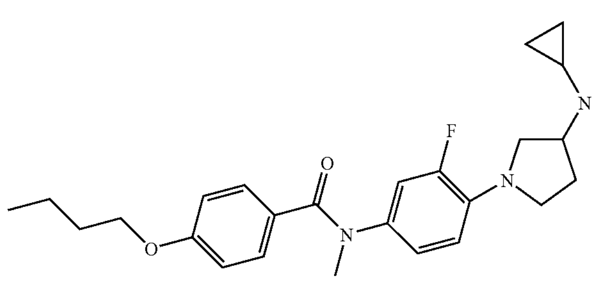 | C25H32FN3O2 | 425.25 | 426 |

TABLE 10-continued

| Ex. No. | Structure | Molecular formula | Monoisotopic molecular wt. | M + H⁺ |
|---|---|---|---|---|
| 1337 | 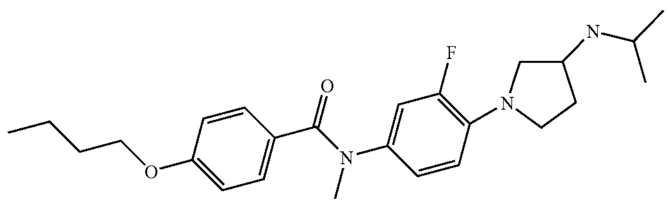 | C25H34FN3O2 | 427.26 | 428 |
| 1338 | 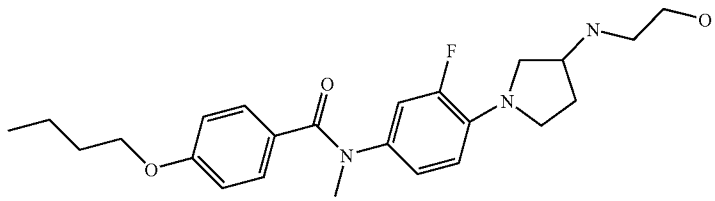 | C24H32FN3O3 | 429.24 | 430 |
| 1339 | 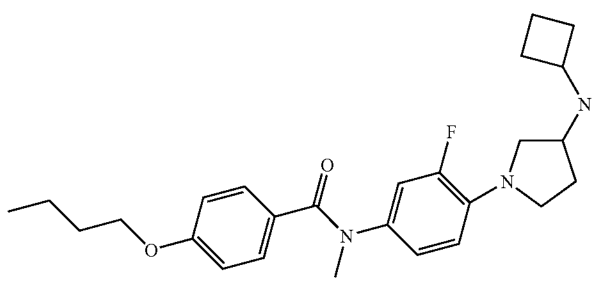 | C26H34FN3O2 | 439.26 | 440 |
| 1340 | 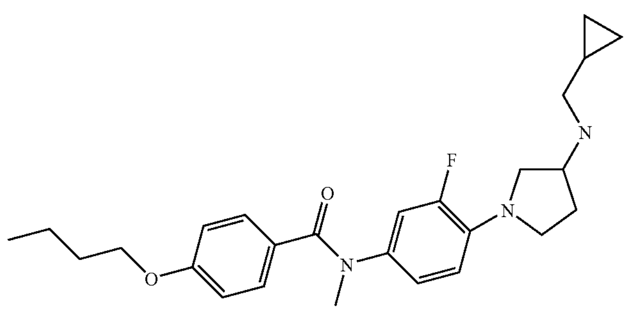 | C26H34FN3O2 | 439.26 | 440 |
| 1341 | 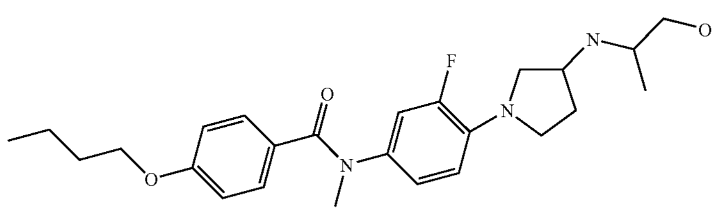 | C25H34FN3O3 | 443.26 | 444 |
| 1342 | 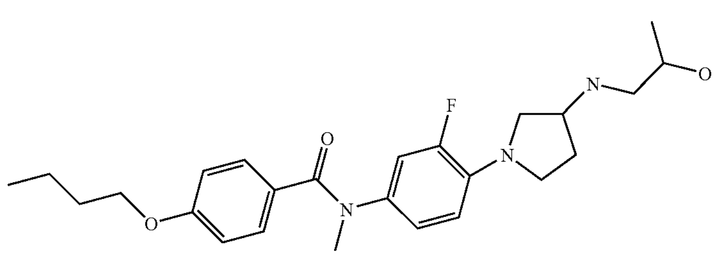 | C25H34FN3O3 | 443.26 | 444 |

TABLE 10-continued

| Ex. No. | Structure | Molecular formula | Monoisotopic molecular wt. | M + H⁺ |
|---|---|---|---|---|
| 1343 | 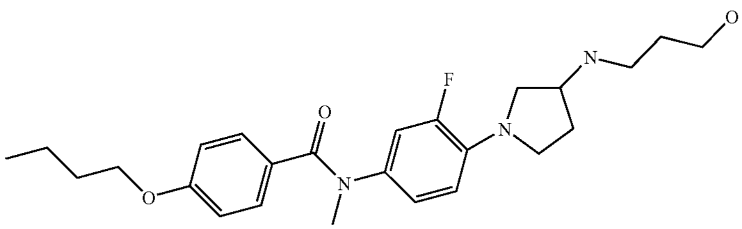 | C25H34FN3O3 | 443.26 | 444 |
| 1344 | 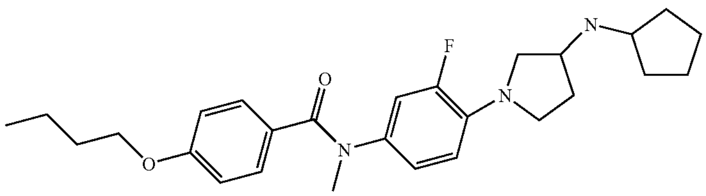 | C27H36FN3O2 | 453.28 | 454 |
| 1345 | 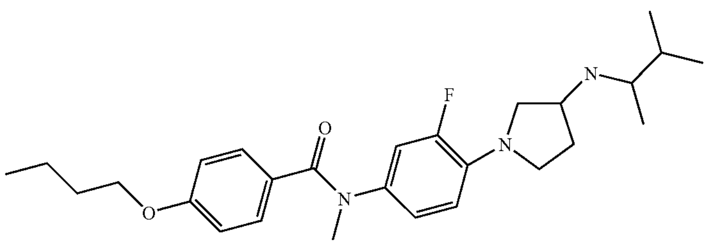 | C27H38FN3O2 | 455.30 | 456 |
| 1346 | 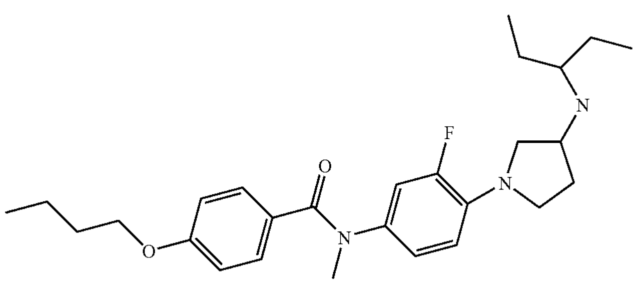 | C27H38FN3O2 | 455.30 | 456 |
| 1347 | 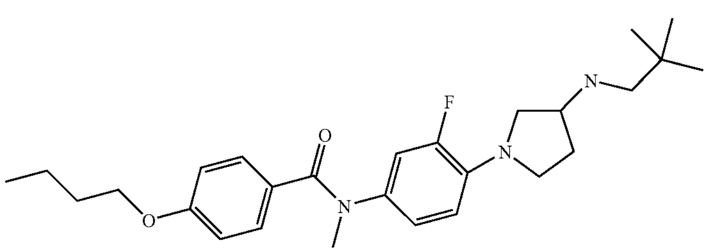 | C27H38FN3O2 | 455.30 | 456 |
| 1348 | 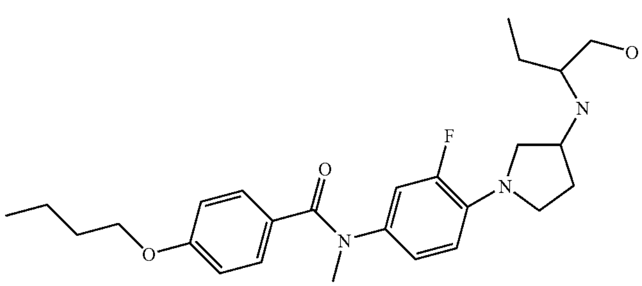 | C26H36FN3O3 | 457.27 | 458 |

TABLE 10-continued
| Ex. No. | Structure | Molecular formula | Monoisotopic molecular wt. | M + H+ |
|---|---|---|---|---|
| 1349 | 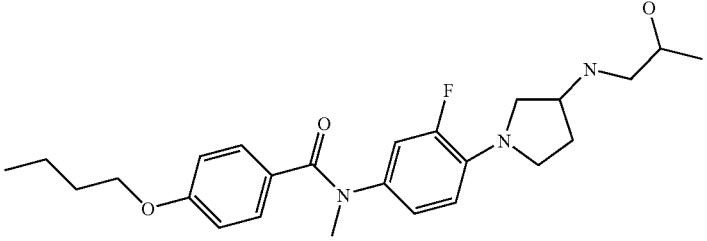 | C26H36FN3O3 | 457.27 | 458 |
| 1350 | 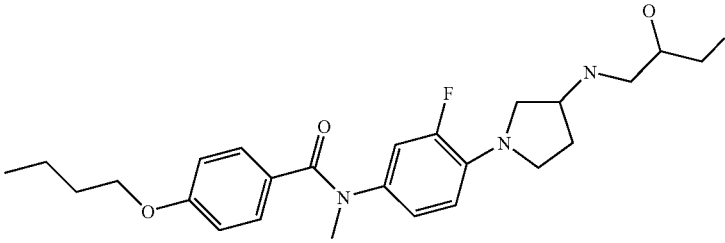 | C25H34FN3O4 | 459.25 | 460 |
| 1351 | 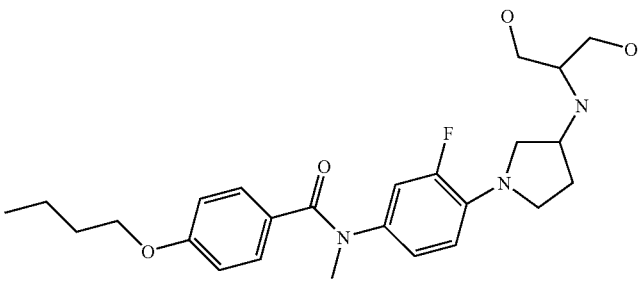 | C25H34FN3O4 | 459.25 | 460 |
| 1352 | 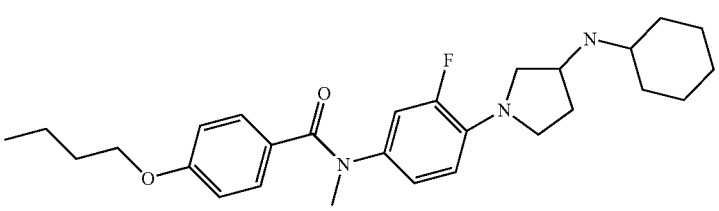 | C28H38FN3O2 | 467.30 | 468 |
| 1353 | 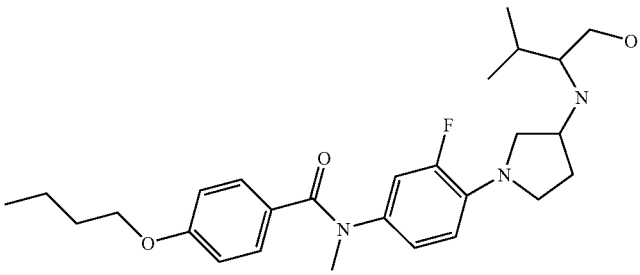 | C27H38FN3O3 | 471.29 | 472 |
| 1354 | 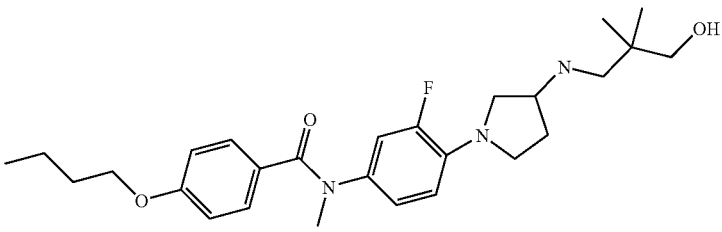 | C27H38FN3O3 | 471.29 | 472 |

TABLE 10-continued
| Ex. No. | Structure | Molecular formula | Monoisotopic molecular wt. | M + H⁺ |
|---|---|---|---|---|
| 1355 | 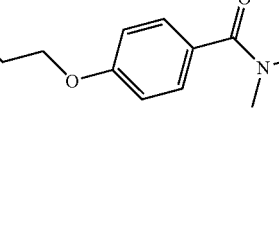 | C27H34FN5O2 | 479.27 | 480 |
| 1356 | 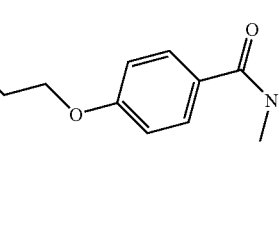 | C29H40FN3O2 | 481.31 | 482 |
| 1357 | 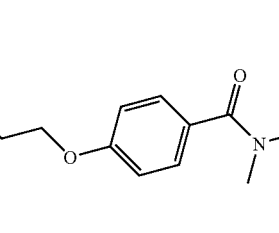 | C29H40FN3O2 | 481.31 | 482 |
| 1358 | 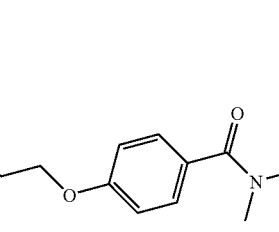 | C28H39FN4O2 | 482.31 | 483 |
| 1359 | 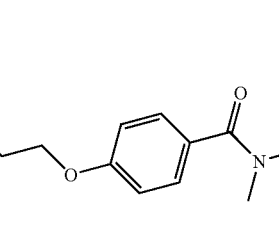 | C28H38FN3O3 | 483.29 | 484 |
| 1360 | 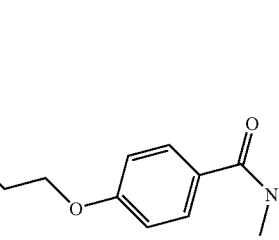 | C28H38FN3O3 | 483.29 | 484 |

TABLE 10-continued
| Ex. No. | Structure | Molecular formula | Monoisotopic molecular wt. | M + H⁺ |
|---|---|---|---|---|
| 1361 | 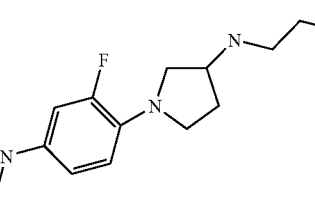 | C28H36FN5O2 | 493.29 | 494 |
| 1362 | 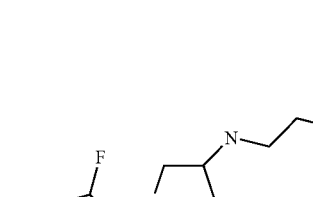 | C27H35FN6O2 | 494.28 | 495 |
| 1363 | 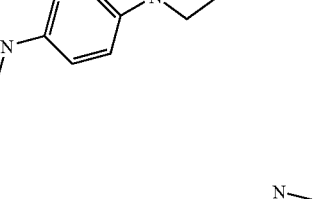 | C28H37FN4O3 | 496.29 | 497 |
| 1364 | 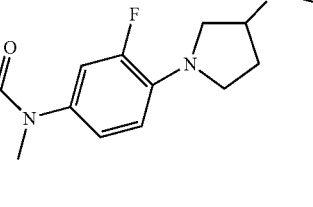 | C29H41FN4O2 | 496.32 | 497 |
| 1365 | 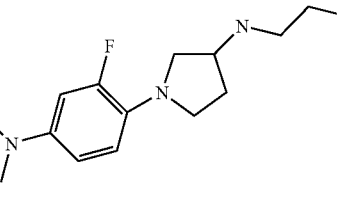 | C28H39FN4O3 | 498.30 | 499 |
| 1366 | 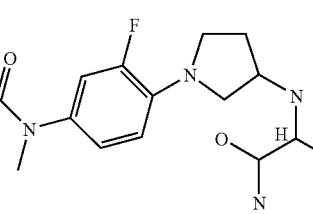 | C26H32FN3O4 | 469.24 | 470 |

TABLE 10-continued

| Ex. No. | Structure | Molecular formula | Monoisotopic molecular wt. | M + H+ |
|---|---|---|---|---|
| 1367 | 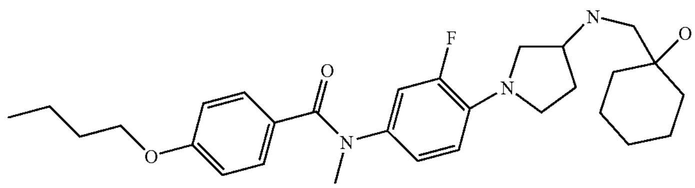 | C29H40FN3O3 | 497.30 | 498 |
| 1368 | 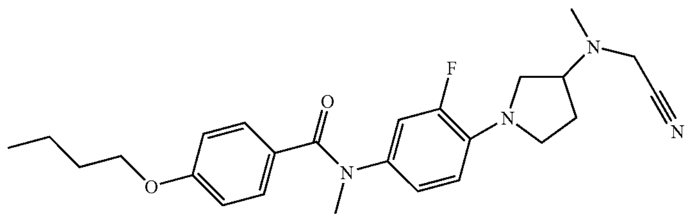 | C25H31FN4O2 | 438.24 | 439 |
| 1369 | 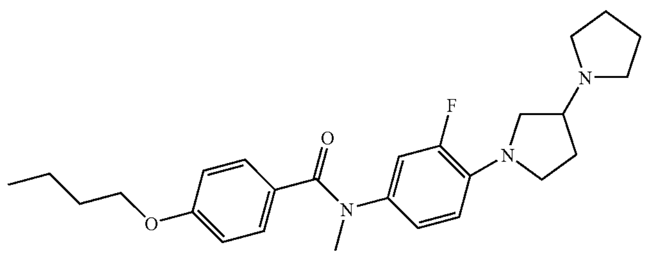 | C26H34FN3O2 | 439.26 | 440 |
| 1370 | 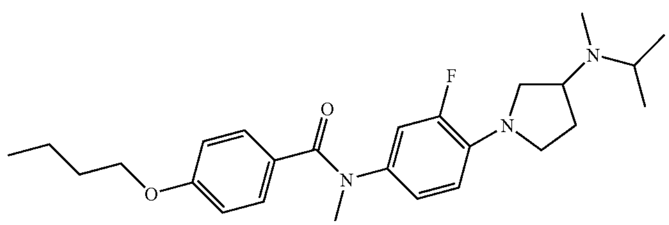 | C26H36FN3O2 | 441.28 | 442 |
| 1371 | 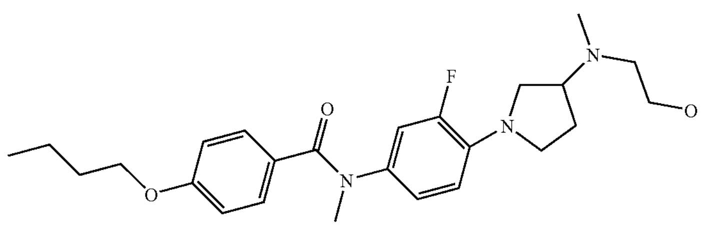 | C25H34FN3O3 | 443.26 | 444 |
| 1372 | 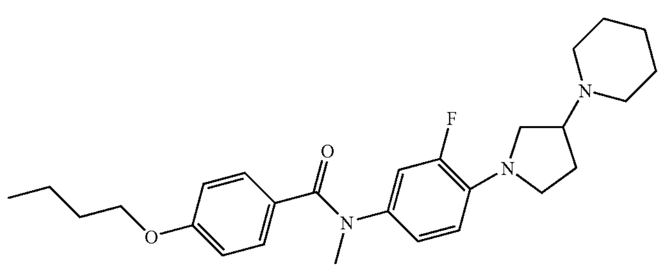 | C27H36FN3O2 | 453.28 | 454 |
| 1373 | 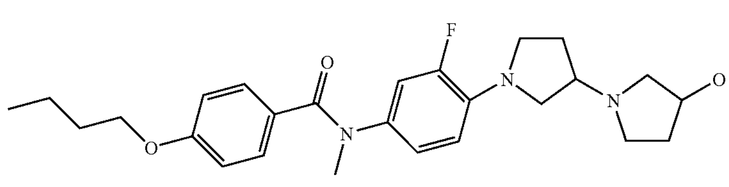 | C26H34FN3O3 | 455.26 | 456 |

TABLE 10-continued

| Ex. No. | Structure | Molecular formula | Monoisotopic molecular wt. | M + H⁺ |
|---|---|---|---|---|
| 1374 | 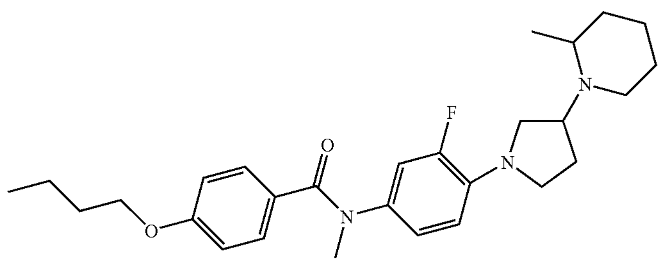 | C28H38FN3O2 | 467.30 | 468 |
| 1375 | 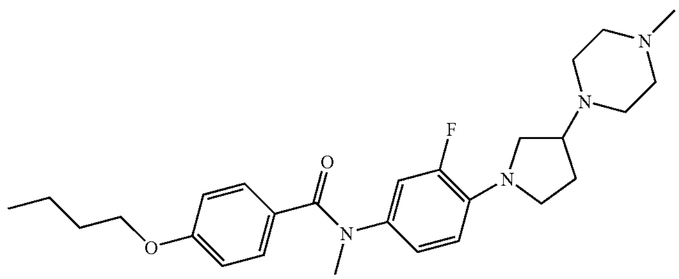 | C27H37FN4O2 | 468.29 | 469 |
| 1376 | 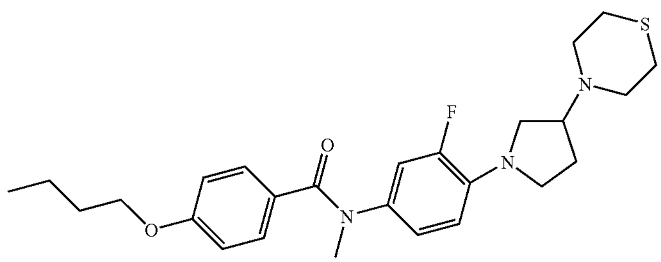 | C26H34FN3O2S | 471.24 | 472 |
| 1377 | 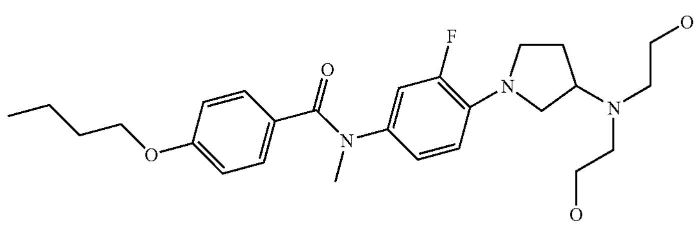 | C26H36FN3O4 | 473.27 | 474 |
| 1378 | 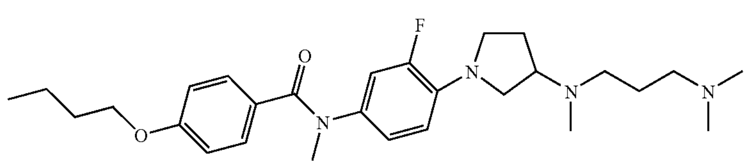 | C28H41FN4O2 | 484.32 | 485 |
| 1379 | 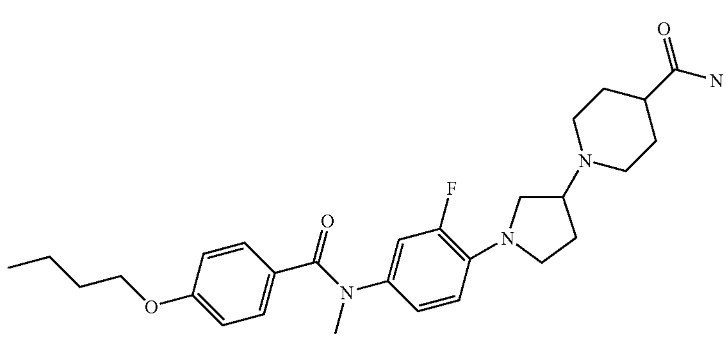 | C28H37FN4O3 | 496.29 | 497 |

TABLE 10-continued

| Ex. No. | Structure | Molecular formula | Monoisotopic molecular wt. | M + H⁺ |
|---|---|---|---|---|
| 1380 | 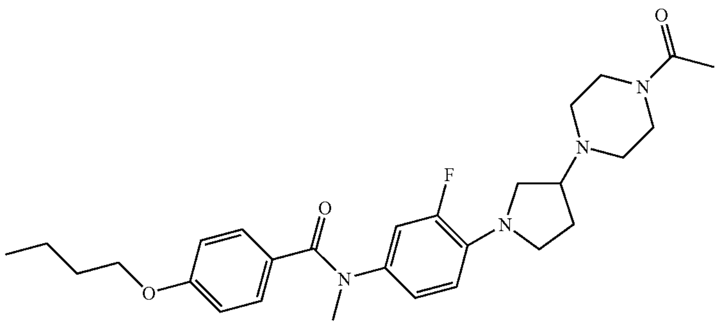 | C28H37FN4O3 | 496.29 | 497 |
| 1381 | 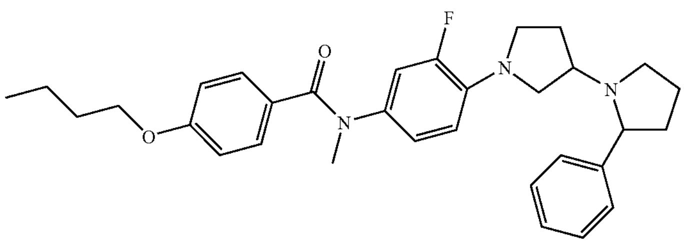 | C32H38FN3O2 | 515.29 | 516 |
| 1382 | 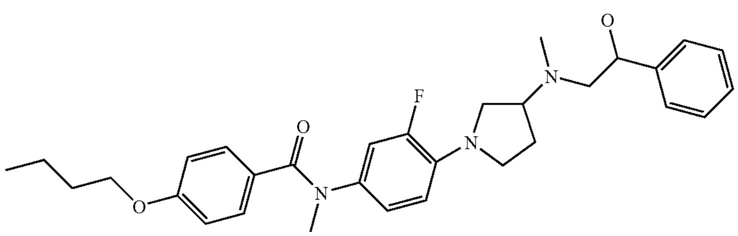 | C31H38FN3O3 | 519.29 | 520 |
| 1383 | 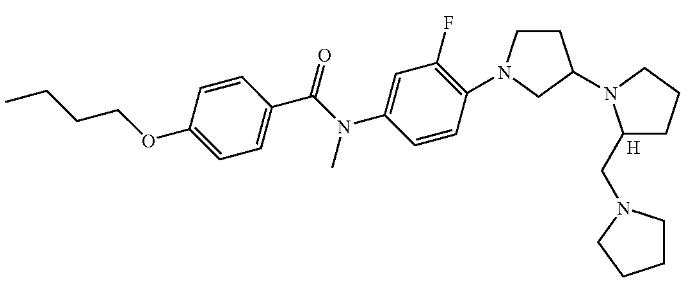 | C31H43FN4O2 | 522.34 | 523 |
| 1384 | 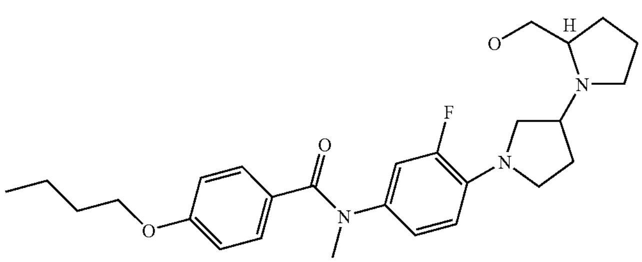 | C27H36FN3O3 | 469.27 | 470 |

TABLE 10-continued
| Ex. No. | Structure | Molecular formula | Monoisotopic molecular wt. | M + H+ |
|---|---|---|---|---|
| 1385 | 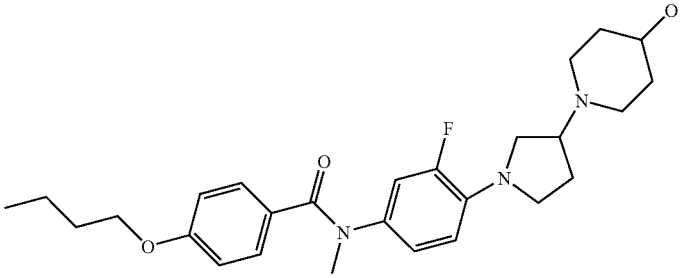 | C27H36FN3O3 | 469.27 | 470 |
| 1386 | 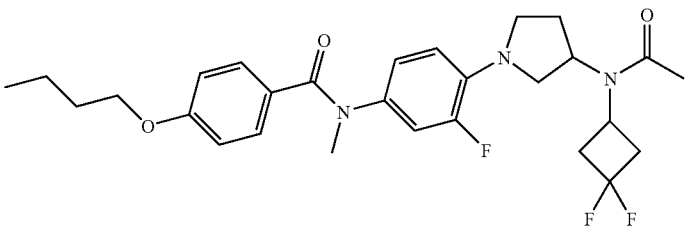 | C28H34F3N3O3 | 517.26 | 518 |
| 1387 | 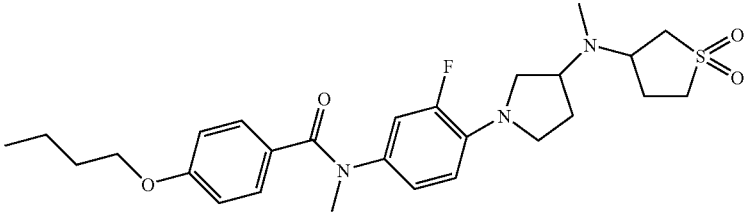 | C27H36FN3O4S | 517.24 | 518 |
| 1388 | 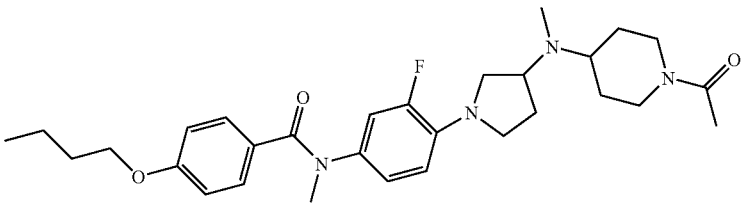 | C30H41FN4O3 | 524.32 | 525 |
| 1389 | 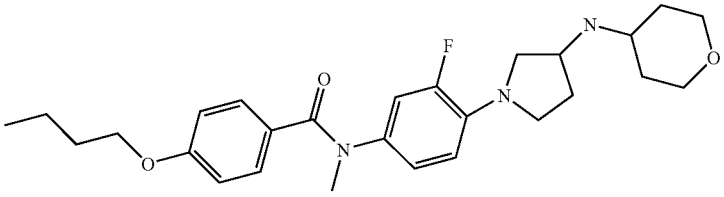 | C27H36FN3O3 | 469.27 | 470 |
| 1390 | 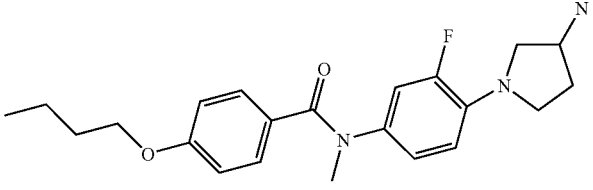 | C22H28FN3O2 | 385.22 | 386 |

TABLE 10-continued

| Ex. No. | Structure | Molecular formula | Monoisotopic molecular wt. | M + H+ |
|---|---|---|---|---|
| 1391 | 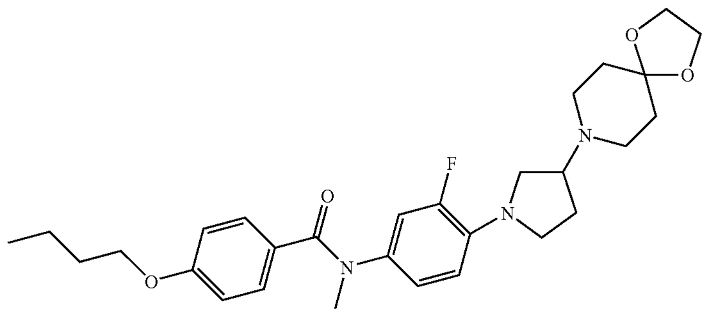 | C29H38FN3O4 | 511.29 | 512 |
| 1392 | 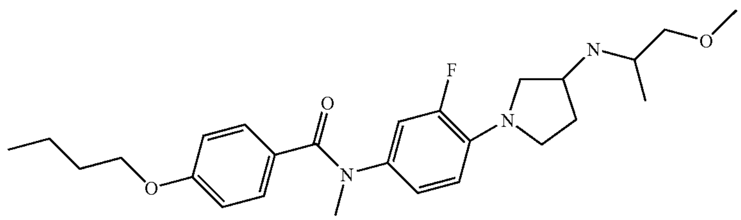 | C26H36FN3O3 | 457.27 | 458 |
| 1393 | 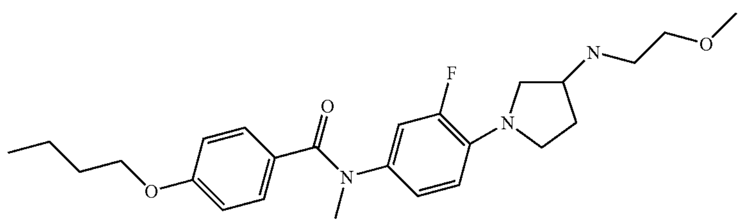 | C25H34FN3O3 | 443.26 | 444 |
| 1394 | 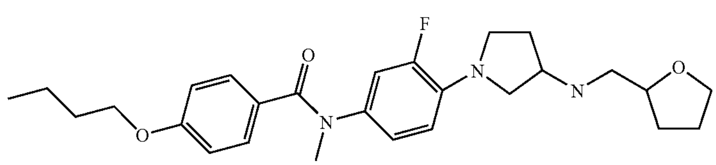 | C27H36FN3O3 | 469.27 | 470 |
| 1395 | 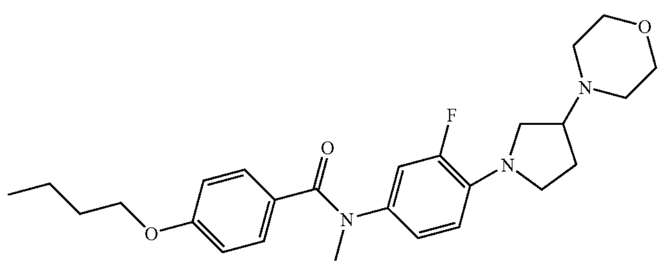 | C26H34FN3O3 | 455.26 | 456 |
| 1396 | 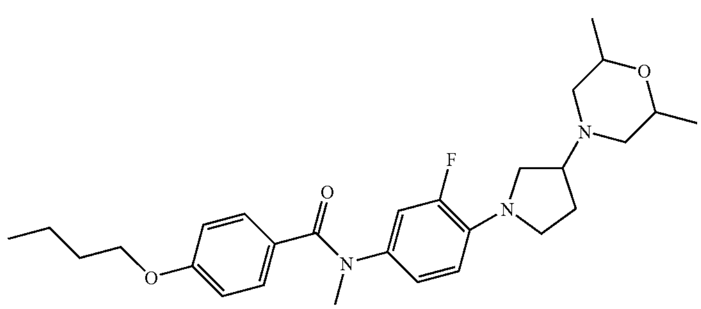 | C28H38FN3O3 | 483.29 | 484 |

TABLE 10-continued

| Ex. No. | Structure | Molecular formula | Monoisotopic molecular wt. | M + H⁺ |
|---|---|---|---|---|
| 1397 | 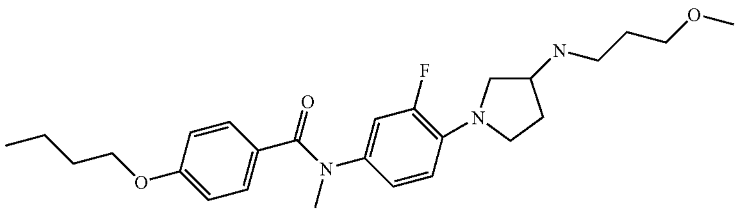 | C26H36FN3O3 | 457.27 | 458 |
| 1398 | 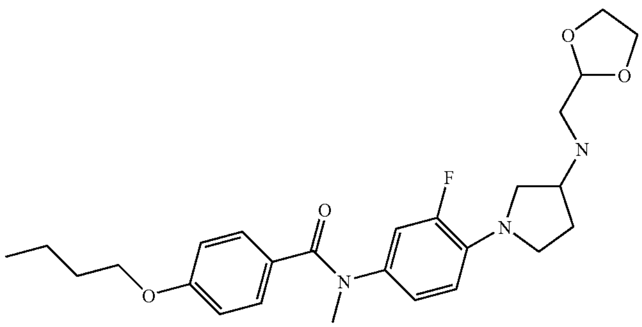 | C26H34FN3O4 | 471.25 | 472 |
| 1399 | 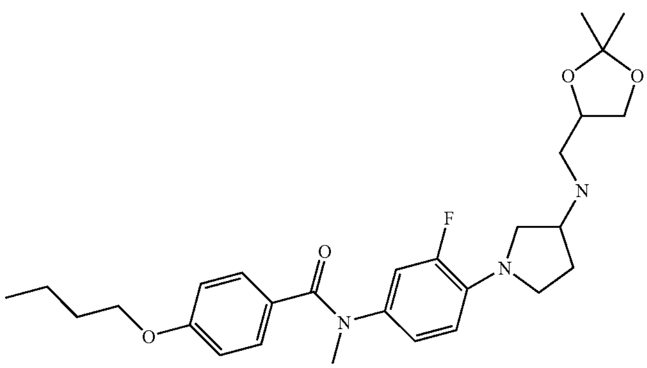 | C28H38FN3O4 | 499.29 | 500 |
| 1400 | 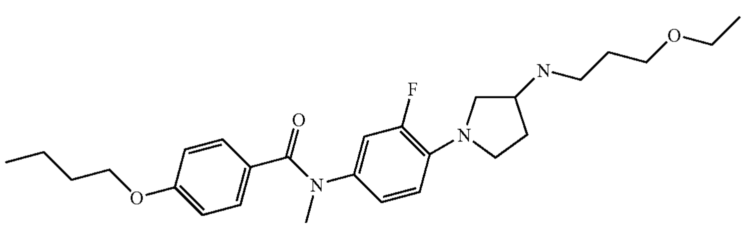 | C27H38FN3O3 | 471.29 | 472 |
| 1401 | 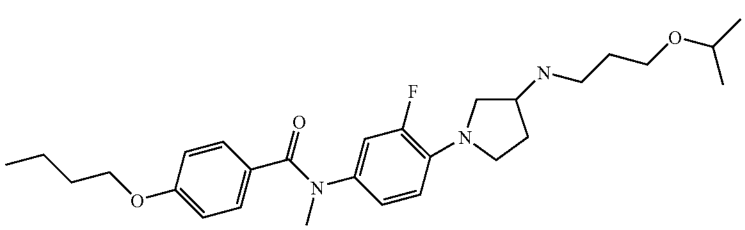 | C28H40FN3O3 | 485.30 | 486 |

TABLE 10-continued
| Ex. No. | Structure | Molecular formula | Monoisotopic molecular wt. | M + H⁺ |
|---|---|---|---|---|
| 1402 | 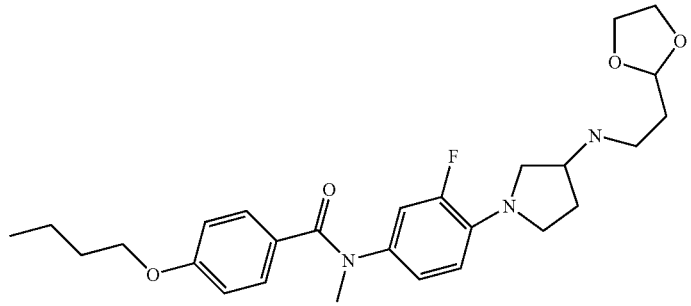 | C27H36FN3O4 | 485.27 | 486 |
| 1403 | 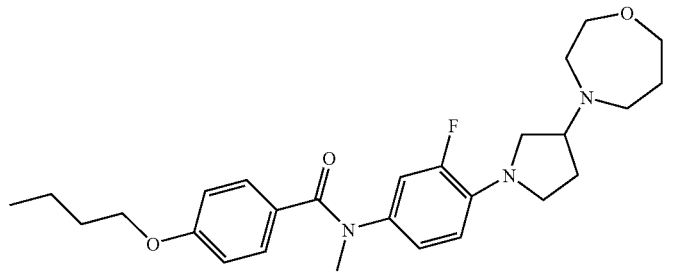 | C27H36FN3O3 | 469.27 | 470 |
TABLE 11
| Ex. No. | Structure | Molecular formula | Monoisotopic molecular wt. | M + H⁺ |
|---|---|---|---|---|
| 1404 | 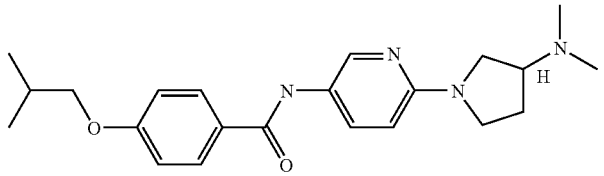 | C22H30N4O2 | 382.24 | 383 |
| 1405 | 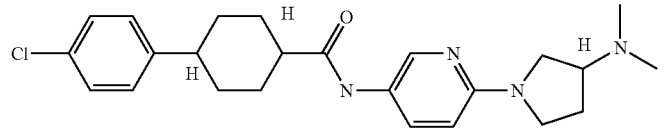 | C24H31ClN4O | 426.22 | 427 |
| 1406 | 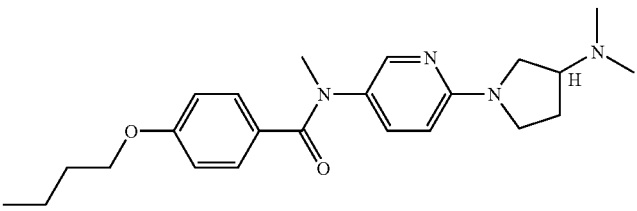 | C23H32N4O2 | 396.25 | 397 |
| 1407 | 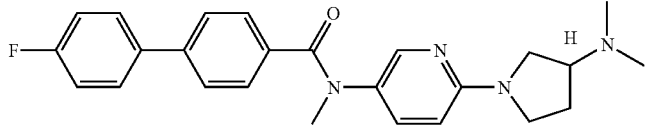 | C25H27FN4O | 418.22 | 410 |

TABLE 11-continued

| Ex. No. | Structure | Molecular formula | Mono-isotopic molecular wt. | M + H⁺ |
|---|---|---|---|---|
| 1408 | 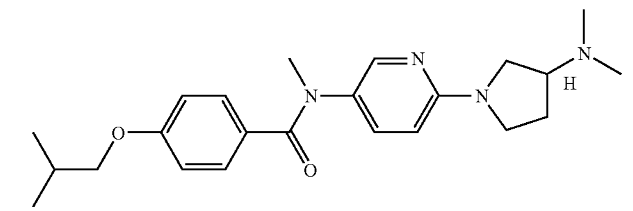 | C23H32N4O2 | 396.25 | 397 |
| 1409 | 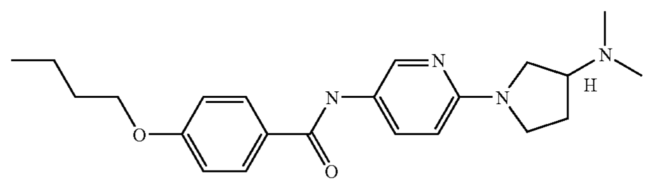 | C22H30N4O2 | 382.24 | 383 |
| 1410 | 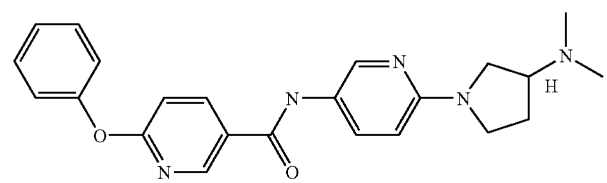 | C23H25N5O2 | 403.20 | 404 |
| 1411 | 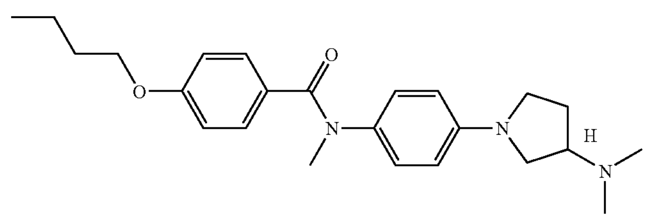 | C24H33N3O2 | 395.26 | 396 |
| 1412 | 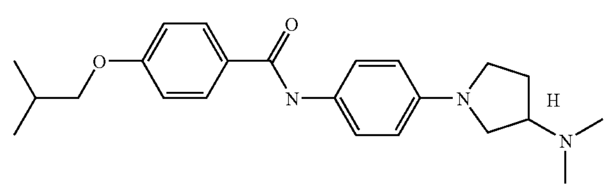 | C23H31N3O2 (S)-Konfiguration | 381.24 | 382 |
| 1413 | 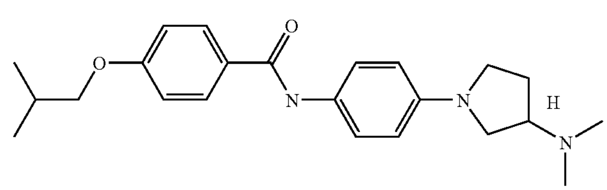 | C23H31N3O2 | 381.24 | 382 |
| 1414 | 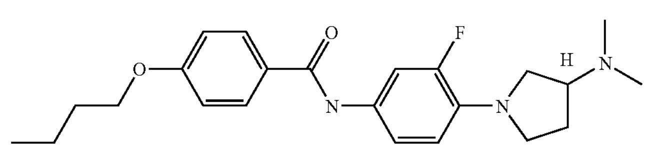 | C23H30FN3O2 | 399.23 | 400 |
| 1415 | 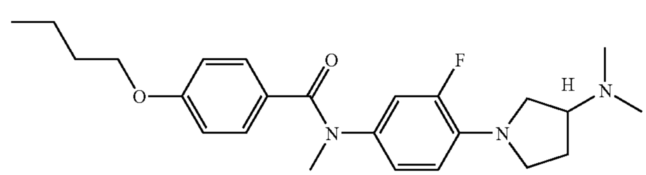 | C24H32FN3O2 | 413.25 | 414 |

TABLE 11-continued

| Ex. No. | Structure | Molecular formula | Mono-isotopic molecular wt. | M + H⁺ |
|---|---|---|---|---|
| 1416 | 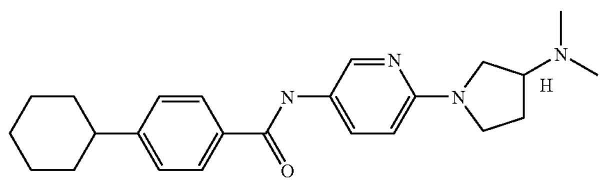 | C24H32N4O | 392.26 | 393 |
| 1417 | 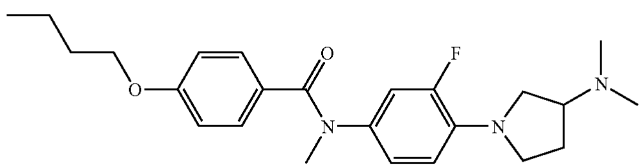 | C24H32FN3O2 | 413.25 | 414 |
| 1418 | 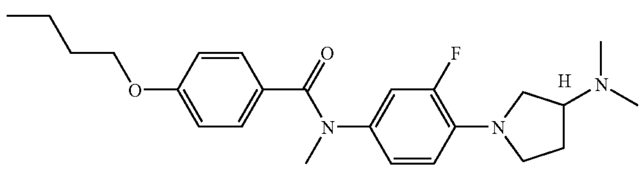 | C24H32FN3O2 (S)-configuration | 413.25 | 414 |
| 1419 | 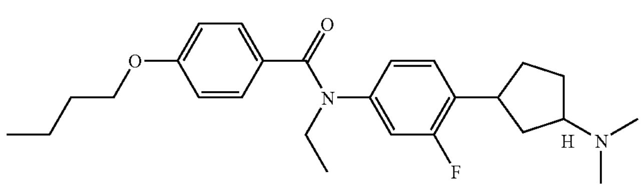 | C25H34FN3O2 | 427.26 | 428 |
| 1420 | 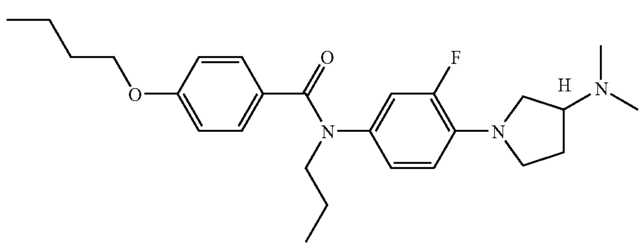 | C26H36FN3O2 | 441.28 | 442 |
| 1421 | 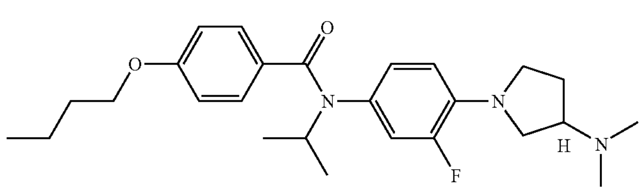 | C26H36FN3O2 | 441.28 | 442 |
| 1422 | 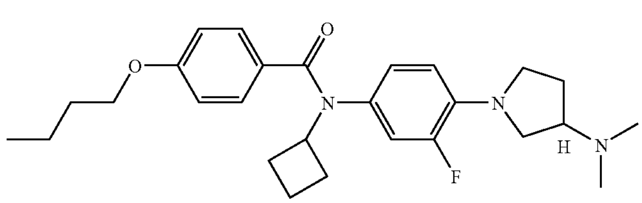 | C27H36FN3O2 | 453.28 | 454 |

TABLE 11-continued
| Ex. No. | Structure | Molecular formula | Mono-isotopic molecular wt. | M + H+ |
|---|---|---|---|---|
| 1423 | 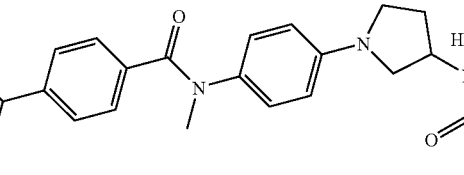 | C27H38FN3O3 | 471.29 | 472 |
TABLE 12
| Ex. No. | Structure | Molecular formula | Mono-isotopic molecular wt. | M + H+ |
|---|---|---|---|---|
| 1424 | 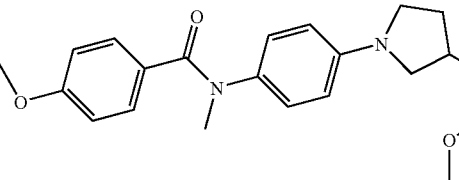 | C27H35N3O2 | 433.27 | 434 |
| 1425 | 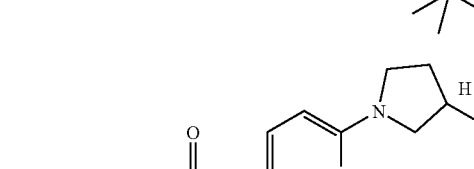 | C28H39N3O4 | 481.29 | 482 |
| 1426 | 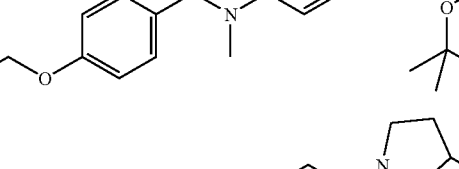 | C27H38N4O4 | 482.29 | 483 |
| 1427 | 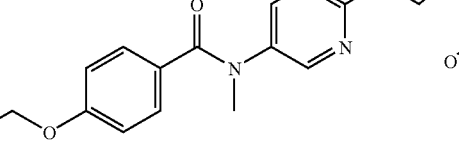 | C24H32N4O3 | 424.25 | 425 |
| 1428 | 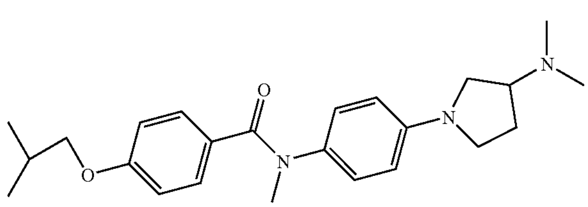 | C24H33N3O2 | 395.26 | 396 |

TABLE 12-continued

| Ex. No. | Structure | Molecular formula | Mono-isotopic molecular wt. | M + H⁺ |
|---|---|---|---|---|
| 1429 | 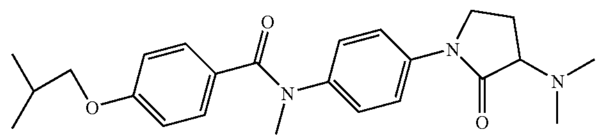 | C24H31N3O3 | 409.24 | 410 |
| 1430 | 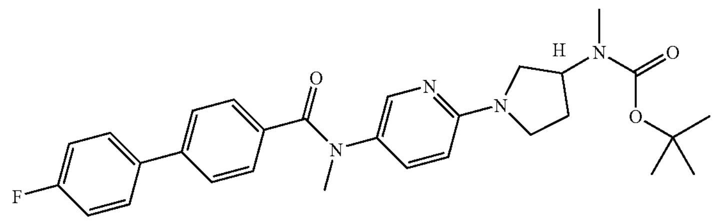 | C29H33FN4O3 | 504.25 | 505 |
| 1431 | 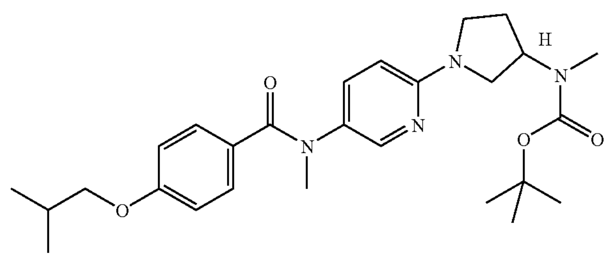 | C27H38N4O4 | 482.29 | 483 |
| 1432 | 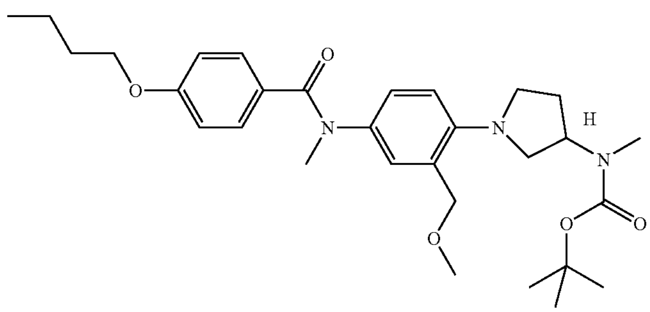 | C30H43N3O5 | 525.32 | 526 |
| 1433 | 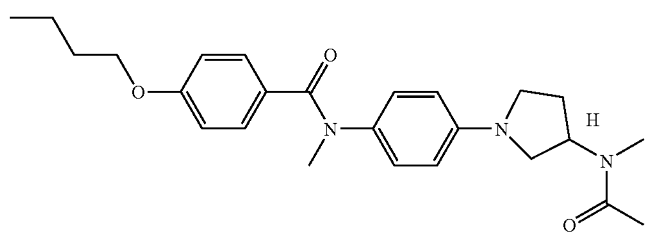 | C25H33N3O3 | 423.25 | 424 |
| 1434 | 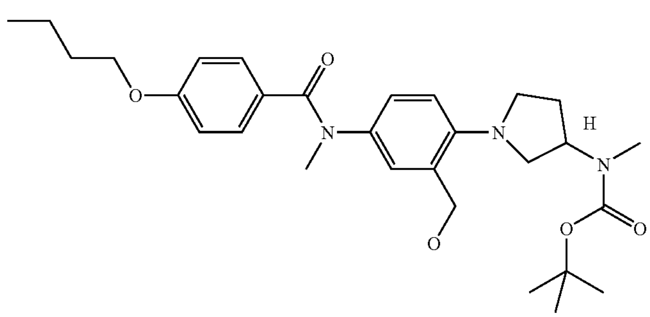 | C29H41N3O5 | 511.30 | 512 |

TABLE 12-continued

| Ex. No. | Structure | Molecular formula | Mono-isotopic molecular wt. | M + H⁺ |
|---|---|---|---|---|
| 1435 | 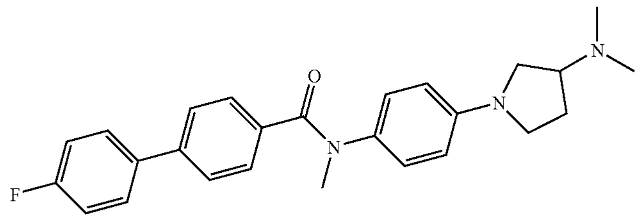 | C26H28FN3O | 417.22 | 418 |
| 1436 | 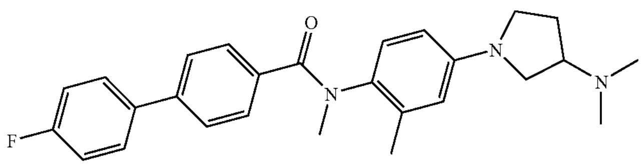 | C27H30FN3O | 431.24 | 432 |
| 1437 | 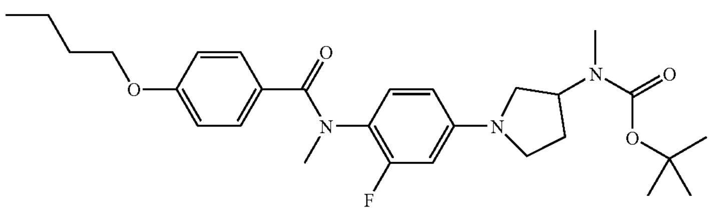 | C28H38FN3O4 | 499.29 | 500 |
| 1438 | 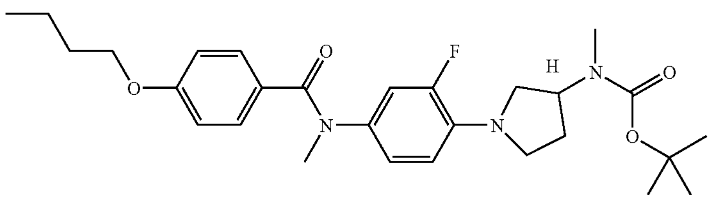 | C28H38FN3O4 | 499.29 | 500 |
| 1439 | 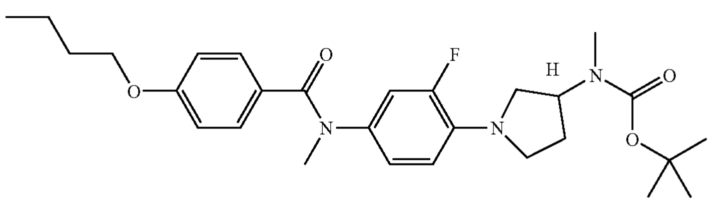 | C28H38FN3O4 (S)-Konfiguration | 499.29 | 500 |
| 1440 | 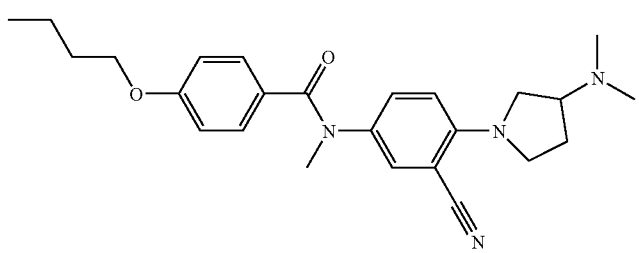 | C25H32N4O2 | 420.25 | 421 |
| 1441 | 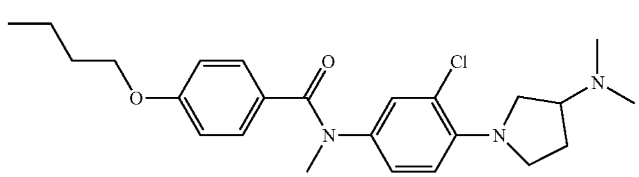 | C24H32ClN3O2 | 429.22 | 430 |

TABLE 12-continued

| Ex. No. | Structure | Molecular formula | Mono-isotopic molecular wt. | M + H⁺ |
|---|---|---|---|---|
| 1442 | 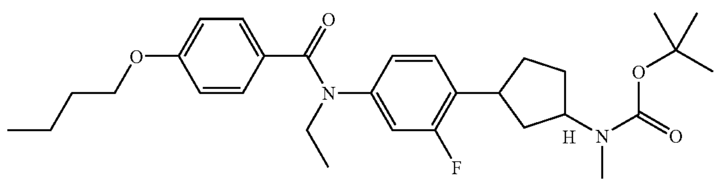 | C29H40FN3O4 | 513.30 | 514 |
| 1443 | 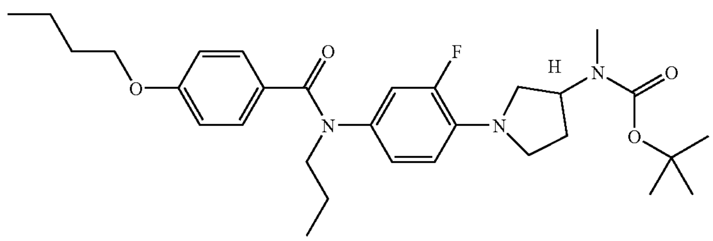 | C30H42FN3O4 | 527.32 | 528 |

TABLE 13

| Ex. No. | Structure | Molecular formula | Mono-isotopic molecular wt. | M + H⁺ |
|---|---|---|---|---|
| 1444 | 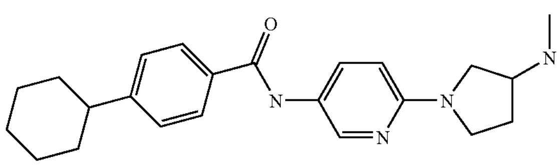 | C23H30N4O | 378.24 | 379 |
| 1445 | 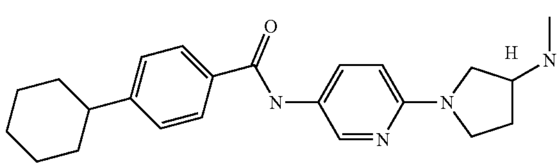 | C23H30N4O | 378.24 | 379 |
| 1446 | 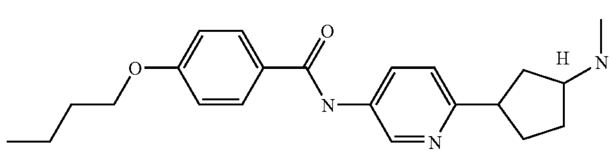 | C21H28N4O2 | 368.22 | 369 |
| 1447 | 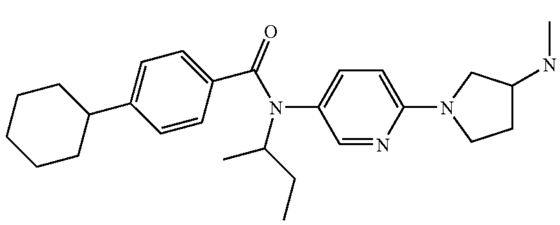 | C27H38N4O | 434.30 | 435 |

TABLE 13-continued

| Ex. No. | Structure | Molecular formula | Mono-isotopic molecular wt. | M + H+ |
|---|---|---|---|---|
| 1448 | 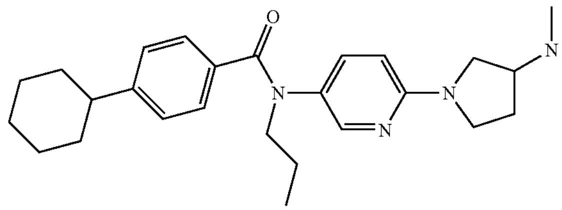 | C26H36N4O | 420.29 | 421 |
| 1449 | 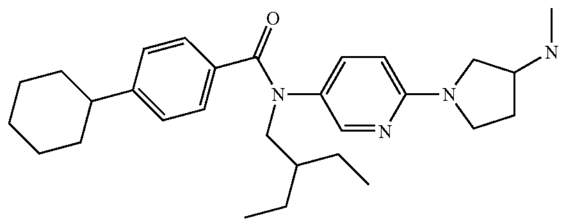 | C29H42N4O | 462.34 | 463 |
| 1450 | 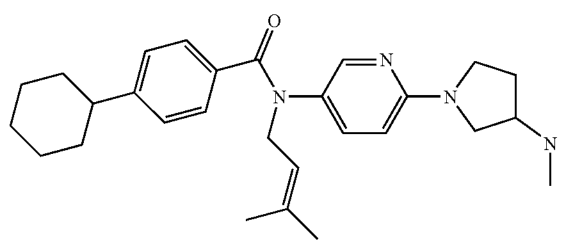 | C28H38N4O | 446.30 | 447 |
| 1451 | 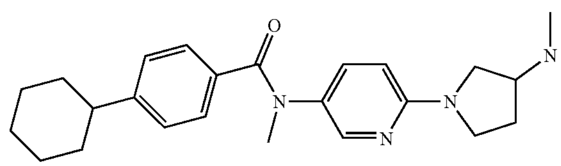 | C24H32N4O | 392.26 | 393 |
| 1452 | 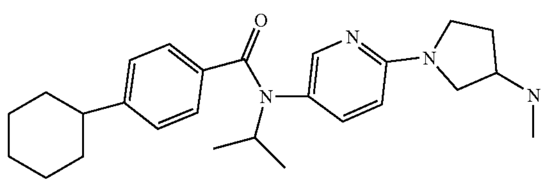 | C26H36N4O | 420.29 | 421 |
| 1453 | 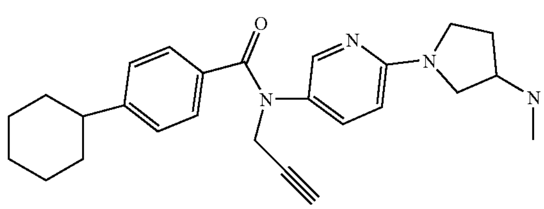 | C26H32N4O | 416.26 | 417 |
| 1454 | 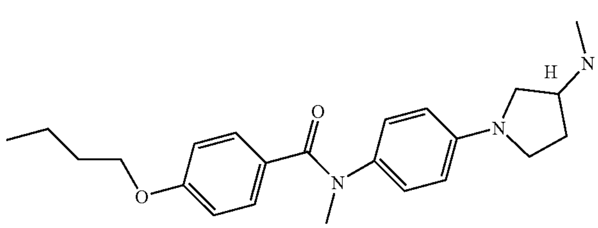 | C23H31N3O2 | 381.24 | 382 |

TABLE 13-continued

| Ex. No. | Structure | Molecular formula | Mono-isotopic molecular wt. | M + H⁺ |
|---|---|---|---|---|
| 1455 | 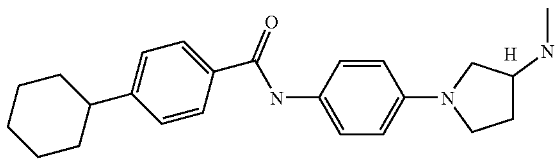 | C24H31N3O | 377.25 | 378 |
| 1456 | 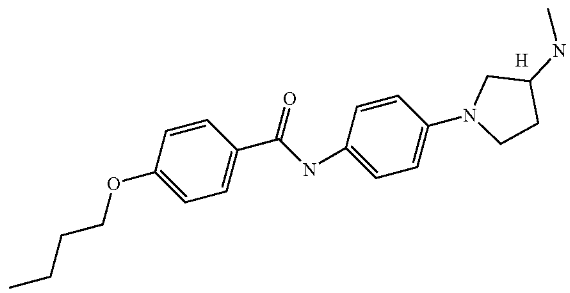 | C22H29N3O2 | 367.23 | 368 |
| 1457 | 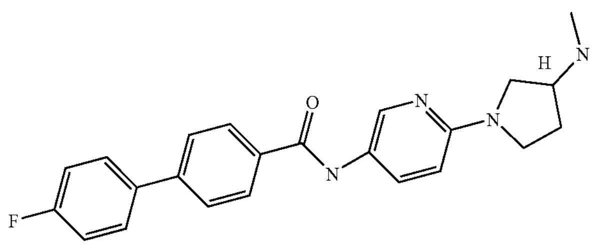 | C22H21FN4O | 376.17 | 377 |
| 1458 | 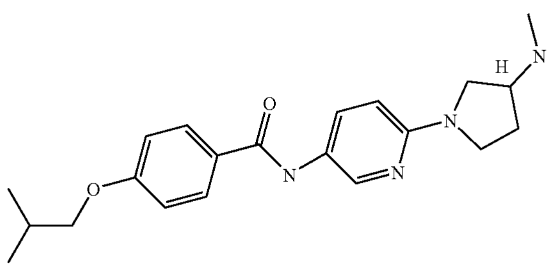 | C20H26N4O2 | 354.21 | 355 |
| 1459 | 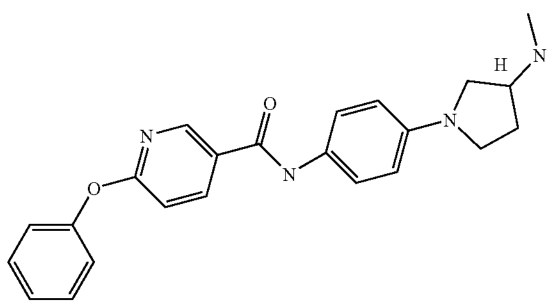 | C23H24N4O2 | 388.19 | 389 |
| 1460 | 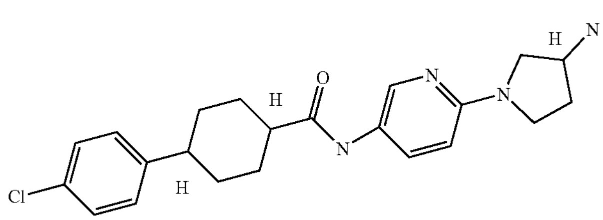 | C22H27ClN4O | 398.19 | 399 |

TABLE 13-continued

| Ex. No. | Structure | Molecular formula | Mono-isotopic molecular wt. | M + H+ |
|---|---|---|---|---|
| 1461 | 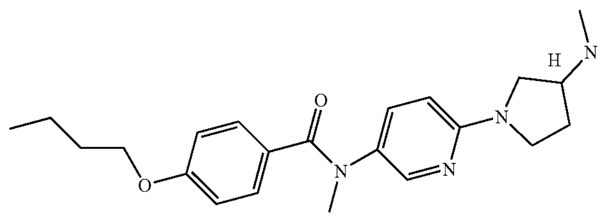 | C22H30N4O2 | 382.24 | 383 |
| 1462 | 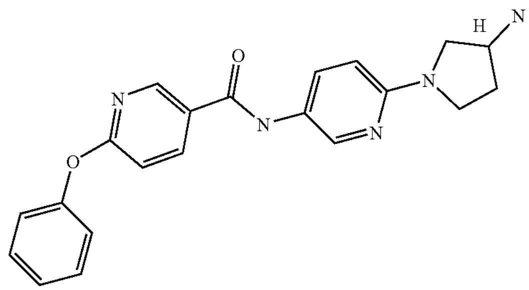 | C21H21N5O2 | 375.17 | 376 |
| 1463 | 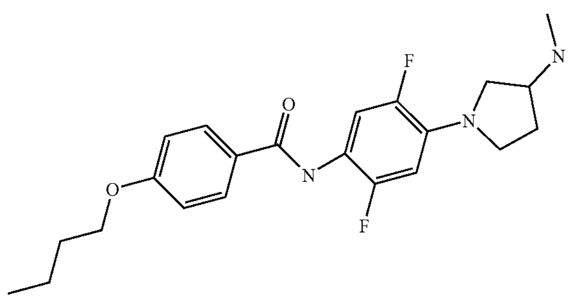 | C22H27F2N3O2 | 403.21 | 404 |
| 1464 | 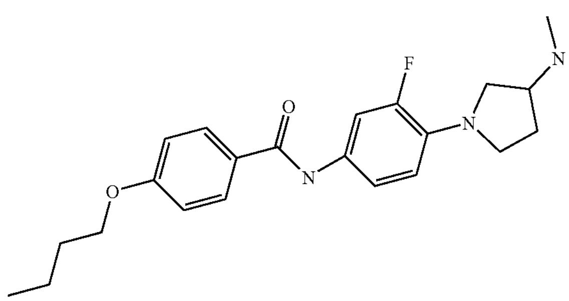 | C22H28FN3O2 | 385.22 | 386 |
| 1465 | 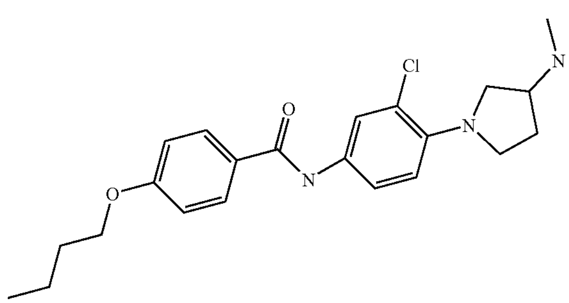 | C22H28ClN3O2 | 401.19 | 402 |

TABLE 13-continued

| Ex. No. | Structure | Molecular formula | Mono-isotopic molecular wt. | M + H+ |
|---|---|---|---|---|
| 1466 | 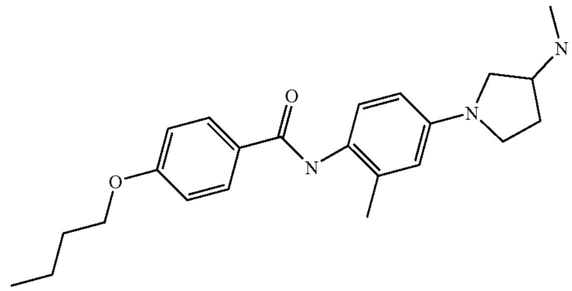 | C23H31N3O2 | 381.24 | 382 |
| 1467 | 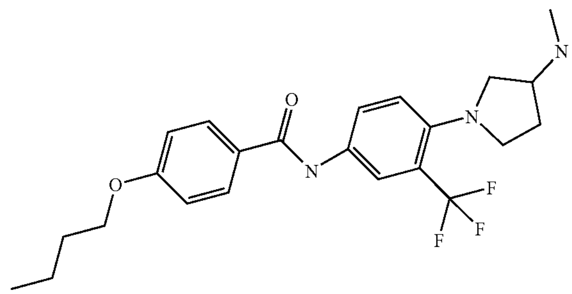 | C23H28F3N3O2 | 435.21 | 436 |
| 1468 | 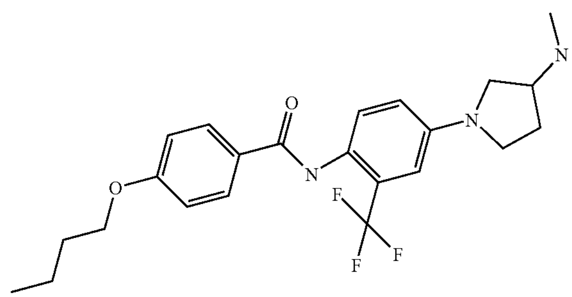 | C23H28F3N3O2 | 435.21 | 436 |
| 1469 | 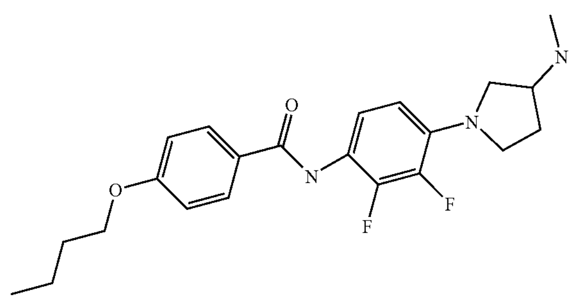 | C22H27F2N3O2 | 403.21 | 404 |
| 1470 | 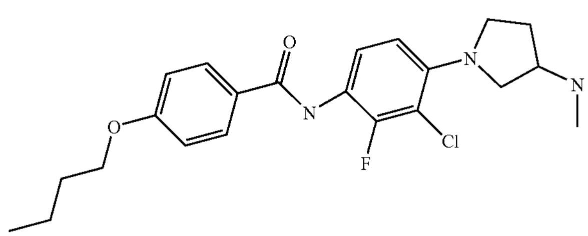 | C22H27ClFN3O2 | 419.18 | 420 |

TABLE 13-continued

| Ex. No. | Structure | Molecular formula | Mono-isotopic molecular wt. | M + H⁺ |
|---|---|---|---|---|
| 1471 | 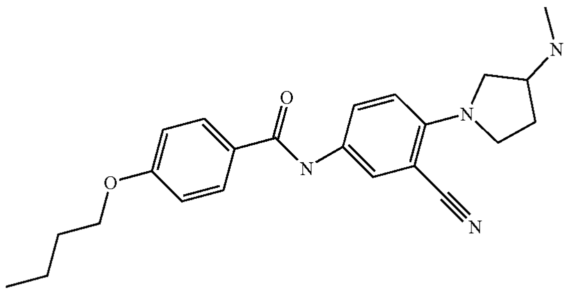 | C23H28N4O2 | 392.22 | 393 |
| 1472 | 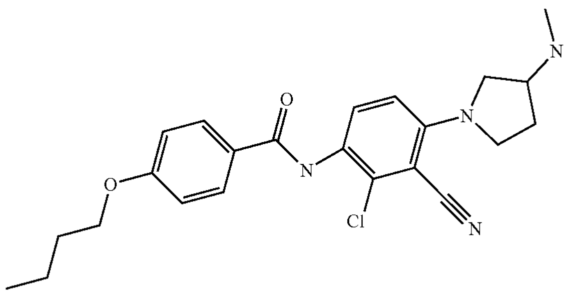 | C23H27C1N4O2 | 426.18 | 427 |
| 1473 | 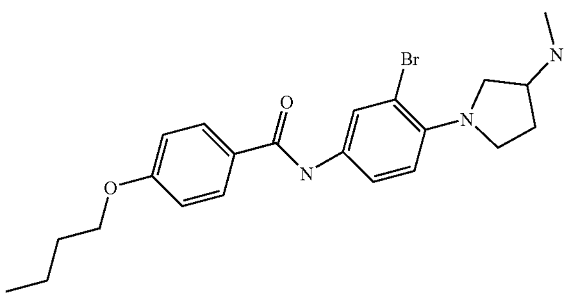 | C22H28BrN3O2 | 445.14 | 446 |
| 1474 | 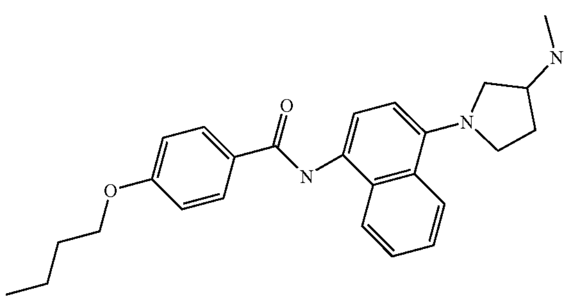 | C26H31N3O2 | 417.24 | 418 |
| 1475 | 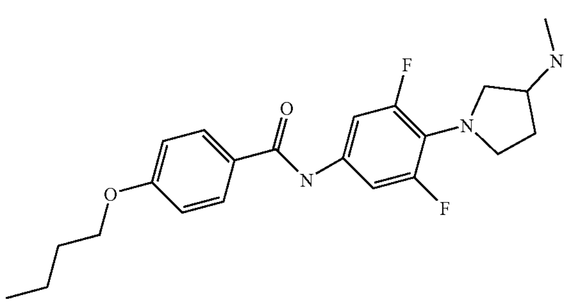 | C22H27F2N3O2 | 403.21 | 404 |

TABLE 13-continued

| Ex. No. | Structure | Molecular formula | Mono-isotopic molecular wt. | M + H⁺ |
|---|---|---|---|---|
| 1476 | 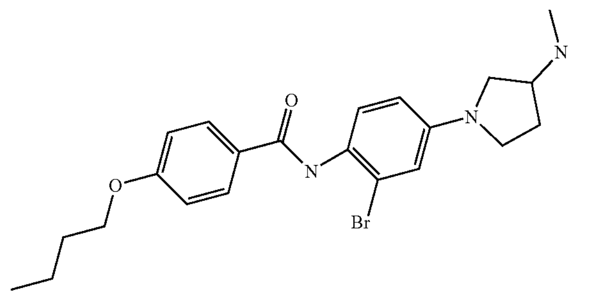 | C22H28BrN3O2 | 445.14 | 446 |
| 1477 | 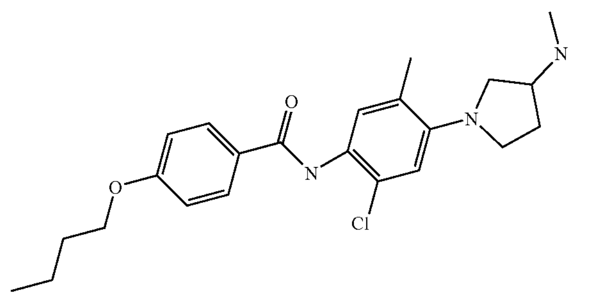 | C23H30ClN3O2 | 415.20 | 416 |
| 1478 | 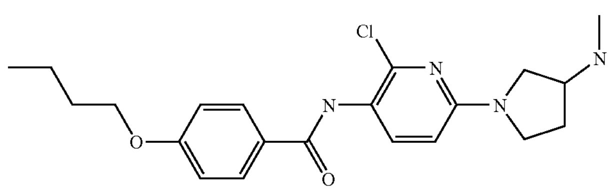 | C21H27ClN4O2 | 402.18 | 403 |
| 1479 | 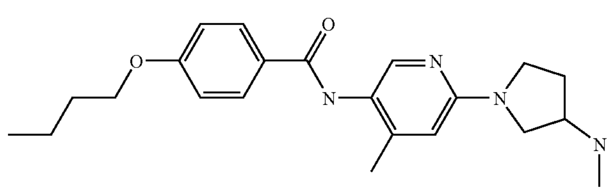 | C22H30N4O2 | 382.24 | 383 |
| 1480 | 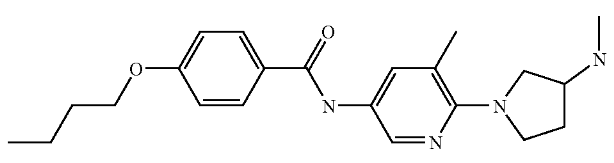 | C22H30N4O2 | 382.24 | 383 |
| 1481 | 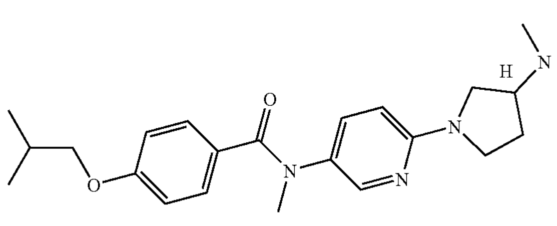 | C22H30N4O2 | 382.24 | 383 |

TABLE 13-continued

| Ex. No. | Structure | Molecular formula | Mono-isotopic molecular wt. | M + H+ |
|---|---|---|---|---|
| 1482 | 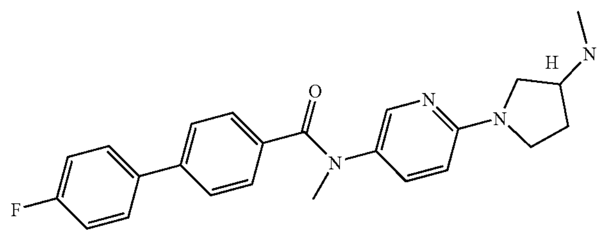 | C24H25FN4O | 404.20 | 405 |
| 1483 | 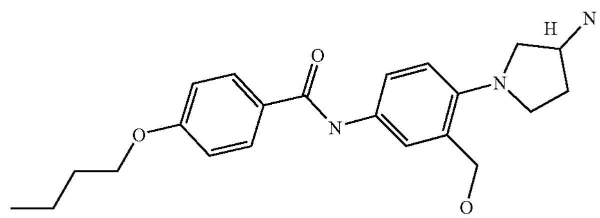 | C22H29N3O3 | 383.22 | 384 |
| 1484 | 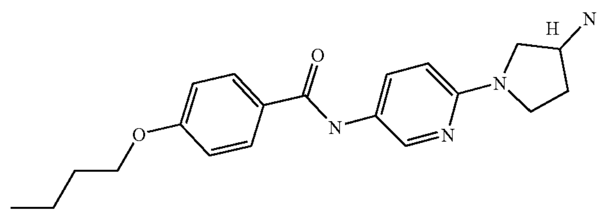 | C20H26N4O2 | 354.21 | 355 |
| 1485 | 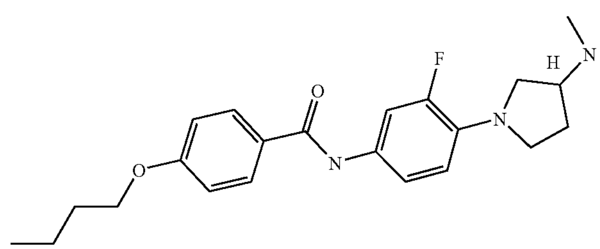 | C22H28FN3O2 | 385.22 | 386 |
| 1486 | 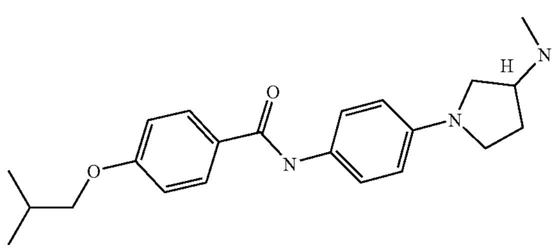 | C22H29N3O2 | 367.23 | 368 |
| 1487 | 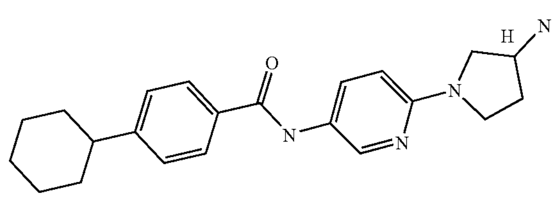 | C22H28N4O | 364.23 | 365 |

TABLE 13-continued

| Ex. No. | Structure | Molecular formula | Mono-isotopic molecular wt. | M + H+ |
|---|---|---|---|---|
| 1488 | 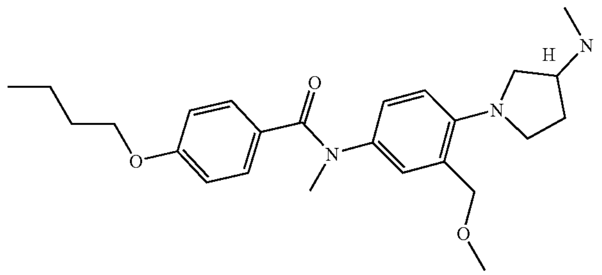 | C25H35N3O3 | 425.27 | 426 |
| 1489 | 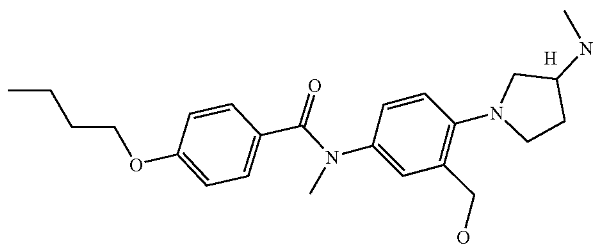 | C24H33N3O3 | 411.25 | 412 |
| 1490 | 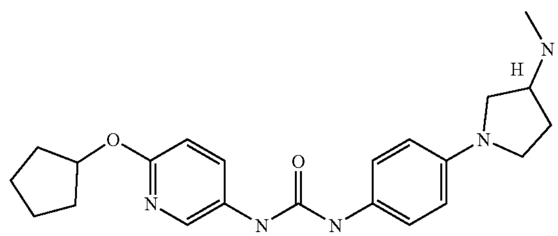 | C22H29N5O2 | 395.23 | 396 |
| 1491 | 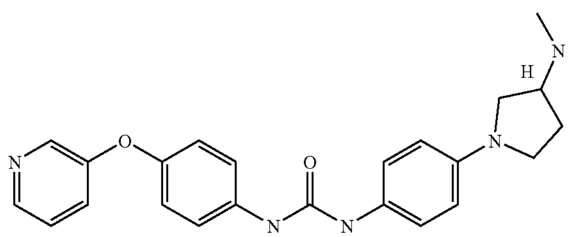 | C23H25N5O2 | 403.20 | 404 |
| 1492 | 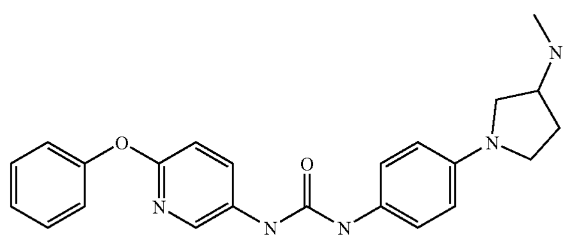 | C23H25N5O2 | 403.20 | 404 |
| 1493 | 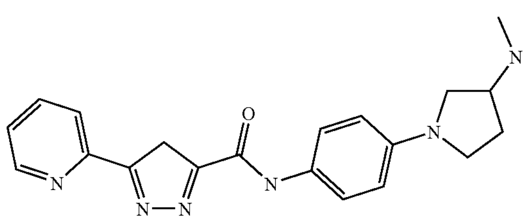 | C20H22N6O | 362.19 | 363 |

TABLE 13-continued

| Ex. No. | Structure | Molecular formula | Mono-isotopic molecular wt. | M + H⁺ |
|---|---|---|---|---|
| 1494 | 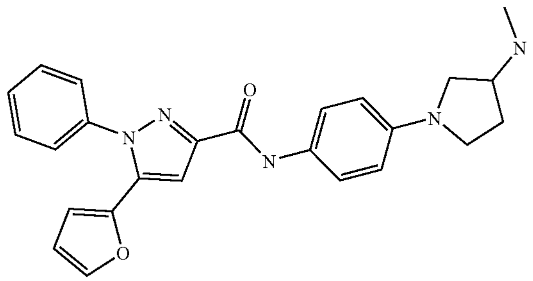 | C25H25N5O2 | 427.20 | 428 |
| 1495 | 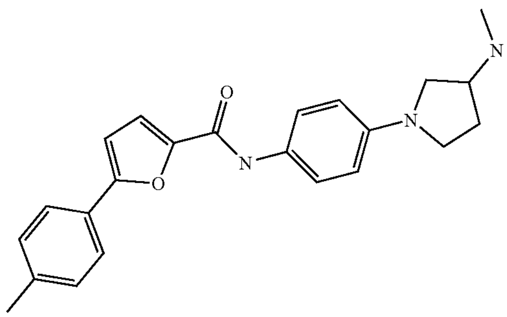 | C23H25N3O2 | 375.20 | 376 |
| 1496 | 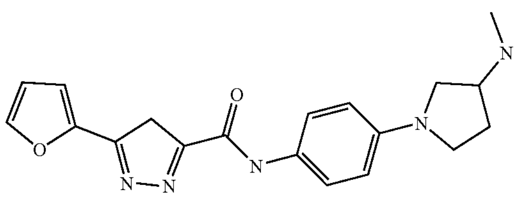 | C19H21N5O2 | 351.17 | 352 |
| 1497 | 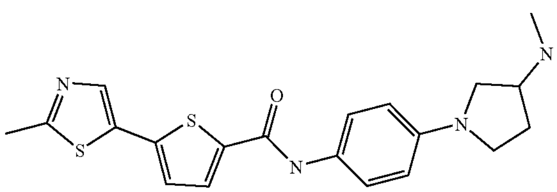 | C20H22N4OS2 | 398.12 | 399 |
| 1498 | 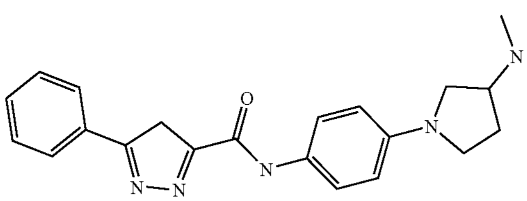 | C21H23N5O | 361.19 | 362 |
| 1499 | 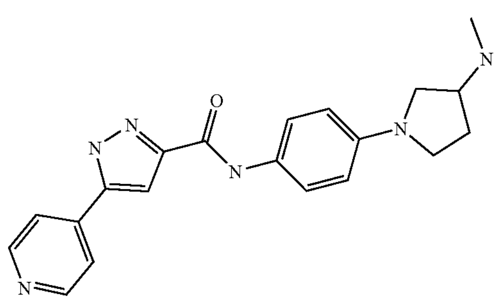 | C20H22N6O | 362.19 | 363 |

TABLE 13-continued

| Ex. No. | Structure | Molecular formula | Mono-isotopic molecular wt. | M + H+ |
|---|---|---|---|---|
| 1500 | 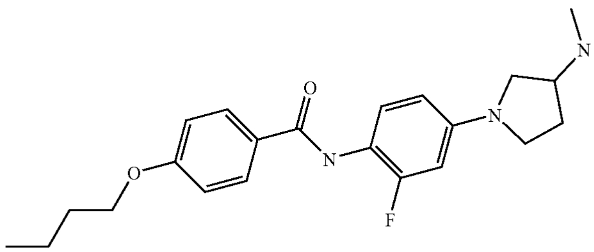 | C22H28FN3O2 | 385.22 | 386 |
| 1501 | 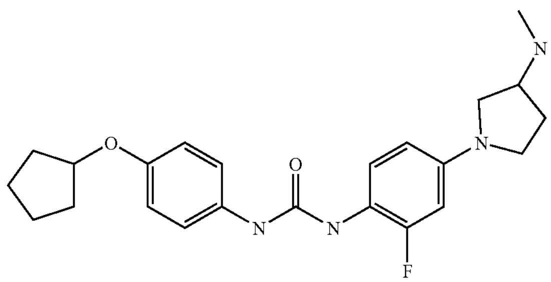 | C23H29FN4O2 | 412.23 | 413 |
| 1502 | 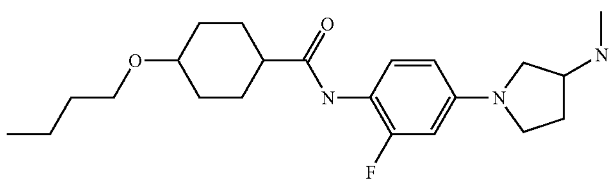 | C22H34FN3O2 | 391.26 | 392 |
| 1503 | 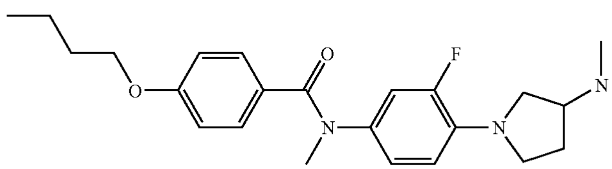 | C23H30FN3O2 | 399.23 | 400 |
| 1504 | 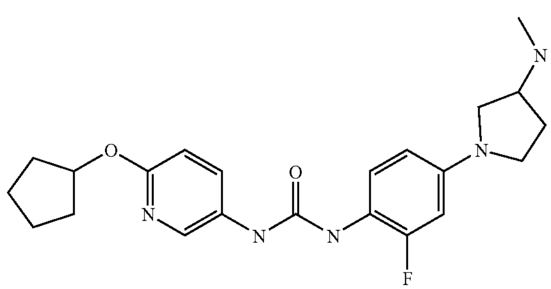 | C22H28FN5O2 | 413.22 | 414 |
| 1505 | 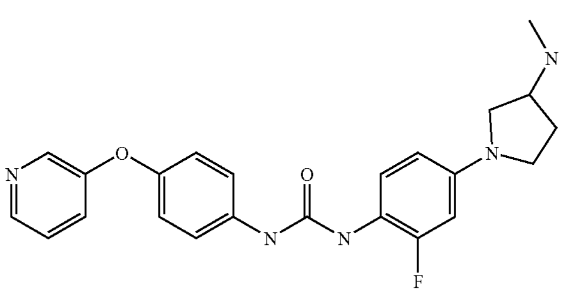 | C23H24FN5O2 | 421.19 | 422 |

TABLE 13-continued

| Ex. No. | Structure | Molecular formula | Mono-isotopic molecular wt. | M + H⁺ |
|---|---|---|---|---|
| 1506 | 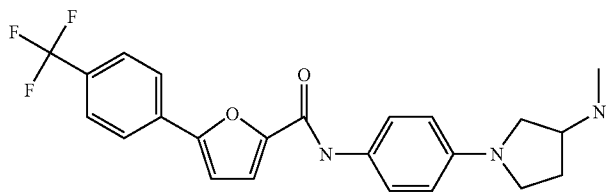 | C23H22F3N3O2 | 429.17 | 430 |
| 1507 | 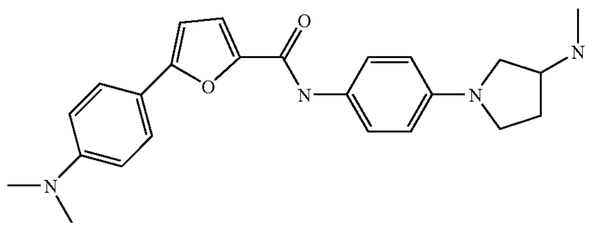 | C24H28N4O2 | 404.22 | 405 |
| 1508 | 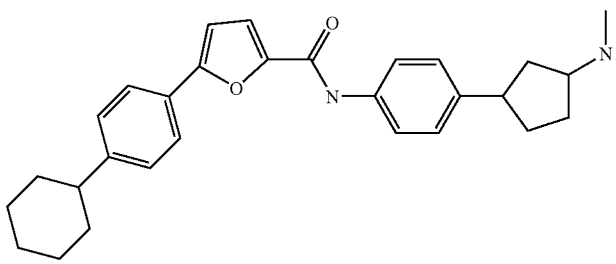 | C28H33N3O2 | 443.26 | 444 |
| 1509 | 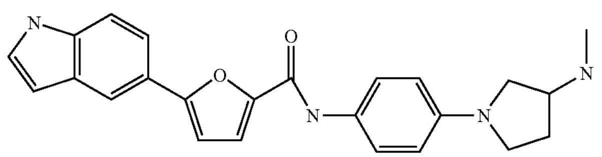 | C24H24N4O2 | 400.19 | 401 |
| 1510 | 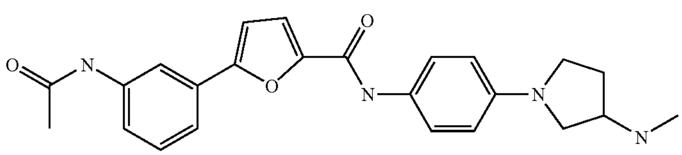 | C24H26N4O3 | 418.20 | 419 |
| 1511 | 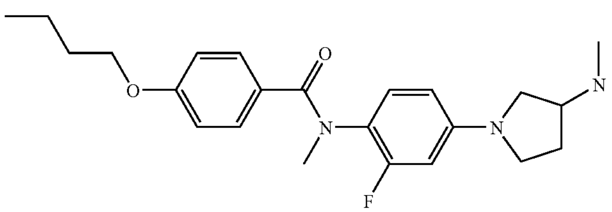 | C23H30FN3O2 | 399.23 | 400 |
| 1512 | 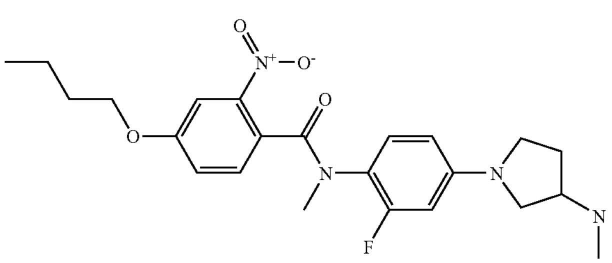 | C22H27FN4O4 | 430.20 | 431 |

TABLE 13-continued

| Ex. No. | Structure | Molecular formula | Mono-isotopic molecular wt. | M + H+ |
|---|---|---|---|---|
| 1513 | 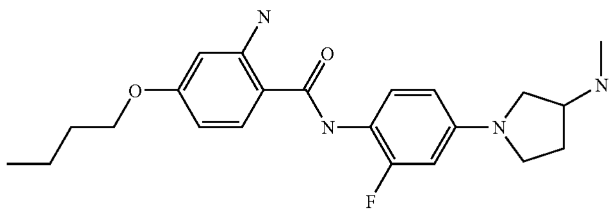 | C22H29FN4O2 | 400.23 | 401 |
| 1514 | 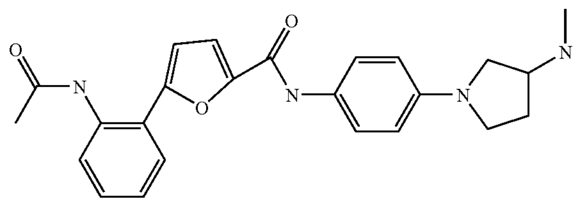 | C24H26N4O3 | 418.20 | 419 |
| 1515 | 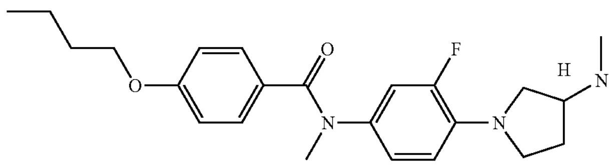 | C23H30FN3O2 | 399.23 | 400 |
| 1516 | 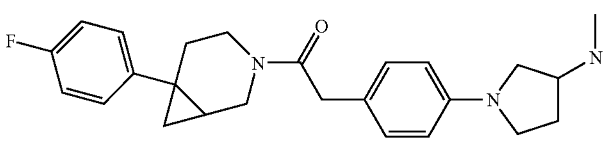 | C24H29FN4O | 408.23 | 409 |
| 1517 | 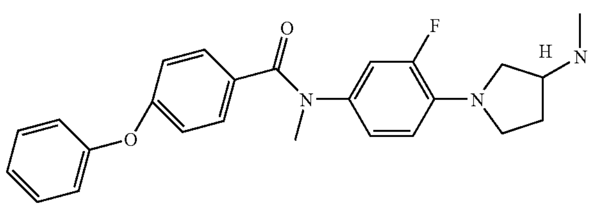 | C25H26FN3O2 | 419.20 | 420 |
| 1518 | 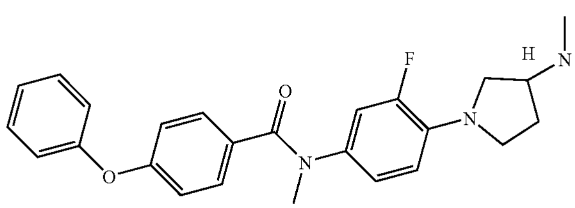 | C25H26FN3O2 | 419.20 | 420 |
| 1519 | 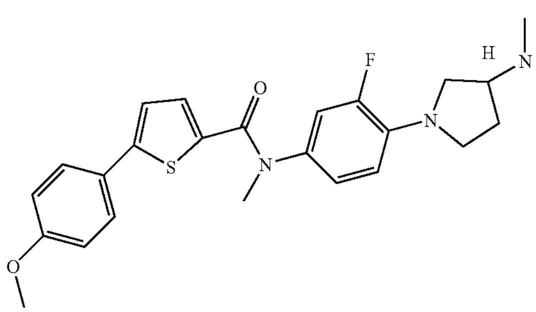 | C24H26FN3O2S | 439.17 | 440 |

TABLE 13-continued

| Ex. No. | Structure | Molecular formula | Mono-isotopic molecular wt. | M + H+ |
|---|---|---|---|---|
| 1520 | 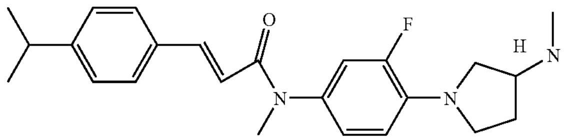 | C24H30FN3O | 395.24 | 396 |
| 1521 | 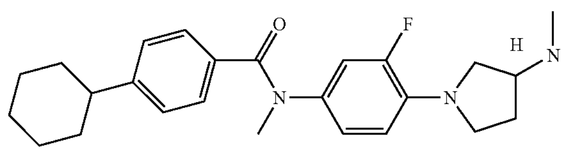 | C25H32FN3O | 409.25 | 410 |
| 1522 | 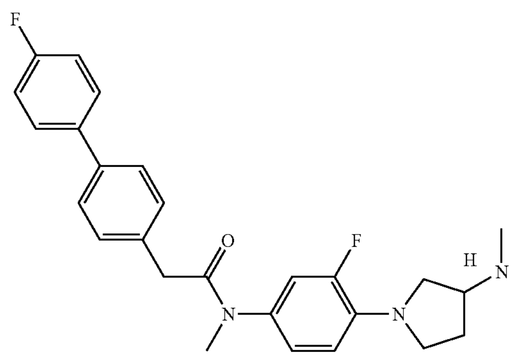 | C26H27F2N3O | 435.21 | 436 |
| 1523 | 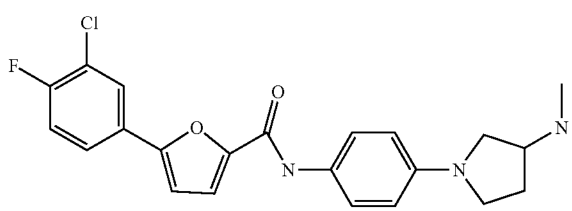 | C22H21ClFN3O2 | 413.13 | 414 |
| 1524 | 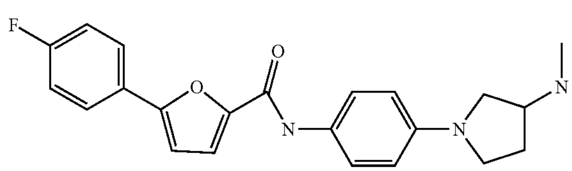 | C22H22FN3O2 | 379.17 | 380 |
| 1525 | 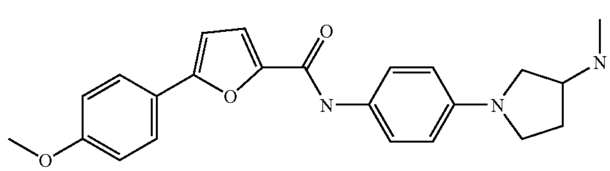 | C23H25N3O3 | 391.19 | 392 |
| 1526 | 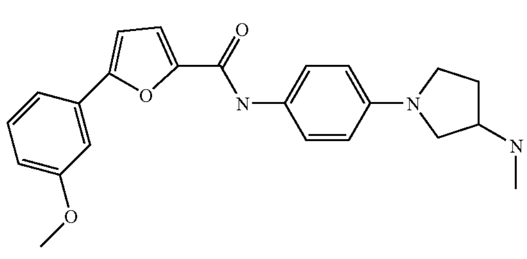 | C23H25N3O3 | 391.19 | 392 |

TABLE 13-continued
| Ex. No. | Structure | Molecular formula | Mono-isotopic molecular wt. | M + H⁺ |
|---|---|---|---|---|
| 1527 | 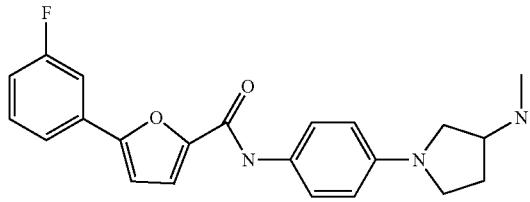 | C22H22FN3O2 | 379.17 | 380 |
| 1528 | 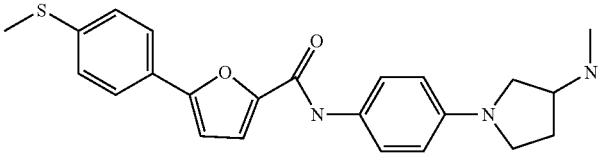 | C23H25N3O2S | 407.17 | 408 |
| 1529 | 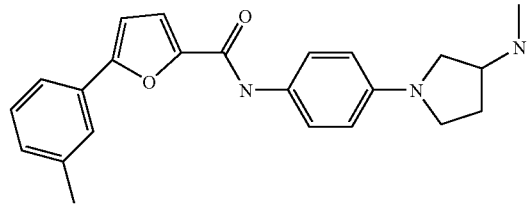 | C23H25N3O2 | 375.20 | 376 |
| 1530 | 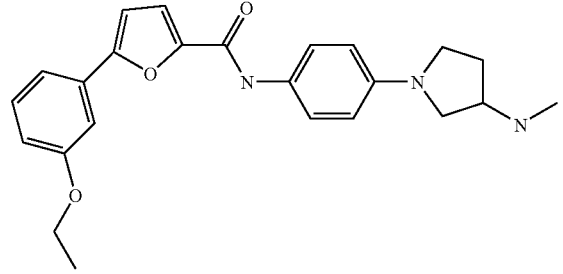 | C24H27N3O3 | 405.20 | 406 |
| 1531 | 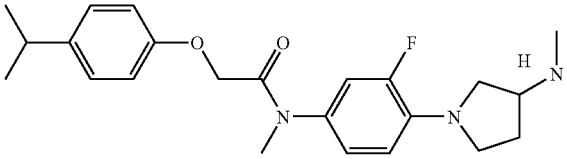 | C23H30FN3O2 | 399.23 | 400 |
| 1532 | 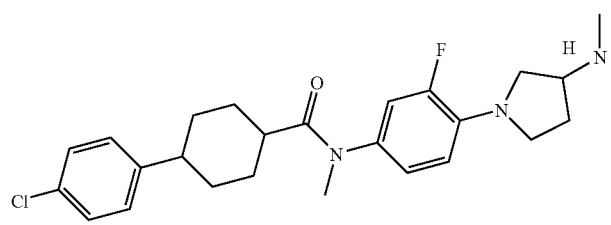 | C25H31ClFN3O | 443.21 | 444 |

TABLE 13-continued
| Ex. No. | Structure | Molecular formula | Mono-isotopic molecular wt. | M + H+ |
|---|---|---|---|---|
| 1533 | 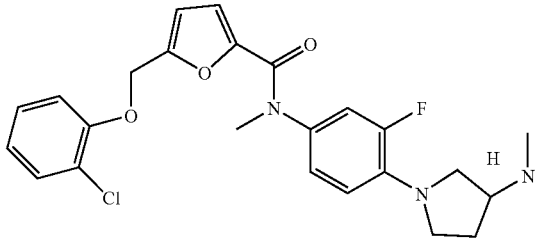 | C24H25ClFN3O3 | 457.16 | 458 |
| 1534 | 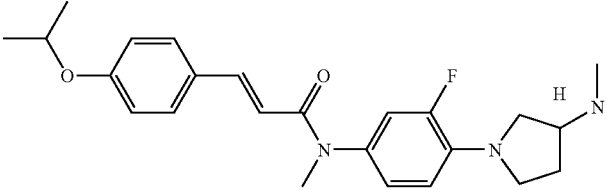 | C24H30FN3O2 | 411.23 | 412 |
| 1535 | 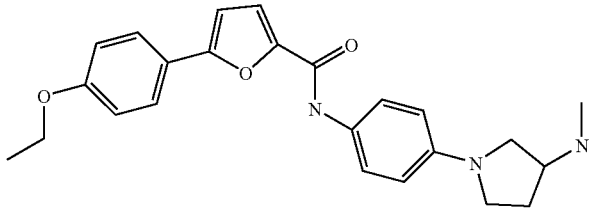 | C24H27N3O3 | 405.20 | 406 |
| 1536 | 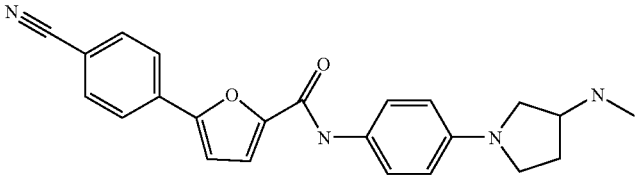 | C23H22N4O2 | 386.17 | 387 |
| 1537 | 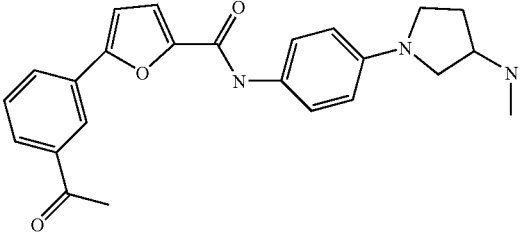 | C24H25N3O3 | 403.19 | 404 |
| 1538 | 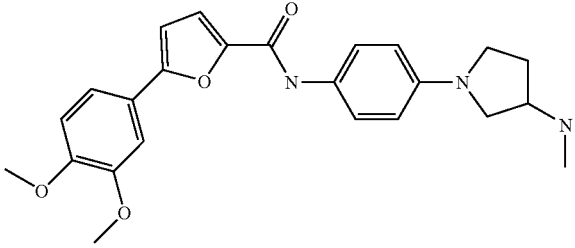 | C24H27N3O4 | 421.20 | 422 |

TABLE 13-continued

| Ex. No. | Structure | Molecular formula | Mono-isotopic molecular wt. | M + H⁺ |
|---|---|---|---|---|
| 1539 | 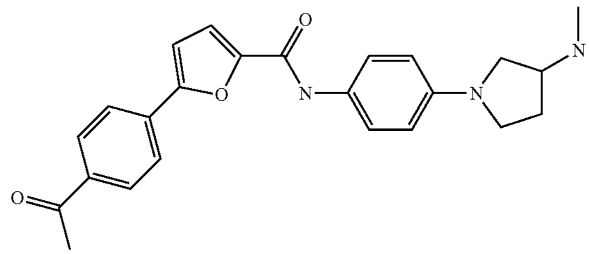 | C24H25N3O3 | 403.19 | 404 |
| 1540 | 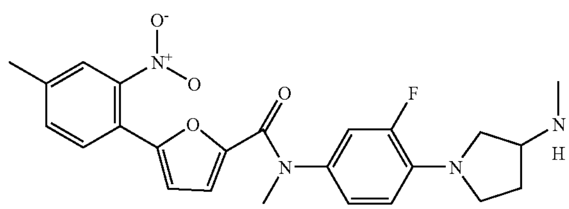 | C24H25FN4O4 | 452.19 | 453 |
| 1541 | 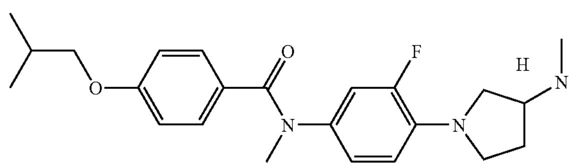 | C23H3OFN3O2 | 399.23 | 400 |
| 1542 | 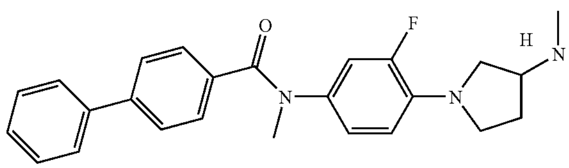 | C25H26FN3O | 403.21 | 404 |
| 1543 | 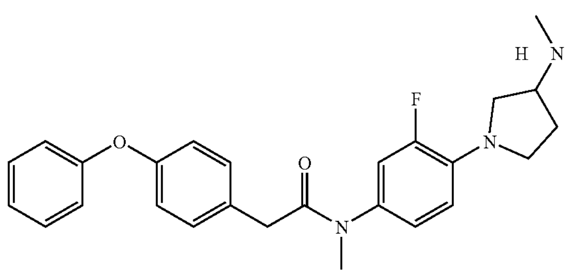 | C26H28FN3O2 | 433.22 | 434 |
| 1544 | 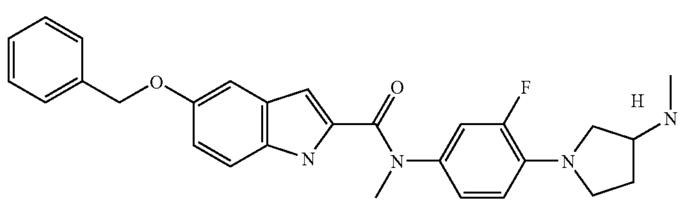 | C28H29FN4O2 | 472.23 | 473 |
| 1545 | 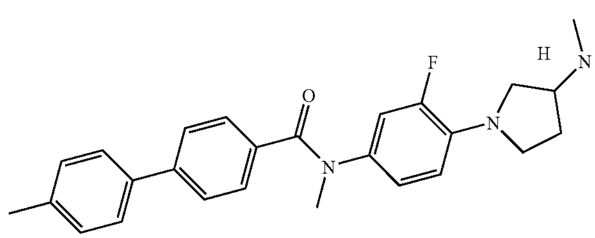 | C26H28FN3O | 417.22 | 418 |

TABLE 13-continued

| Ex. No. | Structure | Molecular formula | Mono-isotopic molecular wt. | M + H+ |
|---|---|---|---|---|
| 1546 | 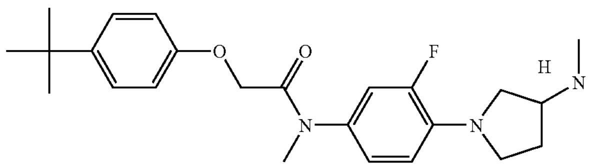 | C24H32FN3O2 | 413.25 | 414 |
| 1547 | 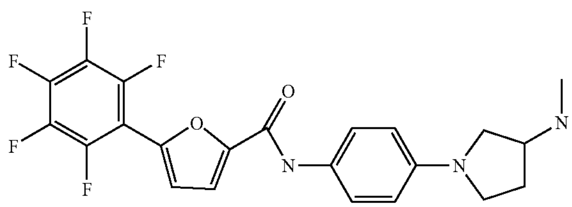 | C22H18F5N3O2 | 451.13 | 452 |
| 1548 | 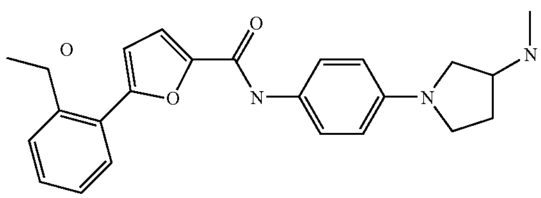 | C24H25N3O3 | 403.19 | 404 |
| 1549 | 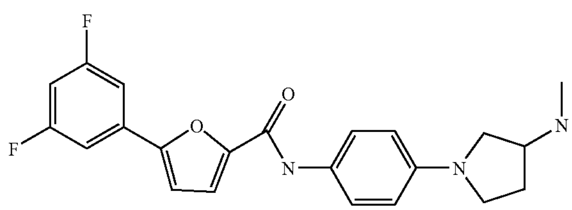 | C22H21F2N3O2 | 397.16 | 398 |
| 1550 | 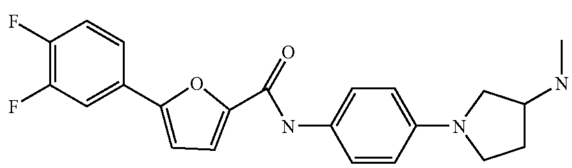 | C22H21F2N3O2 | 397.16 | 398 |
| 1551 | 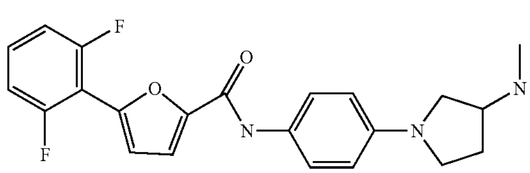 | C22H21F2N3O2 | 397.16 | 398 |
| 1552 | 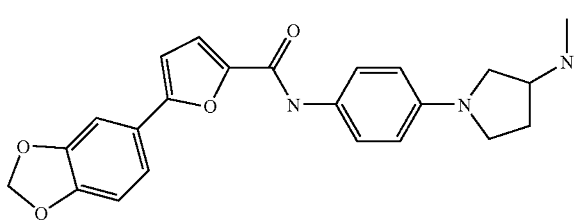 | C23H23N3O4 | 405.17 | 406 |

TABLE 13-continued

| Ex. No. | Structure | Molecular formula | Mono-isotopic molecular wt. | M + H+ |
|---|---|---|---|---|
| 1553 | 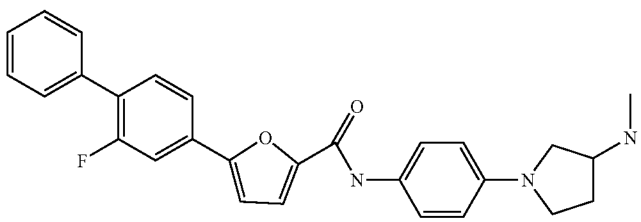 | C28H26FN3O2 | 455.20 | 456 |
| 1554 | 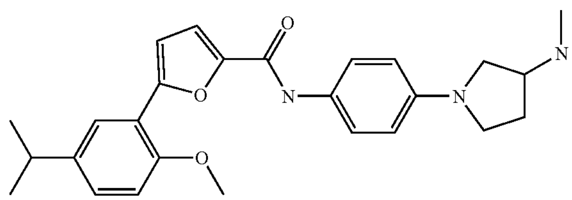 | C26H31N3O3 | 433.24 | 434 |
| 1555 | 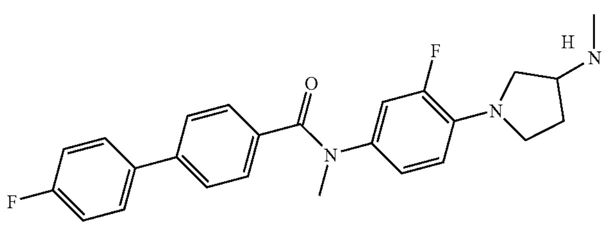 | C25H25F2N3O | 421.20 | 422 |
| 1556 | 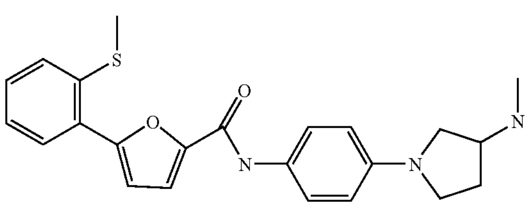 | NC23H25N3O2S | 407.17 | 408 |
| 1557 | 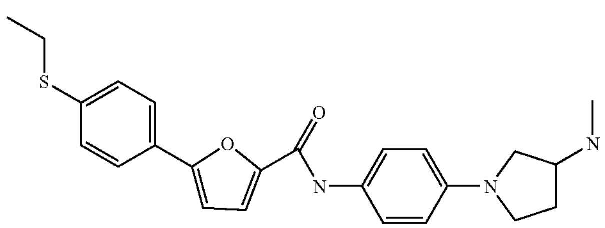 | C24H27N3O2S | 421.18 | 422 |
| 1558 | 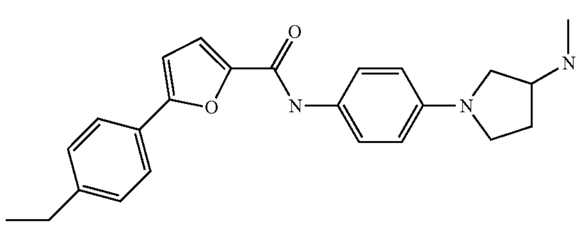 | C24H27N3O2 | 389.21 | 390 |

TABLE 13-continued

| Ex. No. | Structure | Molecular formula | Mono-isotopic molecular wt. | M + H⁺ |
|---|---|---|---|---|
| 1559 | 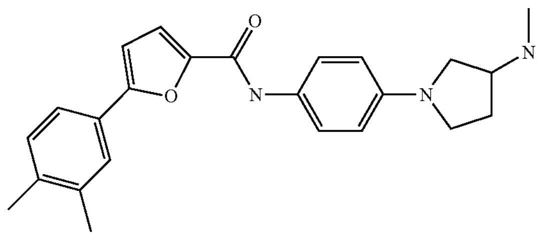 | C24H27N3O2 | 389.21 | 390 |
| 1560 | 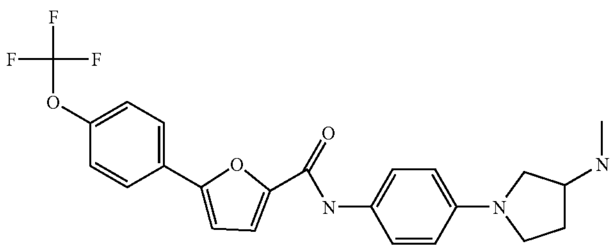 | C23H22F3N3O3 | 445.16 | 446 |
| 1561 | 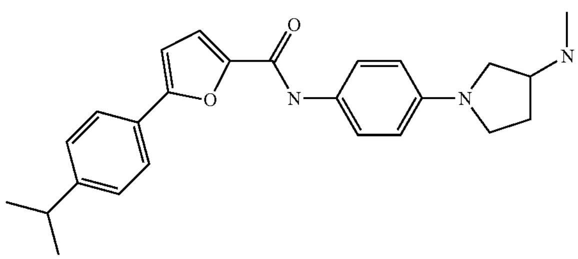 | C25H29N3O2 | 403.23 | 404 |
| 1562 | 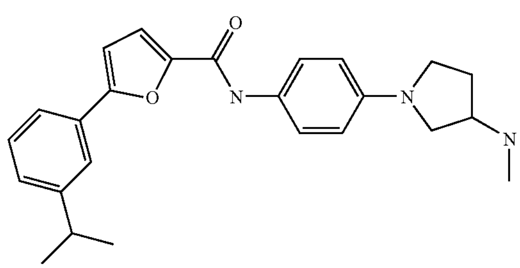 | C25H29N3O2 | 403.23 | 404 |
| 1563 | 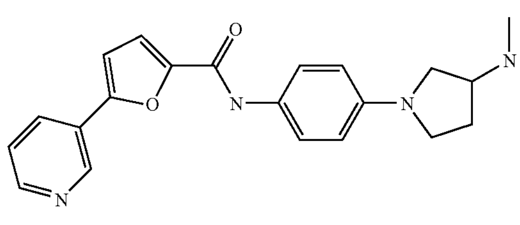 | C21H22N4O2 | 362.17 | 363 |
| 1564 | 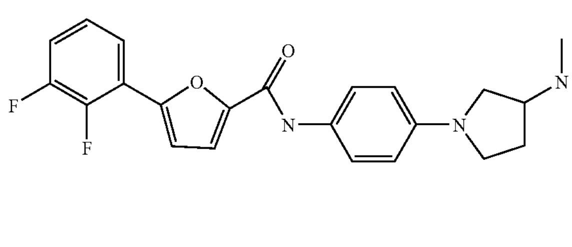 | C22H21F2N3O2 | 397.16 | 398 |

TABLE 13-continued

| Ex. No. | Structure | Molecular formula | Mono-isotopic molecular wt. | M + H⁺ |
|---|---|---|---|---|
| 1565 | 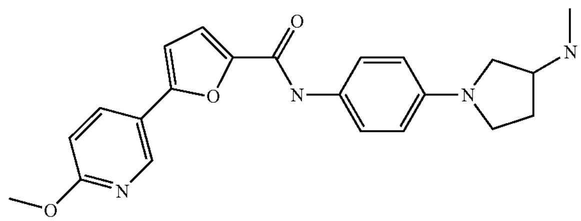 | C22H24N4O3 | 392.18 | 393 |
| 1566 | 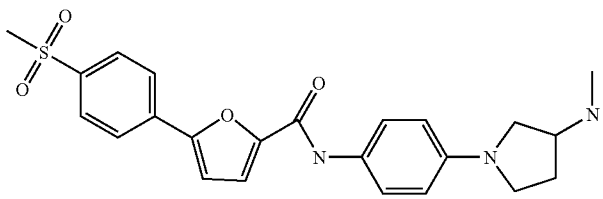 | C23H25N3O4S | 439.16 | 440 |
| 1567 | 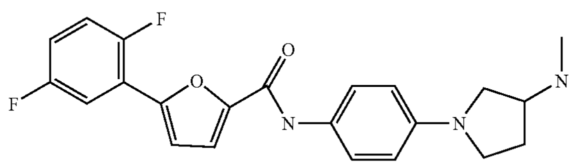 | C22H21F2N3O2 | 397.16 | 398 |
| 1568 | 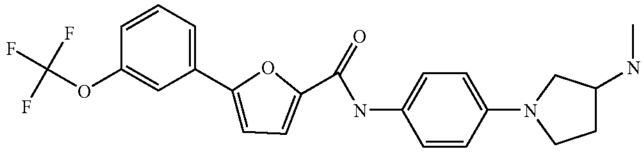 | C23H22F3N3O3 | 445.16 | 446 |
| 1569 | 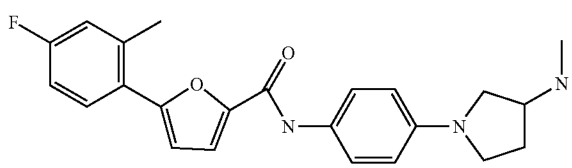 | C23H24FN3O2 | 393.18 | 394 |
| 1570 | 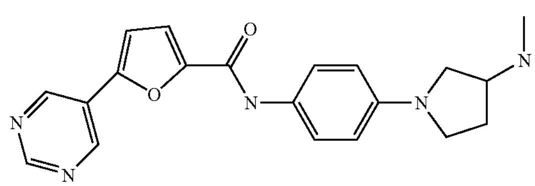 | C20H21N5O2 | 363.17 | 364 |
| 1571 | 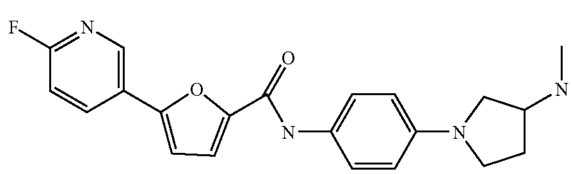 | C21H21FN4O2 | 380.17 | 381 |
| 1572 | 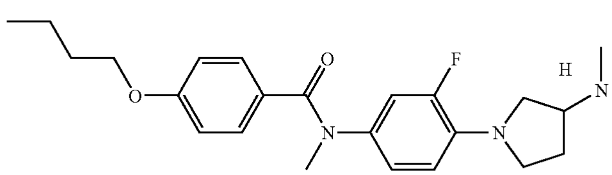 | C23H30FN3O2 | 399.23 | 400 |

TABLE 13-continued

| Ex. No. | Structure | Molecular formula | Mono-isotopic molecular wt. | M + H+ |
|---|---|---|---|---|
| 1573 | 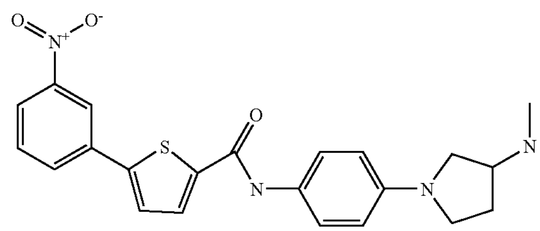 | C22H22N4O3S | 422.14 | 423 |
| 1574 | 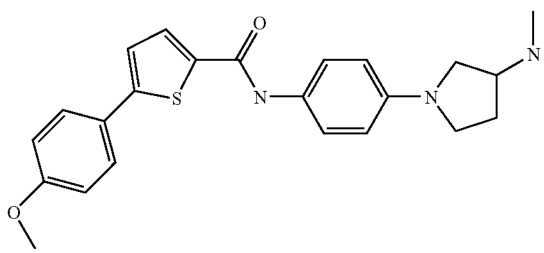 | C23H25N3O2S | 407.17 | 408 |
| 1575 | 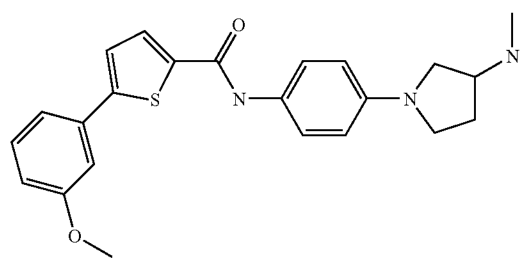 | C23H25N3O2S | 407.17 | 408 |
| 1576 | 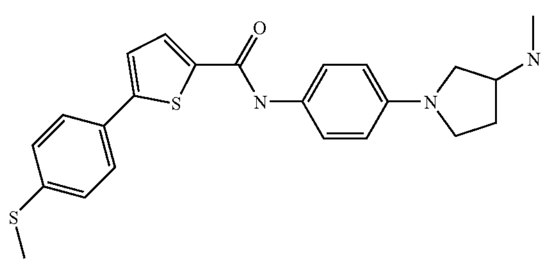 | C23H25N3OS2 | 423.14 | 424 |
| 1577 | 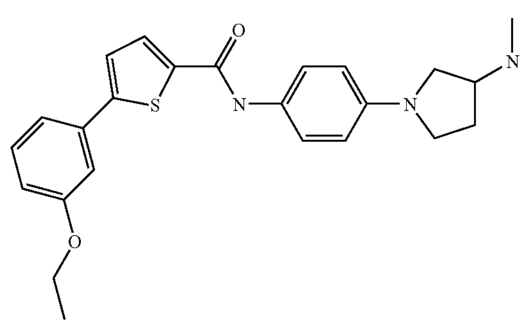 | C24H27N3O2S | 421.18 | 422 |

TABLE 13-continued

| Ex. No. | Structure | Molecular formula | Mono-isotopic molecular wt. | M + H+ |
|---|---|---|---|---|
| 1578 | 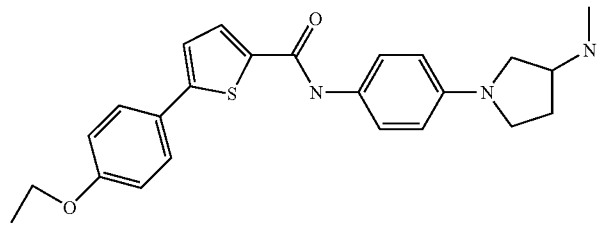 | C24H27N3O2S | 421.18 | 422 |
| 1579 | 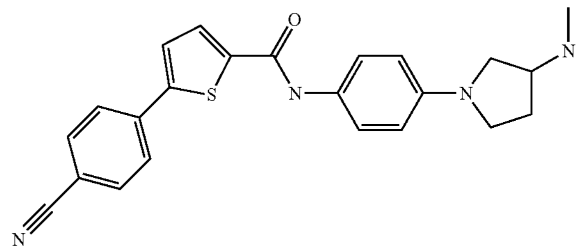 | C23H22N4OS | 402.15 | 403 |
| 1580 | 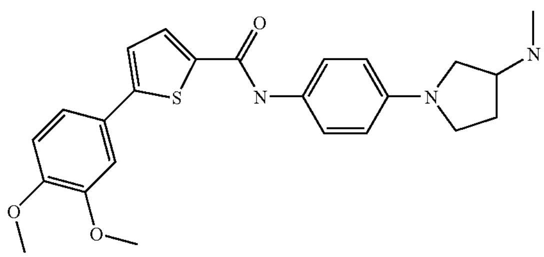 | C24H27N3O3S | 437.18 | 438 |
| 1581 | 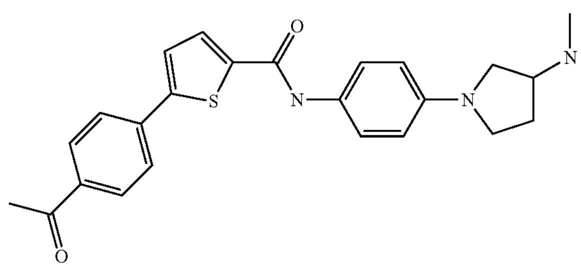 | C24H25N3O2S | 419.17 | 420 |
| 1582 | 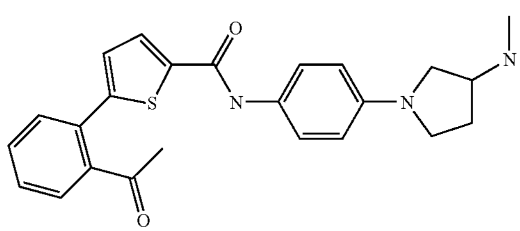 | C24H25N3O2S | 419.17 | 420 |
| 1583 | 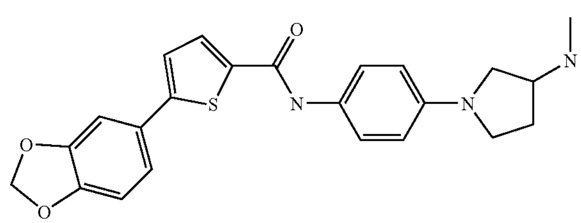 | C23H23N3O3S | 421.15 | 422 |

TABLE 13-continued

| Ex. No. | Structure | Molecular formula | Mono-isotopic molecular wt. | M + H+ |
|---|---|---|---|---|
| 1584 | 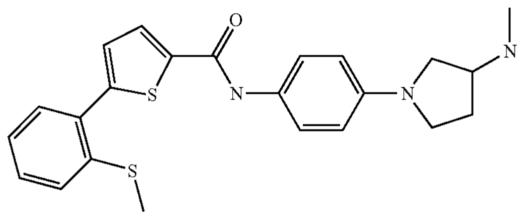 | C23H25N3OS2 | 423.14 | 424 |
| 1585 | 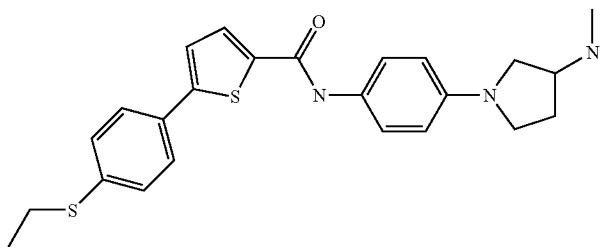 | C24H27N3OS2 | 437.16 | 438 |
| 1586 | 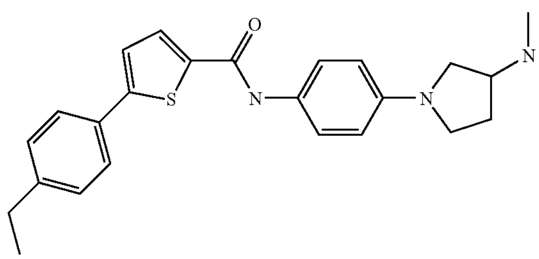 | C24H27N3OS | 405.19 | 406 |
| 1587 | 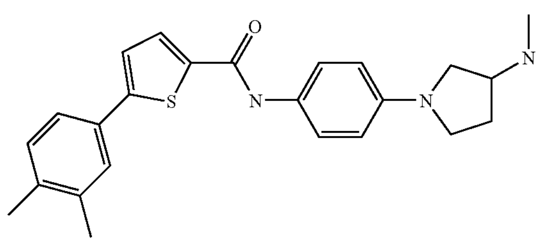 | C24H27N3OS | 405.19 | 406 |
| 1588 | 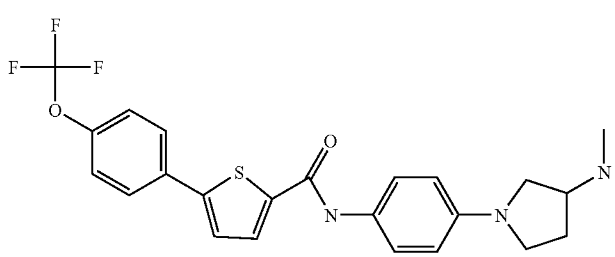 | C23H22F3N3O2S | 461.14 | 462 |
| 1589 | 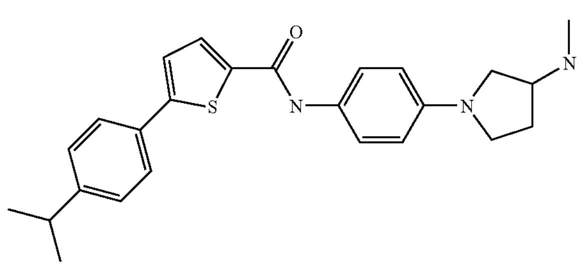 | C25H29N3OS | 419.20 | 420 |

TABLE 13-continued

| Ex. No. | Structure | Molecular formula | Mono-isotopic molecular wt. | M + H+ |
|---|---|---|---|---|
| 1590 | 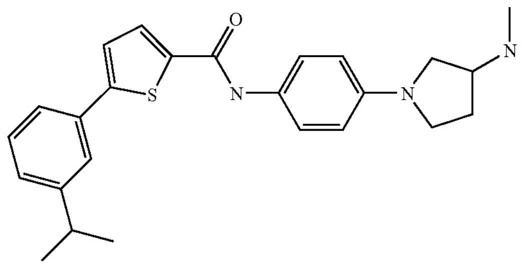 | C25H29N3OS | 419.20 | 420 |
| 1591 | 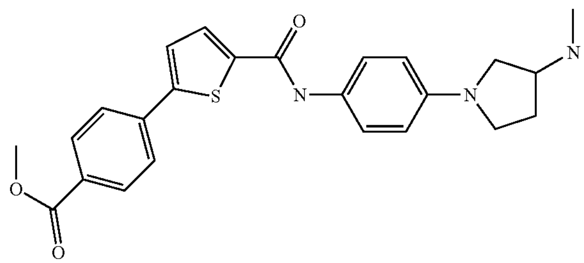 | C24H25N3O3S | 435.16 | 436 |
| 1592 | 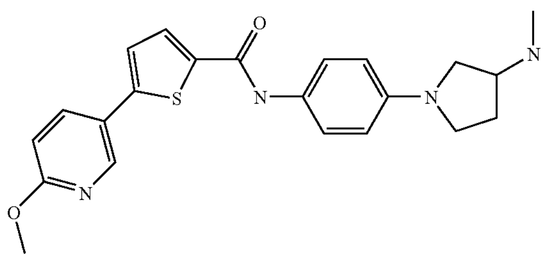 | C22H24N4O2S | 408.16 | 409 |
| 1593 | 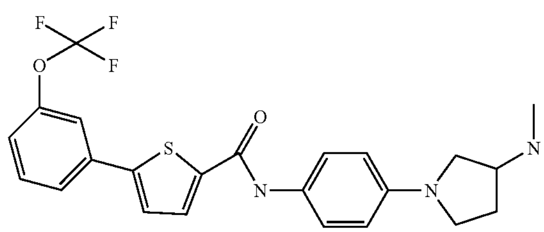 | C23H22F3N3O2S | 461.14 | 462 |
| 1594 | 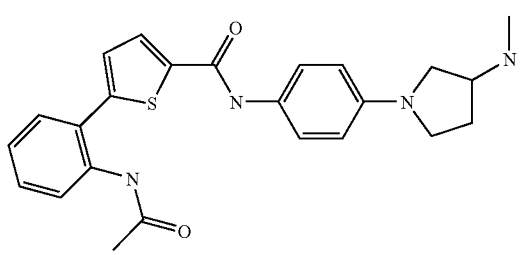 | C24H26N4O2S | 434.18 | 435 |
| 1595 | 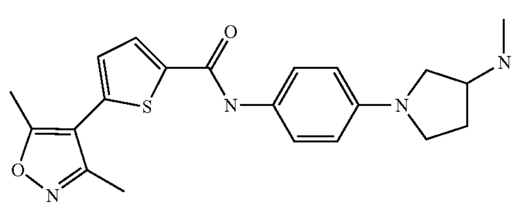 | C21H24N4O2S | 396.16 | 397 |

TABLE 13-continued

| Ex. No. | Structure | Molecular formula | Mono-isotopic molecular wt. | M + H+ |
|---|---|---|---|---|
| 1596 | 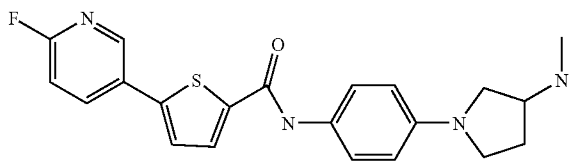 | C21H21FN4OS | 396.14 | 397 |
| 1597 | 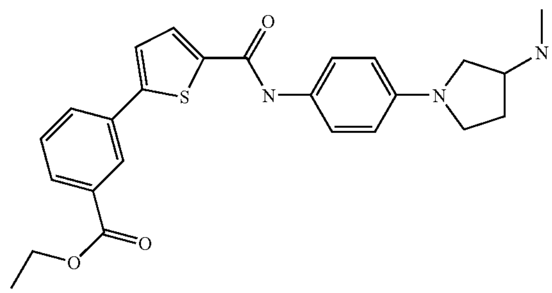 | C25H27N3O3S | 449.18 | 450 |
| 1598 | 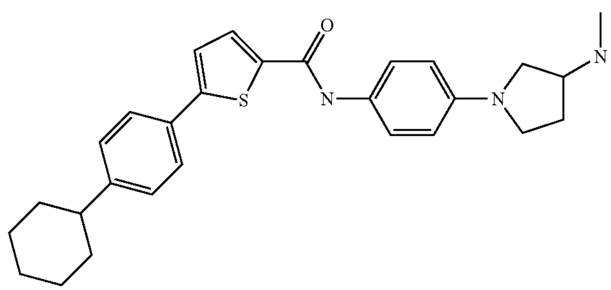 | C28H33N3OS | 459.23 | 460 |
| 1599 | 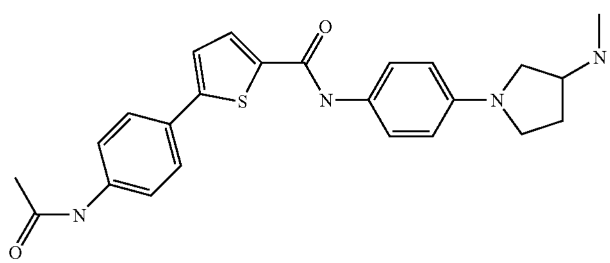 | C24H26N4O2S | 434.18 | 435 |
| 1600 | 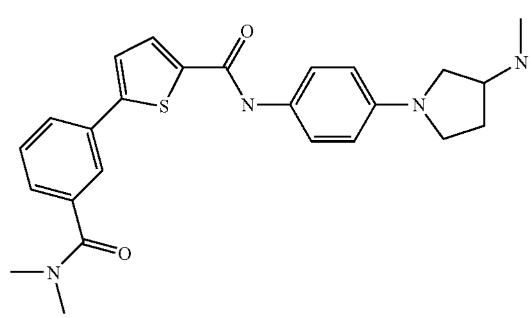 | C25H28N4O2S | 448.19 | 449 |

TABLE 13-continued
| Ex. No. | Structure | Molecular formula | Mono-isotopic molecular wt. | M + H+ |
|---|---|---|---|---|
| 1601 | 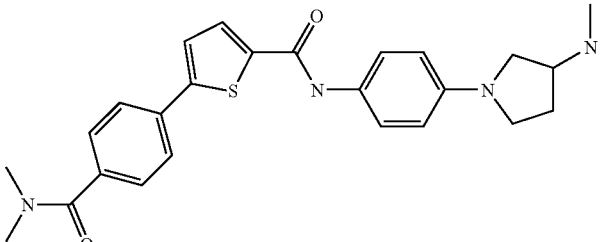 | C25H28N4O2S | 448.19 | 449 |
| 1602 | 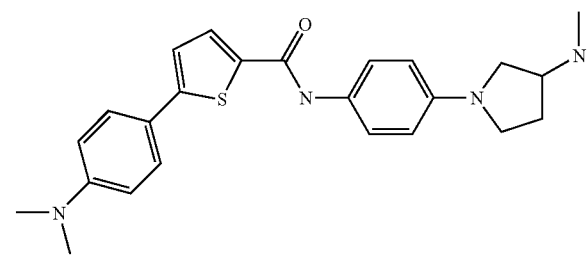 | C24H28N4OS | 420.20 | 421 |
| 1603 | 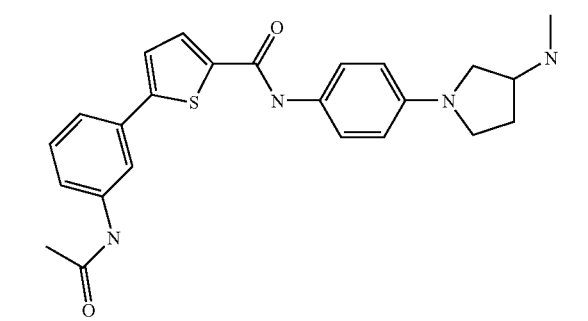 | C24H26N4O2S | 434.18 | 435 |
| 1604 | 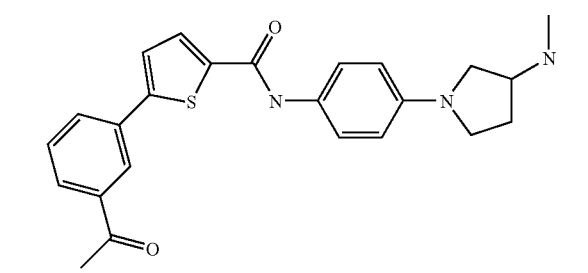 | C24H25N3O2S | 419.17 | 420 |
| 1605 | 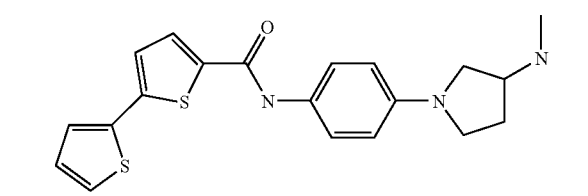 | C20H21N3OS2 | 383.11 | 384 |

TABLE 13-continued

| Ex. No. | Structure | Molecular formula | Mono-isotopic molecular wt. | M + H⁺ |
|---|---|---|---|---|
| 1606 | 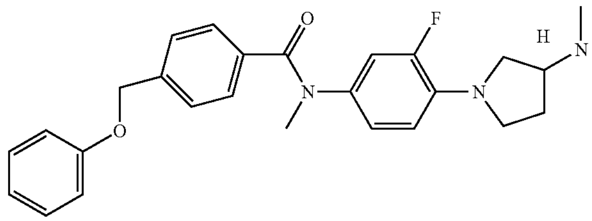 | C26H28FN3O2 | 433.22 | 434 |
| 1607 | 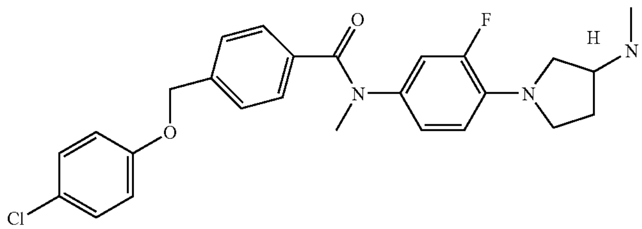 | C26H27ClFN3O2 | 467.18 | 468 |
| 1608 | 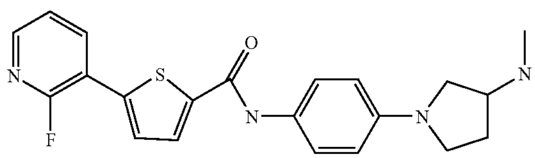 | C21H21FN4OS | 396.14 | 397 |
| 1609 | 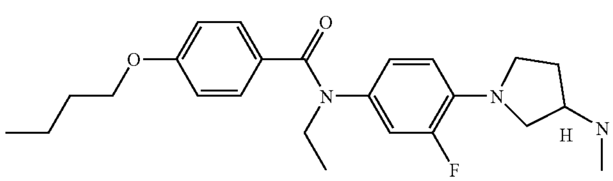 | C24H32FN3O2 | 413.25 | 414 |
| 1610 | 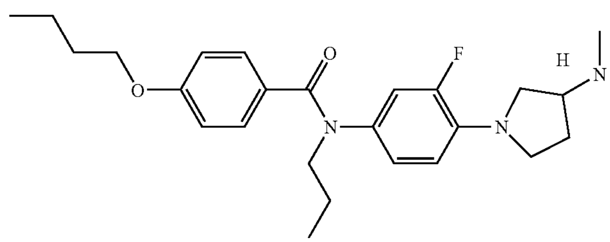 | C25H34FN3O2 | 427.26 | 428 |
| 1611 | 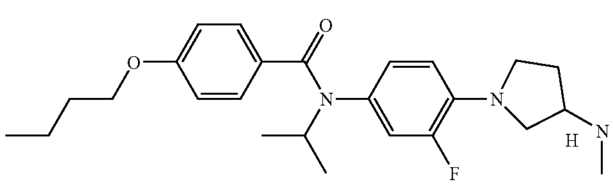 | C25H34FN3O2 | 427.26 | 428 |
| 1612 | 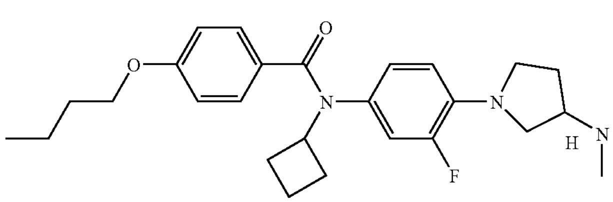 | C26H34FN3O2 | 439.26 | 440 |

TABLE 13-continued

| Ex. No. | Structure | Molecular formula | Mono-isotopic molecular wt. | M + H+ |
|---|---|---|---|---|
| 1613 | 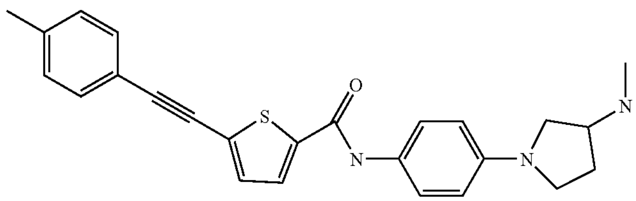 | C25H25N3OS | 415.17 | 416 |
| 1614 | 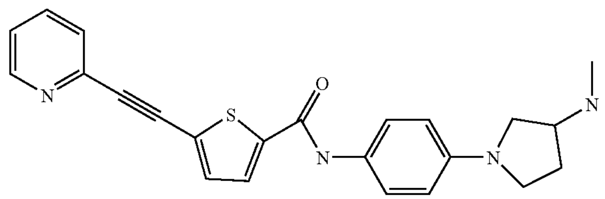 | C23H22N4OS | 402.15 | 403 |
| 1615 | 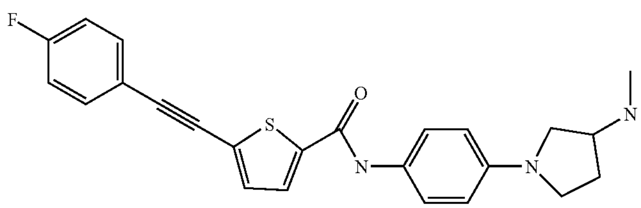 | C24H22FN3OS | 419.15 | 420 |
| 1616 | 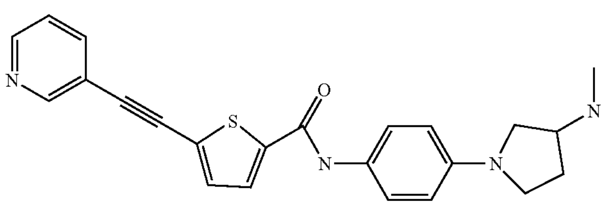 | C23H22N4OS | 402.15 | 403 |
| 1617 | 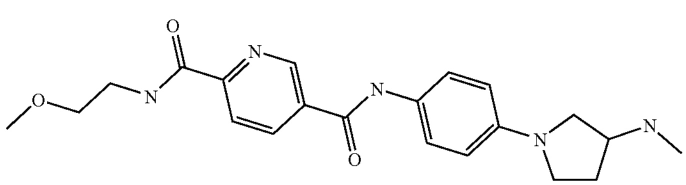 | C21H27N5O3 | 397.21 | 398 |
| 1618 | 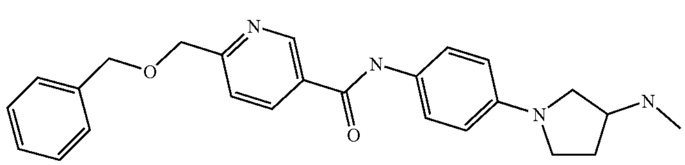 | C25H28N4O2 | 416.22 | 417 |

Synthesis of Pyrrolidinylanilines Required as Intermediates

[1-Amino-2-chlorophenyl)pyrrolidin-3-yl]dimethylamine

Method C-a

3-Dimethylaminopyrrolidine (0.34 g) was slowly added to a solution of 2-chloro-1 fluoro-4-nitrobenzene (0.52 g) in DMF (5 ml). After 1 hour, ethyl acetate (30 ml) was added to the reaction mixture, and it was extracted with 10% hydrochloric acid (2×20 ml). The aqueous phase was washed with ethyl acetate (2×20 ml), adjusted to pH>10 with 10% ammonia and extracted with ethyl acetate. The yellow solution was dried with sodium sulfate, filtered and concentrated in a rotary evaporator. The residue was then dissolved in dichloromethane (50 ml), zinc (10 g) was added, and glacial acetic acid (5 ml) was slowly added dropwise while cooling in ice. The suspension was stirred for 15 minutes, filtered, washed with 10% ammonia (2×20 ml) and concentrated. This resulted in the product with the molecular weight of 239.75 (C12H18ClN3); MS (ESI): 239 (M+H+), 240 (M+H+), 5-Amino-2-(3-dimethylaminopyrrolidin-1-yl)benzonitrile Dimethylaminopyrrolidine was treated with 2-fluoro-5-nitrobenzonitrile and subsequently reduced by method C-a.

This resulted in the product with the molecular weight of 230.32 (C13H18N4); MS (ESI): 231 (M+H+),

[1-(4-Amino-3-chlorophenyl)pyrrolidin-3-yl]dimethylamine

Dimethylaminopyrrolidine was treated with 3-chloro-1-fluoro-4-nitrobenzene and subsequently reduced by method C-a. This resulted in the product with the molecular weight of 239.75 (C12H18ClN3); MS (ESI): 239 (M+H+), 240 (M+H+),

[1-(4-Amino-3-methylphenyl)pyrrolidin-3-yl]dimethylamine

Dimethylaminopyrrolidine was treated with 4-fluoro-2-methyl-1-nitrobenzene and subsequently reduced by method C-a. This resulted in the product with the molecular weight of 219.33 (C13H21N3); MS (ESI): 220 (M+H+).

tert-Butyl (R)-[1-(4-amino-2-fluorophenyl)pyrrolidin-3-yl]methylcarbamate

Method C-b tert-Butyl (R)-(+)-pyrrolidin-3-ylcarbamate (1.86 g) was slowly added to a suspension of 3,4-difluoronitrobenzene (1.59 g) and potassium carbonate (2.8 g) in DMF (10 ml). After 10 minutes, ethyl acetate (50 ml) was added, and the mixture was washed with water (3×50 ml) in a separating funnel, dried with sodium sulfate, filtered and concentrated. The residue was dissolved in DMF (10 ml), and sodium hydride (0.48 g) was added. After 15 minutes, methyl iodide (1.41 g) was then added while cooling in ice. After 30 minutes, ethyl acetate (50 ml) was added, and the mixture was washed with water (3×50 ml) in a separating funnel, dried with sodium sulfate, filtered and concentrated. The substance was then treated as described for method B. This resulted in the product with the molecular weight of 309.39 (C16H24FN3O2); MS (ESI): 310 (M+H+).

tert-Butyl (S)-[1-(4-amino-2-fluorophenyl)pyrrolidin-3-yl]methylcarbamate was obtained analogously.

tert-Butyl (R)-[1-(2-fluoro-4-isopropylaminophenyl)pyrrolidin-3-yl]methylcarbamate tert-Butyl (R)-[1-(4-amino-2-fluorophenyl)pyrrolidin-3-yl]methylcarbamate was alkylated with acetone using triacetoxyborohydride as reducing agent by method N. This resulted in the product with the molecular weight of 351.47 (C19H30FN3O2); MS (ESI): 352 (M+H+).

tert-Butyl (R)-[1-(2-Fluoro-4-cyclobutylaminophenyl)pyrrolidin-3-yl]methylcarbamate tert-Butyl (R)-[1-(4-amino-2-fluorophenyl)pyrrolidin-3-yl]methylcarbamate was alkylated with cyclobutanone using triacetoxyborohydride as reducing agent by method N. This resulted in the product with the molecular weight of 363.48 (C20H30FN3O2); MS (ESI): 364 (M+H+).

tert-Butyl (R)-[1-(2-fluoro-4-methylaminophenyl)pyrrolidin-3-yl]methylcarbamate tert-Butyl (R)-{1-[4-(benzyloxycarbonylmethylamino)-2-fluorophenyl]pyrrolidin-3-yl}-methylcarbamate was treated as described for method B. This resulted in the product with the molecular weight of 323.41 (C17H26FN3O2); MS (ESI): 324 (M+H+).

tert-Butyl (R)-{1-[4-(benzyloxycarbonylmethylamino)-2-fluorophenyl]pyrrolidin-3-yl}-methylcarbamate tert-Butyl (R)-(+)-[1-(4-amino-2-fluorophenyl)pyrrolidin-3-yl]methylcarbamate (0.93 g) was added to a solution of N-(benzyloxycarbonyloxy)succinimide (2.49 g) in dichloromethane (30 ml). After 12 hours, the mixture was washed with water (2×30 ml), dried sodium sulfate, filtered and concentrated. The residue was recrystallized from acetonitrile. The product obtained in this way was dissolved in DMF (10 ml), and sodium hydride (0.24 g) was added. After 15 minutes, methyl iodide (0.71 g) was added while cooling in ice. After 15 minutes, ethyl acetate (50 ml) was added, and the mixture was washed with water (3×30 ml), dried sodium sulfate, filtered and concentrated. This resulted in the product with the molecular weight of 457.55 (C25H32FN3O4); MS (ESI): 458 (M+H+).

(R)-[1-(2-Fluoro-4-methylaminophenyl)pyrrolidin-3-yl]dimethylamine (R)-{1-[4-(Benzyloxycarbonylmethylamino)-2-fluorophenyl]pyrrolidin-3-yl}methylcarbamic acid tert-butyl ester was treated by method G, and the resulting amine was methylated by method M. Finally, hydrogenation was carried out by method B. This resulted in the product with the molecular weight of 237.32 (C13H20FN3); MS (ESI): 238 (M+H+).

Dimethyl-[1-(4-methylaminophenyl)pyrrolidin-3-yl]amine can be prepared analogously.

2-Dimethylamino-N-[1-(2-fluoro-4-methylaminophenyl)pyrrolidin-3-yl]-N-methylacetamide (R)-{1-[4-(Benzyloxycarbonylmethylamino)-2-fluorophenyl]pyrrolidin-3-yl}methylcarbamic acid tert-butyl ester was treated by method G, and the resulting amine was reacted with N,N-dimethylglycine by method E. Finally, hydrogenation was carried out by method B. This resulted in the product with the molecular weight of 308.40 (C16H25FN4O); MS (ESI): 309 (M+H+).

tert-Butyl (R)-[1-(4-amino-3-fluorophenyl)pyrrolidin-3-yl]methylcarbamate 2,4-Difluoronitrobenzene was treated with tert-butyl (R)-(+)-pyrrolidin-3-ylcarbamate, methylated and subsequently hydrogenated by method C-b. This resulted in the product with the molecular weight of 309.39 (C16H24FN3O2); MS (ESI): 310 (M+H+).

tert-Butyl [1-(4-aminonaphthalen-1-yl)pyrrolidin-3-yl]methylcarbamate

Method C-c tert-Butyl methylpyrrolidin-3-ylcarbamate (1.86 g) was slowly added to a suspension of 4-fluoro-1-nitronaphthalene (1.91 g) and potassium carbonate (2.8 g) in DMF (10 ml). After 10 minutes, ethyl acetate (50 ml) was added, and the mixture was washed with water (3×50 ml) in a separating funnel, dried with sodium sulfate, filtered and concentrated. The substance was then treated as described for method B. This resulted in the product with the molecular weight of 341.46 (C20H27N3O2); MS (ESI): 342 (M+H+).

tert-Butyl [1-(4-amino-3-bromophenyl)pyrrolidin-3-yl]methylcarbamate

2-Bromo-4-fluoro-1-nitrobenzene was treated with tert-butyl methylpyrrolidin-3-ylcarbamate and subsequently reduced by method C-a. This resulted in the product with the molecular weight of 370.29 (C16H24BrN3O2); MS (ESI): 370 (M+H+), 372 (M+H+).

Tert-butyl [1-(4-amino-3-cyanophenyl)pyrrolidin-3-yl]methylcarbamate

2-Cyano-4-fluoro-1-nitrobenzene was treated with tert-butyl methylpyrrolidin-3-yl-carbamate and subsequently reduced by method C-a. This resulted in the product with the molecular weight of 316.41 (C17H24N4O2); MS (ESI): 317 (M+H+).

tert-Butyl [1-(5-amino-6-chloropyridin-2-yl)pyrrolidin-3-yl]methylcarbamate

2-Chloro-6-fluoro-3-nitropyridine was treated with tert-butyl methylpyrrolidin-3-ylcarbamate and subsequently reduced by method C-c. This resulted in the product with the molecular weight of 326.83 (C15H23ClN4O2); MS (ESI): 326 (M+H+), 327 (M+H+).

tert-Butyl [1-(4-amino-2,3-difluorophenyl)pyrrolidin-3-yl]methylcarbamate 2,3,4-Trifluoronitrobenzene was treated with tert-butyl methylpyrrolidin-3-ylcarbamate and subsequently reduced by method C-c. This resulted in the product with the molecular weight of 327.38 (C16H23F2N3O2); MS (ESI): 328 (M+H+).

tert-Butyl [1-(4-amino-2-bromophenyl)pyrrolidin-3-yl]methylcarbamate

3-Bromo-4-fluoro-1-nitrobenzene was treated with tert-butyl methylpyrrolidin-3-ylcarbamate and subsequently reduced by method C-a. This resulted in the product with the molecular weight of 370.29 (C16H24BrN3O2); MS (ESI): 370 (M+H+), 372 (M+H+).

tert-Butyl [1-(4-amino-2,6-difluorophenyl)pyrrolidin-3-yl]methylcarbamate 3,4,5-Trifluoronitrobenzene was treated with tert-butyl methylpyrrolidin-3-yl-carbamate and subsequently hydrogenated by method C-c. This resulted in the product with the molecular weight of 327.38 (C16H23F2N3O2); MS (ESI): 328 (M+H+).

tert-Butyl (R)-[1-(4-amino-2-hydroxymethylphenyl)pyrrolidin-3-yl]carbamate (2-Fluoro-5-nitrophenyl)methanol was treated with tert-butyl (R)-(+)-pyrrolidin-3-ylcarbamate and subsequently hydrogenated by method C-c. This resulted in the product with the molecular weight of 307.40 (C16H25N3O3); MS (ESI): 308 (M+H+).

tert-Butyl [1-(4-amino-2-chlorophenyl)pyrrolidin-3-yl]methylcarbamate

2-Chloro-1-fluoro-4-nitrobenzene was treated with tert-butyl methylpyrrolidin-3-ylcarbamate and subsequently hydrogenated by method C-c. This resulted in the product with the molecular weight of 311.81 (C15H22ClN3O2); MS (ESI): 311 (M+H+), 312 (M+H+).

tert-Butyl [1-(4-amino-2,5-difluorophenyl)pyrrolidin-3-yl]methylcarbamate 3,4,6-Trifluoronitrobenzene was treated with tert-butyl methylpyrrolidin-3-ylcarbamate and subsequently hydrogenated by method C-c. This resulted in the product with the molecular weight of 327.38 (C16H23F2N3O2); MS (ESI): 328 (M+H+).

tert-Butyl [1-(4-amino-2-methylphenyl)pyrrolidin-3-yl]methylcarbamate tert-Butyl 4-fluoro-3-methylnitrobenzene was treated with tert-butyl methylpyrrolidin-3-yl-carbamate and subsequently hydrogenated by method C-c. This resulted in the product with the molecular weight of 291.40 (C16H25N3O2); MS (ESI): 292 (M+H+).

tert-Butyl [1-(4-amino-3-trifluoromethylphenyl)pyrrolidin-3-yl]methylcarbamate 4-Fluoro-2-trifluoromethyinitrobenzene was treated with tert-butyl methylpyrrolidin-3-yl-carbamate and subsequently hydrogenated by method C-c. This resulted in the product with the molecular weight of 345.37 (C16H22F3N3O2); MS (ESI): 346 (M+H+).

tert-Butyl [1-(4-amino-2-chloro-3-fluorophenyl)pyrrolidin-3-yl]methylcarbamate 2,4-Difluoro-3-chloronitrobenzene was treated with tert-butyl methylpyrrolidin-3-yl-carbamate and subsequently hydrogenated by method C-c. This resulted in the product with the molecular weight of 329.80 (C15H21ClN3O2); MS (ESI): 329 (M+H+), 330 (M+H+).

tert-Butyl [1-(4-amino-2-cyanophenyl)pyrrolidin-3-yl]methylcarbamate

3-Cyano-4-fluoronitrobenzene was treated with tert-butyl methylpyrrolidin-3-yl-carbamate and subsequently hydrogenated by method C-c. This resulted in the product with the molecular weight of 302.38 (C16H22N4O2); MS (ESI): 303 (M+H+).

tert-Butyl [1-(4-amino-5-chloro-2-methylphenyl)pyrrolidin-3-yl]methylcarbamate 1-Chloro-5-fluoro-4-methyl-2-nitrobenzene was treated with tert-butyl methylpyrrolidin-3-ylcarbamate and subsequently hydrogenated by method C-c. This resulted in the product with the molecular weight of 325.84 (C16H24ClN3O2); MS (ESI): 325 (M+H+), 326 (M+H+).

tert-Butyl (R)-[1-(5-aminopyridin-2-yl)pyrrolidin-3-yl]methylcarbamate

2-Chloro-5-nitropyridine was treated with tert-butyl (R)-(+)-pyrrolidin-3-ylcarbamate and subsequently hydrogenated by method C-b. This resulted in the product with the molecular weight of 322.37 (C16H24FN3O2); MS (ESI): 323 (M+H+).

tert-Butyl [1-(5-aminopyridin-2-yl)pyrrolidin-3-yl] methylcarbamate

2-Chloro-5-nitropyridine was treated with tert-butyl methylpyrrolidin-3-yl-carbamate and subsequently hydrogenated by method C-c. This resulted in the product with the molecular weight of 322.37 (C16H24FN3O2); MS (ESI): 323 (M+H+).

tert-Butyl (R)-[1-(4-aminophenyl)pyrrolidin-3-yl] methylcarbamate

4-Fluoronitrobenzene was treated with tert-butyl (R)-(+)-pyrrolidin-3-yl-carbamate and subsequently hydrogenated by method C-b. This resulted in the product with the molecular weight of 291.40 (C16H25N3O2); MS (ESI): 292 (M+H+).

tert-Butyl [1-(4-amino-2-trifluoromethylphenyl) pyrrolidin-3-yl]methylcarbamate 4-Fluoro-3-trifluoromethylnitrobenzene was treated with tert-butyl methylpyrrolidin-3-yl-carbamate and subsequently hydrogenated by method C-c. This resulted in the product with the molecular weight of 345.37 (C16H22F3N3O2); MS (ESI): 346 (M+H+).

tert-Butyl [1-(5-amino-4-methylpyridin-2-yl)pyrrolidin-3-yl]methylcarbamate

2-Chloro-4-methyl-5-nitropyridine was treated with tert-butyl methylpyrrolidin-3-ylcarbamate and subsequently hydrogenated by method C-c. This resulted in the product with the molecular weight of 306.419 (C16H26N4O2); MS (ESI): 306 (M+H+), 307 (M+H+).

tert-Butyl [1-(5-amino-3-methylpyridin-2-yl)pyrrolidin-3-yl]methylcarbamate

2-Chloro-3-methyl-5-nitropyridine was treated with tert-butyl methylpyrrolidin-3-yl-carbamate and subsequently hydrogenated by method C-c. This resulted in the product with the molecular weight of 306.419 (C16H26N4O2); MS (ESI): 306 (M+H+), 307 (M+H+).

tert-Butyl [1-(4-amino-2-hydroxymethylphenyl) pyrrolidin-3-yl]methylcarbamate (2-Fluoro-5-nitrophenyl)methanol was treated with tert-butyl methylpyrrolidin-3-yl-carbamate and subsequently hydrogenated by method C-c. This resulted in the product with the molecular weight of 321.42 (C17H27N3O3); MS (ESI): 322 (M+H+).

tert-Butyl [1-(4-amino-3-chloro-2-cyanophenyl) pyrrolidin-3-yl]methylcarbamate 2-Chloro-6-fluoro-3-nitrobenzonitrile was treated with tert-butyl methylpyrrolidin-3-yl-carbamate and subsequently hydrogenated by method C-c. This resulted in the product with the molecular weight of 350.5 (C17H23ClN4O2); MS (ESI): 350 (M+H+), 351 (M+H+).

tert-Butyl [1-(4-amino-3-methylphenyl)pyrrolidin-3yl]methylcarbamate

4-Fluoro-2-methylnitrobenzene was treated with tert-butyl methylpyrrolidin-3-ylcarbamate and subsequently -hydrogenated by method C-c. This resulted in the product with the molecular weight of 291.40 (C16H25N3O2); MS (ESI): 292 (M+H+).

tert-Butyl [1-(5-aminopyridin-2-yl)pyrrolidin-3-yl]carbamate

2-Chloro-5-nitropyridine was treated with tert-butyl (R)-(+)-pyrrolidin-3-ylcarbamate and subsequently hydrogenated by method C-c. This resulted in the product with the molecular weight of 278.36 (C14H22N4O2); MS (ESI): 279 (M+H+).

5-(3-Dimethylaminopyrrolidin-1-yl)pyridin-2-ylamine

A suspension of 5-bromo-2-nitropyridine (2 g), 3-(dimethylamino)pyrrolidine (1.14 g), (R)-(+)2,2'-bis(diphenylphosphino)-1,1'-binaphthyl (0.5 g), palladium(II) acetate (0.09 g), cesium carbonate (4.5 g) in toluene (20 ml) was heated at 100° C. for 3 hours. Cooling to room temperature was followed by extraction with 1N hydrochloric acid (2×100 ml). The aqueous phase was adjusted to pH>10 with ammonia, extracted with ethyl acetate (2×100 ml), dried with sodium sulfate, filtered and concentrated. The substance was then treated as described for method B. This resulted in the product with the molecular weight of 206.29 (C11H18FN4); MS (ESI): 207 (M+H+).

N-[1-(4-Aminophenyl)-4-hydroxypyrrolidin-3-yl]-N-methylacetamide trans-N-(4-Hydroxypyrrolidin-3-yl)-N-methylacetamide was reacted with 4-fluoronitrobenzene by method C, and the product was subsequently hydrogenated by method B. This resulted in the product with the molecular weight of 249.32 (C13H19N3O2); MS (ESI): 250 (M+H+).

trans-N-(4-Hydroxypyrrolidin-3-yl)-N-methylacetamide tert-Butyl trans-3-hydroxy-4-methylaminopyrrolidin-1-carboxylate (1.0 g, tetrahedron: Asymmetry 2001, 12, 2989) was mixed with pyridine (1.5 g) and acetic anhydride (0.567 g). After 3 hours, volatile fractions were removed under high vacuum. The residue was treated by method G. This resulted in the product with the molecular weight of 158.20 (C7H14N2O2); MS (ESI): 159 (M+H+).

trans-1-(4-Aminophenyl)-4-dimethylaminopyrrolidin-3-ol tert-Butyl 6-oxa-3-azabicyclo[3.1.0]hexane-3-carboxylate (2.0 g, tetrahedron: Asymmetry 2001, 12, 2989) was stirred with dimethylamine (40% aq., 10 ml) for 12 hours. The mixture was concentrated and partitioned between water and ethyl acetate. The organic phase was dried over magnesium sulfate and concentrated. The crude product was treated by method G. The resulting amine was reacted with 4-fluoronitrobenzene by method C. The resulting nitro compound was hydrogenated by method B. This resulted in the product with the molecular weight of 221 (C12H19N3O); MS (ESI): 222 (M+H+).

[1-(4-Aminophenyl)-4-methoxypyrrolidin-3-yl]dimethylamine

An alternative possibility is for the nitro compound prepared in the preceding method to be alkylated with methyl iodide by method F and then hydrogenated by method B. This resulted in the product with the molecular weight of 235 (C13H21N3O); MS (ESI): 236 (M+H+).

[1-(4-Aminophenyl)pyrrolidin-3-yl]dimethylamine

Dimethylpyrrolidin-3-ylamine was reacted with 4-fluoronitrobenzene by method C, and the product was subsequently hydrogenated by method B. This resulted in the product with the molecular weight of 205.31 (C12H19N3); MS (ESI): 206 (M+H+).

1-(4-Aminophenyl)-3-dimethylaminopyrrolidin-2-one

Trisodium phosphate (3.56 g) was added to a solution of 4-nitroaniline (5.0 g) in acetonitrile (30 ml) and, at 0° C., 2-bromo-4-chlorobutyryl bromide (11 g) was added. After one hour, a solution of sodium hydroxide (3.2 g) in water (10 ml) was added, and the mixture was vigorously stirred at room temperature. After 6 hours, the same amount of sodium hydroxide solution was again added, and the mixture was left to stand overnight. The reaction solution was diluted with water and extracted with ethyl acetate. The organic phase was dried over magnesium sulfate and concentrated. The crude product (0.5 g) was heated with dimethylamine (160 mg) in toluene (20 ml) at 80° C. for 3 hours. The reaction solution was diluted with water and extracted with ethyl acetate. The organic phase was dried over magnesium sulfate and concentrated. The crude product was hydrogenated by method B. This resulted in the product with the molecular weight of 219.29 (C12H17N3O); MS (ESI): 220 (M+H+).

1-(4-Aminophenyl)-3-(7-azabicyclo[2.2.1]hept-7-yl)pyrrolidin-2-one was obtained in an analogous manner.

4-[3-(7-Azabicyclo[2.2.1]hept-7-yl)pyrrolidin-1-yl]phenylamine 1-(4-Nitrophenyl)-3-(7-azabicyclo[2.2.1]hept-7-yl)pyrrolidin-2-one (0.25 g) in THF (10 ml) was mixed with borane-THF complex (1M in THF, 0.83 ml) and boiled under reflux for 3 hours. After the reaction was complete, the mixture was diluted with water and adjusted to pH 9-10 with hydrochloric acid (4N). Extraction in ethyl acetate, drying and concentration of the organic phase afforded a crude product that was hydrogenated by method B. This resulted in the product with the molecular weight of 257.38 (C16H23N3); MS (ESI): 258 (M+H+).

(R)-1'-(4-Aminophenyl)-[1,3']bipyrrolidinyl-2-one tert-Butyl [1-(4-Nitrophenyl)pyrrolidin-3-yl]carbamate was treated by method G. The crude product (1.4 g) was dissolved in acetonitrile (20 ml) and mixed with trisodium phosphate (0.67 g) and 4-chlorobutyryl chloride (1.1 g). After 2 hours, sodium hydroxide (0.6 g) in water (10 ml) was added and the mixture was vigorously stirred. After 12 hours, the same amount of sodium hydroxide solution was again added, and the mixture was stirred for a further 24 hours. The concentrated reaction solution was partitioned between water and ethyl acetate, and the organic phase was dried and concentrated. The residue was hydrogenated by method B. This resulted in the product with the molecular weight of 245.33 (C14H19N3O); MS (ESI): 246 (M+H+).

1-Methylpiperidine-3-carboxylic acid [(R)-1-(4-aminophenyl)pyrrolidin-3-yl]methylamide tert-Butyl (R)-[1-(4-nitrophenyl)pyrrolidin-3-yl]methylcarbamate was treated by method G and reacted with 1-methylpiperidine-3-carboxylic acid by method E. Finally, hydrogenation was also carried out by method E. This resulted in the product with the molecular weight of 316.45 (C18H28N4O); MS (ESI): 317 (M+H+).

(R)-N-[1-(4-Aminophenyl)pyrrolidin-3-yl]-2-dimethylamino-N-methylacetamide was obtained in an analogous manner using N,N-dimethylglycine.

N-[(R)-1-(4-Aminophenyl)pyrrolidin-3-yl]-N-(2-diethylaminoethyl)acetamide

N-(2-Diethylaminoethyl)-N-[(R)-1-(4-nitrophenyl)pyrrolidin-3-yl]acetamide was hydrogenated by method B. This resulted in the product with the molecular weight of 318.47 (C18H30N4O); MS (ESI): 319 (M+H+).

N-(2-Diethylaminoethyl)-N-[(R)-1-(4-nitrophenyl)pyrrolidin-3-yl]acetamide

Acetyl chloride (2.9 g) was dissolved in 50 ml of dry dichloromethane, mixed with 5.3 ml of triethylamine, and after addition of N,N-diethyl-N'-[(R)-1-(4-nitrophenyl)pyrrolidin-3-yl]-ethane-1,2-diamine (5.8 g), stirred at room temperature for 30 minutes. Subsequently, (LCMS check), water (10 ml) was added to the reaction, and the mixture was extracted with dichloromethane (2×10 ml). The combined organic phases were dried over magnesium sulfate, the solvent was removed, and the crude product was separated by chromatography on silica gel (dichloromethane/methanol 10:1). This resulted in the product with the molecular weight of 348.45 (C18H28N4O3); MS (ESI): 349 (M+H+).

N,N-Diethyl-N'-[(R)-1-(4-nitrophenyl)pyrrolidin-3-yl]ethane-1,2-diamine tert-Butyl (2-diethylaminoethyl)-[(R)-1-(4-nitrophenyl)pyrrolidin-3-yl]carbamate (7.9 g) was reacted with trifluoroacetic acid by method G. This resulted in the product with the molecular weight of 306.41 (C16H26N4O2); MS (ESI): 307 (M+H+).

tert-Butyl (2-diethylaminoethyl)-[(R)-1-(4-nitrophenyl)pyrrolidin-3-yl]carbamate tert-Butyl [(R)-1-(4-nitrophenyl)pyrrolidin-3-yl]carbamate (6.0 g) was dissolved in 50 ml of N,N-dimethylformamide and, after addition of sodium hydride (1.1 g), stirred at room temperature for 30 minutes, and subsequently chlorethyldiethylamine hydrochloride (4.1 g) was added. The mixture was subsequently stirred at room temperature with exclusion of moisture for 4 hours. The reaction was stopped by adding water (50 ml), and this was followed by extraction with ethyl acetate (3×50 ml) and drying of the combined organic phases over magnesium sulfate, and removal of the solvent. This resulted in the product with the molecular weight of 406.53 (C21H34N4O4); MS (ESI): 407 (M+H+).

Piperidine-4-carboxylic acid [4-(3-dimethylaminopyrrolidin-1-yl)phenyl]amide Piperidine-1,4-dicarboxylic acid mono-tert-butyl ester was reacted with [1-(4-aminophenyl)pyrrolidin-3-yl]dimethylamine by method E, and the product was then treated by method G. This resulted in the product with the molecular weight of 316.45 (C18H28N4O); MS (ESI): 317 (M+H+).

Synthesis of Amines Required as Intermediates

Spiro[1,3-benzodioxol-2,1'-cyclopentane]-5-amine

A solution of spiro[5-nitro-1,3-benzodioxol-2,1'-cyclopentane] (8.8 g) in methanol (90 ml) was hydrogenated under 6 bar in the presence of palladium on carbon (10%, 0.1 g). After 30 minutes at room temperature, the mixture was filtered and concentrated. This resulted in the product with the molecular weight of 191.23 (C11H13NO2); MS(ESI): 192 (M+H+).

Spiro[5-nitro-1,3-benzodioxol-2,1'-cyclopentane]

A solution of spiro[1,3-benzodioxol-2,1'-cyclopentane] (8.5 g) in 20 ml of dichloromethane was added dropwise at 10° C. to 65% strength nitric acid (65 ml). After 2 hours at 5-10° C., the mixture was diluted with water, the organic phase was separated off, and the aqueous phase was extracted twice with dichloromethane. The combined organic phases were washed with water until neutral, dried over sodium sulfate, concentrated and crystallized from heptane. This resulted in the product with the molecular weight of 221.21 (C11H11NO4); MS(ESI): 222 (M+H+).

Spiro[1,3-benzodioxol-2,1'-cyclopentane]

Catechol (11 g) and cyclopentanone (9 ml) were heated under reflux in toluene (150 ml) with p-toluenesulfonic acid (0.18 g) with a water trap. After 18 hours, the mixture was concentrated and purified by chromatography (silica gel, heptane/ethyl acetate 4:1). This resulted in the product with the molecular weight of 176.22 (C11H12O2); MS(ESI): 177 (M+H+).

5-Chloro-2',3',5',6'-tetrahydro-1'H-[2,4']bipyridinyl-4'-ol

Butyllithium (15% in hexane; 7.6 ml) was added dropwise to a solution of 2-bromo-5-chloropyridine (2.0 g) in diethyl ether (50 ml) at −78° C. and, after one hour, a solution of N-tert-butoxycarbonyl-4-piperidinone (2.1 g) in diethyl ether (10 ml) was added dropwise. After 30 minutes, water was cautiously added, and the mixture was extracted with ethyl acetate. The organic phase was dried over sodium sulfate, filtered and concentrated. The residue was treated by method G. This resulted in the product with the molecular weight of 212.68 (C10H13ClN2O); MS(ESI): 213 (M+H+).

The following were obtained analogously:
5-Fluoro-2',3',5',6'-tetrahydro-1'H-[2,4']bipyridinyl-4'-ol
6-Chloro-2',3',5',6'-tetrahydro-1'H-[3,4']bipyridinyl-4'-ol.

6-Cyclopentyloxypyridin-3-ylamine

A mixture of 2-hydroxy-5-nitropyridine (1.4 g), cyclopentyl bromide (1.5 g) and potassium carbonate (3 g) was heated in DMF (20 ml) at 80° C. for 6 hours. The mixture was diluted with water and extracted with ethyl acetate. The organic phase was dried over magnesium sulfate and concentrated. The residue was purified by chromatography on silica gel (mobile phase ethyl acetate/heptane 1:2). The nitro compound obtained in this way was hydrogenated by method B. This resulted in the product with the molecular weight of 178.24 (C10H14N2O2); MS(ESI): 179 (M+H+).

6-(4-Fluorophenyl)-3-azabicyclo[4.1.0]heptane

Diethylzinc (1M in hexane, 19 ml) in dichloromethane (100 ml) was mixed with trifluoroacetic acid (3 ml) at 0° C. After 20 minutes, diiodomethane (3 ml) in dichloromethane (10 ml) was added. Then 4-(4-fluorophenyl)-1,2,3,6-tetrahydropyridine (3.0 g) in dichloromethane (10 ml) was added, and the mixture was stirred at room temperature overnight. After addition of hydrochloric acid (1N), the phases were separated and the organic phase was washed with water, dried over magnesium sulfate and concentrated. This resulted in the product with the molecular weight of 191.25 (C12H14FN); MS(ESI): 192 (M+H+).

Synthesis of Carboxylic Acids Required as Intermediates

4-(4-Methylpiperidin-1-yl)benzoic acid 4-(4-Methylpiperidin1-yl)benzonitrile (1.2 g) was heated to reflux with potassium hydroxide (0.7 g) in water (2 ml) and ethylene glycol (8 ml) for 3 hours. The mixture was diluted with water, washed with ethyl acetate and acidified with 2N hydrochloric acid. The precipitated product was filtered off with suction, dissolved in dichloromethane, dried over sodium sulfate, concentrated and crystallized from diethyl ether. This resulted in the product with the molecular weight of 219.29 (C13H17NO2); MS(ESI): 220 (M+H+).

4-(4-Methylpiperidin1-yl)benzonitrile

4-Fluorobenzonitrile (1.21 g) was heated with 4-methylpiperidine (1.00 g) at 180° C. for 1 hour. The mixture was then taken up in ethyl acetate, washed with water, 2N sodium hydroxide solution and saturated sodium bicarbonate solution, dried over sodium sulfate, concentrated and crystallized from n-pentane. This resulted in the product with the molecular weight of 200.29 (C13H16N2); MS(ESI): 201 (M+H+).

4-Butoxycyclohexanecarboxylic acid

Sodium hydride (2.78 g) was added to a solution of ethyl 4-hydroxycyclocarboxylate (10 g) and butyl iodide (10.6 g) in DMF while cooling in ice under argon. After 12 hours, the mixture was poured onto ice (200 g), extracted with ethyl acetate (100 ml) and then washed with water (3×50 ml). The organic phase was concentrated and mixed with ethanol (50 ml) and 5N sodium hydroxide (30 ml). The solution was heated at 60° C. for 4 hours. Cooling to room temperature was followed by adjustment to pH<2 with 2N hydrochloric acid, extraction with ethyl acetate (3×50 ml), drying with magnesium sulfate, filtration and concentration. This resulted in the product with the molecular weight of 200.28 (C11H20O3); MS (ESI): 201 (M+H+).

1-Benzyl-1H-[1,2,3]triazole-4-carboxylic acid

Methyl 1-benzyl-1H-[1,2,3]triazol-4-carboxylate (217 mg) was dissolved in 4 ml of methanol and hydrolyzed with 2 ml of 2N sodium hydroxide solution. After acidification with 4 ml of 2N hydrochloric acid, the resulting precipitate was filtered off, taken up in 5 ml of ethyl acetate and purified by preparative HPLC. This resulted in the product with the molecular weight of 203.2 (C10H9N3O2); MS (ESI): 204 (M+H+).

Methyl 1-benzyl-1H-[1,2,3]triazole-4-carboxylate

Benzyl azide (266 mg) was dissolved together with sodium ascorbate (20 mg) and copper sulfate (5 mg) in 8 ml of the solvent mixture (tert-butanol/water 3:1), and methyl propionate (336 mg) was added. The solution was stirred at room temperature for 2 hours. A white precipitate separated out and was filtered off with suction on a frit and subsequently dried. This resulted in the product with the molecular weight of 217.23 (C11H11N3O2); MS (ESI): 218 (M+H+).

1-Biphenyl-4-yl-1H-[1,2,3]triazole-4-carboxylic acid was prepared analogously from 4-Ethynylbiphenyl and ethyl azidoacetate.

1-Butyl-1H-indole-5-carboxylic acid

Sodium hydride (50% in oil, 1.4 g) was added to methyl 1H-indole-5-carboxylate (5.0 g) in DMF (100 ml) and, after gas evolution ceased, bromobutane (3.9 g) was added. After 12 hours, the reaction solution was diluted with ethyl acetate and washed three times with water. The organic phase was dried over magnesium sulfate and concentrated. The residue was purified by chromatography on silica gel (mobile phase ethyl acetate/heptane 1:6). The resulting ester was dissolved in methanol (10 ml) and boiled under reflux with sodium hydroxide (0.6 g ) in water (10 ml) for 12 hours. The mixture was diluted with water and acidified with hydrochloric acid, followed by extraction with ethyl acetate. The organic phase was dried over magnesium sulfate and concentrated. This resulted in the product with the molecular weight of 217.27 (C13H15NO2); MS (ESI): 218 (M+H+).

3'-Acetylaminobiphenyl-4-carboxylic acid

3'-Aminobiphenyl-4-carboxylic acid (0.2 g) was mixed with pyridine (0.7 g) and acetic anhydride (180 mg) and, after 14 hours, volatile fractions were removed. The residue was taken up in sodium hydroxide solution (2N) and washed with diethyl ether. The aqueous phase was acidified with hydrochloric acid and extracted with ethyl acetate. The organic phase was dried over magnesium sulfate and concentrated. This resulted in the product with the molecular weight of 255.28 (C15H13NO3); MS (ESI): 256 (M+H+).

3'-Isobutyrylaminobiphenyl-4-carboxylic acid

3'-Aminobiphenyl-4-carboxylic acid (0.2 g) was mixed in dichloromethane with potassium carbonate (121 mg) and isobutyryl chloride (94 mg). After 12 hours, the mixture was diluted with sodium hydroxide solution and washed with diethyl ether. The aqueous phase was acidified with hydrochloric acid and extracted with ethyl acetate. The organic phase was dried over magnesium sulfate and concentrated. This resulted in the product with the molecular weight of 283.33 (C17H17NO3); MS (ESI): 284 (M+H+).

5-Butoxypyridine-2-carboxylic acid

Sodium hydride (50% in oil, 250 mg) was added to benzhydryl 5-hydroxypyridine-2-carboxylate (2.0 g) dissolved in DMF (20 ml) and, after gas evolution ceased, 1-bromobutane (0.72 g) was added. The mixture was heated at 90° C. for 6 hours. It was diluted with water and extracted with ethyl acetate. The organic phase was dried over magnesium sulfate and concentrated. The residue was hydrogenated in analogy to method B. This resulted in the product with the molecular weight of 195.22 (C10H13NO3); MS (ESI): 196 (M+H+).

4-Methyl-3,4,5,6-tetrahydro-2H-[1,3']bipyridinyl-6'-carboxylic acid

Benzhydryl 5-trifluoromethanesulfonyloxypyridine-2-carboxylate (3.0 g) was heated with 4-methylpiperidine (1.4 g) at 80° C. for one hour. The reaction mixture was immediately purified by preparative HPLC and then hydrogenated in analogy to method. This resulted in the product with the molecular weight of 220.27 (C12H16N2O2); MS (ESI): 221 (M+H+).

N-[4-(3-Dimethylaminopyrrolidin-1-yl)phenyl] terephthalamic acid

Method P-a
N-[4-(3-Dimethylaminopyrrolidin-1-yl)phenyl]terephthalamic acid methyl ester (1.7 g) dissolved in methanol (20 ml) was stirred with sodium hydroxide solution (2N, 15 ml) at room temperature for 24 hours. If conversion is incomplete, it is also possible to heat to reflux. The organic solvent was distilled off, and the mixture was acidified with hydrochloric acid. The precipitate which separated out was filtered off with suction and dried. This resulted in the product with the molecular weight of 353.42 (C20H23N3O3); MS (ESI): 354 (M+H+).

N-[4-(3-Dimethylaminopyrrolidin-1-yl)phenyl] terephthalamic acid methyl ester

[1-(4-Aminophenyl)pyrrolidin-3-yl]dimethylamine was reacted with terephthalic acid monomethyl ester by method E. This resulted in the product with the molecular weight of 367.45 (C21H25N3O3); MS (ESI): 368 (M+H+).

4-(Cyclopentanecarbonylmethylamino)benzoic acid

Methyl 4-methylaminobenzoate was reacted with cyclopentanecarboxylic acid by method E and then hydrolyzed by method P-a. This resulted in the product with the molecular weight of 247.30 (C14H17NO3); MS (ESI): 248 (M+H+).

The following compounds were obtained analogously:
4-(Cyclopentanecarbonylamino)-3-methoxybenzoic acid
2-Chloro-4-(cyclopentanecarbonylamino)benzoic acid
2-Fluoro-4-(cyclopentanecarbonylamino)benzoic acid
4-(Cyclopentanecarbonylamino)-3-methylbenzoic acid
4-(Cyclopentanecarbonylamino)benzoic acid
4-(Cyclopentanecarbonylamino)-3-trifluoromethoxybenzoic acid
3-Chloro-4-(cyclopentanecarbonylamino)benzoic acid
5-Chloro-4-(cyclopentanecarbonylamino)-2-methoxybenzoic acid
4-[(Cyclohex-1-enecarbonyl)amino]benzoic acid
4-[(Cyclopent-1-enecarbonyl)amino]benzoic acid 3-Fluoro-4-(1-methylbutoxy)benzoic Acid A solution of 0.449 g of 1-[3-fluoro-4-(1-methylbutoxy) phenyl]ethanone in 6.8 ml of dioxane was dropped dropwise into 1.36 g of NaOH, 1.6 g of bromine in 6.8 ml of water. The mixture was stirred at room temperature for 30 minutes and then heated at 50° C. for 1 h. The excess bromide was decomposed by adding a sodium disulfite solution, and then the solution was poured into 25% strength hydrochloric acid solution and stirred for 20 minutes. The solution was extracted with ethyl acetate. The combined organic phases dried over sodium sulfate, concentrated in vacuo and purified by preparative HPLC. This resulted in the product with the molecular weight of 226.1 (C12H15FO3); MS (ESI): 227 (M+H+).

1-[3-Fluoro-4-(1-methylbutoxy)phenyl]ethanone 0.058 g of NaH was added to a solution of 0.176 g of 2-pentanol in 2 ml of DMF, and the solution was stirred at room temperature for 1 hour. Then 0.312 g of 3,4-difluoroacetophenone was added, and the mixture was stirred at room temperature overnight. The reaction solution was taken up in ethyl acetate and washed twice with water. The organic phase was dried over sodium sulfate and concentrated in vacuo. The resulting compound was reacted further without further purification.

The following compounds were obtained analogously:
4-Cyclobutoxy-3-fluorobenzoic acid
3-Fluoro-4-(2-methylcyclopropylmethoxy)benzoic acid
4-(2-Cyclopropylethoxy)-3-fluorobenzoic acid
3-Fluoro-4-(1-methylpiperidin-3-yloxy)benzoic acid
4-(1-Acetylpiperidin-3-yloxy)-3-fluorobenzoic acid
3-Fluoro-4-(1-methylpyrrolidin-3-yloxy)benzoic acid
4-(1-Acetylpyrrolidin-3-yloxy)-3-fluorobenzoic acid
3-Fluoro-4-(1-methylpiperidin-3-ylmethoxy)benzoic acid

4-(2,4-Difluorophenoxy)benzoic Acid 0.518 g of potassium hydroxide was added to a solution of 0.428 g of ethyl 4-(2,4-difluorophenoxy)benzoate in 2 ml of THF/water (1:1). The solution was heated at 110° C. for 6 hours. The THF was then removed in vacuo, and the aqueous phase was freeze dried and purified by preparative HPLC. This resulted in the product with the molecular weight of 250.04 (C13H8F2O3); MS (ESI): 251 (M+H+).

Ethyl 4-(2,4-difluorophenoxy)benzoate 0.018 g of NaH was added to a solution of 0.1 g of 2,4-difluorophenol in 0.5 ml of DMF. The reaction was stirred at room temperature for 45 minutes. Then 0.129 g of ethyl 4-fluorobenzoate in 0.5 ml of DMF was added dropwise. The reaction was heated at 110° C. overnight. After cooling concentrated in vacuo and the residue taken up in ethyl acetate/water. The ethyl acetate phase was washed three times with water, dried over sodium sulfate, concentrated in vacuo and purified by preparative HPLC. This resulted in the product with the molecular weight of 278.08 (C15H12F2O3); MS (ESI): 279 (M+H+)

4-(2,4-Difluorophenoxy)benzoic acid was reacted with [1-(4-aminophenyl)pyrrolidin-3-yl]-dimethylamine by method E-b. This resulted in the product with the molecular weight of 437.19 (C25H25F2N3O2); MS (ESI): 438 (M+H+) as hydrotrifluoroacetate.

4-Butoxy-3-methoxybenzoic acid

Methyl 4-hydroxy-3-methoxybenzoate was alkylated with bromobutane by method H and hydrolyzed by method P-a. This resulted in the product with the molecular weight of 224.26 (C12H16O4); MS (ESI): 225 (M+H+).

The following compounds were prepared analogously:
4-Butoxy-3,5-dichlorobenzoic acid
4-Butoxy-3-nitrobenzoic acid
4-Butoxy-3-chlorobenzoic acid
4-Butoxy-3,5-dimethylbenzoic acid
4-Butoxy-2,3-dichloro-5-methoxybenzoic acid
4-Butoxy-2,3,5,6-tetrafluorobenzoic acid
4-Butoxy-3-fluorobenzoic acid
3-Acetyl-4-butoxybenzoic acid
2,4-Dibutoxybenzoic acid
4-Butoxy-2-chlorobenzoic acid

4-Propoxymethylbenzoic Acid

Sodium hydride (50% in oil; 0.42 g) was cautiously added to a solution of propanol (0.6 g) in DMF (8 ml). After gas evolution ceased, methyl 4-bromomethylbenzoate (1.0 g) was added. After 4 hours, the mixture was partitioned between water and ethyl acetate. The organic phase was dried over magnesium sulfate and concentrated. The residue was hydrolyzed by method P-a. This resulted in the product with the molecular weight of 194.23 (C11H14O3); MS (ESI): 195 (M+H+).

The following compounds were prepared analogously:
4-Ethoxymethylbenzoic acid
4-Butoxymethylbenzoic acid
4-Isobutoxymethylbenzoic acid
4-Phenoxymethylbenzoic acid
4-(Pyridin-3-yloxymethyl)benzoic acid
4-(Pyridin-2-yloxymethyl)benzoic acid
4-Benzoimidazol-1-ylmethylbenzoic acid
4-Indol-1-ylmethylbenzoic acid
4-Phenylsulfanylmethylbenzoic acid
4-(Pyrimidin-2-ylsulfanylmethyl)benzoic acid
4-(Pyridin-2-ylsulfanylmethyl)benzoic acid
4-(2-Cyanophenoxymethyl)benzoic acid
4-(2-Chlorophenoxymethyl)benzoic acid
4-Cyclobutoxymethylbenzoic acid
4-Cyclopentyloxymethylbenzoic acid
4-Cyclohexyloxymethylbenzoic acid
4-sec-Butoxymethylbenzoic acid
4-Pentoxymethylbenzoic acid

4-(3-Oxo-3a,4,5,6-tetrahydro-3H-cyclopentapyrazol-2-yl)benzoic acid

A solution of 4-hydrazinobenzoic acid (0.3 g), ethyl-2-oxocyclopentanecarboxylate (0.31 g) and p-toluenesulfonic acid (340 mg) in ethanol (12 ml) was boiled under reflux for 12 hours. The concentrated reaction solution was purified by preparative HPLC. The isolated reaction product (as ethyl ester) was hydrolyzed by method P-a. This resulted in the product with the molecular weight of 244.25 (C13H12N2O3); MS (ESI): 245 (M+H+).

4-Butoxy-2-methoxybenzoic acid

4-Hydroxy-2-methoxybenzaldehyde was alkylated with 1-bromobutane by method H. The resulting aldehyde (6.4 g) in dioxane (100 ml) was mixed with sodium dihydrogen phosphate (14.4 g) and sulfuric acid (2.4 ml), and the solution was cooled to 10° C. A solution of sodium chlorite (3.61 g) in water (100 ml) was added in such a way that the temperature did not exceed 10° C. 15 minutes after the addition was complete, sodium sulfite (4.6 g) was added.

After a further 15 minutes, the pH was adjusted to 2 with hydrochloric acid and the dioxane was removed in a rotary evaporator. The aqueous phase was extracted with ethyl acetate. The organic phase was dried over magnesium sulfate, filtered and concentrated. The residue was purified by preparative HPLC. This resulted in the product with the molecular weight of 224.26 (C12H16O4); MS (ESI): 225 (M+H+). 4-Butoxy-5-chloro-2-methoxybenzoic acid was obtained as by-product.

4-(1-Propoxyethyl)benzoic acid

Methyl 4-(1-hydroxyethyl)benzoate (2.0 g) dissolved in DMF (30 ml) was mixed with propyl iodide (3.8 g), and then sodium hydride (50% in oil, 0.53 g) was added. After the end of the exothermic reaction, the mixture was stirred for 1 hour and then water was cautiously added. It was extracted with ethyl acetate, and the organic phase was dried over sodium sulfate, filtered and concentrated. The residue was hydrolyzed by method P-a. This resulted in the product with the molecular weight of 208.26 (C12H16O3); MS (ESI): 209 (M+H+).

We claim:

1. A compound of the formula I

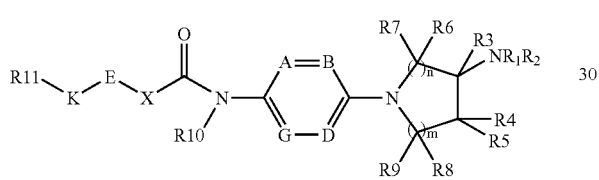

I wherein

R1, R2 are each independently H, $(C_1-C_8)$-alkyl, -$(CR78R79)_o$-R12, $(C_1-C_4)$-alkoxy-$(C_1-C_4)$-alkyl, aryloxy-$(C_1-C_4)$-alkyl, $(C_3-C_8)$-alkenyl, $(C_3-C_8)$-alkynyl, CO—$(C_1-C_8)$-alkyl, —CO—$(CH_2)_o$—R12, CO-aryloxy-$(C_1-C_4)$-alkyl, CO—$(C_2-C_8)$-alkenyl, CO—$(C_2-C_8)$-alkynyl, COCH=CH(R13), COCC(R14), CO—$(C_1-C_4)$-alkyl-S(O)$_p$—$(C_1-C_4)$-alkyl, CO(C(R15)(R16))$_q$N(R17)(R18), CO(C(R19)(R20))$_r$CON(R21)(R22) or CO(C(R23)(R24))$_s$O(R25); or R1 and R2, together with the nitrogen atom to which they are attached, form a 4-, 5-, 6-, 7-, 8-, 9- or 10-membered mono-, bi- or spirocyclic ring which, apart from said nitrogen atom of attachment, optionally contains 1, 2, 3 or 4 additional heteroatoms selected from the group of oxygen, nitrogen and sulfur, and is optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R26), CON(R27)(R28), hydroxy, COO(R29), N(R30)CO$(C_1-C_6)$-alkyl, N(R31)(R32) or $SO_2CH_3$;

wherein o is 0, 1, 2, 3, 4, 5 or 6;

p is 0, 1 or 2 q, r, s are each independently 0, 1, 2, 3 or 4;

R13, R14 are each independently a 5-, 6-, 7-, 8-, 9- or 10-membered aromatic ring system optionally containing 1 or 2 heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R15, R16, R17, R19, R20, R21, R22, R23, R24, R25, R26, R27, R28, R29, R30, R31, R32 are each independently H or $(C_1-C_6)$-alkyl;

R18 is H, $(C_1-C_6)$-alkyl, CO$(C_1-C_6)$-alkyl or CO(R33); or substituent pairs R17 and R18, R21 and R22, R27 and R28, and R31 and R32, independently of one another and taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur;

R33 is a 5-, 6-, 7-, 8-, 9- or 10-membered aromatic ring system which optionally contains 1 or 2 heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R12 is OH, O—$(C_1-C_6)$-alkyl, O$(C_0-C_8)$-alkylene-aryl, CN, S—$(C_1-C_6)$-alkyl, COO(R80), CON(R81)(R93), N(R82)(R83) or a 3-, 4-, 5-, 6-, 7-, 8-, 9-, 10-, 11-, or 12-membered mono-, bi- or spirocyclic ring which optionally contains one or more heteroatoms selected from the group of N, O and S, and is optionally substituted with F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, O—$(C_0-C_8)$-alkylene-aryl, N(R34)(R35), COCH=CH(R36), (C(R37)(R38))$_t$(R39), CO(C(R37)(R38))$_t$(R39), CO$(C_1-C_6)$-alkyl, COCOO$(C_1-C_6)$-alkyl, COO(R40), S(O)$_u$(R41) or COOH;

t is 0, 1, 2, 3, 4, 5 or 6;

u is 0, 1 or 2;

R34, R35, R37, R38 are each independently H or $(C_1-C_8)$-alkyl; or

R34 and R35, taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur, and is optionally substituted by 1 or 2 oxo groups;

R36, R39 are each independently $(C_3-C_8)$-cycloalkyl or a 5-, 6-, 7-, 8-, 9- or 10-membered aromatic ring system wherein said aromatic ring system optionally contains one or two additional heteroatoms selected from the group of nitrogen, oxygen and sulfur, and is optionally substituted by F, Cl, Br, $CF_3$, $NO_2$, CN, $(C_1-C_6)$-alkyl or O—$(C_1-C_8)$-alkyl;

R40 is H, $(C_1-C_8)$-alkyl, $(C_2-C_6)$-alkenyl or $(C_0-C_8)$-alkylene-aryl;

R41 is $(C_1-C_6)$-alkyl or a 5-, 6-, 7-, 8-, 9-, or 10-membered aromatic ring system optionally containing one or two heteroatoms from the group of nitrogen, oxygen and sulfur, and optionally substituted by F, Cl, Br, $CF_3$, $NO_2$, CN, $(C_1-C_6)$-alkyl or O—$(C_1-C_8)$-alkyl;

R78, R79 are each independently H, $(C_1-C_8)$-alkyl, hydroxy-$(C_1-C_4)$-alkyl, OH or $(C_1-C_4)$-alkoxy-$(C_1-C_4)$-alkyl;

R80, R81, R93 are each independently $(C_1-C_8)$-alkyl, $(C_2-C_6)$-alkenyl or $(C_0-C_8)$-alkylene-aryl;

R82, R83 are each independently H or $(C_1-C_6)$-alkyl; or

R82 and R83, taken together with the nitrogen atom to which they are attached, optionally form a 5- or 6-membered ring which, apart from said nitrogen atom of attachment, optionally contains one additional heteroatom component selected from the group of N—$(C_1-C_6)$-alkyl, oxygen and sulfur, and is optionally substituted by 1 or 2 oxo groups;

R3 is H or $(C_1-C_6)$-alkyl;

R4, R5 are each independently H, $(C_1-C_6)$-alkyl, OH, O—$(C_1-C_6)$-alkyl, O—CO$(C_1-C_6)$-alkyl or S—$(C_1-C_6)$-alkyl;

R6, R7, R8, R9 are each independently H or $(C_1-C_8)$-alkyl; or substituent pairs R6 and R7, and R8 and R9, optionally form, independently of one another, an oxo group;

n, m are each independently 0, 1 or 2;

A, B, D, G are each independently N or C(R42); or said radicals A and B, or said radicals D and G are each C(R42) and, taken together, optionally form a 5- or 6 membered carbocyclic or heterocyclic radical resulting in an overall bicyclic ring system;

wherein

R42 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R43)(R44), $SO_2$—$CH_3$, COOH, COO—$(C_1-C_6)$-alkyl, CON(R45)(R46), N(R47)CO(R48), N(R49)$SO_2$(R50), CO(R51) or -(CR84R85)$_x$-O(R86);

wherein

R43, R44, R45, R46, R47, R49 are each independently H or $(C_1-C_8)$-alkyl; or substituent pairs R43 and R44, and R45 and R46, independently of one another and taken together with the nitrogen atom to which they are attached, optionally form a 5- or 6-membered ring which, apart from said nitrogen atom of attachment, optionally contains an additional heteroatom component selected from the group of N—$(C_1-C_6)$-alkyl, oxygen and sulfur;

R48, R50, R51 are each independently H, $(C_1-C_8)$-alkyl or aryl;

R84, R85 are each independently H or $(C_1-C_8)$-alkyl;

R86 is H, $(C_1-C_6)$-alkyl or aryl;

x is 1, 2, 3, 4, 5 or 6;

R10 is H, $(C_1-C_8)$-alkyl, $(C_3-C_6)$-alkenyl or $(C_3-C_6)$-alkynyl;

X is N(R52) or O;

wherein

R52 is H or $(C_1-C_8)$-alkyl;

E is a 3, 4, 5, 6, 7, 8, 9, 10, 11, 12, 13- or 14-membered bivalent carbo- or heterocyclic ring structure with 0, 1, 2, 3 or 4 heteroatoms selected from the group of N, O and S, and optionally substituted with H, F, Cl, Br, I, OH, $CF_3$, $NO_2$, CN, $OCF_3$, oxo, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R57)(R58), $SO_2$—$CH_3$, COOH, COO—$(C_1-C_6)$-alkyl, CON(R59)(R60), N(R61)CO(R62), N(R63)$SO_2$(R64) or CO(R65), and wherein said bivalent carbo- or heterocyclic ring structure is mono- or bicyclic;

wherein

R57, R58, R59, R60, R61, R63 are each independently H or $(C_1-C_8)$-alkyl; or substituent pairs R57 and R58, and R59 and R60, independently of one another and taken together with the nitrogen atom to which they are attached, optionally form a 5- or 6-membered ring which, apart from said nitrogen atom of attachment, optionally contains one further heteroatom component selected from the group of N—$(C_1-C_6)$-alkyl, oxygen and sulfur;

R62, R64, R65 are each independently H, $(C_1-C_8)$-alkyl or aryl;

K is a bond, O, $OCH_2$, $CH_2O$, S, SO, SO2, N(R66), N(R67)CO, CON(R68), $(C(R69)(R70))_v$, CO, C≡C, C=C or a group of the formula -(CR90R91)$_z$- in which one or more of the -(CR90R91)- units contained in said group of the formula -(CR90R91)$_z$- is optionally replaced by Z;

wherein v is 1, 2, 3 or 4

R66, R67, R68, R69, R70 are each independently H or $(C_1-C_8)$-alkyl;

Z is O, S, N(R92), CO, SO or $SO_2$;

R90, R91 are each independently H, $(C_1-C_8)$-alkyl, hydroxy-$(C_1-C_4)$-alkyl, hydroxy or $(C_1-C_4)$-alkoxy-$(C_1-C_4)$-alkyl, and wherein R90 and R91 may be defined the same or differently in each of said -(CR90R91)- units contained in said group of formula -(CR90R91)$_z$-;

z is 2, 3, 4, 5 or 6;

R92 is H or $(C_1-C_8)$-alkyl;

R11 is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl or a 3-, 4-, 5-, 6-, 7-, 8-, 9- or 10-membered mono-, bi- or spirocyclic ring, optionally containing 1, 2, 3 or 4 heteroatoms selected from the group of oxygen, nitrogen and sulfur, and optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R71), CON(R72)(R73), hydroxy, hydroxy-$(C_1-C_4)$-alkyl, COO(R74), N(R75)CO$(C_1-C_6)$-alkyl, N(R76)(R77), $SO_2CH_3$ or $SCF_3$;

wherein

R71, R72, R73, R74, R75, R76, R77 are each independently H or $(C_1-C_8)$-alkyl; or substituent pairs R72 and R73, and R76 and R77, independently of one another and taken together with the nitrogen atom to which they are attached, optionally form a 5- or 6-membered ring which, apart from the nitrogen atom, optionally contain one additional heteroatom component selected from the group of N—$(C_1-C_6)$-alkyl, oxygen and sulfur; or E, K and R11 taken together form a tricyclic system where each of the rings in said tricyclic system are, independently of one another, saturated, partially saturated or unsaturated, and wherein each ring is comprised of 3-8 ring atoms;

and the N-oxides and pharmaceutically acceptable salts thereof.

2. The compound of claim 1 of formula 1:

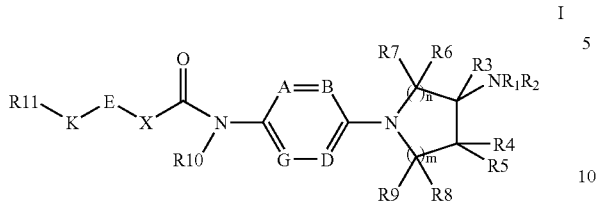

wherein
R1, R2 are each independently H, (C$_1$-C$_8$)-alkyl, —(CR78R79)$_o$—R12, (C$_1$-C$_4$)-alkoxy-(C$_1$-C$_4$)-alkyl, aryloxy-(C$_1$-C$_4$)-alkyl, (C$_3$-C$_8$)-alkenyl, (C$_3$-C$_8$)-alkynyl, CO—(C$_1$-C$_8$)-alkyl, —CO—(CH$_2$)$_o$—R12, CO-aryloxy-(C$_1$-C$_4$)-alkyl, CO—(C$_2$-C$_8$)-alkenyl, CO—(C$_2$-C$_8$)-alkynyl, COCH=CH(R13), COCC(R14), CO—(C$_1$-C$_4$)-alkyl-S(O)$_p$—(C$_1$-C$_4$)-alkyl, CO(C(R15)(R16))$_q$N(R17)(R18), CO(C(R19)(R20))$_r$, CON(R21)(R22) or CO(C(R23)(R24))$_s$O(R25); or R1 and R2, together with the nitrogen atom to which they are attached, form a 4-, 5-, 6-, 7-, 8-, 9- or 10-membered mono-, bi- or spirocyclic ring which, apart from said nitrogen atom of attachment, optionally contains 1, 2, 3 or 4 additional heteroatoms selected from the group of oxygen, nitrogen and sulfur, and is optionally substituted by F, Cl, Br, CF$_3$, NO$_2$, CN, (C$_1$-C$_6$)-alkyl, O—(C$_1$-C$_8$)-alkyl, (C$_1$-C$_4$)-alkoxy-(C$_1$-C$_4$)-alkyl, (C$_0$-C$_8$)-alkylene-aryl, oxo, CO(R26), CON(R27)(R28), hydroxy, COO(R29), N(R30)CO(C$_1$-C$_6$)-alkyl, N(R31)(R32) or SO$_2$CH$_3$;

wherein
o is 0, 1, 2, 3, 4, 5 or 6;
p is 0, 1 or 2
q, r, s are each independently 0, 1, 2, 3 or 4;
R13, R14 are each independently a 5-, 6-, 7-, 8-, 9- or 10-membered aromatic ring system optionally containing 1 or 2 heteroatoms selected from the group of nitrogen, oxygen and sulfur, and is optionally substituted by F, Cl, Br, CF$_3$, NO$_2$, CN, (C$_1$-C$_6$)-alkyl or O—(C$_1$-C$_8$)-alkyl;
R15, R16, R17, R19, R20, R21, R22, R23, R24, R25, R26, R27, R28, R29, R30, R31, R32 are each independently H or (C$_1$-C$_6$)-alkyl;
R18 is H, (C$_1$-C$_6$)-alkyl, CO(C$_1$-C$_6$)-alkyl or CO(R33); or
substituent pairs R17 and R18, R21 and R22, R27 and R28, and R31 and R32, independently of one another and taken together with the nitrogen atom to which they are attached, optionally form a 5- or 6-membered ring which, apart from said nitrogen atom of attachment, optionally contains one additional heteroatom component selected from the group of N—(C$_1$-C$_6$)-alkyl, oxygen and sulfur;
R33 is a 5-, 6-, 7-, 8-, 9- or 10-membered aromatic ring system which optionally contains 1 or 2 heteroatoms selected from the group of nitrogen, oxygen and sulfur, and is optionally substituted by F, Cl, Br, CF$_3$, NO$_2$, CN, (C$_1$-C$_6$)-alkyl or O—(C$_1$-C$_8$)-alkyl;
R12 is OH or a 3-, 4-, 5-, 6-, 7-, 8-, 9-, 10-, 11-, or 12-membered mono-, bi- or spirocyclic ring which optionally contains one or more heteroatoms selected from the group of N, O and S, and is optionally substituted with F, Cl, Br, I, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, O—(C$_3$-C$_8$)-cycloalkenyl, (C$_2$-C$_6$)-alkynyl, O—(C$_0$-C$_8$)-alkylene-aryl, N(R34)(R35), COCH=CH(R36), (C(R37)(R38))$_t$(R39), CO(C(R37)(R38))$_t$(R39), CO(C$_1$-C$_6$)-alkyl, COCOO(C$_1$-C$_6$)-alkyl, COO(R40), S(O)$_u$(R41) or COOH;
t is 0, 1, 2, 3, 4, 5 or 6;
u is 0, 1 or 2;
R34, R35, R37, R38 are each independently H or (C$_1$-C$_8$)-alkyl; or
R34 and R35, taken together with the nitrogen atom to which they are attached, optionally form a 5- or 6-membered ring which, apart from said nitrogen atom of attachment, optionally contains one additional heteroatom component selected from the group of N—(C$_1$-C$_6$)-alkyl, oxygen and sulfur, and is optionally substituted by 1 or 2 oxo groups;
R36, R39 are each independently (C$_3$-C$_8$)-cycloalkyl or a 5-, 6-, 7-, 8-, 9- or 10-membered aromatic ring system wherein said aromatic ring system optionally contains one or two additional heteroatoms selected from the group of nitrogen, oxygen and sulfur, and is optionally substituted by F, Cl, Br, CF$_3$, NO$_2$, CN, (C$_1$-C$_6$)-alkyl or O—(C$_1$-C$_8$)-alkyl;
R40 is H, (C$_1$-C$_8$)-alkyl, (C$_2$-C$_6$)-alkenyl or (C$_0$-C$_8$)-alkylene-aryl;
R41 is (C$_1$-C$_6$)-alkyl or a 5-, 6-, 7-, 8-, 9-, or 10-membered aromatic ring system optionally containing one or two heteroatoms from the group of nitrogen, oxygen and sulfur, and optionally substituted by F, Cl, Br, CF$_3$, NO$_2$, CN, (C$_1$-C$_6$)-alkyl or O—(C$_1$-C$_8$)-alkyl;
R3 is H or (C$_1$-C$_6$)-alkyl;
R4, R5 are each independently H, (C$_1$-C$_6$)-alkyl, OH, O—(C$_1$-C$_6$)-alkyl, O—CO(C$_1$-C$_6$)-alkyl or S—(C$_1$-C$_6$)-alkyl;
R6, R7, R8, R9 are each independently H or (C$_1$-C$_8$)-alkyl; or
substituent pairs R6 and R7, and R8 and R9, optionally form, independently of one another, an oxo group;
n, m are each independently 0, 1 or 2;
A, B, D, G are each independently N or C(R42);
wherein
R42 is H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, O—(C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R43)(R44), SO$_2$—CH$_3$, COOH, COO—(C$_1$-C$_6$)-alkyl, CON(R45)(R46), N(R47)CO(R48), N(R49)SO$_2$(R50) or CO(R51);
wherein
R43, R44, R45, R46, R47, R49 are each independently H or (C$_1$-C$_8$)-alkyl; or
substituent pairs R43 and R44, and R45 and R46, independently of one another and taken together with the nitrogen atom to which they are attached, optionally form a 5- or 6-membered ring which, apart from said nitrogen atom of attachment, optionally contains an additional heteroatom component selected from the group of N—(C$_1$-C$_6$)-alkyl, oxygen and sulfur;

R48, R50, R51 are each independently H, $(C_1-C_8)$-alkyl or aryl;

R10 is H, $(C_1-C_8)$-alkyl, $(C_3-C_6)$-alkenyl or $(C_3-C_6)$-alkynyl;

X is N(R52) or O;
wherein
R52 is H or $(C_1-C_8)$-alkyl;

E is a 3, 4, 5, 6, 7 or 8-membered bivalent carbo- or heterocyclic ring structure with 0, 1, 2, 3 or 4 heteroatoms selected from the group of N, O and S, and optionally substituted with H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R57)(R58), $SO_2$—$CH_3$, COOH, COO—$(C_1-C_6)$-alkyl, CON(R59)(R60), N(R61)CO(R62), N(R63)$SO_2$(R64) or CO(R65), and wherein said bivalent carbo- or heterocyclic ring structure is mono- or bicyclic;
wherein
R57, R58, R59, R60, R61, R63 are each independently H or $(C_1-C_8)$-alkyl; or
substituent pairs R57 and R58, and R59 and R60, independently of one another and taken together with the nitrogen atom to which they are attached, optionally form a 5- or 6-membered ring which, apart from said nitrogen atom of attachment, optionally contains one further heteroatom component selected from the group of N—$(C_1-C_6)$-alkyl, oxygen and sulfur;
R62, R64, R65 are each independently H, $(C_1-C_8)$-alkyl or aryl;

K is a bond, O, $OCH_2$, $CH_2O$, S, SO, $SO_2$, N(R66), N(R67)CO, CON(R68), (C(R69)(R70))$_v$, CO or C≡C;
wherein
v is 1, 2, 3 or 4
R66, R67, R68, R69, R70 are each independently H or $(C_1-C_8)$-alkyl;

R11 is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl or a 3-, 4-, 5-, 6-, 7-, 8-, 9- or 10-membered mono-, bi- or spirocyclic ring, optionally containing 1, 2, 3 or 4 heteroatoms selected from the group of oxygen, nitrogen and sulfur, and optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R71), CON(R72)(R73), hydroxy, COO(R74), N(R75)CO$(C_1-C_6)$-alkyl, N(R76)(R77) or $SO_2CH_3$;
wherein
R71, R72, R73, R74, R75, R76, R77 are each independently H or $(C_1-C_8)$-alkyl; or
substituent pairs R72 and R73, and R76 and R77, independently of one another and taken together with the nitrogen atom to which they are attached, optionally form a 5- or 6-membered ring which, apart from the nitrogen atom, optionally contain one additional heteroatom component selected from the group of N—$(C_1-C_6)$-alkyl, oxygen and sulfur; or
E, K and R11 taken together form a tricyclic system where each of the rings in said tricyclic system are, independently of one another, saturated, partially saturated or unsaturated, and wherein each ring is comprised of 3-8 ring atoms;

and the N-oxides and pharmaceutically acceptable salts thereof.

3. The compound of claim 2 wherein

R1, R2 are each independently H, $(C_1-C_8)$-alkyl, —$(CH_2)_o$—R12, $(C_1-C_4)$-alkoxy-$(C_1-C_4)$-alkyl, CO—$(C_1-C_8)$-alkyl, —CO—$(CH_2)_o$—R12, COCH═CH(R13), COCC(R14), CO—$(C_1-C_4)$-alkyl-S(O)$_p$—$(C_1-C_4)$-alkyl, CO(C(R15)(R16))$_q$N(R17)(R18), CO(C(R19)(R20))$_r$CON(R21)(R22) or CO(C(R23)(R24))$_s$O(R25); or R1 and R2, together with the nitrogen atom to which they are attached, form a 4-, 5-, 6-, 7-, 8-, 9- or 10-membered mono-, bi- or spirocyclic ring which, apart from said nitrogen atom of attachment, optionally contains 1 or 2 additional heteroatoms selected from the group of oxygen, nitrogen and sulfur, and is optionally substituted by F, $(C_1-C_6)$-alkyl, O—$(C_1-C_8)$-alkyl, $(C_0-C_8)$-alkylene-aryl, oxo, CO(R26), CON(R27)(R28), hydroxy, COO(R29), N(R30)CO$(C_1-C_6)$-alkyl, N(R31)(R32) or $SO_2CH_3$;

o 0, 1, 2, 3 or 4;

p 0, 1 or 2;

q, r, s are each independently 0, 1, 2 or 3;

R13, R14 are each independently a 5-, 6-, 7-, 8-, 9- or 10 membered aromatic ring system optionally containing a further heteroatom selected from the group of nitrogen, oxygen and sulfur and optionally substituted by F, Cl, $(C_1-C_6)$-alkyl, O—$(C_1-C_8)$-alkyl;

R15, R16, R17, R19, R20, R21, R22, R23, R24, R25, R26, R27, R28, R29, R30, R31, R32 are each independently H or $(C_1-C_6)$-alkyl;

R18 is H, $(C_1-C_6)$-alkyl, CO$(C_1-C_6)$-alkyl or CO(R33); or substituent pairs R17 and R18, R21 and R22, R27 and R28, and R31 and R32, independently of one another and taken together with the nitrogen atom to which they are attached, optionally form a 5- or 6 membered ring which, apart from said nitrogen atom of attachment, optionally contains one further heteroatom selected from the group of N—$(C_1-C_6)$-alkyl, oxygen and sulfur;

R33 is a 5-, 6-, 7-, 8-, 9- or 10 membered aromatic ring system which optionally contains a further heteroatom selected from the group of nitrogen, oxygen and sulfur and is optionally substituted by F, Cl, $(C_1-C_6)$-alkyl or O—$(C_1-C_8)$-alkyl;

R12 is OH or a 3-, 4-, 5-, 6, 7-, 8-, 9-, 10-, 11- or 12 membered mono-, bi- or spirocyclic ring which optionally contains one or more heteroatoms from the group of N, O and S, and is optionally substituted by F, Cl, $CF_3$, CN, oxo, O—$(C_1-C_6)$-alkyl, $(C_1-C_6)$-alkyl, O—$(C_0-C_8)$-alkylene-aryl, N(R34)(R35), COCH═CH(R36), (C(R37)(R38))$_t$(R39), CO(C(R37)(R38))$_t$(R39), CO$(C_1-C_6)$-alkyl, COCOO$(C_1-C_6)$-alkyl, COO(R40) or S(O)$_u$(R41);

t 0, 1, 2, 3 or 4;

u 0, 1 or 2;

R34, R35, R37, R38 are each independently H or $(C_1-C_8)$-alkyl; or
R34 and R35, taken together with the nitrogen atom to which they are attached, optionally form a 5- or 6-membered ring which, apart from said nitrogen atom of attachment, optionally contains one further heteroatom component selected from the group of N—$(C_1-C_6)$-alkyl, oxygen and sulfur, and is optionally substituted by 1 or 2 oxo groups;

R36, R39 are each independently $(C_3-C_8)$-cycloalkyl or a 5-, 6-, 7-, 8-, 9- or 10-membered aromatic ring system wherein said aromatic ring system optionally contains a further heteroatom selected from the group of nitrogen, oxygen and sulfur, and is optionally substituted by F, Cl, $(C_1-C_6)$-alkyl, O—$(C_1-C_8)$-alkyl;

R40 is H, $(C_1-C_8)$-alkyl, $(C_2-C_6)$-alkenyl or $(C_0-C_8)$-alkylene-aryl;

R41 is $(C_1-C_6)$-alkyl or a 5-, 6-, 7-, 8-, 9- or 10-membered aromatic ring system optionally containing one or two heteroatoms selected from the group of nitrogen, oxygen and sulfur, and optionally substituted by F, Cl, $(C_1-C_6)$-alkyl or O—$(C_1-C_8)$-alkyl;

R3 is H or $(C_1-C_6)$-alkyl;

R4, R5 are each independently H, $(C_1-C_6)$-alkyl, OH, O—$(C_1-C_6)$-alkyl or O—CO$(C_1-C_6)$-alkyl;

R6, R7, R8, R9 are each independently H or $(C_1-C_8)$-alkyl; or substituent pairs R6 and R7, and R8 and R9, optionally form, independently of one another, an oxo group;

n, m are each independently 0, 1 or 2;

A, B, D, G are each independently N or C(R42);

R42 is H, F, Cl, Br, $CF_3$, CN, O—$(C_1-C_6)$-alkyl, $(C_1-C_6)$-alkyl, $(C_3-C_8)$-cycloalkyl, $(C_0-C_2)$-alkylene-aryl, O—$(C_0-C_2)$-alkylene-aryl, N(R43)(R44), $SO_2$—$CH_3$, COO—$(C_1-C_6)$-alkyl, CON(R45)(R46), N(R47)CO(R48), N(R49)$SO_2$(R50) or CO(R51);

R43, R44, R45, R46, R47, R49 are each independently H or $(C_1-C_8)$-alkyl; or substituent pairs R43 and R44, and R45 and R46, independently of one another and taken together with the nitrogen atom to which they are attached, optionally form a 5 or 6 membered ring which, apart from said nitrogen atom of attachment, optionally contains an additional heteroatom component selected from the group of N—$(C_1-C_6)$-alkyl, oxygen and sulfur;

R48, R50, R51 are each independently H, $(C_1-C_8)$-alkyl or aryl;

R10 is H or $(C_1-C_8)$-alkyl;

X is N(R52) or O;

R52 is H or $(C_1-C_8)$-alkyl;

E is a 3-, 4-, 5-, 6-, 7- or 8 membered bivalent carbo- or heterocyclic ring structure with 0, 1, 2, 3, or 4 heteroatoms from the group of N, O and S, and optionally substituted with H, F, Cl, $CF_3$, $NO_2$, OH, CN, O—$(C_1-C_6)$-alkyl, $(C_1-C_6)$-alkyl, $(C_0-C_8)$-alkylene-aryl, O—$(C_0-C_8)$-alkylene-aryl, N(R57)(R58), $SO_2$—$CH_3$, COO—$(C_1-C_6)$-alkyl, CON(R59)(R60), N(R61)CO(R62), N(R63)$SO_2$(R64) or CO(R65), and wherein said bivalent carbo- or heterocyclic ring is mono- or bicyclic;

R57, R58, R59, R60, R61, R63 are each independently H or $(C_1-C_8)$-alkyl; or substituent pairs R57 and R58, and R59 and R60, independently of one another and taken together with the nitrogen atom to which they are attached, optionally form a 5 or 6 membered ring which, apart from said nitrogen atom of attachment, optionally contains one further heteroatom component selected from the group of N—$(C_1-C_6)$-alkyl, oxygen and sulfur;

R62, R64, R65 are each independently H, $(C_1-C_8)$-alkyl or aryl;

K is a bond, O, $CH_2O$, N(R66), (C(R69)(R70))$_v$ or C≡C;

v is 1 or 2;

R66, R67, R68, R69, R70 are each independently H or $(C_1-C_8)$-alkyl;

R11 is H, $(C_1-C_8)$-alkyl, $(C_1-C_4)$-alkoxy-$(C_1-C_4)$-alkyl, $(C_3-C_8)$-alkenyl, a 3-, 4-, 5-, 6-, 7-, 8-, 9-, or 10-membered mono-, bi- or spirocyclic ring, optionally containing 1, 2, 3 or 4 heteroatoms selected from the group of oxygen, nitrogen and sulfur, and optionally substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R71), CON(R72)(R73), hydroxy, COO(R74), N(R75)CO$(C_1-C_6)$-alkyl, N(R76)(R77) or $SO_2CH_3$;

R71, R72, R73, R74, R75, R76, R77 are each independently H or $(C_1-C_8)$-alkyl; or substituent pairs R72 and R73, and R76 and R77, independently of one another and taken together with the nitrogen atom to which they are attached, optionally form a 5 or 6 membered ring which, apart from said nitrogen atom of attachment, optionally contain one additional heteroatom component selected from the group of N—$(C_1-C_6)$-alkyl, oxygen and sulfur.

4. The compound of claim 3, wherein

A, B, D, G are each independently N or C(R42), and the total number of nitrogen atoms in said ring is 0-2.

5. The compound of claim 4, wherein n is 1 and m is 1 or 2.

6. The compound of claim 1 wherein

R1, R2 are each independently H, $(C_1-C_8)$-alkyl, —(CR78R79)$_o$-R12, $(C_1-C_4)$-alkoxy-$(C_1-C_4)$-alkyl, $(C_3-C_8)$-alkenyl, CO—$(C_1-C_8)$-alkyl, —CO—(CH$_2$)$_o$—R12, CO-aryloxy-$(C_1-C_4)$-alkyl, COCH═CH(R13), COCC(R14), CO(C(R15)(R16))$_q$N(R17)(R18), CO(C(R19)(R20))$_r$CON(R21)(R22), CO(C(R23)(R24))$_s$O(R25); or R1 and R2, taken together with the nitrogen atom to which they are attached, optionally form a 4-, 5-, 6-, 7-, 8-, 9-, or 10-membered mono-, bi- or spirocyclic ring which, apart from said nitrogen atom of attachment, optionally comprises one or two additional heteroatoms selected from the group of oxygen, nitrogen and sulfur, and is optionally substituted by F, Cl, $CF_3$, $(C_1-C_6)$-alkyl, O—$(C_1-C_4)$-alkyl, $(C_1-C_4)$-alkoxy-$(C_1-C_4)$-alkyl, hydroxy-$(C_1-C_4)$-alkyl, $(C_0-C_2)$-alkylene-aryl, oxo, CO(R26), CON(R27)(R28), hydroxy, COO(R29), N(R30)CO$(C_1-C_6)$-alkyl, N(R31)(R32) or $SO_2CH_3$;

o is 0, 1, 2, 3, 4, 5 or 6;

q, r are independently of one another 1, 2 or 3;

s is 0, 1, 2, 3 or 4;

R13, R14 are each independently an aryl ring optionally comprising one nitrogen atom;

R15, R16, R17, R19, R20, R21, R22, R23, R24, R25, R26, R27, R28, R29, R30, R31, R32 are each independently H or $(C_1-C_6)$-alkyl;

R18 is H, $(C_1-C_6)$-alkyl, CO$(C_1-C_6)$-alkyl or CO(R33); or substituent pairs R17 and R18, R21 and R22, R27 and R28, R31 and R32, independently of one another and taken together with the nitrogen atom to which they are attached, optionally form a 5 or 6 membered ring which, apart from said nitrogen atom of attachment, optionally contains 1 further heteroatom component selected from the group of N—$(C_1-C_6)$-alkyl, oxygen and sulfur;

R33 is a 5-, 6-, 7-, 8-, 9- or 10 membered aromatic ring system optionally comprising one additional heteroatom selected from the group of nitrogen, oxygen and sulfur and optionally substituted by F, Cl, $(C_1-C_6)$-alkyl or O—$(C_1-C_8)$-alkyl;

R12 is OH, O—$(C_1-C_6)$-alkyl, O—$(C_0-C_8)$-alkylene-aryl, CN, S—$(C_1-C_6)$-alkyl, COO(R80), CON(R81)(R82), or a 3-, 4-, 5-, 6-, 7-, 8-, 9-, 10, 11- or 12 membered mono-, bi- or spirocyclic ring which optionally contains one or more heteroatoms from the group of N, O and S, and is optionally substituted by F, Cl, Br, OH, $CF_3$, CN, oxo, O—$(C_1-C_6)$-alkyl, $(C_1-C_4)$-alkoxy-$(C_1-C_4)$-alkyl, $(C_1-C_6)$-alkyl, O—$(C_0-C_8)$-alkylene-aryl, $(C_0-C_8)$-alkylene-aryl, N(R34)(R35), COCH=CH(R36), (C(R37)(R38))$_t$(R39), CO(C(R37)(R38))$_t$(R39), CO($C_1-C_6$)-alkyl, COCOO($C_1-C_6$)-alkyl, COO(R40) or S(O)$_u$(R41);

t is 0, 1, 2, 3, 4, 5 or 6;

u is 0, 1 or 2;

R34, R35, R37, R38 are independently of one another H or $(C_1-C_8)$-alkyl; or substituent pair R34 and R35, taken together with the nitrogen atom to which they are attached, optionally form a 5 or 6 membered ring which, apart from said nitrogen atom of attachment, optionally contains one additional heteroatom component selected from the group of N—$(C_1-C_6)$-alkyl, oxygen and sulfur, and is optionally substituted by 1 or 2 oxo groups;

R36, R39 are each independently $(C_3-C_8)$-cycloalkyl or a 5-10 membered aromatic ring system which may comprise 0-2 further heteroatoms from the group of nitrogen, oxygen and sulfur and may be substituted by F, Cl, $(C_1-C_6)$-alkyl or O—$(C_1-C_8)$-alkyl;

R40 is H, $(C_1-C_8)$-alkyl, $(C_2-C_6)$-alkenyl or $(C_0-C_8)$-alkylene-aryl;

R41 is $(C_1-C_6)$-alkyl or a 5-10 membered aromatic ring system which may comprise 0-2 further heteroatoms from the group of nitrogen, oxygen and sulfur and may be substituted by F, Cl, $(C_1-C_6)$-alkyl, O—$(C_1-C_8)$-alkyl;

R78, R79 are independently of one another H, $(C_1-C_8)$-alkyl, hydroxy-$(C_1-C_4)$-alkyl, OH or $(C_1-C_4)$-alkoxy-$(C_1-C_4)$-alkyl;

R80, R81 are independently of one another H or $(C_1-C_8)$-alkyl;

R3 is H or $(C_1-C_6)$-alkyl;

R4, R5 are independently of one another H, $(C_1-C_6)$-alkyl, OH, O—$(C_1-C_6)$-alkyl, O—CO$(C_1-C_6)$-alkyl or S—$(C_1-C_6)$-alkyl;

R6, R7, R8, R9 is H; or
substituent pairs R6 and R7, and R8 and R9, independently of one another, optionally form oxo;

n is 1;

m is 1 or 2;

A, B, D, G are independently of one another N or C(R42); or
the groups A and B or D and G are each C(R42) and together form an ortho-phenylene unit to result overall in a 1,4-bisubstituted naphthalene system;

R42 is H, F, Cl, Br, $CF_3$, CN, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_0-C_8)$-alkylene-aryl, O—$(C_0-C_8)$-alkylene-aryl, N(R43)(R44), $SO_2$—$CH_3$, CON(R45)(R46), N(R47)CO(R48), CO(R51) or —(CR84R85)$_x$—O(R86);

R43, R44, R45, R46, R47 are independently of one another H, $(C_1-C_8)$-alkyl; or
substituent pairs R43 and R44, and R45 and R46, independently of one another, taken together with the nitrogen atom to which they are attached, optionally form a 5-6 membered ring which, apart from said nitrogen atom of attachment, optionally contain one additional heteroatom component selected from the group of N—$(C_1-C_6)$-alkyl, oxygen and sulfur;

R48, R50, R51 are each independently H, $(C_1-C_8)$-alkyl or aryl;

R84, R85 are H;

R86 is H or $(C_1-C_6)$-alkyl;

x is 0, 1 or 2;

R10 is H or $(C_1-C_8)$-alkyl;

X is N(R52) or a bond;

R52 is H or $(C_1-C_8)$-alkyl;

E is a 3-8 membered bivalent carbo- or heterocyclic ring structure with 0-4 heteroatoms from the group of N, O and S, which may optionally have substituents from the group of H, F, Cl, Br, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R57)(R58), $SO_2$—$CH_3$, N(R61)CO(R62), N(R63)$SO_2$(R64) or CO(R65) and wherein said carbo- or heterocyclic ring structure may be mono- or bicyclic;

R57, R58, R61, R63 are each independently H or $(C_1-C_8)$-alkyl;

R62, R64, R65 are each independently H, $(C_1-C_8)$-alkyl or aryl;

K is a bond, O, $OCH_2$, $CH_2O$, S, SO, $SO_2$, N(R66), N(R67)CO, CON(R68), (C(R69)(R70))$_v$, CO, C=C, C≡C, $SCH_2$ or $SO_2CH_2$;

v is 1, 2, 3 or 4;

R66, R67, R68, R69, R70 are independently of one another H or $(C_1-C_8)$-alkyl;

R11 is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, a 3 to 10-membered mono-, bi-, tri- or spirocyclic ring which may comprise 0 to 4 heteroatoms selected from the group of oxygen, nitrogen and sulfur, where the ring system may additionally be substituted by F, Cl, Br, $CF_3$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R71), CON(R72)(R73), hydroxy, COO(R74), N(R75)CO$(C_1-C_6)$-alkyl, N(R76)(R77) or $SO_2CH_3$;

R71, R72, R73, R74, R75, R76, R77 are independently of one another H or $(C_1-C_8)$-alkyl; or
substituent pairs R72 and R73, and R76 and R77, independently of one another and taken together with the nitrogen atom to which they are attached, optionally form a 5-6 membered ring which, apart from said nitrogen atom of attachment, optionally contains an additional heteroatom component selected from the group of N—$(C_1-C_6)$-alkyl, oxygen and sulfur; or the N-oxides and the pharmaceutically acceptable salts thereof.

7. The compound of claim 6 having the formula Ia

Ia wherein
R1, R2 are independently of one another H, $(C_1-C_8)$-alkyl, —(CR78R79)$_o$—R12, $(C_1-C_4)$-alkoxy-$(C_1-C_4)$-alkyl, or R1 and R2 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, $(C_1-C_6)$-alkyl, O—$(C_1-C_4)$-alkyl, $(C_1-C_4)$-alkoxy-$(C_1-C_4)$-alkyl, hydroxy-$(C_1-C_4)$-alkyl, $(C_0-C_2)$-alkylene-aryl, oxo, CO(R26), CON(R27)(R28), hydroxy, N(R31)(R32) or $SO_2CH_3$; where $R^1$ and $R^2$ are not both CO(R26);

o is 0, 1, 2, 3 or 4;

q is 1, 2 or 3;

s 0, 1 or 2;

R15, R16, R17, R18, R23, R24, R25, R26, R27, R28, R31, R32 are independently of one another H or $(C_1-C_6)$-alkyl; or substituent pairs R17 and R18, R27 and R28, and R31 and R32, independently of one another and taken together with the nitrogen atom to which they are attached, optionally form a 5-6 membered ring which, apart from said nitrogen atom of attachment, optionally comprises one additional heteroatom component selected from the group of N—$(C_1-C_6)$-alkyl, oxygen and sulfur;

R12 is OH, O—$(C_1-C_6)$-alkyl, O—$(C_0-C_2)$-alkylene-aryl, CN, S—$(C_1-C_6)$-alkyl, 3-12 membered mono-, bi- or spirocyclic ring which optionally comprises 1 to 3 heteroatoms selected from the group of N, O and S, and optionally substituted by F, OH, $CF_3$, CN, oxo, $(C_1-C_6)$-alkyl, $(C_0-C_2)$-alkylene-aryl, N(R34)(R35), COO(R40) or CO($C_1-C_6$)-alkyl;

R34, R35 are independently of one another H or $(C_1-C_4)$-alkyl;

R40 is H, $(C_1-C_6)$-alkyl or $(C_0-C_2)$-alkylene-aryl;

R78, R79 are each independently H, $(C_1-C_8)$-alkyl, hydroxy-$(C_1-C_4)$-alkyl, OH or $(C_1-C_4)$-alkoxy-$(C_1-C_4)$-alkyl;

R42, R42' are each independently H, F, Cl, Br, $CF_3$, CN or $(C_1-C_6)$-alkyl;

R10 is H or $(C_1-C_8)$-alkyl;

X is N(R52);

R52 is H or $(C_1-C_8)$-alkyl;

E is a 5-7 membered bivalent carbo- or heterocyclic ring structure with 0-3 heteroatoms from the group of N, O and S, and optionally substituted by H, F, Cl, Br, $CF_3$, OH, CN, $OCF_3$, $NO_2$, O—$(C_1-C_6)$-alkyl, $(C_1-C_6)$-alkyl, $SO_2$—$CH_3$ or CO(R65);

R65 is H or $(C_1-C_8)$-alkyl;

K is a bond, O, $OCH_2$, $CH_2O$, S, $SO_2$, N(R66), N(R67)CO, CON(R68), $(C(R69)(R70))_v$, CO, C≡C, $SCH_2$ or $SO_2CH_2$;

v is 1, 2 or 3,

R66, R67, R68, R69, R70 are each independently H or $(C_1-C_8)$-alkyl;

R11 is $(C_1-C_8)$-alkyl, $(C_1-C_4)$-alkoxy-$(C_1-C_4)$-alkyl, a 3 to 10-membered mono-, bi-, tri- or spirocyclic ring optionally comprising 1 to 4 heteroatoms selected from the group of oxygen, nitrogen and sulfur, and optionally substituted by F, Cl, Br, $CF_3$, CN, $(C_1-C_6)$-alkyl, O—$(C_1-C_8)$-alkyl, oxo, CO(R71), hydroxy, N(R75)CO$(C_1-C_6)$-alkyl, or $SO_2CH_3$;

R71, R72, R73, R74, R75, R76, R77 is each independently H or $(C_1-C_8)$-alkyl; or substituent pairs R72 and R73, and R76 and R77, independently of one another and taken together with the nitrogen atom to which they are attached, optionally form a 5 or 6 membered ring which, apart from said nitrogen atom of attachment, optionally contains one additional heteroatom component selected from the group of N—$(C_1-C_6)$-alkyl, oxygen and sulfur; or the N-oxides or pharmaceutically acceptable salts thereof.

8. A pharmaceutical composition comprising a compound of claim 1 and a pharmaceutically acceptable carrier.

9. The pharmaceutical composition of claim 8 further comprising one or more anorectic active ingredients.

10. A method of treating obesity comprising administering to a patient in need thereof a compound of claim 1.

11. A method of treating obesity comprising administering to a patient in need thereof a compound of claim 1 in combination with at least one further anorectic active ingredient.

12. A method of treating type II diabetes comprising administering to a patient in need thereof a compound of claim 1.

13. A method of treating type II diabetes comprising administering to a patient in need thereof a compound of claim 1 in combination with at least one further anorectic active ingredient.

14. A method of reducing weight in mammals comprising administering to a patient in need thereof a compound of claim 1.

* * * * *